United States Patent
Falb et al.

(10) Patent No.: US 10,195,234 B2
(45) Date of Patent: *Feb. 5, 2019

(54) BACTERIA ENGINEERED TO REDUCE HYPERPHENYLALANINEMIA

(71) Applicant: Synlogic Operating Company, Inc., Cambridge, MA (US)

(72) Inventors: Dean Falb, Sherborn, MA (US); Vincent M. Isabella, Cambridge, MA (US); Jonathan W. Kotula, Somerville, MA (US); Paul F. Miller, Salem, CT (US); Sarah Rowe, Somerville, MA (US); Yves Millet, Newton, MA (US)

(73) Assignee: Synlogic Operating Company, Inc., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/301,324

(22) PCT Filed: May 13, 2016

(86) PCT No.: PCT/US2016/032562
§ 371 (c)(1),
(2) Date: Sep. 30, 2016

(87) PCT Pub. No.: WO2016/183531
PCT Pub. Date: Nov. 17, 2016

(65) Prior Publication Data
US 2017/0312320 A1    Nov. 2, 2017

Related U.S. Application Data

(60) Provisional application No. 62/161,137, filed on May 13, 2015, provisional application No. 62/256,052, filed on Nov. 16, 2015.

(51) Int. Cl.
| | | |
|---|---|---|
| *A61K 35/74* | (2015.01) | |
| *C07K 14/245* | (2006.01) | |
| *C12N 9/88* | (2006.01) | |
| *C12N 15/70* | (2006.01) | |
| *C12N 9/06* | (2006.01) | |
| *A61K 35/741* | (2015.01) | |
| *C07K 14/195* | (2006.01) | |
| *A61K 39/02* | (2006.01) | |
| *A61K 35/00* | (2006.01) | |
| *A61K 38/00* | (2006.01) | |

(52) U.S. Cl.
CPC ............ *A61K 35/74* (2013.01); *A61K 35/741* (2013.01); *A61K 39/02* (2013.01); *C07K 14/195* (2013.01); *C07K 14/245* (2013.01); *C12N 9/0014* (2013.01); *C12N 9/0022* (2013.01); *C12N 9/88* (2013.01); *C12N 15/70* (2013.01); *C12Y 104/03002* (2013.01); *C12Y 403/01024* (2013.01); *A61K 38/00* (2013.01); *A61K 2035/11* (2013.01); *Y02A 50/473* (2018.01)

(58) Field of Classification Search
None
See application file for complete search history.

(56) References Cited

U.S. PATENT DOCUMENTS

| | | |
|---|---|---|
| 5,589,168 A | 12/1996 | Allen et al. |
| 5,989,463 A | 11/1999 | Tracy et al. |
| 6,203,797 B1 | 3/2001 | Perry |
| 6,835,376 B1 | 12/2004 | Neeser et al. |
| 7,731,976 B2 | 6/2010 | Cobb et al. |
| 2014/0079701 A1 | 3/2014 | Miller et al. |
| 2015/0238545 A1 | 8/2015 | Borody |
| 2015/0246085 A1* | 9/2015 | Al-Hafid ............ C12N 9/88 424/490 |
| 2015/0359894 A1 | 12/2015 | Weinrich et al. |
| 2016/0177274 A1* | 6/2016 | Falb ............ C12R 1/19 424/93.2 |

FOREIGN PATENT DOCUMENTS

| | | |
|---|---|---|
| CN | 1154845 A | 7/1997 |
| WO | WO 2009/004595 A2 | 1/2009 |
| WO | WO 2013/192543 A2 | 12/2013 |
| WO | WO 2014/018832 A1 | 1/2014 |
| WO | WO 2014/066945 A1 | 5/2014 |
| WO | WO 2014/138324 A1 | 9/2014 |
| WO | WO 2016/183531 A1 | 11/2016 |
| WO | WO 2016/183532 A1 | 11/2016 |
| WO | WO 2016/210373 A2 | 12/2016 |

OTHER PUBLICATIONS

Olier et al Genotoxicity of *Escherichia coli* Nissle 1917 strain cannot be dissociated from its probiotic activity; Gut Microbes 3:6, 501-509.*

Altenhoefer et al., The probiotic *Escherichia coli* strain Nissle 1917 interferes with invasion of human intestinal epithelial cells by different enteroinvasive bacterial pathogens FEMS Immunology and Medical Microbiology 40 (2004) 223-229.*

Sat et al., The *Escherichia coli* mazEF Suicide Module Mediates Thymineless Death Journal of Bacteriology, Mar. 2003, p. 1803-1807.*

Al Hafid et al Phenylketonuria: a review of current and future treatments Transl Pediatr 2014;3:49-62.*

Widhalm et al., Identification of a plastidial phenylalanine exporter that influences flux distribution through the phenylalanine biosynthetic network Nature Communications pp. 1-11.*

Ma et al Oral Administration of Recombinant *Lactococcus lactis* Expressing HSP65 and Tandemly Repeated P277 Reduces the Incidence of Type I Diabetes in Non-Obese Diabetic Mice PLoS One 2014; 9:105701.*

(Continued)

*Primary Examiner* — Maria G Leavitt
(74) *Attorney, Agent, or Firm* — Finnegan, Henderson, Farabow, Garrett & Dunner, LLP; Chang B. Hong

(57) ABSTRACT

Genetically engineered bacteria, pharmaceutical compositions thereof, and methods of modulating and treating diseases associated with hyperphenylalaninemia are disclosed.

15 Claims, 81 Drawing Sheets

Specification includes a Sequence Listing.

(56) References Cited

OTHER PUBLICATIONS

Drouault et al., Oral Treatment with Lactococcus lactis Expressing *Staphylococcus hyicus* Lipase Enhances Lipid Digestion in Pigs with Induced Pancreatic Insufficiency Applied and Environmental Microbiology, Jun. 2002, p. 3166-3168.*
Blau, N. and N. Longo (2015) "Alternative therapies to address the unmet medical needs of patients with phenylketonuria" *Expert Opin Pharmacother*, 16(6):791-800.
Coban, H.B. et al. (2014) "Screening of phenylpyruvic acid producers and optimization of culture conditions in bench scale bioreactors" *Bioprocess Biosyst Eng*, 37:2343-2352.
International Patent Application No. PCT/US2016/062369, filed Nov. 16, 2016, by Synlogic, Inc.: International Search Report and Written Opinion; dated Mar. 10, 2017.
Jia, X. et al. (2000) "A new strategeutics of gene therapy for hyperphenylalaninemia rats" *National Medical Journal of China*, 2000 Issue 06, English Abstract. [online]. Retrieved from: http://en.cnki.com.cn/Article_en/CJFDTOTAL-ZHYX200006029.htm, on Jan. 30, 2017 (3 pages).
Jia, X. et al. (2000) "A new strategeutics of gene therapy for hyperphenylalaninemia rats" *National Medical Journal of China*, 2000 Issue 06. English translation, Phoenix Translations, Elgin, TX: Nov. 2015 (15 pages).
Al Hafid, N and J. Christodoulou (Oct. 2015) "Phenylketonuria: a review of current and future treatments" *Transl Pediatr*, 4(4):304-317.
Albiniak, A.M. et al. (2013) "High-level secretion of a recombinant protein to the culture medium with a *Bacillus subtilis* twin-arginine translocation system in *Escherichia coli*" *FEBS J*, 280:3810-3821.
Altenhoefer et al. (Apr. 9, 2004) "The probiotic *Escherichia coli* strain Nissie 1917 interferes with invasion of human intestinal epithelial cells by different enteroinvasive bacterial pathogens" *FEMS Immunol Med Microbiol*, 40(3):223-229.
Andersen, P.S. et al. (Apr. 1995) "Uracil uptake in *Escherichia coli* K-12: isolation of uraA mutants and cloning of the gene" *J Bacteriol*, 177(8):2008-2013.
Arai et al. (Aug. 28, 1995) "Expression of the nir and nor genes for denitrification of Pseudomonas aeruginosa requires a novel CRP/FNR-related transcriptional regulator, DNR, in addition to ANR" *FEBS Lett*, 371(1):73-76.
Argos, P. (1989) "A possible homology between immunodeficiency virus p24 core protein and picornaviral VP2 coat protein: prediction of HIV p24 antigenic sites" *EMBO J*, 8(3):779-785.
Arthur et al. (Oct. 5, 2012) "Intestinal inflammation targets cancer-inducing activity of the microbiota" *Science*, 338(6103):120-123. NIH Public Access Author Manuscript: available in PMC May 6, 2013 (11 pages).
Baek, J.O. et al. (Apr. 2011) "Expression and characterization of a second L-amino acid deaminase isolated from *Proteus mirabilis* in *Escherichia coli*" *J Basic Microbiol*, 51:129-135.
Bifulco, D. et al. (2013) "A thermostable L-aspartate oxidase: a new tool for biotechnological applications" *Appl Microbiol Biotechnol*, 97:7285-7295.
Boysen, A. et al. (Apr. 2010) "Translational Regulation of Gene Expression by an Anaerobically Induced Small Non-coding RNA in *Escherichia coli*" *J Biol Chem*, 285(14):10690-10702.
Callura et al. (Sep. 7, 2010) "Tracking, turning, and terminating microbial physiology using synthetic riboregulators" *Proc Natl Acad Sci USA*, 107(36):15898-15903.
Castiglione et al. (Sep. 2009) "The transcription factor DNR from *Pseudomonas aeruginosa* specifically requires nitric oxide and haem for the activation of a target promoter in *Escherichia coli*" *Microbiology*, 155(Pt 9):2838-2844.
Chang (2007) "Use of Enzyme Artificial Cells for Genetic Enzyme Defects" In *Artificial Cells: Biotechnology, Nanomedicine, Regenerative Medicine, Blood Substitutes, Bioencapsulation, and Cell/Stem Cell Therapy, Regenerative Medicine, Artificial Cells and Nanomedicine*—vol. 1, Singapore: World Scientific Publishing, pp. 147-159.
Chen et al. (Mar. 2006) "High-level Expression Phenylalanine Ammonia-lyase in *Lactococcus lactis* via Synthesized Sequence Based on Bias Codons" *Chin J Biotech*, 22(2):187-190.
Christoloulou et al. (2012) "Enzyme substitution therapy for phenylketonuria delivered orally using a genetically modified probiotic: proof of principle" 62nd Annual Meeting of the American Society of Human Genetics, Nov. 6-10, 2012, San Francisco, CA, USA; Abstract 166.
Clarkson et al. (1971) "Diaminopimelic Acid and Lysine Auxotrophs of *Pseudomonas aeruginosa* 8602" *J Gen Microbiol*, 66:161-169.
Collinson, I. et al. (2015) "Channel crossing: how are proteins shipped across the bacterial plasma membrane?" *Philos Trans R Soc B*, 370:20150025 [online]. Retrieve from: http://rstb.royalsocietypublishing.org/, on Jun. 16, 2016 (13 pages).
Costa, T.R.D. et al. (May 2015) "Secretion systems in Gram-negative bacteria: structural and mechanistic insights" *Nat Rev Microbiol*, 13(6):343-359.
Cuevas-Ramos et al. (Jun. 22, 2010) "*Escherichia coli* induces DNA damage in vivo and triggers genomic instability in mammalian cells" *Proc Natl Acad Sci USA*, 107(25):11537-11542.
Danino, T. et al. (May 2015) "Programmable probiotics for detection of cancer in urine" *Sci Transl Med*,7(289):289ra84 [online]. Retrieved from: www.sciencetranslational medicine.org, on Jul. 30, 2015 (11 pages).
Deutscher (Apr. 2008) "The mechanisms of carbon catabolite repression in bacteria" *Curr Opin Microbiol*, 11(2):87-93.
Dinleyici et al. (Nov. 2014) "*Saccharomyces boulardii* CNCM I-745 in different clinical conditions" *Expert Opin Biol Ther*, 14(11):1593-1609.
Dobbelaere, D. et al. (2003) "Evaluation of nutritional status and pathophysiology of growth retardation in patients with phenylketonuria" *J Inherit Metab Dis*, 26(1):1-11.
Duerre, J. and S. Chakrabarty (Feb. 1975) "L-Amino Acid Oxidases of *Proteus rettgeri*," *J Bacteriol*, 121(2):656-663.
Durand, S. and G. Storz (Mar. 2010) "Reprogramming of Anaerobic Metabolism by the FnrS Small RNA" *Mol Microbiol*, 75(5):1215-1231. NIH Public Access Author Manuscript; available in PMC Sep. 17, 2010 (28 pages).
Eiglmeier et al. (Jul. 1989) "Molecular genetic analysis of FNR-dependent promoters" *Mol Microbiol*, 3(7):869-878.
Estrem, S.T. et al. (Aug. 1998) "Identification of an UP element consensus sequence for bacterial promoters" *Proc Natl Acad Sci USA*, 95(17):9761-9766.
Galimand et al. (Mar. 1991) "Positive FNR-like control of anaerobic arginine degradation and nitrate respiration in *Pseudomonas aeruginosa*" *J Bacteriol*, 173(5):1598-1606.
Gardner et al. (2000) "Construction of a genetic toggle switch in *Escherichia coli*" *Nature*, 403:339-342.
Genbank Database Accession No. AAA86752 (Feb. 3, 1996) "amino acid deaminase [Proteus mirabilis HI4320" [online]. National Center for Biotechnology Information (NCBI), U.S. National Library of Medicine; http://www.ncbi.nlm.nih.gov/protein/AAA86752 (1 page).
Genbank Database Accession No. AAH26251.1 (Jul. 15, 2006) "Phenylalanine hydroxylase [*Homo sapiens*]" [online]. National Center for Biotechnology Information (NCBI), U.S. National Library of Medicine; http://www.ncbi.nlm.nih.gov/protein/AAH26251 (2 pages).
Genbank Database Accession No. ABA23593.1 (Jan. 28, 2014) "histidine ammonia-lyase [Anabaena variabilis ATCC 29413]" [online]. National Center for Biotechnology Information (NCBI), U.S. National Library of Medicine; http://www.ncbi.nlm.nih.gov/protein/ABA23593 (2 pages).
Genbank Database Accession No. ACD36582.1 (Aug. 15, 2011) "L-amino acid deaminase [Proteus mirabilis]" [online]. National Center for Biotechnology Information (NCBI), U.S. National Library of Medicine; http://www.ncbi.nlm.nih.gov/protein/ACD36582 (1 page).
Genbank Database Accession No. BAA90864.1 (Feb. 18, 2000) "L-amino acid deaminase [Proteus vulgaris]" [online]. National

(56) References Cited

OTHER PUBLICATIONS

Center for Biotechnology Information (NCBI), U.S. National Library of Medicine; http://www.ncbi.nlm.nih.gov/protein/BAA90864 (1 page).
Genbank Database Accession No. CAE15566.1 (Feb. 27, 2015) "Histidine ammonia-lyase (histidase) [*Photorhabdus luminescens* subsp. *laumondii* TTO1]" [online]. National Center for Biotechnology Information (NCBI). U.S. National Library of Medicine; http://www.ncbi.nlm.nih.gov/protein/CAE15566 (2 pages).
Genbank Database Accession No. EDV65095.1 (Jun. 20, 2008) "aromatic amino acid transport protein AroP [*Escherichia coli* F11]" [online]. National Center for Biotechnology Information (NCBI), U.S. National Library of Medicine; http://www.ncbi.nlm.nih.gov/protein/EDV65095 (2 pages).
Genbank Database Accession No. EU669819.1 (Aug. 15, 2011) "Proteus mirabilis L-amino acid deaminase gene, complete cds" [online]. National Center for Biotechnology Information (NCBI), U.S. National Library of Medicine; http://www.ncbi.nlm.nih.gov/nuccore/EU669819 (2 pages).
Genbank Database Accession No. U35383.1 (Feb. 3, 1996) "Proteus mirabilis amino acid deaminase (aad) gene, complete cds" [online], National Center for Biotechnology Information (NCBI), U.S. National Library of Medicine; http://www.ncbi.nlm.nih.gov/nuccore/U35383 (2 pages).
Gerdes et al. (Oct. 2006) "Essential genes on metabolic maps" *Curr Opin Biotechnol*, 17(5):448-456.
Gilbert, H.J. et al. (Jan. 1985) "Molecular cloning of the phenylalanine ammonia lyase gene from *Rhodosporidium toruloides* in *Escherichia coli* K-12" *J Bacteriol*, 161(1):314-320.
Gorke and Stülke. (Aug. 2008) "Carbon catabolite repression in bacteria: many ways to make the most out of nutrients" *Nat Rev Microbiol*, 6(8):613-624.
Hasegawa et al. (Sep. 15, 1998) "Activation of a consensus FNR-dependent promoter by DNR of *Pseudomonas aeruginosa* in response to nitrite" *FEMS Microbiol Lett*, 166(2):213-217.
He, G. et al. (Apr. 13, 1999) "Noninvasive measurement of anatomic structure and intraluminal oxygenation in the gastrointestinal tract of iiving mice with spatial and spectral EPR imaging" *Proc Natl Acad Sci USA*, 96(8):4586-4591.
Hoeks, M.P. et al. (Jan. 2009) "Adult issues in phenylketonuria" *Neth J Med*, 67(1):2-7.
Hoeren et al. (Nov. 15, 1993) "Sequence and expression of the gene encoding the respiratory nitrous-oxide reductase from *Paracocous denitrificans*" *Eur J Biochem*, 218(1):49-57.
Hosseini et al. (May 2011) "Propionate as a health-promoting microbial metabolite in the human gut" *Nutr Rev*, 69(5):245-258.
Hou, Y. et al. (Oct. 2015) "Production of phenylpyruvic acid from L-phenylalanine using an L-amino acid deaminase from *Proteus mirabilis*: comparison of enzymatic and whole-cell biotransformation approaches" *Appl Microbiol Biotechnol*, 99(20):8391-8402.
International Patent Application No. PCT/US2016/032562, filed May 13, 2016, by Synlogic, Inc.: International Search Report and Written Opinion, dated Aug. 22, 2016.
Isabella et al. (Jan. 20, 2011) "Deep sequencing-based analysis of the anaerobic stimulon in *Neisseria gonorrhoeae*" *BMC Genomics*, 12:51 (24 pages).
Ivanovska, V. et al. (2014) "Pediatric Drug Formulations: A Review of Challenges and Progress" *Pediatrics*, 134:361-372.
Kang et al. (2010) "Converting an injectable protein therapeutic into an oral form: Phenylalanine ammonia lyase for phenylketonuria" *Mol Genet Metab*, 99:4-9.
Kobe, B. et al. (Jun. 1997) "Regulation and Crystallization of phosphorylated and dephosphorylated forms of truncated dimeric phenylalanine hydroxylase" *Protein Sci*, 6(6):1352-1357.
Kwok, S.C. et al. (Jan. 29, 1985) "Nucleotide sequence of a full-length complementary DNA clone and amino acid sequence of human phenylalanine hydroxylase" *Biochemistry*, 24(3):556-561.

Lee, D.H. et al. (2011) "Cumulative Number of Cell Divisions as a Meaningful Timescale for Adaptive Laboratory Evolution of *Escherichia coli*" *PLoS One*, 6:e26172, http://dx.doi.org/10.1371/journal.pone.0026172 (8 pages).
Leonard, "Disorders of the urea cycle and related enzymes" in *Inborn Metabolic Diseases*, 4th ed. Heidelberg: Springer Medizin Verlag, 2006; pp. 263-272.
Liu et al. (2002) "Study on a Novel Strategy to Treatment of Phenylketonuria" *Art Cells, Blood Subs, and Immob Biotech*. 30(4):243-257.
Longo, N. et al. (Jul. 5, 2014) "Phase 1 Trial of Subcutaneous rAvPAL-PEG in Subjects with Phenylketonuria" *Lancet*, 384(9937):37-44. HHS Public Access Author Manuscript; available in PMC Jul. 5, 2015 (18 pages).
Lopez and Anderson (Dec. 2015) "Synthetic Auxotrophs with Ligand-Dependent Essential Genes for a BL21(DE3) Biosafety Strain" *ACS Synthetic Biology*, 4(12):1279-1286.
MacDonald, M.J. and G.B D'Cunha (2007) "A modern view of phenylalanine ammonia lyase" *Biochem Cell Biol*, 85(3):273-282.
MacLeod, E.L. et al. (Jun. 2010) "Nutritional Management of Phenylketonuria" *Ann Nestle Eng*, 66(2):58-69.
Meadow, P. and E. Work (1959) "Biosynthesis of diaminopimelic acid and lysine in *Escherichia coli*" *Biochem J*, 72(3):396-400.
Moffitt, M.C. et al. (Jan. 30, 2007) "Discovery of two cyanobacterial phenylalanine ammonia lyases: kinetic and structural characterization" *Biochemistry*, 46(4):1004-1012.
Moore et al. (Nov. 3, 2006) "Regulation of FNR dimerization by subunit charge repulsion" *J Biol Chem*, 281(44):33268-33275.
Nougayrede et al. (Aug. 11, 2006) "*Escherichia coli* induces DNA double-strand breaks in eukaryotic cells" *Science*, 313(5788):848-851.
Olier et al. (Nov.-Dec. 2012) "Genotoxicity of *Escherichia coli* Nissle 1917 strain cannot be dissociated from its probiotic activity" *Gut Microbes*, 3(6):501-509.
Pelmont, J. et al. (1972) "L-aminoacide oxydases des enveloppes de *Proteus mirabilis*: propriétés générales (L-amino acid oxidases of *Proteus mirabilis*: general properties)" *Biochimie* 54(10):1359-1374 (French; English summary on p. 1359).
Pi, J. et al. (Jun. 1991) "Cloning and sequencing of the pheP gene, which encodes the phenylalanine-specific transport system of *Escherichia coli*" *J Bacteriol*, 173(12):3622-3629.
Pi, J. et al. (Nov. 1998) "Functional consequences of changing proline residues in the phenylalanine-specific permease of *Escherichia coli*" *J Bacteriol*, 180(21):5515-5519.
Pi, J. and J. Pittard (May 1996) "Topology of the phenylalanine-specific permease of *Escherichia coli*" *J Bacteriol*; 178(9):2650-2655.
Pugsley, A.P. (Mar. 1993) "The complete general secretory pathway in gram-negative bacteria" *Microbiol Rev*, 57(1):50-108.
Purcell, O. et al. (2013) "Towards a whole-cell modeling approach for synthetic biology" *Chaos*, 23(2):025112 (8 pages).
Ray et al. (Nov. 15, 1997) "The effects of mutation of the anr gene on the aerobic respiratory chain of *Pseudomonas aeruginosa*" *FEMS Microbiol Lett*, 156(2):227-232.
Reeves, A.Z. et al. (Apr. 2015) "Engineering *E. coli* into a protein delivery system for mammalian cells" *ACS Synth Biol*, Just Accepted Manuscript, DOI: 10.1021/acssynbio.5b00002 [online], Retrieved from: http://pubs.acs.org, on Apr. 20, 2015 (26 pages), Final publication in vol. 5, pp. 644-654.
Reister et al. (Oct. 10, 2014) "Complete genome sequence of the Gram-negative probiotic *Escherichia coli* strain Nissle 1917" *J Biotechnol*, 187:106-107.
Rembacken et al. (Aug. 21, 1999) "Non-pathogenic *Escherichia coli* versus mesalazine for the treatment of ulcerative colitis: a randomised trial" *Lancet*, 354(9179):635-639.
REFSEQ Database Accession No. NP_415108.1 (Dec. 16, 2014) "phenylalanine transporter [*Escherichla coli* str. K-12 substr. MG1655]" [online]. National Center for Biotechnology Information (NCBI), U.S. National Library of Medicine; http://www.ncbi.nlm.nih.gov/protein/NP_415108 (3 pages).
REFSEQ Database Accession No. WP_011146484.1 (May 24, 2013) "histidine ammonia-lyase [*Photorhabdus luminescens*]" [online].

(56) References Cited

OTHER PUBLICATIONS

National Center for Biotechnology Information (NCBI), U.S. National Library of Medicine; http://www.ncbi.nlm.nih.gov/protein/WP_011146464 (1 page).
Rigel, N.W. and Braunstein (2008) "A new twist on an old pathway—accessory secretion systems" *Mol Microbiol*, 69(2):291-302.
Saier Jr., M.H. (2006) "Protein Secretion and Membrane Insertion Systems in Gram-Negative Bacteria" *J Membrane Biol*, 214:75-90.
Saier Jr., M.H. (2006) "Protein Secretion Systems in Gram-Negative Bacteria. Gram-negative bacteria possess many protein secretion-membrane insertion systems that apparently evolved independently" *Microbe*, 1(9):414-419.
Salmon, K. et al. (Aug. 8, 2003) "Global gene expression profiling in *Escherichia coli* K12. The effects of oxygen availability and FNR" *J Biol Chem*. 278(32):29837-29855.
Sarkissian, C.N. et al. (Mar. 1999) "A different approach to treatment of phenylketonuria: Phenylalanine degradation with recombinant phenylalanine ammonia lyase" *Proc Natl Acad Sci USA*, 96(5):2339-2344.
Sarkissian, C.N. et al. (Jun. 2007) "Quantitation of phenylalanine and its trans-cinnamic, benzoic and hippuric acid metabolites in biological fluids in a single GC-MS analysis" *J Mass Spectrom*, 42(6):811-817.
Sarkissian, C.N. et al. (Nov. 2011) "Evaluation of orally administered PEGylated phenylalanine ammonia lyase in mice for the treatment of Phenylketonuria" *Mol Genet Metab*, 104(3): 249-254. NIH Public Access Author Manuscript, available in PMC Nov. 1, 2012 (15 pages).
Sat et al. (Mar. 2003) "The *Escherichia coli* mazEF suicide module mediates thymineless death" *J Bacteriol*, 185(6):1803-1807.
Sawers (Jun. 1991) "Identification and molecular characterization of a transcriptional regulator from *Pseudomonas aeruginosa* PAO1 exhibiting structural and functional similarity to the FNR protein of *Escherichia coli*" *Mol Microbiol*, 5(6):1469-1481.
Schultz (Jul. 2008) "Clinical use of *E. coli* Nissle 1917 in inflammatory bowel disease" *Inflamm Bowel Dis*, 14(7):1012-1018.
Silhavy, T.J. et al. (2010) "The bacterial cell envelope" *Cold Spring Harb Perspect Biol*, 2, a000414 (17 pages).
Sonnenborn and Schulze (2009) "The non-pathogenic *Escherichia coli* strain Nissle 1917—features of a versatile probiotic" *Microbial Ecology in Health and Disease*, 21:122-158.
Stanley, S.A. et al. (Oct. 2003) "Acute infection and macrophage subversion by *Mycobacterium tuberculosis* require a specialized secretion system" *PNAS*, 100(22):13001-13006.
Steele, R.D. (Jun. 1986) "Blood-brain barrier transport of the alpha-keto acid analogs of amino acids" *Fed Proc*, 45(7):2060-2064.
Trunk et al. (Jun. 2010) "Anaerobic adaptation in *Pseudomonas aeruginosa*: definition of the Anr and Dnr regulons" *Environ Microbiol*, 12(6):1719-1733.
Ukena et al. (Dec. 12, 2007) "Probiotic *Escherichia coli* Nissle 1917 inhibits leaky gut by enhancing mucosal integrity" *PLoS One*, 2(12):e1308. [online] DOI: 10.1371/journal.pone.0001308 (11 pages).
Unden et al. (Jul. 4, 1997) "Alternative respiratory pathways of *Escherichia coli*: energetics and transcriptional regulation in response to electron acceptors" *Biochim Biophys Acta*, 1320(3):217-234.
UNIPROTKB/Swiss-Prot Database Accession No. Q3M5Z3.1 (Nov. 11, 2015) "RecName: Full=Phenylalanine ammonia-lyase" National Center for Biotechnology Information (NCBI), U.S. National Library of Medicine, http://www.ncbi.nlm.nih.gov/protein/Q3M5Z3 (7 pages).
Vockley, J. et al. (Feb. 2014) "Phenylalanine hydroxylase deficiency: diagnosis and management guideline" *Genet Med*, 16(2):188-200.
Wanner, L.A. et al. (Jan. 1995) "The phenylalanine ammonia-lyase gene family in *Arabidopsis thaliana*" *Plant Mol Biol*, 27(2):327-338.
Williams, J.S. et al. (Aug. 2005) "The gene stlA encodes a phenylalanine ammonia-lyase that is involved in the production of a stilbene antibiotic in *Photorhabdus luminescens* TT01" *Microbiology*, 151(Pt 8):2543-2550.
Winteler et al. (Mar. 1996) "The homologous regulators ANR of *Pseudomonas aeruginosa* and FNR of *Escherichia coli* have overlapping but distinct specificities for anaerobically inducible promoters" *Microbiology*, 142(Pt 3):685-693.
Wright et al. (Mar. 20, 2015) "GeneGuard: A modular plasmid system designed for biosafety" *ACS Synth Biol*, 4(3):307-316.
Wu et al. (Oct. 7, 2015) "Direct regulation of the natural competence regulator gene tfoX by cyclic AMP (cAMP) and cAMP receptor protein in *Vibrios*" *Sci Rep*. 5:14921 (15 pages).
Xiang, L and B.S. Moore (Jun. 2005) "Biochemical characterization of a prokaryotic phenylalanine ammonia lyase" *J Bacteriol*, 187(12):4286-4289.
Zhang and Lin (2009) "DEG 5.0, a database of essential genes in both prokaryotes and eukaryotes" *Nucl Acids Res*, 37(suppl. 1):D455-D458.
U.S. Appl. No. 62/183,935, filed Jun. 24, 2015, by Kotula et al.
U.S. Appl. No. 62/184,811, filed Jun. 25, 2015, by Falb et al.
U.S. Appl. No. 62/263,329, filed Dec. 4, 2015, by Kotula et al.

\* cited by examiner

• PAL = phenylalanine ammonia lyase from an Enterobacteriaciae species
• PheP = high affinity phenylalanine transporter

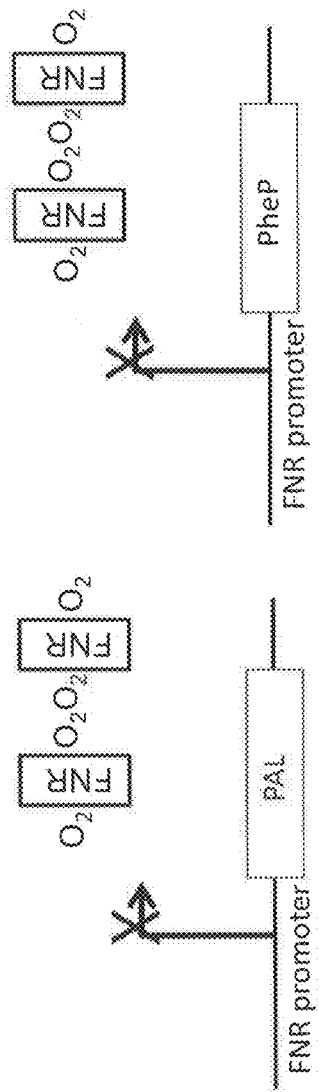
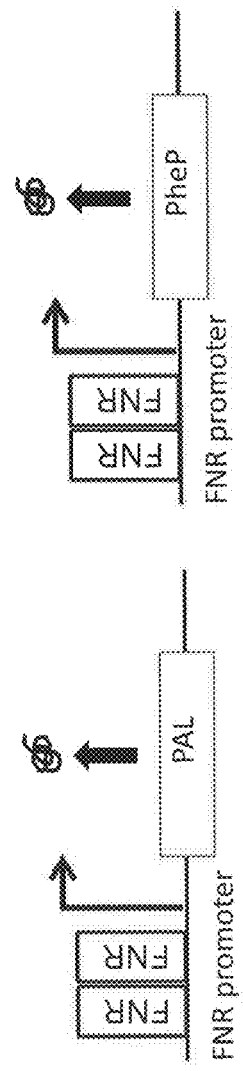
Fig. 17A
Fig. 17B

P-values: ANOVA with Tukey pairwise comparison
* p<0.05,  p<0.01, * p<0.001, **** p<0.0001

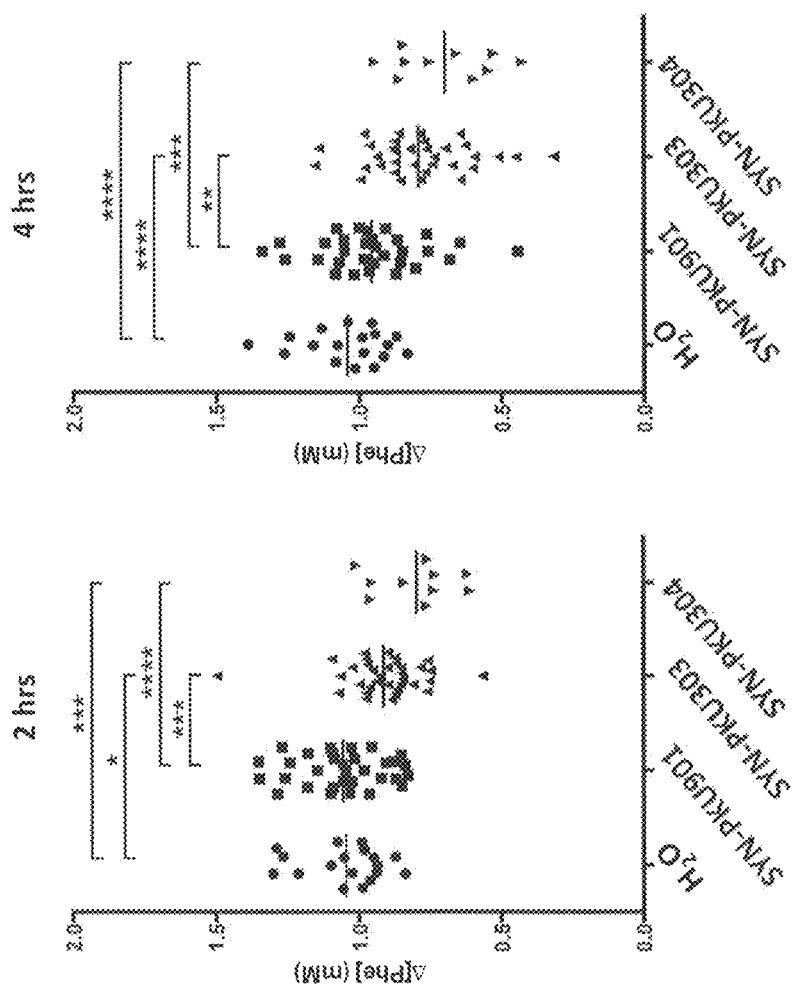

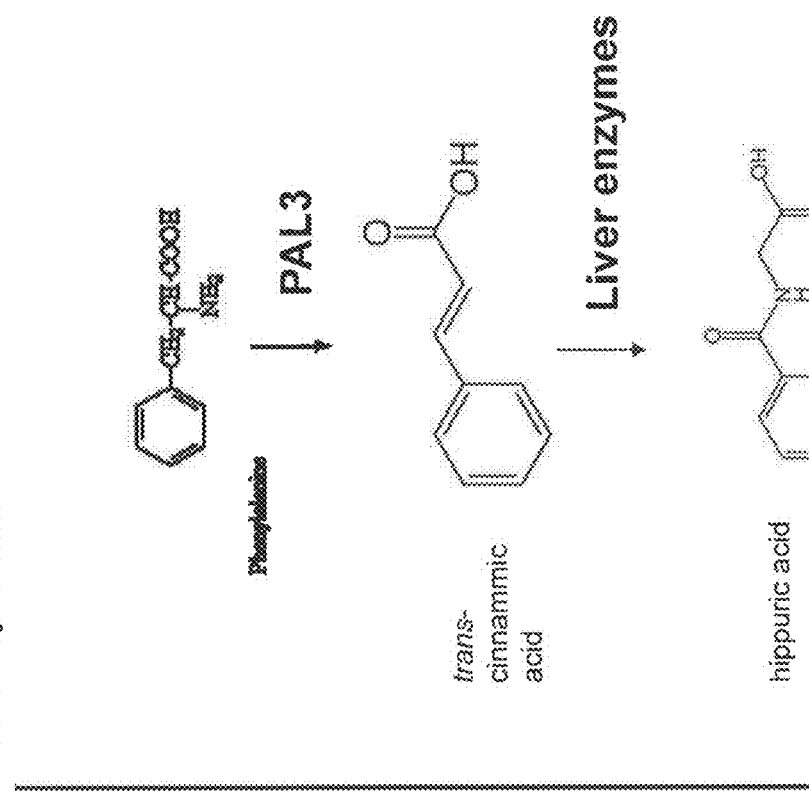
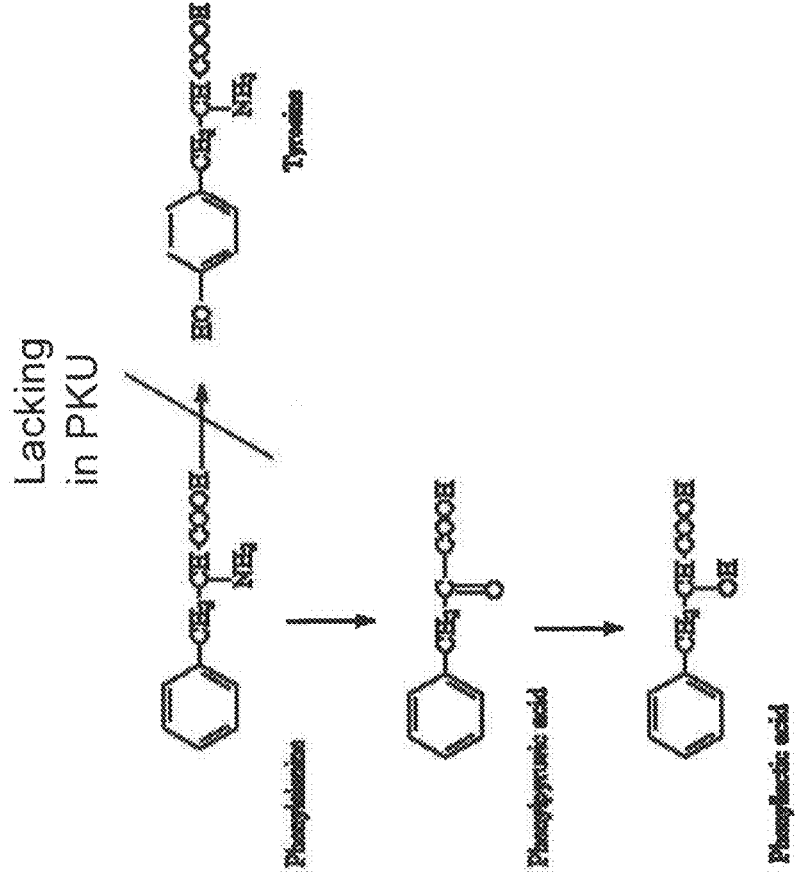
Fig. 31B
Fig. 31A

Brightness of constitutive RFP integrated in three locations:
1. AraB/C
2. MalE/K
3. MetY/ArgG
4. Nissle (non-fluorescent)

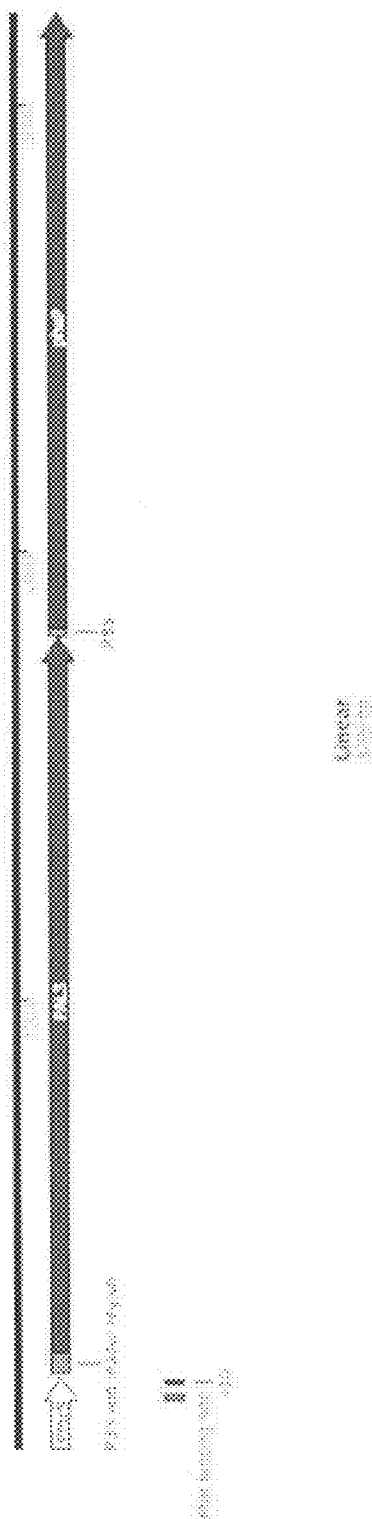

Fig. 49

BACTERIA ENGINEERED TO REDUCE HYPERPHENYLALANINEMIA

This is a national stage application under 35 U.S.C. § 371 of International Application No. PCT/US2016/032562, filed May 13, 2016, which designated the U.S. and which claims the benefit of U.S. Provisional Application No. 62/161,137, filed May 13, 2015, and U.S. Provisional Application No. 62/256,052, filed Nov. 16, 2015, all of which are incorporated herein by reference.

The present application claims the benefit of priority to U.S. Provisional Patent Application No. 62/161,137, filed May 13, 2015, and U.S. Provisional Patent Application No. 62/256,052, filed Nov. 16, 2015, the contents of which are hereby incorporated by reference herein in their entirety.

His disclosure relates to compositions and therapeutic methods for reducing hyperphenylalaninemia. In certain aspects, the disclosure relates to genetically engineered bacteria that are capable of reducing hyperphenylalaninemia in a mammal. In certain aspects, the compositions and methods disclosed herein may be used for treating diseases associated with hyperphenylalaninemia, e.g., phenylketonuria.

Phenylalanine is an essential amino acid primarily found in dietary protein. Typically, a small amount is utilized for protein synthesis, and the remainder is hydroxylated to tyrosine in an enzymatic pathway that requires phenylalanine hydroxylase (PAH) and the cofactor tetrahydrobiopterin. Hyperphenylalaninemia is a group of diseases associated with excess levels of phenylalanine, which can be toxic and cause brain damage. Primary hyperphenylalaninemia is caused by deficiencies in PAH activity that result from mutations in the PAH gene and/or a block in cofactor metabolism.

Phenylketonuria (PKU) is a severe form of hyperphenylalaninemia caused by mutations in the PAH gene. PKU is an autosomal recessive genetic disease that ranks as the most common inborn error of metabolism worldwide (1 in 3,000 births), and affects approximately 13,000 patients in the United States. More than 400 different PAH gene mutations have been identified (Hoeks et al., 2009). Current PKU therapies require substantially modified diets consisting of protein restriction. Treatment from birth generally reduces brain damage and mental retardation (Hoeks et al., 2009; Sarkissian et al., 1999). However, the protein-restricted diet must be carefully monitored, and essential amino acids as well as vitamins must be supplemented in the diet. Furthermore, access to low protein foods is a challenge as they are more costly than their higher protein, nonmodified counterparts (Vockley et al., 2014).

In children with PKU, growth retardation is common on a low-phenylalanine diet (Dobbelaere et al., 2003). In adulthood, new problems such as osteoporosis, maternal PKU, and vitamin deficiencies may occur (Hoeks et al., 2009). Excess levels of phenylalanine in the blood, which can freely penetrate the blood-brain barrier, can also lead to neurological impairment, behavioral problems (e.g., irritability, fatigue), and/or physical symptoms (e.g., convulsions, skin rashes, musty body odor). International guidelines recommend lifelong dietary phenylalanine restriction, which is widely regarded as difficult and unrealistic (Sarkissian et al., 1999), and "continued efforts are needed to overcome the biggest challenge to living with PKU—lifelong adherence to the low-phe diet" (Macleod et al., 2010).

In a subset of patients with residual PAH activity, oral administration of the cofactor tetrahydrobiopterin (also referred to as THB, BH4, Kuvan, or sapropterin) may be used together with dietary restriction to lower blood phenylalanine levels. However, cofactor therapy is costly and only suitable for mild forms of phenylketonuria. The annual cost of Kuvan, for example, may be as much as $57,000 per patient. Additionally, the side effects of Kuvan can include gastritis and severe allergic reactions (e.g., wheezing, light-headedness, nausea, flushing of the skin).

The enzyme phenylalanine ammonia lyase (PAL) is capable of metabolizing phenylalanine to non-toxic levels of ammonia and transcinnamic acid. Unlike PAH, PAL does not require THB cofactor activity in order to metabolize phenylalanine. Studies of oral enzyme therapy using PAL have been conducted, but "human and even the animal studies were not continued because PAL was not available in sufficient amounts at reasonable cost" (Sarkissian et al., 1999). A pegylated form of recombinant PAL (PEG-PAL) is also in development as an injectable form of treatment. However, most subjects dosed with PEG-PAL have suffered from injection site reactions and/or developed antibodies to this therapeutic enzyme (Longo et al., 2014). Thus, there is significant unmet need for effective, reliable, and/or long-term treatment for diseases associated with hyperphenylalaninemia, including PKU.

L-amino acid deaminase (LAAD) catalyzes oxidative deamination of phenylalanine to generate phenylpyruvate, and trace amounts of ammonia and hydrogen peroxide. Phenylpyruvic acid (PPA) is widely used in the pharmaceutical, food, and chemical industries, and PPA is the starting material for the synthesis of D-phenylalanine, a raw intermediate in the production of many chiral drugs and food additives. LAAD has therefore been studied in the context of industrial PPA production (Hou et al. 2015, Appl Microbiol Biotechnol. 2015 October; 99(20):8391-402; "Production of phenylpyruvic acid from L-phenylalanine using an L-amino acid deaminase from *Proteus mirabilis*: comparison of enzymatic and whole-cell biotransformation approaches"). Phenylpyruvate is unable to cross the blood brain barrier (Steele, Fed Proc. 1986 June; 45(7):2060-4; "Blood-brain barrier transport of the alpha-keto acid analogs of amino acids.," indicating that this conversion is useful in controlling the neurological phenotypes of PKU.

In some embodiments, the disclosure provides genetically engineered bacteria that encode and express a phenylalanine metabolizing enzyme (PME). In some embodiments, the disclosure provides genetically engineered bacteria that encode and express phenylalanine ammonia lyase and/or phenylalanine hydroxylase and/or L-aminoacid deaminase and are capable of reducing hyperphenylalaninemia.

In certain embodiments, the genetically engineered bacteria are non-pathogenic and may be introduced into the gut in order to reduce toxic levels of phenylalanine. In certain embodiments, the phenylalanine ammonia lyase and/or phenylalanine hydroxylase and/or L-aminoacid deaminase is stably produced by the genetically engineered bacteria, and/or the genetically engineered bacteria are stably maintained in vivo and/or in vitro. In certain embodiments, the genetically engineered bacteria further comprise a phenylalanine transporter gene to increase their uptake of phenylalanine. The invention also provides pharmaceutical compositions comprising the genetically engineered bacteria, and methods of modulating and treating disorders associated with hyperphenylalaninemia.

BRIEF DESCRIPTION OF THE FIGURES

FIG. 13 depicts schematic diagrams of non-limiting embodiments of the disclosure.

FIGS. 17A and 17B depict the state of one non-limiting embodiment of the PAL construct under non-inducing (FIG. 17A) and inducing (FIG. 17B) conditions. FIG. 17A depicts relatively low PAL and PheP production under aerobic conditions due to oxygen ($O_2$) preventing FNR from dimerizing and activating PAL and/or pheP gene expression. FIG. 17B depicts up-regulated PAL and PheP production under anaerobic conditions due to FNR dimerizing and inducing FNR promoter-mediated expression of PAL and pheP (squiggle above "PAL" and "pheP"). Arrows adjacent to a single rectangle, or a cluster of rectangles, depict the promoter responsible for driving transcription (in the direction of the arrow) of such gene(s). Arrows above each rectangle depict the expression product of each gene.

FIG. 25A depicts phenylalanine concentrations under aerobic conditions using two cell densities. A and B are duplicates under the same experimental conditions. The activity in aerobic conditions is ~50 umol/hr./1e9cells. FIG. 25B depicts phenylalanine concentrations of aerobically, microaerobically, or anaerobically grown cells.

FIGS. 27A and 27B show blood phenylalanine concentrations at 2 hrs and 4 hrs post-phenylalanine injection, respectively. These data indicate that oral administration of the engineered probiotic strain SYN-PKU303 significantly reduces blood phenylalanine levels in mice, compared to mice administered mock treatment ($H_2O$) or the parental strain (SYN-PKU901) (*, $p<0.05$; *, $p<0.001$; **, $p<0.00001$). SYN-PKU303 is capable of intercepting enterorecirculating phenylalanine.

FIGS. 23A and 23B Blood phenylalanine concentrations post phenylalanine injection indicate that SYN-PKU304 (low copy plasmid containing fnrS-PAL) is at least as effective as SYN-PKU303 (high copy plasmid containing Tet-PAL) in reducing circulating Phe levels in the enterorecirculation model.

FIGS. 29A and 29B show blood phenylalanine concentrations at 2 hrs and 4 hrs post-phenylalanine injection, respectively. These data indicate that oral administration of engineered probiotic strains SYN-PKU303 and SYN-PKU304 significantly reduces blood phenylalanine levels in mice compared to mice administered mock treatment (H2O) or the parental strain (SYN-PKU901) (*, $p<0.05$; , $p<0.01$; *, $p<0.001$; ****, $p<0.0001$). FIGS. 29C and 29D depict scatter plots of the data shown in FIGS. 29A and 29B.

FIGS. 30A and 30B show a dose-dependent decrease in blood phenylalanine levels in SYN-PKU304-treated mice compared to mice administered mock treatment (H2O) or the parental strain (SYN-PKU901) (* 30% decrease; $p<0.05$). This experiment represents one of eight studies of this same design, and each one shows that SYN-PKU304 is capable of intercepting enterorecirculating phenylalanine.

FIGS. 31A and 31B depicts a schematic of PKU specific and PAL specific phenylalanine metabolites. FIG. 31A depicts a schematic of the conversion of phenylalanine to phenylpyruvic acid and phenyllactic acid in the absence of functional PAH. FIG. 31B depicts a schematic of the conversion of phenylalanine to trans-cinnamic acid by PAL3, which is further metabolized to hippuric acid by liver enzymes. These metabolites can be detected by mass spectrometry as described in Examples 24-26 or by other means.

FIG. 32A depicts blood phenylalanine concentrations relative to baseline; total metabolic activity for SYN-PKU304 was calculated as 81.2 umol/hr. and the total reduction in Δphe was 45% relative to SYN-PKU901 (P<0.05). FIG. 32B depicts the blood phenylalanine concentration at 0 and 4 hours post phenylalanine injection. FIG. 32C depicts the blood phenylpyruvate concentration at 0 and 4 hours post phenylalanine injection. FIG. 32D depicts the blood phenyllactate concentration at 0 and 4 hours post phenylalanine injection. FIG. 32E depicts the blood t-cinnamic acid concentration at 0 and 4 hours post phenylalanine injection. FIG. 32F depicts the blood hippuric acid concentration at 0 and 4 hours post phenylalanine injection.

FIG. 33A depicts blood phenylalanine concentrations relative to baseline; total metabolic activity for SYN-PKU517 was calculated as 39.6 umol/hr. and the total reduction in Δphe was 17% relative to SYN-PKU801 (P<0.05). FIG. 33B depicts the blood phenylalanine concentration at 0 and 4 hours post phenylalanine injection. FIG. 33C depicts the blood phenylpyruvate concentration at 0 and 4 hours post phenylalanine injection. FIG. 33D depicts the blood phenyllactate concentration at 0 and 4 hours post phenylalanine injection. FIG. 33E depicts the blood t-cinnamic acid concentration at 0 and 4 hours post phenylalanine injection. FIG. 33F depicts the blood hippuric acid concentration at 0 and 4 hours post phenylalanine injection.

FIG. 34A depicts blood phenylalanine concentrations relative to baseline; total metabolic activity for SYN-PKU705 was calculated as 133.2 umol/hr. and the total reduction in Δphe was 30% relative to SYN-PKU901 (P<0.05). FIG. 34B depicts the blood phenylalanine concentration at 0 and 4 hours post phenylalanine injection. FIG. 34C depicts the blood phenylpyruvate concentration at 0 and 4 hours post phenylalanine injection. FIG. 34D depicts the blood phenyllactate concentration at 0 and 4 hours post phenylalanine injection. FIG. 34E depicts the blood t-cinnamic acid concentration at 0 and 4 hours post phenylalanine injection. FIG. 34F depicts the blood hippuric acid concentration at 0 and 4 hours post phenylalanine injection.

FIG. 41 depicts the gene organization of an exemplary construct in which the PAL3 and pheP genes are co-transcribed under the control of an exemplary FNR promoter ($P_{fnrS}$).

FIG. 42A depicts a schematic diagram of the PAL3 gene, flanked by Int5 sites, in the OFF orientation (3' to 5'). When Int5 gene expression is activated under anaerobic conditions, recombinatorial flipping of PAL3 to the ON orientation (5' to 3'; FIG. 42B) leads to the production of PAL3 and to phenylalanine metabolism. Any strong constitutive promoter sequence may be used.

FIG. 43A depicts a schematic diagram of the T7 RNA polymerase gene, flanked by Int5 sites, in the OFF orientation. When Int5 gene expression is activated under anaerobic conditions, the T7 RNA polymerase gene is flipped to the ON orientation (FIG. 43B). In engineered bacterial strains comprising a copy of PAL3 under the control of a T7-driven promoter ($P_{T7}$; FIG. 43C), T7 RNA polymerase expression leads to the production of PAL3 and to phenylalanine metabolism.

FIG. 43A depicts a schematic diagram of the T7 RNA polymerase gene, flanked by Int5 sites, in the OFF orientation. When Int5 gene expression is activated under anaerobic conditions, the T7 RNA polymerase gene is flipped to the ON orientation (FIG. 43B). In engineered bacterial strains comprising a copy of PAL3 under the control of a T7-driven promoter ($P_{T7}$; FIG. 43C), T7 RNA polymerase expression leads to the production of PAL3 and to phenylalanine metabolism.

FIG. 46A also depicts another non-limiting embodiment of the disclosure, wherein the expression of an essential gene not found in the recombinant bacteria is activated by an exogenous environmental signal. In the absence of arabinose, the AraC transcription factor adopts a conformation that represses transcription of the essential gene under the control of the araBAD promoter and the bacterial cell cannot survive. In the presence of arabinose, the AraC transcription factor undergoes a conformational change that allows it to bind to and activate the araBAD promoter, which induces expression of the essential gene and maintains viability of the bacterial cell.

FIG. 49 depicts exemplary sequences of a wild-type clbA construct and a clbA knockout construct.

FIGS. 55A, B, C, D, and E depict a schematic of non-limiting manufacturing processes for upstream and downstream production of the genetically engineered bacteria of the present disclosure. FIG. 55A depicts the parameters for starter culture 1 (SC1): loop full—glycerol stock, duration overnight, temperature 37° C., shaking at 250 rpm. FIG. 55B depicts the parameters for starter culture 2 (SC2): 1/100 dilution from SC1, duration 1.5 hours, temperature 37° C., shaking at 250 rpm. FIG. 55C depicts the parameters for the production bioreactor: inoculum—SC2, temperature 37° C., pH set point 7.00, pH dead band 0.05, dissolved oxygen set point 50%, dissolved oxygen cascade agitation/gas FLO, agitation limits 300-1200 rpm, gas FLO limits 0.5-20 standard liters per minute, duration 24 hours. FIG. 55D depicts the parameters for harvest: centrifugation at speed 4000 rpm and duration 30 minutes, wash 1×10% glycerol/PBS, centrifugation, re-suspension 10% glycerol/PBS. FIG. 55E depicts the parameters for vial fill/storage: 1-2 mL aliquots, −80° C.

DESCRIPTION OF EMBODIMENTS

Figure 1:
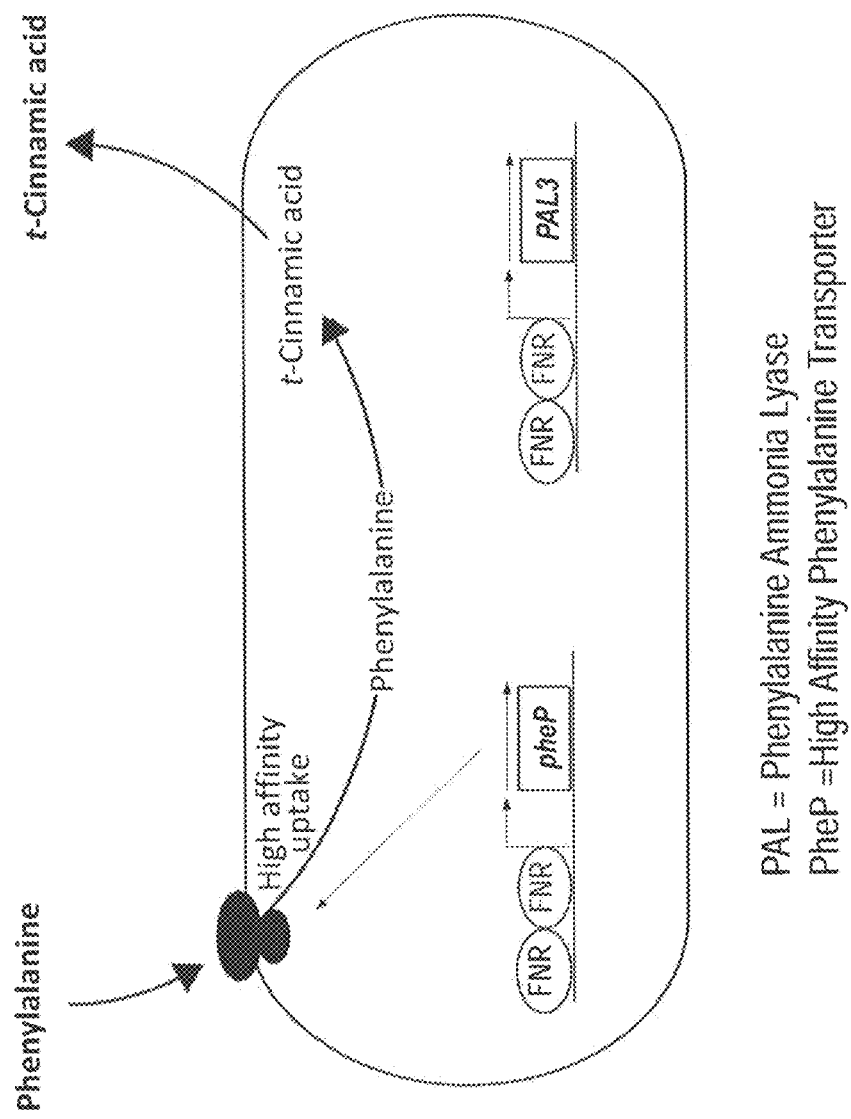
FIG. 1 depicts a synthetic biotic for treating phenylketonuria (PKU) and disorders characterized by hyperphenylalaninemia.
Figure 2A:
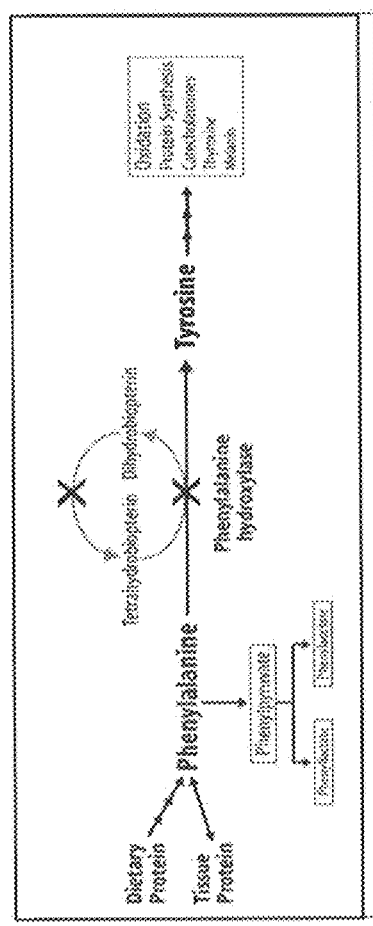
FIG. 2A depicts a schematic of phenylalanine hydroxylase action in phenylketonuria (PKU).
Figure 2B:
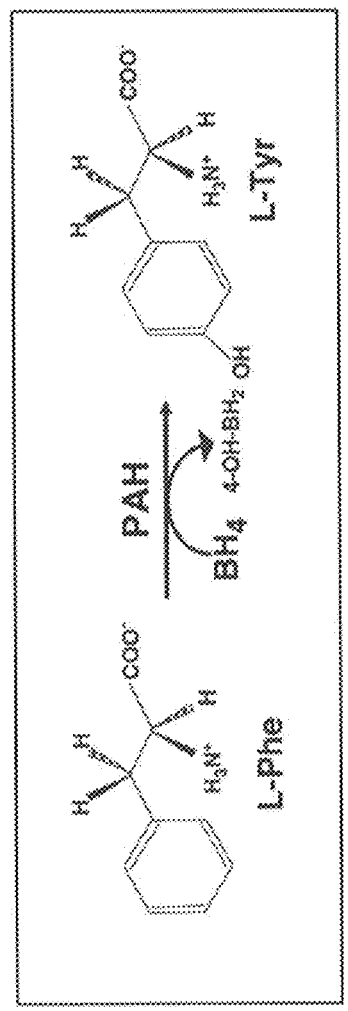
FIG. 2B depicts a schematic of phenylalanine hydroxylase (PAH) action.
Figure 2C:
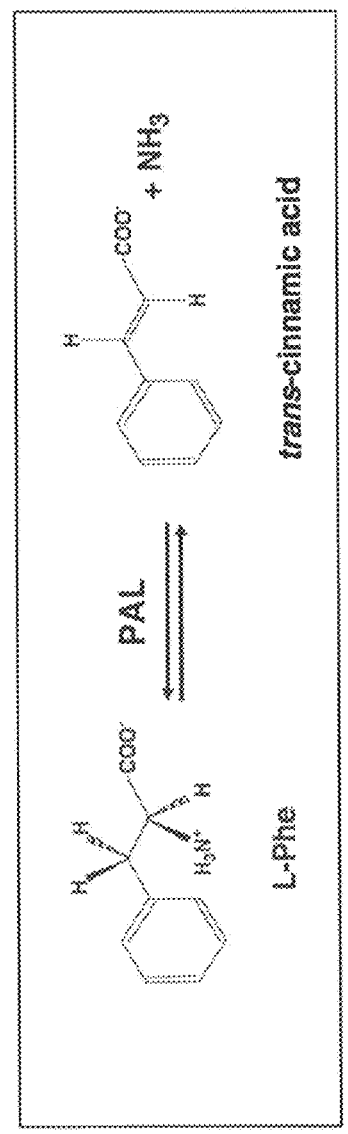
FIG. 2C depicts a schematic of phenylalanine ammonia lyase (PAL) action.
Figure 2D:
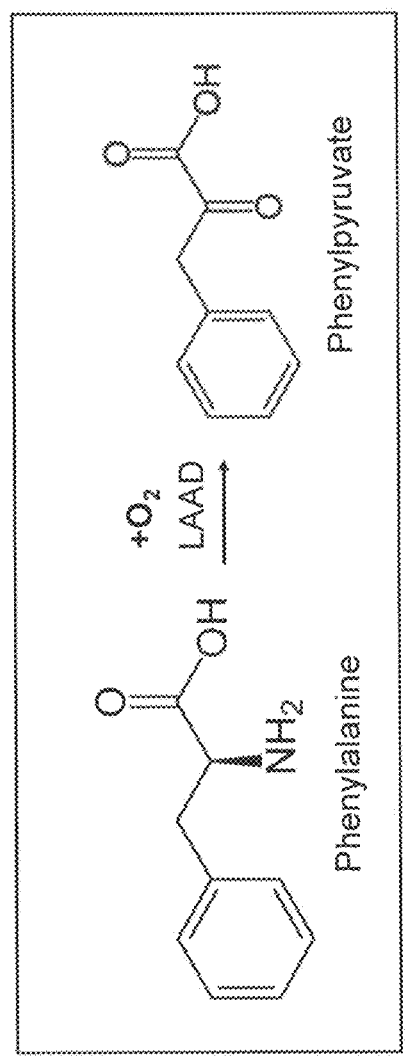
FIG. 2D depicts a schematic of L-amino acid deaminase (LAAD; e.g., from *Proteus mirabilis*) action.
Figure 3:
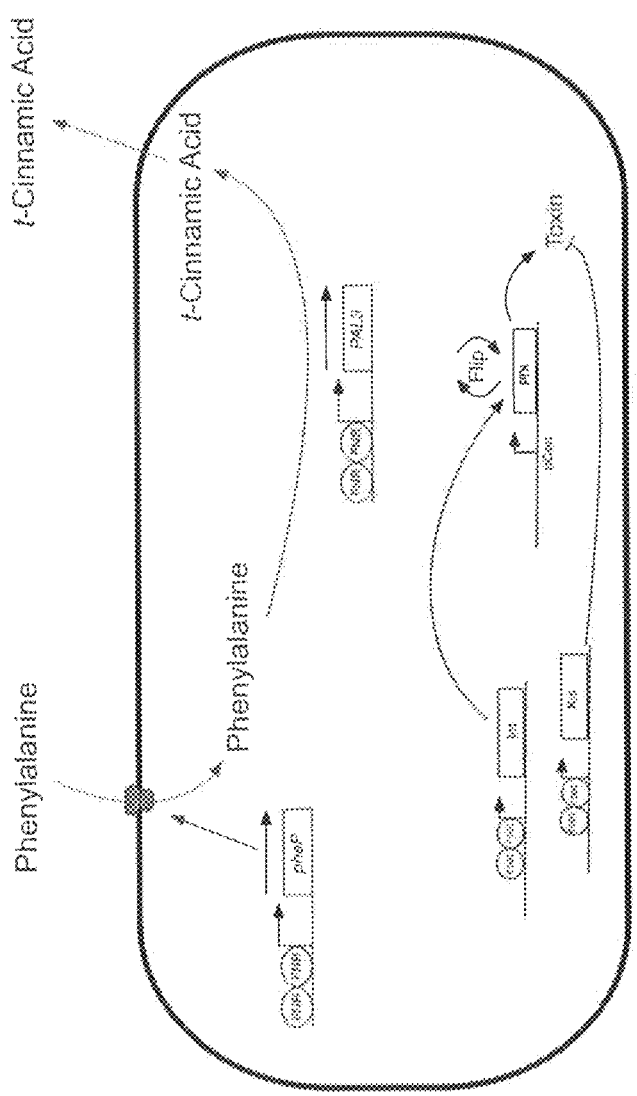
FIG. 3 depicts a synthetic biotic for treating phenylketonuria (PKU) and disorders characterized by hyperphenylalaninemia.
Figure 4:
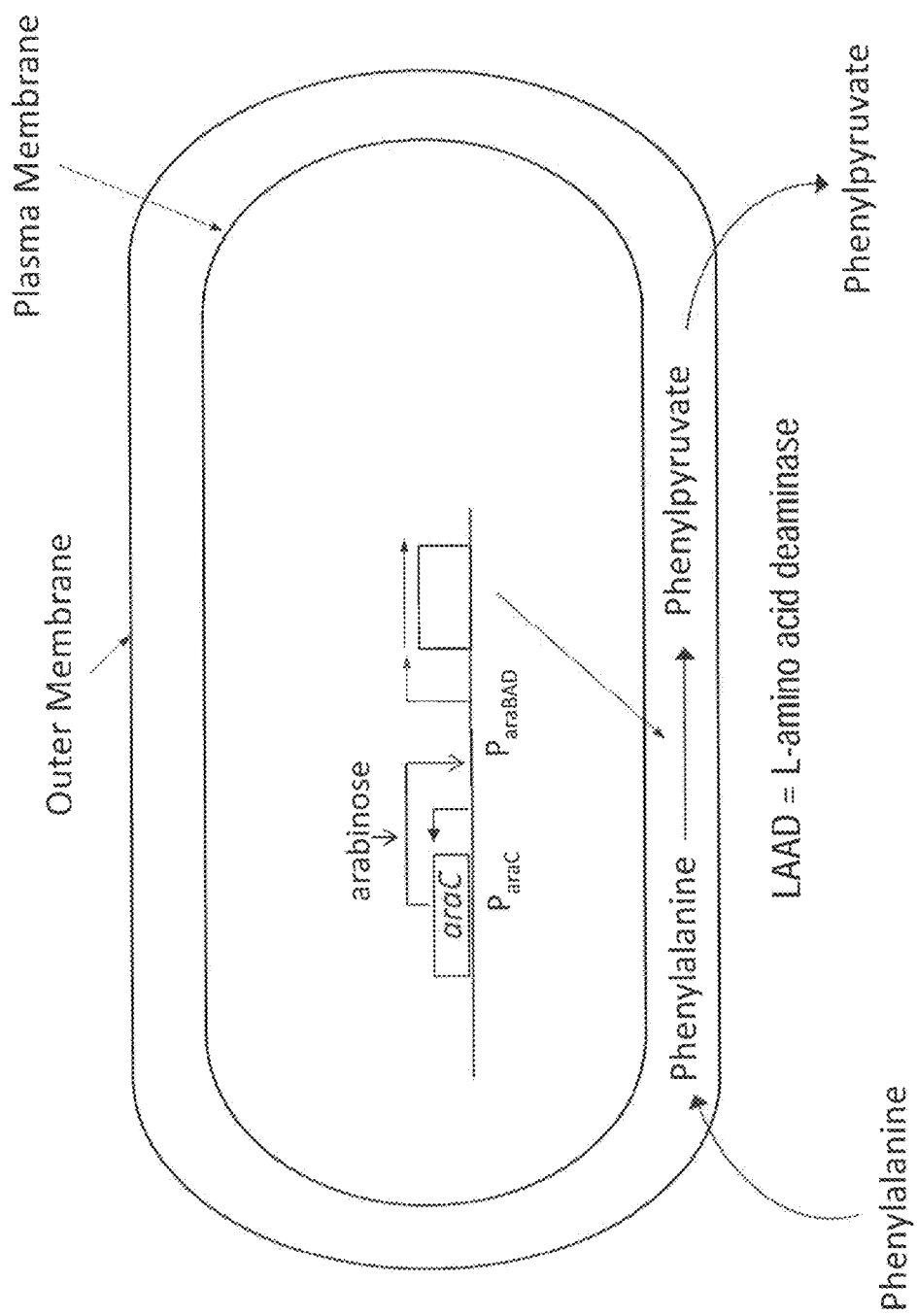
FIG. 4 depicts a synthetic biotic for treating phenylketonuria (PKU) and disorders characterized by hyperphenylalaninemia.
Figure 5:
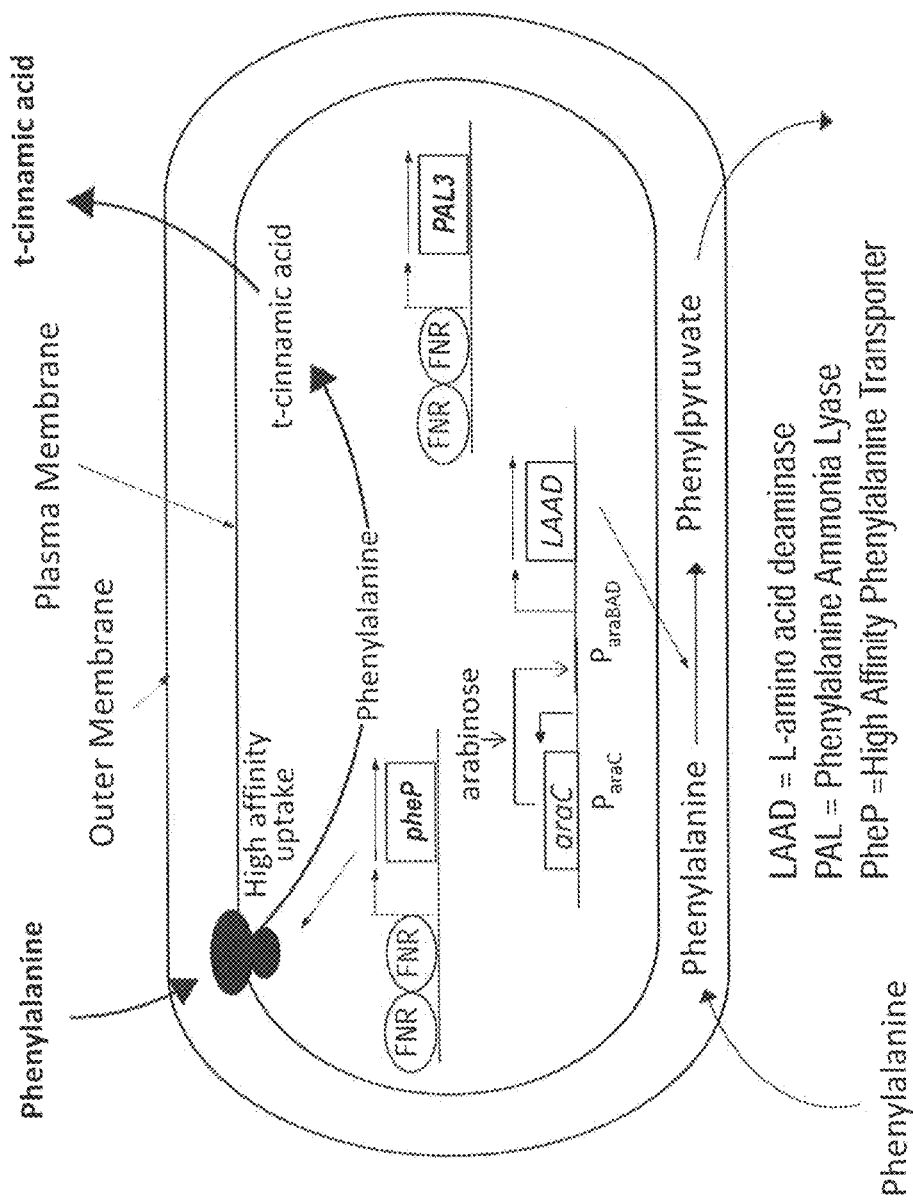
FIG. 5 depicts a synthetic biotic for treating phenylketonuria (PKU) and disorders characterized by hyperphenylalaninemia.
Figure 6:
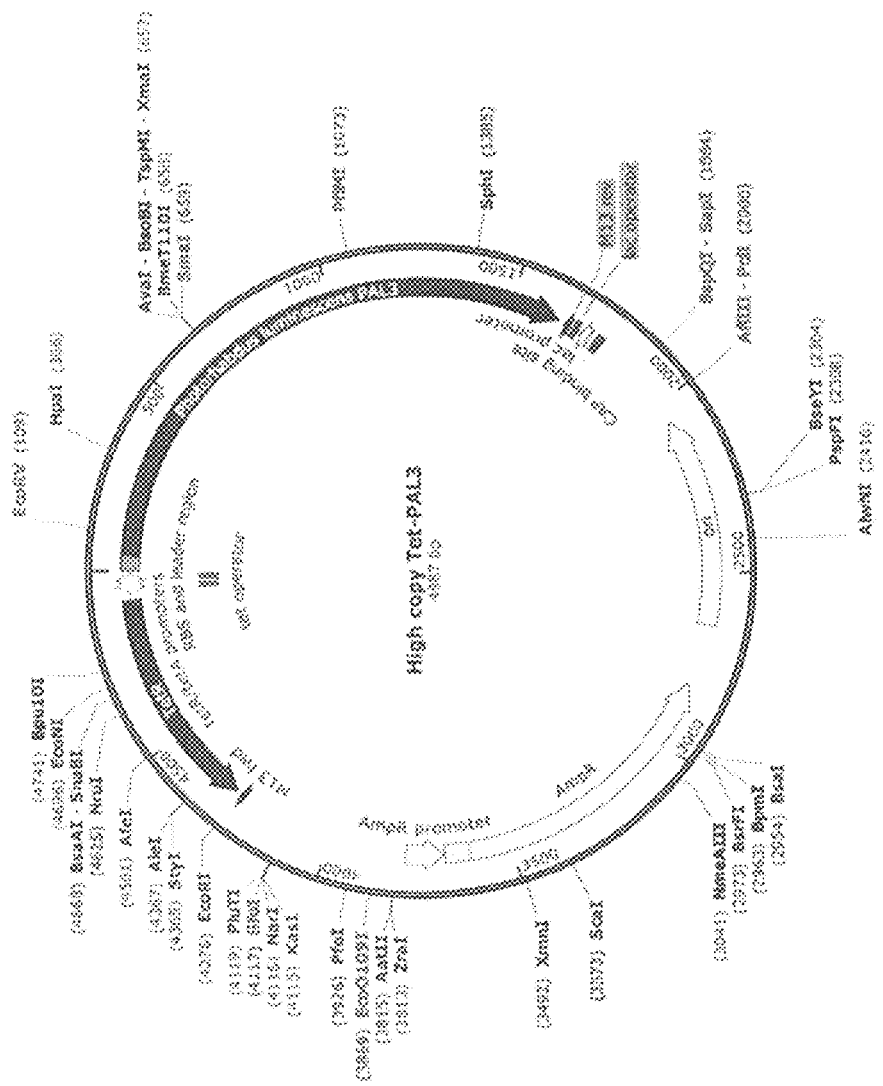
FIG. 6 depicts the gene organization of an exemplary construct comprising a gene encoding PAL3 and a Tet promoter sequence on a high-copy plasmid e.g., as comprised in SYN-PKU202, SYN-PKU303.
Figure 7:
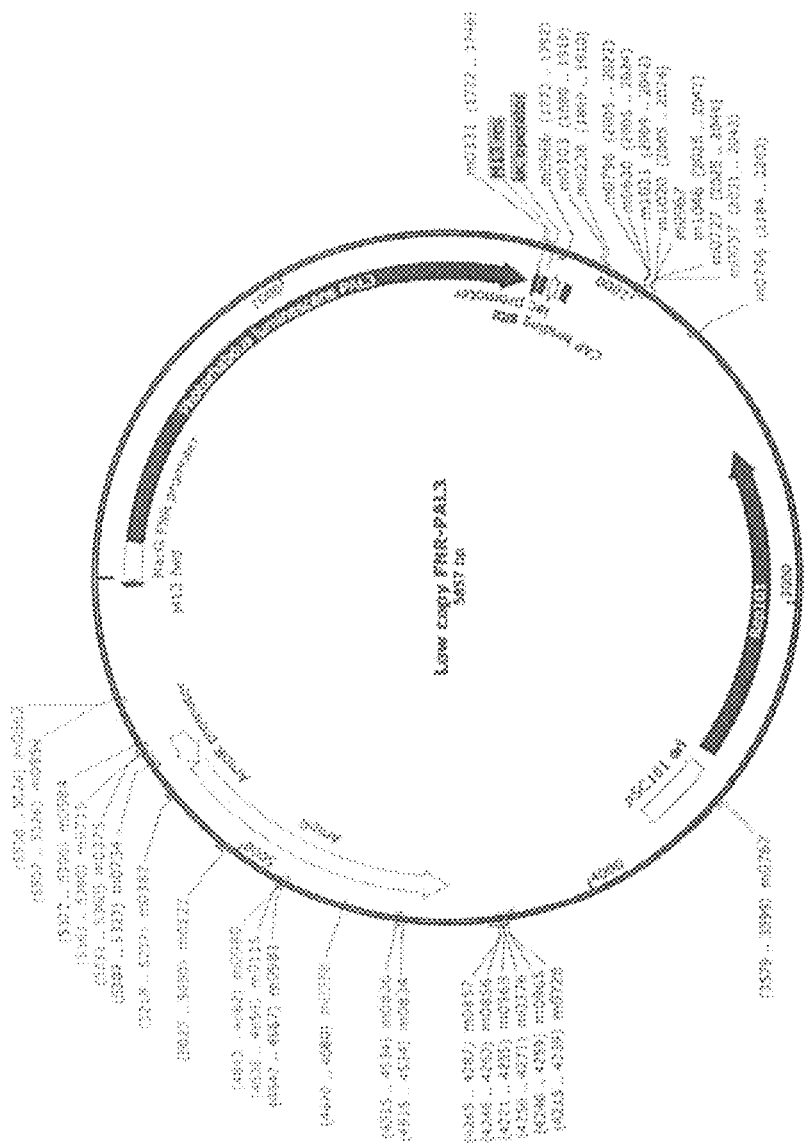
FIG. 7 depicts the gene organization of an exemplary construct comprising a gene encoding PAL3 and an FNR promoter sequence on a low-copy plasmid, e.g., as comprised in SYN-PKU304, SYN-PKU307, SYN-PKU305, SYN-PKU306.
Figure 8:
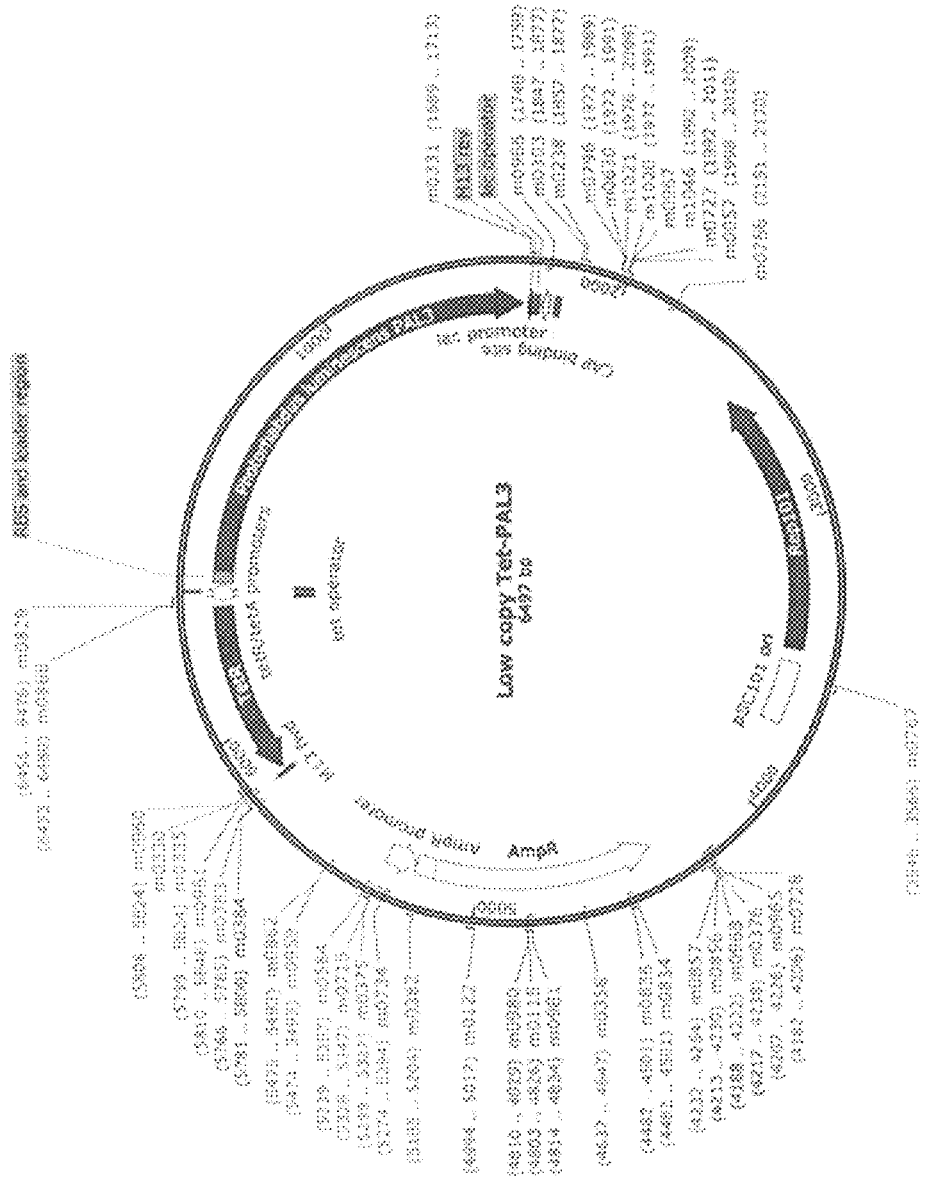
FIG. 8 depicts the gene organization of an exemplary construct comprising a gene encoding PAL3 and a Tet promoter sequence on a low-copy plasmid, e.g., SYN-PKU302, SYN-PKU201.
Figure 9:
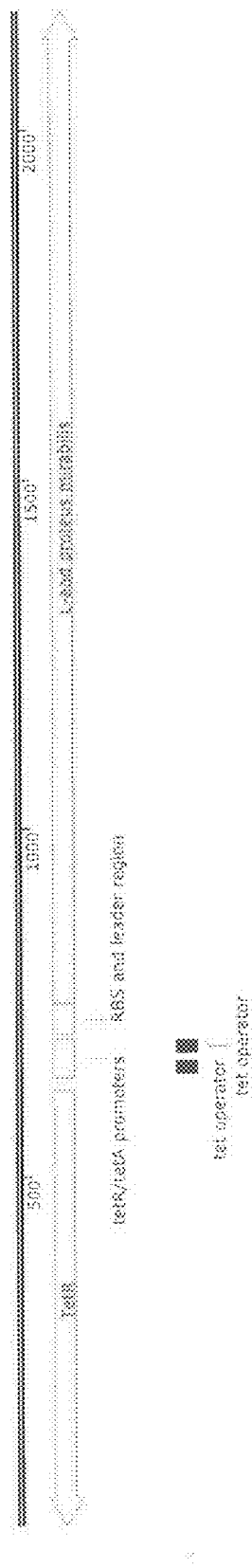
FIG. 9 depicts the gene organization of an exemplary construct, e.g., comprised in SYN-PKU401, comprising a cloned LAAD gene under the control of a Tet promoter sequence and a Tet repressor gene.

The present disclosure includes genetically engineered bacteria, pharmaceutical compositions thereof, and methods of modulating and treating disorders associated with hyperphenylalaninemia. In some embodiments, the genetically engineered bacteria comprise a gene encoding non-native phenylalanine ammonia lyase (PAL) and are capable of processing and reducing phenylalanine in a mammal. Thus, the genetically engineered bacteria and pharmaceutical compositions comprising those bacteria may be used to metabolize phenylalanine in the body into non-toxic molecules in order to treat and/or prevent conditions associated with hyperphenylalaninemia, including PKU. In certain aspects, the compositions comprising the genetically engineered bacteria may be used in the methods of the disclosure to treat and/or prevent disorders associated with hyperphenylalaninemia.

In order that the disclosure may be more readily understood, certain terms are first defined. These definitions should be read in light of the remainder of the disclosure and as understood by a person of ordinary skill in the art. Unless defined otherwise, all technical and scientific terms used herein have the same meaning as commonly understood by a person of ordinary skill in the art. Additional definitions are set forth throughout the detailed description.

"Hyperphenylalaninemia," "hyperphenylalaninemic," and "excess phenylalanine" are used interchangeably herein to refer to increased or abnormally high concentrations of phenylalanine in the body. In some embodiments, a diagnostic signal of hyperphenylalaninemia is a blood phenylalanine level of at least 2 mg/dL, at least 4 mg/dL, at least 6 mg/dL, at least 8 mg/dL, at least 10 mg/dL, at least 12 mg/dL, at least 14 mg/dL, at least 16 mg/dL, at least 18 mg/dL, at least 20 mg/dL, or at least 25 mg/dL. As used herein, diseases associated with hyperphenylalaninemia include, but are not limited to, phenylketonuria, classical or typical phenylketonuria, atypical phenylketonuria, permanent mild hyperphenylalaninemia, nonphenylketonuric hyperphenylalaninemia, phenylalanine hydroxylase deficiency, cofactor deficiency, dihydropteridine reductase deficiency, tetrahydropterin synthase deficiency, and Segawa's disease. Affected individuals can suffer progressive and irreversible neurological deficits, mental retardation, encephalopathy, epilepsy, eczema, reduced growth, microcephaly, tremor, limb spasticity, and/or hypopigmentation (Leonard 2006). Hyperphenylalaninemia can also be secondary to other conditions, e.g., liver diseases.

"Phenylalanine ammonia lyase" and "PAL" are used to refer to a phenylalanine metabolizing enzyme (PME) that converts or processes phenylalanine to trans-cinnamic acid and ammonia. Trans-cinnamic acid has low toxicity and is converted by liver enzymes in mammals to hippuric acid, which is secreted in the urine. PAL may be substituted for the enzyme PAH to metabolize excess phenylalanine. PAL enzyme activity does not require THB cofactor activity. In some embodiments, PAL is encoded by a PAL gene derived from a prokaryotic species. In alternate embodiments, PAL is encoded by a PAL gene derived from a eukaryotic species. In some embodiments, PAL is encoded by a PAL gene derived from a bacterial species, including but not limited to, *Achromobacter xylosoxidans, Pseudomonas aeruginosa, Photorhabdus luminescens, Anabaena variabilis,* and *Agrobacterium tumefaciens*. In some embodiments, PAL is encoded by a PAL gene derived from *Anabaena variabilis* and referred to as "PAL1" herein (Moffitt et al., 2007). In some embodiments, PAL is encoded by a PAL gene derived from *Photorhabdus luminescens* and referred to as "PAL3" herein (Williams et al., 2005). In some embodiments, PAL is encoded by a PAL gene derived from a yeast species, e.g., *Rhodosporidium toruloides* (Gilbert et al., 1985). In some embodiments, PAL is encoded by a PAL gene derived from a plant species, e.g., *Arabidopsis thaliana* (Wanner et al., 1995). Any suitable nucleotide and amino acid sequences of PAL, or functional fragments thereof, may be used.

"Phenylalanine hydroxylase" and "PAH" are used to refer to an enzyme that catalyzes the hydroxylation of the aromatic side chain of phenylalanine to create tyrosine in the human body in conjunction with the cofactor tetrahydrobiopterin. The human gene encoding PAH is located on the long (q) arm of chromosome 12 between positions 22 and 24.2. The amino acid sequence of PAH is highly conserved among mammals. Nucleic acid sequences for human and mammalian PAH are well known and widely available. The full-length human cDNA sequence for PAH was reported in 1985 (Kwok et al. 1985). Active fragments of PAH are also well known (e.g., Kobe et al. 1997).

"L-Aminoacid Deaminase" and "LAAD" are used to refer to an enzyme that catalyzes the stereospecific oxidative deamination of L-amino acids to generate their respective keto acids, ammonia, and hydrogen peroxide. For example, LAAD catalyzes the conversion of phenylalanine to phenylpyruvate. Multiple LAAD enzymes are known in the art, many of which are derived from bacteria, such as *Proteus, Providencia,* and *Morganella,* or venom. LAAD is characterized by fast reaction rate of phenylalanine degradation (Hou et al., Appl Microbiol Technol. 2015 October; 99(20): 8391-402; "Production of phenylpyruvic acid from L-phenylalanine using an L-amino acid deaminase from *Proteus mirabilis:* comparison of enzymatic and whole-cell biotransformation approaches"). Most eukaryotic and prokaryotic L-amino acid deaminases are extracellular; however, *Proteus* species LAAD are localized to the plasma membrane (inner membrane), facing outward into the periplasmic space, in which the enzymatic activity resides. As a consequence of this localization, phenylalanine transport through the inner membrane into the cytoplasm is not required for *Proteus* LAAD mediated phenylalanine degradation. Phenylalanine is readily taken up through the outer membrane into the periplasm without a transporter, eliminating the need for a transporter to improve substrate availability.

In some embodiments, the genetically engineered bacteria comprise a LAAD gene derived from a bacterial species, including but not limited to, *Proteus, Providencia,* and *Morganella* bacteria. In some embodiments, the bacterial species is *Proteus mirabilis*. In some embodiments, the bacterial species is *Proteus vulgaris*. In some embodiments, the LAAD encoded by the genetically engineered bacteria is localized to the plasma membrane, facing into the periplasmic space and with the catalytic activity occurring in the periplasmic space.

"Phenylalanine metabolizing enzyme" or "PME" are used to refer to an enzyme which is able to degrade phenylalanine. Any phenylalanine metabolizing enzyme known in the art may be encoded by the genetically engineered bacteria. PMEs include, but are not limited to, phenylalanine hydroxylase (PAH), phenylalanine ammonia lyase (PAL), aminotransferase, L-amino acid deaminase (L-AAD), and phenylalanine dehydrogenases.

Reactions with phenylalanine hydroxylases, phenylalanine dehydrogenases or aminotransferases require cofactors, while L-AAD and PAL do not require any additional cofactors. In some embodiments, the PME encoded by the genetically engineered bacteria requires a cofactor. In some embodiments, this cofactor is provided concurrently or sequentially with the administration of the genetically engineered bacteria. In other embodiments, the genetically engineered bacteria can produce the cofactor. In some embodiments, the genetically engineered bacteria encode a phenylalanine hydroxylase. In some embodiments, the genetically engineered bacteria encode a phenylalanine dehydrogenase. In some embodiments, the genetically engineered bacteria encode an aminotransferase. In some embodiments, the PME encoded by the genetically engineered bacteria does not require a cofactor. Without wishing to be bound by theory, the lack of need for a cofactor means that the rate of phenylalanine degradation by the enzyme is dependent on the availability of the substrate and is not limited by the availability of the cofactor. In some embodiments, the PME produced by the genetically engineered bacteria is PAL. In some embodiments, the PME produced by the genetically engineered bacteria is LAAD. In some embodiments, the genetically engineered bacteria encode combinations of PMEs.

In some embodiments, the catalytic activity of the PME is dependent on oxygen levels. In some embodiments, the PME is catalytically active under microaerobic conditions. As a non-limiting example, LAAD catalytic activity is dependent on oxygen. In some embodiments, LAAD is active under low oxygen conditions, such as microaerobic conditions. In some embodiments, of the invention, the PME functions at very low levels of oxygen or in the absence of oxygen, e.g. as found in the colon. As a non-limiting example, PAL activity is not dependent on the presence of oxygen.

In certain embodiments, new or improved PMEs can be identified according to methods known in the art or described herein, and are encoded by the genetically engineered bacteria. In some embodiments, the enzyme encoded by the genetically engineered bacteria is a wild type enzyme isolated from a viral, prokaryotic or eukaryotic organism. In some embodiments, the enzyme sequence has been further modified or mutated to increase one or more specific properties of the enzyme, such as stability or catalytic activity.

"Phenylalanine metabolite" refers to a metabolite that is generated as a result of the degradation of phenylalanine. The metabolite may be generated directly from phenylalanine, by the enzyme using phenylalanine as a substrate, or indirectly by a different enzyme downstream in the metabolic pathway, which acts on a phenylalanine metabolite substrate. In some embodiments, phenylalanine metabolites are produced by the genetically engineered bacteria encoding a PME.

In some embodiments, the phenylalanine metabolite results directly or indirectly from PAH activity, e.g., from PAH produced by the genetically engineered bacteria. In some embodiments, the metabolite is tyrosine. In some embodiments, the phenylalanine metabolite accumulates in the blood or the urine of a PKU patient, due to defective PAH activity. Non-limiting examples of such PKU metabolites are phenylpyruvic acid and phenyl-lactic acid. Other examples include phenylacetate, phenylethylamine, and phenylacetyl glutamine.

In some embodiments, the phenylalanine metabolite results directly or indirectly from PAL action, e.g., from PAL produced by the genetically engineered bacteria. Non-limiting examples of such PAL metabolites are trans-cinnamic acid and hippuric acid. In some embodiments, the phenylalanine metabolite results directly or indirectly from LAAD action, e.g., from LAAD produced by the genetically engineered bacteria. Examples of such LAAD metabolites are phenylpyruvate and phenyllactic acid.

"Phenylalanine transporter" is used to refer to a membrane transport protein that is capable of transporting phenylalanine into bacterial cells (see, e.g., Pi et al., 1991). In *Escherichia coli,* the pheP gene encodes a high affinity phenylalanine-specific permease responsible for phenylalanine transport (Pi et al., 1998). In some embodiments, the phenylalanine transporter is encoded by a pheP gene derived from a bacterial species, including but not limited to, *Acinetobacter calcoaceticus, Salmonella enterica,* and *Escherichia coli*. Other phenylalanine transporters include Aageneral amino acid permease, encoded by the aroP gene, transports three aromatic amino acids, including phenylalanine, with high affinity, and is thought, together with PheP, responsible for the lion share of phenylalanine import. Additionally, a low level of phenylalanine transport activity has been traced to the activity of the LIV-I/LS system, which is a branched-chain amino acid transporter consisting of two periplasmic binding proteins, the LIV-binding protein (LIV-I system) and LS-binding protein (LS system), and membrane components, LivHMGF. In some embodiments, the phenylalanine transporter is encoded by a aroP gene derived from a bacterial species. In some embodiments, the phenylalanine transporter is encoded by LIV-binding protein and LS-binding protein and LivHMGF genes derived from a bacterial species. In some embodiments, the genetically engineered bacteria comprise more than one type of phenylalanine transporter, selected from pheP, aroP, and the LIV-I/LS system.

"Phenylalanine" and "Phe" are used to refer to an amino acid with the formula $C_6H_5CH_2CH(NH_2)COOH$. Phenylalanine is a precursor for tyrosine, dopamine, norepinephrine, and epinephrine. L-phenylalanine is an essential amino acid and the form of phenylalanine primarily found in dietary protein; the stereoisomer D-phenylalanine is found is lower amounts in dietary protein; DL-phenylalanine is a combination of both forms. Phenylalanine may refer to one or more of L-phenylalanine, D-phenylalanine, and DL-phenylalanine.

"Operably linked" refers a nucleic acid sequence, e.g., a gene encoding PAL, that is joined to a regulatory region sequence in a manner which allows expression of the nucleic acid sequence, e.g., acts in cis. A regulatory region is a nucleic acid that can direct transcription of a gene of interest and may comprise promoter sequences, enhancer sequences, response elements, protein recognition sites, inducible elements, promoter control elements, protein binding sequences, 5' and 3' untranslated regions, transcriptional start sites, termination sequences, polyadenylation sequences, and introns.

An "inducible promoter" refers to a regulatory region that is operably linked to one or more genes, wherein expression of the gene(s) is increased in the presence of an inducer of said regulatory region.

A "directly inducible promoter" refers to a regulatory region, wherein the regulatory region is operably linked to a gene encoding a phenylalanine-metabolizing enzyme, e.g., PAL; in the presence of an inducer of said regulatory region, the phenylalanine-metabolizing enzyme is expressed. An "indirectly inducible promoter" refers to a regulatory system comprising two or more regulatory regions, for example, a first regulatory region that is operably linked to a gene encoding a first molecule, e.g., a transcriptional regulator, which is capable of regulating a second regulatory region that is operably linked to a gene encoding a phenylalanine-metabolizing enzyme. In the presence of an inducer of the first regulatory region, the second regulatory region may be activated or repressed, thereby activating or repressing expression of the phenylalanine-metabolizing enzyme. Both a directly inducible promoter and an indirectly inducible promoter are encompassed by "inducible promoter."

"Exogenous environmental conditions" refer to settings or circumstances under which the promoter described above is directly or indirectly induced. In some embodiments, the exogenous environmental conditions are specific to the gut of a mammal. In some embodiments, the exogenous environmental conditions are specific to the upper gastrointestinal tract of a mammal. In some embodiments, the exogenous environmental conditions are specific to the lower gastrointestinal tract of a mammal. In some embodiments, the exogenous environmental conditions are specific to the small intestine of a mammal. In some embodiments, exogenous environmental conditions refer to the presence of molecules or metabolites that are specific to the mammalian gut in a healthy or disease state, e.g., propionate. In some embodiments, the exogenous environmental conditions are low-oxygen, microaerobic, or anaerobic conditions, such as the environment of the mammalian gut.

"Exogenous environmental condition(s)" refer to setting(s) or circumstance(s) under which the promoter described herein is induced. The phrase "exogenous environmental conditions" is meant to refer to the environmental conditions external to the engineered microorganism, but endogenous or native to the host subject environment. Thus, "exogenous" and "endogenous" may be used interchangeably to refer to environmental conditions in which the environmental conditions are endogenous to a mammalian body, but external or exogenous to an intact microorganism cell. In some embodiments, the exogenous environmental conditions are specific to the gut of a mammal. In some embodiments, the exogenous environmental conditions are specific to the upper gastrointestinal tract of a mammal. In some embodiments, the exogenous environmental conditions are specific to the lower gastrointestinal tract of a mammal. In some embodiments, the exogenous environmental conditions are specific to the small intestine of a mammal. In some embodiments, the exogenous environmental conditions are low-oxygen, microaerobic, or anaerobic conditions, such as the environment of the mammalian gut. In some embodiments, exogenous environmental conditions are molecules or metabolites that are specific to the mammalian gut, e.g., propionate. In some embodiments, the exogenous environmental condition is a tissue-specific or disease-specific metabolite or molecule(s). In some embodiments, the exogenous environmental condition is a low-pH environment. In some embodiments, the genetically engineered microorganism of the disclosure comprises a pH-dependent promoter. In some embodiments, the genetically engineered microorganism of the disclosure comprises an oxygen level-dependent promoter. In some aspects, bacteria have evolved transcription factors that are capable of sensing oxygen levels. Different signaling pathways may be triggered by different oxygen levels and occur with different kinetics.

An "oxygen level-dependent promoter" or "oxygen level-dependent regulatory region" refers to a nucleic acid sequence to which one or more oxygen level-sensing transcription factors is capable of binding, wherein the binding and/or activation of the corresponding transcription factor activates downstream gene expression.

Examples of oxygen level-dependent transcription factors include, but are not limited to, FNR, ANR, and DNR. Corresponding FNR-responsive promoters, ANR-responsive promoters, and DNR-responsive promoters are known in the art (see, e.g., Castiglione et al., 2009; Eiglmeier et al., 1989; Galimand et al., 1991; Hasegawa et al., 1998; Hoeren et al., 1993; Salmon et al., 2003). Non-limiting examples are shown in Table 1.

In a non-limiting example, a promoter ($P_{fnrS}$) was derived from the *E. coli* Nissle fumarate and nitrate reductase gene S (fnrS) that is known to be highly expressed under conditions of low or no environmental oxygen (Durand and Storz, 2010; Boysen et al, 2010). The PfnrS promoter is activated under anaerobic conditions by the global transcriptional regulator FNR that is naturally found in Nissle. Under anaerobic conditions, FNR forms a dimer and binds to specific sequences in the promoters of specific genes under its control, thereby activating their expression. However, under aerobic conditions, oxygen reacts with iron-sulfur clusters in FNR dimers and converts them to an inactive form. In this way, the PfnrS inducible promoter is adopted to modulate the expression of proteins or RNA. PfnrS is used interchangeably in this application as FNRS, fnrS, FNR, P-FNRS promoter and other such related designations to indicate the promoter PfnrS.

TABLE 1

Examples of transcription factors and responsive genes and regulatory regions

| Transcription factor | Examples of responsive genes, promoters, and/or regulatory regions: |
|---|---|
| FNR | nirB, ydfZ, pdhR, focA, ndH, hlyE, narK, narX, narG, yfiD, tdcD |
| ANR | arcDABC |
| DNR | norb, norC |

As used herein, a "non-native" nucleic acid sequence refers to a nucleic acid sequence not normally present in a bacterium, e.g., an extra copy of an endogenous sequence, or a heterologous sequence such as a sequence from a different species, strain, or substrain of bacteria, or a sequence that is modified and/or mutated as compared to the unmodified sequence from bacteria of the same subtype. In some embodiments, the non-native nucleic acid sequence is a synthetic, non-naturally occurring sequence (see, e.g., Purcell et al., 2013). The non-native nucleic acid sequence may be a regulatory region, a promoter, a gene, and/or one or more genes in a gene cassette. In some embodiments, "non-native" refers to two or more nucleic acid sequences that are not found in the same relationship to each other in nature. The non-native nucleic acid sequence may be present on a plasmid or chromosome. In addition, multiple copies of any regulatory region, promoter, gene, and/or gene cassette may be present in the bacterium, wherein one or more copies of the regulatory region, promoter, gene, and/or gene cassette may be mutated or otherwise altered as described herein. In some embodiments, the genetically engineered bacteria are engineered to comprise multiple copies of the same regulatory region, promoter, gene, and/or gene cassette in order to enhance copy number or to comprise multiple different components of a gene cassette performing multiple different functions. In some embodiments, the genetically engineered bacteria of the invention comprise a gene encoding a phenylalanine-metabolizing enzyme that is operably linked to a directly or indirectly inducible promoter that is not associated with said gene in nature, e.g., an FNR promoter operably linked to a gene encoding PAL or a ParaBAD promoter operably linked to LAAD.

"Constitutive promoter" refers to a promoter that is capable of facilitating continuous transcription of a coding sequence or gene under its control and/or to which it is operably linked. Constitutive promoters and variants are well known in the art and include, but are not limited to, BBa_J23100, a constitutive *Escherichia coli* $\sigma^S$ promoter (e.g., an osmY promoter (International Genetically Engineered Machine (iGEM) Registry of Standard Biological Parts Name BBa_J45992; BBa_J45993)), a constitutive *Escherichia coli* $\sigma^{32}$ promoter (e.g., htpG heat shock promoter (BBa_J45504)), a constitutive *Escherichia coli* $\sigma^{70}$ promoter (e.g., lacq promoter (BBa_J54200; BBa_J56015), *E. coli* CreABCD phosphate sensing operon promoter (BBa_J64951), GlnRS promoter (BBa_K088007), lacZ promoter (BBa_K119000; BBa_K119001); M13K07 gene I promoter (BBa_M13101); M13K07 gene II promoter (BBa_M13102), M13K07 gene III promoter (BBa_M13103), M13K07 gene IV promoter (BBa_M13104), M13K07 gene V promoter (BBa_M13105), M13K07 gene VI promoter (BBa_M13106), M13K07 gene VIII promoter (BBa_M13108), M13110 (BBa_M13110)), a constitutive *Bacillus subtilis* $\sigma^A$ promoter (e.g., promoter veg (BBa_K143013), promoter 43 (BBa_K143013), $P_{liaG}$ (BBa_K823000), $P_{lepA}$ (BBa_K823002), $P_{veg}$ (BBa_K823003)), a constitutive *Bacillus subtilis* $\sigma^B$ promoter (e.g., promoter ctc (BBa_K143010), promoter gsiB (BBa_K143011)), a *Salmonella* promoter (e.g., Pspv2 from *Salmonella* (BBa_K112706), Pspv from *Salmonella* (BBa_K112707)), a bacteriophage T7 promoter (e.g., T7 promoter (BBa_I712074; BBa_I719005; BBa_J34814; BBa_J64997; BBa_K113010; BBa_K113011; BBa_K113012; BBa_R0085; BBa_R0180; BBa_R0181; BBa_R0182; BBa_R0183; BBa_Z0251; BBa_Z0252; BBa_Z0253)), a bacteriophage SP6 promoter (e.g., SP6 promoter (BBa_J64998)), and functional fragments thereof.

"Gut" refers to the organs, glands, tracts, and systems that are responsible for the transfer and digestion of food, absorption of nutrients, and excretion of waste. In humans, the gut comprises the gastrointestinal (GI) tract, which starts at the mouth and ends at the anus, and additionally comprises the esophagus, stomach, small intestine, and large intestine. The gut also comprises accessory organs and glands, such as the spleen, liver, gallbladder, and pancreas. The upper gastrointestinal tract comprises the esophagus, stomach, and duodenum of the small intestine. The lower gastrointestinal tract comprises the remainder of the small intestine, i.e., the jejunum and ileum, and all of the large intestine, i.e., the cecum, colon, rectum, and anal canal. Bacteria can be found throughout the gut, e.g., in the gastrointestinal tract, and particularly in the intestines.

As used herein, the term "gene sequence" is meant to refer to a genetic sequence, e.g., a nucleic acid sequence. The gene sequence or genetic sequence is meant to include a complete gene sequence or a partial gene sequence. The gene sequence or genetic sequence is meant to include sequence that encodes a protein or polypeptide and is also menat to include genetic sequence that does not encode a protein or polypeptide, e.g., a regulatory sequence, leader sequence, signal sequence, or other non-protein coding sequence.

"Microorganism" refers to an organism or microbe of microscopic, submicroscopic, or ultramicroscopic size that typically consists of a single cell. Examples of microorganisms include bacteria, viruses, parasites, fungi, certain algae, and protozoa. In some aspects, the microorganism is engineered ("engineered microorganism") to produce one or more therapeutic molecules or proteins of interest. In certain aspects, the microorganism is engineered to take up and catabolize certain metabolites or other compounds from its environment, e.g., the gut. In certain aspects, the microorganism is engineered to synthesize certain beneficial metabolites or other compounds (synthetic or naturally occurring) and release them into its environment. In certain embodiments, the engineered microorganism is an engineered bacterium. In certain embodiments, the engineered microorganism is an engineered virus.

"Non-pathogenic bacteria" refer to bacteria that are not capable of causing disease or harmful responses in a host. In some embodiments, non-pathogenic bacteria are Gram-negative bacteria. In some embodiments, non-pathogenic bacteria are Gram-positive bacteria. In some embodiments, non-pathogenic bacteria are commensal bacteria, which are present in the indigenous microbiota of the gut. Examples of non-pathogenic bacteria include, but are not limited to, *Bacillus, Bacteroides, Bifidobacterium, Brevibacteria, Clostridium, Enterococcus, Escherichia, Lactobacillus, Lactococcus, Saccharomyces,* and *Staphylococcus,* e.g., *Bacillus coagulans, Bacillus subtilis, Bacteroides fragilis, Bacteroides subtilis, Bacteroides thetaiotaomicron, Bifidobacterium bifidum, Bifidobacterium infantis, Bifidobacterium lactis, Bifidobacterium longum, Clostridium butyricum, Enterococcus faecium, Escherichia coli, Lactobacillus acidophilus, Lactobacillus bulgaricus, Lactobacillus casei, Lactobacillus johnsonii, Lactobacillus paracasei, Lactobacillus plantarum, Lactobacillus reuteri, Lactobacillus rhamnosus, Lactococcus lactis,* and *Saccharomyces boulardii* (Sonnenborn et al., 2009; Dinleyici et al., 2014; U.S. Pat. Nos. 6,835,376; 6,203,797; 5,589,168; 7,731,976). Naturally pathogenic bacteria may be genetically engineered to provide reduce or eliminate pathogenicity.

"Probiotic" is used to refer to live, non-pathogenic microorganisms, e.g., bacteria, which can confer health benefits to a host organism that contains an appropriate amount of the microorganism. In some embodiments, the host organism is a mammal. In some embodiments, the host organism is a human. Some species, strains, and/or subtypes of non-pathogenic bacteria are currently recognized as probiotic. Examples of probiotic bacteria include, but are not limited to, *Bifidobacteria, Escherichia, Lactobacillus,* and *Saccharomyces,* e.g., *Bifidobacterium bifidum, Enterococcus faecium, Escherichia coli, Escherichia coli* strain Nissle, *Lactobacillus acidophilus, Lactobacillus bulgaricus, Lactobacillus paracasei, Lactobacillus plantarum,* and *Saccharomyces boulardii* (Dinleyici et al., 2014; U.S. Pat. Nos. 5,589,168; 6,203,797; 6,835,376). The probiotic may be a variant or a mutant strain of bacterium (Arthur et al., 2012; Cuevas-Ramos et al., 2010; Olier et al., 2012; Nougayrede et al., 2006). Non-pathogenic bacteria may be genetically engineered to enhance or improve desired biological properties, e.g., survivability. Non-pathogenic bacteria may be genetically engineered to provide probiotic properties. Probiotic bacteria may be genetically engineered to enhance or improve probiotic properties.

As used herein, "stably maintained" or "stable" bacterium is used to refer to a bacterial host cell carrying non-native genetic material, e.g., a PAL gene, which is incorporated into the host genome or propagated on a self-replicating extra-chromosomal plasmid, such that the non-native genetic material is retained, expressed, and/or propagated. The stable bacterium is capable of survival and/or growth in vitro, e.g., in medium, and/or in vivo, e.g., in the gut. For example, the stable bacterium may be a genetically modified bacterium comprising a PAL gene, in which the plasmid or chromosome carrying the PAL gene is stably maintained in the host cell, such that PAL can be expressed in the host cell, and the host cell is capable of survival and/or growth in vitro and/or in vivo. In some embodiments, copy number affects the stability of expression of the non-native genetic material, e.g., a PAL gene or a PAH gene. In some embodiments, copy number affects the level of expression of the non-native genetic material, e.g., a PAL gene or a PAH gene.

As used herein, the terms "modulate" and "treat" and their cognates refer to an amelioration of a disease, disorder, and/or condition, or at least one discernible symptom thereof. In another embodiment, "modulate" and "treat" refer to an amelioration of at least one measurable physical parameter, not necessarily discernible by the patient. In another embodiment, "modulate" and "treat" refer to inhibiting the progression of a disease, disorder, and/or condition, either physically (e.g., stabilization of a discernible symptom), physiologically (e.g., stabilization of a physical parameter), or both. In another embodiment, "modulate" and "treat" refer to slowing the progression or reversing the progression of a disease, disorder, and/or condition. As used herein, "prevent" and its cognates refer to delaying the onset or reducing the risk of acquiring a given disease, disorder and/or condition or a symptom associated with such disease, disorder, and/or condition.

Those in need of treatment may include individuals already having a particular medical disease, as well as those at risk of having, or who may ultimately acquire the disease. The need for treatment is assessed, for example, by the presence of one or more risk factors associated with the development of a disease, the presence or progression of a disease, or likely receptiveness to treatment of a subject having the disease. Primary hyperphenylalaninemia, e.g., PKU, is caused by inborn genetic mutations for which there are no known cures. Hyperphenylalaninemia can also be secondary to other conditions, e.g., liver diseases. Treating hyperphenylalaninemia may encompass reducing or eliminating excess phenylalanine and/or associated symptoms, and does not necessarily encompass the elimination of the underlying disease.

As used herein a "pharmaceutical composition" refers to a preparation of genetically engineered bacteria of the invention with other components such as a physiologically suitable carrier and/or excipient.

The phrases "physiologically acceptable carrier" and "pharmaceutically acceptable carrier" which may be used interchangeably refer to a carrier or a diluent that does not cause significant irritation to an organism and does not abrogate the biological activity and properties of the administered bacterial compound. An adjuvant is included under these phrases.

The term "excipient" refers to an inert substance added to a pharmaceutical composition to further facilitate administration of an active ingredient. Examples include, but are not limited to, calcium bicarbonate, calcium phosphate, various sugars and types of starch, cellulose derivatives, gelatin, vegetable oils, polyethylene glycols, and surfactants, including, for example, polysorbate 20.

The terms "therapeutically effective dose" and "therapeutically effective amount" are used to refer to an amount of a compound that results in prevention, delay of onset of symptoms, or amelioration of symptoms of a condition, e.g., hyperphenylalaninemia. A therapeutically effective amount may, for example, be sufficient to treat, prevent, reduce the severity, delay the onset, and/or reduce the risk of occurrence of one or more symptoms of a disease or condition associated with excess phenylalanine levels. A therapeutically effective amount, as well as a therapeutically effective frequency of administration, can be determined by methods known in the art and discussed below.

As used herein, the term "polypeptide" includes "polypeptide" as well as "polypeptides," and refers to a molecule composed of amino acid monomers linearly linked by amide bonds (i.e., peptide bonds). The term "polypeptide" refers to any chain or chains of two or more amino acids, and does not refer to a specific length of the product. Thus, "peptides," "dipeptides," "tripeptides," "oligopeptides," "protein," "amino acid chain," or any other term used to refer to a chain or chains of two or more amino acids, are included within the definition of "polypeptide," and the term "polypeptide" may be used instead of, or interchangeably with any of these terms. The term "dipeptide" refers to a peptide of two linked amino acids. The term "tripeptide" refers to a peptide of three linked amino acids. The term "polypeptide" is also intended to refer to the products of post-expression modifications of the polypeptide, including but not limited to glycosylation, acetylation, phosphorylation, amidation, derivatization, proteolytic cleavage, or modification by non-naturally occurring amino acids. A polypeptide may be derived from a natural biological source or produced by recombinant technology. In other embodiments, the polypeptide is produced by the genetically engineered bacteria or virus of the current invention. A polypeptide of the invention may be of a size of about 3 or more, 5 or more, 10 or more, 20 or more, 25 or more, 50 or more, 75 or more, 100 or more, 200 or more, 500 or more, 1,000 or more, or 2,000 or more amino acids. Polypeptides may have a defined three-dimensional structure, although they do not necessarily have such structure. Polypeptides with a defined three-dimensional structure are referred to as folded, and polypeptides, which do not possess a defined three-dimensional structure, but rather can adopt a large number of different conformations, are referred to as unfolded. The term "peptide" or "polypeptide" may refer to an amino acid sequence that corresponds to a protein or a portion of a protein or may refer to an amino acid sequence that corresponds with non-protein sequence, e.g., a sequence selected from a regulatory peptide sequence, leader peptide sequence, signal peptide sequence, linker peptide sequence, and other peptide sequence.

An "isolated" polypeptide or a fragment, variant, or derivative thereof refers to a polypeptide that is not in its natural milieu. No particular level of purification is required. Recombinantly produced polypeptides and proteins expressed in host cells, including but not limited to bacterial or mammalian cells, are considered isolated for purposed of the invention, as are native or recombinant polypeptides which have been separated, fractionated, or partially or substantially purified by any suitable technique. Recombinant peptides, polypeptides or proteins refer to peptides, polypeptides or proteins produced by recombinant DNA techniques, i.e. produced from cells, microbial or mammalian, transformed by an exogenous recombinant DNA expression construct encoding the polypeptide. Proteins or peptides expressed in most bacterial cultures will typically be free of glycan. Fragments, derivatives, analogs or variants of the foregoing polypeptides, and any combination thereof are also included as polypeptides. The terms "fragment," "variant," "derivative" and "analog" include polypeptides having an amino acid sequence sufficiently similar to the amino acid sequence of the original peptide and include any polypeptides, which retain at least one or more properties of the corresponding original polypeptide. Fragments of polypeptides of the present invention include proteolytic fragments, as well as deletion fragments. Fragments also include specific antibody or bioactive fragments or immunologically active fragments derived from any polypeptides described herein. Variants may occur naturally or be non-naturally occurring. Non-naturally occurring variants may be produced using mutagenesis methods known in the art. Variant polypeptides may comprise conservative or non-conservative amino acid substitutions, deletions or additions.

Polypeptides also include fusion proteins. As used herein, the term "variant" includes a fusion protein, which comprises a sequence of the original peptide or sufficiently similar to the original peptide. As used herein, the term "fusion protein" refers to a chimeric protein comprising amino acid sequences of two or more different proteins. Typically, fusion proteins result from well known in vitro recombination techniques. Fusion proteins may have a similar structural function (but not necessarily to the same extent), and/or similar regulatory function (hut not necessarily to the same extent), and/or similar biochemical function (but not necessarily to the same extent) and/or immunological activity (but not necessarily to the same extent) as the individual original proteins which are the components of the fusion proteins. "Derivatives" include but are not limited to peptides, which contain one or more naturally occurring amino acid derivatives of the twenty standard amino acids. "Similarity" between two peptides is determined by comparing the amino acid sequence of one peptide to the sequence of a second peptide. An amino acid of one peptide is similar to the corresponding amino acid of a second peptide if it is identical or a conservative amino acid substitution. Conservative substitutions include those described in Dayhoff, M. O., ed., The Atlas of Protein Sequence and Structure 5, National Biomedical Research Foundation, Washington, D.C. (1978), and in Argos, EMBO J. 8 (1989), 779-785. For example, amino acids belonging to one of the following groups represent conservative changes or substitutions: -Ala, Pro, Gly, Gln, Asn, Ser, Thr; -Cys, Ser, Tyr, Thr; Ile. Leu, Met, Ala, Phe; -Lys, Arg, His; -Phe, Tyr, Trp, His; and -Asp, Glu.

As used herein, the term "sufficiently similar" means a first amino acid sequence that contains a sufficient or minimum number of identical or equivalent amino acid residues relative to a second amino acid sequence such that the first and second amino acid sequences have a common structural domain and/or common functional activity. For example, amino acid sequences that comprise a common structural domain that is at least about 45%, at least about 50%, at least about 55%, at least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or at least about 100%, identical are defined herein as sufficiently similar. Preferably, variants will be sufficiently similar to the amino acid sequence of the peptides of the invention. Such variants generally retain the functional activity of the peptides of the present invention. Variants include peptides that differ in amino acid sequence from the native and wt peptide, respectively, by way of one or more amino acid deletion(s), addition(s), and/or substitution(s). These may be naturally occurring variants as well as artificially designed ones.

As used herein the term "linker", "linker peptide" or "peptide linkers" or "linker" refers to synthetic or non-native or non-naturally-occurring amino acid sequences that connect or link two polypeptide sequences, e.g., that link two polypeptide domains. As used herein the term "synthetic" refers to amino acid sequences that are not naturally occurring. Exemplary linkers are described herein. Additional exemplary linkers are provided in US 20140079701, the contents of which are herein incorporated by reference in its entirety.

As used herein the term "codon-optimized sequence" refers to a sequence, which was modified from an existing coding sequence, or designed, for example, to improve translation in an expression host cell or organism of a transcript RNA molecule transcribed from the coding sequence, or to improve transcription of a coding sequence. Codon optimization includes, but is not limited to, processes including selecting codons for the coding sequence to suit the codon preference of the expression host organism.

Many organisms display a bias or preference for use of particular codons to code for insertion of a particular amino acid in a growing polypeptide chain. Codon preference or codon bias, differences in codon usage between organisms, is allowed by the degeneracy of the genetic code, and is well documented among many organisms. Codon bias often correlates with the efficiency of translation of messenger RNA (mRNA), which is in turn believed to be dependent on, inter alia, the properties of the codons being translate(and the availability of particular transfer RNA (tRNA) molecules. The predominance of selected tRNAs in a cell is generally a reflection of the codons used most frequently in peptide synthesis. Accordingly, genes can be tailored for optimal gene expression in a given organism based on codon optimization.

As used herein, the terms "secretion system" or "secretion protein" refers to a native or non-native secretion mechanism capable of secreting or exporting the protein(s) of interest or therapeutic protein(s) from the microbial, e.g., bacterial cytoplasm. The secretion system may comprise a single protein or may comprise two or more proteins assembled in a complex e.g., HlyBD. Non-limiting examples of secretion systems for gram negative bacteria include the modified type III flagellar, type I (e.g., hemolysin secretion system), type II, type IV, type V, type VI, and type VII secretion systems, resistance-nodulation-division (RND) multi-drug efflux pumps, various single membrane secretion systems. Non-liming examples of secretion systems for gram positive bacteria include Sec and TAT secretion systems. In some embodiments, the proteins of interest include a "secretion tag" of either RNA or peptide origin to direct the protein(s) of interest or therapeutic protein(s) to specific secretion systems. In some embodiments, the secretion system is able to remove this tag before secreting the protein(s) of interest from the engineered bacteria. For example, in Type V auto-secretion-mediated secretion the N-terminal peptide secretion tag is removed upon translocation of the "passenger" peptide from the cytoplasm into the periplasmic compartment by the native Sec system. Further, once the auto-secretor is translocated across the outer membrane the C-terminal secretion tag can be removed by either an autocatalytic or protease-catalyzed e.g., OmpT cleavage thereby releasing the protein(s) of interest into the extracellular milieu.]]

As used herein, the term "transporter" is meant to refer to a mechanism, e.g., protein or proteins, for importing a molecule, e.g., amino acid, toxin, metabolite, substrate, etc. into the microorganism from the extracellular milieu.

The articles "a" and "an," as used herein, should be understood to mean "at least one," unless clearly indicated to the contrary.

The phrase "and/or," when used between elements in a list, is intended to mean either (1) that only a single listed element is present, or (2) that more than one element of the list is present. For example, "A, B, and/or C" indicates that the selection may be A alone; B alone; C alone; A and B; A and C; B and C; or A, B, and C. The phrase "and/or" may be used interchangeably with "at least one of" or "one or more of" the elements in a list.

Bacteria

The genetically engineered bacteria of the invention are capable of reducing excess phenylalanine. In some embodiments, the genetically engineered bacteria are non-pathogenic bacteria. In some embodiments, the genetically engineered bacteria are commensal bacteria. In some embodiments, the genetically engineered bacteria are probiotic bacteria. In some embodiments, the genetically engineered bacteria are naturally pathogenic bacteria that are modified or mutated to reduce or eliminate pathogenicity. In some embodiments, non-pathogenic bacteria are Gram-negative bacteria. In some embodiments, non-pathogenic bacteria are Gram-positive bacteria. Exemplary bacteria include, but are not limited to, *Bacillus, Bacteroides, Bifidobacterium, Brevibacteria, Clostridium, Enterococcus, Escherichia coli, Lactobacillus, Lactococcus, Saccharomyces,* and *Staphylococcus,* e.g., *Bacillus coagulans, Bacillus subtilis, Bacteroides fragilis, Bacteroides subtilis, Bacteroides thetaiotaomicron, Bifidobacterium bifidum, Bifidobacterium infantis, Bifidobacterium lactis, Bifidobacterium longum, Clostridium butyricum, Enterococcus faecium, Lactobacillus acidophilus, Lactobacillus bulgaricus, Lactobacillus casei, Lactobacillus johnsonii, Lactobacillus paracasei, Lactobacillus plantarum, Lactobacillus reuteri, Lactobacillus rhamnosus, Lactococcus lactis,* and *Saccharomyces boulardii*. In certain embodiments, the genetically engineered bacteria are selected from the group consisting of *Bacteroides fragilis, Bacteroides thetaiotaomicron, Bacteroides subtilis, Bifidobacterium bifidum, Bifidobacterium infantis, Bifidobacterium lactis, Clostridium butyricum,*

*Escherichia coli* Nissle, *Lactobacillus acidophilus, Lactobacillus plantarum, Lactobacillus reuteri,* and *Lactococcus lactis*.

In some embodiments, the genetically engineered bacteria are *Escherichia coli* strain Nissle 1917 (*E. coli* Nissle), a Gram-negative bacterium of the Enterobacteriaceae family that has evolved into one of the best characterized probiotics (Ukena et al., 2007). The strain is characterized by its complete harmlessness (Schultz, 2008), and has GRAS (generally recognized as safe) status (Reister et al., 2014, emphasis added). Genomic sequencing confirmed that *E. coli* Nissle lacks prominent virulence factors (e.g., *E. coli* α-hemolysin, P-fimbrial adhesins) (Schultz, 2008). In addition, it has been shown that *E. coli* Nissle does not carry pathogenic adhesion factors, does not produce any enterotoxins or cytotoxins, is not invasive, and is not uropathogenic (Sonnenborn et al., 2009). As early as in 1917, *E. coli* Nissle was packaged into medicinal capsules, called Mutaflor, for therapeutic use. It is commonly accepted that *E. coli* Nissle's therapeutic efficacy and safety have convincingly been proven (Ukena et al., 2007).

One of ordinary skill in the art would appreciate that the genetic modifications disclosed herein may be adapted for other species, strains, and subtypes of bacteria. Furthermore, genes from one or more different species can be introduced into one another, e.g., the PAL gene from *Rhodosporidium toruloides* can be expressed in *Escherichia coli* (Sarkissian et al., 1999), and it is known that prokaryotic and eukaryotic phenylalanine ammonia lyases share sequence homology (Xiang and Moore, 2005).

Unmodified *E. coli* Nissle and the genetically engineered bacteria of the invention may be destroyed, e.g., by defense factors in the gut or blood serum (Sonnenborn et al., 2009) or by activation of a kill switch, several hours or days after administration. Thus, the genetically engineered bacteria may require continued administration. In some embodiments, the residence time is calculated for a human subject. Residence time in vivo may be calculated for the genetically engineered bacteria of the invention (see, e.g., FIG. 38).

In some embodiments, the genetically engineered bacteria of the invention comprise a gene encoding PAL, wherein the PAL gene is operably linked to a directly or indirectly inducible promoter. In some embodiments, the bacteria comprise a non-native PAL gene. In some embodiments, the bacteria comprise additional copies of a native PAL gene. In some embodiments, the promoter is not associated with the PAL gene in nature. In some embodiments, the genetically engineered bacteria of the invention comprise a gene encoding PAH, wherein the PAH gene is operably linked to a directly or indirectly inducible promoter. In some embodiments, the bacteria comprise a non-native PAH gene. In some embodiments, the bacteria comprise additional copies of a native PAH gene. In some embodiments, the promoter is not associated with the PAH gene in nature.

The genetically engineered bacteria further comprise a gene encoding a phenylalanine transporter (PheP). In certain embodiments, the bacteria comprise additional copies of a native gene encoding a phenylalanine transporter, wherein the phenylalanine transporter gene is operably linked to a directly or indirectly inducible promoter. In alternate embodiments, the bacteria comprise a gene encoding a non-native phenylalanine transporter, wherein the phenylalanine transporter gene is operably linked to a directly or indirectly inducible promoter. Both embodiments are encompassed by the term "non-native" phenylalanine transporter. In some embodiments, the promoter is not associated with the pheP gene in nature. In some embodiments, the same promoter controls expression of PheP and PAL or PAH.

In some embodiments, the promoter that is operably linked to PAL, PAH, and/or pheP is directly or indirectly induced by exogenous environmental conditions. In some embodiments, the promoter is directly or indirectly induced by exogenous environmental conditions specific to the gut of a mammal. In some embodiments, the promoter is directly or indirectly induced by exogenous environmental conditions specific to the small intestine of a mammal. In some embodiments, the promoter is directly or indirectly induced by low-oxygen or anaerobic conditions such as the environment of the mammalian gut. In some embodiments, the promoter is directly or indirectly induced by the presence of molecules or metabolites that are specific to the gut of a mammal, e.g., propionate. In some embodiments, the promoter is directly or indirectly induced by exposure to tetracycline. In some embodiments, the promoter is directly or indirectly induced by a molecule that is co-administered with the genetically engineered bacteria of the invention.

Reducing Hyperphenylalaninemia

The genetically engineered bacteria of the invention comprise a gene encoding a phenylalanine-metabolizing enzyme (PME) and are capable of reducing hyperphenylalaninemia.

Examples of phenylalanine metabolizing enzymes include, but are not limited to, phenylalanine hydroxylase (PAH), phenylalanine ammonia lyase (PAL), aminotransferases, L-amino acid deaminase (L-AAD), and phenylalanine dehydrogenases. Reactions with phenylalanine hydroxylases, phenylalanine dehydrogenases or aminotransferases require cofactors, while L-AAD and PAL do not require any extra cofactor. Without wishing to be bound by theory, the lack of need for a cofactor means that phenylalanine degradation by the enzyme encoded by the genetically engineered bacteria is dependent on the availability of the substrate and is not limited by the availability of the cofactor.

Phenylalanine ammonia lyase (PAL; EC 4.3.1.24) is an enzyme that catalyzes a reaction converting L-phenylalanine to ammonia and trans-cinnamic acid. Phenylalanine ammonia lyase is specific for L-Phe, and to a lesser extent, L-Tyrosine. The reaction catalyzed by PAL is the spontaneous, non-oxidative deamination of L-phenylalanine to yield trans-cinnamic acid and ammonia. Unlike the mammalian enzyme (PAH), PAL is a monomer and requires no cofactors (MacDonald et al., Biochem Cell Biol 2007; 85:273-82. A modern view of phenylalanine ammonia lyase). In microorganisms, it has a catabolic role, allowing them to utilize L-phenylalanine (L-Phe) as a sole source of carbon and nitrogen. In one embodiment, the genetically engineered bacteria of the invention comprise a PAL gene. PAL is capable of converting phenylalanine to non-toxic levels of transcinnamic acid and ammonia. Trans-cinnamic acid (TCA) can further be converted to TCA metabolites benzoic and hippuric acids (Sarkissian et al., J Mass Spectrom. 2007 June; 42(6):811-7; Quantitation of phenylalanine and its trans-cinnamic, benzoic and hippuric acid metabolites in biological fluids in a single GC-MS analysis). PAL enzyme activity does not require THB cofactor activity.

In some embodiments, PAL is encoded by a PAL gene derived from a bacterial species, including but not limited to, *Achromobacter xylosoxidans, Pseudomonas aeruginosa, Photorhabdus luminescens, Anabaena variabilis,* and *Agrobacterium tumefaciens*. In some embodiments, the bacterial species is *Photorhabdus luminescens*. In some embodiments, the bacterial species is *Anabaena variabilis*. In some embodiments, PAL is encoded by a PAL gene derived from a eukaryotic species, e.g., a yeast species, a plant species. Multiple distinct PAL proteins are known in the art. The genetically engineered bacteria convert more phenylalanine when the PAL gene is expressed than unmodified bacteria of the same bacterial subtype under the same conditions. Thus, the genetically engineered bacteria comprising PAL may be used to metabolize phenylalanine in the body into non-toxic molecules in order to treat conditions associated with hyperphenylalaninemia, including PKU. In some embodiments, the genetically engineered bacteria express *Anabaena variabilis* PAL ("PAL1"). In some embodiments, the genetically engineered bacteria express *Photorhabdus luminescens* PAL ("PAL3"). Non-limiting examples of PAL sequences of interest are shown in Table 2.

LAAD catalyzes the stereospecific oxidative, i.e., oxygen consuming, deamination of L-amino acids to α-keto acids along with the production of ammonia and hydrogen peroxide via an imino acid intermediate. L-AADs are found in snake venoms, and in many bacteria (Bifulco et al. 2013), specifically in the cytomembranes of the *Proteus, Providencia,* and *Morganella* bacteria. L-AADs (EC 1.4.3.2) are flavoenzymes with a dimeric structure. Each subunit contains a non-covalently-bound flavin adenine dinucleotide (FAD) cofactor and do not require any external cofactors. *Proteus mirabilis* contains two types of L-AADs (Duerre and Chakrabarty 1975). One has broad substrate specificity and catalyzes the oxidation of aliphatic and aromatic L-amino acids to keto acids, typically L-phenylalanine (GenBank: U35383.1) (Baek et al., Journal of Basic Microbiology 2011, 51, 129-135; "Expression and characterization of a second L-amino acid deaminase isolated from *Proteus mirabilis* in *Escherichia coli*"). The other type acts mainly on basic L-amino acids (GenBank: EU669819.1). LAADs from bacterial, fungal, and plant sources appear to be involved in the utilization of L-amino acids (i.e., ammonia produced by the enzymatic activity) as a nitrogen source. Most eukaryotic and prokaryotic L-amino acid deaminases are extracellularly secreted, with the exception of from *Proteus* species LAADs, which are membrane-bound. In *Proteus mirabilis,* L-AADs have been reported to be located in the plasma membrane, facing outward into the periplasmic space, in which the enzymatic activity resides (Pelmont J et al., (1972) "L-amino acid oxidases of *Proteus mirabilis:* general properties" Biochimie 54: 1359-1374).

In one embodiment, the genetically engineered bacteria of the invention comprise a LAAD gene. LAAD is capable of converting phenylalanine to non-toxic levels of phenylpyruvate, which can also further be degraded, e.g., by liver enzymes, to phenyllactate. Phenylpyruvate cannot cross the blood brain barrier, which allows LAAD to reduce the levels of phenylalanine in the brain without allowing the accumulation of another potentially toxic metabolite. In some embodiments, LAAD is encoded by a LAAD gene derived from a bacterial species, including but not limited to, *Proteus, Providencia,* and *Morganella* bacteria. In some embodiments, the bacterial species is *Proteus mirabilis*. In some embodiments, the bacterial species is *Proteus vulgaris*. In some embodiments, the genetically engineered bacteria express *Proteus mirabilis* LAAD enzyme GenBank: U35383.1. Non-limiting examples of LAAD sequences of interest are shown in Table 2. In some embodiments, the LAAD enzyme is derived from snake venom. According to the invention, genetically engineered bacteria convert more phenylalanine when the LAAD gene is expressed than unmodified bacteria of the same bacterial subtype under the same conditions. Thus, the genetically engineered bacteria comprising LAAD may be used to metabolize phenylalanine in the body into non-toxic molecules in order to treat conditions associated with hyperphenylalaninemia, including PKU.

In some embodiments, the genetically engineered bacteria encode a wild type enzyme as it occurs in nature. In some embodiments, the genetically engineered bacteria encode an enzyme which comprises mutations relative to the wild type sequence. In some embodiments, the mutations increase stability of the enzyme. In some embodiments, the mutations increase the catalytic activity of the enzyme. In some embodiments, the genetically engineered bacteria comprise a gene encoding one or more of the proteins listed in Table 2. In some embodiments, the genetically engineered bacteria comprise gene sequence(s) encoding one or more of the polypeptides comprising sequence of any of SEQ ID Nos: 1-8. In some embodiments, the genetically engineered bacteria comprise gene sequence(s) encoding a polypeptide having at least 80%, 81%, 82%, 83%, 84%, 85%, 86%, 87%, 88%, 89%, 90%, 91%, 92%, 93%, 94%, 95%,96%, 97%, 98%, or 99% identity with any of the sequences of SEQ ID Nos: 1-8. In some embodiments, the genetically engineered bacteria encode one or more enzymes from Table 2, which comprise a mutation. In some embodiments, the genetically engineered bacteria comprise a gene encoding wild type PAH. In some embodiments, the genetically engineered bacteria encode a mutated PAH with increased stability and/or activity. In some embodiments, the genetically engineered bacteria comprise a gene encoding wild type PAL. In some embodiments, the genetically engineered bacteria encode a mutated PAL with increased stability and/or activity. In some embodiments, the genetically engineered bacteria comprise a gene encoding wild type LAAD. In some embodiments, the genetically engineered bacteria encode a mutated LAAD with increased stability and/or activity. Methods for screening for enzymes with desirable properties are known in the art and described herein.

TABLE 2

Sequences of Phenylalanine Metabolizing Enzymes

| Description | Sequence | SEQ ID NO |
|---|---|---|
| Phenylalanine ammonia-lyase (*Anabaena variabilis*) Acc. No.: Q3M5Z3.1 | MKTLSQAQSKTSSQQFSFTGNSSANVIIGNQKLTIN DVARVARNGTLVSLTNNTDILQGIQASCDYINNAV ESGEPIYGVTSGFGGMANVAISREQASELQTNLVW FLKTGAGNKLPLADVRAAMLLRANSHMRGASGIR LELIKRMEIFLNAGVTPYVYEFGSIGASGDLVPLSYI TGSLIGLDPSFKVDFNGKEMDAPTALRQLNLSPLTL LPKEGLAMMNGTSVMTGIAANCVYDTQILTAIAM GVHALDIQALNGTNQSFHPFIHNSKPHPGQLWAAD QMISLLANSQLVRDELDGKHDYRDHELIQDRYSLR | SEQ ID NO: 1 |

TABLE 2-continued

Sequences of Phenylalanine Metabolizing Enzymes

| Description | Sequence | SEQ ID NO |
|---|---|---|
| | CLPQYLGPIVDGISQIAKQIEIEINSVTDNPLIDVDNQ<br>ASYHGGNFLGQYVGMGMDHLRYYIGLLAKHLDV<br>QIALLASPEFSNGLPPSLLGNRERKVNMGLKGLQIC<br>GNSIMPLLTFYGNSIADRFPTHAEQFNQNINSQGYT<br>SATLARRSVDIFQNYVAIALMFGVQAVDLRTYKKT<br>GHYDARACLSPATERLYSAVRHVVGQKPTSDRPYI<br>WNDNEQGLDEHIARISADIAAGGVIVQAVQDILPCL<br>H | |
| histidine ammonia-lyase [Anabaena variabilis ATCC 29413](Acc. NO. ABA23593.1) | MKTLSQAQSKTSSQQFSFTGNSSANVIIGNQKLTIN<br>DVARVARNGTLVSLTNNTDILQGIQASCDYINNAV<br>ESGEPIYGVTSGFGGMANVAISREQASELQTNLVW<br>FLKTGAGNKLPLADVRAAMLLRANSHMRGASGIR<br>LELIKRMEIFLNAGVTPYVYEFGSIGASGDLVPLSYI<br>TGSLIGLDPSFKVDFNGKEMDAPTALRQLNLSPLTL<br>LPKEGLAMMNGTSVMTGIAANCVYDTQILTAIAM<br>GVHALDIQALNGTNQSFHPFIHNSKPHPGQLWAAD<br>QMISLLANSQLVRDELDGKHDYRDHELIQDRYSLR<br>CLPQYLGPIVDGISQIAKQIEIEINSVTDNPLIDVDNQ<br>ASYHGGNFLGQYVGMGMDHLRYYIGLLAKHLDV<br>QIALLASPEFSNGLPPSLLGNRERKVNMGLKGLQIC<br>GNSIMPLLTFYGNSIADRFPTHAEQFNQNINSQGYT<br>SATLARRSVDIFQNYVAIALMFGVQAVDLRTYKKT<br>GHYDARACLSPATERLYSAVRHVVGQKPTSDRPYI<br>WNDNEQGLDEHIARISADIAAGGVIVQAVQDILPCL<br>H | SEQ ID NO: 2 |
| histidine ammonia-lyase [Photorhabdus luminescens] (WP_011146484) | MKAKDVQPTIIINKNGLISLEDIYDIAIKQKKVEISTE<br>ITELLTHGREKLEEKLNSGEVIYGINTGFGGNANLV<br>VPFEKIAEHQQNLLTFLSAGTGDYMSKPCIKASQFT<br>MLLSVCKGWSATRPIVAQAIVDHINHDIVPLVPRYG<br>SVGASGDLIPLSYIARALCGIGKVYYMGAEIDAAEA<br>IKRAGLTPLSLKAKEGLALINGTRVMSGISAITVIKL<br>EKLFKASISAIALAVEALLASHEHYDARIQQVKNHP<br>GQNAVASALRNLLAGSTQVNLLSGVKEQANKACR<br>HQEITQLNDTLQEVYSIRCAPQVLGIVPESLATARKI<br>LEREVISANDNPLIDPENGDVLHGGNFMGQYVART<br>MDALKLDIALIANHLHAIVALMMDNRFSRGLPNSL<br>SPTPGMYQGFKGVQLSQTALVAAIRHDCAASGIHT<br>LATEQYNQDIVSLGLHAAQDVLEMEQKLRNIVSMT<br>ILVVCQAIHLRGNISEIAPETAKFYHAVREISSPLITD<br>RALDEDIIRIADAIINDQLPLPEIMLEE | SEQ ID NO: 3 |
| Histidine ammonia lyase (Photorhabdus luminescens) Acc. NO: CAE15566 | MKQLTIYPGKLTLDELRQVYLQPVKITLDSQIFPAIE<br>RSVECVNAILAENRTAYGINTGFGLLASTRIEEDNL<br>EKLQRSLVVSHAAGVGKALDDNMTRLIMVLKINSL<br>SRGYSGIRLAVIQALIALVNAEIYPHIPCKGSVGASG<br>DLAPLAHMSLLLLGEGQARYQGEWLPAKEALAKA<br>NLQPITLAAKEGLALLNGTQVSTAFALRGLFEAEDL<br>LAAAIVCGSLSVEAALGSRKPFDARVHVVRGQQGQ<br>IDVAALYRHVLEESSELSDSHINCPKVQDPYSLRCQ<br>PQVMGACLTQLRHAADVILTEANAVSDNPLVFAEQ<br>GEVISGGNFHAEPVAMASDNLALVLAEIGALSERRI<br>ALLMDSHMSQLPPFLVENGGVNSGFMIAQVTAAAL<br>ASENKALAHPASVDSLPTSANQEDHVSMAPAAGRR<br>LWEMAENTRGILAIEWLSACQGIDFRNGLKSSPILE<br>EARVILRAKVDYYDQDRFFAPDIDAAVKLLAEQHL<br>SSLLPSGQILQRKNNR | SEQ ID NO: 4 |
| amino acid deaminase (Proteus mirabilis) Acc. No: ACD36582 | MAISRRKFILGGTVVAAGAGVLTPMLTREGRFV<br>PGTPRHGFVEGTGGPLPKQDDVVVIGAGILGIMTAI<br>NLAERGLSVTIVEKGNIAGEQSSRFYGQAISYKMPD<br>ETFLLHHLGKHRWREMNAKVGIDTTYRTQGRVEV<br>PLDEEDLENVRKWIDAKSKDVGSDIPFRTKMIEGAE<br>LKQRLRGATTDWKIAGFEEDSGSFDPEVATFVMAE<br>YAKKMGIKIFTNCAARGLETQAGVISDVVTEKGPIK<br>TSRVVVAGGVGSRLFMQNLNVDVPTLPAYQSQQLI<br>SAAPNAPGGNVALPGGIFFRDQADGTYATSPRVIVA<br>PVVKESFTYGYKYLPLLALPDFPVHISLNEQLINSFM<br>QSTHWDLNEESPFEKYRDMTALPDLPELNASLEKL<br>KKEFPAFKESTLIDQWSGAMAIAPDENPIISDVKEYP<br>GLVINTATGWGMTESPVSAEITADLLLGKKPVLDA<br>KPFSLYRF | SEQ ID NO: 5 |

TABLE 2-continued

Sequences of Phenylalanine Metabolizing Enzymes

| Description | Sequence | SEQ ID NO |
|---|---|---|
| amino acid deaminase [Proteus mirabilis HI4320]) Acc. No.: AAA86752.1 | MNISRRKLLLGVGAAGVLAGGAALVPMVRRDGKF VEAKSRASFVEGTQGALPKEADVVIIGAGIQGIMTA INLAERGMSVTILEKGQIAGEQSGRAYSQIISYQTSP EIFPLHHYGKILWRGMNEKIGADTSYRTQGRVEAL ADEKALDKAQAWIKTAKEAAGFDTPLNTRIIKGEE LSNRLVGAQTPWTVAAFEEDSGSVDPETGTPALAR YAKQIGVKIYTNCAVRGIETAGGKISDVVSEKGAIK TSQVVLAGGIWSRLFMGNMGIDIPTLNVYLSQQRV SGVPGAPRGNVHLPNGIHFREQADGTYAVAPRIFTS SIVKDSFLLGPKFMHLLGGGELPLEFSIGEDLFNSFK MPTSWNLDEKTPFEQFRVATATQNTQHLDAVFQR MKTEFPVFEKSEVVERWGAVVSPTFDELPIISEVKE YPGLVINTATVWGMTEGPAAGEVTADIVMGKKPVI DPTPFSLDRFKK | SEQ ID NO: 6 |
| L-AAD from Proteus vulgaris; (Acc. NO: BAA90864) | MAISRRKFIIGGTVVAVAAGAGILTPMLTREGRFVP GTPRHGFVEGTEGALPKQADVVVVGAGILGIMTAI NLVERGLSVVIVEKGNIAGEQSSRFYGQAISYKMPD ETFLLHHLGKHRWREMNAKVGIDTTYRTQGRVEV PLDEEDLVNVRKWIDERSKNVGSDIPFKTRIIEGAEL NQRLRGATTDWKIAGFEEDSGSFDPEVATFVMAEY AKKMGVRIYTQCAARGLETQAGVISDVVTEKGAIK TSQVVVAGGVWSRLFMQNLNVDVPTLPAYQSQQL ISGSPTAPGGNVALPGGIFFREQADGTYATSPRVIVA PVVKESFTYGYKYLPLLALPDFPVHISLNEQLINSFM QSTHWNLDEVSPFEQFRNMTALPDLPELNASLEKL KAEFPAFKESKLIDQWSGAMAIAPDENPIISEVKEYP GLVINTATGWGMTESPVSAELTADLLLGKKPVLDP KPFSLYRF | SEQ ID NO: 7 |
| Phenylalanine hydroxylase [Homo sapiens] (Acc. No. AAH26251] | MSTAVLENPGLGRKLSDFGQETSYIEDNCNQNGAIS LIFSLKEEVGALAKVLRLFEENDVNLTHIESRPSRLK KDEYEFFTHLDKRSLPALTNIIKILRHDIGATVHELS RDKKKDTVPWFPRTIQELDRFANQILSYGAELDAD HPGFKDPVYRARRKQFADIAYNYRHGQPIPRVEYM EEGKKTWGTVFKTLKSLYKTHACYEYNHIFPLLEK YCGFHEDNIPQLEDVSQFLQTCTGFRLRPVAGLLSS RDFLGGLAFRVFHCTQYIRHGSKPMYTPEPDICHEL LGHVPLFSDRSFAQFSQEIGLASLGAPDEYIEKLATI YWFTVEFGLCKQGDSIKAYGAGLLSSFGELQYCLS EKPKLLPLELEKTAIQNYTVTEFQPLYYVAESFNDA KEKVRNFAATIPRPFSVRYDPYTQRIEVLDNTQQLK ILADSINSEIGILCSALQKIK | SEQ ID NO: 8 |

The PME, e.g., PAL, LAAD, or PAH, gene may be present on a plasmid or chromosome in the genetically engineered bacteria. In some embodiments, the PME gene is expressed under the control of a constitutive promoter. In some embodiments, the PME gene is expressed under the control of a promoter that is directly or indirectly induced by exogenous environmental conditions, as described herein. In some embodiments, the PME gene is expressed under the control of a promoter that is directly or indirectly induced by exogenous environmental conditions, such as in the presence of molecules or metabolites specific to the gut of a mammal. In one embodiment, the PME gene is expressed under the control of a promoter that is directly or indirectly induced by low-oxygen, microaerobic, or anaerobic conditions, wherein expression of the PME gene, e.g., the PAL gene, is activated under low-oxygen or anaerobic environments, such as the environment of the mammalian gut.

In one embodiment, the genetically engineered bacteria encode a PAL gene which is directly or indirectly induced by low-oxygen or anaerobic conditions, such as the mammalian gut. In one embodiment, the genetically engineered bacteria encode a LAAD gene which is directly or indirectly induced by oxygenated, low oxygen, or microaerobic conditions, such as conditions found in the the proximal intestine, including but not limited to the stomach, duodenum, and ileum. In other embodiments, the genetically engineered bacteria encode a PME gene which is directly or indirectly induced by an environmental factor that is naturally present in a mammalian gut. In other embodiments, the genetically engineered bacteria encode a PME gene which is directly or indirectly induced by an environmental factor that is not naturally present in a mammalian gut, e.g., arabinose. In other embodiments, the genetically engineered bacteria encode a PME gene which is directly or indirectly induced by an environmental factor that is naturally present in a mammalian gut under inflammatory conditions.

Bacteria have evolved transcription factors that are capable of sensing oxygen levels. Different signaling pathways may be triggered by different oxygen levels and occur with different kinetics. An oxygen level-dependent promoter is a nucleic acid sequence to which one or more oxygen level-sensing transcription factors is capable of binding, wherein the binding and/or activation of the corresponding transcription factor activates downstream gene expression. In one embodiment, the PME gene is expressed under the control of an oxygen level-dependent promoter. In a more specific aspect, the PAL gene is under the control of an oxygen level-dependent promoter that is activated under low-oxygen or anaerobic environments, such as the environment of the mammalian gut.

In certain embodiments, the genetically engineered bacteria comprise a PME, e.g., PAL, expressed under the control of the fumarate and nitrate reductase regulator (FNR) promoter. In *E. coli*, FNR is a major transcriptional activator that controls the switch from aerobic to anaerobic metabolism (Unden et al., 1997). In the anaerobic state, FNR dimerizes into an active DNA binding protein that activates hundreds of genes responsible for adapting to anaerobic growth. In the aerobic state, FNR is prevented from dimerizing by oxygen and is inactive. In some embodiments, multiple distinct FNR nucleic acid sequences are inserted in the genetically engineered bacteria. In alternate embodiments, the genetically engineered bacteria comprise a PME, e.g., PAL, expressed under the control of an alternate oxygen level-dependent promoter, e.g., an ANR promoter (Ray et al., 1997), a DNR promoter (Trunk et al., 2010). In some embodiments, phenylalanine metabolism is particularly activated in a low-oxygen or anaerobic environment, such as in the gut.

In *P. aeruginosa*, the anaerobic regulation of arginine deiminase and nitrate reduction (ANR) transcriptional regulator is "required for the expression of physiological functions which are inducible under oxygen-limiting or anaerobic conditions" (Winteler et al., 1996; Sawers 1991). *P. aeruginosa* ANR is homologous with *E. coli* FNR, and "the consensus FNR site (TTGAT - - - ATCAA) was recognized efficiently by ANR and FNR" (Winteler et al., 1996). Like FNR, in the anaerobic state, ANR activates numerous genes responsible for adapting to anaerobic growth. In the aerobic state, ANR is inactive. *Pseudomonas fluorescens, Pseudomonas putida, Pseudomonas syringae,* and *Pseudomonas mendocina* all have functional analogs of ANR (Zimmermann et al., 1991). Promoters that are regulated by ANR are known in the art, e.g., the promoter of the arcDABC operon (see, e.g., Hasegawa et al., 1998).

The FNR family also includes the dissimilatory nitrate respiration regulator (DNR) (Arai et al., 1995), a transcriptional regulator which is required in conjunction with ANR for "anaerobic nitrate respiration of *Pseudomonas aeruginosa*" (Hasegawa et al., 1998). For certain genes, the FNR-binding motifs "are probably recognized only by DNR" (Hasegawa et al., 1998). Any suitable transcriptional regulator that is controlled by exogenous environmental conditions and corresponding regulatory region may be used. Non-limiting examples include ArcA/B, ResD/E, NreA/B/C, and AirSR, and others are known in the art.

FNR promoter sequences are known in the art, and any suitable FNR promoter sequence(s) may be used in the genetically engineered bacteria of the invention. Any suitable FNR promoter(s) may be combined with any suitable PAL. Non-limiting FNR promoter sequences are provided in Table 3, and non-limiting PAL sequences are also provided herein. In some embodiments, the genetically engineered bacteria of the invention comprise one or more of: SEQ ID NO: 9, SEQ ID NO: 10, nirB1 promoter (SEQ ID NO: 11), nirB2 promoter (SEQ ID NO: 12), nirB3 promoter (SEQ ID NO: 13), ydfZ promoter (SEQ ID NO: 14), nirB promoter fused to a strong ribosome binding site (SEQ ID NO: 15), ydfZ promoter fused to a strong ribosome binding site (SEQ ID NO: 16), fnrS, an anaerobically induced small RNA gene (fnrS1 promoter SEQ ID NO: 9 or fnrS2 promoter SEQ ID NO: 17), nirB promoter fused to a crp binding site (SEQ ID NO: 18), and fnrS fused to a crp binding site (SEQ ID NO: 19).

In some embodiments, genetically engineered bacteria comprise a nucleic acid sequence that is at least about 80%, at least about 85%, at least about 90%, at least about 95%, or at least about 99% homologous to the DNA sequence of SEQ ID NO: 9, 10, 11, 12, 13, 14, 15, 16, 17, 18, 19, or 20 or a functional fragment thereof.

TABLE 3

FNR Sequences

| SEQ ID NO | FNR-responsive regulatory region Sequence |
| --- | --- |
| SEQ ID NO: 9 | ATCCCCATCACTCTTGATGGAGATCAATTCCCCAAGCTGCTAGAGCGTTA<br>CCTTGCCCTTAAACATTAGCAATGTCGATTTATCAGAGGGCCGACAGGCT<br>CCCACAGGAGAAAACCG |
| SEQ ID NO: 10 | CTCTTGATCGTTATCAATTCCCACGCTGTTTCAGAGCGTTACCTTGCCCT<br>TAAACATTAGCAATGTCGATTTATCAGAGGGCCGACAGGCTCCCACAGGA<br>GAAAACCG |
| nirB1<br>SEQ ID NO: 11 | GTCAGCATAACACCCTGACCTCTCATTAATTGTTCATGCCGGGCGGCACT<br>ATCGTCGTCCGGCCTTTTCCTCTCTTACTCTGCTACGTACATCTATTTCT<br>ATAAATCCGTTCAATTTGTCTGTTTTTTGCACAAACATGAAATATCAGAC<br>AATTCCGTGACTTAAGAAAATTTATACAAATCAGCAATATACCCCTTAAG<br>GAGTATATAAAGGTGAATTTGATTTACATCAATAAGCGGGGTTGCTGAAT<br>CGTTAAGGTAGGCGGTAATAG<u>AAAAGAAATCGAGGCAAAA</u> |
| nirB2<br>SEQ ID NO: 12 | CGGCCCGATCGTTGAACATAGCGGTCCGCAGGCGGCACTGCTTACAGCAA<br>ACGGTCTGTACGCTGTCGTCTTTGTGATGTGCTTCCTGTTAGGTTTCGTC<br>AGCCGTCACCGTCAGCATAACACCCTGACCTCTCATTAATTGCTCATGCC<br>GGACGGCACTATCGTCGTCCGGCCTTTTCCTCTCTTCCCCCGCTACGTGC<br>ATCTATTTCTATAAACCCGCTCATTTTGTCTATTTTTTGCACAAACATGA<br>AATATCAGACAATTCCGTGACTTAAGAAAATTTATACAAATCAGCAATAT<br>ACCCATTAAGGAGTATATAAAGGTGAATTTGATTTACATCAATAAGCGGG<br>GTTGCTGAATCGTTAAGGTAGGCGGTAATAGAAAAGAAATCGAGGCAAAA<br>atgtttgtttaactttaagaaggagatatacat |
| nirB3<br>SEQ ID NO: 13 | GTCAGCATAACACCCTGACCTCTCATTAATTGCTCATGCGGACGGCACT<br>ATCGTCGTCCGGCCTTTTCCTCTCTTCCCCCGCTACGTGCATCTATTTCT<br>ATAAACCCGCTCATTTTGTCTATTTTTTGCACAAACATGAAATATCAGAC<br>AATTCCGTGACTTAAGAAAATTTATACAAATCAGCAATATACCCATTAAG |

TABLE 3-continued

FNR Sequences

| SEQ ID NO | FNR-responsive regulatory region Sequence |
|---|---|
|  | GAGTATATAAAGGTGAATTTGATTTACATCAATAAGCGGGGTTGCTGAAT CGTTAAGGTAGGCGGTAATAGAAAAGAAATCGAGGCAAAA |
| ydfZ<br>SEQ ID NO: 14 | ATTTCCTCTCATCCCATCCGGGGTGAGAGTCTTTTCCCCCGACTTATGGC TCATGCATGCATCAAAAAAGATGTGAGCTTGATCAAAAACAAAAAATATT TCACTCGACAGGAGTATTTATATTGCGCCCGTTACGTGGGCTTCGACTGT AAATCAGAAAGGAGAAAACACCT |
| nirB + RBS<br>SEQ ID NO: 15 | GTCAGCATAACACCCTGACCTCTCATTATTGTTCATGCCGGGCGGCACT ATCGTCGTCCGGCCTTTTCCTCTCTTACTCTGCTACGTACATCTATTTCT ATAAATCCGTTCAATTTGTCTGTTTTTTGCACAAACATGAAATATCAGAC AATTCCGTGACTTAAGAAAATTTATACAAATCAGCAATATACCCCTTAAG GAGTATATAAAGGTGAATTTGATTTACATCAATAAGCGGGGTTGCTGAAT CGTTAAGGATCCCTCTAGAAATAATTTTGTTTAACTTTAAGAAGGAGATA TACAT |
| ydfZ + RBS<br>SEQ ID NO: 16 | CATTTCCTCTCATCCCATCCGGGGTGAGAGTCTTTTCCCCCGACTTATGG CTCATGCATGCATCAAAAAAGATGTGAGCTTGATCAAAAACAAAAAATAT TTCACTCGACAGGAGTATTTATATTGCGCCCGGATCCCTCTAGAAATAAT TTTGTTTAACTTTAAGAAGGAGATATACAT |
| fnrS1<br>SEQ ID NO: 17 | AGTTGTTCTTATTGGTGGTGTTGCTTTATGGTTGCATCGTAGTAAATGGT TGTAACAAAAGCAATTTTTCCGGCTGTCTGTATACAAAAACGCCGTAAAG TTTGAGCGAAGTCAATAAACTCTCTACCCATTCAGGGCAATATCTCTCTT GGATCCCTCTAGAAATAATTTTGTTTAACTTTAAGAAGGAGATATACAT |
| fnrS2<br>SEQ ID NO: 18 | AGTTGTTCTTATTGGTGGTGTTGCTTTATGGTTGCATCGTAGTAAATGGT TGTAACAAAAGCAATTTTTCCGGCTGTCTGTATACAAAAACGCCGCAAAG TTTGAGCGAAGTCAATAAACTCTCTACCCATTCAGGGCAATATCTCTCTT GGATCCAAAGTGAACTCTAGAAATAATTTTGTTTAACTTTAAGAAGGAGA TATACAT |
| nirB + crp<br>SEQ ID NO: 19 | TCGTCTTTGTGATGTGCTTCCTGTTAGGTTTCGTCAGCCGTCACCGTCAG CATAACACCCTGACCTCTCATTAATTGCTCATGCCGGACGGCACTATCGT CGTCCGGCCTTTTCCTCTCTTCCCCCGCTACGTGCATCTATTTCTATAAA CCCGCTCATTTTGTCTATTTTTTGCACAAACATGAAATATCAGACAATTC CGTGACTTAAGAAAATTTATACAAATCAGCAATATACCCATTAAGGAGTA TATAAAGGTGAATTTGATTTACATCAATAAGCGGGGTTGCTGAATCGTTA AGGTAGaaatgtgatctagttcacatttGCGGTAATAGAAAAGAAATCGA GGCAAAAatgtttgtttaactttaagaaggagatatacat |
| fnrS + crp<br>SEQ ID NO: 20 | AGTTGTTCTTATTGGTGGTGTTGCTTTATGGTTGCATCGTAGTAAATGGT TGTAACAAAAGCAATTTTTCCGGCTGTCTGTATACAAAAACGCCGCAAAG TTTGAGCGAAGTCAATAAACTCTCTACCCATTCAGGGCAATATCTCTCaa atgtgatctagttcacattttttgtttaactttaagaaggagatatacat |

In other embodiments, a PME, e.g., PAL, is expressed under the control of an oxygen level-dependent promoter fused to a binding site for a transcriptional activator, e.g., CRP. CRP (cyclic AMP receptor protein or catabolite activator protein or CAP) plays a major regulatory role in bacteria by repressing genes responsible for the uptake, metabolism, and assimilation of less favorable carbon sources when rapidly metabolizable carbohydrates, such as glucose, are present (Wu et al., 2015). This preference for glucose has been termed glucose repression, as well as carbon catabolite repression (Deutscher, 2008; Görke and Stülke, 2008). In some embodiments, PME, e.g., PAL, expression is controlled by an oxygen level-dependent promoter fused to a CRP binding site. In some embodiments, PAL expression is controlled by an FNR promoter fused to a CRP binding site. In these embodiments, cyclic AMP binds to CRP when no glucose is present in the environment. This binding causes a conformational change in CRP, and allows CRP to bind tightly to its binding site. CRP binding then activates transcription of the PME gene, e.g., PAL gene, by recruiting RNA polymerase to the FNR promoter via direct protein-protein interactions. In the presence of glucose, cyclic AMP does not bind to CRP and a PME, e.g., PAL, gene transcription is repressed. In some embodiments, an oxygen level-dependent promoter (e.g., an FNR promoter) fused to a binding site for a transcriptional activator is used to ensure that a PME, e.g., PAL, is not expressed under anaerobic conditions when sufficient amounts of glucose are present, e.g., by adding glucose to growth media in vitro.

In another embodiment, a PME, e.g., LAAD, is expressed under the control of an inducible promoter fused to a binding site for a transcriptional activator, e.g., CRP, such that expression is repressed in the presence of glucose.

In some embodiments, LAAD is not under the control of an FNRs promoter. LAAD requires oxygen to catalyze the degradation of phenylalanine to phenylpyruvate. Therefore, it would not be desirable to induce LAAD expression under strictly anaerobic conditions where it would be minimally active (FIG. 25).

In some embodiments, a PME, e.g., PAL or LAAD, is expressed under the control of an inducible promoter that is responsive to specific molecules or metabolites in the environment, e.g., the mammalian gut. For example, the short-chain fatty acid propionate is a major microbial fermentation metabolite localized to the gut (Hosseini et al., 2011). In one embodiment, PAL gene expression is under the control of a propionate-inducible promoter. In a more specific embodiment, PME gene expression is under the control of a propionate-inducible promoter that is activated by the presence of propionate in the mammalian gut. Any molecule or metabolite found in the mammalian gut, in a healthy and/or disease state, may be used to induce PME gene expression. Non-limiting examples include propionate, bilirubin, aspartate aminotransferase, alanine aminotransferase, blood coagulation factors II, VII, IX, and X, alkaline phosphatase, gamma glutamyl transferase, hepatitis antigens and antibodies, alpha fetoprotein, anti-mitochondrial, smooth muscle, and anti-nuclear antibodies, iron, transferrin, ferritin, copper, ceruloplasmin, ammonia, and manganese. In alternate embodiments, PME, e.g., PAL and/or LAAD, gene expression is under the control of a $P_{araBAD}$ promoter, which is activated in the presence of the sugar arabinose. In one embodiment, LAAD expression is under the control of the $P_{araBAD}$ promoter. In one embodiment, expression of LAAD occurs under aerobic or microaerobic conditions.

In some embodiments, the PAL gene is expressed under the control of a promoter that is induced by exposure to tetracycline. In some embodiments, gene expression is further optimized by methods known in the art, e.g., by optimizing ribosomal binding sites, manipulating transcriptional regulators, and/or increasing mRNA stability.

In some embodiments, the genetically engineered bacteria comprise a stably maintained plasmid or chromosome carrying the PAL gene, such that PAL can be expressed in the host cell, and the host cell is capable of survival and/or growth in vitro, e.g., in medium, and/or in vivo, e.g., in the gut. In some embodiments, the genetically engineered bacteria comprise two or more distinct PAL genes. In some embodiments, the genetically engineered bacteria comprise multiple copies of the same PAL gene. In some embodiments, the PAL gene is present on a plasmid and operably linked to a directly or indirectly inducible promoter. In some embodiments, the PAL gene is present on a plasmid and operably linked to a promoter that is induced under low-oxygen or anaerobic conditions. In some embodiments, the PAL gene is present on a chromosome and operably linked to a directly or indirectly inducible promoter. In some embodiments, the PAL gene is present in the chromosome and operably linked to a promoter that is induced under low-oxygen or anaerobic conditions. In some embodiments, the PAL gene is present on a plasmid and operably linked to a promoter that is induced by exposure to tetracycline.

In some embodiments, the genetically engineered bacteria comprise a stably maintained plasmid or chromosome carrying the LAAD gene, such that LAAD can be expressed in the host cell, and the host cell is capable of survival and/or growth in vitro, e.g., in medium, and/or in vivo, e.g., in the gut. In some embodiments, the genetically engineered bacteria comprise two or more distinct LAAD genes. In some embodiments, the genetically engineered bacteria comprise multiple copies of the same LAAD gene. In some embodiments, the LAAD gene is present on a plasmid and operably linked to a directly or indirectly inducible promoter. In some embodiments, the LAAD gene is present on a plasmid and operably linked to a promoter that is inducible, e.g., by arabinose or tetracycline. In some embodiments, the LAAD gene is present on a chromosome and operably linked to a directly or indirectly inducible promoter. In some embodiments, the LAAD gene is present in the chromosome and operably linked to a promoter that is induced, e.g., by arabinose. In some embodiments, the LAAD gene is present on a plasmid and operably linked to a promoter that is induced by exposure to tetracycline.

In some embodiments, the genetically engineered bacteria comprise an oxygen-level dependent transcriptional regulator, e.g., FNR, ANR, or DNR, and corresponding promoter from a different bacterial species. The non-native oxygen-level dependent transcriptional regulator and promoter increase the transcription of genes operably linked to said promoter, e.g., PAL, in a low-oxygen or anaerobic environment, as compared to the native transcriptional regulator and promoter in the bacteria under the same conditions. In certain embodiments, the non-native oxygen-level dependent transcriptional regulator is an FNR protein from N. gonorrhoeae (see, e.g., Isabella et al., 2011). In some embodiments, the corresponding wild-type transcriptional regulator is left intact and retains wild-type activity. In alternate embodiments, the corresponding wild-type transcriptional regulator is deleted or mutated to reduce or eliminate wild-type activity.

In some embodiments, the genetically engineered bacteria comprise a wild-type oxygen-level dependent transcriptional regulator, e.g., FNR, ANR, or DNR, and corresponding promoter that is mutated relative to the wild-type promoter from bacteria of the same subtype. The mutated promoter enhances binding to the wild-type transcriptional regulator and increases the transcription of genes operably linked to said promoter, e.g., PAL, in a low-oxygen or anaerobic environment, as compared to the wild-type promoter under the same conditions. In some embodiments, the genetically engineered bacteria comprise a wild-type oxygen-level dependent promoter, e.g., FNR, ANR, or DNR promoter, and corresponding transcriptional regulator that is mutated relative to the wild-type transcriptional regulator from bacteria of the same subtype. The mutated transcriptional regulator enhances binding to the wild-type promoter and increases the transcription of genes operably linked to said promoter, e.g., PAL, in a low-oxygen or anaerobic environment, as compared to the wild-type transcriptional regulator under the same conditions. In certain embodiments, the mutant oxygen-level dependent transcriptional regulator is an FNR protein comprising amino acid substitutions that enhance dimerization and FNR activity (see, e.g., Moore et al., 2006).

In some embodiments, the genetically engineered bacteria of the invention comprise multiple copies of the endogenous gene encoding the oxygen level-sensing transcriptional regulator, e.g., the FNR gene. In some embodiments, the gene encoding the oxygen level-sensing transcriptional regulator is present on a plasmid. In some embodiments, the gene encoding the oxygen level-sensing transcriptional regulator and the gene encoding PAL are present on different plasmids. In some embodiments, the gene encoding the oxygen level-sensing transcriptional regulator and the gene encoding PAL are present on the same plasmid. In some embodiments, the gene encoding the oxygen level-sensing transcriptional regulator is present on a chromosome. In some embodiments, the gene encoding the oxygen level-sensing transcriptional regulator and the gene encoding PAL are present on different chromosomes. In some embodiments, the gene encoding the oxygen level-sensing transcriptional regulator and the gene encoding PAL are present on the same chromosome. In some instances, it may be advantageous to express the oxygen level-sensing transcriptional regulator under the control of an inducible promoter in order to enhance expression stability. In some embodiments, expression of the transcriptional regulator is controlled by a different promoter than the promoter that controls expression of the gene encoding the phenylalanine-metabolizing enzyme. In some embodiments, expression of the transcriptional regulator is controlled by the same promoter that controls expression of the phenylalanine-metabolizing enzyme. In some embodiments, the transcriptional regulator and the phenylalanine-metabolizing enzyme are divergently transcribed from a promoter region.

Figure 16A:
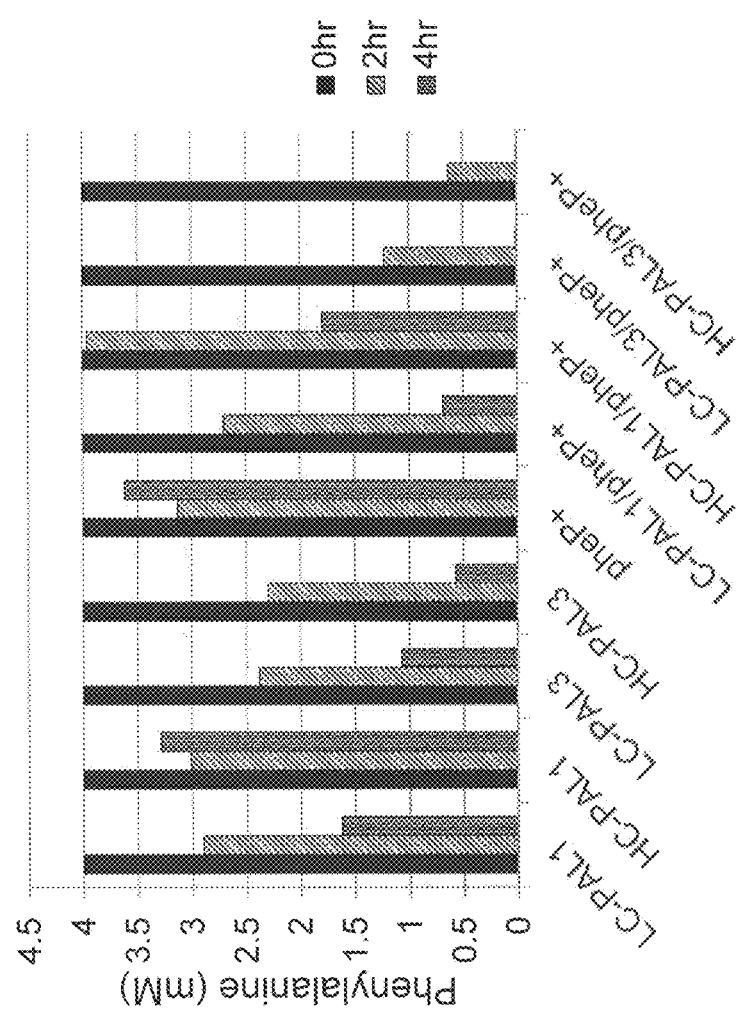
FIG. 16A depicts phenylalanine concentrations in samples comprising bacteria expressing PAL1 or PAL3 on low-copy (LC) or high-copy (HC) plasmids, or further comprising a copy of pheP driven by the Tet promoter integrated into the chromosome. Bacteria were induced with ATC, and then grown in culture medium supplemented with 4 mM (660,000 ng/mL) of phenylalanine to an $OD_{600}$ of 2.0. Samples were removed at 0 hrs, 2 hrs, and 4 hrs post-induction and phenylalanine concentrations were determined by mass spectrometry. Notably, the additional copy of pheP permitted the degradation of phenylalanine (4 mM) in 4 hrs.
Figure 16B:
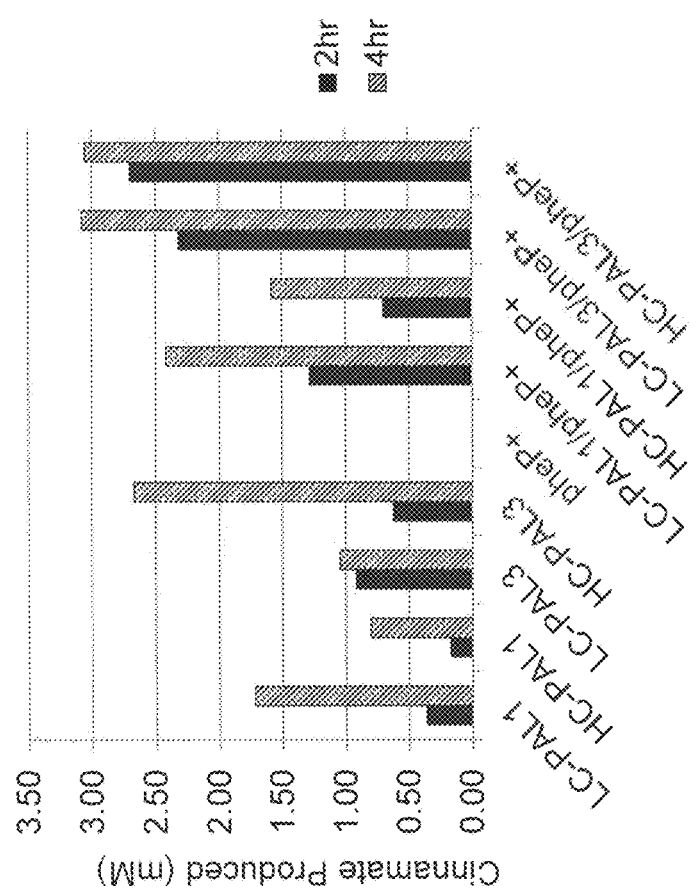
FIG. 16B depicts cinnamate levels in samples at 2 hrs and 4 hrs post-induction. In some embodiments, cinnamate may be used as an alternative biomarker for strain activity. PheP overexpression improves phenylalanine metabolism in engineered bacteria. Strains analyzed in this data set are SYN-PKU101, SYN-PKU102, SYN-PKU202, SYN-PKU201, SYN-PKU401, SYN-PKU402, SYN-PKU203, SYN-PKU302, SYN-PKU303.

In some embodiments, the genetically engineered bacteria of the invention produce PAL under exogenous environmental conditions, such as the low-oxygen environment of the mammalian gut, to reduce blood phenylalanine by at least about 1.5-fold, at least about 2-fold, at least about 3-fold, at least about 4-fold, at least about 5-fold, at least about 6-fold, at least about 7-fold, at least about 8-fold, at least about 9-fold, at least about 10-fold, at least about 15-fold, at least about 20-fold, at least about 30-fold, at least about 40-fold, or at least about 50-fold as compared to unmodified bacteria of the same subtype under the same conditions. Certain unmodified bacteria will not have appreciable levels of phenylalanine processing. In embodiments using genetically modified forms of these bacteria, PAL-mediated processing of phenylalanine will be appreciable under exogenous environmental conditions. Phenylalanine may be measured by methods known in the art, e.g., blood sampling and mass spectrometry. In some embodiments, cinnamate is measured by methods known in the art to assess PAL activity. Cinnamate production is directly correlated with phenylalanine degradation, and in some embodiments, that cinnamate may be used as an alternative biomarker for strain activity (FIG. 16B). Cinnamate can be further degraded to hippuric acid by liver enzymes; both can be measured as described in Example 24-26. In some embodiments, PAL expression is measured by methods known in the art to assess PAL activity.

In some embodiments, the genetically engineered bacteria of the invention produce LAAD, to reduce blood phenylalanine by at least about 1.5-fold, at least about 2-fold, at least about 3-fold, at least about 4-fold, at least about 5-fold, at least about 6-fold, at least about 7-fold, at least about 8-fold, at least about 9-fold, at least about 10-fold, at least about 15-fold, at least about 20-fold, at least about 30-fold, at least about 40-fold, or at least about 50-fold as compared to unmodified bacteria of the same subtype under the same conditions. Certain unmodified bacteria will not have appreciable levels of phenylalanine processing. In embodiments using genetically modified forms of these bacteria, LAAD-mediated processing of phenylalanine will be appreciable under exogenous environmental conditions. Phenylalanine may be measured by methods known in the art, e.g., blood sampling and mass spectrometry. Pyruvic acid and phenylpyruvate, the LAAD generated degradation products can be measured using masspectrometry as described in Examples 24-26, and can be used as an additional readout of LAAD activity.

Figure 15A:
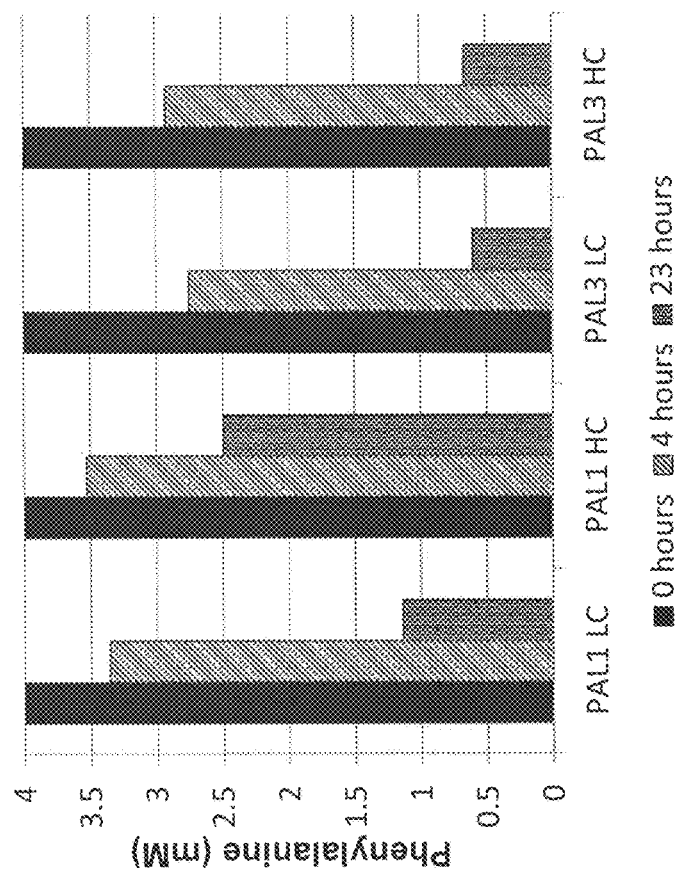
FIG. 15A depicts phenylalanine concentrations in samples comprising bacteria expressing PAL1 or on low-copy (LC; SYN-PKU101) or high-copy (HC; SYN-PKU102) plasmids or PAL3 on low-copy (LC; SYN-PKU201) or high-copy (HC; SYN-PKU202) plasmids, induced with anhydrous tetracycline (ATC), and then grown in culture medium supplemented with 4 mM (660,000 ng/mL) of phenylalanine. Samples were removed at 0 hrs, 4 hrs, and 23 hrs. Phenylalanine concentrations were determined by mass spectrometry.
Figure 15B:
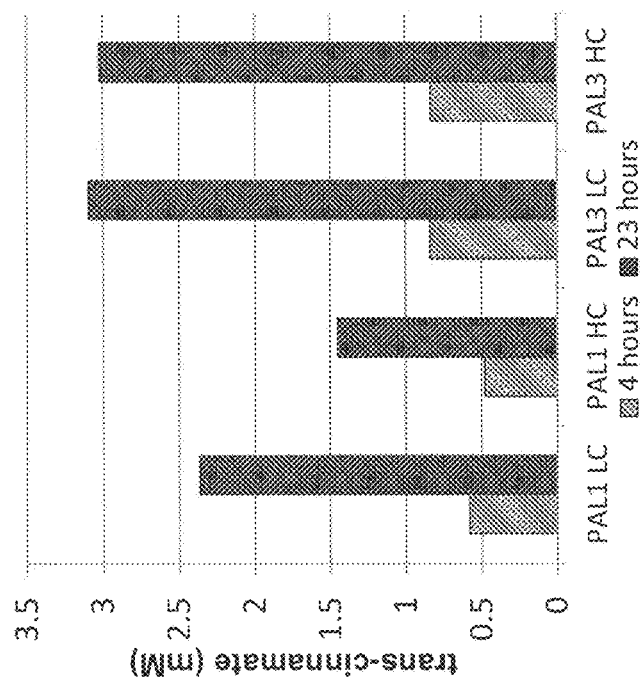
FIG. 15B depicts cinnamate levels in samples at 4 hrs and 23 hrs post-induction. In PAL3-expressing strains, the PAL3 gene is derived from *Photorhabdus luminescens*, an enterobacterium in the same taxonomic subdivision as *Escherichia coli*.

In some embodiments, the PME, e.g., PAL, LAAD, and/or PAH, is expressed on a low-copy plasmid. In some embodiments, the low-copy plasmid may be useful for increasing stability of expression. In some embodiments, the low-copy plasmid may be useful for decreasing leaky expression under non-inducing conditions. In some embodiments, the PME, e.g., PAL, LAAD, and/or PAH, is expressed on a high-copy plasmid. In some embodiments, the high-copy plasmid may be useful for increasing the PME, e.g., PAL, LAAD, and/or PAH, expression, thereby increasing the metabolism of phenylalanine and reducing hyperphenylalaninemia. In some embodiments, a genetically engineered bacterium comprising a the PME, e.g., PAL, LAAD, and/or PAH, expressed on a high-copy plasmid does not increase phenylalanine metabolism or decrease phenylalanine levels as compared to a genetically engineered bacterium comprising the same PME, e.g., PAL, LAAD, and/or PAH, expressed on a low-copy plasmid in the absence of heterologous pheP and additional copies of a native pheP. Genetically engineered bacteria comprising the same the PME gene, e.g., PAL, LAAD, and/or PAH gene on high and low copy plasmids were generated. For example, either PAL1 or PAL3 on a high-copy plasmid and a low-copy plasmid were generated, and each metabolized and reduced phenylalanine to similar levels (FIG. 15). Thus, in some embodiments, the rate-limiting step of phenylalanine metabolism is phenylalanine availability (see, e.g., FIG. 16). In these embodiments, it may be advantageous to increase phenylalanine transport into the cell, thereby enhancing phenylalanine metabolism. In conjunction with pheP, even low-copy PAL plasmids are capable of almost completely eliminating Phe from a test sample (see, e.g., FIG. 16A). Furthermore, in some embodiments, that incorporate pheP, there may be additional advantages to using a low-copy PAL-expressing plasmid in conjunction in order to enhance the stability of PAL expression while maintaining high phenylalanine metabolism, and to reduce negative selection pressure on the transformed bacterium. In alternate embodiments, the phenylalanine transporter is used in conjunction with the high-copy plasmid.

In some embodiments, a transporter may not increase phenylalanine degradation. For example, *Proteus mirabilis* LAAD is localized to the plasma membrane, with the enzymatic catalysis occurring in the periplasm. Phenylalanine can readily traverse the outer membrane without the need of a transporter. Therefore, in embodiments, in which the genetically engineered bacteria express LAAD, a transporter may not be needed or improve phenylalanine metabolism.

Figure 36:
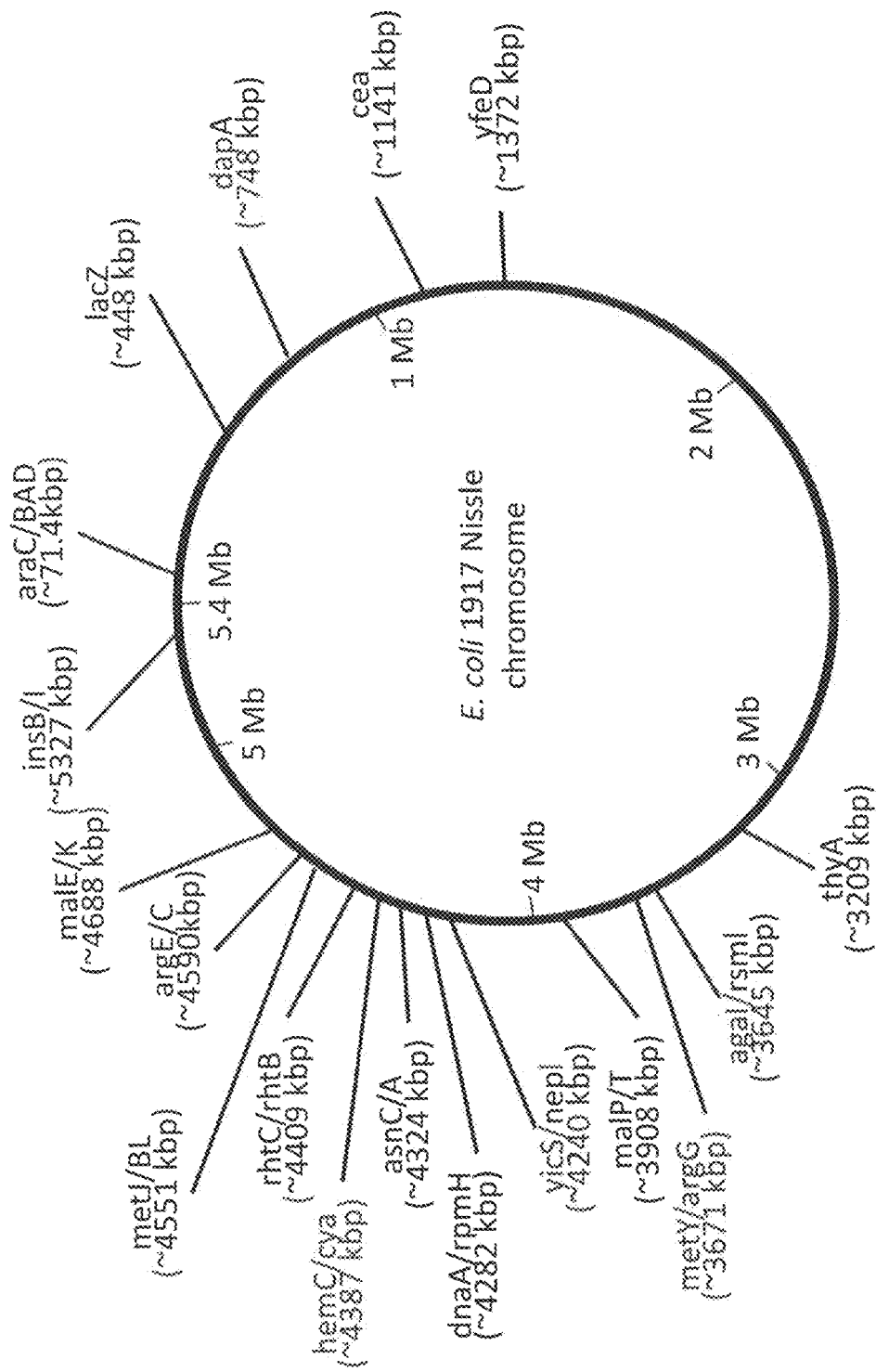
FIG. 36 depicts a map of exemplary integration sites within the E. coli 1917 Nissle chromosome. These sites indicate regions where circuit components may be inserted into the chromosome without interfering with essential gene expression. Backslashes (/) are used to show that the insertion will occur between divergently or convergently expressed genes. Insertions within biosynthetic genes, such as thyA, can be useful for creating nutrient auxotrophies. In some embodiments, an individual circuit component is inserted into more than one of the indicated sites.
Figure 37:
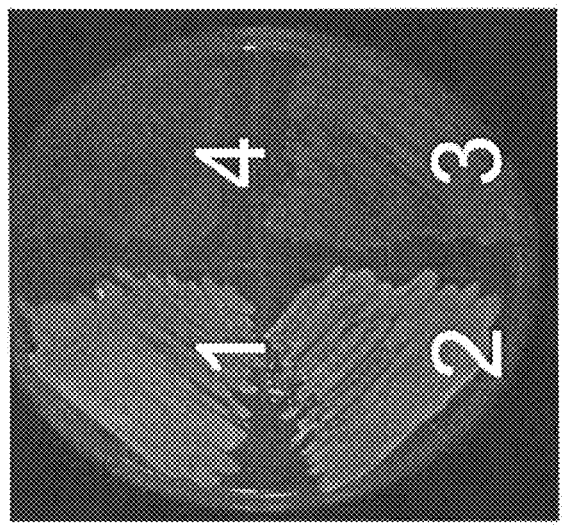
FIG. 37 depicts three bacterial strains which constitutively express red fluorescent protein (RFP). In strains 1-3, the rfp gene has been inserted into different sites within the bacterial chromosome, and results in varying degrees of brightness under fluorescent light. Unmodified E. coli Nissle (strain 4) is non-fluorescent.

In some embodiments, the PME, e.g., PAL, LAAD, and/or PAH, gene is expressed on a chromosome. In some embodiments, expression from the chromosome may be useful for increasing stability of expression of the PME. In some embodiments, the PME gene, e.g., PAL, LAAD, and/or PAH gene(s), is integrated into the bacterial chromosome at one or more integration sites in the genetically engineered bacteria. In some embodiments, the PME gene, e.g., PAL, LAAD, and/or PAH gene(s) is inserted into the bacterial genome at one or more of the following insertion sites in *E. coli* Nissle: malE/K, insB/I, araC/BAD, lacZ, agal/rsml, thyA, and malP/T. Any suitable insertion site may be used (see, e.g., FIG. 36). The insertion site may be anywhere in the genome, e.g., in a gene required for survival and/or growth, such as thyA (to create an auxotroph); in an active area of the genome, such as near the site of genome replication; and/or in between divergent promoters in order to reduce the risk of unintended transcription, such as between AraB and AraC of the arabinose operon. In some embodiments, more than one copy, e.g., two, three, four, five, six, seven, eight, nine, ten or more copies of the PME gene, e.g., PAL, PAH, and/or LAAD is integrated into the bacterial chromosome at one or more integration sites in the genetically engineered bacteria. The more than one copy of a PME gene may be more then one copy of the same PME gene or more than one copy of different PME genes.

Exemplary constructs are shown in 4-13 below. Table 4 shows the sequence of an exemplary construct comprising a gene encoding PheP and an FNR promoter sequence for chromosomal insertion (SEQ ID NO: 21), with the pheP sequence underlined and the FNR promoter sequence bolded. Table 5 shows the sequence of an exemplary construct comprising a gene encoding PAL1 and an FNR promoter sequence on a high-copy plasmid (SEQ ID NO: 22), with the PAL1 sequence underlined and the FNR promoter sequence bolded. Table 6 shows the sequence of an exemplary construct comprising a gene encoding PAL3 and an FNR promoter sequence on a high-copy plasmid (SEQ ID NO: 23), with the PAL3 sequence underlined and the FNR promoter sequence bolded. Table 7 shows the sequence of an exemplary construct comprising a gene encoding PAL1 and a Tet promoter sequence on a high-copy plasmid (SEQ ID NO: 24), with the PAL1 sequence underlined and the Tet promoter sequence bolded. Table 8 shows the sequence of an exemplary construct comprising a gene encoding PAL3 and a Tet promoter sequence on a high-copy plasmid (SEQ ID NO: 25), with the PAL3 sequence underlined and the Tet promoter sequence bolded. Table 9 shows the sequence of an exemplary construct comprising a gene encoding PAL1 and an FNR promoter sequence on a low-copy plasmid (SEQ ID NO: 26), with the PAL1 sequence underlined and the FNR promoter sequence bolded. Table 10 shows the sequence of an exemplary construct comprising a gene encoding PAL3 and an FNR promoter sequence on a low-copy plasmid (SEQ ID NO: 27), with the PAL3 sequence underlined and the FNR promoter sequence bolded. Table 11 shows the sequence of an exemplary construct comprising a gene encoding PAL1 and a Tet promoter sequence on a low-copy plasmid (SEQ ID NO: 28), with the PAL1 sequence underlined and the Tet promoter sequence bolded. Table 12 shows the sequence of an exemplary construct comprising a gene encoding PAL3 and a Tet promoter sequence on a low-copy plasmid (SEQ ID NO: 29), with the PAL3 sequence underlined and the Tet promoter sequence bolded. Table 13 shows the sequence of an exemplary construct comprising a gene encoding PheP, a gene coding TetR, and a Tet promoter sequence for chromosomal insertion (SEQ ID NO: 30), with the pheP sequence underlined, the TetR sequence boxed, and the FNR promoter sequence bolded.

TABLE 4

Nucleotide sequences of FNR promoter-PheP construct (SEQ ID NO: 21)

CTCTTGATCGTTATCAATTCCCACGCTGTTTCAGAGCGTTACCTTGCCCTTAAACATTA

GCAATGTCGATTTATCAGAGGGCCGACAGGCTCCCACAGGAGAAAACCGATGAAAAACG

CGTCAACCGTATCGGAAGATACTGCGTCGAATCAAGAGCCGACGCTTCATCGCGGATTA

CATAACCGTCATATTCAACTGATTGCGTTGGGTGGCGCAATTGGTACTGGTCTGTTTCT

TGGCATTGGCCCGGCGATTCAGATGGCGGGTCCGGCTGTATTGCTGGGCTACGGCGTCG

CCGGGATCATCGCTTTCCTGATTATGCGCCAGCTTGGCGAAATGGTGGTTGAGGAGCCG

GTATCCGGTTCATTTGCCCACTTTGCCTATAAATACTGGGGACCGTTTGCGGGCTTCCT

CTCTGGCTGGAACTACTGGGTAATGTTCGTGCTGGTGGGAATGGCAGAGCTGACCGCTG

CGGGCATCTATATGCAGTACTGGTTCCCGGATGTTCCAACGTGGATTTGGGCTGCCGCC

TTCTTTATTATCATCAACGCCGTTAACCTGGTGAACGTGCGCTTATATGGCGAAACCGA

GTTCTGGTTTGCGTTGATTAAAGTGCTGGCAATCATCGGTATGATCGGCTTTGGCCTGT

GGCTGCTGTTTTCTGGTCACGGCGGCGAGAAAGCCAGTATCGACAACCTCTGGCGCTAC

GGTGGTTTCTTCGCCACCGGCTGGAATGGGCTGATTTTGTCGCTGGCGGTAATTATGTT

CTCCTTCGGCGGTCTGGAGCTGATTGGGATTACTGCCGCTGAAGCGCGCGATCCGGAAA

AAAGCATTCCAAAAGCGGTAAATCAGGTGGTGTATCGCATCCTGCTGTTTTACATCGGT

TCACTGGTGGTTTTACTGGCGCTCTATCCGTGGGTGGAAGTGAAATCCAACAGTAGCCC

GTTTGTGATGATTTTCCATAATCTCGACAGCAACGTGGTAGCTTCTGCGCTGAACTTCG

TCATTCTGGTAGCATCGCTGTCAGTGTATAACAGCGGGGTTTACTCTAACAGCCGCATG

CTGTTTGGCCTTTCTGTGCAGGGTAATGCGCCGAAGTTTTTGACTCGCGTCAGCCGTCG

CGGTGTGCCGATTAACTCGCTGATGCTTTCCGGAGCGATCACTTCGCTGGTGGTGTTAA

TCAACTATCTGCTGCCGCAAAAAGCGTTTGGTCTGCTGATGGCGCTGGTGGTAGCAACG

CTGCTGTTGAACTGGATTATGATCTGTCTGGCGCATCTGCGTTTTCGTGCAGCGATGCG

ACGTCAGGGGCGTGAAACACAGTTTAAGGCGCTGCTCTATCCGTTCGGCAACTATCTCT

GCATTGCCTTCCTCGGCATGATTTTGCTGCTGATGTGCACGATGGATGATATGCGCTTG

TCAGCGATCCTGCTGCCGGTGTGGATTGTATTCCTGTTTATGGCATTTAAAACGCTGCG

TCGGAAATAA

TABLE 5

Nucleotide sequences of FNR promoter-PAL1 construct, high-copy (SEQ ID NO: 22)

CTCTTGATCGTTATCAATTCCCACGCTGTTTCAGAGCGTTACCTTGCCCTTAAACATTA

GCAATGTCGATTTATCAGAGGGCCGACAGGCTCCCACAGGAGAAAACCGATGAAAACAC

TATCACAGGCCCAATCTAAAACTTCTTCACAGCAATTCAGCTTTACCGGGAACTCGTCT

GCGAATGTAATTATCGGCAATCAAAAGCTGACCATTAATGATGTAGCTCGCGTTGCCCG

GAATGGCACTTTGGTGTCACTGACGAACAATACCGACATTCTGCAAGGTATTCAAGCTA

GCTGCGATTATATCAATAACGCCGTTGAATCTGGCGAGCCAATCTACGGGGTAACAAGC

GGTTTTGGTGGGATGGCGAACGTTGCCATTAGCCGTGAACAGGCGAGCGAACTTCAGAC

CAACCTCGTTTGGTTCCTAAAGACAGGAGCTGGTAATAAGTTACCTCTGGCTGACGTAA

GAGCCGCGATGCTGCTTCGCGCTAATAGTCACATGCGCGGCGCCAGTGGTATCCGTCTT

GAGCTTATCAAGAGGATGGAAATCTTCCTCAACGCGGGTGTCACACCATATGTTTATGA

GTTTGGTAGTATCGGAGCCAGTGGTGATCTTGTTCCCCTGAGTTATATTACGGGTTCAT

TGATTGGTTTAGACCCGTCCTTTAAAGTGGATTTTAACGGGAAAGAAATGGACGCCCCG

ACCGCTTTACGACAGCTTAATCTGAGCCCACTTACTTTGCTCCCTAAAGAAGGTCTTGC

CATGATGAATGGCACCTCTGTGATGACTGGAATTGCCGCGAATTGTGTGTATGACACGC

AGATCCTAACGGCCATTGCCATGGGTGTTCACGCGTTGGACATTCAAGCCCTGAATGGT

ACAAACCAGTCGTTTCATCCGTTTATCCATAATTCAAAACCCCATCCGGGACAGCTTTG

GGCTGCTGATCAGATGATCTCACTCCTGGCCAATAGTCAACTGGTTCGGGACGAGCTCG

ACGGCAAACATGATTATCGCGATCATGAGCTCATCCAGGACCGGTATTCACTTCGTTGT

CTCCCACAATACCTGGGGCCTATCGTTGATGGTATATCTCAAATTGCGAAGCAAATTGA

AATTGAGATCAATAGCGTAACCGACAACCCGCTTATCGATGTTGATAATCAGGCCTCTT

ATCACGGTGGCAATTTTCTGGGCCAGTATGTTGGTATGGGGATGGATCACCTGCGGTAC

TATATTGGGCTTCTGGCTAAACATCTTGATGTGCAGATTGCCTTATTAGCTTCACCAGA

ATTTTCAAATGGACTGCCGCCATCATTGCTCGGTAACAGAGAAAGGAAAGTAAATATGG

GCCTTAAGGGCCTTCAGATATGTGGTAACTCAATCATGCCCCTCCTGACCTTTTATGGG

AACTCAATTGCTGATCGTTTTCCGACACATGCTGAACAGTTTAACCAAAACATTAACTC

ACAGGGCTATACATCCGCGACGTTAGCGCGTCGGTCCGTGGATATCTTCCAGAATTATG

TTGCTATCGCTCTGATGTTCGGCGTACAGGCCGTTGATTTGCGCACTTATAAAAAAACC

GGTCACTACGATGCTCGGGCTTGCCTGTCGCCTGCCACCGAGCGGCTTTATAGCGCCGT

ACGTCATGTTGTGGGTCAGAAACCGACGTCGGACCGCCCCTATATTTGGAATGATAATG

AACAAGGGCTGGATGAACACATCGCCCGGATATCTGCCGATATTGCCGCCGGAGGTGTC

ATCGTCCAGGCGGTACAAGACATACTTCCTTGCCTGCATTAAGCTTGGCGTAATCATGG

TCATAGCTGTTTCCTGTGTGAAATTGTTATCCGCTCACAATTCCACACAACATACGAGC

CGGAAGCATAAAGTGTAAAGCCTGGGGTGCCTAATGAGTGAGCTAACTCACATTAATTG

CGTTGCGCTCACTGCCCGCTTTCCAGTCGGGAAACCTGTCGTGCCAGCTGCATTAATGA

ATCGGCCAACGCGCGGGGAGAGGCGGTTTGCGTATTGGGCGCTCTTCCGCTTCCTCGCT

CACTGACTCGCTGCGCTCGGTCGTTCGGCTGCGGCGAGCGGTATCAGCTCACTCAAAGG

CGGTAATACGGTTATCCACAGAATCAGGGGATAACGCAGGAAAGAACATGTGAGCAAAA

GGCCAGCAAAAGGCCAGGAACCGTAAAAAGGCCGCGTTGCTGGCGTTTTTCCATAGGCT

CCGCCCCCCTGACGAGCATCACAAAAATCGACGCTCAAGTCAGAGGTGGCGAAACCCGA

TABLE 5-continued

Nucleotide sequences of FNR promoter-PAL1 construct, high-copy (SEQ ID NO: 22)

```
CAGGACTATAAAGATACCAGGCGTTTCCCCCTGGAAGCTCCCTCGTGCGCTCTCCTGTT
CCGACCCTGCCGCTTACCGGATACCTGTCCGCCTTTCTCCCTTCGGGAAGCGTGGCGCT
TTCTCATAGCTCACGCTGTAGGTATCTCAGTTCGGTGTAGGTCGTTCGCTCCAAGCTGG
GCTGTGTGCACGAACCCCCCGTTCAGCCCGACCGCTGCGCCTTATCCGGTAACTATCGT
CTTGAGTCCAACCCGGTAAGACACGACTTATCGCCACTGGCAGCAGCCACTGGTAACAG
GATTAGCAGAGCGAGGTATGTAGGCGGTGCTACAGAGTTCTTGAAGTGGTGGCCTAACT
ACGGCTACACTAGAAGAACAGTATTTGGTATCTGCGCTCTGCTGAAGCCAGTTACCTTC
GGAAAAAGAGTTGGTAGCTCTTGATCCGGCAAACAAACCACCGCTGGTAGCGGTGGTTT
TTTTGTTTGCAAGCAGCAGATTACGCGCAGAAAAAAAGGATCTCAAGAAGATCCTTTGA
TCTTTTCTACGGGTCTGACGCTCAGTGGAACGAAAACTCACGTTAAGGGATTTTGGTC
ATGAGATTATCAAAAAGGATCTTCACCTAGATCCTTTTAAATTAAAAATGAAGTTTTAA
ATCAATCTAAAGTATATATGAGTAAACTTGGTCTGACAGTTACCAATGCTTAATCAGTG
AGGCACCTATCTCAGCGATCTGTCTATTTCGTTCATCCATAGTTGCCTGACTCCCCGTC
GTGTAGATAACTACGATACGGGAGGGCTTACCATCTGGCCCCAGTGCTGCAATGATACC
GCGAGACCCACGCTCACCGGCTCCAGATTTATCAGCAATAAACCAGCCAGCCGGAAGGG
CCGAGCGCAGAAGTGGTCCTGCAACTTTATCCGCCTCCATCCAGTCTATTAATTGTTGC
CGGGAAGCTAGAGTAAGTAGTTCGCCAGTTAATAGTTTGCGCAACGTTGTTGCCATTGC
TACAGGCATCGTGGTGTCACGCTCGTCGTTTGGTATGGCTTCATTCAGCTCCGGTTCCC
AACGATCAAGGCGAGTTACATGATCCCCCATGTTGTGCAAAAAAGCGGTTAGCTCCTTC
GGTCCTCCGATCGTTGTCAGAAGTAAGTTGGCCGCAGTGTTATCACTCATGGTTATGGC
AGCACTGCATAATTCTCTTACTGTCATGCCATCCGTAAGATGCTTTTCTGTGACTGGTG
AGTACTCAACCAAGTCATTCTGAGAATAGTGTATGCGGCGACCGAGTTGCTCTTGCCCG
GCGTCAATACGGGATAATACCGCGCCACATAGCAGAACTTTAAAAGTGCTCATCATTGG
AAAACGTTCTTCGGGGCGAAAACTCTCAAGGATCTTACCGCTGTTGAGATCCAGTTCGA
TGTAACCCACTCGTGCACCCAACTGATCTTCAGCATCTTTTACTTTCACCAGCGTTTCT
GGGTGAGCAAAAACAGGAAGGCAAAATGCCGCAAAAAAGGGAATAAGGGCGACACGGAA
ATGTTGAATACTCATACTCTTCCTTTTTCAATATTATTGAAGCATTTATCAGGGTTATT
GTCTCATGAGCGGATACATATTTGAATGTATTTAGAAAAATAAACAAATAGGGGTTCCG
CGCACATTTCCCCGAAAAGTGCCACCTGACGTCTAAGAAACCATTATTATCATGACATT
AACCTATAAAAATAGGCGTATCACGAGGCCCTTTCGTCTCGCGCGTTTCGGTGATGACG
GTGAAAACCTCTGACACATGCAGCTCCCGGAGACGGTCACAGCTTGTCTGTAAGCGGAT
GCCGGGAGCAGACAAGCCCGTCAGGGCGCGTCAGCGGGTGTTGGCGGGTGTCGGGCTG
GCTTAACTATGCGGCATCAGAGCAGATTGTACTGAGAGTGCACCATATGCGGTGTGAAA
TACCGCACAGATGCGTAAGGAGAAAATACCGCATCAGGCGCCATTCGCCATTCAGGCTG
CGCAACTGTTGGGAAGGGCGATCGGTGCGGGCCTCTTCGCTATTACGCCAGCTGGCGAA
AGGGGGATGTGCTGCAAGGCGATTAAGTTGGGTAACGCCAGGGTTTTCCCAGTCACGAC
GTT
```

TABLE 6

Nucleotide sequences of FNR promoter-PAL3 construct, high-copy (SEQ ID NO: 23)

CTCTTGATCGTTATCAATTCCCACGCTGTTTCAGAGCGTTACCTTGCCCTTAAACATTA

GCAATGTCGATTTATCAGAGGGCCGACAGGCTCCCACAGGAGAAAACCG<u>ATGAAAGCTA</u>

<u>AAGATGTTCAGCCAACCATTATTATTAATAAAAATGGCCTTATCTCTTTGGAAGATATC</u>

<u>TATGACATTGCGATAAAACAAAAAAAAGTAGAAATATCAACGGAGATCACTGAACTTTT</u>

<u>GACGCATGGTCGTGAAAAATTAGAGGAAAAATTAAATTCAGGAGAGGTTATATATGGAA</u>

<u>TCAATACAGGATTTGGAGGGAATGCCAATTTAGTTGTGCCATTTGAGAAAATCGCAGAG</u>

<u>CATCAGCAAAATCTGTTAACTTTTCTTTCTGCTGGTACTGGGGACTATATGTCCAAACC</u>

<u>TTGTATTAAAGCGTCACAATTTACTATGTTACTTTCTGTTTGCAAAGGTTGGTCTGCAA</u>

<u>CCAGACCAATTGTCGCTCAAGCAATTGTTGATCATATTAATCATGACATTGTTCCTCTG</u>

<u>GTTCCTCGCTATGGCTCAGTGGGTGCAAGCGGTGATTTAATTCCTTTATCTTATATTGC</u>

<u>ACGAGCATTATGTGGTATCGGCAAAGTTTATTATATGGGCGCAGAAATTGACGCTGCTG</u>

<u>AAGCAATTAAACGTGCAGGGTTGACACCATTATCGTTAAAAGCCAAAGAAGGTCTTGCT</u>

<u>CTGATTAACGGCACCCGGGTAATGTCAGGAATCAGTGCAATCACCGTCATTAAACTGGA</u>

<u>AAAACTATTTAAAGCCTCAATTTCTGCGATTGCCCTTGCTGTTGAAGCATTACTTGCAT</u>

<u>CTCATGAACATTATGATGCCCGGATTCAACAAGTAAAAAATCATCCTGGTCAAAACGCG</u>

<u>GTGGCAAGTGCATTGCGTAATTTATTGGCAGGTTCAACGCAGGTTAATCTATTATCTGG</u>

<u>GGTTAAAGAACAAGCCAATAAAGCTTGTCGTCATCAAGAAATTACCCAACTAAATGATA</u>

<u>CCTTACAGGAAGTTTATTCAATTCGCTGTGCACCACAAGTATTAGGTATAGTGCCAGAA</u>

<u>TCTTTAGCTACCGCTCGGAAAATATTGGAACGGGAAGTTATCTCAGCTAATGATAATCC</u>

<u>ATTGATAGATCCAGAAAATGGCGATGTTCTACACGGTGGAAATTTTATGGGGCAATATG</u>

<u>TCGCCCGAACAATGGATGCATTAAAACTGGATATTGCTTTAATTGCCAATCATCTTCAC</u>

<u>GCCATTGTGGCTCTTATGATGGATAACCGTTTCTCTCGTGGATTACCTAATTCACTGAG</u>

<u>TCCGACACCCGGCATGTATCAAGGTTTTAAAGGCGTCCAACTTTCTCAAACCGCTTTAG</u>

<u>TTGCTGCAATTCGCCATGATTGTGCTGCATCAGGTATTCATACCCTCGCCACAGAACAA</u>

<u>TACAATCAAGATATTGTCAGTTTAGGTCTGCATGCCGCTCAAGATGTTTTAGAGATGGA</u>

<u>GCAGAAATTACGCAATATTGTTTCAATGACAATTCTGGTAGTTTGTCAGGCCATTCATC</u>

<u>TTCGCGGCAATATTAGTGAAATTGCGCCTGAAACTGCTAAATTTTACCATGCAGTACGC</u>

<u>GAAATCAGTTCTCCTTTGATCACTGATCGTGCGTTGGATGAAGATATAATCCGCATTGC</u>

<u>GGATGCAATTATTAATGATCAACTTCCTCTGCCAGAAATCATGCTGGAAGAATAA</u>GCTT

GGCGTAATCATGGTCATAGCTGTTTCCTGTGTGAATTGTTATCCGCTCACAATTCCAC

ACAACATACGAGCCGGAAGCATAAAGTGTAAAGCCTGGGGTGCCTAATGAGTGAGCTAA

CTCACATTAATTGCGTTGCGCTCACTGCCCGCTTTCCAGTCGGGAAACCTGTCGTGCCA

GCTGCATTAATGAATCGGCCAACGCGCGGGGAGAGGCGGTTTGCGTATTGGGCGCTCTT

CCGCTTCCTCGCTCACTGACTCGCTGCGCTCGGTCGTTCGGCTGCGGCGAGCGGTATCA

GCTCACTCAAAGGCGGTAATACGGTTATCCACAGAATCAGGGGATAACGCAGGAAAGAA

CATGTGAGCAAAAGGCCAGCAAAAGGCCAGGAACCGTAAAAAGGCCGCGTTGCTGGCGT

TTTTCCATAGGCTCCGCCCCCCTGACGAGCATCACAAAAATCGACGCTCAAGTCAGAGG

TGGCGAAACCCGACAGGACTATAAAGATACCAGGCGTTTCCCCCTGGAAGCTCCCTCGT

GCGCTCTCCTGTTCCGACCCTGCCGCTTACCGGATACCTGTCCGCCTTTCTCCCTTCGG

TABLE 6-continued

Nucleotide sequences of FNR promoter-PAL3 construct, high-copy (SEQ ID NO: 23)

GAAGCGTGGCGCTTTCTCATAGCTCACGCTGTAGGTATCTCAGTTCGGTGTAGGTCGTT

CGCTCCAAGCTGGGCTGTGTGCACGAACCCCCCGTTCAGCCCGACCGCTGCGCCTTATC

CGGTAACTATCGTCTTGAGTCCAACCCGGTAAGACACGACTTATCGCCACTGGCAGCAG

CCACTGGTAACAGGATTAGCAGAGCGAGGTATGTAGGCGGTGCTACAGAGTTCTTGAAG

TGGTGGCCTAACTACGGCTACACTAGAAGAACAGTATTTGGTATCTGCGCTCTGCTGAA

GCCAGTTACCTTCGGAAAAAGAGTTGGTAGCTCTTGATCCGGCAAACAAACCACCGCTG

GTAGCGGTGGTTTTTTTGTTTGCAAGCAGCAGATTACGCGCAGAAAAAAAGGATCTCAA

GAAGATCCTTTGATCTTTTCTACGGGGTCTGACGCTCAGTGGAACGAAAACTCACGTTA

AGGGATTTTGGTCATGAGATTATCAAAAAGGATCTTCACCTAGATCCTTTTAAATTAAA

AATGAAGTTTTAAATCAATCTAAAGTATATATGAGTAAACTTGGTCTGACAGTTACCAA

TGCTTAATCAGTGAGGCACCTATCTCAGCGATCTGTCTATTTCGTTCATCCATAGTTGC

CTGACTCCCCGTCGTGTAGATAACTACGATACGGGAGGGCTTACCATCTGGCCCCAGTG

CTGCAATGATACCGCGAGACCCACGCTCACCGGCTCCAGATTTATCAGCAATAAACCAG

CCAGCCGGAAGGGCCGAGCGCAGAAGTGGTCCTGCAACTTTATCCGCCTCCATCCAGTC

TATTAATTGTTGCCGGGAAGCTAGAGTAAGTAGTTCGCCAGTTAATAGTTTGCGCAACG

TTGTTGCCATTGCTACAGGCATCGTGGTGTCACGCTCGTCGTTTGGTATGGCTTCATTC

AGCTCCGGTTCCCAACGATCAAGGCGAGTTACATGATCCCCCATGTTGTGCAAAAAAGC

GGTTAGCTCCTTCGGTCCTCCGATCGTTGTCAGAAGTAAGTTGGCCGCAGTGTTATCAC

TCATGGTTATGGCAGCACTGCATAATTCTCTTACTGTCATGCCATCCGTAAGATGCTTT

TCTGTGACTGGTGAGTACTCAACCAAGTCATTCTGAGAATAGTGTATGCGGCGACCGAG

TTGCTCTTGCCCGGCGTCAATACGGGATAATACCGCGCCACATAGCAGAACTTTAAAAG

TGCTCATCATTGGAAAACGTTCTTCGGGGCGAAAACTCTCAAGGATCTTACCGCTGTTG

AGATCCAGTTCGATGTAACCCACTCGTGCACCCAACTGATCTTCAGCATCTTTTACTTT

CACCAGCGTTTCTGGGTGAGCAAAAACAGGAAGGCAAAATGCCGCAAAAAAGGGAATAA

GGGCGACACGGAAATGTTGAATACTCATACTCTTCCTTTTTCAATATTATTGAAGCATT

TATCAGGGTTATTGTCTCATGAGCGGATACATATTTGAATGTATTTAGAAAAATAAACA

AATAGGGGTTCCGCGCACATTTCCCCGAAAAGTGCCACCTGACGTCTAAGAAACCATTA

TTATCATGACATTAACCTATAAAAATAGGCGTATCACGAGGCCCTTTCGTCTCGCGCGT

TTCGGTGATGACGGTGAAAACCTCTGACACATGCAGCTCCCGGAGACGGTCACAGCTTG

TCTGTAAGCGGATGCCGGGAGCAGACAAGCCCGTCAGGGCGCGTCAGCGGGTGTTGGCG

GGTGTCGGGGCTGGCTTAACTATGCGGCATCAGAGCAGATTGTACTGAGAGTGCACCAT

ATGCGGTGTGAAATACCGCACAGATGCGTAAGGAGAAAATACCGCATCAGGCGCCATTC

GCCATTCAGGCTGCGCAACTGTTGGGAAGGGCGATCGGTGCGGGCCTCTTCGCTATTAC

GCCAGCTGGCGAAAGGGGGATGTGCTGCAAGGCGATTAAGTTGGGTAACGCCAGGGTTT

TCCCAGTCACGACGTT

TABLE 7

Nucleotide sequences of Tet promoter-PAL1 construct, high-copy (SEQ ID NO: 24)

CTCTAGAAATAATTTTGTTTAACTTTAAGAAGGAGATATACAT<u>ATGAAAACACTATCAC</u>

<u>AGGCCCAATCTAAAACTTCTTCACAGCAATTCAGCTTTACCGGGAACTCGTCTGCGAAT</u>

<u>GTAATTATCGGCAATCAAAAGCTGACCATTAATGATGTAGCTCGCGTTGCCCGGAATGG</u>

<u>CACTTTGGTGTCACTGACGAACAATACCGACATTCTGCAAGGTATTCAAGCTAGCTGCG</u>

<u>ATTATATCAATAACGCCGTTGAATCTGGCGAGCCAATCTACGGGGTAACAAGCGGTTTT</u>

<u>GGTGGGATGGCGAACGTTGCCATTAGCCGTGAACAGGCGAGCGAACTTCAGACCAACCT</u>

<u>CGTTTGGTTCCTAAAGACAGGAGCTGGTAATAAGTTACCTCTGGCTGACGTAAGAGCCG</u>

<u>CGATGCTGCTTCGCGCTAATAGTCACATGCGCGGCGCCAGTGGTATCCGTCTTGAGCTT</u>

<u>ATCAAGAGGATGGAAATCTTCCTCAACGCGGGTGTCACACCATATGTTTATGAGTTTGG</u>

<u>TAGTATCGGAGCCAGTGGTGATCTTGTTCCCCTGAGTTATATTACGGGTTCATTGATTG</u>

<u>GTTTAGACCCGTCCTTTAAAGTGGATTTTAACGGGAAAGAAATGGACGCCCCGACCGCT</u>

<u>TTACGACAGCTTAATCTGAGCCCACTTACTTTGCTCCCTAAAGAAGGTCTTGCCATGAT</u>

<u>GAATGGCACCTCTGTGATGACTGGAATTGCCGCGAATTGTGTGTATGACACGCAGATCC</u>

<u>TAACGGCCATTGCCATGGGTGTTCACGCGTTGGACATTCAAGCCCTGAATGGTACAAAC</u>

<u>CAGTCGTTTCATCCGTTTATCCATAATTCAAAACCCCATCCGGGACAGCTTTGGGCTGC</u>

<u>TGATCAGATGATCTCACTCCTGGCCAATAGTCAACTGGTTCGGGACGAGCTCGACGGCA</u>

<u>AACATGATTATCGCGATCATGAGCTCATCCAGGACCGGTATTCACTTCGTTGTCTCCCA</u>

<u>CAATACCTGGGGCCTATCGTTGATGGTATATCTCAAATTGCGAAGCAAATTGAAATTGA</u>

<u>GATCAATAGCGTAACCGACAACCCGCTTATCGATGTTGATAATCAGGCCTCTTATCACG</u>

<u>GTGGCAATTTTCTGGGCCAGTATGTTGGTATGGGGATGGATCACCTGCGGTACTATATT</u>

<u>GGGCTTCTGGCTAAACATCTTGATGTGCAGATTGCCTTATTAGCTTCACCAGAATTTTC</u>

<u>AAATGGACTGCCGCCATCATTGCTCGGTAACAGAGAAAGGAAAGTAAATATGGGCCTTA</u>

<u>AGGGCCTTCAGATATGTGGTAACTCAATCATGCCCCTCCTGACCTTTTATGGGAACTCA</u>

<u>ATTGCTGATCGTTTTCCGACACATGCTGAACAGTTTAACCAAAACATTAACTCACAGGG</u>

<u>CTATACATCCGCGACGTTAGCGCGTCGGTCCGTGGATATCTTCCAGAATTATGTTGCTA</u>

<u>TCGCTCTGATGTTCGGCGTACAGGCCGTTGATTTGCGCACTTATAAAAAACCGGTCAC</u>

<u>TACGATGCTCGGGCTTGCCTGTCGCCTGCCACCGAGCGGCTTTATAGCGCCGTACGTCA</u>

<u>TGTTGTGGGTCAGAAACCGACGTCGGACCGCCCCTATATTTGGAATGATAATGAACAAG</u>

<u>GGCTGGATGAACACATCGCCCGGATATCTGCCGATATTGCCGCCGGAGGTGTCATCGTC</u>

<u>CAGGCGGTACAAGACATACTTCCTTGCCTGCATTAA</u>GCTTGGCGTAATCATGGTCATAG

CTGTTTCCTGTGTGAAATTGTTATCCGCTCACAATTCCACACAACATACGAGCCGGAAG

CATAAAGTGTAAAGCCTGGGGTGCCTAATGAGTGAGCTAACTCACATTAATTGCGTTGC

GCTCACTGCCCGCTTTCCAGTCGGGAAACCTGTCGTGCCAGCTGCATTAATGAATCGGC

CAACGCGCGGGAGAGGCGGTTTGCGTATTGGGCGCTCTTCCGCTTCCTCGCTCACTGA

CTCGCTGCGCTCGGTCGTTCGGCTGCGGCGAGCGGTATCAGCTCACTCAAAGGCGGTAA

TACGGTTATCCACAGAATCAGGGGATAACGCAGGAAAGAACATGTGAGCAAAAGGCCAG

CAAAAGGCCAGGAACCGTAAAAAGGCCGCGTTGCTGGCGTTTTTCCATAGGCTCCGCCC

CCCTGACGAGCATCACAAAAATCGACGCTCAAGTCAGAGGTGGCGAAACCCGACAGGAC

TATAAAGATACCAGGCGTTTCCCCCTGGAAGCTCCCTCGTGCGCTCTCCTGTTCCGACC

TABLE 7-continued

Nucleotide sequences of Tet promoter-PAL1 construct, high-copy (SEQ ID NO: 24)

```
CTGCCGCTTACCGGATACCTGTCCGCCTTTCTCCCTTCGGGAAGCGTGGCGCTTTCTCA
TAGCTCACGCTGTAGGTATCTCAGTTCGGTGTAGGTCGTTCGCTCCAAGCTGGGCTGTG
TGCACGAACCCCCCGTTCAGCCCGACCGCTGCGCCTTATCCGGTAACTATCGTCTTGAG
TCCAACCCGGTAAGACACGACTTATCGCCACTGGCAGCAGCCACTGGTAACAGGATTAG
CAGAGCGAGGTATGTAGGCGGTGCTACAGAGTTCTTGAAGTGGTGGCCTAACTACGGCT
ACACTAGAAGAACAGTATTTGGTATCTGCGCTCTGCTGAAGCCAGTTACCTTCGGAAAA
AGAGTTGGTAGCTCTTGATCCGGCAAACAAACCACCGCTGGTAGCGGTGGTTTTTTTGT
TTGCAAGCAGCAGATTACGCGCAGAAAAAAAGGATCTCAAGAAGATCCTTTGATCTTTT
CTACGGGGTCTGACGCTCAGTGGAACGAAAACTCACGTTAAGGGATTTTGGTCATGAGA
TTATCAAAAAGGATCTTCACCTAGATCCTTTTAAATTAAAAATGAAGTTTTAAATCAAT
CTAAAGTATATATGAGTAAACTTGGTCTGACAGTTACCAATGCTTAATCAGTGAGGCAC
CTATCTCAGCGATCTGTCTATTTCGTTCATCCATAGTTGCCTGACTCCCCGTCGTGTAG
ATAACTACGATACGGGAGGGCTTACCATCTGGCCCCAGTGCTGCAATGATACCGCGAGA
CCCACGCTCACCGGCTCCAGATTTATCAGCAATAAACCAGCCAGCCGGAAGGGCCGAGC
GCAGAAGTGGTCCTGCAACTTTATCCGCCTCCATCCAGTCTATTAATTGTTGCCGGGAA
GCTAGAGTAAGTAGTTCGCCAGTTAATAGTTTGCGCAACGTTGTTGCCATTGCTACAGG
CATCGTGGTGTCACGCTCGTCGTTTGGTATGGCTTCATTCAGCTCCGGTTCCCAACGAT
CAAGGCGAGTTACATGATCCCCCATGTTGTGCAAAAAAGCGGTTAGCTCCTTCGGTCCT
CCGATCGTTGTCAGAAGTAAGTTGGCCGCAGTGTTATCACTCATGGTTATGGCAGCACT
GCATAATTCTCTTACTGTCATGCCATCCGTAAGATGCTTTTCTGTGACTGGTGAGTACT
CAACCAAGTCATTCTGAGAATAGTGTATGCGGCGACCGAGTTGCTCTTGCCCGGCGTCA
ATACGGGATAATACCGCGCCACATAGCAGAACTTTAAAAGTGCTCATCATTGGAAAACG
TTCTTCGGGGCGAAAACTCTCAAGGATCTTACCGCTGTTGAGATCCAGTTCGATGTAAC
CCACTCGTGCACCCAACTGATCTTCAGCATCTTTTACTTTCACCAGCGTTTCTGGGTGA
GCAAAAACAGGAAGGCAAAATGCCGCAAAAAAGGGAATAAGGGCGACACGGAAATGTTG
AATACTCATACTCTTCCTTTTTCAATATTATTGAAGCATTTATCAGGGTTATTGTCTCA
TGAGCGGATACATATTTGAATGTATTTAGAAAAATAAACAAATAGGGGTTCCGCGCACA
TTTCCCCGAAAAGTGCCACCTGACGTCTAAGAAACCATTATTATCATGACATTAACCTA
TAAAAATAGGCGTATCACGAGGCCCTTTCGTCTCGCGCGTTTCGGTGATGACGGTGAAA
ACCTCTGACACATGCAGCTCCCGGAGACGGTCACAGCTTGTCTGTAAGCGGATGCCGGG
AGCAGACAAGCCCGTCAGGGCGCGTCAGCGGGTGTTGGCGGGTGTCGGGGCTGGCTTAA
CTATGCGGCATCAGAGCAGATTGTACTGAGAGTGCACCATATGCGGTGTGAAATACCGC
ACAGATGCGTAAGGAGAAAATACCGCATCAGGCGCCATTCGCCATTCAGGCTGCGCAAC
TGTTGGGAAGGGCGATCGGTGCGGGCCTCTTCGCTATTACGCCAGCTGGCGAAAGGGGG
ATGTGCTGCAAGGCGATTAAGTTGGGTAACGCCAGGGTTTTCCCAGTCACGACGTTGTA
AAACGACGGCCAGTGAATTCGTTAAGACCCACTTTCACATTTAAGTTGTTTTTCTAATC
CGCATATGATCAATTCAAGGCCGAATAAGAAGGCTGGCTCTGCACCTTGGTGATCAAAT
AATTCGATAGCTTGTCGTAATAATGGCGGCATACTATCAGTAGTAGGTGTTTCCCTTTC
```

TABLE 7-continued

Nucleotide sequences of Tet promoter-PAL1 construct, high-copy (SEQ ID NO: 24)

TTCTTTAGCGACTTGATGCTCTTGATCTTCCAATACGCAACCTAAAGTAAAATGCCCCA

CAGCGCTGAGTGCATATAATGCATTCTCTAGTGAAAAACCTTGTTGGCATAAAAAGGCT

AATTGATTTTCGAGAGTTTCATACTGTTTTTCTGTAGGCCGTGTACCTAAATGTACTTT

TGCTCCATCGCGATGACTTAGTAAAGCACATCTAAAACTTTTAGCGTTATTACGTAAAA

AATCTTGCCAGCTTTCCCCTTCTAAAGGGCAAAAGTGAGTATGGTGCCTATCTAACATC

TCAATGGCTAAGGCGTCGAGCAAAGCCCGCTTATTTTTTACATGCCAATACAATGTAGG

CTGCTCTACACCTAGCTTCTGGGCGAGTTTACGGGTTGTTAAACCTTCGATTCCGACCT

CATTAAGCAGCTCTAATGCGCTGTTAATCACTTTACTTTTATCTAATCTAGACATCATT

AATTCCTAATTTTTGTTGACACTCTATCATTGATAGAGTTATTTTACCACTCCCTATCA

GTGATAGAGAAAAGTGAA

TABLE 8

Nucleotide sequences of Tet promoter-PAL3, high-copy construct (SEQ ID NO: 25)

CTCTAGAAATAATTTTGTTTAACTTTAAGAAGGAGATATACAT<u>ATGAAAGCTAAAGATG</u>

<u>TTCAGCCAACCATTATTATTAATAAAAATGGCCTTATCTCTTTGGAAGATATCTATGAC</u>

<u>ATTGCGATAAAACAAAAAAAGTAGAAATATCAACGGAGATCACTGAACTTTTGACGCA</u>

<u>TGGTCGTGAAAAATTAGAGGAAAAATTAAATTCAGGAGAGGTTATATATGGAATCAATA</u>

<u>CAGGATTTGGAGGGAATGCCAATTTAGTTGTGCCATTTGAGAAAATCGCAGAGCATCAG</u>

<u>CAAAATCTGTTAACTTTTCTTTCTGCTGGTACTGGGGACTATATGTCCAAACCTTGTAT</u>

<u>TAAAGCGTCACAATTTACTATGTTACTTTCTGTTTGCAAAGGTTGGTCTGCAACCAGAC</u>

<u>CAATTGTCGCTCAAGCAATTGTTGATCATATTAATCATGACATTGTTCCTCTGGTTCCT</u>

<u>CGCTATGGCTCAGTGGGTGCAAGCGGTGATTTAATTCCTTTATCTTATATTGCACGAGC</u>

<u>ATTATGTGGTATCGGCAAAGTTTATTATATGGGCGCAGAAATTGACGCTGCTGAAGCAA</u>

<u>TTAAACGTGCAGGGTTGACACCATTATCGTTAAAAGCCAAAGAAGGTCTTGCTCTGATT</u>

<u>AACGGCACCCGGGTAATGTCAGGAATCAGTGCAATCACCGTCATTAAACTGGAAAAACT</u>

<u>ATTTAAAGCCTCAATTTCTGCGATTGCCCTTGCTGTTGAAGCATTACTTGCATCTCATG</u>

<u>AACATTATGATGCCCGGATTCAACAAGTAAAAAATCATCCTGGTCAAAACGCGGTGGCA</u>

<u>AGTGCATTGCGTAATTTATTGGCAGGTTCAACGCAGGTTAATCTATTATCTGGGGTTAA</u>

<u>AGAACAAGCCAATAAAGCTTGTCGTCATCAAGAAATTACCCAACTAAATGATACCTTAC</u>

<u>AGGAAGTTTATTCAATTCGCTGTGCACCACAAGTATTAGGTATAGTGCCAGAATCTTTA</u>

<u>GCTACCGCTCGGAAAATATTGGAACGGGAAGTTATCTCAGCTAATGATAATCCATTGAT</u>

<u>AGATCCAGAAAATGGCGATGTTCTACACGGTGGAAATTTTATGGGGCAATATGTCGCCC</u>

<u>GAACAATGGATGCATTAAAACTGGATATTGCTTTAATTGCCAATCATCTTCACGCCATT</u>

<u>GTGGCTCTTATGATGGATAACCGTTTCTCTCGTGGATTACCTAATTCACTGAGTCCGAC</u>

<u>ACCCGGCATGTATCAAGGTTTTAAAGGCGTCCAACTTTCTCAAACCGCTTTAGTTGCTG</u>

<u>CAATTCGCCATGATTGTGCTGCATCAGGTATTCATACCCTCGCCACAGAACAATACAAT</u>

<u>CAAGATATTGTCAGTTTAGGTCTGCATGCCGCTCAAGATGTTTTAGAGATGGAGCAGAA</u>

<u>ATTACGCAATATTGTTTCAATGACAATTCTGGTAGTTTGTCAGGCCATTCATCTTCGCG</u>

TABLE 8-continued

Nucleotide sequences of Tet promoter-PAL3, high-copy construct
(SEQ ID NO: 25)

<u>GCAATATTAGTGAAATTGCGCCTGAAACTGCTAAATTTTACCATGCAGTACGCGAAATC</u>

<u>AGTTCTCCTTTGATCACTGATCGTGCGTTGGATGAAGATATAATCCGCATTGCGGATGC</u>

<u>AATTATTAATGATCAACTTCCTCTGCCAGAAATCATGCTGGAAGAATAA</u>GCTTGGCGTA

ATCATGGTCATAGCTGTTTCCTGTGTGAAATTGTTATCCGCTCACAATTCCACACAACA

TACGAGCCGGAAGCATAAAGTGTAAAGCCTGGGGTGCCTAATGAGTGAGCTAACTCACA

TTAATTGCGTTGCGCTCACTGCCCGCTTTCCAGTCGGGAAACCTGTCGTGCCAGCTGCA

TTAATGAATCGGCCAACGCGCGGGGAGAGGCGGTTTGCGTATTGGGCGCTCTTCCGCTT

CCTCGCTCACTGACTCGCTGCGCTCGGTCGTTCGGCTGCGGCGAGCGGTATCAGCTCAC

TCAAAGGCGGTAATACGGTTATCCACAGAATCAGGGGATAACGCAGGAAAGAACATGTG

AGCAAAAGGCCAGCAAAAGGCCAGGAACCGTAAAAAGGCCGCGTTGCTGGCGTTTTTCC

ATAGGCTCCGCCCCCCTGACGAGCATCACAAAAATCGACGCTCAAGTCAGAGGTGGCGA

AACCCGACAGGACTATAAAGATACCAGGCGTTTCCCCCTGGAAGCTCCCTCGTGCGCTC

TCCTGTTCCGACCCTGCCGCTTACCGGATACCTGTCCGCCTTTCTCCCTTCGGGAAGCG

TGGCGCTTTCTCATAGCTCACGCTGTAGGTATCTCAGTTCGGTGTAGGTCGTTCGCTCC

AAGCTGGGCTGTGTGCACGAACCCCCCGTTCAGCCCGACCGCTGCGCCTTATCCGGTAA

CTATCGTCTTGAGTCCAACCCGGTAAGACACGACTTATCGCCACTGGCAGCAGCCACTG

GTAACAGGATTAGCAGAGCGAGGTATGTAGGCGGTGCTACAGAGTTCTTGAAGTGGTGG

CCTAACTACGGCTACACTAGAAGAACAGTATTTGGTATCTGCGCTCTGCTGAAGCCAGT

TACCTTCGGAAAAAGAGTTGGTAGCTCTTGATCCGGCAAACAAACCACCGCTGGTAGCG

GTGGTTTTTTTGTTTGCAAGCAGCAGATTACGCGCAGAAAAAAAGGATCTCAAGAAGAT

CCTTTGATCTTTTCTACGGGGTCTGACGCTCAGTGGAACGAAAACTCACGTTAAGGGAT

TTTGGTCATGAGATTATCAAAAAGGATCTTCACCTAGATCCTTTTAAATTAAAAATGAA

GTTTTAAATCAATCTAAAGTATATATGAGTAAACTTGGTCTGACAGTTACCAATGCTTA

ATCAGTGAGGCACCTATCTCAGCGATCTGTCTATTTCGTTCATCCATAGTTGCCTGACT

CCCCGTCGTGTAGATAACTACGATACGGGAGGGCTTACCATCTGGCCCCAGTGCTGCAA

TGATACCGCGAGACCCACGCTCACCGGCTCCAGATTTATCAGCAATAAACCAGCCAGCC

GGAAGGGCCGAGCGCAGAAGTGGTCCTGCAACTTTATCCGCCTCCATCCAGTCTATTAA

TTGTTGCCGGGAAGCTAGAGTAAGTAGTTCGCCAGTTAATAGTTTGCGCAACGTTGTTG

CCATTGCTACAGGCATCGTGGTGTCACGCTCGTCGTTTGGTATGGCTTCATTCAGCTCC

GGTTCCCAACGATCAAGGCGAGTTACATGATCCCCCATGTTGTGCAAAAAAGCGGTTAG

CTCCTTCGGTCCTCCGATCGTTGTCAGAAGTAAGTTGGCCGCAGTGTTATCACTCATGG

TTATGGCAGCACTGCATAATTCTCTTACTGTCATGCCATCCGTAAGATGCTTTTCTGTG

ACTGGTGAGTACTCAACCAAGTCATTCTGAGAATAGTGTATGCGGCGACCGAGTTGCTC

TTGCCCGGCGTCAATACGGGATAATACCGCGCCACATAGCAGAACTTTAAAAGTGCTCA

TCATTGGAAAACGTTCTTCGGGGCGAAAACTCTCAAGGATCTTACCGCTGTTGAGATCC

AGTTCGATGTAACCCACTCGTGCACCCAACTGATCTTCAGCATCTTTTACTTTCACCAG

CGTTTCTGGGTGAGCAAAAACAGGAAGGCAAAATGCCGCAAAAAAGGGAATAAGGGCGA

CACGGAAATGTTGAATACTCATACTCTTCCTTTTTCAATATTATTGAAGCATTTATCAG

TABLE 8-continued

Nucleotide sequences of Tet promoter-PAL3, high-copy construct (SEQ ID NO: 25)

GGTTATTGTCTCATGAGCGGATACATATTTGAATGTATTTAGAAAAATAAACAAATAGG

GGTTCCGCGCACATTTCCCCGAAAAGTGCCACCTGACGTCTAAGAAACCATTATTATCA

TGACATTAACCTATAAAAATAGGCGTATCACGAGGCCCTTTCGTCTCGCGCGTTTCGGT

GATGACGGTGAAAACCTCTGACACATGCAGCTCCCGGAGACGGTCACAGCTTGTCTGTA

AGCGGATGCCGGGAGCAGACAAGCCCGTCAGGGCGCGTCAGCGGGTGTTGGCGGGTGTC

GGGGCTGGCTTAACTATGCGGCATCAGAGCAGATTGTACTGAGAGTGCACCATATGCGG

TGTGAAATACCGCACAGATGCGTAAGGAGAAAATACCGCATCAGGCGCCATTCGCCATT

CAGGCTGCGCAACTGTTGGGAAGGGCGATCGGTGCGGGCCTCTTCGCTATTACGCCAGC

TGGCGAAAGGGGGATGTGCTGCAAGGCGATTAAGTTGGGTAACGCCAGGGTTTTCCCAG

TCACGACGTTGTAAAACGACGGCCAGTGAATTCGTTAAGACCCACTTTCACATTTAAGT

TGTTTTTCTAATCCGCATATGATCAATTCAAGGCCGAATAAGAAGGCTGGCTCTGCACC

TTGGTGATCAAATAATTCGATAGCTTGTCGTAATAATGGCGGCATACTATCAGTAGTAG

GTGTTTCCCTTTCTTCTTTAGCGACTTGATGCTCTTGATCTTCCAATACGCAACCTAAA

GTAAAATGCCCCACAGCGCTGAGTGCATATAATGCATTCTCTAGTGAAAAACCTTGTTG

GCATAAAAAGGCTAATTGATTTTCGAGAGTTTCATACTGTTTTTCTGTAGGCCGTGTAC

CTAAATGTACTTTTGCTCCATCGCGATGACTTAGTAAAGCACATCTAAAACTTTTAGCG

TTATTACGTAAAAAATCTTGCCAGCTTTCCCCTTCTAAAGGGCAAAAGTGAGTATGGTG

CCTATCTAACATCTCAATGGCTAAGGCGTCGAGCAAAGCCCGCTTATTTTTTACATGCC

AATACAATGTAGGCTGCTCTACACCTAGCTTCTGGGCGAGTTTACGGGTTGTTAAACCT

TCGATTCCGACCTCATTAAGCAGCTCTAATGCGCTGTTAATCACTTTACTTTTATCTAA

TCTAGACATCATTAATTCCTAATTTTTGTTGACACTCTATCATTGATAGAGTTATTTTA

CCACTCCCTATCAGTGATAGAGAAAAGTGAA

TABLE 9

Nucleotide sequences of FNR promoter-PAL1 construct, low-copy (SEQ ID NO: 26)

CTCTTGATCGTTATCAATTCCCACGCTGTTTCAGAGCGTTACCTTGCCCTTAAACATTA

GCAATGTCGATTTATCAGAGGGCCGACAGGCTCCCACAGGAGAAAACCGATGAAACAC

TATCACAGGCCCAATCTAAAACTTCTTCACAGCAATTCAGCTITACCGGGAACTCGTCT

GCGAATGTAATTATCGGCAATCAAAAGCTGACCATTAATGATGTAGCTCGCGTTGCCCG

GAATGGCACTTTGGTGTCACTGACGAACAATACCGACATTCTGCAAGGTATTCAAGCTA

GCTGCGATTATATCAATAACGCCGTTGAATCTGGCGAGCCAATCTACGGGGTAACAAGC

GGTTTTGGTGGGATGGCGAACGTTGCCATTAGCCGTGAACAGGCGAGCGAACTTCAGAC

CAACCTCGTTTGGTTCCTAAAGACAGGAGCTGGTAATAAGTTACCTCTGGCTGACGTAA

GAGCCGCGATGCTGCTTCGCGCTAATAGTCACATGCGCGGCGCCAGTGGTATCCGTCTT

GAGCTTATCAAGAGGATGGAAATCTTCCTCAACGCGGGTGTCACACCATATGTTTATGA

GTTTGGTAGTATCGGAGCCAGTGGTGATCTTGTTCCCCTGAGTTATATTACGGGTTCAT

TGATTGGTTTAGACCCGTCCTTTAAAGTGGATTTTAACGGGAAAGAAATGGACGCCCCG

ACCGCTTTACGACAGCTTAATCTGAGCCCACTTACTTTGCTCCCTAAAGAAGGTCTTGC

TABLE 9-continued

Nucleotide sequences of FNR promoter-PAL1 construct, low-copy
(SEQ ID NO: 26)

CATGATGAATGGCACCTCTGTGATGACTGGAATTGCCGCGAATTGTGTGTATGACACGC

AGATCCTAACGGCCATTGCCATGGGTGTTCACGCGTTGGACATTCAAGCCCTGAATGGT

ACAAACCAGTCGTTTCATCCGTTTATCCATAATTCAAAACCCCATCCGGGACAGCTTTG

GGCTGCTGATCAGATGATCTCACTCCTGGCCAATAGTCAACTGGTTCGGGACGAGCTCG

ACGGCAAACATGATTATCGCGATCATGAGCTCATCCAGGACCGGTATTCACTTCGTTGT

CTCCCACAATACCTGGGGCCTATCGTTGATGGTATATCTCAAATTGCGAAGCAAATTGA

AATTGAGATCAATAGCGTAACCGACAACCCGCTTATCGATGTTGATAATCAGGCCTCTT

ATCACGGTGGCAATTTTCTGGGCCAGTATGTTGGTATGGGGATGGATCACCTGCGGTAC

TATATTGGGCTTCTGGCTAAACATCTTGATGTGCAGATTGCCTTATTAGCTTCACCAGA

ATTTTCAAATGGACTGCCGCCATCATTGCTCGGTAACAGAGAAAGGAAAGTAAATATGG

GCCTTAAGGGCCTTCAGATATGTGGTAACTCAATCATGCCCCTCCTGACCTTTTATGGG

AACTCAATTGCTGATCGTTTTCCGACACATGCTGAACAGTTTAACCAAAACATTAACTC

ACAGGGCTATACATCCGCGACGTTAGCGCGTCGGTCCGTGGATATCTTCCAGAATTATG

TTGCTATCGCTCTGATGTTCGGCGTACAGGCCGTTGATTTGCGCACTTATAAAAAAACC

GGTCACTACGATGCTCGGGCTTGCCTGTCGCCTGCCACCGAGCGGCTTTATAGCGCCGT

ACGTCATGTTGTGGGTCAGAAACCGACGTCGGACCGCCCCTATATTTGGAATGATAATG

AACAAGGGCTGGATGAACACATCGCCCGGATATCTGCCGATATTGCCGCCGGAGGTGTC

ATCGTCCAGGCGGTACAAGACATACTTCCTTGCCTGCATTAAGCTTGGCGTAATCATGG

TCATAGCTGTTTCCTGTGTGAAATTGTTATCCGCTCACAATTCCACACAACATACGAGC

CGGAAGCATAAAGTGTAAAGCCTGGGGTGCCTAATGAGTGAGCTAACTCACATTAATTG

CGTTGCGCTCACTGCCCGCTTTCCAGTCGGGAAACCTGTCGTGCCAGCTGCATTAATGA

ATCGGCCAACGCGCGGGGAGAGGCGGTTTGCGTATTGGGCGCTCTTCCGCTTCCTCGCT

CACTGACTCGCTGCGCTCGGTCGTTCGGCTGCGGCGAGCGGTATCAGCTCACTCAAAGG

CGGTAGTACGGGTTTTGCTGCCCGCAAACGGGCTGTTCTGGTGTTGCTAGTTTGTTATC

AGAATCGCAGATCCGGCTTCAGGTTTGCCGGCTGAAAGCGCTATTTCTTCCAGAATTGC

CATGATTTTTTCCCCACGGGAGGCGTCACTGGCTCCCGTGTTGTCGGCAGCTTTGATTC

GATAAGCAGCATCGCCTGTTTCAGGCTGTCTATGTGTGACTGTTGAGCTGTAACAAGTT

GTCTCAGGTGTTCAATTTCATGTTCTAGTTGCTTTGTTTTACTGGTTTCACCTGTTCTA

TTAGGTGTTACATGCTGTTCATCTGTTACATTGTCGATCTGTTCATGGTGAACAGCTTT

AAATGCACCAAAAACTCGTAAAAGCTCTGATGTATCTATCTTTTTTACACCGTTTTCAT

CTGTGCATATGGACAGTTTTCCCTTTGATATCTAACGGTGAACAGTTGTTCTACTTTTG

TTTGTTAGTCTTGATGCTTCACTGATAGATACAAGAGCCATAAGAACCTCAGATCCTTC

CGTATTTAGCCAGTATGTTCTCTAGTGTGGTTCGTTGTTTTTGCGTGAGCCATGAGAAC

GAACCATTGAGATCATGCTTACTTTGCATGTCACTCAAAAATTTTGCCTCAAAACTGGT

GAGCTGAATTTTTGCAGTTAAAGCATCGTGTAGTGTTTTTCTTAGTCCGTTACGTAGGT

AGGAATCTGATGTAATGGTTGTTGGTATTTTGTCACCATTCATTTTTATCTGGTTGTTC

TCAAGTTCGGTTACGAGATCCATTTGTCTATCTAGTTCAACTTGGAAAATCAACGTATC

AGTCGGGCGGCCTCGCTTATCAACCACCAATTTCATATTGCTGTAAGTGTTTAAATCTT

TABLE 9-continued

Nucleotide sequences of FNR promoter-PAL1 construct, low-copy
(SEQ ID NO: 26)

TACTTATTGGTTTCAAAACCCATTGGTTAAGCCTTTTAAACTCATGGTAGTTATTTTCA

AGCATTAACATGAACTTAAATTCATCAAGGCTAATCTCTATATTTGCCTTGTGAGTTTT

CTTTTGTGTTAGTTCTTTTAATAACCACTCATAAATCCTCATAGAGTATTTGTTTTCAA

AAGACTTAACATGTTCCAGATTATATTTTATGAATTTTTTTAACTGGAAAAGATAAGGC

AATATCTCTTCACTAAAAACTAATTCTAATTTTTCGCTTGAGAACTTGGCATAGTTTGT

CCACTGGAAAATCTCAAAGCCTTTAACCAAAGGATTCCTGATTTCCACAGTTCTCGTCA

TCAGCTCTCTGGTTGCTTTAGCTAATACACCATAAGCATTTTCCCTACTGATGTTCATC

ATCTGAGCGTATTGGTTATAAGTGAACGATACCGTCCGTTCTTTCCTTGTAGGGTTTTC

AATCGTGGGGTTGAGTAGTGCCACACAGCATAAAATTAGCTTGGTTTCATGCTCCGTTA

AGTCATAGCGACTAATCGCTAGTTCATTTGCTTTGAAAACAACTAATTCAGACATACAT

CTCAATTGGTCTAGGTGATTTTAATCACTATACCAATTGAGATGGGCTAGTCAATGATA

ATTACTAGTCCTTTTCCTTTGAGTTGTGGGTATCTGTAAATTCTGCTAGACCTTTGCTG

GAAAACTTGTAAATTCTGCTAGACCCTCTGTAAATTCCGCTAGACCTTTGTGTGTTTTT

TTTGTTTATATTCAAGTGGTTATAATTTATAGAATAAAGAAAGAATAAAAAAAGATAAA

AAGAATAGATCCCAGCCCTGTGTATAACTCACTACTTTAGTCAGTTCCGCAGTATTACA

AAAGGATGTCGCAAACGCTGTTTGCTCCTCTACAAAACAGACCTTAAAACCCTAAAGGC

TTAAGTAGCACCCTCGCAAGCTCGGGCAAATCGCTGAATATTCCTTTTGTCTCCGACCA

TCAGGCACCTGAGTCGCTGTCTTTTTCGTGACATTCAGTTCGCTGCGCTCACGGCTCTG

GCAGTGAATGGGGGTAAATGGCACTACAGGCGCCTTTTATGGATTCATGCAAGGAAACT

ACCCATAATACAAGAAAAGCCCGTCACGGGCTTCTCAGGGCGTTTTATGGCGGGTCTGC

TATGTGGTGCTATCTGACTTTTTGCTGTTCAGCAGTTCCTGCCCTCTGATTTTCCAGTC

TGACCACTTCGGATTATCCCGTGACAGGTCATTCAGACTGGCTAATGCACCCAGTAAGG

CAGCGGTATCATCAACAGGCTTACCCGTCTTACTGTCTTTTCTACGGGGTCTGACGCTC

AGTGGAACGAAAACTCACGTTAAGGGATTTTGGTCATGAGATTATCAAAAAGGATCTTC

ACCTAGATCCTTTTAAATTAAAAATGAAGTTTTAAATCAATCTAAAGTATATATGAGTA

AACTTGGTCTGACAGTTACCAATGCTTAATCAGTGAGGCACCTATCTCAGCGATCTGTC

TATTTCGTTCATCCATAGTTGCCTGACTCCCCGTCGTGTAGATAACTACGATACGGGAG

GGCTTACCATCTGGCCCCAGTGCTGCAATGATACCGCGAGACCCACGCTCACCGGCTCC

AGATTTATCAGCAATAAACCAGCCAGCCGGAAGGGCCGAGCGCAGAAGTGGTCCTGCAA

CTTTATCCGCCTCCATCCAGTCTATTAATTGTTGCCGGGAAGCTAGAGTAAGTAGTTCG

CCAGTTAATAGTTTGCGCAACGTTGTTGCCATTGCTACAGGCATCGTGGTGTCACGCTC

GTCGTTTGGTATGGCTTCATTCAGCTCCGGTTCCCAACGATCAAGGCGAGTTACATGAT

CCCCCATGTTGTGCAAAAAAGCGGTTAGCTCCTTCGGTCCTCCGATCGTTGTCAGAAGT

AAGTTGGCCGCAGTGTTATCACTCATGGTTATGGCAGCACTGCATAATTCTCTTACTGT

CATGCCATCCGTAAGATGCTTTTCTGTGACTGGTGAGTACTCAACCAAGTCATTCTGAG

AATAGTGTATGCGGCGACCGAGTTGCTCTTGCCCGGCGTCAATACGGGATAATACCGCG

CCACATAGCAGAACTTTAAAAGTGCTCATCATTGGAAAACGTTCTTCGGGGCGAAAACT

CTCAAGGATCTTACCGCTGTTGAGATCCAGTTCGATGTAACCCACTCGTGCACCCAACT

GATCTTCAGCATCTTTTACTTTCACCAGCGTTTCTGGGTGAGCAAAAACAGGAAGGCAA

TABLE 9-continued

Nucleotide sequences of FNR promoter-PAL1 construct, low-copy
(SEQ ID NO: 26)

AATGCCGCAAAAAGGGAATAAGGGCGACACGGAAATGTTGAATACTCATACTCTTCCT

TTTTCAATATTATTGAAGCATTTATCAGGGTTATTGTCTCATGAGCGGATACATATTTG

AATGTATTTAGAAAAATAAACAAATAGGGGTTCCGCGCACATTTCCCCGAAAAGTGCCA

CCTGACGTCTAAGAAACCATTATTATCATGACATTAACCTATAAAAATAGGCGTATCAC

GAGGCCCTTTCGTCTCGCGCGTTTCGGTGATGACGGTGAAAACCTCTGACACATGCAGC

TCCCGGAGACGGTCACAGCTTGTCTGTAAGCGGATGCCGGGAGCAGACAAGCCCGTCAG

GGCGCGTCAGCGGGTGTTGGCGGGTGTCGGGGCTGGCTTAACTATGCGGCATCAGAGCA

GATTGTACTGAGAGTGCACCATATGCGGTGTGAAATACCGCACAGATGCGTAAGGAGAA

AATACCGCATCAGGCGCCATTCGCCATTCAGGCTGCGCAACTGTTGGGAAGGGCGATCG

GTGCGGGCCTCTTCGCTATTACGCCAGCTGGCGAAAGGGGGATGTGCTGCAAGGCGATT

AAGTTGGGTAACGCCAGGGTTTTCCCAGTCACGACGTTGTAAAACGACGGCCAGTGAAT

TCG

TABLE 10

Nucleotide sequences of FNR promoter-PAL3 construct, low-copy
(SEQ ID NO: 27)

CTCTTGATCGTTATCAATTCCCACGCTGTTTCAGAGCGTTACCTTGCCCTTAAACATTA

GCAATGTCGATTTATCAGAGGGCCGACAGGCTCCCACAGGAGAAAACCGATGAAAGCTA

AAGATGTTCAGCCAACCATTATTATTAATAAAAATGGCCTTATCTCTTTGGAAGATATC

TATGACATTGCGATAAAACAAAAAAAGTAGAAATATCAACGGAGATCACTGAACTTTT

GACGCATGGTCGTGAAAAATTAGAGGAAAAATTAAATTCAGGAGAGGTTATATATGGAA

TCAATACAGGATTTGGAGGGAATGCCAATTTAGTTGTGCCATTTGAGAAAATCGCAGAG

CATCAGCAAAATCTGTTAACTTTTCTTTCTGCTGGTACTGGGGACTATATGTCCAAACC

TTGTATTAAAGCGTCACAATTTACTATGTTACTTTCTGTTTGCAAAGGTTGGTCTGCAA

CCAGACCAATTGTCGCTCAAGCAATTGTTGATCATATTAATCATGACATTGTTCCTCTG

GTTCCTCGCTATGGCTCAGTGGGTGCAAGCGGTGATTTAATTCCTTTATCTTATATTGC

ACGAGCATTATGTGGTATCGGCAAAGTTTATTATATGGGCGCAGAAATTGACGCTGCTG

AAGCAATTAAACGTGCAGGGTTGACACCATTATCGTTAAAAGCCAAAGAAGGTCTTGCT

CTGATTAACGGCACCCGGGTAATGTCAGGAATCAGTGCAATCACCGTCATTAAACTGGA

AAAACTATTTAAAGCCTCAATTTCTGCGATTGCCCTTGCTGTTGAAGCATTACTTGCAT

CTCATGAACATTATGATGCCCGGATTCAACAAGTAAAAAATCATCCTGGTCAAAACGCG

GTGGCAAGTGCATTGCGTAATTTATTGGCAGGTTCAACGCAGGTTAATCTATTATCTGG

GGTTAAAGAACAAGCCAATAAAGCTTGTCGTCATCAAGAAATTACCCAACTAAATGATA

CCTTACAGGAAGTTTATTCAATTCGCTGTGCACCACAAGTATTAGGTATAGTGCCAGAA

TCTTTAGCTACCGCTCGGAAAATATTGGAACGGGAAGTTATCTCAGCTAATGATAATCC

ATTGATAGATCCAGAAAATGGCGATGTTCTACACGGTGGAAATTTTATGGGGCAATATG

TCGCCCGAACAATGGATGCATTAAAACTGGATATTGCTTTAATTGCCAATCATCTTCAC

GCCATTGTGGCTCTTATGATGGATAACCGTTTCTCTCGTGGATTACCTAATTCACTGAG

TABLE 10-continued

Nucleotide sequences of FNR promoter-PAL3 construct, low-copy
(SEQ ID NO: 27)

<u>TCCGACACCCGGCATGTATCAAGGTTTTAAAGGCGTCCAACTTTCTCAAACCGCTTTAG</u>

<u>TTGCTGCAATTCGCCATGATTGTGCTGCATCAGGTATTCATACCCTCGCCACAGAACAA</u>

<u>TACAATCAAGATATTGTCAGTTTAGGTCTGCATGCCGCTCAAGATGTTTTAGAGATGGA</u>

<u>GCAGAAATTACGCAATATTGTTTCAATGACAATTCTGGTAGTTTGTCAGGCCATTCATC</u>

<u>TTCGCGGCAATATTAGTGAAATTGCGCCTGAAACTGCTAAATTTTACCATGCAGTACGC</u>

<u>GAAATCAGTTCTCCTTTGATCACTGATCGTGCGTTGGATGAAGATATAATCCGCATTGC</u>

<u>GGATGCAATTATTAATGATCAACTTCCTCTGCCAGAAATCATGCTGGAAGAATAA</u>GCTT

GGCGTAATCATGGTCATAGCTGTTTCCTGTGTGAAATTGTTATCCGCTCACAATTCCAC

ACAACATACGAGCCGGAAGCATAAAGTGTAAAGCCTGGGGTGCCTAATGAGTGAGCTAA

CTCACATTAATTGCGTTGCGCTCACTGCCCGCTTTCCAGTCGGGAAACCTGTCGTGCCA

GCTGCATTAATGAATCGGCCAACGCGCGGGGAGAGGCGGTTTGCGTATTGGGCGCTCTT

CCGCTTCCTCGCTCACTGACTCGCTGCGCTCGGTCGTTCGGCTGCGGCGAGCGGTATCA

GCTCACTCAAAGGCGGTAGTACGGGTTTTGCTGCCCGCAAACGGGCTGTTCTGGTGTTG

CTAGTTTGTTATCAGAATCGCAGATCCGGCTTCAGGTTTGCCGGCTGAAAGCGCTATTT

CTTCCAGAATTGCCATGATTTTTTCCCCACGGGAGGCGTCACTGGCTCCCGTGTTGTCG

GCAGCTTTGATTCGATAAGCAGCATCGCCTGTTTCAGGCTGTCTATGTGTGACTGTTGA

GCTGTAACAAGTTGTCTCAGGTGTTCAATTTCATGTTCTAGTTGCTTTGTTTTACTGGT

TTCACCTGTTCTATTAGGTGTTACATGCTGTTCATCTGTTACATTGTCGATCTGTTCAT

GGTGAACAGCTTTAAATGCACCAAAAACTCGTAAAAGCTCTGATGTATCTATCTTTTTT

ACACCGTTTTCATCTGTGCATATGGACAGTTTTCCCTTTGATATCTAACGGTGAACAGT

TGTTCTACTTTTGTTTGTTAGTCTTGATGCTTCACTGATAGATACAAGAGCCATAAGAA

CCTCAGATCCTTCCGTATTTAGCCAGTATGTTCTCTAGTGTGGTTCGTTGTTTTTGCGT

GAGCCATGAGAACGAACCATTGAGATCATGCTTACTTTGCATGTCACTCAAAAATTTTG

CCTCAAAACTGGTGAGCTGAATTTTTGCAGTTAAAGCATCGTGTAGTGTTTTTCTTAGT

CCGTTACGTAGGTAGGAATCTGATGTAATGGTTGTTGGTATTTTGTCACCATTCATTTT

TATCTGGTTGTTCTCAAGTTCGGTTACGAGATCCATTTGTCTATCTAGTTCAACTTGGA

AAATCAACGTATCAGTCGGGCGGCCTCGCTTATCAACCACCAATTTCATATTGCTGTAA

GTGTTTAAATCTTTACTTATTGGTTTCAAAACCCATTGGTTAAGCCTTTTAAACTCATG

GTAGTTATTTTCAAGCATTAACATGAACTTAAATTCATCAAGGCTAATCTCTATATTTG

CCTTGTGAGTTTTCTTTTGTGTTAGTTCTTTTAATAACCACTCATAAATCCTCATAGAG

TATTTGTTTTCAAAAGACTTAACATGTTCCAGATTATATTTTATGAATTTTTTTAACTG

GAAAAGATAAGGCAATATCTCTTCACTAAAAACTAATTCTAATTTTTCGCTTGAGAACT

TGGCATAGTTTGTCCACTGGAAAATCTCAAAGCCTTTAACCAAAGGATTCCTGATTTCC

ACAGTTCTCGTCATCAGCTCTCTGGTTGCTTTAGCTAATACACCATAAGCATTTTCCCT

ACTGATGTTCATCATCTGAGCGTATTGGTTATAAGTGAACGATACCGTCCGTTCTTTCC

TTGTAGGGTTTTCAATCGTGGGGTTGAGTAGTGCCACACAGCATAAAATTAGCTTGGTT

TCATGCTCCGTTAAGTCATAGCGACTAATCGCTAGTTCATTTGCTTTGAAAACAACTAA

TTCAGACATACATCTCAATTGGTCTAGGTGATTTTAATCACTATACCAATTGAGATGGG

CTAGTCAATGATAATTACTAGTCCTTTTCCTTTGAGTTGTGGGTATCTGTAAATTCTGC

TABLE 10-continued

Nucleotide sequences of FNR promoter-PAL3 construct, low-copy
(SEQ ID NO: 27)

```
TAGACCTTTGCTGGAAAACTTGTAAATTCTGCTAGACCCTCTGTAAATTCCGCTAGACC

TTTGTGTGTTTTTTTTGTTTATATTCAAGTGGTTATAATTTATAGAATAAAGAAAGAAT

AAAAAAAGATAAAAAGAATAGATCCCAGCCCTGTGTATAACTCACTACTTTAGTCAGTT

CCGCAGTATTACAAAAGGATGTCGCAAACGCTGTTTGCTCCTCTACAAAACAGACCTTA

AAACCCTAAAGGCTTAAGTAGCACCCTCGCAAGCTCGGGCAAATCGCTGAATATTCCTT

TTGTCTCCGACCATCAGGCACCTGAGTCGCTGTCTTTTTCGTGACATTCAGTTCGCTGC

GCTCACGGCTCTGGCAGTGAATGGGGGTAAATGGCACTACAGGCGCCTTTTATGGATTC

ATGCAAGGAAACTACCCATAATACAAGAAAAGCCCGTCACGGGCTTCTCAGGGCGTTTT

ATGGCGGGTCTGCTATGTGGTGCTATCTGACTTTTTGCTGTTCAGCAGTTCCTGCCCTC

TGATTTTCCAGTCTGACCACTTCGGATTATCCCGTGACAGGTCATTCAGACTGGCTAAT

GCACCCAGTAAGGCAGCGGTATCATCAACAGGCTTACCCGTCTTACTGTCTTTTCTACG

GGGTCTGACGCTCAGTGGAACGAAAACTCACGTTAAGGGATTTTGGTCATGAGATTATC

AAAAAGGATCTTCACCTAGATCCTTTTAAATTAAAAATGAAGTTTTAAATCAATCTAAA

GTATATATGAGTAAACTTGGTCTGACAGTTACCAATGCTTAATCAGTGAGGCACCTATC

TCAGCGATCTGTCTATTTCGTTCATCCATAGTTGCCTGACTCCCCGTCGTGTAGATAAC

TACGATACGGGAGGGCTTACCATCTGGCCCCAGTGCTGCAATGATACCGCGAGACCCAC

GCTCACCGGCTCCAGATTTATCAGCAATAAACCAGCCAGCCGGAAGGGCCGAGCGCAGA

AGTGGTCCTGCAACTTTATCCGCCTCCATCCAGTCTATTAATTGTTGCCGGGAAGCTAG

AGTAAGTAGTTCGCCAGTTAATAGTTTGCGCAACGTTGTTGCCATTGCTACAGGCATCG

TGGTGTCACGCTCGTCGTTTGGTATGGCTTCATTCAGCTCCGGTTCCCAACGATCAAGG

CGAGTTACATGATCCCCCATGTTGTGCAAAAAAGCGGTTAGCTCCTTCGGTCCTCCGAT

CGTTGTCAGAAGTAAGTTGGCCGCAGTGTTATCACTCATGGTTATGGCAGCACTGCATA

ATTCTCTTACTGTCATGCCATCCGTAAGATGCTTTTCTGTGACTGGTGAGTACTCAACC

AAGTCATTCTGAGAATAGTGTATGCGGCGACCGAGTTGCTCTTGCCCGGCGTCAATACG

GGATAATACCGCGCCACATAGCAGAACTTTAAAAGTGCTCATCATTGGAAAACGTTCTT

CGGGGCGAAAACTCTCAAGGATCTTACCGCTGTTGAGATCCAGTTCGATGTAACCCACT

CGTGCACCCAACTGATCTTCAGCATCTTTTACTTTCACCAGCGTTTCTGGGTGAGCAAA

AACAGGAAGGCAAAATGCCGCAAAAAAGGGAATAAGGGCGACACGGAAATGTTGAATAC

TCATACTCTTCCTTTTTCAATATTATTGAAGCATTTATCAGGGTTATTGTCTCATGAGC

GGATACATATTTGAATGTATTTAGAAAAATAAACAAATAGGGGTTCCGCGCACATTTCC

CCGAAAAGTGCCACCTGACGTCTAAGAAACCATTATTATCATGACATTAACCTATAAAA

ATAGGCGTATCACGAGGCCCTTTCGTCTCGCGCGTTTCGGTGATGACGGTGAAAACCTC

TGACACATGCAGCTCCCGGAGACGGTCACAGCTTGTCTGTAAGCGGATGCCGGGAGCAG

ACAAGCCCGTCAGGGCGCGTCAGCGGGTGTTGGCGGGTGTCGGGGCTGGCTTAACTATG

CGGCATCAGAGCAGATTGTACTGAGAGTGCACCATATGCGGTGTGAAATACCGCACAGA

TGCGTAAGGAGAAAATACCGCATCAGGCGCCATTCGCCATTCAGGCTGCGCAACTGTTG

GGAAGGGCGATCGGTGCGGGCCTCTTCGCTATTACGCCAGCTGGCGAAAGGGGGATGTG
```

TABLE 10-continued

Nucleotide sequences of FNR promoter-PAL3 construct, low-copy (SEQ ID NO: 27)

CTGCAAGGCGATTAAGTTGGGTAACGCCAGGGTTTTCCCAGTCACGACGTTGTAAAACG

ACGGCCAGTGAATTCG

TABLE 11

Nucleotide sequences of Tet promoter-PAL1 construct, low-copy (SEQ ID NO: 28)

ACCACTCCCTATCAGTGATAGAGAAAAGTGAACTCTAGAAATAATTTTGTTTAACTTTA

AGAAGGAGATATACAT<u>ATGAAAACACTATCACAGGCCCAATCTAAAACTTCTTCACAGC</u>

<u>AATTCAGCTTTACCGGGAACTCGTCTGCGAATGTAATTATCGGCAATCAAAAGCTGACC</u>

<u>ATTAATGATGTAGCTCGCGTTGCCCGGAATGGCACTTTGGTGTCACTGACGAACAATAC</u>

<u>CGACATTCTGCAAGGTATTCAAGCTAGCTGCGATTATATCAATAACGCCGTTGAATCTG</u>

<u>GCGAGCCAATCTACGGGGTAACAAGCGGTTTTGGTGGGATGGCGAACGTTGCCATTAGC</u>

<u>CGTGAACAGGCGAGCGAACTTCAGACCAACCTCGTTTGGTTCCTAAAGACAGGAGCTGG</u>

<u>TAATAAGTTACCTCTGGCTGACGTAAGAGCCGCGATGCTGCTTCGCGCTAATAGTCACA</u>

<u>TGCGCGGCGCCAGTGGTATCCGTCTTGAGCTTATCAAGAGGATGGAAATCTTCCTCAAC</u>

<u>GCGGGTGTCACACCATATGTTTATGAGTTTGGTAGTATCGGAGCCAGTGGTGATCTTGT</u>

<u>TCCCCTGAGTTATATTACGGGTTCATTGATTGGTTTAGACCCGTCCTTTAAAGTGGATT</u>

<u>TTAACGGGAAAGAAATGGACGCCCCGACCGCTTTACGACAGCTTAATCTGAGCCCACTT</u>

<u>ACTTTGCTCCCTAAAGAAGGTCTTGCCATGATGAATGGCACCTCTGTGATGACTGGAAT</u>

<u>TGCCGCGAATTGTGTGTATGACACGCAGATCCTAACGGCCATTGCCATGGGTGTTCACG</u>

<u>CGTTGGACATTCAAGCCCTGAATGGTACAAACCAGTCGTTTCATCCGTTTATCCATAAT</u>

<u>TCAAAACCCCATCCGGGACAGCTTTGGGCTGCTGATCAGATGATCTCACTCCTGGCCAA</u>

<u>TAGTCAACTGGTTCGGGACGAGCTCGACGGCAAACATGATTATCGCGATCATGAGCTCA</u>

<u>TCCAGGACCGGTATTCACTTCGTTGTCTCCCACAATACCTGGGGCCTATCGTTGATGGT</u>

<u>ATATCTCAAATTGCGAAGCAAATTGAAATTGAGATCAATAGCGTAACCGACAACCCGCT</u>

<u>TATCGATGTTGATAATCAGGCCTCTTATCACGGTGGCAATTTTCTGGGCCAGTATGTTG</u>

<u>GTATGGGGATGGATCACCTGCGGTACTATATTGGGCTTCTGGCTAAACATCTTGATGTG</u>

<u>CAGATTGCCTTATTAGCTTCACCAGAATTTTCAAATGGACTGCCGCCATCATTGCTCGG</u>

<u>TAACAGAGAAAGGAAAGTAAATATGGGCCTTAAGGGCCTTCAGATATGTGGTAACTCAA</u>

<u>TCATGCCCCTCCTGACCTTTTATGGGAACTCAATTGCTGATCGTTTTCCGACACATGCT</u>

<u>GAACAGTTTAACCAAAACATTAACTCACAGGGCTATACATCCGCGACGTTAGCGCGTCG</u>

<u>GTCCGTGGATATCTTCCAGAATTATGTTGCTATCGCTCTGATGTTCGGCGTACAGGCCG</u>

<u>TTGATTTGCGCACTTATAAAAAAACCGGTCACTACGATGCTCGGGCTTGCCTGTCGCCT</u>

<u>GCCACCGAGCGGCTTTATAGCGCCGTACGTCATGTTGTGGGTCAGAAACCGACGTCGGA</u>

<u>CCGCCCCTATATTTGGAATGATAATGAACAAGGGCTGGATGAACACATCGCCCGGATAT</u>

<u>CTGCCGATATTGCCGCCGGAGGTGTCATCGTCCAGGCGGTACAAGACATACTTCCTTGC</u>

<u>CTGCATTAA</u>GCTTGGCGTAATCATGGTCATAGCTGTTTCCTGTGTGAAATTGTTATCCG

CTCACAATTCCACACAACATACGAGCCGGAAGCATAAAGTGTAAAGCCTGGGGTGCCTA

TABLE 11-continued

Nucleotide sequences of Tet promoter-PAL1 construct, low-copy
(SEQ ID NO: 28)

```
ATGAGTGAGCTAACTCACATTAATTGCGTTGCGCTCACTGCCCGCTTTCCAGTCGGGAA
ACCTGTCGTGCCAGCTGCATTAATGAATCGGCCAACGCGCGGGGAGAGGCGGTTTGCGT
ATTGGGCGCTCTTCCGCTTCCTCGCTCACTGACTCGCTGCGCTCGGTCGTTCGGCTGCG
GCGAGCGGTATCAGCTCACTCAAAGGCGGTAGTACGGGTTTTGCTGCCCGCAAACGGGC
TGTTCTGGTGTTGCTAGTTTGTTATCAGAATCGCAGATCCGGCTTCAGGTTTGCCGGCT
GAAAGCGCTATTTCTTCCAGAATTGCCATGATTTTTTCCCCACGGGAGGCGTCACTGGC
TCCCGTGTTGTCGGCAGCTTTGATTCGATAAGCAGCATCGCCTGTTTCAGGCTGTCTAT
GTGTGACTGTTGAGCTGTAACAAGTTGTCTCAGGTGTTCAATTTCATGTTCTAGTTGCT
TTGTTTTACTGGTTTCACCTGTTCTATTAGGTGTTACATGCTGTTCATCTGTTACATTG
TCGATCTGTTCATGGTGAACAGCTTTAAATGCACCAAAAACTCGTAAAAGCTCTGATGT
ATCTATCTTTTTACACCGTTTTCATCTGTGCATATGGACAGTTTTCCCTTTGATATCT
AACGGTGAACAGTTGTTCTACTTTTGTTTGTTAGTCTTGATGCTTCACTGATAGATACA
AGAGCCATAAGAACCTCAGATCCTTCCGTATTTAGCCAGTATGTTCTCTAGTGTGGTTC
GTTGTTTTGCGTGAGCCATGAGAACGAACCATTGAGATCATGCTTACTTTGCATGTCA
CTCAAAAATTTTGCCTCAAAACTGGTGAGCTGAATTTTTGCAGTTAAAGCATCGTGTAG
TGTTTTTCTTAGTCCGTTACGTAGGTAGGAATCTGATGTAATGGTTGTTGGTATTTTGT
CACCATTCATTTTTATCTGGTTGTTCTCAAGTTCGGTTACGAGATCCATTTGTCTATCT
AGTTCAACTTGGAAAATCAACGTATCAGTCGGGCGGCCTCGCTTATCAACCACCAATTT
CATATTGCTGTAAGTGTTTAAATCTTTACTTATTGGTTTCAAAACCCATTGGTTAAGCC
TTTTAAACTCATGGTAGTTATTTTCAAGCATTAACATGAACTTAAATTCATCAAGGCTA
ATCTCTATATTTGCCTTGTGAGTTTTCTTTTGTGTTAGTTCTTTTAATAACCACTCATA
AATCCTCATAGAGTATTTGTTTTCAAAAGACTTAACATGTTCCAGATTATATTTTATGA
ATTTTTTTAACTGGAAAAGATAAGGCAATATCTCTTCACTAAAAACTAATTCTAATTTT
TCGCTTGAGAACTTGGCATAGTTTGTCCACTGGAAAATCTCAAAGCCTTTAACCAAAGG
ATTCCTGATTTCCACAGTTCTCGTCATCAGCTCTCTGGTTGCTTTAGCTAATACACCAT
AAGCATTTCCCTACTGATGTTCATCATCTGAGCGTATTGGTTATAAGTGAACGATACC
GTCCGTTCTTTCCTTGTAGGGTTTTCAATCGTGGGGTTGAGTAGTGCCACACAGCATAA
AATTAGCTTGGTTTCATGCTCCGTTAAGTCATAGCGACTAATCGCTAGTTCATTTGCTT
TGAAAACAACTAATTCAGACATACATCTCAATTGGTCTAGGTGATTTTAATCACTATAC
CAATTGAGATGGGCTAGTCAATGATAATTACTAGTCCTTTTCCTTTGAGTTGTGGGTAT
CTGTAAATTCTGCTAGACCTTTGCTGGAAAACTTGTAAATTCTGCTAGACCCTCTGTAA
ATTCCGCTAGACCTTTGTGTGTTTTTTTGTTTATATTCAAGTGGTTATAATTTATAGA
ATAAAGAAAGAATAAAAAAAGATAAAAAGAATAGATCCCAGCCCTGTGTATAACTCACT
ACTTTAGTCAGTTCCGCAGTATTACAAAAGGATGTCGCAAACGCTGTTTGCTCCTCTAC
AAAACAGACCTTAAAACCCTAAAGGCTTAAGTAGCACCCTCGCAAGCTCGGGCAAATCG
CTGAATATTCCTTTTGTCTCCGACCATCAGGCACCTGAGTCGCTGTCTTTTTCGTGACA
TTCAGTTCGCTGCGCTCACGGCTCTGGCAGTGAATGGGGGTAAATGGCACTACAGGCGC
CTTTTATGGATTCATGCAAGGAAACTACCCATAATACAAGAAAAGCCCGTCACGGGCTT
CTCAGGGCGTTTTATGGCGGGTCTGCTATGTGGTGCTATCTGACTTTTTGCTGTTCAGC
```

TABLE 11-continued

Nucleotide sequences of Tet promoter-PAL1 construct, low-copy
(SEQ ID NO: 28)

```
AGTTCCTGCCCTCTGATTTTCCAGTCTGACCACTTCGGATTATCCCGTGACAGGTCATT

CAGACTGGCTAATGCACCCAGTAAGGCAGCGGTATCATCAACAGGCTTACCCGTCTTAC

TGTCTTTTCTACGGGGTCTGACGCTCAGTGGAACGAAAACTCACGTTAAGGGATTTTGG

TCATGAGATTATCAAAAAGGATCTTCACCTAGATCCTTTTAAATTAAAAATGAAGTTTT

AAATCAATCTAAAGTATATATGAGTAAACTTGGTCTGACAGTTACCAATGCTTAATCAG

TGAGGCACCTATCTCAGCGATCTGTCTATTTCGTTCATCCATAGTTGCCTGACTCCCCG

TCGTGTAGATAACTACGATACGGGAGGGCTTACCATCTGGCCCCAGTGCTGCAATGATA

CCGCGAGACCCACGCTCACCGGCTCCAGATTTATCAGCAATAAACCAGCCAGCCGGAAG

GGCCGAGCGCAGAAGTGGTCCTGCAACTTTATCCGCCTCCATCCAGTCTATTAATTGTT

GCCGGGAAGCTAGAGTAAGTAGTTCGCCAGTTAATAGTTTGCGCAACGTTGTTGCCATT

GCTACAGGCATCGTGGTGTCACGCTCGTCGTTTGGTATGGCTTCATTCAGCTCCGGTTC

CCAACGATCAAGGCGAGTTACATGATCCCCCATGTTGTGCAAAAAAGCGGTTAGCTCCT

TCGGTCCTCCGATCGTTGTCAGAAGTAAGTTGGCCGCAGTGTTATCACTCATGGTTATG

GCAGCACTGCATAATTCTCTTACTGTCATGCCATCCGTAAGATGCTTTTCTGTGACTGG

TGAGTACTCAACCAAGTCATTCTGAGAATAGTGTATGCGGCGACCGAGTTGCTCTTGCC

CGGCGTCAATACGGGATAATACCGCGCCACATAGCAGAACTTTAAAAGTGCTCATCATT

GGAAAACGTTCTTCGGGGCGAAAACTCTCAAGGATCTTACCGCTGTTGAGATCCAGTTC

GATGTAACCCACTCGTGCACCCAACTGATCTTCAGCATCTTTTACTTTCACCAGCGTTT

CTGGGTGAGCAAAAACAGGAAGGCAAAATGCCGCAAAAAAGGGAATAAGGGCGACACGG

AAATGTTGAATACTCATACTCTTCCTTTTTCAATATTATTGAAGCATTTATCAGGGTTA

TTGTCTCATGAGCGGATACATATTTGAATGTATTTAGAAAAATAAACAAATAGGGGTTC

CGCGCACATTTCCCCGAAAAGTGCCACCTGACGTCTAAGAAACCATTATTATCATGACA

TTAACCTATAAAAATAGGCGTATCACGAGGCCCTTTCGTCTCGCGCGTTTCGGTGATGA

CGGTGAAAACCTCTGACACATGCAGCTCCCGGAGACGGTCACAGCTTGTCTGTAAGCGG

ATGCCGGGAGCAGACAAGCCCGTCAGGGCGCGTCAGCGGGTGTTGGCGGGTGTCGGGGC

TGGCTTAACTATGCGGCATCAGAGCAGATTGTACTGAGAGTGCACCATATGCGGTGTGA

AATACCGCACAGATGCGTAAGGAGAAAATACCGCATCAGGCGCCATTCGCCATTCAGGC

TGCGCAACTGTTGGGAAGGGCGATCGGTGCGGGCCTCTTCGCTATTACGCCAGCTGGCG

AAAGGGGGATGTGCTGCAAGGCGATTAAGTTGGGTAACGCCAGGGTTTTCCCAGTCACG

ACGTTGTAAAACGACGGCCAGTGAATTCGTTAAGACCCACTTTCACATTTAAGTTGTTT

TTCTAATCCGCATATGATCAATTCAAGGCCGAATAAGAAGGCTGGCTCTGCACCTTGGT

GATCAAATAATTCGATAGCTTGTCGTAATAATGGCGGCATACTATCAGTAGTAGGTGTT

TCCCTTTCTTCTTTAGCGACTTGATGCTCTTGATCTTCCAATACGCAACCTAAAGTAAA

ATGCCCCACAGCGCTGAGTGCATATAATGCATTCTCTAGTGAAAAACCTTGTTGGCATA

AAAAGGCTAATTGATTTTCGAGAGTTTCATACTGTTTTTCTGTAGGCCGTGTACCTAAA

TGTACTTTTGCTCCATCGCGATGACTTAGTAAAGCACATCTAAAACTTTTAGCGTTATT

ACGTAAAAAATCTTGCCAGCTTTCCCCTTCTAAAGGGCAAAAGTGAGTATGGTGCCTAT

CTAACATCTCAATGGCTAAGGCGTCGAGCAAAGCCCGCTTATTTTTTACATGCCAATAC
```

TABLE 11-continued

Nucleotide sequences of Tet promoter-PAL1 construct, low-copy
(SEQ ID NO: 28)

AATGTAGGCTGCTCTACACCTAGCTTCTGGGCGAGTTTACGGGTTGTTAAACCTTCGAT

TCCGACCTCATTAAGCAGCTCTAATGCGCTGTTAATCACTTTACTTTTATCTAATCTAG

ACATCATTAATTCCTAATTTTTGTTGACACTCTATCATTGATAGAGTTATTTT

TABLE 12

Nucleotide sequences of Tet promoter-PAL3 construct, low-copy
(SEQ ID NO: 29)

ACCACTCCCTATCAGTGATAGAGAAAAGTGAACTCTAGAAATAATTTTGTTTAACTTTA

AGAAGGAGATATACAT<u>ATGAAAGCTAAAGATGTTCAGCCAACCATTATTATTAATAAAA</u>

<u>ATGGCCTTATCTCTTTGGAAGATATCTATGACATTGCGATAAAACAAAAAAAAGTAGAA</u>

<u>ATATCAACGGAGATCACTGAACTTTTGACGCATGGTCGTGAAAAATTAGAGGAAAAATT</u>

<u>AAATTCAGGAGAGGTTATATATGGAATCAATACAGGATTTGGAGGGAATGCCAATTTAG</u>

<u>TTGTGCCATTTGAGAAAATCGCAGAGCATCAGCAAAATCTGTTAACTTTTCTTTCTGCT</u>

<u>GGTACTGGGGACTATATGTCCAAACCTTGTATTAAAGCGTCACAATTTACTATGTTACT</u>

<u>TTCTGTTTGCAAAGGTTGGTCTGCAACCAGACCAATTGTCGCTCAAGCAATTGTTGATC</u>

<u>ATATTAATCATGACATTGTTCCTCTGGTTCCTCGCTATGGCTCAGTGGGTGCAAGCGGT</u>

<u>GATTTAATTCCTTTATCTTATATTGCACGAGCATTATGTGGTATCGGCAAAGTTTATTA</u>

<u>TATGGGCGCAGAAATTGACGCTGCTGAAGCAATTAAACGTGCAGGGTTGACACCATTAT</u>

<u>CGTTAAAAGCCAAAGAAGGTCTTGCTCTGATTAACGGCACCCGGGTAATGTCAGGAATC</u>

<u>AGTGCAATCACCGTCATTAAACTGGAAAAACTATTTAAAGCCTCAATTTCTGCGATTGC</u>

<u>CCTTGCTGTTGAAGCATTACTTGCATCTCATGAACATTATGATGCCCGGATTCAACAAG</u>

<u>TAAAAAATCATCCTGGTCAAAACGCGGTGGCAAGTGCATTGCGTAATTTATTGGCAGGT</u>

<u>TCAACGCAGGTTAATCTATTATCTGGGGTTAAAGAACAAGCCAATAAAGCTTGTCGTCA</u>

<u>TCAAGAAATTACCCAACTAAATGATACCTTACAGGAAGTTTATTCAATTCGCTGTGCAC</u>

<u>CACAAGTATTAGGTATAGTGCCAGAATCTTTAGCTACCGCTCGGAAAATATTGGAACGG</u>

<u>GAAGTTATCTCAGCTAATGATAATCCATTGATAGATCCAGAAAATGGCGATGTTCTACA</u>

<u>CGGTGGAAATTTTATGGGGCAATATGTCGCCCGAACAATGGATGCATTAAAACTGGATA</u>

<u>TTGCTTTAATTGCCAATCATCTTCACGCCATTGTGGCTCTTATGATGGATAACCGTTTC</u>

<u>TCTCGTGGATTACCTAATTCACTGAGTCCGACACCCGGCATGTATCAAGGTTTTAAAGG</u>

<u>CGTCCAACTTTCTCAAACCGCTTTAGTTGCTGCAATTCGCCATGATTGTGCTGCATCAG</u>

<u>GTATTCATACCCTCGCCACAGAACAATACAATCAAGATATTGTCAGTTTAGGTCTGCAT</u>

<u>GCCGCTCAAGATGTTTTAGAGATGGAGCAGAAATTACGCAATATTGTTTCAATGACAAT</u>

<u>TCTGGTAGTTTGTCAGGCCATTCATCTTCGCGGCAATATTAGTGAAATTGCGCCTGAAA</u>

<u>CTGCTAAATTTTACCATGCAGTACGCGAAATCAGTTCTCCTTTGATCACTGATCGTGCG</u>

<u>TTGGATGAAGATATAATCCGCATTGCGGATGCAATTATTAATGATCAACTTCCTCTGCC</u>

<u>AGAAATCATGCTGGAAGAATAAGCTTGGCGTAATCATGGTCATAGCTGTTTCCTGTGTG</u>

AAATTGTTATCCGCTCACAATTCCACACAACATACGAGCCGGAAGCATAAAGTGTAAAG

CCTGGGGTGCCTAATGAGTGAGCTAACTCACATTAATTGCGTTGCGCTCACTGCCCGCT

TTCCAGTCGGGAAACCTGTCGTGCCAGCTGCATTAATGAATCGGCCAACGCGCGGGGAG

TABLE 12-continued

Nucleotide sequences of Tet promoter-PAL3 construct, low-copy
(SEQ ID NO: 29)

```
AGGCGGTTTGCGTATTGGGCGCTCTTCCGCTTCCTCGCTCACTGACTCGCTGCGCTCGG

TCGTTCGGCTGCGGCGAGCGGTATCAGCTCACTCAAAGGCGGTAGTACGGGTTTTGCTG

CCCGCAAACGGGCTGTTCTGGTGTTGCTAGTTTGTTATCAGAATCGCAGATCCGGCTTC

AGGTTTGCCGGCTGAAAGCGCTATTTCTTCCAGAATTGCCATGATTTTTTCCCCACGGG

AGGCGTCACTGGCTCCCGTGTTGTCGGCAGCTTTGATTCGATAAGCAGCATCGCCTGTT

TCAGGCTGTCTATGTGTGACTGTTGAGCTGTAACAAGTTGTCTCAGGTGTTCAATTTCA

TGTTCTAGTTGCTTTGTTTTACTGGTTTCACCTGTTCTATTAGGTGTTACATGCTGTTC

ATCTGTTACATTGTCGATCTGTTCATGGTGAACAGCTTTAAATGCACCAAAAACTCGTA

AAAGCTCTGATGTATCTATCTTTTTTACACCGTTTTCATCTGTGCATATGGACAGTTTT

CCCTTTGATATCTAACGGTGAACAGTTGTTCTACTTTTGTTTGTTAGTCTTGATGCTTC

ACTGATAGATACAAGAGCCATAAGAACCTCAGATCCTTCCGTATTTAGCCAGTATGTTC

TCTAGTGTGGTTCGTTGTTTTTGCGTGAGCCATGAGAACGAACCATTGAGATCATGCTT

ACTTTGCATGTCACTCAAAAATTTTGCCTCAAAACTGGTGAGCTGAATTTTTGCAGTTA

AAGCATCGTGTAGTGTTTTTCTTAGTCCGTTACGTAGGTAGGAATCTGATGTAATGGTT

GTTGGTATTTTGTCACCATTCATTTTTATCTGGTTGTTCTCAAGTTCGGTTACGAGATC

CATTTGTCTATCTAGTTCAACTTGGAAAATCAACGTATCAGTCGGGCGGCCTCGCTTAT

CAACCACCAATTTCATATTGCTGTAAGTGTTTAAATCTTTACTTATTGGTTTCAAAACC

CATTGGTTAAGCCTTTTAAACTCATGGTAGTTATTTTCAAGCATTAACATGAACTTAAA

TTCATCAAGGCTAATCTCTATATTTGCCTTGTGAGTTTTCTTTTGTGTTAGTTCTTTTA

ATAACCACTCATAAATCCTCATAGAGTATTTGTTTTCAAAAGACTTAACATGTTCCAGA

TTATATTTTATGAATTTTTTTAACTGGAAAAGATAAGGCAATATCTCTTCACTAAAAAC

TAATTCTAATTTTTCGCTTGAGAACTTGGCATAGTTTGTCCACTGGAAAATCTCAAAGC

CTTTAACCAAAGGATTCCTGATTTCCACAGTTCTCGTCATCAGCTCTCTGGTTGCTTTA

GCTAATACACCATAAGCATTTTCCCTACTGATGTTCATCATCTGAGCGTATTGGTTATA

AGTGAACGATACCGTCCGTTCTTTCCTTGTAGGGTTTTCAATCGTGGGGTTGAGTAGTG

CCACACAGCATAAAATTAGCTTGGTTTCATGCTCCGTTAAGTCATAGCGACTAATCGCT

AGTTCATTTGCTTTGAAAACAACTAATTCAGACATACATCTCAATTGGTCTAGGTGATT

TTAATCACTATACCAATTGAGATGGGCTAGTCAATGATAATTACTAGTCCTTTTCCTTT

GAGTTGTGGGTATCTGTAAATTCTGCTAGACCTTTGCTGGAAAACTTGTAAATTCTGCT

AGACCCTCTGTAAATTCCGCTAGACCTTTGTGTGTTTTTTTGTTTATATTCAAGTGGT

TATAATTTATAGAATAAAGAAAGAATAAAAAAAGATAAAAAGAATAGATCCCAGCCCTG

TGTATAACTCACTACTTTAGTCAGTTCCGCAGTATTACAAAAGGATGTCGCAAACGCTG

TTTGCTCCTCTACAAAACAGACCTTAAAACCCTAAAGGCTTAAGTAGCACCCTCGCAAG

CTCGGGCAAATCGCTGAATATTCCTTTTGTCTCCGACCATCAGGCACCTGAGTCGCTGT

CTTTTTCGTGACATTCAGTTCGCTGCGCTCACGGCTCTGGCAGTGAATGGGGGTAAATG

GCACTACAGGCGCCTTTTATGGATTCATGCAAGGAAACTACCCATAATACAAGAAAAGC

CCGTCACGGGCTTCTCAGGGCGTTTTATGGCGGGTCTGCTATGTGGTGCTATCTGACTT

TTTGCTGTTCAGCAGTTCCTGCCCTCTGATTTTCCAGTCTGACCACTTCGGATTATCCC
```

TABLE 12-continued

Nucleotide sequences of Tet promoter-PAL3 construct, low-copy
(SEQ ID NO: 29)

```
GTGACAGGTCATTCAGACTGGCTAATGCACCCAGTAAGGCAGCGGTATCATCAACAGGC

TTACCCGTCTTACTGTCTTTTCTACGGGGTCTGACGCTCAGTGGAACGAAAACTCACGT

TAAGGGATTTTGGTCATGAGATTATCAAAAAGGATCTTCACCTAGATCCTTTTAAATTA

AAAATGAAGTTTTAAATCAATCTAAAGTATATATGAGTAAACTTGGTCTGACAGTTACC

AATGCTTAATCAGTGAGGCACCTATCTCAGCGATCTGTCTATTTCGTTCATCCATAGTT

GCCTGACTCCCCGTCGTGTAGATAACTACGATACGGGAGGGCTTACCATCTGGCCCCAG

TGCTGCAATGATACCGCGAGACCCACGCTCACCGGCTCCAGATTTATCAGCAATAAACC

AGCCAGCCGGAAGGGCCGAGCGCAGAAGTGGTCCTGCAACTTTATCCGCCTCCATCCAG

TCTATTAATTGTTGCCGGGAAGCTAGAGTAAGTAGTTCGCCAGTTAATAGTTTGCGCAA

CGTTGTTGCCATTGCTACAGGCATCGTGGTGTCACGCTCGTCGTTTGGTATGGCTTCAT

TCAGCTCCGGTTCCCAACGATCAAGGCGAGTTACATGATCCCCCATGTTGTGCAAAAAA

GCGGTTAGCTCCTTCGGTCCTCCGATCGTTGTCAGAAGTAAGTTGGCCGCAGTGTTATC

ACTCATGGTTATGGCAGCACTGCATAATTCTCTTACTGTCATGCCATCCGTAAGATGCT

TTTCTGTGACTGGTGAGTACTCAACCAAGTCATTCTGAGAATAGTGTATGCGGCGACCG

AGTTGCTCTTGCCCGGCGTCAATACGGGATAATACCGCGCCACATAGCAGAACTTTAAA

AGTGCTCATCATTGGAAAACGTTCTTCGGGGCGAAAACTCTCAAGGATCTTACCGCTGT

TGAGATCCAGTTCGATGTAACCCACTCGTGCACCCAACTGATCTTCAGCATCTTTTACT

TTCACCAGCGTTTCTGGGTGAGCAAAAACAGGAAGGCAAAATGCCGCAAAAAAGGGAAT

AAGGGCGACACGGAAATGTTGAATACTCATACTCTTCCTTTTTCAATATTATTGAAGCA

TTTATCAGGGTTATTGTCTCATGAGCGGATACATATTTGAATGTATTTAGAAAAATAAA

CAAATAGGGGTTCCGCGCACATTTCCCCGAAAAGTGCCACCTGACGTCTAAGAAACCAT

TATTATCATGACATTAACCTATAAAAATAGGCGTATCACGAGGCCCTTTCGTCTCGCGC

GTTTCGGTGATGACGGTGAAAACCTCTGACACATGCAGCTCCCGGAGACGGTCACAGCT

TGTCTGTAAGCGGATGCCGGGAGCAGACAAGCCCGTCAGGGCGCGTCAGCGGGTGTTGG

CGGGTGTCGGGGCTGGCTTAACTATGCGGCATCAGAGCAGATTGTACTGAGAGTGCACC

ATATGCGGTGTGAAATACCGCACAGATGCGTAAGGAGAAAATACCGCATCAGGCGCCAT

TCGCCATTCAGGCTGCGCAACTGTTGGGAAGGGCGATCGGTGCGGGCCTCTTCGCTATT

ACGCCAGCTGGCGAAAGGGGGATGTGCTGCAAGGCGATTAAGTTGGGTAACGCCAGGGT

TTTCCCAGTCACGACGTTGTAAAACGACGGCCAGTGAATTCGTTAAGACCCACTTTCAC

ATTTAAGTTGTTTTTCTAATCCGCATATGATCAATTCAAGGCCGAATAAGAAGGCTGGC

TCTGCACCTTGGTGATCAAATAATTCGATAGCTTGTCGTAATAATGGCGGCATACTATC

AGTAGTAGGTGTTTCCCTTTCTTCTTTAGCGACTTGATGCTCTTGATCTTCCAATACGC

AACCTAAAGTAAAATGCCCCACAGCGCTGAGTGCATATAATGCATTCTCTAGTGAAAAA

CCTTGTTGGCATAAAAAGGCTAATTGATTTTCGAGAGTTTCATACTGTTTTTCTGTAGG

CCGTGTACCTAAATGTACTTTTGCTCCATCGCGATGACTTAGTAAAGCACATCTAAAAC

TTTTAGCGTTATTACGTAAAAAATCTTGCCAGCTTTCCCCTTCTAAAGGGCAAAAGTGA

GTATGGTGCCTATCTAACATCTCAATGGCTAAGGCGTCGAGCAAAGCCCGCTTATTTTT

TACATGCCAATACAATGTAGGCTGCTCTACACCTAGCTTCTGGGCGAGTTTACGGGTTG

TTAAACCTTCGATTCCGACCTCATTAAGCAGCTCTAATGCGCTGTTAATCACTTTACTT
```

TABLE 12-continued

Nucleotide sequences of Tet promoter-PAL3 construct, low-copy (SEQ ID NO: 29)

TTATCTAATCTAGACATCATTAATTCCTAATTTTTGTTGACACTCTATCATTGATAGAG

TTATTTT

TABLE 13

Nucleotide sequences of TetR-PheP construct, low-copy (SEQ ID NO: 30)

ccagtgaattcg|ttaagacccactttcacatttaagttgttttg|

|taatccgcatatgatcaattcaaggccgaataagaaggctggctc|

|tgcaccttggtgatcaaataattcgatagcttgtcgtaataatgg|

|cggcatactatcagtagtaggtgtttcccttttcttctttagcgac|

|ttgatgctcttgatcttccaatacgcaacctaaagtaaaatgccc|

|cacagcgctgagtgcatataatgcattctctagtgaaaaaccttg|

|ttggcataaaaaggctaattgattttcgagagtttcatactgttt|

|ttctgtaggccgtgtacctaaatgtacttttgctccatcgcgatg|

|acttagtaaagcacatctaaaacttttagcgttattacgtaaaaa|

|atcttgccagctttccccttctaaagggcaaaagtgagtatggtg|

|cctatctaacatctcaatggctaaggcgtcgagcaaagcccgctt|

|atttttacatgccaatacaatgtaggctgctctacacctagctt|

|ctgggcgagtttacgggttgttaaaccttcgattccgacctcatt|

|aagcagctctaatgcgctgttaatcactttacttttatctaatct|

|agacat|cattaattcctaatttttgttgacactctatcattgata gagttatttaccactccctatcagtgatagagaaaagtgaactc tagaaataattttgtttaactttaagaaggagatatacatATGAA

AAACGCGTCAACCGTATCGGAAGATACTGCGTCGAATCAAGAGCC

GACGCTTCATCGCGGATTACATAACCGTCATATTCAACTGATTGC

GTTGGGTGGCGCAATTGGTACTGGTCTGTTTCTTGGCATTGGCCC

GGCGATTCAGATGGCGGGTCCGGCTGTATTGCTGGGCTACGGCGT

CGCCGGGATCATCGCTTTCCTGATTATGCGCCAGCTTGGCGAAAT

GGTGGTTGAGGAGCCGGTATCCGGTTCATTTGCCCACTTTGCCTA

TAAATACTGGGGACCGTTTGCGGGCTTCCTCTCTGGCTGGAACTA

CTGGGTAATGTTCGTGCTGGTGGGAATGGCAGAGCTGACCGCTGC

GGGCATCTATATGCAGTACTGGTTCCCGGATGTTCCAACGTGGAT

TTGGGCTGCCGCCTTCTTTATTATCATCAACGCCGTTAACCTGGT

GAACGTGCGCTTATATGGCGAAACCGAGTTCTGGTTTGCGTTGAT

TAAAGTGCTGGCAATCATCGGTATGATCGGCTTTGGCCTGTGGCT

GCTGTTTTCTGGTCACGGCGGCGAGAAAGCCAGTATCGACAACCT

TABLE 13-continued

Nucleotide sequences of TetR-PheP construct, low-copy (SEQ ID NO: 30)

CTGGCGCTACGGTGGTTTCTTCGCCACCGGCTGGAATGGGCTGAT

TTTGTCGCTGGCGGTAATTATGTTCTCCTTCGGCGGTCTGGAGCT

GATTGGGATTACTGCCGCTGAAGCGCGCGATCCGGAAAAAAGCAT

TCCAAAAGCGGTAAATCAGGTGGTGTATCGCATCCTGCTGTTTTA

CATCGGTTCACTGGTGGTTTTACTGGCGCTCTATCCGTGGGTGGA

AGTGAAATCCAACAGTAGCCCGTTTGTGATGATTTTCCATAATCT

CGACAGCAACGTGGTAGCTTCTGCGCTGAACTTCGTCATTCTGGT

AGCATCGCTGTCAGTGTATAACAGCGGGGTTTACTCTAACAGCCG

CATGCTGTTTGGCCTTTCTGTGCAGGGTAATGCGCCGAAGTTTTT

GACTCGCGTCAGCCGTCGCGGTGTGCCGATTAACTCGCTGATGCT

TTCCGGAGCGATCACTTCGCTGGTTGGTGGGTGTTAATCAACTAT

CTGCTGCCGCAAAAAGCGTTTGGTCTGCTGATGGCGCGTAGCAAC

GCTGCTGTTGAACTGGATTATGATCTGTCTGGCGCATCTGCGTTT

TCGTGCAGCGATGCGACGTCAGGGGCGTGAAACACAGTTTAAGGC

GCTGCTCTATCCGTTCGGCAACTATCTCTGCATTGCCTTCCTCGG

CATGATTTTGCTGCTGATGTGCACGATGGATGATATGCGCTTGTC

AGCGATCCTGCTGCCGGTGTGGATTGTATTCCTGTTTATGGCATT

TAAAACGCTGCGTCGGAAATAA

In some embodiments, the genetically engineered bacteria contain gene sequence(s) comprising one or more sequence(s) of any of SEQ ID Nos: 21-30. In some embodiments, the genetically engineered bacteria contain gene sequence(s) comprising one or more sequence(s) having at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identity with any of the sequences of SEQ ID Nos: 21-30.

Phenylalanine Transport

Each of PAL1 and PAL3 was expressed on a high-copy plasmid and a low-copy plasmid in genetically engineered *E. coli* Nissle. Surprisingly, each construct metabolized and reduced phenylalanine to similar levels (FIG. 15), and the rate-limiting step of phenylalanine metabolism was phenylalanine availability (FIG. 16). Thus, in some embodiments, it is advantageous to increase phenylalanine transport into the cell, thereby enhancing phenylalanine metabolism. Unexpectedly, even low-copy PAL plasmids are capable of almost completely eliminating Phe from a test sample when expressed in conjunction with pheP (FIG. 16A). Furthermore, there may be additional advantages to using a low-copy PAL-expressing plasmid in conjunction with pheP in order to enhance the stability of PAL expression while maintaining high phenylalanine metabolism, and to reduce negative selection pressure on the transformed bacterium. In alternate embodiments, the phenylalanine transporter is used in conjunction with the high-copy plasmid.

The genetically engineered bacteria further comprise a gene encoding a phenylalanine transporter. Phenylalanine transporters may be expressed or modified in the genetically engineered bacteria of the invention in order to enhance phenylalanine transport into the cell.

PheP is a membrane transport protein that is capable of transporting phenylalanine into bacterial cells (see, e.g., Pi et al., 1991). In some embodiments, the native pheP gene in the genetically modified bacteria of the invention is not modified. In some embodiments, the genetically engineered bacteria of the invention comprise multiple copies of the native pheP gene. In some embodiments, the genetically engineered bacteria of the invention comprise multiple copies of a non-native pheP gene. In some embodiments, the genetically engineered bacteria of the invention comprise a pheP gene that is controlled by its native promoter, an inducible promoter, a promoter that is stronger than the native promoter, e.g., the GlnRS promoter or the P(Bla) promoter, or a constitutive promoter. In some embodiments, expression of the pheP gene is controlled by a different promoter than the promoter that controls expression of the gene encoding the phenylalanine-metabolizing enzyme and/or the transcriptional regulator. In some embodiments, expression of the pheP gene is controlled by the same promoter that controls expression of the phenylalanine-metabolizing enzyme and/or the transcriptional regulator. In some embodiments, the pheP gene and the phenylalanine-metabolizing enzyme and/or the transcriptional regulator are divergently transcribed from a promoter region. In some embodiments, expression of each of the genes encoding PheP, the phenylalanine-metabolizing enzyme, and the transcriptional regulator is controlled by a different promoter. In some embodiments, expression of the genes encoding PheP, the phenylalanine-metabolizing enzyme, and the transcriptional regulator is controlled by the same promoter.

In some embodiments, the native pheP gene in the genetically modified bacteria is not modified, and one or more additional copies of the native pheP gene are inserted into the genome under the control of the same inducible promoter that controls expression of PAL, e.g., the FNR promoter, or a different inducible promoter than the one that controls expression of PAL, or a constitutive promoter. In alternate embodiments, the native pheP gene is not modified, and a copy of a non-native pheP gene from a different bacterial species is inserted into the genome under the control of the same inducible promoter that controls expression of PAL, e.g., the FNR promoter, or a different inducible promoter than the one that controls expression of PAL, or a constitutive promoter.

In some embodiments, the native pheP gene in the genetically modified bacteria is not modified, and one or more additional copies of the native pheP gene are present in the bacteria on a plasmid and under the control of the same inducible promoter that controls expression of PAL, e.g., the FNR promoter, or a different inducible promoter than the one that controls expression of the PME, or a constitutive promoter. In alternate embodiments, the native pheP gene is not modified, and a copy of a non-native pheP gene from a different bacterial species is present in the bacteria on a plasmid and under the control of the same inducible promoter that controls expression of PAL, e.g., the FNR promoter, or a different inducible promoter than the one that controls expression of PAL, or a constitutive promoter.

In some embodiments, the native pheP gene is mutagenized, mutants exhibiting increased phenylalanine transport are selected, and the mutagenized pheP gene is isolated and inserted into the genetically engineered bacteria (see, e.g., Pi et al., 1996; Pi et al., 1998). The phenylalanine transporter modifications described herein may be present on a plasmid or chromosome.

In some embodiments, the genetically engineered bacterium is *E. coli* Nissle, and the native pheP gene in *E. coli* Nissle is not modified; one or more additional copies the native *E. coli* Nissle pheP genes are inserted into the *E. coli* Nissle genome under the control of the same inducible promoter that controls expression of PAL, e.g., the FNR promoter, or a different inducible promoter than the one that controls expression of PAL, or a constitutive promoter. In an alternate embodiment, the native pheP gene in *E. coli* Nissle is not modified, and a copy of a non-native pheP gene from a different bacterium is inserted into the *E. coli* Nissle genome under the control of the same inducible promoter that controls expression of PAL, e.g., the FNR promoter, or a different inducible promoter than the one that controls expression of PAL, or a constitutive promoter. In some embodiments, the genetically engineered bacterium is *E. coli* Nissle, and the native pheP gene in *E. coli* Nissle is not modified; one or more additional copies the native *E. coli* Nissle pheP genes are present in the bacterium on a plasmid and under the control of the same inducible promoter that controls expression of PAL, e.g., the FNR promoter, or a different inducible promoter than the one that controls expression of PAL, or a constitutive promoter. In an alternate embodiment, the native pheP gene in *E. coli* Nissle is not modified, and a copy of a non-native pheP gene from a different bacterium, are present in the bacterium on a plasmid and under the control of the same inducible promoter that controls expression of PAL, e.g., the FNR promoter, or a different inducible promoter than the one that controls expression of PAL, or a constitutive promoter.

It has been reported that *Escherichia coli* has five distinct transport systems (AroP, Mtr, PheP, TnaB, and TyrP) for the accumulation of aromatic amino acids. A general amino acid permease, encoded by the aroP gene, transports three aromatic amino acids, including phenylalanine, with high affinity, and is thought, together with PheP, responsible for the lion share of phenylalanine import. Additionally, a low level of accumulation of phenylalanine was observed in an aromatic amino acid transporter-deficient *E. coli* strain ($\Delta$aroP $\Delta$pheP $\Delta$mtr $\Delta$tna $\Delta$tyrP), and was traced to the activity of the LIV-I/LS system, which is a branched-chain amino acid transporter consisting of two periplasmic binding proteins, the LIV-binding protein (LIV-I system) and LS-binding protein (LS system), and membrane components, LivHMGF (Koyanagi et al., and references therein; Identification of the LIV-I/LS System as the Third Phenylalanine Transporter in *Escherichia coli* K-12).

In some embodiments, the genetically engineered bacteria comprise an aroP gene. In some embodiments, the genetically engineered bacterium is *E. coli* Nissle, and the native aroP gene in *E. coli* Nissle is not modified; one or more additional copies of the native *E. coli* Nissle aroP genes are present in the bacterium on a plasmid or in the chromosome and under the control of the same inducible promoter that controls expression of the PME, e.g., the FNR promoter, or the araBAD promoter, a different inducible promoter than the one that controls expression of the PME, or a constitutive promoter. In an alternate embodiment, the native aroP gene in *E. coli* Nissle is not modified, and a copy of a non-native aroP gene from a different bacterium, are present in the bacterium on a plasmid or in the chromosome and under the control of the same inducible promoter that controls expression of the PME, e.g., the FNR promoter or the AraBAD promoter, or a different inducible promoter than the one that controls expression of the PME, or a constitutive promoter.

In other embodiments, the genetically engineered bacteria comprise AroP and PheP, under the control of the same or different inducible or constitutive promoters.

In some embodiments, the pheP gene is expressed on a chromosome. In some embodiments, expression from the chromosome may be useful for increasing stability of expression of pheP. In some embodiments, the pheP gene is integrated into the bacterial chromosome at one or more integration sites in the genetically engineered bacteria. In some embodiments, the pheP gene is inserted into the bacterial genome at one or more of the following insertion sites in *E. coli* Nissle: malE/K, insB/I, araC/BAD, lacZ, agaI/rsmI, thyA, and malP/T. Any suitable insertion site may be used (see, e.g., FIG. 36). The insertion site may be anywhere in the genome, e.g., in a gene required for survival and/or growth, such as thyA (to create an auxotroph); in an active area of the genome, such as near the site of genome replication; and/or in between divergent promoters in order to reduce the risk of unintended transcription, such as between AraB and AraC of the arabinose operon.

In some embodiments, the genetically engineered bacterium comprises multiple mechanisms of action and/or one or more auxotrophies. In certain embodiments, the bacteria are genetically engineered to comprise five copies of PAL under the control of an oxygen level-dependent promoter (e.g., $P_{fnrS}$-PAL3) inserted at different integration sites on the chromosome (e.g., malE/K, yicS/nepI, malP/T, agaI/rsmI, and cea), and one copy of a phenylalanine transporter gene under the control of an oxygen level-dependent promoter (e.g., $P_{fnrS}$-pheP) inserted at a different integration site on the chromosome (e.g., lacZ). In a more specific aspect, the bacteria are genetically engineered to further include a kanamycin resistance gene, and a thyA auxotrophy, in which the thyA gene is deleted and/or replaced with an unrelated gene.

Multiple Mechanisms of Action

Figure 13A:
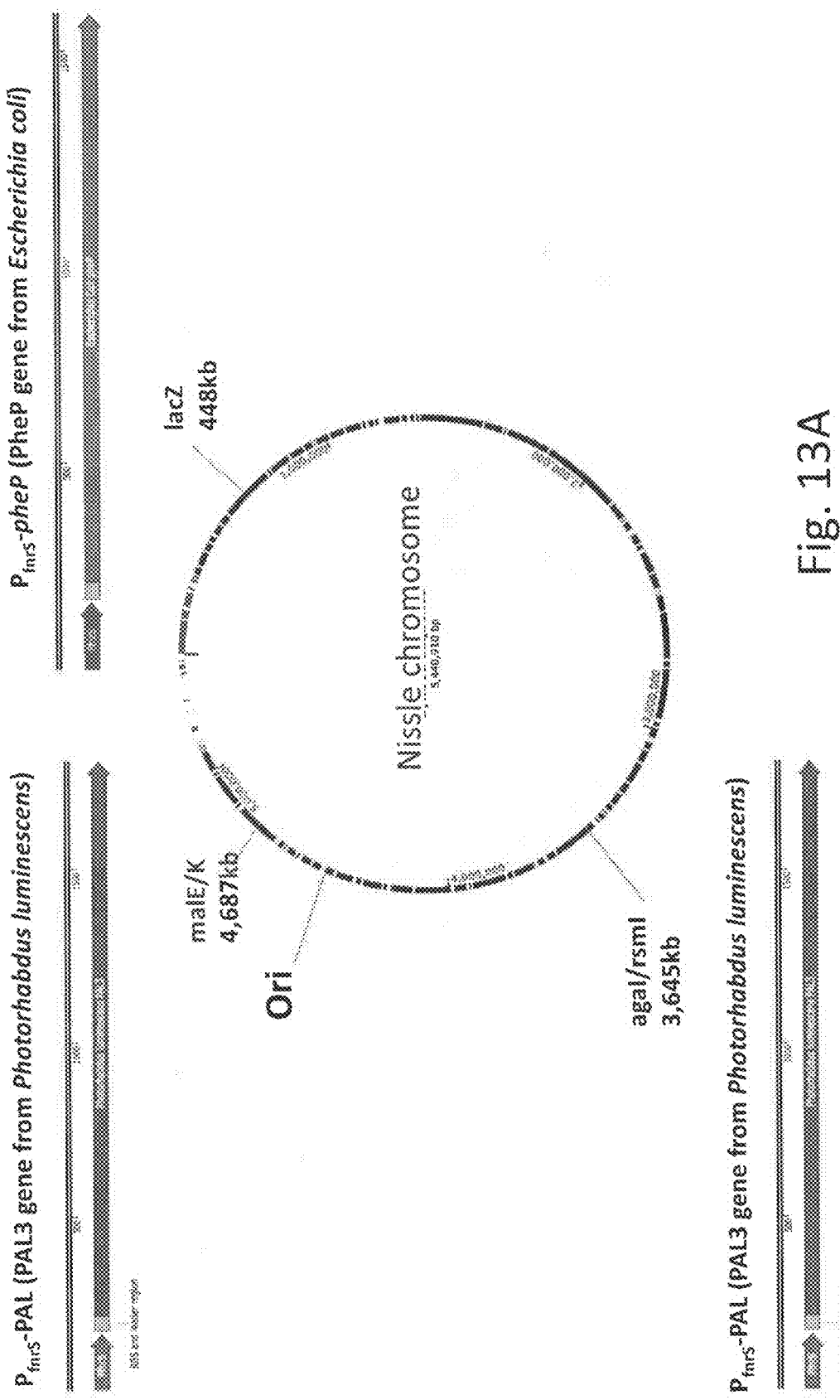
FIG. 13A depicts phenylalanine degradation components integrated into the *E. coli* Nissle chromosome. In some embodiments, engineered plasmid-free bacterial strains are used to prevent plasmid conjugation in vivo. In some embodiments, multiple insertions of the PAL gene result in increased copy number and/or increased phenylalanine degradation activity. In some embodiments, a copy of the endogenous *E. coli* high affinity phenylalanine transporter, pheP, is driven by the PfnrS promoter and is inserted into the lacZ locus.
Figure 13B:
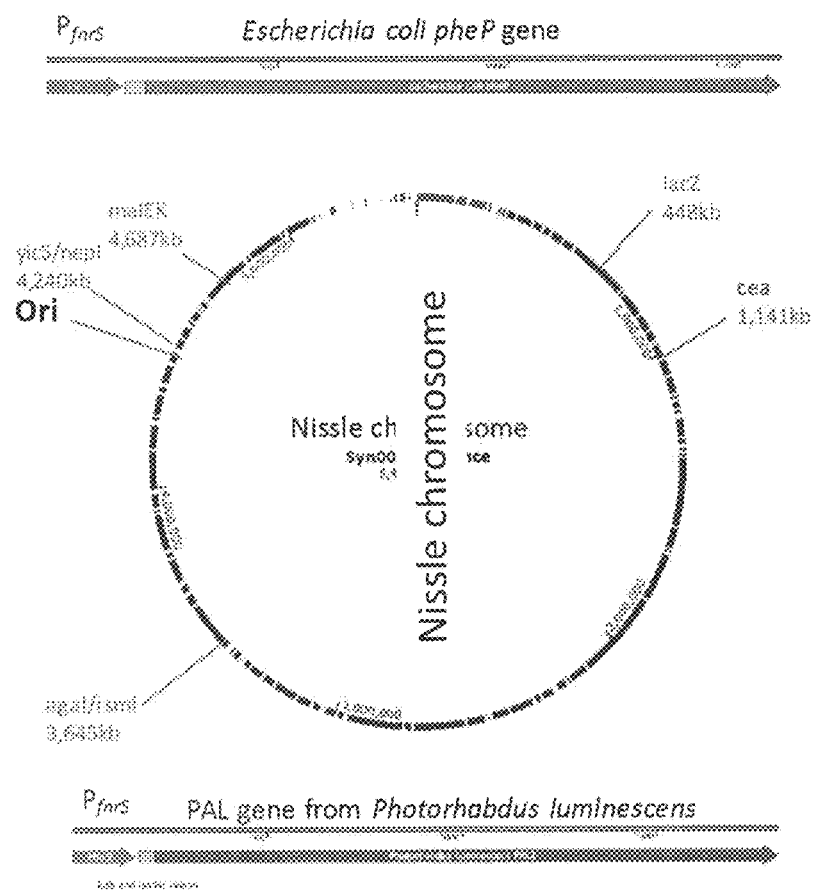
FIG. 13B depicts a schematic diagram of one non-limiting embodiment of the disclosure, wherein the *E. coli* Nissle chromosome is engineered to contain four copies of PfnrS-PAL inserted at four different insertion sites across the genome (malE/K, yicS/nepI, agaI/rsmI, and cea), and one copy of a phenylalanine transporter gene inserted at a different insertion site (lacZ). In this embodiment, the PAL gene is PAL3 derived from *P. luminescens*, and the phenylalanine transporter gene is pheP derived from *E. coli*. In one embodiment, the strain is SYN-PKU511.
Figure 13C:
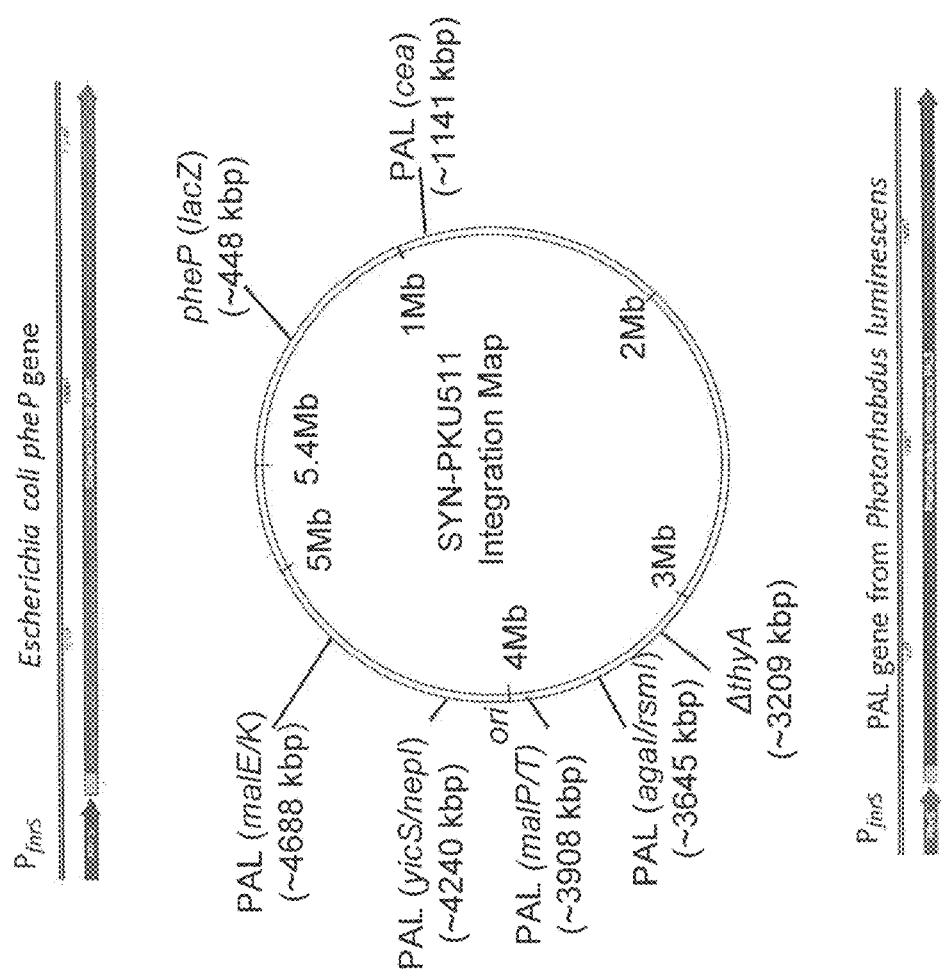
FIG. 13C depicts a schematic diagram of one preferred embodiment of the disclosure, wherein the *E. coli* Nissle chromosome is engineered to contain five copies of PAL under the control of an oxygen level-dependent promoter (e.g., PfnrS-PAL3) inserted at different integration sites on the chromosome (malE/K, yicS/nepI, malP/T, agaI/rsmI, and cea), and one copy of a phenylalanine transporter gene under the control of an oxygen level-dependent promoter (e.g., PfnrS-pheP) inserted at a different integration site on the chromosome (lacZ). The genome is further engineered to include a thyA auxotrophy, in which the thyA gene is deleted and/or replaced with an unrelated gene, as well as a kanamycin resistance gene.
Figure 14:
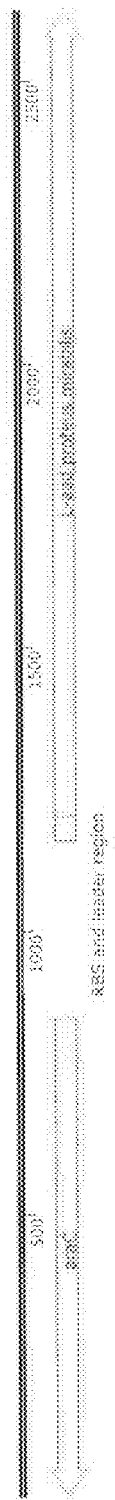
FIG. 14 depicts the gene organization of a non-limiting exemplary construct comprising a gene encoding araC and a gene encoding LAAD from *Proteus mirabilis* and an arabinose inducible promoter (ParaBAD) sequence for chromosomal insertion into the endogenous arabinose operon for chromosomal integration, e.g., as comprised in SYN-PKU705.

In some embodiments, the bacteria are genetically engineered to include multiple mechanisms of action (MoAs), e.g., circuits producing multiple copies of the same product (e.g., to enhance copy number) or circuits performing multiple different functions. Examples of insertion sites include, but are not limited to, malE/K, yicS/nepI, insB/I, araC/BAD, lacZ, agaI/rsmI, thyA, malP/T, dapA, and cea, and others shown in FIG. 36. For example, the genetically engineered bacteria may include four copies of PAL inserted at four different insertion sites, e.g., malE/K, araC/BAD, and lacZ. The genetically engineered bacteria may also include four copies of PAL inserted at four different insertion sites, e.g., malE/K, yicS/nepI, agaI/rsmI, and cea, and one copy of a phenylalanine transporter gene inserted at a different insertion site, e.g., lacZ (FIG. 13B). Alternatively, the genetically engineered bacteria may include three copies of PAL inserted at three different insertion sites, e.g., malE/K, insB/I, and lacZ, and three copies of a phenylalanine transporter gene inserted at three different insertion sites, e.g., dapA, cea, and araC/BAD.

In some embodiments, the genetically engineered bacteria comprise one or more of (1) PAL, PAH, LAAD for degradation of phenylalanine, in wild type or in a mutated form (for increased stability or metabolic activity) (2) transporter PheP or AroP for uptake of phenylalanine, in wild type or in mutated form (for increased stability or metabolic activity) (3) PAL, PAH, LAAD, and/or PheP for secretion and extracellular phenylalanine degradation, (4) components of secretion machinery, as described herein (5) Auxotrophy, e.g., deltaThyA (6) antibiotic resistance, including but not limited to, kanamycin or chloramphenicol resistance (7) mutations/deletions in genes involved in oxygen metabolism, as described herein and (8) mutations/deletions in genes of the endogenous Nissle phenylalanine synthesis pathway (e.g., delta PheA for Phe auxotrophy).

In one embodiment, the genetically engineered bacteria comprise one or more copies of PAL3, (e.g., under the control of a Pfnr promoter) and one or more copies of PAL1 (e.g. under the control of a Pfnr promoter). In one embodiment, the genetically engineered bacteria comprise one or more copies of PAL3, (e.g., under the control of a Pfnr promoter) and one or more copies of PAL1 (e.g. under the control of a Pfnr promoter); and further comprises one or more copies of a phenylalanine transporter (e.g., PheP and/or AroP, e.g., under the control of a Pfnr promoter). In one embodiment, the genetically engineered bacteria comprise one or more copies of PAL3, (e.g., under the control of a Pfnr promoter) and one or more copies of LAAD (e.g., under the control of the ParaBAD promoter). In one embodiment, the genetically engineered bacteria comprise one or more copies of PAL3, (e.g., under the control of a Pfnr promoter) and one or more copies of LAAD (e.g., under the control of the ParaBAD promoter); and further comprises one or more copies of a phenylalanine transporter (e.g., PheP and/or AroP, e.g., under the control of a Pfnr promoter). In one embodiment, the genetically engineered bacteria comprise one or more copies of PAL3, (e.g., under the control of a Pfnr promoter) and one or more copies of PAH. In one embodiment, the genetically engineered bacteria comprise one or more copies of PAL3, (e.g., under the control of a Pfnr promoter) and one or more copies of PAH; and further comprises one or more copies of a phenylalanine transporter (e.g., PheP and/or AroP, e.g., under the control of a Pfnr promoter). In one embodiment, the genetically engineered bacteria comprise one or more copies of PAL1, (e.g., under the control of a Pfnr promoter) and one or more copies of LAAD (e.g., under the control of the ParaBAD promoter). In one embodiment, the genetically engineered bacteria comprise one or more copies of PAL1, (e.g., under the control of a Pfnr promoter) and one or more copies of LAAD (e.g., under the control of the ParaBAD promoter); and further comprises one or more copies of a phenylalanine transporter (e.g., PheP and/or AroP, e.g., under the control of a Pfnr promoter). In one embodiment, the genetically engineered bacteria comprise one or more copies of PAL1 (e.g., under the control of a Pfnr promoter) and one or more copies of PAH. In one embodiment, the genetically engineered bacteria comprise one or more copies of PAL1 (e.g., under the control of a Pfnr promoter) and one or more copies of PAH; and further comprises one or more copies of a phenylalanine transporter (e.g., PheP and/or AroP, e.g., under the control of a Pfnr promoter). In one embodiment, the genetically engineered bacteria comprise one or more copies of PAH and one or more copies of LAAD (e.g., under the control of the ParaBAD promoter). In one embodiment, the genetically engineered bacteria comprise one or more copies of PAH and one or more copies of LAAD (e.g., under the control of the ParaBAD promoter); and further comprises one or more copies of a phenylalanine transporter (e.g., PheP and/or AroP, e.g., under the control of a Pfnr promoter). PMEs and transporters may be integrated into any of the insertion sites described herein.

In one embodiment, the genetically engineered bacteria comprise one or more copies of PAL3, e.g. (e.g., under the control of a Pfnr promoter), one or more copies of LAAD (e.g., under the control of the ParaBAD promoter), and one or more copies of PAH. In one embodiment, the genetically engineered bacteria comprise one or more copies of PAL3, e.g. (e.g., under the control of a Pfnr promoter), one or more copies of LAAD (e.g., under the control of the ParaBAD promoter), and one or more copies of PAH; and further comprise one or more copies of a phenylalanine transporter (e.g., PheP and/or AroP, e.g., under the control of a Pfnr promoter). In one embodiment, the genetically engineered bacteria comprise one or more copies of PAL3, e.g. (e.g., under the control of a Pfnr promoter), one or more copies of LAAD (e.g., under the control of the ParaBAD promoter), and one or more copies of PAL1 (e.g., under the control of a Pfnr promoter). In one embodiment, the genetically engineered bacteria comprise one or more copies of PAL3, e.g. (e.g., under the control of a Pfnr promoter), one or more copies of LAAD (e.g., under the control of the ParaBAD promoter), and one or more copies of PAL1 (e.g., under the control of a Pfnr promoter); and further comprise one or more copies of a phenylalanine transporter (e.g., PheP and/or AroP, e.g., under the control of a Pfnr promoter). In one embodiment, the genetically engineered bacteria comprise one or more copies of PAL3, e.g. (e.g., under the control of a Pfnr promoter), one or more copies of PAL1 (e.g., under the control of a Pfnr promoter), and one or more copies of PAH. In one embodiment, the genetically engineered bacteria comprise one or more copies of PAL3, e.g. (e.g., under the control of a Pfnr promoter), one or more copies of PAL1 (e.g., under the control of a Pfnr promoter), and one or more copies of PAH; and further comprise one or more copies of a phenylalanine transporter (e.g., PheP and/or AroP, e.g., under the control of a Pfnr promoter). In one embodiment, the genetically engineered bacteria comprise one or more copies of LAAD (e.g., under the control of the ParaBAD promoter), one or more copies of PAH, and one or more copies of PAL1 (e.g., under the control of an Pfnr promoter). In one embodiment, the genetically engineered bacteria comprise one or more copies of LAAD (e.g., under the control of the ParaBAD promoter), one or more copies of PAH, and one or more copies of PAL1 (e.g., under the control of an Pfnr promoter); and further comprise one or more copies of a phenylalanine transporter (e.g., PheP and/or AroP, e.g., under the control of a Pfnr promoter). PMEs and/or transporters may be integrated into any of the insertion sites described herein. Alternatively, PMEs and/or transporters may be comprised on low or high copy plasmids. PMEs and/or transporters may be integrated into any of the insertion sites described herein in combination with PMEs and/or transporters that are comprised on low or high copy plasmids.

In one embodiment, the genetically engineered bacteria comprise one or more copies of PAL3, e.g. (e.g., under the control of a Pfnr promoter), one or more copies of PAL1, e.g. (e.g., under the control of a Pfnr promoter), one or more copies of LAAD (e.g., under the control of the ParaBAD promoter), and one or more copies of PAH. In one embodiment, the genetically engineered bacteria comprise one or more copies of PAL3, e.g. (e.g., under the control of a Pfnr promoter), one or more copies of PAL1, e.g. (e.g., under the control of a Pfnr promoter), one or more copies of LAAD (e.g., under the control of the ParaBAD promoter), and one or more copies of PAH; and further comprise one or more copies of a phenylalanine transporter (e.g., PheP and/or AroP, e.g., under the control of a Pfnr promoter). PMEs and transporters may be integrated into any of the insertion sites described herein. Alternatively, PMEs and/or transporters may be comprised on low or high copy plasmids.

In one embodiment, the genetically engineered bacteria comprise one copy of PAL, (e.g., PAL1 or PAL3, e.g., under the control of a Pfnr promoter) one copy of PheP (e.g., under the control of a Pfnr promoter), and one copy of LAAD (e.g., under the control of the ParaBAD promoter). In one embodiment, the genetically engineered bacteria comprise one copy of PAL, (e.g., PAL1 or PAL3, e.g., under the control of a Pfnr promoter) two copies of PheP (e.g., under the control of a Pfnr promoter), and one copy of LAAD (e.g., under the control of the ParaBAD promoter). In one embodiment, the genetically engineered bacteria comprise one copy of PAL, (e.g., PAL1 or PAL3, e.g., under the control of a Pfnr promoter) one copy of PheP (e.g., under the control of a Pfnr promoter), and two copies of LAAD (e.g., under the control of the ParaBAD promoter). In one embodiment, the genetically engineered bacteria comprise one copy of PAL, (e.g., PAL1 or PAL3, e.g., under the control of a Pfnr promoter) two copies of PheP (e.g., under the control of a Pfnr promoter), and two copies of LAAD (e.g., under the control of the ParaBAD promoter). PMEs and transporters may be integrated into any of the insertion sites described herein. Alternatively, located PMEs and/or transporters may be comprised on low or high copy plasmids.

In one embodiment, the genetically engineered bacteria comprise two copies of PAL (e.g., PAL1 or PAL3, e.g., under the control of a Pfnr promoter) one copy of PheP (e.g., under the control of a Pfnr promoter), and one copy of LAAD (e.g., under the control of the ParaBAD promoter). In one embodiment, the genetically engineered bacteria comprise two copies of PAL, (e.g., PAL1 or PAL3, e.g., under the control of a Pfnr promoter) two copies of PheP (e.g., under the control of a Pfnr promoter), and one copy of LAAD (e.g., under the control of the ParaBAD promoter). In one embodiment, the genetically engineered bacteria comprise two copies of PAL, (e.g., PAL1 or PAL3, e.g., under the control of a Pfnr promoter) one copy of PheP (e.g., under the control of a Pfnr promoter), and two copies of LAAD (e.g., under the control of the ParaBAD promoter). In one embodiment, the genetically engineered bacteria comprise two copies of PAL, (e.g., PAL1 or PAL3, e.g., under the control of a Pfnr promoter) two copies of PheP (e.g., under the control of a Pfnr promoter), and two copies of LAAD (e.g., under the control of the ParaBAD promoter).

In one embodiment, the genetically engineered bacteria comprise three copies of PAL, (e.g., PAL1 or PAL3, e.g., under the control of a Pfnr promoter) one copy of PheP (e.g., under the control of a Pfnr promoter), and one copy of LAAD (e.g., under the control of the ParaBAD promoter). In one embodiment, the genetically engineered bacteria comprise three copies of PAL, (e.g., PAL1 or PAL3, e.g., under the control of a Pfnr promoter) two copies of PheP (e.g., under the control of a Pfnr promoter), and one copy of LAAD (e.g., under the control of the ParaBAD promoter). In one embodiment, the genetically engineered bacteria comprise three copies of PAL, (e.g., PAL1 or PAL3, e.g., under the control of a Pfnr promoter) one copy of PheP (e.g., under the control of a Pfnr promoter), and two copies of LAAD (e.g., under the control of the ParaBAD promoter). In one embodiment, the genetically engineered bacteria comprise three copies of PAL, (e.g., PAL1 or PAL3, e.g., under the control of a Pfnr promoter) two copies of PheP (e.g., under the control of a Pfnr promoter), and two copies of LAAD (e.g., under the control of the ParaBAD promoter). In one embodiment, the genetically engineered bacteria comprise three copies of PAL, (e.g., PAL1 or PAL3, e.g., under the control of a Pfnr promoter), three copies of PheP (e.g., under the control of a Pfnr promoter), and two copies of LAAD (e.g., under the control of the ParaBAD promoter). In one embodiment, the genetically engineered bacteria comprise three copies of PAL, (e.g., PAL1 or PAL3, e.g., under the control of a Pfnr promoter), three copies of PheP (e.g., under the control of a Pfnr promoter), and one copy of LAAD (e.g., under the control of the ParaBAD promoter).

In one embodiment, the genetically engineered bacteria comprise four copies of PAL, (e.g., PAL1 or PAL3, e.g., under the control of a Pfnr promoter) one copy of PheP (e.g., under the control of a Pfnr promoter), and one copy of LAAD (e.g., under the control of the ParaBAD promoter). In one embodiment, the genetically engineered bacteria comprise four copies of PAL, (e.g., PAL1 or PAL3, e.g., under the control of a Pfnr promoter) two copies of PheP (e.g., under the control of a Pfnr promoter), and one copy of LAAD (e.g., under the control of the ParaBAD promoter). In one embodiment, the genetically engineered bacteria comprise four copies of PAL, (e.g., PAL1 or PAL3, e.g., under the control of a Pfnr promoter) one copy of PheP (e.g., under the control of a Pfnr promoter), and two copies of LAAD (e.g., under the control of the ParaBAD promoter). In one embodiment, the genetically engineered bacteria comprise four copies of PAL, (e.g., PAL1 or PAL3, e.g., under the control of a Pfnr promoter) two copies of PheP (e.g., under the control of a Pfnr promoter), and two copies of LAAD (e.g., under the control of the ParaBAD promoter).

In one embodiment, the genetically engineered bacteria comprise five copies of PAL, (e.g., PAL1 or PAL3, e.g., under the control of a Pfnr promoter) one copy of PheP (e.g., under the control of a Pfnr promoter), and one copy of LAAD (e.g., under the control of the ParaBAD promoter). In one embodiment, the genetically engineered bacteria comprise five copies of PAL, (e.g., PAL1 or PAL3, e.g., under the control of a Pfnr promoter) two copies of PheP (e.g., under the control of a Pfnr promoter), and one copy of LAAD (e.g., under the control of the ParaBAD promoter). In one embodiment, the genetically engineered bacteria comprise five copies of PAL, (e.g., PAL1 or PAL3, e.g., under the control of a Pfnr promoter) one copy of PheP (e.g., under the control of a Pfnr promoter), and two copies of LAAD (e.g., under the control of the ParaBAD promoter). In one embodiment, the genetically engineered bacteria comprise five copies of PAL, (e.g., PAL1 or PAL3, e.g., under the control of a Pfnr promoter) two copies of PheP (e.g., under the control of a Pfnr promoter), and two copies of LAAD (e.g., under the control of the ParaBAD promoter).

In one embodiment, the genetically engineered bacteria comprise one or more PMEs for metabolizing phenylalanine in combination with one or more PMEs for secretion. In one embodiment, the genetically engineered bacteria comprise one or more PMEs for metabolizing phenylalanine and a phenylalanine transporter in combination with one or more PMEs for secretion. In one embodiment, the genetically engineered bacteria comprise one or more PMEs for metabolizing phenylalanine and a phenylalanine transporter in combination with one or more PMEs for secretion, and also include an auxotrophy and/or an antibiotic resistance. Secretion systems described herein are utilized to secrete the PMEs in the genetically engineered bacteria with multiple mechanisms of action.

In one embodiment, the genetically engineered bacteria comprise two additional copies of PheP (in addition to the wild type gene). This provides redundancy, in case one of the PheP genes acquires a mutation. In one embodiment, the PheP genes are inserted at lacZ and agal/rsml. In one embodiment, the two copies of PheP are under the control of the PfnrS promoter. In one embodiment, the genetically engineered bacteria comprise three copies of PAL3. In one embodiment, the genetically engineered bacteria comprise three copies of PAL3, inserted at malEK, malPT, yicS/nepI. In one embodiment, the expression of the three copies of PAL3 is under the control of the PfnrS promoter. In one embodiment, the genetically engineered bacteria comprise one or more copies of LAAD. In one embodiment, the genetically engineered bacteria comprise one copy of LAAD, inserted in the arabinose operon. In one embodiment, LAAD is under the control of the endogenous ParaBAD promoter. In one embodiment, the genetically engineered bacteria comprise an auxotrophy, e.g., deltaThyA. In one embodiment, the genetically engineered bacteria comprise an antibiotic resistance. In one embodiment the genetically engineered bacteria comprise an antibiotic resistance and an auxotrophy, e.g., deltaThyA. In one embodiment, the genetically engineered bacteria do not comprise an auxotrophy, e.g., deltaThyA. In one embodiment, the genetically engineered bacteria do not comprise an antibiotic resistance. In one embodiment the genetically engineered bacteria comprise neither an antibiotic resistance nor an auxotrophy, e.g., deltaThyA.

In one embodiment, the genetically engineered bacteria comprise three copies of PAL, e.g., PAL3, 2 copies of PheP (in addition to the endogenous PheP), and one copy of LAAD. In one embodiment, the genetically engineered bacteria comprise three copies of PAL, e.g., PAL3, 2 copies of PheP (in addition to the endogenous PheP), and one copy of LAAD, and an auxotrophy, e.g., delta ThyA. In one embodiment, the genetically engineered bacteria comprise three copies of PAL, 2 copies of PheP (in addition to the endogenous PheP), and one copy of LAAD, and an antibiotic resistance gene. In one embodiment, the genetically engineered bacteria comprise three copies of PAL, 2 copies of PheP (in addition to the endogenous PheP), and one copy of LAAD, and an antibiotic resistance gene and an auxotrophy, e.g., delta ThyA.

In one embodiment, the genetically engineered bacteria comprise three copies of PAL (each under control of a PfnrS promoter), 2 copies of PheP (each under control of a PfnrS promoter), and one copy of LAAD (under the control of the endogenous ParaBAD promoter). In one embodiment, the genetically engineered bacteria comprise three copies of PAL (each under control of a PfnrS promoter), 2 copies of PheP (each under control of a PfnrS promoter), and one copy of LAAD (under the control of the endogenous ParaBAD promoter), and an antibiotic resistance. In one embodiment, the genetically engineered bacteria comprise three copies of PAL (each under control of a PfnrS promoter), 2 copies of PheP (each under control of a PfnrS promoter), and one copy of LAAD (under the control of the endogenous ParaBAD promoter), and an auxotrophy, e.g., delta ThyA. In one embodiment, the genetically engineered bacteria comprise three copies of PAL (each under control of a PfnrS promoter), 2 copies of PheP (each under control of a PfnrS promoter), and one copy of LAAD (under the control of the endogenous ParaBAD promoter), and an antibiotic resistance and an auxotrophy, e.g., deltaThyA.

In one embodiment, the genetically engineered bacteria comprise three copies of PAL (each under control of a PfnrS promoter and inserted at the malEK, malPT, and yicS/nepI sites), 2 copies of PheP (each under control of a PfnrS promoter and inserted at the LacZ and agaI/rsmI sites), and one copy of LAAD (under the control of the endogenous ParaBAD promoter, and inserted in the endogenous arabinose operon). In one embodiment, the genetically engineered bacteria comprise three copies of PAL (each under control of a PfnrS promoter and inserted at the malEK, malPT, and yicS/nepI sites), 2 copies of PheP (each under control of a PfnrS promoter and inserted at the LacZ and agaI/rsmI sites), and one copy of LAAD (under the control of the endogenous ParaBAD promoter, and inserted in the endogenous arabinose operon), and further comprise an antibiotic resistance. In one embodiment, the genetically engineered bacteria comprise three copies of PAL (each under control of a PfnrS promoter and inserted at the malEK, malPT, and yicS/nepI sites), 2 copies of PheP (each under control of a PfnrS promoter and inserted at the LacZ and agaI/rsmI sites), and one copy of LAAD (under the control of the endogenous ParaBAD promoter, and inserted in the endogenous arabinose operon) and further comprise an auxotrophy, e.g., deltaThyA. In one embodiment, the genetically engineered bacteria comprise three copies of PAL (each under control of a PfnrS promoter and inserted at the malEK, malPT, and yicS/nepI sites), 2 copies of PheP (each under control of a PfnrS promoter and inserted at the LacZ and agaI/rsmI sites), and one copy of LAAD (under the control of the endogenous ParaBAD promoter, and inserted in the endogenous arabinose operon), and further comprise an antibiotic resistance and an auxotrophy, e.g., deltaThyA.

In one embodiment, the genetically engineered bacteria are SYN-PKU705. In one embodiment, SYN-PKU705 further comprises an antibiotic resistance. In one embodiment, SYN-PKU705 further comprises an auxotrophy, e.g., deltaThyA. In one embodiment, SYN-PKU705 further comprises an antibiotic resistance and auxotrophy, e.g., deltaThyA.

Table 14 contains non-limiting examples of the genetically engineered bacteria of the disclosure. In certain embodiments, the genetically engineered bacteria of Table 14 further contain a PME for secretion.

TABLE 14

Non-limiting Examples of Embodiments of the Disclosure

| Strain Name | Genotype |
|---|---|
| Plasmid -based strains | |
| SYN-PKU101 | Low copy pSC101-Ptet::PAL1, ampicillin resistant |
| SYN-PKU102 | High copy pColE1-Ptet::PAL1, ampicillin resistant, |
| SYN-PKU201 | Low copy pSC101-Ptet::PAL3, ampicillin resistant |
| SYN-PKU202 | High copy pColE1-Ptet::PAL3, ampicillin resistant, |
| SYN-PKU203 | lacZ::Ptet-pheP::cam |
| SYN-PKU401 | Low copy pSC101-Ptet::PAL1, ampicillin resistant, chromosomal lacZ::Ptet-pheP::cam |
| SYN-PKU402 | High copy pColE1-Ptet::PAL1, ampicillin resistant, chromosomal lacZ::Ptet-pheP::cam |
| SYN-PKU302 | Low Copy pSC101-Ptet::PAL3, ampicillin resistant; chromosomal lacZ::Ptet-pheP::cam |
| SYN-PKU303 | High copy pColE1-Ptet::PAL3, ampicillin resistant, chromosomal lacZ::Ptet-pheP::cam |
| SYN-PKU304 | Low Copy pSC101-PfnrS::PAL3, ampicillin resistant; chromosomal lacZ::PfnrS-pheP::cam |
| SYN-PKU305 | Low Copy pSC101-PfnrS::PAL3, kanamycin resistant; chromosomal lacZ::PfnrS-pheP::cam |

TABLE 14-continued

Non-limiting Examples of Embodiments of the Disclosure

| Strain Name | Genotype |
|---|---|
| SYN-PKU306 | Low Copy pSC101-PfnrS::PAL3, kanamycin resistant; thyA |
| SYN-PKU307 | Low Copy pSC101-PfnrS::PAL3, ampicillin resistant; |
| SYN-PKU308 | Low Copy pSC101-PfnrS::PAL3, kanamycin resistant; |
| SYN-PKU401 | High Copy pUC57-Ptet::LAAD; kanamycin resistant |
| Integrated strains | |
| SYN-PKU501 | malPT:: PfnrS::PAL3::kan |
| SYN-PKU502 | malPT:: PfnrS::PAL3::kan; bicistronic lacZ:: PfnrS::PAL3-pheP::cam |
| SYN-PKU503 | malEK::PfnrS::PAL3::cam |
| SYN-PKU504 | agaI/rsmI::PfnrS::PAL3 |
| SYN-PKU505 | cea::PfnrS::PAL3 |
| SYN-PKU506 | malEK::PfnrS::PAL3; agaI/rsmI::PfnrS::PAL3; cea::PfnrS::PAL3 |
| SYN-PKU507 | malEK:: PfnrS::PAL3; agaI/rsmI::PfnrS::PAL3; cea::PfnrS::PAL3; lacZ::Pfnr-pheP::cam |
| SYN-PKU508 | malEK::PfnrS::PAL3; pheA auxotroph |
| SYN-PKU509 | malEK::PfnrS::PAL3; agaI/rsmI::PfnrS::PAL3; cea::PfnrS::PAL3; lacZ::Pfnr-pheP:: cam |
| SYN-PKU601 | malPT::PfnrS-INT5::kan, rrnBUP -[PAL3]; lacZ::Pfnr-pheP::cam (recombinase based strain) |
| SYN-PKU510 | malEK::PfnrS::PAL3;agaI/rsmI::PfnrS::PAL3; cea::PfnrS::PAL3; |
| SYN-PKU511 | malEK:: PfnrS::PAL3; agaI/rsmI::PfnrS::PAL3; cea::PfnrS::PAL3; yicS/nepI::PfnrS-PAL3::kan; malPT::PfnrS::P AL3; lacZ::Pfnr-pheP; 4 thyA |
| SYN-PKU204 | lacZ::Pfnr-pheP::cam |
| SYN-PKU512 | malEK::PfnrS::PAL3; agaI/rsmI::PfnrS::PAL3; cea::PfnrS::PAL3; malPT::PfnrS::PAL3; lacZ::Pfnr-pheP::cam; 4 thyA |
| SYN-PKU513 | malEK:: PfnrS::PAL3; agaI/rsmI::PfnrS::PAL3; cea::PfnrS::PAL3; lacZ::Pfnr-pheP; 4 thyA |
| SYN-PKU514 | malEK:: PfnrS::PAL3; agaI/rsmI::PfnrS::PAL3; cea::PfnrS::PAL3; malPT::PfnrS::PAL3; 4 thyA |
| SYN-PKU515 | malEK:: PfnrS::PAL3; agaI/rsmI::PfnrS::PAL3; cea::PfnrS::PAL3; 4 thyA |
| SYN-PKU516 | agaI/rsmI::PfnrS::PAL3::kan |
| SYN-PKU517 | malEK:: PfnrS::PAL3:: cam; malPT::PfnrS::P AL3 ::kan; lacZ::PfnrS-pheP; ΔthyA |
| SYN-PKU518 | malEK-PfnrS::PAL3::cam; PfnrS::pheP::kan |
| SYN-PKU519 | ParaBC-PAL3::cam; PfnrS-pheP::kan |
| SYN-PKU520 | agaI/rsmI::PfnrS::PAL3::kan;PfnrS-PheP::cam |
| SYN-PKU801 | ΔargR; thyA::cam |
| SYN-PKU701 | ParaBC-LAAD::cam; malEK-PfnrS-PAL3; malPT::PfnrS-PAL3::kan; PfnrS-pheP |
| SYN-PKU521 | yicS/nepI::PfnrS-PAL3::kan; lacZ::Pfnr-pheP::cam |
| SYN-PKU522 | cea::PfnrS-PAL3::kan; lacZ::Pfnr-pheP::cam |
| SYN-PKU523 | malPT::PfnrS-PAL3::kan; lacZ::Pfnr-pheP::cam |
| SYN-PKU524 | malEK:: PfnrS::PAL3;malPT::PfnrS::PAL3; lacZ::Pfnr-pheP |
| SYN-PKU702 | malEK:: PfnrS::PAL3; lacZ::Pfnr-pheP; Para::LAAD |
| SYN-PKU703 | malEK:: PfnrS::PAL3;malPT::PfnrS::PAL3; lacZ::Pfnr-pheP; agaI/rsmI::PfnrS::pheP; Para::LAAD |
| SYN-PKU704 | malEK:: PfnrS::PAL3;malPT::PfnrS::PAL3; yicS/nepI::PfnrS-PAL3; lacZ::Pfnr-pheP; Para::LAAD |
| SYN-PKU705 | malEK:: PfnrS::PAL3;malPT::PfnrS::PAL3; yicS/nepI::PfnrS-PAL3::kan; lacZ::Pfnr-pheP; agaI/rsmf:PfnrS::pheP Para. :LAAD |
| SYN-PKU602 | malEK:: PT7::PAL3; Para::INT5::cam (recombinase); lacZ::Pfnr-pheP; malPT::Pconstitutive::T7 polymerase (unflipped); |
| SYN-PKU901 | Nissle with streptomycin resistance |

Secretion

In some embodiments, the genetically engineered bacteria further comprise a native secretion mechanism (e.g., gram positive bacteria) or non-native secretion mechanism (e.g., gram negative bacteria) that is capable of secreting the protein(s) of interest or therapeutic protein(s), e.g., PAH, PAL or LAAD, from the bacterial cytoplasm. Many bacteria have evolved sophisticated secretion systems to transport substrates across the bacterial cell envelope. Substrates, such as small molecules, proteins, and DNA, may be released into the extracellular space or periplasm (such as the gut lumen or other space), injected into a target cell, or associated with the bacterial membrane.

In Gram-negative bacteria, secretion machineries may span one or both of the inner and outer membranes. In some embodiments, the genetically engineered bacteria further comprise a non-native double membrane-spanning secretion system. Double membrane-spanning secretion systems include, but are not limited to, the type I secretion system (T1SS), the type II secretion system (T2SS), the type III secretion system (T3SS), the type IV secretion system (T4SS), the type VI secretion system (T6SS), and the resistance-nodulation-division (RND) family of multi-drug efflux pumps (Pugsley 1993; Gerlach et al., 2007; Collinson et al., 2015; Costa et al., 2015; Reeves et al., 2015; WO2014138324A1, incorporated herein by reference). Examples of such secretion systems are shown in FIGS. 3-6. Mycobacteria, which have a Gram-negative-like cell envelope, may also encode a type VII secretion system (T7SS) (Stanley et al., 2003). With the exception of the T2SS, double membrane-spanning secretions generally transport substrates from the bacterial cytoplasm directly into the extracellular space or into the target cell. In contrast, the T2SS and secretion systems that span only the outer membrane may use a two-step mechanism, wherein substrates are first translocated to the periplasm by inner membrane-spanning transporters, and then transferred to the outer membrane or secreted into the extracellular space. Outer membrane-spanning secretion systems include, but are not limited to, the type V secretion or autotransporter system (T5SS), the curli secretion system, and the chaperone-usher pathway for pili assembly (Saier, 2006; Costa et al., 2015).

In some embodiments, the genetically engineered bacteria of the invention further comprise a type III or a type III-like secretion system (T3SS) from *Shigella, Salmonella, E. coli, Bivrio, Burkholderia, Yersinia, Chlamydia,* or *Pseudomonas.* The T3SS is capable of transporting a protein from the bacterial cytoplasm to the host cytoplasm through a needle complex. The T3SS may be modified to secrete the molecule from the bacterial cytoplasm, but not inject the molecule into the host cytoplasm. Thus, the molecule is secreted into the gut lumen or other extracellular space. In some embodiments, the genetically engineered bacteria comprise said modified T3SS and are capable of secreting the protein(s) of interest or therapeutic protein(s) from the bacterial cytoplasm. In some embodiments, the secreted molecule, such as a heterologous protein or peptide, e.g., the protein of interest or therapeutic protein e.g., PAH, PAL or LAAD, comprises a type III secretion sequence that allows the protein(s) of interest or therapeutic protein(s) to be secreted from the bacteria.

In some embodiments, a flagellar type III secretion pathway is used to secrete the molecule of interest, e.g., PAH, PAL or LAAD. In some embodiments, an incomplete flagellum is used to secrete a therapeutic peptide of interest, e.g., PAH, PAL or LAAD, by recombinantly fusing the peptide to an N-terminal flagellar secretion signal of a native flagellar component. In this manner, the intracellularly expressed chimeric peptide can be mobilized across the inner and outer membranes into the surrounding host environment.

Figure 10:
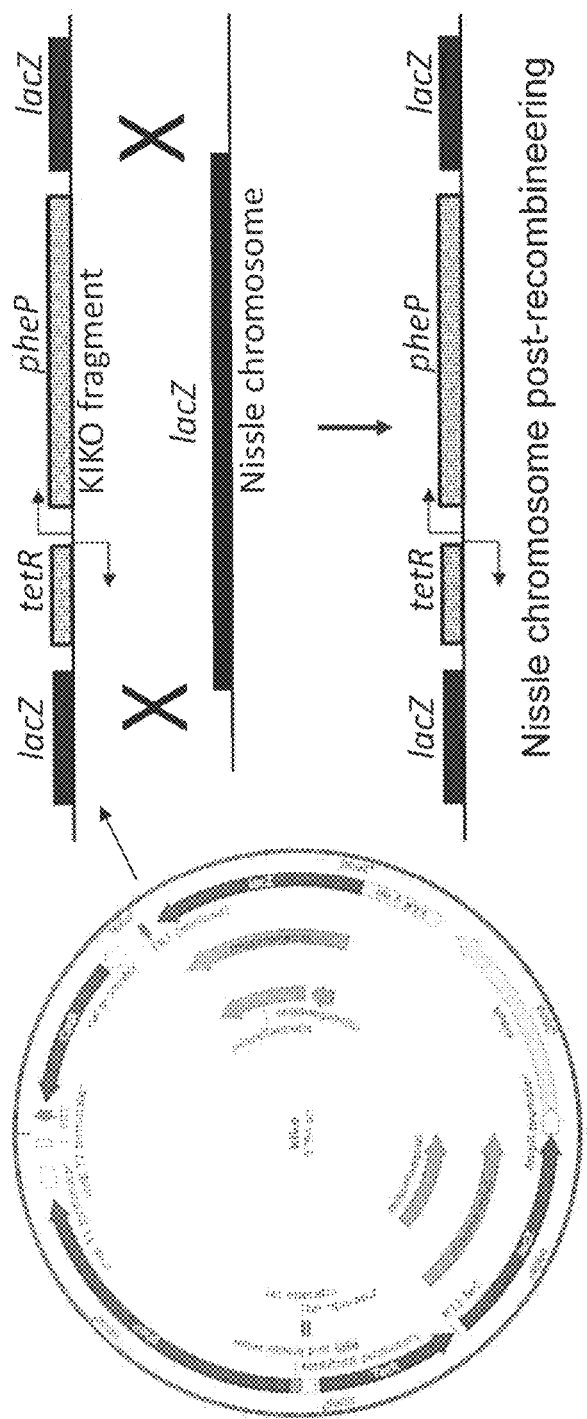
FIG. 10 depicts a schematic representation of the construction of a pheP knock-in strain, wherein recombineering is used to insert a second copy of pheP into the Nissle lacZ gene.

In some embodiments, a Type V Autotransporter Secretion System is used to secrete the therapeutic peptide, e.g., PAH, PAL or LAAD. Due to the simplicity of the machinery and capacity to handle relatively large protein fluxes, the Type V secretion system is attractive for the extracellular production of recombinant proteins. As shown in FIG. 10, a therapeutic peptide (star) can be fused to an N-terminal secretion signal, a linker, and the beta-domain of an autotransporter. The N-terminal signal sequence directs the protein to the SecA-YEG machinery which moves the protein across the inner membrane into the periplasm, followed by subsequent cleavage of the signal sequence. The Beta-domain is recruited to the Bam complex ('Beta-barrel assembly machinery') where the beta-domain is folded and inserted into the outer membrane as a beta-barrel structure. The therapeutic peptide, e.g., PAH, PAL or LAAD, is threaded through the hollow pore of the beta-barrel structure ahead of the linker sequence. Once exposed to the extracellular environment, the therapeutic peptide, e.g., PAH, PAL or LAAD, can be freed from the linker system by an autocatalytic cleavage (left side of Bam complex) or by targeting of a membrane-associated peptidase (black scissors; right side of Bam complex) to a complimentary protease cut site in the linker. Thus, in some embodiments, the secreted molecule, such as a heterologous protein or peptide, e.g., the protein of interest or therapeutic protein, comprises an N-terminal secretion signal, a linker, and beta-domain of an autotransporter so as to allow the molecule to be secreted from the bacteria.

Figure 11:
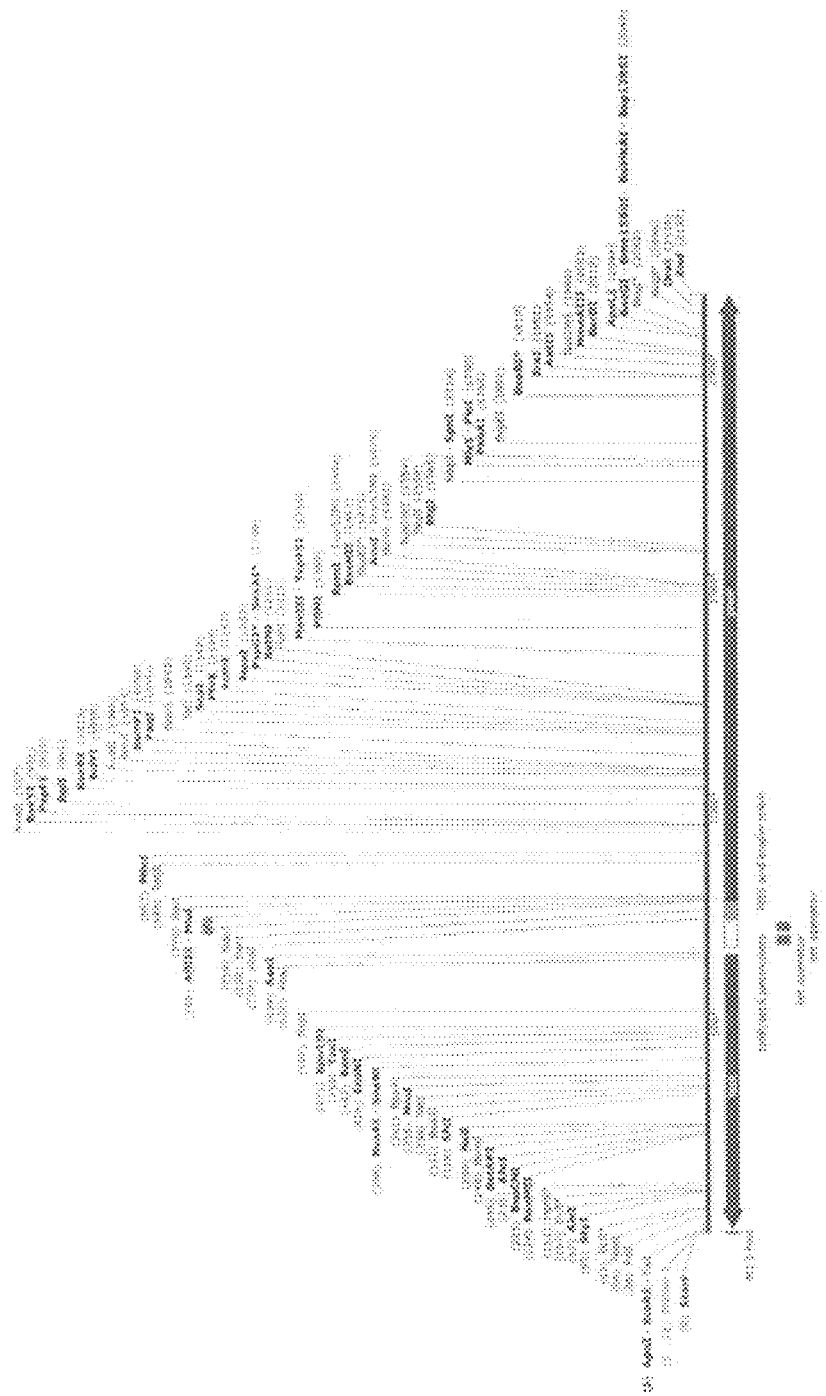
FIG. 11 depicts the gene organization of an exemplary construct comprising a gene encoding PheP, a gene encoding TetR, and a tet promoter sequence for chromosomal insertion e.g., as for example comprised in SYN-PKU203, SYN-PKU401, SYN-PKU402, SYN-PKU302, and SYN-PKU303.
Figure 12A:
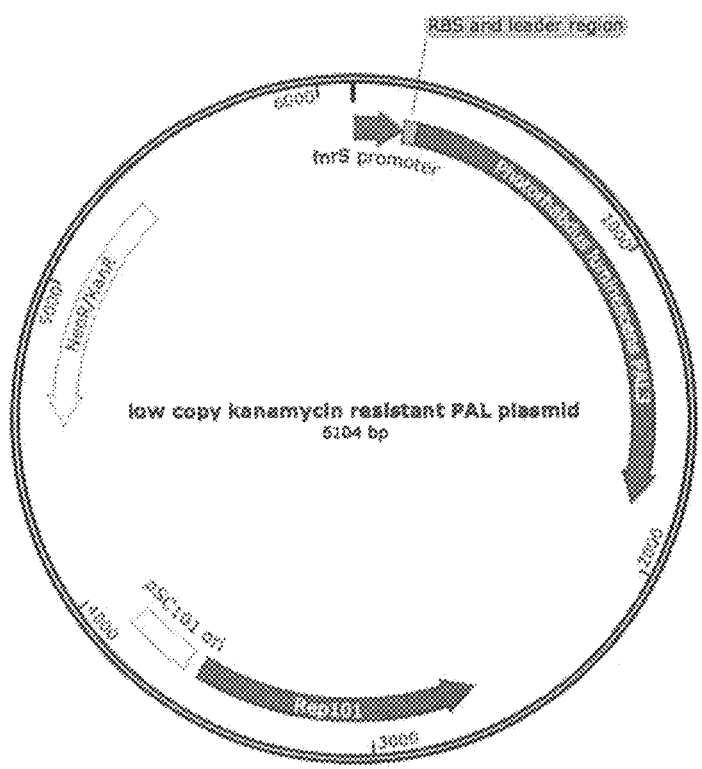
FIG. 12 depicts the gene organization of an exemplary construct, comprising a cloned PAL3 gene under the control of an FNR promoter sequence, on a low-copy, kanamycin-resistant plasmid (pSC101 origin of replication, (FIG. 12A). Under anaerobic conditions, PAL3 degrades phenylalanine to non-toxic trans-cinnamate.
FIG. 12B depicts an additional copy of the endogenous *E. coli* high affinity phenylalanine transporter, pheP, driven by the PfnrS promoter and inserted into the lacZ locus on the Nissle chromosome.
Figure 12B:
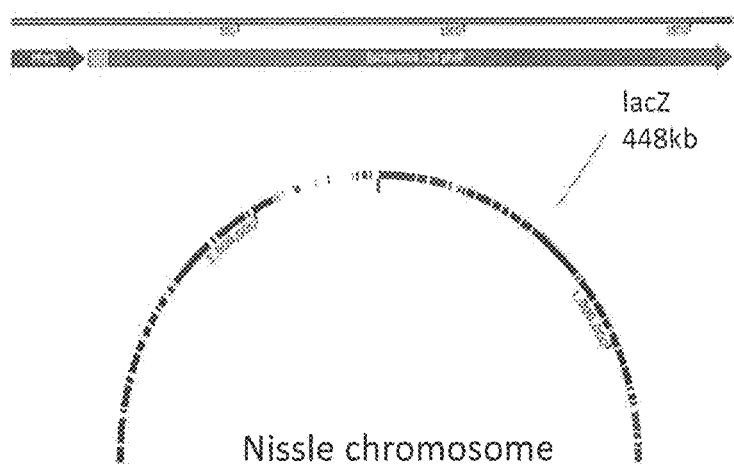

In some embodiments, a Hemolysin-based Secretion System is used to secrete the molecule of interest, e.g., e.g., PAH, PAL or LAAD. Type I Secretion systems offer the advantage of translocating their passenger peptide directly from the cytoplasm to the extracellular space, obviating the two-step process of other secretion types. FIG. 11 shows the alpha-hemolysin (HlyA) of uropathogenic *Escherichia coli.* This pathway uses HlyB, an ATP-binding cassette transporter; HlyD, a membrane fusion protein; and TolC, an outer membrane protein. The assembly of these three proteins forms a channel through both the inner and outer membranes. Natively, this channel is used to secrete HlyA, however, to secrete the therapeutic peptide of the present disclosure, the secretion signal-containing C-terminal portion of HlyA is fused to the C-terminal portion of a therapeutic peptide (star) to mediate secretion of this peptide.

In alternate embodiments, the genetically engineered bacteria further comprise a non-native single membrane-spanning secretion system. Single membrane-spanning exporters may act as a component of a secretion system, or may export substrates independently. Such exporters include, but are not limited to, ATP-binding cassette translocases, flagellum/virulence-related translocases, conjugation-related translocases, the general secretory system (e.g., the SecYEG complex in *E. coli*), the accessory secretory system in mycobacteria and several types of Gram-positive bacteria (e.g., *Bacillus anthracis, Lactobacillus johnsonii, Corynebacterium glutamicum, Streptococcus gordonii, Staphylococcus aureus*), and the twin-arginine translocation (TAT) system (Saier, 2006; Rigel and Braunstein, 2008; Albiniak et al., 2013). It is known that the general secretory and TAT systems can both export substrates with cleavable N-terminal signal peptides into the periplasm, and have been explored in the context of biopharmaceutical production. The TAT system may offer particular advantages, however, in that it is able to transport folded substrates, thus eliminating the potential for premature or incorrect folding. In certain embodiments, the genetically engineered bacteria comprise a TAT or a TAT-like system and are capable of secreting the protein(s) of interest or therapeutic protein(s), e.g., PAH, PAL or LAAD, from the bacterial cytoplasm. One of ordinary skill in the art would appreciate that the secretion systems disclosed herein may be modified to act in different species, strains, and subtypes of bacteria, and/or adapted to deliver different payloads.

In order to translocate a protein, e.g., therapeutic polypeptide, e.g., PAH, PAL or LAAD, to the extracellular space, the polypeptide must first be translated intracellularly, mobilized across the inner membrane and finally mobilized across the outer membrane. Many effector proteins (e.g., therapeutic polypeptides)—particularly those of eukaryotic origin—contain disulphide bonds to stabilize the tertiary and quaternary structures. While these bonds are capable of correctly forming in the oxidizing periplasmic compartment with the help of periplasmic chaperones, in order to translocate the polypeptide across the outer membrane the disulphide bonds must be reduced and the protein unfolded again.

One way to secrete properly folded proteins in gram-negative bacteria—particularly those requiring disulphide bonds—is to target the periplasm in a bacterium with a destabilized outer membrane. In this manner the protein is mobilized into the oxidizing environment and allowed to fold properly. In contrast to orchestrated extracellular secretion systems, the protein is then able to escape the periplasmic space in a correctly folded form by membrane leakage. These "leaky" gram-negative mutants are therefore capable of secreting bioactive, properly disulphide-bonded polypeptides. In some embodiments, the genetically engineered bacteria have a "leaky" or destabilized outer membrane. Destabilizing the bacterial outer membrane to induce leakiness can be accomplished by deleting or mutagenizing genes responsible for tethering the outer membrane to the rigid peptidoglycan skeleton, including for example, lpp, ompC, ompA, ompF, tolA, tolB, pal, degS, degP, and nlpI. Lpp is the most abundant polypeptide in the bacterial cell existing at ~500,000 copies per cell and functions as the primary 'staple' of the bacterial cell wall to the peptidoglycan. Silhavy, T. J., Kahne, D. & Walker, S. The bacterial cell envelope. *Cold Spring Harb Perspect Biol* 2, a000414 (2010). TolA-PAL and OmpA complexes function similarly to Lpp and are other deletion targets to generate a leaky phenotype. Additionally, leaky phenotypes have been observed when periplasmic proteases are deactivated. The periplasm is very densely packed with protein and therefore encode several periplasmic proteins to facilitate protein turnover. Removal of periplasmic proteases such as degS, degP or nlpI can induce leaky phenotypes by promoting an excessive build-up of periplasmic protein. Mutation of the proteases can also preserve the effector polypeptide by preventing targeted degradation by these proteases. Moreover, a combination of these mutations may synergistically enhance the leaky phenotype of the cell without major sacrifices in cell viability. Thus, in some embodiments, the engineered bacteria have one or more deleted or mutated membrane genes. In some embodiments, the engineered bacteria have a deleted or mutated lpp gene. In some embodiments, the engineered bacteria have one or more deleted or mutated gene(s), selected from ompA, ompA, and ompF genes. In some embodiments, the engineered bacteria have one or more deleted or mutated gene(s), selected from tolA, tolB, and pal genes. In some embodiments, the engineered bacteria have one or more deleted or mutated periplasmic protease genes. In some embodiments, the engineered bacteria have one or more deleted or mutated periplasmic protease genes selected from degS, degP, and nlpI. In some embodiments, the engineered bacteria have one or more deleted or mutated gene(s), selected from lpp, ompA, ompA, ompF, tolA, tolB, pal, degS, degP, and nlpI genes.

To minimize disturbances to cell viability, the leaky phenotype can be made inducible by placing one or more membrane or periplasmic protease genes, e.g., selected from lpp, ompA, ompA, ompF, tolA, tolB, pal, degS, degP, and nlpI, under the control of an inducible promoter. For example, expression of lpp or other cell wall stability protein or periplasmic protease can be repressed in conditions where the therapeutic polypeptide needs to be delivered (secreted). For instance, under inducing conditions a transcriptional repressor protein or a designed antisense RNA can be expressed which reduces transcription or translation of a target membrane or periplasmic protease gene. Conversely, overexpression of certain peptides can result in a destabilized phenotype, e.g., overexpression of colicins or the third topological domain of TolA, wherein peptide overexpression can be induced in conditions in which the therapeutic polypeptide needs to be delivered (secreted). These sorts of strategies would decouple the fragile, leaky phenotypes from biomass production. Thus, in some embodiments, the engineered bacteria have one or more membrane and/or periplasmic protease genes under the control of an inducible promoter.

Table 15 and Table 16 list secretion systems for Gram positive bacteria and Gram negative bacteria. These can be used to secrete polypeptides, proteins of interest or therapeutic protein(s) from the engineered bacteria, which are reviewed in Milton H. Saier, Jr. Microbe/Volume 1, Number 9, 2006 "Protein Secretion Systems in Gram-Negative Bacteria Gram-negative bacteria possess many protein secretion-membrane insertion systems that apparently evolved independently", the contents of which is herein incorporated by reference in its entirety.

TABLE 15

Secretion systems for gram positive bacteria

| Bacterial Strain | Relevant Secretion System |
|---|---|
| C. novyi-NT (Gram+) | Sec pathway |
| | Twin-arginine (TAT) pathway |
| C. butryicum (Gram+) | Sec pathway |
| | Twin-arginine (TAT) pathway |
| Listeria monocytogenes (Gram+) | Sec pathway |
| | Twin-arginine (TAT) pathway |

TABLE 16

Secretion Systems for Gram negative bacteria
Protein secretary pathways (SP) in gram-negative bacteria and their descendants

| Type (Abbreviation) | Name | TC #2 | Bacteria | Archaea | Eukarya | # Proteins/ System | Energy Source |
|---|---|---|---|---|---|---|---|
| IMPS - Gram-negative bacterial inner membrane channel-forming translocases | | | | | | | |
| ABC (SIP) | ATP binding cassette translocase | 3.A.1 | + | + | + | 3-4 | ATP |
| SEC (IISP) | General secretory translocase | 3.A.5 | + | + | + | ~12 | GTP OR ATP +PMF |
| Fla/Path (IIISP) | Flagellum/virulence-related translocase | 3.A.6 | + | − | − | >10 | ATP |
| Conj (IVSP) | Conjugation-related translocase | 3.A.7 | + | − | − | >10 | ATP |
| Tat (IISP) | Twin-arginine targeting translocase | 2.A.64 | + | + | + (chloroplasts) | 2-4 | PMF |
| Oxa1 (YidC) | Cytochrome oxidase biogenesis family | 2.A.9 | + | + | + (mitochondria chloroplasts) | 1 or PMF | None |
| MscL | Large conductance mechanosensitive channel family | 1.A.22 | + | + | + | 1 | None |
| Holins | Holin functional superfamily | 1.E.1• 21 | + | − | − | 1 | None |
| Eukaryotic Organelles | | | | | | | |
| MPT | Mitochondrial protein translocase | 3.A.B | − | − | + (mitochondrial) | ≥20 | ATP |
| CEPT | Chloroplast envelope protein translocase | 3.A.9 | (+) | − | + (chloroplasts) | ≥3 | GTP |
| Bcl-2 | Eukaryotic Bcl-2 family (programmed cell death) | 1.A.21 | − | − | + | 1? | None |
| Gram-negative bacterial outer membrane channel-forming translocases | | | | | | | |
| MTB (IISP) | Main terminal branch of the general secretory translocase | 3.A.15 | +[b] | − | − | ~14 | ATP; PMF |
| FUP AT-1 | Fimbrial usher protein Autotransporter-1 | 1.B.11 1.B.12 | +[b] +[b] | − − | − − | 1 1 | None None |
| AT-2 OMF (ISP) | Autotransporter-2 | 1.B.40 1.B.17 | +[b] +[b] | − − | − +(?) | 1 1 | None None |
| TPS Secretin (IISP and IISP) | | 1.B.20 1.B.22 | + +[b] | − − | + − | 1 1 | None None |
| OmpIP | Outer membrane insertion porin | 1.B.33 | + | − | + (mitochondria; chloroplasts) | ≥4 | None? |

In some embodiments, the genetically engineered bacterial comprise a native or non-native secretion system described herein for the secretion of a PME, e.g., PAH, PAL and/or LAAD. In some embodiments, the secretion system is selected from the modified type III flagellar, type I (e.g., hemolysin secretion system), type II, type IV, type V, type VI, and type VII secretion systems, resistance-nodulation-division (RND) multi-drug efflux pumps, a single membrane secretion system, Sec and, TAT secretion systems.

In some embodiments, the PMEs secreted by the genetically engineered bacteria are modified to increase resistance to proteases. For example, in some embodiments, the one or more PME administered is modified as described in Sakissian et al., 2011, Mol Genet Metab. 2011 November; 104(3): 249-254, the contents of which is herein incorporated by reference in its entirety. In some embodiments, the secreted PAL is Av-p.C503S/p.C565S/p.F18A PAL. In some embodiments, the secreted PAL is PEG-Av-p.C503 S/p.C565S/p.F18A PAL.

In some embodiments, the one or more PMEs for secretion are under the control of an inducible promoter, as described herein. In one example, the one or more PMEs are under the control of the FNR promoter and are produced and secreted under anaerobic conditions. In some embodiments, the PMEs for secretion are under the control of the ParaBAD promoter. In some embodiments, the PMEs for secretion are under the control of a constitutive promoter.

In some embodiments in which the one or more PMEs are secreted or exported from the microorganism, the engineered microorganism comprises gene sequence(s) that includes a secretion tag. In some embodiments, the PME(s) include a "secretion tag" of either RNA or peptide origin to direct the PME(s) to specific secretion systems. For example, a secretion tag for the Type I Hemolysin secretion system is encoded in the C-terminal 53 amino acids of the alpha hemolysin protein (HlyA). HlyA secretion signal.

HlyB inserts into inner membrane to form a pore, HlyD aligns HlyB with TolC (outer membrane pore) thereby forming a channel through inner and outer membrane. The C-terminal secretion tag can be removed by either an autocatalytic or protease-catalyzed e.g., OmpT cleavage thereby releasing the PME(s) into the extracellular milieu.

The Type V Auto-secretion System utilizes an N-terminal Sec-dependent peptide tag (inner membrane) and C-terminal tag (outer-membrane). This uses Sec-system to get from cytoplasm to periplasm. C-terminal tag then inserts into the outer membrane forming a pore through which the "passenger protein" threads through. Once across the outer membrane, the passenger (anti-cancer molecule) is released from the membrane-embedded C-terminal tag by either an autocatalytic, intein-like mechanism or via a membrane-bound protease (I.e., OmpT). The N-terminal tag is removed by the Sec system. Thus, in some embodiments, the secretion system is able to remove this tag before secreting the PME(s), e.g., PAL, PAH, and/or LAAD from the engineered bacteria. In the Type V auto-secretion-mediated secretion the N-terminal peptide secretion tag is removed upon translocation of the "passenger" peptide from the cytoplasm into the periplasmic compartment by the native Sec system. Further, once the auto-secretor is translocated across the outer membrane the C-terminal secretion tag can be removed by either an autocatalytic or protease-catalyzed e.g., OmpT cleavage thereby releasing the anti-cancer molecule(s) into the extracellular milieu.

In the Flagellar modified Type III Secretion, the tag is encoded in 5'untranslated region of the mRNA and thus there is no peptide tag to cleave/remove. This modified system does not contain the "syringe" portion and instead uses the basal body of the flagella structure as the pore to translocate across both membranes and out through the forming flagella. If the fliC/fliD genes (encoding the flagella "tail"/whip) are disrupted the flagella cannot fully form and this promotes overall secretion. In some embodiments, the tail portion can be removed entirely. In the Type III traditional secretion system, the basal body closely resembles the flagella, however, instead of a "tail"/whip, the traditional T3SS has a syringe to inject the passenger proteins into host cells. The secretion tag is encoded by an N-terminal peptide (lengths vary and there are several different tags, see PCT/US14/020972). The N-terminal tag is not removed from the polypeptides in this secretion system.

In some embodiments the PME contains expressed as fusion protein with the 53 amino acids of the C termini of alpha-hemolysin (hlyA) of E. coli CFT073 (C terminal secretion tag).

Oxygen Consuming Enzymes

LAAD catalytic activity is dependent on oxygen, and therefore may not be active in anaerobic environments in the intestine, e.g., the colon. Oxygen is present in more proximal compartments of the GI tract.

The oxygen tension as measured in healthy mice is shown in Table 17. He et al., Proc Natl Acad Sci USA. 1999 Apr. 13; 96(8):4586-91; "Noninvasive measurement of anatomic structure and intraluminal oxygenation in the gastrointestinal tract of living mice with spatial and spectral EPR imaging", the contents of which is herein incorporated by reference in its entirety. A marked oxygen gradient from the proximal to the distal GI tract. As noted by He et al., the observed oxygen gradient seen along the GI tract can be explained by a combination of processes. Without wishing to be bound by theory, food, when swallowed, is initially equilibrated with the oxygen tension of ambient room air. On passage to the stomach and later the small intestine, the oxygen levels may fall as oxygen diffuses across the mucosal membrane. A gradual process of equilibration with the capillary levels of oxygen (i.e., 5-10 torr; ref. 9) may occur. On passage to the colon, with its heavy bacterial colonization, further decreases in oxygenation occur. Finally, the lumen of the distal colon displays marked hypoxia, as expected, based on the abundance of anaerobic bacteria at this site.

TABLE 17

Oxygen Tension in Gastrointestinal Tract Compartments

| Compartment | Oxygen Tension |
| --- | --- |
| Ambient Air | 159 Torr |
| stomach | ~60 torr |
| duodenum and first part of jejunum | (~30 torr); ~20% oxygen in ambient air |
| ileum | (~10 torr); ~6% oxygen in ambient air |
| colon | (<2 torr) |

Figure 25A:
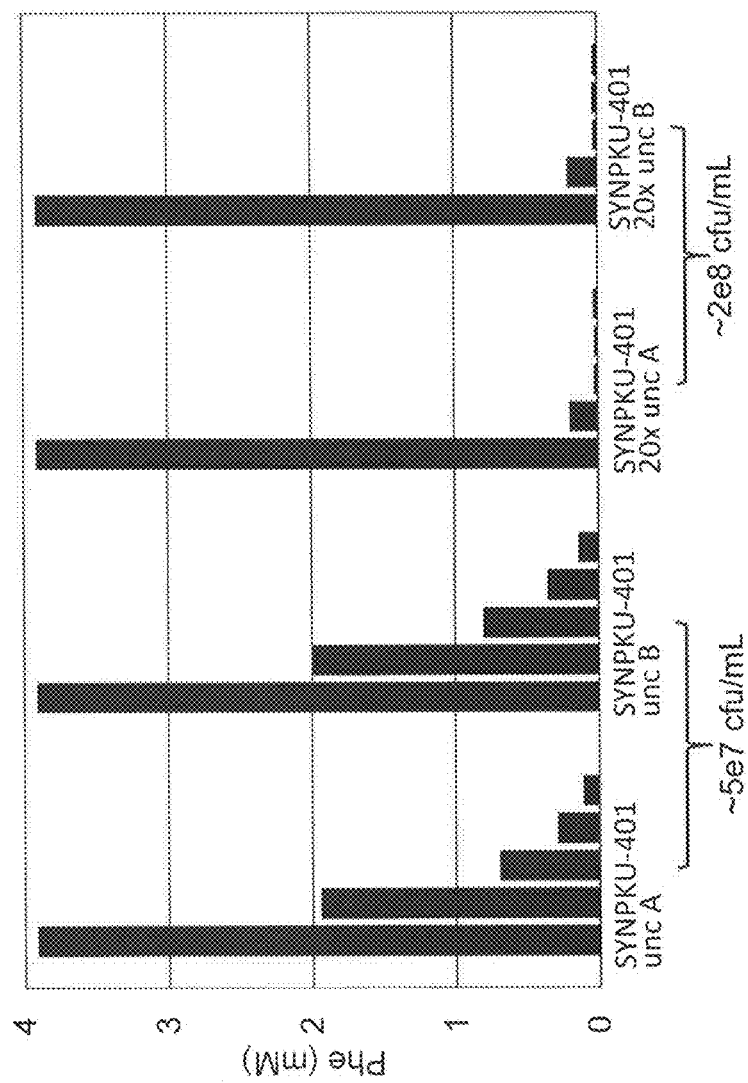
FIGS. 25A and 25B depict phenylalanine concentrations in cultures of a synthetic probiotic strain, SYN-PKU401, which comprises a high copy pUC57-plasmid with LAAD driven by a Tet inducible promoter, cells were grown in flasks shaking at 37 C, and induced with TCA at early log phase for a duration of 2 hours. Cells were spun down and re-suspended in assay buffer containing phenylalanine. Cells were measured at various cell concentrations and at varying oxygen levels. Cells were either incubated aerobically (1 ml) in a 14 ml culture tube, shaking at 250 rpm. For microaerobic conditions, cells (1 ml) were incubated in a 1.7 ml conical tube without shaking. Cells were incubated anaerobically in a Coy anaerobic chamber supplying 90% N2, 5% CO2, and 5% H2. Aliquots were removed from cell assays every 30 min for 2 hrs for phenylalanine quantification by mass spectrometry.
Figure 25B:
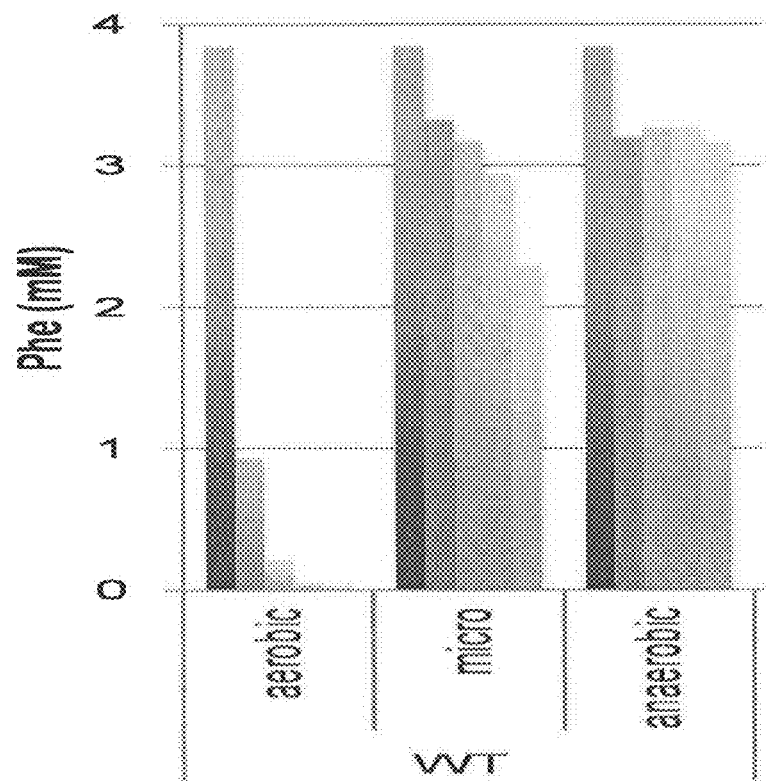

As shown in FIG. 25B, LAAD activity is retained in microaerobic conditions, albeit at lower levels than under aerobic conditions (FIG. 25A and FIG. 25B). LAAD therefore may be active in the more proximal areas of the intestine, such as stomach, duodenum, jejunum, and ileum. It is contemplated as part of this disclosure that LAAD expressed by the genetically engineered bacteria may advantageously be active in a different compartment than PAL, which may be expressed in the colon if under the control of an FNR promoter. In one embodiment, the genetically engineered bacteria express two enzymes, which have different oxygen requirements and/or are induced under different oxygen conditions, such that an PME is expressed and active throughout the entire gastrointestinal system. For example, the first enzyme, e.g., LAAD, which is dependent on the presence of oxygen, is expressed in one or more of stomach, duodenum and ileum under the control of a constitutive or inducible promoter (such as ParaBAD), and the second enzyme, e.g., PAL, is expressed in the colon under the control of an FNR promoter.

Several strategies can be employed to further increase LAAD activity under oxygen limiting conditions. For example, the activity of other enzymes that consume large amounts of oxygen can be reduced or extinguished. One such enzyme is NADH dehydrogenase. E. coli has two NADH dehydrogenases; nuo and ndh2, and is has been shown that knock out of both of these enzymes reduces oxygen consumption by 80%. In some embodiments, additional measures are taken to conserve limiting oxygen, i.e., to allow LAAD to function under lower exogenous oxygen conditions in the genetically engineered bacteria expressing LAAD. In some embodiments, the genetically engineered bacteria further comprise a mutation in one or more genes involved in oxygen consumption. In some embodiments, one or both E. coli NADH dehydrogenases are knocked out. In some embodiments, the knocked out NADH dehydrogenase is nuo. In some embodiments the knocked out NADH dehydrogenase is ndh2. In some embodiments nuo and ndh2 are knocked out. Other enzymes involved in E. coli oxygen metabolism may also be knocked out, including enzymes in the respiratory chain, such as cydB (a subunit of high affinity terminal oxidase), cydD (an enzyme required to make cytochrome D), and cyoABC (subunits of low affinity cytochrome oxidase). In some embodiments, the genetically engineered bacteria harbor a knock out mutation/deletion in one more genes selected from cydB, cydD, and cyoABC.

In one embodiment, the one or more PME encoded by the genetically engineered bacteria are expressed and show activity in the stomach. In one embodiment, the one or more PME encoded by the genetically engineered bacteria are expressed and show activity in the duodenum. In one embodiment, the one or more PME encoded by the genetically engineered bacteria are expressed and show activity in the jejunum. In one embodiment, the one or more PME encoded by the genetically engineered bacteria are expressed and show activity in the ileum. In one embodiment, the one or more PME encoded by the genetically engineered bacteria are expressed and show activity in the colon.

Essential Genes and Auxotrophs

As used herein, the term "essential gene" refers to a gene that is necessary for cell growth and/or survival. Bacterial essential genes are well known to one of ordinary skill in the art, and can be identified by directed deletion of genes and/or random mutagenesis and screening (see, e.g., Zhang and Lin, "DEG 5.0, a database of essential genes in both prokaryotes and eukaryotes," Nucl Acids Res, 2009; 37:D455-D458 and Gerdes et al., "Essential genes on metabolic maps," Curr Opin Biotechnol, 2006; 17(5):448-456, the entire contents of each of which are expressly incorporated herein by reference).

An "essential gene" may be dependent on the circumstances and environment in which an organism lives. For example, a mutation of, modification of, or excision of an essential gene may result in the genetically engineered bacteria of the disclosure becoming an auxotroph. An auxotrophic modification is intended to cause bacteria to die in the absence of an exogenously added nutrient essential for survival or growth because they lack the gene(s) necessary to produce that essential nutrient. In some embodiments, any of the genetically engineered bacteria described herein also comprise a deletion or mutation in a gene required for cell survival and/or growth. In one embodiment, the essential gene is a DNA synthesis gene, for example, thyA. In another embodiment, the essential gene is a cell wall synthesis gene, for example, dapA. In yet another embodiment, the essential gene is an amino acid gene, for example, serA or MetA. Any gene required for cell survival and/or growth may be targeted, including but not limited to, cysE, glnA, ilvD, leuB, lysA, serA, metA, glyA, hisB, ilvA, pheA, proA, thrC, trpC, tyrA, thyA, uraA, dapA, dapB, dapD, dapE, dapF, flhD, metB, metC, proAB, and thi1, as long as the corresponding wild-type gene product is not produced in the bacteria. Table 18 lists exemplary bacterial genes which may be disrupted or deleted to produce an auxotrophic strain. These include, but are not limited to, genes required for oligonucleotide synthesis, amino acid synthesis, and cell wall synthesis.

TABLE 18

Non-limiting Examples of Bacterial Genes Useful for Generation of an Auxotroph

| Amino Acid | Oligonucleotide | Cell Wall |
|---|---|---|
| cysE | thyA | dapA |
| glnA | uraA | dapB |
| ilvD | | dapD |
| leuB | | dapE |
| lysA | | dapF |
| serA | | |
| metA | | |
| glyA | | |
| hisB | | |
| ilvA | | |
| pheA | | |
| proA | | |
| thrC | | |
| trpC | | |
| tyrA | | |

Table 19 shows the survival of various amino acid auxotrophs in the mouse gut, as detected 24 hrs and 48 hrs post-gavage. These auxotrophs were generated using BW25113, a non-Nissle strain of E. coli.

TABLE 19

Survival of amino acid auxotrophs in the mouse gut

| Gene | AA Auxotroph | Pre-Gavage | 24 hours | 48 hours |
|---|---|---|---|---|
| argA | Arginine | Present | Present | Absent |
| cysE | Cysteine | Present | Present | Absent |
| glnA | Glutamine | Present | Present | Absent |
| glyA | Glycine | Present | Present | Absent |
| hisB | Histidine | Present | Present | Present |
| ilvA | Isoleucine | Present | Present | Absent |
| leuB | Leucine | Present | Present | Absent |
| lysA | Lysine | Present | Present | Absent |
| metA | Methionine | Present | Present | Present |
| pheA | Phenylalanine | Present | Present | Present |
| proA | Proline | Present | Present | Absent |
| serA | Serine | Present | Present | Present |
| thrC | Threonine | Present | Present | Present |
| trpC | Tryptophan | Present | Present | Present |
| tyrA | Tyrosine | Present | Present | Present |
| ilvD | Valine/Isoleucine/Leucine | Present | Present | Absent |
| thyA | Thiamine | Present | Absent | Absent |
| uraA | Uracil | Present | Absent | Absent |
| flhD | FlhD | Present | Present | Present |

For example, thymine is a nucleic acid that is required for bacterial cell growth; in its absence, bacteria undergo cell death. The thyA gene encodes thymidylate synthetase, an enzyme that catalyzes the first step in thymine synthesis by converting dUMP to dTMP (Sat et al., 2003). In some embodiments, the bacterial cell of the disclosure is a thyA auxotroph in which the thyA gene is deleted and/or replaced with an unrelated gene. A thyA auxotroph can grow only when sufficient amounts of thymine are present, e.g., by adding thymine to growth media in vitro, or in the presence of high thymine levels found naturally in the human gut in vivo. In some embodiments, the bacterial cell of the disclosure is auxotrophic in a gene that is complemented when the bacterium is present in the mammalian gut. Without sufficient amounts of thymine, the thyA auxotroph dies. In some embodiments, the auxotrophic modification is used to ensure that the bacterial cell does not survive in the absence of the auxotrophic gene product (e.g., outside of the gut).

Diaminopimelic acid (DAP) is an amino acid synthetized within the lysine biosynthetic pathway and is required for bacterial cell wall growth (Meadow et al., 1959; Clarkson et al., 1971). In some embodiments, any of the genetically engineered bacteria described herein is a dapD auxotroph in which dapD is deleted and/or replaced with an unrelated gene. A dapD auxotroph can grow only when sufficient amounts of DAP are present, e.g., by adding DAP to growth media in vitro, or in the presence of high DAP levels found naturally in the human gut in vivo. Without sufficient amounts of DAP, the dapD auxotroph dies. In some embodiments, the auxotrophic modification is used to ensure that the bacterial cell does not survive in the absence of the auxotrophic gene product (e.g., outside of the gut).

In other embodiments, the genetically engineered bacterium of the present disclosure is a uraA auxotroph in which uraA is deleted and/or replaced with an unrelated gene. The uraA gene codes for UraA, a membrane-bound transporter that facilitates the uptake and subsequent metabolism of the pyrimidine uracil (Andersen et al., 1995). A uraA auxotroph can grow only when sufficient amounts of uracil are present, e.g., by adding uracil to growth media in vitro, or in the presence of high uracil levels found naturally in the human gut in vivo. Without sufficient amounts of uracil, the uraA auxotroph dies. In some embodiments, auxotrophic modifications are used to ensure that the bacteria do not survive in the absence of the auxotrophic gene product (e.g., outside of the gut).

In complex communities, it is possible for bacteria to share DNA. In very rare circumstances, an auxotrophic bacterial strain may receive DNA from a non-auxotrophic strain, which repairs the genomic deletion and permanently rescues the auxotroph. Therefore, engineering a bacterial strain with more than one auxotroph may greatly decrease the probability that DNA transfer will occur enough times to rescue the auxotrophy. In some embodiments, the genetically engineered bacteria of the invention comprise a deletion or mutation in two or more genes required for cell survival and/or growth.

Other examples of essential genes include, but are not limited to, yhbV, yagG, hemB, secD, secF, ribD, ribE, thiL, dxs, ispA, dnaX, adk, hemH, lpxH, cysS, fold, rplT, infC, thrS, nadE, gapA, yeaZ, aspS, argS, pgsA, yefM, metG, folE, yejM, gyrA, nrdA, nrdB, folC, accD, fabB, gltX, ligA, zipA, dapE, dapA, der, hisS, ispG, suhB, tadA, acpS, era, rnc, ftsB, eno, pyrG, chpR, lgt, fbaA, pgk, yqgD, metK, yqgF, plsC, ygiT, pare, ribB, cca, ygjD, tdcF, yraL, yihA, ftsN, murI, murB, birA, secE, nusG, rplJ, rplL, rpoB, rpoC, ubiA, plsB, lexA, dnaB, ssb, alsK, groS, psd, orn, yjeE, rpsR, chpS, ppa, valS, yjgP, yjgQ, dnaC, ribF, lspA, ispH, dapB, folA, imp, yabQ, ftsL, ftsI, murE, murF, mraY, murD, ftsW, murG, murC, ftsQ, ftsA, ftsZ, lpxC, secM, secA, can, folK, hemL, yadR, dapD, map, rpsB, infB, nusA, ftsH, obgE, rpmA, rplU, ispB, murA, yrbB, yrbK, yhbN, rpsI, rplM, degS, mreD, mreC, mreB, accB, accC, yrdC, def, fmt, rplQ, rpoA, rpsD, rpsK, rpsM, entD, mrdB, mrdA, nadD, hlepB, rpoE, pssA, yfiO, rplS, trmD, rpsP, ffh, grpE, yljB, csrA, ispF, ispD, rplW, rplD, rplC, rpsD, fusA, rpsG, rpsL, trpS, yrfF, asd, rpoH, ftsX, ftsE, ftsY, frr, dxr, ispU, rfaK, kdtA, coaD, rpmB, dfp, dut, gmk, spot, gyrB, dnaN, dnaA, rpmH, rnpA, yidC, tnaB, glmS, glmU, wzyE, hemD, hemC, yigP, ubiB, ubiD, hemG, secY, rplO, rpmD, rpsE, rplR, rplF, rpsH, rpsN, rplE, rplX, rplN, rpsQ, rpmC, rplP, rpsC, rplV, rpsS, rplB, cdsA, yaeL, yaeT, lpxD, fabZ, lpxA, lpxB, dnaE, accA, tilS, proS, yafF, tsf, pyrH, olA, rlpB, leuS, lnt, glnS, fidA, cydA, infA, cydC, ftsK, lolA, serS, rpsA, msbA, lpxK, kdsB, mukF, mukE, mukB, asnS, fabA, mviN, me, yceQ, fabD, fabG, acpP, tmk, holB, lolC, lolD, lolE, purB, ymfK, minE, mind, pth, rsA, ispE, lolB, hemA, prfA, prmC, kdsA, topA, ribA, fabI, racR, dicA, ydfB, tyrS, ribC, ydiL, pheT, pheS, yhhQ, bcsB, glyQ, yibJ, and gpsA. Other essential genes are known to those of ordinary skill in the art.

In some embodiments, the genetically engineered bacterium of the present disclosure is a synthetic ligand-dependent essential gene (SLiDE) bacterial cell. SLiDE bacterial cells are synthetic auxotrophs with a mutation in one or more essential genes that only grow in the presence of a particular ligand (see Lopez and Anderson, "Synthetic Auxotrophs with Ligand-Dependent Essential Genes for a BL21 (DE3) Biosafety Strain," ACS Synth Biol 2015; 4(12):1279-1286, the entire contents of which are expressly incorporated herein by reference).

In some embodiments, the SLiDE bacterial cell comprises a mutation in an essential gene. In some embodiments, the essential gene is selected from the group consisting of pheS, dnaN, tyrS, metG, and adk. In some embodiments, the essential gene is dnaN comprising one or more of the following mutations: H191N, R240C, I317S, F319V, L340T, V3471, and S345C. In some embodiments, the essential gene is dnaN comprising the mutations H191N, R240C, I317S, F319V, L340T, V3471, and S345C. In some embodiments, the essential gene is pheS comprising one or more of the following mutations: F125G, P183T, P184A, R186A, and I188L. In some embodiments, the essential gene is pheS comprising the mutations F125G, P183T, P184A, R186A, and I188L. In some embodiments, the essential gene is tyrS comprising one or more of the following mutations: L36V, C38A, and F40G. In some embodiments, the essential gene is tyrS comprising the mutations L36V, C38A, and F40G. In some embodiments, the essential gene is metG comprising one or more of the following mutations: E45Q, N47R, I49G, and A51C. In some embodiments, the essential gene is metG comprising the mutations E45Q, N47R, I49G, and A51C. In some embodiments, the essential gene is adk comprising one or more of the following mutations: I4L, L5I, and L6G. In some embodiments, the essential gene is adk comprising the mutations I4L, L5I, and L6G.

In some embodiments, the genetically engineered bacterium is complemented by a ligand. In some embodiments, the ligand is selected from the group consisting of benzothiazole, indole, 2-aminobenzothiazole, indole-3-butyric acid, indole-3-acetic acid, and L-histidine methyl ester. For example, bacterial cells comprising mutations in metG (E45Q, N47R, I49G, and A51C) are complemented by benzothiazole, indole, 2-aminobenzothiazole, indole-3-butyric acid, indole-3-acetic acid, or L-histidine methyl ester. Bacterial cells comprising mutations in dnaN (H191N, R240C, I317S, F319V, L340T, V3471, and S345C) are complemented by benzothiazole, indole, or 2-aminobenzothiazole. Bacterial cells comprising mutations in pheS (F125G, P183T, P184A, R186A, and I188L) are complemented by benzothiazole or 2-aminobenzothiazole. Bacterial cells comprising mutations in tyrS (L36V, C38A, and F40G) are complemented by benzothiazole or 2-aminobenzothiazole. Bacterial cells comprising mutations in adk (I4L, L5I and L6G) are complemented by benzothiazole or indole.

In some embodiments, the genetically engineered bacterium comprises more than one mutant essential gene that renders it auxotrophic to a ligand. In some embodiments, the bacterial cell comprises mutations in two essential genes. For example, in some embodiments, the bacterial cell comprises mutations in tyrS (L36V, C38A, and F40G) and metG (E45Q, N47R, I49G, and A51C). In other embodiments, the bacterial cell comprises mutations in three essential genes. For example, in some embodiments, the bacterial cell comprises mutations in tyrS (L36V, C38A, and F40G), metG (E45Q, N47R, I49G, and A51C), and pheS (F125G, P183T, P184A, R186A, and I188L).

In some embodiments, the genetically engineered bacterium is a conditional auxotroph whose essential gene(s) is replaced using the arabinose system shown in FIGS. 43-47.

In some embodiments, the genetically engineered bacterium of the disclosure is an auxotroph and also comprises kill switch circuitry, such as any of the kill switch components and systems described herein. For example, the genetically engineered bacteria may comprise a deletion or mutation in an essential gene required for cell survival and/or growth, for example, in a DNA synthesis gene, for example, thyA, cell wall synthesis gene, for example, dapA and/or an amino acid gene, for example, serA or MetA and may also comprise a toxin gene that is regulated by one or more transcriptional activators that are expressed in response to an environmental condition(s) and/or signal(s) (such as the described arabinose system) or regulated by one or more recombinases that are expressed upon sensing an exogenous environmental condition(s) and/or signal(s) (such as the recombinase systems described herein). Other embodiments are described in Wright et al., "GeneGuard: A Modular Plasmid System Designed for Biosafety," ACS Synth Biol, 2015; 4(3):307-316, the entire contents of which are expressly incorporated herein by reference). In some embodiments, the genetically engineered bacterium of the disclosure is an auxotroph and also comprises kill switch circuitry, such as any of the kill switch components and systems described herein, as well as another biosecurity system, such a conditional origin of replication (Wright et al., 2015).

The addition of a Phe-auxotrophy may also have utility for increasing the rate of phenylalanine degradation. For example, the deletion of the pheA gene confers phenylalanine auxotrophy. By turning off endogenous bacterial phenylalanine production, this may drive increased uptake from the environment and also result in increased degradation of phenylalanine taken up from the environment.

Genetic Regulatory Circuits

In some embodiments, the genetically engineered bacteria comprise multi-layered genetic regulatory circuits for expressing the constructs described herein (see, e.g., U.S. Provisional Application No. 62/184,811, incorporated herein by reference in its entirety). The genetic regulatory circuits are useful to screen for mutant bacteria that produce a phenylalanine-metabolizing enzyme or rescue an auxotroph. In certain embodiments, the invention provides methods for selecting genetically engineered bacteria that produce one or more genes of interest.

In some embodiments, the invention provides genetically engineered bacteria comprising a gene or gene cassette for producing a phenylalanine-metabolizing enzyme (e.g., PAL or PAH) and a T7 polymerase-regulated genetic regulatory circuit. For example, the genetically engineered bacteria comprise a first gene encoding a T7 polymerase, wherein the first gene is operably linked to an FNR-responsive promoter; a second gene or gene cassette for producing a phenylalanine-metabolizing enzyme, wherein the second gene or gene cassette is operably linked to a T7 promoter that is induced by the T7 polymerase; and a third gene encoding an inhibitory factor, lysY, that is capable of inhibiting the T7 polymerase. In the presence of oxygen, FNR does not bind the FNR-responsive promoter, and the phenylalanine-metabolizing enzyme is not expressed. LysY is expressed constitutively (P-lac constitutive) and further inhibits T7 polymerase. In the absence of oxygen, FNR dimerizes and binds to the FNR-responsive promoter, T7 polymerase is expressed at a level sufficient to overcome lysY inhibition, and the phenylalanine-metabolizing enzyme is expressed. In some embodiments, the lysY gene is operably linked to an additional FNR binding site. In the absence of oxygen, FNR dimerizes to activate T7 polymerase expression as described above, and also inhibits lysY expression.

In some embodiments, the invention provides genetically engineered bacteria comprising a gene or gene cassette for producing a phenylalanine-metabolizing enzyme (e.g., PAL or PAH) and a protease-regulated genetic regulatory circuit. For example, the genetically engineered bacteria comprise a first gene encoding an mf-lon protease, wherein the first gene is operably linked to an FNR-responsive promoter; a second gene or gene cassette for producing a phenylalanine-metabolizing enzyme operably linked to a Tet regulatory region (TetO); and a third gene encoding an mf-lon degradation signal linked to a Tet repressor (TetR), wherein the TetR is capable of binding to the Tet regulatory region and repressing expression of the second gene or gene cassette. The mf-lon protease is capable of recognizing the mf-lon degradation signal and degrading the TetR. In the presence of oxygen, FNR does not bind the FNR-responsive promoter, the repressor is not degraded, and the phenylalanine-metabolizing enzyme is not expressed. In the absence of oxygen, FNR dimerizes and binds the FNR-responsive promoter, thereby inducing expression of the mf-lon protease. The mf-lon protease recognizes the mf-lon degradation signal and degrades the TetR, and the phenylalanine-metabolizing enzyme is expressed.

In some embodiments, the invention provides genetically engineered bacteria comprising a gene or gene cassette for producing a phenylalanine-metabolizing enzyme (e.g., PAL or PAH) and a repressor-regulated genetic regulatory circuit. For example, the genetically engineered bacteria comprise a first gene encoding a first repressor, wherein the first gene is operably linked to an FNR-responsive promoter; a second gene or gene cassette for producing a phenylalanine-metabolizing enzyme operably linked to a first regulatory region comprising a constitutive promoter; and a third gene encoding a second repressor, wherein the second repressor is capable of binding to the first regulatory region and repressing expression of the second gene or gene cassette. The third gene is operably linked to a second regulatory region comprising a constitutive promoter, wherein the first repressor is capable of binding to the second regulatory region and inhibiting expression of the second repressor. In the presence of oxygen, FNR does not bind the FNR-responsive promoter, the first repressor is not expressed, the second repressor is expressed, and the phenylalanine-metabolizing enzyme is not expressed. In the absence of oxygen, FNR dimerizes and binds the FNR-responsive promoter, the first repressor is expressed, the second repressor is not expressed, and the phenylalanine-metabolizing enzyme is expressed.

Examples of repressors useful in these embodiments include, but are not limited to, ArgR, TetR, ArsR, AscG, LacI, CscR, DeoR, DgoR, FruR, GalR, GatR, CI, LexA, RafR, QacR, and PtxS (US20030166191).

In some embodiments, the invention provides genetically engineered bacteria comprising a gene or gene cassette for producing a phenylalanine-metabolizing enzyme (e.g., PAL or PAH) and a regulatory RNA-regulated genetic regulatory circuit. For example, the genetically engineered bacteria comprise a first gene encoding a regulatory RNA, wherein the first gene is operably linked to an FNR-responsive promoter, and a second gene or gene cassette for producing a phenylalanine-metabolizing enzyme. The second gene or gene cassette is operably linked to a constitutive promoter and further linked to a nucleotide sequence capable of producing an mRNA hairpin that inhibits translation of the phenylalanine-metabolizing enzyme. The regulatory RNA is capable of eliminating the mRNA hairpin and inducing translation via the ribosomal binding site. In the presence of oxygen, FNR does not bind the FNR-responsive promoter, the regulatory RNA is not expressed, and the mRNA hairpin prevents the phenylalanine-metabolizing enzyme from being translated. In the absence of oxygen, FNR dimerizes and binds the FNR-responsive promoter, the regulatory RNA is expressed, the mRNA hairpin is eliminated, and the phenylalanine-metabolizing enzyme is expressed.

In some embodiments, the invention provides genetically engineered bacteria comprising a gene or gene cassette for producing a phenylalanine-metabolizing enzyme (e.g., PAL or PAH) and a CRISPR-regulated genetic regulatory circuit. For example, the genetically engineered bacteria comprise a Cas9 protein; a first gene encoding a CRISPR guide RNA, wherein the first gene is operably linked to an FNR-responsive promoter; a second gene or gene cassette for producing a phenylalanine-metabolizing enzyme, wherein the second gene or gene cassette is operably linked to a regulatory region comprising a constitutive promoter; and a third gene encoding a repressor operably linked to a constitutive promoter, wherein the repressor is capable of binding to the regulatory region and repressing expression of the second gene or gene cassette. The third gene is further linked to a CRISPR target sequence that is capable of binding to the CRISPR guide RNA, wherein said binding to the CRISPR guide RNA induces cleavage by the Cas9 protein and inhibits expression of the repressor. In the presence of oxygen, FNR does not bind the FNR-responsive promoter, the guide RNA is not expressed, the repressor is expressed, and the phenylalanine-metabolizing enzyme is not expressed. In the absence of oxygen, FNR dimerizes and binds the FNR-responsive promoter, the guide RNA is expressed, the repressor is not expressed, and the phenylalanine-metabolizing enzyme is expressed.

In some embodiments, the invention provides genetically engineered bacteria comprising a gene or gene cassette for producing a phenylalanine-metabolizing enzyme (e.g., PAL or PAH) and a recombinase-regulated genetic regulatory circuit. For example, the genetically engineered bacteria comprise a first gene encoding a recombinase, wherein the first gene is operably linked to an FNR-responsive promoter, and a second gene or gene cassette for producing a phenylalanine-metabolizing enzyme operably linked to a constitutive promoter. The second gene or gene cassette is inverted in orientation (3' to 5') and flanked by recombinase binding sites, and the recombinase is capable of binding to the recombinase binding sites to induce expression of the second gene or gene cassette by reverting its orientation (5' to 3'). In the presence of oxygen, FNR does not bind the FNR-responsive promoter, the recombinase is not expressed, the gene or gene cassette remains in the 3' to 5' orientation, and no functional phenylalanine-metabolizing enzyme is produced. In the absence of oxygen, FNR dimerizes and binds the FNR-responsive promoter, the recombinase is expressed, the gene or gene cassette is reverted to the 5' to 3' orientation, and a functional phenylalanine-metabolizing enzyme is produced (see, e.g., FIG. 42).

In some embodiments, the invention provides genetically engineered bacteria comprising a gene or gene cassette for producing a phenylalanine-metabolizing enzyme (e.g., PAL or PAH) and a polymerase- and recombinase-regulated genetic regulatory circuit. For example, the genetically engineered bacteria comprise a first gene encoding a recombinase, wherein the first gene is operably linked to an FNR-responsive promoter; a second gene or gene cassette for producing a phenylalanine-metabolizing enzyme operably linked to a T7 promoter; a third gene encoding a T7 polymerase, wherein the T7 polymerase is capable of binding to the T7 promoter and inducing expression of the phenylalanine-metabolizing enzyme. The third gene encoding the T7 polymerase is inverted in orientation (3' to 5') and flanked by recombinase binding sites, and the recombinase is capable of binding to the recombinase binding sites to induce expression of the T7 polymerase gene by reverting its orientation (5' to 3'). In the presence of oxygen, FNR does not bind the FNR-responsive promoter, the recombinase is not expressed, the T7 polymerase gene remains in the 3' to 5' orientation, and the phenylalanine-metabolizing enzyme is not expressed. In the absence of oxygen, FNR dimerizes and binds the FNR-responsive promoter, the recombinase is expressed, the T7 polymerase gene is reverted to the 5' to 3' orientation, and the phenylalanine-metabolizing enzyme is expressed (see, e.g., FIG. 43).

Synthetic gene circuits expressed on plasmids may function well in the short term but lose ability and/or function in the long term (Danino et al., 2015). In some embodiments, the genetically engineered bacteria comprise stable circuits for expressing genes of interest over prolonged periods. In some embodiments, the genetically engineered bacteria are capable of producing a phenylalanine-metabolizing enzyme (e.g., PAL or PAH) and further comprise a toxin-anti-toxin system that simultaneously produces a toxin (hok) and a short-lived anti-toxin (sok), wherein loss of the plasmid causes the cell to be killed by the long-lived toxin (Danino et al., 2015). In some embodiments, the genetically engineered bacteria further comprise alp7 from *B. subtilis* plasmid pL20 and produces filaments that are capable of pushing plasmids to the poles of the cells in order to ensure equal segregation during cell division (Danino et al., 2015).

Host-Plasmid Mutual Dependency

In some embodiments, the genetically engineered bacteria of the invention also comprise a plasmid that has been modified to create a host-plasmid mutual dependency. In certain embodiments, the mutually dependent host-plasmid platform is GeneGuard (Wright et al., 2015). In some embodiments, the GeneGuard plasmid comprises (i) a conditional origin of replication, in which the requisite replication initiator protein is provided in trans; (ii) an auxotrophic modification that is rescued by the host via genomic translocation and is also compatible for use in rich media; and/or (iii) a nucleic acid sequence which encodes a broad-spectrum toxin. The toxin gene may be used to select against plasmid spread by making the plasmid DNA itself disadvantageous for strains not expressing the anti-toxin (e.g., a wild-type bacterium). In some embodiments, the GeneGuard plasmid is stable for at least 100 generations without antibiotic selection. In some embodiments, the GeneGuard plasmid does not disrupt growth of the host. The GeneGuard plasmid is used to greatly reduce unintentional plasmid propagation in the genetically engineered bacteria of the invention.

The mutually dependent host-plasmid platform may be used alone or in combination with other biosafety mechanisms, such as those described herein (e.g., kill switches, auxotrophies). In some embodiments, the genetically engineered bacteria comprise a GeneGuard plasmid. In other embodiments, the genetically engineered bacteria comprise a GeneGuard plasmid and/or one or more kill switches. In other embodiments, the genetically engineered bacteria comprise a GeneGuard plasmid and/or one or more auxotrophies. In still other embodiments, the genetically engineered bacteria comprise a GeneGuard plasmid, one or more kill switches, and/or one or more auxotrophies.

Kill Switch

In some embodiments, the genetically engineered bacteria of the invention also comprise a kill switch (see, e.g., U.S. Provisional Application Nos. 62/183,935 and 62/263,329, incorporated herein by reference in their entireties). The kill switch is intended to actively kill genetically engineered bacteria in response to external stimuli. As opposed to an auxotrophic mutation where bacteria die because they lack an essential nutrient for survival, the kill switch is triggered by a particular factor in the environment that induces the production of toxic molecules within the microbe that cause cell death.

Bacteria comprising kill switches have been engineered for in vitro research purposes, e.g., to limit the spread of a biofuel-producing microorganism outside of a laboratory environment. Bacteria engineered for in vivo administration to treat a disease may also be programmed to die at a specific time after the expression and delivery of a heterologous gene or genes, for example, a phenylalanine-metabolizing enzyme, or after the subject has experienced the therapeutic effect. For example, in some embodiments, the kill switch is activated to kill the bacteria after a period of time following oxygen level-dependent expression of the phenylalanine-metabolizing enzyme (e.g., PAL or PAH) and/or the phenylalanine transporter gene. In some embodiments, the kill switch is activated in a delayed fashion following oxygen level-dependent expression of the phenylalanine-metabolizing enzyme and/or phenylalanine transporter gene. Alternatively, the bacteria may be engineered to die after the bacterium has spread outside of a disease site. Specifically, it may be useful to prevent long-term colonization of subjects by the microorganism, spread of the microorganism outside the area of interest (for example, outside the gut) within the subject, or spread of the microorganism outside of the subject into the environment (for example, spread to the environment through the stool of the subject). Examples of such toxins that can be used in kill switches include, but are not limited to, bacteriocins, lysins, and other molecules that cause cell death by lysing cell membranes, degrading cellular DNA, or other mechanisms. Such toxins can be used individually or in combination. The switches that control their production can be based on, for example, transcriptional activation (toggle switches; see, e.g., Gardner et al., 2000), translation (riboregulators), or DNA recombination (recombinase-based switches), and can sense environmental stimuli such as anaerobiosis or reactive oxygen species. These switches can be activated by a single environmental factor or may require several activators in AND, OR, NAND and NOR logic configurations to induce cell death. For example, an AND riboregulator switch is activated by tetracycline, isopropyl β-D-1-thiogalactopyranoside (IPTG), and arabinose to induce the expression of lysins, which permeabilize the cell membrane and kill the cell. IPTG induces the expression of the endolysin and holin mRNAs, which are then derepressed by the addition of arabinose and tetracycline. All three inducers must be present to cause cell death. Examples of kill switches are known in the art (Callura et al., 2010).

Kill switches can be designed such that a toxin is produced in response to an environmental condition or external signal (e.g., the bacteria is killed in response to an external cue) or, alternatively designed such that a toxin is produced once an environmental condition no longer exists or an external signal is ceased.

Thus, in some embodiments, the genetically engineered bacteria of the disclosure are further programmed to die after sensing an exogenous environmental signal, for example, in a low-oxygen environment. In some embodiments, the genetically engineered bacteria of the present disclosure comprise one or more genes encoding one or more recombinase(s), whose expression is induced in response to an environmental condition or signal and causes one or more recombination events that ultimately leads to the expression of a toxin which kills the cell. In some embodiments, the at least one recombination event is the flipping of an inverted heterologous gene encoding a bacterial toxin which is then constitutively expressed after it is flipped by the first recombinase. In one embodiment, constitutive expression of the bacterial toxin kills the genetically engineered bacterium. In these types of kill switch systems once the engineered bacterial cell senses the exogenous environmental condition and expresses the heterologous gene of interest, the recombinant bacterial cell is no longer viable.

In another embodiment in which the genetically engineered bacteria of the present disclosure express one or more recombinase(s) in response to an environmental condition or signal causing at least one recombination event, the genetically engineered bacterium further expresses a heterologous gene encoding an anti-toxin in response to an exogenous environmental condition or signal. In one embodiment, the at least one recombination event is flipping of an inverted heterologous gene encoding a bacterial toxin by a first recombinase. In one embodiment, the inverted heterologous gene encoding the bacterial toxin is located between a first forward recombinase recognition sequence and a first reverse recombinase recognition sequence. In one embodiment, the heterologous gene encoding the bacterial toxin is constitutively expressed after it is flipped by the first recombinase. In one embodiment, the anti-toxin inhibits the activity of the toxin, thereby delaying death of the genetically engineered bacterium. In one embodiment, the genetically engineered bacterium is killed by the bacterial toxin when the heterologous gene encoding the anti-toxin is no longer expressed when the exogenous environmental condition is no longer present.

In another embodiment, the at least one recombination event is flipping of an inverted heterologous gene encoding a second recombinase by a first recombinase, followed by the flipping of an inverted heterologous gene encoding a bacterial toxin by the second recombinase. In one embodiment, the inverted heterologous gene encoding the second recombinase is located between a first forward recombinase recognition sequence and a first reverse recombinase recognition sequence. In one embodiment, the inverted heterologous gene encoding the bacterial toxin is located between a second forward recombinase recognition sequence and a second reverse recombinase recognition sequence. In one embodiment, the heterologous gene encoding the second recombinase is constitutively expressed after it is flipped by the first recombinase. In one embodiment, the heterologous gene encoding the bacterial toxin is constitutively expressed after it is flipped by the second recombinase. In one embodiment, the genetically engineered bacterium is killed by the bacterial toxin. In one embodiment, the genetically engineered bacterium further expresses a heterologous gene encoding an anti-toxin in response to the exogenous environmental condition. In one embodiment, the anti-toxin inhibits the activity of the toxin when the exogenous environmental condition is present, thereby delaying death of the genetically engineered bacterium. In one embodiment, the genetically engineered bacterium is killed by the bacterial toxin when the heterologous gene encoding the anti-toxin is no longer expressed when the exogenous environmental condition is no longer present.

In one embodiment, the at least one recombination event is flipping of an inverted heterologous gene encoding a second recombinase by a first recombinase, followed by flipping of an inverted heterologous gene encoding a third recombinase by the second recombinase, followed by flipping of an inverted heterologous gene encoding a bacterial toxin by the third recombinase.

In one embodiment, the at least one recombination event is flipping of an inverted heterologous gene encoding a first excision enzyme by a first recombinase. In one embodiment, the inverted heterologous gene encoding the first excision enzyme is located between a first forward recombinase recognition sequence and a first reverse recombinase recognition sequence. In one embodiment, the heterologous gene encoding the first excision enzyme is constitutively expressed after it is flipped by the first recombinase. In one embodiment, the first excision enzyme excises a first essential gene. In one embodiment, the programmed recombinant bacterial cell is not viable after the first essential gene is excised.

In one embodiment, the first recombinase further flips an inverted heterologous gene encoding a second excision enzyme. In one embodiment, the inverted heterologous gene encoding the second excision enzyme is located between a second forward recombinase recognition sequence and a second reverse recombinase recognition sequence. In one embodiment, the heterologous gene encoding the second excision enzyme is constitutively expressed after it is flipped by the first recombinase. In one embodiment, the genetically engineered bacterium dies or is no longer viable when the first essential gene and the second essential gene are both excised. In one embodiment, the genetically engineered bacterium dies or is no longer viable when either the first essential gene is excised or the second essential gene is excised by the first recombinase.

In one embodiment, the genetically engineered bacterium dies after the at least one recombination event occurs. In another embodiment, the genetically engineered bacterium is no longer viable after the at least one recombination event occurs.

In any of these embodiment, the recombinase can be a recombinase selected from the group consisting of: BxbI, PhiC31, TP901, BxbI, PhiC31, TP901, HK022, HP1, R4, Int1, Int2, Int3, Int4, Int5, Int6, Int7, Int8, Int9, Int10, Int11, Int12, Int13, Int14, Int15, Int16, Int17, Int18, Int19, Int20, Int21, Int22, Int23, Int24, Int25, Int26, Int27, Int28, Int29, Int30, Int31, Int32, Int33, and Int34, or a biologically active fragment thereof.

In the above-described kill switch circuits, a toxin is produced in the presence of an environmental factor or signal. In another aspect of kill switch circuitry, a toxin may be repressed in the presence of an environmental factor (i.e., not produced) and then produced once the environmental condition or external signal is no longer present. Such kill switches are called repression-based kill switches and represent systems in which the bacterial cells are viable only in the presence of an external factor or signal, such as arabinose or other sugar. Exemplary kill switch designs in which the toxin is repressed in the presence of an external factor or signal (and activated once the external signal is removed) is shown in FIGS. 43-47. The disclosure provides recombinant bacterial cells which express one or more heterologous gene(s) upon sensing arabinose or other sugar in the exogenous environment. In this aspect, the recombinant bacterial cells contain the araC gene, which encodes the AraC transcription factor, as well as one or more genes under the control of the araBAD promoter (ParaBAD). In the absence of arabinose, the AraC transcription factor adopts a conformation that represses transcription of genes under the control of the araBAD promoter. In the presence of arabinose, the AraC transcription factor undergoes a conformational change that allows it to bind to and activate the araBAD promoter, which induces expression of the desired gene, for example TetR, which represses expression of a toxin gene. In this embodiment, the toxin gene is repressed in the presence of arabinose or other sugar. In an environment where arabinose is not present, the TetR gene is not activated and the toxin is expressed, thereby killing the bacteria. The arabinose system can also be used to express an essential gene, in which the essential gene is only expressed in the presence of arabinose or other sugar and is not expressed when arabinose or other sugar is absent from the environment.

Thus, in some embodiments, in which one or more heterologous gene(s) are expressed upon sensing arabinose in the exogenous environment, the one or more heterologous genes are directly or indirectly under the control of the araBAD promoter. In some embodiments, the expressed heterologous gene is selected from one or more of the following: a heterologous therapeutic gene, a heterologous gene encoding an anti-toxin, a heterologous gene encoding a repressor protein or polypeptide, for example, a TetR repressor, a heterologous gene encoding an essential protein not found in the bacterial cell, and/or a heterologous encoding a regulatory protein or polypeptide.

Arabinose inducible promoters are known in the art, including $P_{ara}$, $P_{araB}$, $P_{araC}$, and ParaBAD. In one embodiment, the arabinose inducible promoter is from *E. coli*. In some embodiments, the $P_{araC}$ promoter and the $P_{araBAD}$ promoter operate as a bidirectional promoter, with the $P_{araBAD}$ promoter controlling expression of a heterologous gene(s) in one direction, and the $P_{araC}$ (in close proximity to, and on the opposite strand from the $P_{araBAD}$ promoter), controlling expression of a heterologous gene(s) in the other direction. In the presence of arabinose, transcription of both heterologous genes from both promoters is induced. However, in the absence of arabinose, transcription of both heterologous genes from both promoters is not induced.

In one exemplary embodiment of the disclosure, the genetically engineered bacteria of the present disclosure contain a kill switch having at least the following sequences: a $P_{araBAD}$ promoter operably linked to a heterologous gene encoding a tetracycline repressor (TetR) protein, a $P_{araC}$ promoter operably linked to a heterologous gene encoding the AraC transcription factor, and a heterologous gene encoding a bacterial toxin operably linked to a promoter which is repressed by the TetR protein. In the presence of arabinose, the AraC transcription factor activates the $P_{araBAD}$ promoter, which activates transcription of the TetR protein which, in turn, represses transcription of the toxin. In the absence of arabinose, however, AraC suppresses transcription from the $P_{araBAD}$ promoter and no TetR protein is expressed. In this case, expression of the heterologous toxin gene is activated, and the toxin is expressed. The toxin builds up in the recombinant bacterial cell, and the recombinant bacterial cell is killed. In one embodiment, the araC gene encoding the AraC transcription factor is under the control of a constitutive promoter and is therefore constitutively expressed.

In one embodiment of the disclosure, the genetically engineered bacterium further comprises an anti-toxin under the control of a constitutive promoter. In this situation, in the presence of arabinose, the toxin is not expressed due to repression by TetR protein, and the anti-toxin protein builds-up in the cell. However, in the absence of arabinose, TetR protein is not expressed, and expression of the toxin is induced. The toxin begins to build-up within the recombinant bacterial cell. The recombinant bacterial cell is no longer viable once the toxin protein is present at either equal or greater amounts than that of the anti-toxin protein in the cell, and the recombinant bacterial cell will be killed by the toxin.

In another embodiment of the disclosure, the genetically engineered bacterium further comprises an anti-toxin under the control of the $P_{araBAD}$ promoter. In this situation, in the presence of arabinose, TetR and the anti-toxin are expressed, the anti-toxin builds up in the cell, and the toxin is not expressed due to repression by TetR protein. However, in the absence of arabinose, both the TetR protein and the anti-toxin are not expressed, and expression of the toxin is induced. The toxin begins to build-up within the recombinant bacterial cell. The recombinant bacterial cell is no longer viable once the toxin protein is expressed, and the recombinant bacterial cell will be killed by the toxin.

In another exemplary embodiment of the disclosure, the genetically engineered bacteria of the present disclosure contain a kill switch having at least the following sequences: a $P_{araBAD}$ promoter operably linked to a heterologous gene encoding an essential polypeptide not found in the recombinant bacterial cell (and required for survival), and a $P_{araC}$ promoter operably linked to a heterologous gene encoding the AraC transcription factor. In the presence of arabinose, the AraC transcription factor activates the $P_{araBAD}$ promoter, which activates transcription of the heterologous gene encoding the essential polypeptide, allowing the recombinant bacterial cell to survive. In the absence of arabinose, however, AraC suppresses transcription from the $P_{araBAD}$ promoter and the essential protein required for survival is not expressed. In this case, the recombinant bacterial cell dies in the absence of arabinose. In some embodiments, the sequence of $P_{araBAD}$ promoter operably linked to a heterologous gene encoding an essential polypeptide not found in the recombinant bacterial cell can be present in the bacterial cell in conjunction with the TetR/toxin kill switch system described directly above. In some embodiments, the sequence of $P_{araBAD}$ promoter operably linked to a heterologous gene encoding an essential polypeptide not found in the recombinant bacterial cell can be present in the bacterial cell in conjunction with the TetR/toxin/anti-toxin kill switch system described directly above.

In yet other embodiments, the bacteria may comprise a plasmid stability system with a plasmid that produces both a short-lived anti-toxin and a long-lived toxin. In this system, the bacterial cell produces equal amounts of toxin and anti-toxin to neutralize the toxin. However, if/when the cell loses the plasmid, the short-lived anti-toxin begins to decay. When the anti-toxin decays completely the cell dies as a result of the longer-lived toxin killing it.

In some embodiments, the engineered bacteria of the present disclosure further comprise the gene(s) encoding the components of any of the above-described kill switch circuits.

In any of the above-described embodiments, the bacterial toxin is selected from the group consisting of a lysin, Hok, Fst, TisB, LdrD, Kid, SymE, MazF, FlmA, Ibs, XCV2162, dinJ, CcdB, MazF, ParE, YafO, Zeta, hicB, relB, yhaV, yoeB, chpBK, hipA, microcin B, microcin B17, microcin C, microcin C7-051, microcin J25, microcin ColV, microcin 24, microcin L, microcin D93, microcin L, microcin E492, microcin H47, microcin 147, microcin M, colicin A, colicin E1, colicin K, colicin N, colicin U, colicin B, colicin Ia, colicin Ib, colicin 5, colicin10, colicin S4, colicin Y, colicin E2, colicin E7, colicin E8, colicin E9, colicin E3, colicin E4, colicin E6, colicin E5, colicin D, colicin M, and cloacin DF13, or a biologically active fragment thereof.

In any of the above-described embodiments, the anti-toxin is selected from the group consisting of an anti-lysin, Sok, RNAII, IstR, RdlD, Kis, SymR, MazE, FlmB, Sib, ptaRNA1, yafQ, CcdA, MazE, ParD, yafN, Epsilon, HicA, relE, prlF, yefM, chpBI, hipB, MccE, $MccE^{CTD}$, MccF, Cai, ImmE1, Cki, Cni, Cui, Cbi, Iia, Imm, Cfi, Im10, Csi, Cyi, Im2, Im7, Im8, Im9, Im3, Im4, ImmE6, cloacin immunity protein (Cim), ImmE5, ImmD, and Cmi, or a biologically active fragment thereof.

In one embodiment, the bacterial toxin is bactericidal to the genetically engineered bacterium. In one embodiment, the bacterial toxin is bacteriostatic to the genetically engineered bacterium.

In some embodiments, the genetically engineered bacterium provided herein is an auxotroph. In one embodiment, the genetically engineered bacterium is an auxotroph selected from a cysE, glnA, ilvD, leuB, lysA, serA, metA, glyA, hisB, ilvA, pheA, proA, thrC, trpC, tyrA, thyA, uraA, dapA, dapB, dapD, dapE, dapF, flhD, metB, metC, proAB, and thi1 auxotroph. In some embodiments, the engineered bacteria have more than one auxotrophy, for example, they may be a ΔthyA and ΔdapA auxotroph.

In some embodiments, the genetically engineered bacterium provided herein further comprises a kill switch circuit, such as any of the kill switch circuits provided herein. For example, in some embodiments, the genetically engineered bacteria further comprise one or more genes encoding one or more recombinase(s) under the control of an inducible promoter and an inverted toxin sequence. In some embodiments, the genetically engineered bacteria further comprise one or more genes encoding an anti-toxin. In some embodiments, the engineered bacteria further comprise one or more genes encoding one or more recombinase(s) under the control of an inducible promoter and one or more inverted excision genes, wherein the excision gene(s) encode an enzyme that deletes an essential gene. In some embodiments, the genetically engineered bacteria further comprise one or more genes encoding an anti-toxin. In some embodiments, the engineered bacteria further comprise one or more genes encoding a toxin under the control of a promoter having a TetR repressor binding site and a gene encoding the TetR under the control of an inducible promoter that is induced by arabinose, such as $P_{araBAD}$. In some embodiments, the genetically engineered bacteria further comprise one or more genes encoding an anti-toxin.

In some embodiments, the genetically engineered bacterium is an auxotroph comprising a gene encoding a phenylalanine-metabolizing enzyme and further comprises a kill switch circuit, such as any of the kill switch circuits described herein.

In some embodiments, of the above described genetically engineered bacteria, the gene or gene cassette for producing the phenylalanine-metabolizing enzyme is present on a plasmid in the bacterium and operatively linked on the plasmid to the promoter that is induced under low-oxygen or anaerobic conditions. In other embodiments, the gene or gene cassette for producing the phenylalanine-metabolizing enzyme is present in the bacterial chromosome and is operatively linked in the chromosome to the promoter that is induced under low-oxygen or anaerobic conditions.

Pharmaceutical Compositions and Formulations

Pharmaceutical compositions comprising the genetically engineered bacteria of the invention may be used to treat, manage, ameliorate, and/or prevent diseases associated with hyperphenylalaninemia, e.g., PKU. Pharmaceutical compositions of the invention comprising one or more genetically engineered bacteria, alone or in combination with prophylactic agents, therapeutic agents, and/or and pharmaceutically acceptable carriers are provided. In certain embodiments, the pharmaceutical composition comprises one species, strain, or subtype of bacteria that are engineered to comprise the genetic modifications described herein. In alternate embodiments, the pharmaceutical composition comprises two or more species, strains, and/or subtypes of bacteria that are each engineered to comprise the genetic modifications described herein.

The pharmaceutical compositions described herein may be formulated in a conventional manner using one or more physiologically acceptable carriers comprising excipients and auxiliaries, which facilitate processing of the active ingredients into compositions for pharmaceutical use. Methods of formulating pharmaceutical compositions are known in the art (see, e.g., "Remington's Pharmaceutical Sciences," Mack Publishing Co., Easton, Pa.). In some embodiments, the pharmaceutical compositions are subjected to tabletting, lyophilizing, direct compression, conventional mixing, dissolving, granulating, levigating, emulsifying, encapsulating, entrapping, or spray drying to form tablets, granulates, nanoparticles, nanocapsules, microcapsules, microtablets, pellets, or powders, which may be enterically coated or uncoated. Appropriate formulation depends on the route of administration.

The genetically engineered bacteria described herein may be formulated into pharmaceutical compositions in any suitable dosage form (e.g., liquids, capsules, sachet, hard capsules, soft capsules, tablets, enteric coated tablets, suspension powders, granules, or matrix sustained release formations for oral administration) and for any suitable type of administration (e.g., oral, topical, injectable, immediate-release, pulsatile-release, delayed-release, or sustained release). Suitable dosage amounts for the genetically engineered bacteria may range from about $10^5$ to $10^{12}$ bacteria, e.g., approximately $10^5$ bacteria, approximately $10^6$ bacteria, approximately $10^7$ bacteria, approximately $10^8$ bacteria, approximately $10^9$ bacteria, approximately $10^{10}$ bacteria, approximately $10^{11}$ bacteria, or approximately $10^{11}$ bacteria. The composition may be administered once or more daily, weekly, or monthly. The composition may be administered before, during, or following a meal. In one embodiment, the pharmaceutical composition is administered before the subject eats a meal. In one embodiment, the pharmaceutical composition is administered currently with a meal. In one embodiment, the pharmaceutical composition is administered after the subject eats a meal.

The genetically engineered bacteria may be formulated into pharmaceutical compositions comprising one or more pharmaceutically acceptable carriers, thickeners, diluents, buffers, buffering agents, surface active agents, neutral or cationic lipids, lipid complexes, liposomes, penetration enhancers, carrier compounds, and other pharmaceutically acceptable carriers or agents. For example, the pharmaceutical composition may include, but is not limited to, the addition of calcium bicarbonate, sodium bicarbonate, calcium phosphate, various sugars and types of starch, cellulose derivatives, gelatin, vegetable oils, polyethylene glycols, and surfactants, including, for example, polysorbate 20. In some embodiments, the genetically engineered bacteria of the invention may be formulated in a solution of sodium bicarbonate, e.g., 1 molar solution of sodium bicarbonate (to buffer an acidic cellular environment, such as the stomach, for example). The genetically engineered bacteria may be administered and formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

The genetically engineered bacteria disclosed herein may be administered topically and formulated in the form of an ointment, cream, transdermal patch, lotion, gel, shampoo, spray, aerosol, solution, emulsion, or other form well-known to one of skill in the art. See, e.g., "Remington's Pharmaceutical Sciences," Mack Publishing Co., Easton, Pa. In an embodiment, for non-sprayable topical dosage forms, viscous to semi-solid or solid forms comprising a carrier or one or more excipients compatible with topical application and having a dynamic viscosity greater than water are employed. Suitable formulations include, but are not limited to, solutions, suspensions, emulsions, creams, ointments, powders, liniments, salves, etc., which may be sterilized or mixed with auxiliary agents (e.g., preservatives, stabilizers, wetting agents, buffers, or salts) for influencing various properties, e.g., osmotic pressure. Other suitable topical dosage forms include sprayable aerosol preparations wherein the active ingredient in combination with a solid or liquid inert carrier, is packaged in a mixture with a pressurized volatile (e.g., a gaseous propellant, such as freon) or in a squeeze bottle. Moisturizers or humectants can also be added to pharmaceutical compositions and dosage forms. Examples of such additional ingredients are well known in the art. In one embodiment, the pharmaceutical composition comprising the recombinant bacteria of the invention may be formulated as a hygiene product. For example, the hygiene product may be an antibacterial formulation, or a fermentation product such as a fermentation broth. Hygiene products may be, for example, shampoos, conditioners, creams, pastes, lotions, and lip balms.

The genetically engineered bacteria disclosed herein may be administered orally and formulated as tablets, pills, dragees, capsules, liquids, gels, syrups, slurries, suspensions, etc. Pharmacological compositions for oral use can be made using a solid excipient, optionally grinding the resulting mixture, and processing the mixture of granules, after adding suitable auxiliaries if desired, to obtain tablets or dragee cores. Suitable excipients include, but are not limited to, fillers such as sugars, including lactose, sucrose, mannitol, or sorbitol; cellulose compositions such as maize starch, wheat starch, rice starch, potato starch, gelatin, gum tragacanth, methyl cellulose, hydroxypropylmethyl-cellulose, sodium carbomethylcellulose; and/or physiologically acceptable polymers such as polyvinylpyrrolidone (PVP) or polyethylene glycol (PEG). Disintegrating agents may also be added, such as cross-linked polyvinylpyrrolidone, agar, alginic acid or a salt thereof such as sodium alginate.

Tablets or capsules can be prepared by conventional means with pharmaceutically acceptable excipients such as binding agents (e.g., pregelatinised maize starch, polyvinylpyrrolidone, hydroxypropyl methylcellulose, carboxymethylcellulose, polyethylene glycol, sucrose, glucose, sorbitol, starch, gum, kaolin, and tragacanth); fillers (e.g., lactose, microcrystalline cellulose, or calcium hydrogen phosphate); lubricants (e.g., calcium, aluminum, zinc, stearic acid, polyethylene glycol, sodium lauryl sulfate, starch, sodium benzoate, L-leucine, magnesium stearate, talc, or silica); disintegrants (e.g., starch, potato starch, sodium starch glycolate, sugars, cellulose derivatives, silica powders); or wetting agents (e.g., sodium lauryl sulphate). The tablets may be coated by methods well known in the art. A coating shell may be present, and common membranes include, but are not limited to, polylactide, polyglycolic acid, polyanhydride, other biodegradable polymers, alginate-polylysine-alginate (APA), alginate-polymethylene-co-guanidine-alginate (A-PMCG-A), hydroymethylacrylate-methyl methacrylate (HEMA-MMA), multilayered HEMA-MMA-MAA, polyacrylonitrilevinylchloride (PAN-PVC), acrylonitrile/sodium methallylsulfonate (AN-69), polyethylene glycol/poly pentamethylcyclopentasiloxane/polydimethylsiloxane (PEG/PD5/PDMS), poly N,N-dimethyl acrylamide (PDMAAm), siliceous encapsulates, cellulose sulphate/sodium alginate/polymethylene-co-guanidine (CS/A/PMCG), cellulose acetate phthalate, calcium alginate, k-carrageenan-locust bean gum gel beads, gellan-xanthan beads, poly(lactide-co-glycolides), carrageenan, starch poly-anhydrides, starch polymethacrylates, polyamino acids, and enteric coating polymers.

In some embodiments, the genetically engineered bacteria are enterically coated for release into the gut or a particular region of the gut, for example, the large intestine. The typical pH profile from the stomach to the colon is about 1-4 (stomach), 5.5-6 (duodenum), 7.3-8.0 (ileum), and 5.5-6.5 (colon). In some diseases, the pH profile may be modified. In some embodiments, the coating is degraded in specific pH environments in order to specify the site of release. In some embodiments, at least two coatings are used. In some embodiments, the outside coating and the inside coating are degraded at different pH levels.

Liquid preparations for oral administration may take the form of solutions, syrups, suspensions, or a dry product for constitution with water or other suitable vehicle before use. Such liquid preparations may be prepared by conventional means with pharmaceutically acceptable agents such as suspending agents (e.g., sorbitol syrup, cellulose derivatives, or hydrogenated edible fats); emulsifying agents (e.g., lecithin or acacia); non-aqueous vehicles (e.g., almond oil, oily esters, ethyl alcohol, or fractionated vegetable oils); and preservatives (e.g., methyl or propyl-p-hydroxybenzoates or sorbic acid). The preparations may also contain buffer salts, flavoring, coloring, and sweetening agents as appropriate. Preparations for oral administration may be suitably formulated for slow release, controlled release, or sustained release of the genetically engineered bacteria described herein.

In one embodiment, the genetically engineered bacteria of the disclosure may be formulated in a composition suitable for administration to pediatric subjects. As is well known in the art, children differ from adults in many aspects, including different rates of gastric emptying, pH, gastrointestinal permeability, etc. (Ivanovska et al., 2014). Moreover, pediatric formulation acceptability and preferences, such as route of administration and taste attributes, are critical for achieving acceptable pediatric compliance. Thus, in one embodiment, the composition suitable for administration to pediatric subjects may include easy-to-swallow or dissolvable dosage forms, or more palatable compositions, such as compositions with added flavors, sweeteners, or taste blockers. In one embodiment, a composition suitable for administration to pediatric subjects may also be suitable for administration to adults.

In one embodiment, the composition suitable for administration to pediatric subjects may include a solution, syrup, suspension, elixir, powder for reconstitution as suspension or solution, dispersible/effervescent tablet, chewable tablet, gummy candy, lollipop, freezer pop, troche, chewing gum, oral thin strip, orally disintegrating tablet, sachet, soft gelatin capsule, sprinkle oral powder, or granules. In one embodiment, the composition is a gummy candy, which is made from a gelatin base, giving the candy elasticity, desired chewy consistency, and longer shelf-life. In some embodiments, the gummy candy may also comprise sweeteners or flavors.

In one embodiment, the composition suitable for administration to pediatric subjects may include a flavor. As used herein, "flavor" is a substance (liquid or solid) that provides a distinct taste and aroma to the formulation. Flavors also help to improve the palatability of the formulation. Flavors include, but are not limited to, strawberry, vanilla, lemon, grape, bubble gum, and cherry.

In certain embodiments, the genetically engineered bacteria may be orally administered, for example, with an inert diluent or an assimilable edible carrier. The compound may also be enclosed in a hard or soft shell gelatin capsule, compressed into tablets, or incorporated directly into the subject's diet. For oral therapeutic administration, the compounds may be incorporated with excipients and used in the form of ingestible tablets, buccal tablets, troches, capsules, elixirs, suspensions, syrups, wafers, and the like. To administer a compound by other than parenteral administration, it may be necessary to coat the compound with, or co-administer the compound with, a material to prevent its inactivation.

In another embodiment, the pharmaceutical composition comprising the recombinant bacteria of the invention may be a comestible product, for example, a food product. In one embodiment, the food product is milk, concentrated milk, fermented milk (yogurt, sour milk, frozen yogurt, lactic acid bacteria-fermented beverages), milk powder, ice cream, cream cheeses, dry cheeses, soybean milk, fermented soybean milk, vegetable-fruit juices, fruit juices, sports drinks, confectionery, candies, infant foods (such as infant cakes), nutritional food products, animal feeds, or dietary supplements. In one embodiment, the food product is a fermented food, such as a fermented dairy product. In one embodiment, the fermented dairy product is yogurt. In another embodiment, the fermented dairy product is cheese, milk, cream, ice cream, milk shake, or kefir. In another embodiment, the recombinant bacteria of the invention are combined in a preparation containing other live bacterial cells intended to serve as probiotics. In another embodiment, the food product is a beverage. In one embodiment, the beverage is a fruit juice-based beverage or a beverage containing plant or herbal extracts. In another embodiment, the food product is a jelly or a pudding. Other food products suitable for administration of the recombinant bacteria of the invention are well known in the art. See, e.g., US 2015/0359894 and US 2015/0238545, the entire contents of each of which are expressly incorporated herein by reference. In yet another embodiment, the pharmaceutical composition of the invention is injected into, sprayed onto, or sprinkled onto a food product, such as bread, yogurt, or cheese.

In some embodiments, the composition is formulated for intraintestinal administration, intrajejunal administration, intraduodenal administration, intraileal administration, gastric shunt administration, or intracolic administration, via nanoparticles, nanocapsules, microcapsules, or microtablets, which are enterically coated or uncoated. The pharmaceutical compositions may also be formulated in rectal compositions such as suppositories or retention enemas, using, e.g., conventional suppository bases such as cocoa butter or other glycerides. The compositions may be suspensions, solutions, or emulsions in oily or aqueous vehicles, and may contain suspending, stabilizing and/or dispersing agents.

The genetically engineered bacteria described herein may be administered intranasally, formulated in an aerosol form, spray, mist, or in the form of drops, and conveniently delivered in the form of an aerosol spray presentation from pressurized packs or a nebuliser, with the use of a suitable propellant (e.g., dichlorodifluoromethane, trichlorofluoromethane, dichlorotetrafluoroethane, carbon dioxide or other suitable gas). Pressurized aerosol dosage units may be determined by providing a valve to deliver a metered amount. Capsules and cartridges (e.g., of gelatin) for use in an inhaler or insufflator may be formulated containing a powder mix of the compound and a suitable powder base such as lactose or starch.

The genetically engineered bacteria may be administered and formulated as depot preparations. Such long acting formulations may be administered by implantation or by injection, including intravenous injection, subcutaneous injection, local injection, direct injection, or infusion. For example, the compositions may be formulated with suitable polymeric or hydrophobic materials (e.g., as an emulsion in an acceptable oil) or ion exchange resins, or as sparingly soluble derivatives (e.g., as a sparingly soluble salt).

In some embodiments, disclosed herein are pharmaceutically acceptable compositions in single dosage forms. Single dosage forms may be in a liquid or a solid form. Single dosage forms may be administered directly to a patient without modification or may be diluted or reconstituted prior to administration. In certain embodiments, a single dosage form may be administered in bolus form, e.g., single injection, single oral dose, including an oral dose that comprises multiple tablets, capsule, pills, etc. In alternate embodiments, a single dosage form may be administered over a period of time, e.g., by infusion.

Single dosage forms of the pharmaceutical composition may be prepared by portioning the pharmaceutical composition into smaller aliquots, single dose containers, single dose liquid forms, or single dose solid forms, such as tablets, granulates, nanoparticles, nanocapsules, microcapsules, microtablets, pellets, or powders, which may be enterically coated or uncoated. A single dose in a solid form may be reconstituted by adding liquid, typically sterile water or saline solution, prior to administration to a patient.

In other embodiments, the composition can be delivered in a controlled release or sustained release system. In one embodiment, a pump may be used to achieve controlled or sustained release. In another embodiment, polymeric materials can be used to achieve controlled or sustained release of the therapies of the present disclosure (see, e.g., U.S. Pat. No. 5,989,463). Examples of polymers used in sustained release formulations include, but are not limited to, poly(-hydroxy ethyl methacrylate), poly(methyl methacrylate), poly(acrylic acid), poly(ethylene-co-vinyl acetate), poly (methacrylic acid), polyglycolides (PLG), polyanhydrides, poly(N-vinyl pyrrolidone), poly(vinyl alcohol), polyacrylamide, poly(ethylene glycol), polylactides (PLA), poly(lactide-co-glycolides) (PLGA), and polyorthoesters. The polymer used in a sustained release formulation may be inert, free of leachable impurities, stable on storage, sterile, and biodegradable. In some embodiments, a controlled or sustained release system can be placed in proximity of the prophylactic or therapeutic target, thus requiring only a fraction of the systemic dose. Any suitable technique known to one of skill in the art may be used.

Dosage regimens may be adjusted to provide a therapeutic response. Dosing can depend on several factors, including severity and responsiveness of the disease, route of administration, time course of treatment (days to months to years), and time to amelioration of the disease. For example, a single bolus may be administered at one time, several divided doses may be administered over a predetermined period of time, or the dose may be reduced or increased as indicated by the therapeutic situation. The specification for the dosage is dictated by the unique characteristics of the active compound and the particular therapeutic effect to be achieved. Dosage values may vary with the type and severity of the condition to be alleviated. For any particular subject, specific dosage regimens may be adjusted over time according to the individual need and the professional judgment of the treating clinician. Toxicity and therapeutic efficacy of compounds provided herein can be determined by standard pharmaceutical procedures in cell culture or animal models. For example, $LD_{50}$, $ED_{50}$, $EC_{50}$, and $IC_{50}$ may be determined, and the dose ratio between toxic and therapeutic effects ($LD_{50}/ED_{50}$) may be calculated as the therapeutic index. Compositions that exhibit toxic side effects may be used, with careful modifications to minimize potential damage to reduce side effects. Dosing may be estimated initially from cell culture assays and animal models. The data obtained from in vitro and in vivo assays and animal studies can be used in formulating a range of dosage for use in humans.

The ingredients are supplied either separately or mixed together in unit dosage form, for example, as a dry lyophilized powder or water-free concentrate in a hermetically sealed container such as an ampoule or sachet indicating the quantity of active agent. If the mode of administration is by injection, an ampoule of sterile water for injection or saline can be provided so that the ingredients may be mixed prior to administration.

The pharmaceutical compositions may be packaged in a hermetically sealed container such as an ampoule or sachet indicating the quantity of the agent. In one embodiment, one or more of the pharmaceutical compositions is supplied as a dry sterilized lyophilized powder or water-free concentrate in a hermetically sealed container and can be reconstituted (e.g., with water or saline) to the appropriate concentration for administration to a subject. In an embodiment, one or more of the prophylactic or therapeutic agents or pharmaceutical compositions is supplied as a dry sterile lyophilized powder in a hermetically sealed container stored between 2° C. and 8° C. and administered within 1 hour, within 3 hours, within 5 hours, within 6 hours, within 12 hours, within 24 hours, within 48 hours, within 72 hours, or within one week after being reconstituted. Cryoprotectants can be included for a lyophilized dosage form, principally 0-10% sucrose (optimally 0.5-1.0%). Other suitable cryoprotectants include trehalose and lactose. Other suitable bulking agents include glycine and arginine, either of which can be included at a concentration of 0-0.05%, and polysorbate-80 (optimally included at a concentration of 0.005-0.01%). Additional surfactants include but are not limited to polysorbate 20 and BRIJ surfactants. The pharmaceutical composition may be prepared as an injectable solution and can further comprise an agent useful as an adjuvant, such as those used to increase absorption or dispersion, e.g., hyaluronidase.

Methods of Treatment

Another aspect of the invention provides methods of treating a disease associated with hyperphenylalaninemia or symptom(s) associated with hyperphenylalaninemia. In some embodiments, the disease is selected from the group consisting of: phenylketonuria, classical or typical phenylketonuria, atypical phenylketonuria, permanent mild hyperphenylalaninemia, nonphenylketonuric hyperphenylalaninemia, phenylalanine hydroxylase deficiency, cofactor deficiency, dihydropteridine reductase deficiency, tetrahydropterin synthase deficiency, and Segawa's disease. In some embodiments, hyperphenylalaninemia is secondary to other conditions, e.g., liver diseases. In some embodiments, the invention provides methods for reducing, ameliorating, or eliminating one or more symptom(s) associated with these diseases, including but not limited to neurological deficits, mental retardation, encephalopathy, epilepsy, eczema, reduced growth, microcephaly, tremor, limb spasticity, and/or hypopigmentation. In some embodiments, the subject to be treated is a human patient.

In certain embodiments, the genetically engineered bacteria are capable of metabolizing phenylalanine in the diet in order to treat a disease or disorder associated with hyperphenylalaninemia, e.g., PKU. In some embodiments, the genetically engineered bacteria are delivered simultaneously with dietary protein. In other embodiments, the genetically engineered bacteria are not delivered simultaneously with dietary protein. Studies have shown that pancreatic and other glandular secretions into the intestine contain high levels of proteins, enzymes, and polypeptides, and that the amino acids produced as a result of their catabolism are reabsorbed back into the blood in a process known as "enterorecirculation" (Chang, 2007; Sarkissian et al., 1999). Thus, high intestinal levels of phenylalanine may be partially independent of food intake, and are available for breakdown by PAL. In some embodiments, the genetically engineered bacteria and dietary protein are delivered after a period of fasting or phenylalanine-restricted dieting. In these embodiments, a patient suffering from hyperphenylalaninemia may be able to resume a substantially normal diet, or a diet that is less restrictive than a phenylalanine-free diet. In some embodiments, the genetically engineered bacteria may be capable of metabolizing phenylalanine from additional sources, e.g., the blood, in order to treat a disease associated with hyperphenylalaninemia, e.g., PKU. In these embodiments, the genetically engineered bacteria need not be delivered simultaneously with dietary protein, and a phenylalanine gradient is generated, e.g., from blood to gut, and the genetically engineered bacteria metabolize phenylalanine and reduce phenylalaninemia.

The method may comprise preparing a pharmaceutical composition with at least one genetically engineered species, strain, or subtype of bacteria described herein, and administering the pharmaceutical composition to a subject in a therapeutically effective amount. In some embodiments, the genetically engineered bacteria of the invention are administered orally, e.g., in a liquid suspension. In some embodiments, the genetically engineered bacteria of the invention are lyophilized in a gel cap and administered orally. In some embodiments, the genetically engineered bacteria of the invention are administered via a feeding tube or gastric shunt. In some embodiments, the genetically engineered bacteria of the invention are administered rectally, e.g., by enema. In some embodiments, the genetically engineered bacteria of the invention are administered topically, intraintestinally, intrajejunally, intraduodenally, intraileally, and/or intracolically.

In certain embodiments, the pharmaceutical composition described herein is administered to reduce phenylalanine levels in a subject. In some embodiments, the methods of the present disclosure reduce the phenylalanine levels in a subject by at least about 10%, 20%, 25%, 30%, 40%, 50%, 60%, 70%, 75%, 80%, 85%, 90%, 95%, or more as compared to levels in an untreated or control subject. In some embodiments, reduction is measured by comparing the phenylalanine level in a subject before and after administration of the pharmaceutical composition. In some embodiments, the method of treating or ameliorating hyperphenylalaninemia allows one or more symptoms of the condition or disorder to improve by at least about 10%, 20%, 30%, 40%, 50%, 60%, 70%, 80%, 90%, 95%, or more.

Before, during, and after the administration of the pharmaceutical composition, phenylalanine levels in the subject may be measured in a biological sample, such as blood, serum, plasma, urine, peritoneal fluid, cerebrospinal fluid, fecal matter, intestinal mucosal scrapings, a sample collected from a tissue, and/or a sample collected from the contents of one or more of the following: the stomach, duodenum, jejunum, ileum, cecum, colon, rectum, and anal canal. In some embodiments, the methods may include administration of the compositions of the invention to reduce phenylalanine. In some embodiments, the methods may include administration of the compositions of the invention to reduce phenylalanine to undetectable levels in a subject. In some embodiments, the methods may include administration of the compositions of the invention to reduce phenylalanine concentrations to undetectable levels, or to less than about 1%, 2%, 5%, 10%, 20%, 25%, 30%, 40%, 50%, 60%, 70%, 75%, or 80% of the subject's phenylalanine levels prior to treatment.

Figure 38:
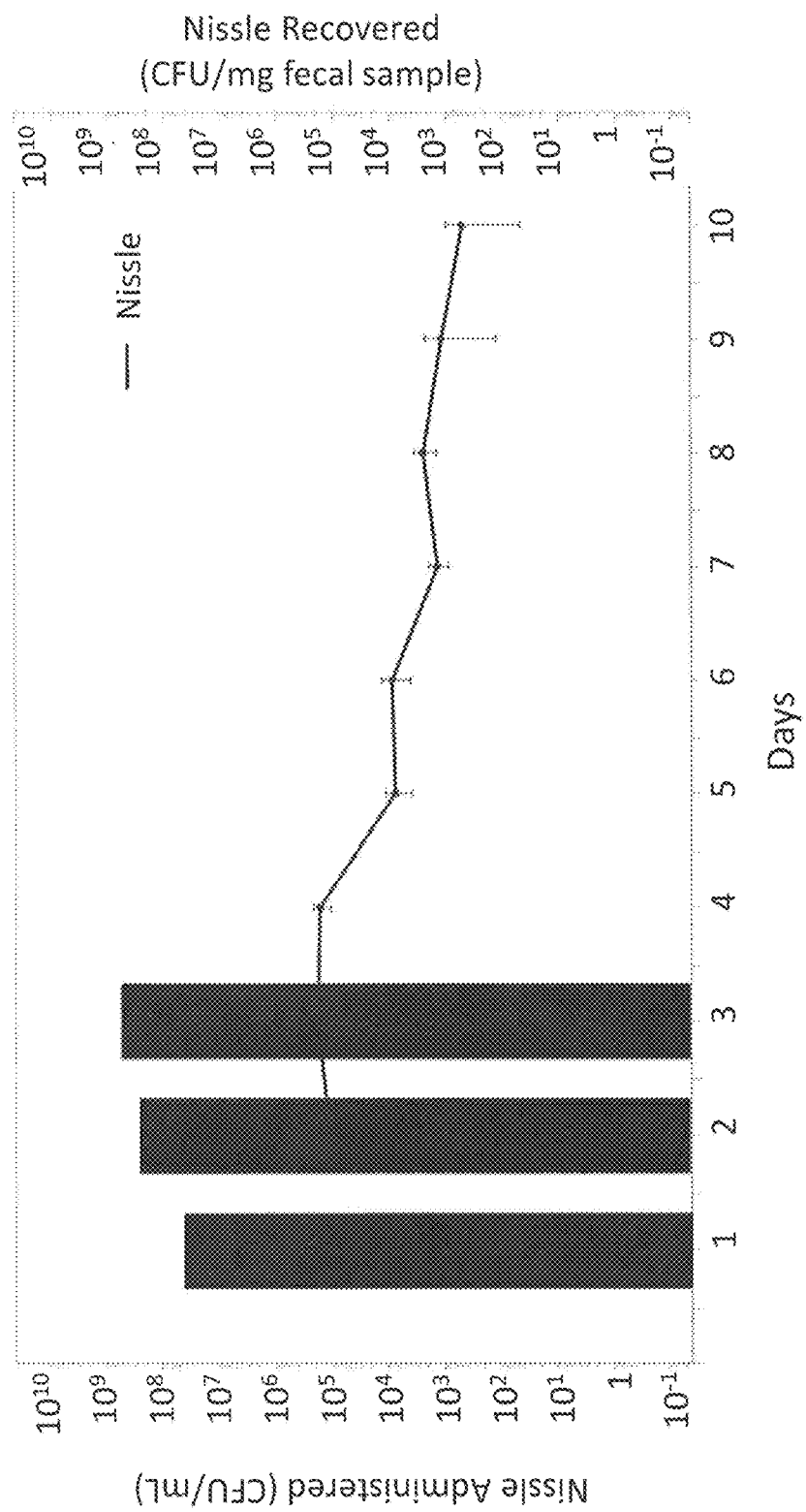
FIG. 38 depicts a graph of Nissle residence in vivo. Streptomycin-resistant Nissle was administered to mice via oral gavage without antibiotic pre-treatment. Fecal pellets from 6 total mice were monitored post-administration to determine the amount of administered Nissle still residing within the mouse gastrointestinal tract. The bars represent the number of bacteria administered to the mice. The line represents the number of Nissle recovered from the fecal samples each day for 10 consecutive days.

In certain embodiments, the genetically engineered bacteria are *E. coli* Nissle. The genetically engineered bacteria may be destroyed, e.g., by defense factors in the gut or blood serum (Sonnenborn et al., 2009) or by activation of a kill switch, several hours or days after administration. Thus, the pharmaceutical composition comprising the genetically engineered bacteria may be re-administered at a therapeutically effective dose and frequency. Length of Nissle residence in vivo in mice is shown in FIG. 38. In alternate embodiments, the genetically engineered bacteria are not destroyed within hours or days after administration and may propagate and colonize the gut.

The methods of the invention may comprise administration of the pharmaceutical composition alone or in combination with one or more additional therapeutic agents. In some embodiments, the pharmaceutical composition is administered in conjunction with the cofactor tetrahydrobiopterin (e.g., Kuvan/sapropterin), large neutral amino acids (e.g., tyrosine, tryptophan), glycomacropeptides, a probiotic (e.g., VSL3), an enzyme (e.g., pegylated-PAL), and/or other agents used in the treatment of phenylketonuria (Al Hafid and Christodoulou, 2015).

In some embodiments, the genetically engineered bacteria are administered in combination with one or more recombinantly produced PME enzymes, e.g. recombinant PAL, LAAD or PAH. In some embodiments, the recombinant enzymes are further formulated for improved stability and/or delivery. In some embodiments, the one or more PME enzyme administered in combination with the genetically engineered bacteria is pegylated. In some embodiments, the one or more PME enzyme administered in combination with the genetically engineered bacteria is delivered as a fusion protein. A non-limiting example of such a fusion protein is a fusion between a PME and a transduction domain for uptake into cells. A non-limiting example of such transduction domain or cell penetrating peptide is the TAT peptide. In some embodiments, the one or more PME enzyme administered in combination with the genetically engineered bacteria is formulated in a nanoparticle. A non-limiting example of such a nanoparticle is a dextran sulfate/chitosan PME nanoparticle. In some embodiments, the one or more PME enzyme administered in combination with the genetically engineered bacteria is delivered as a PME microsphere. A non-limiting example of such a microsphere is a barium alginate PME microsphere. In some embodiments, the one or more PME enzyme administered in combination with the genetically engineered bacteria is delivered as amorphous silica PME particles.

In some embodiments, the genetically engineered bacteria are administered in combination with PAL. In some embodiments, the genetically engineered bacteria are administered in combination with PAH. In some embodiments, the genetically engineered bacteria are administered in combination with LAAD. In some embodiments, the genetically engineered bacteria are administered in combination with PAL and PAH. In some embodiments, the genetically engineered bacteria are administered in combination with PAL and LAAD. In some embodiments, the genetically engineered bacteria are administered in combination with PAH and LAAD. In some embodiments, the genetically engineered bacteria are administered in combination with PAL, PAH, and LAAD.

In some embodiments, the genetically engineered bacteria are administered in combination with pegylated PAL. In some embodiments, the genetically engineered bacteria are administered in combination with pegylated PAH. In some embodiments, the genetically engineered bacteria are administered in combination with pegylated LAAD. In some embodiments, the genetically engineered bacteria are administered in combination with a PAL fusion protein, e.g., a cell penetrating peptide. In some embodiments, the genetically engineered bacteria are administered in combination with a PAH fusion protein, e.g., a cell penetrating peptide. In some embodiments, the genetically engineered bacteria are administered in combination with a LAAD fusion protein, e.g., a cell penetrating peptide. In some embodiments, the genetically engineered bacteria are administered in combination with PAL-nanoparticles. In some embodiments, the genetically engineered bacteria are administered in combination with PAH-nanoparticles. In some embodiments, the genetically engineered bacteria are administered in combination with LAAD nanoparticles. In some embodiments, the genetically engineered bacteria are administered in combination with PAL-microspheres. In some embodiments, the genetically engineered bacteria are administered in combination with PAH-microspheres. In some embodiments, the genetically engineered bacteria are administered in combination with LAAD-microspheres. In some embodiments, the genetically engineered bacteria are administered in combination with PAL-silica particles. In some embodiments, the genetically engineered bacteria are administered in combination with PAH-silica particles. In some embodiments, the genetically engineered bacteria are administered in combination with LAAD-silica particles.

In some embodiments, a recombinant enzyme replacement therapy or substitution therapy, e.g. PAL, PAH, and/or LAAD is administered without the genetically engineered bacteria.

In some embodiments, the one or more PME administered is PAL. In some embodiments, PAL is modified as described in Sakissian et al., 2011, Mol Genet Metab. 2011 November; 104(3): 249-254, the contents of which is herein incorporated by reference in its entirety. In some embodiments, the PAL is Av-p.C503S/p.C565S/p.F18A PAL. In some embodiments, the PAL is PEG-Av-p.C503S/p.C565S/p.F18A PAL.

In some embodiments, the PAL is PEGylated. In one embodiment, the pegylated PAL is from *Anabaena variabilis*. In one embodiment, the pegylated PAL is from *Photorhabdus luminescens*. In some embodiments, the one or more PME administered is PAH. In one embodiment, PAH is human PAH. In some embodiments, the one or more PME administered is LAAD. In one embodiment, the LAAD protein administered is derived from *Proteus mirabilis*. In some embodiments, the one or more PME administered in combination with PAL and PAH. In some embodiments, the one or more PME administered is PAL and LAAD. In some embodiments, the one or more PME administered is PAH and LAAD. In some embodiments, the one or more PME administered is PAL, PAH, and LAAD.

In some embodiments, the recombinant enzymes are further formulated for improved stability and/or delivery. In some embodiments, the one or more PME enzyme administered is pegylated. In some embodiments, the one or more PME enzyme administered is delivered as a fusion protein. A non-limiting example of such a fusion protein is a fusion between a PME and a transduction domain for uptake into cells. A non-limiting example of such transduction domain or cell penetrating peptide is the TAT peptide. In some embodiments, the one or more PME enzyme administered is formulated in a nanoparticle. A non-limiting example of such a nanoparticle is a dextran sulfate/chitosan PME nanoparticle. In some embodiments, the one or more PME enzyme administered is delivered as a PME microsphere. A non-limiting example of such a microsphere is a barium alginate PME microsphere. In some embodiments, the one or more PME enzyme administered is delivered as amorphous silica PME particles.

In some embodiments, pegylated PAL is administered. In some embodiments, pegylated LAAD is administered. In some embodiments pegylated LAAD from *Proteus mirabilis* is administered. In some embodiments, pegylated PAH is administered.

In one embodiment, a PAL fusion protein, e.g., with a cell penetrating peptide, is administered. In one embodiment, a LAAD fusion protein, e.g., with a cell penetrating peptide, is administered. In one embodiment, a PAH fusion protein, e.g., with a cell penetrating peptide, is administered. In some embodiments, PAL-nanoparticles are administered. In some embodiments, PAH-nanoparticles are administered. In some embodiments, LAAD-nanoparticles are administered. In some embodiments, PAL-microspheres are administered. In some embodiments, PAH-microspheres are administered. In some embodiments, LAAD-microspheres are administered. In some embodiments, PAL-silica particles are administered. In some embodiments, PAH-silica particles are administered. In some embodiments, LAAD-silica particles are administered.

In some embodiments the PME, e.g., PAH, PAL, and/or LAAD is formulated with aprotinin, e.g., 40 mg/ml aprotinin.

In some embodiments the PMEs are delivered as gene therapy. In some embodiments, a CRISPR technology is used. In some embodiments a gene therapy vector is used to deliver the one or more PME, e.g., PAL, LAAD, and/or PAH. Gene therapy vectors are known in the art and include, but are not limited to, retroviral vectors, adenoviral vectors, adeno-associated viral vectors. Alternatively, formulated or naked PME gene DNA or RNA can be delivered.

An important consideration in the selection of the one or more additional therapeutic agents is that the agent(s) should be compatible with the genetically engineered bacteria of the invention, e.g., the agent(s) must not interfere with or kill the bacteria. In some embodiments, the pharmaceutical composition is administered with food. In alternate embodiments, the pharmaceutical composition is administered before or after eating food. The pharmaceutical composition may be administered in combination with one or more dietary modifications, e.g., low-phenylalanine diet. The dosage of the pharmaceutical composition and the frequency of administration may be selected based on the severity of the symptoms and the progression of the disease. The appropriate therapeutically effective dose and/or frequency of administration can be selected by a treating clinician.

The methods of the invention also include kits comprising the pharmaceutical composition described herein. The kit can include one or more other elements including, but not limited to: instructions for use; other reagents, e.g., a label, an additional therapeutic agent; devices or materials for measuring phenylalanine levels, or levels of other molecules or metabolites associated with hyperphenylalaninemia, in a subject; devices or other materials for preparing the pharmaceutical composition of the invention for administration; and devices or other materials for administration to a subject. Instructions for use can include guidance for therapeutic application, such as suggested dosages and/or modes of administration, e.g., in a patient with hyperphenylalaninemia. The kit can further contain at least one additional therapeutic agent, and/or one or more additional genetically engineered bacterial strains of the invention, formulated as appropriate, in one or more separate pharmaceutical preparations.

In some embodiments, the kit is used for administration of the pharmaceutical composition to a subject. In some embodiments, the kit is used for administration of the pharmaceutical composition, alone or in combination with one or more additional therapeutic agents, to a subject. In some embodiments, the kit is used for measuring phenylalanine levels (e.g., blood phenylalanine levels) in a subject before, during, or after administration of the pharmaceutical composition to the subject. In certain embodiments, the kit is used for administration and/or re-administration of the pharmaceutical composition, alone or in combination with one or more additional therapeutic agents, when blood phenylalanine levels are increased or abnormally high. In some embodiments, a diagnostic signal of hyperphenylalaninemia is a blood phenylalanine level of at least 2 mg/dL, at least 4 mg/dL, at least 6 mg/dL, at least 8 mg/dL, at least 10 mg/dL, at least 12 mg/dL, at least 14 mg/dL, at least 16 mg/dL, at least 18 mg/dL, at least 20 mg/dL, or at least 25 mg/dL.

Table 20 shows non-limiting examples of target degradation rates, based on levels of phenylalanine on average in classical PKU patients.

TABLE 20

| | | | | | | | | | |
|---|---|---|---|---|---|---|---|---|---|
| Target Degradation Rates | | | | | | | | | |
| Age (years) | 0-6 months | 7-12 months | 1-3 | 4-8 | 9-13 | 14-18 (M) | 14-18 (F) | >18 (M) | >18 (F) |
| RDA Protein (g/d) | 9.1 | 11 | 13 | 19 | 34 | 52 | 46 | 56 | 46 |
| Daily PHE (mg)- Healthy subject (1g protein= 47mg PHE) | 428 | 517 | 611 | 893 | 1598 | 2444 | 2162 | 2632 | 2162 |
| Daily PHE tolerance (mg) (Classical PKU) | 250 | 250 | 250 | 250 | 250 | 250 | 250 | 250 | 250 |
| Target Reduction (mg) | 178 | 267 | 361 | 643 | 1348 | 2194 | 1912 | 2382 | 1912 |
| Target Reduction (mmol) | 1.08 | 1.62 | 2.19 | 3.89 | 8.16 | 13.28 | 11.57 | 14.42 | 11.57 |
| Target degradation rate ($\mu$mol/$10^9$ CFUs/hr) (based on $3.10^{11}$ CFUs/day dose) assuming all dose functioning for 24 hours | 0.15 | 0.22 | 0.3 | 0.54 | 1.13 | 1.84 | 1.61 | 2 | 1.61 |

TABLE 20-continued

| | Target Degradation Rates | | | | | | | | |
|---|---|---|---|---|---|---|---|---|---|
| Age (years) | 0-6 months | 7-12 months | 1-3 | 4-8 | 9-13 | 14-18 (M) | 14-18 (F) | >18 (M) | >18 (F) |
| Target degradation rate 2 hrs transit time ($\mu mol/10^9$ CFUs/hr) assuming 2 hour transit time per dose | 0.6 | 0.9 | 1.21 | 2.16 | 4.53 | 7.38 | 6.43 | 8.01 | 6.43 |
| Target degradation rate 6 hrs transit time ($\mu mol/10^9$ CFUs/hr) assuming 6 hour transit time per dose | 0.2 | 0.3 | 0.4 | 0.72 | 1.51 | 2.46 | 2.14 | 2.67 | 2.14 |

In some embodiments, the genetically engineered bacteria achieve a target degradation rate of about 0.15 to about 8.01 $\mu mol/10^9$ CFUs/hr. In some embodiments, the genetically engineered bacteria achieve a target degradation rate of about 0.15 to about 2 $\mu mol/10^9$ CFUs/hr. In some embodiments, the genetically engineered bacteria achieve a target degradation rate of about 0.6 to about 8.01 $\mu mol/10^9$ CFUs/hr. In some embodiments, the genetically engineered bacteria achieve a target degradation rate of about 0.2 to about 2.67 $\mu mol/10^9$ CFUs/hr.

In some embodiments, the genetically engineered bacteria achieve a target degradation rate of about 0.15 to about 0.6 $\mu mol/10^9$ CFUs/hr. In some embodiments, the genetically engineered bacteria achieve a target degradation rate of about 0.22 to about 0.9 $\mu mol/10^9$ CFUs/hr. In some embodiments, the genetically engineered bacteria achieve a target degradation rate of about 0.3 to about 1.21 $\mu mol/10^9$ CFUs/hr. In some embodiments, the genetically engineered bacteria achieve a target degradation rate of about 0.54 to about 2.16 $\mu mol/10^9$ CFUs/hr. In some embodiments, the genetically engineered bacteria achieve a target degradation rate of about 1.13 to about 4.53 $\mu mol/10^9$ CFUs/hr. In some embodiments, the genetically engineered bacteria achieve a target degradation rate of about 1.84 to about 7.38 $\mu mol/10^9$ CFUs/hr. In some embodiments, the genetically engineered bacteria achieve a target degradation rate of about 1.61 to about 6.43 $\mu mol/10^9$ CFUs/hr. In some embodiments, the genetically engineered bacteria achieve a target degradation rate of about 2 to about 8.01 $\mu mol/10^9$ CFUs/hr.

In some embodiments, the genetically engineered bacteria achieve a target degradation rate of about 0.1 to about 1 $\mu mol/10^9$ CFUs/hr. In some embodiments, the genetically engineered bacteria achieve a target degradation rate of about 1 to about 2 $\mu mol/10^9$ CFUs/hr. In some embodiments, the genetically engineered bacteria achieve a target degradation rate of about 2 to about 3 $\mu mol/10^9$ CFUs/hr. In some embodiments, the genetically engineered bacteria achieve a target degradation rate of about 3 to about 4 $\mu mol/10^9$ CFUs/hr. In some embodiments, the genetically engineered bacteria achieve a target degradation rate of about 4 to about 5 $\mu mol/10^9$ CFUs/hr. In some embodiments, the genetically engineered bacteria achieve a target degradation rate of about 5 to about 6 $\mu mol/10^9$ CFUs/hr. In some embodiments, the genetically engineered bacteria achieve a target degradation rate of about 6 to about 7 $\mu mol/10^9$ CFUs/hr. In some embodiments, the genetically engineered bacteria achieve a target degradation rate of about 7 to about 8 $\mu mol/10^9$ CFUs/hr.

In some embodiments, the genetically engineered bacteria achieve a target reduction rate of less than 0.15 $\mu mol/10^9$ CFUs/hr. In some embodiments, the genetically engineered bacteria achieve a target degradation rate of greater than 8.01 $\mu mol/10^9$ CFUs/hr.

In some embodiments, the genetically engineered bacteria achieve a target reduction of between about 178 mg and 2382 mg. In some embodiments, the genetically engineered bacteria achieve a target reduction of 1.08 mmol to 14.42 mmol. In some embodiments, the reduction is less than 1.08 mmol. In some embodiments, the reduction is greater than 14.42 mmol.

In some embodiments, target reduction and target degradation rates are based on classical PKU phenylalanine levels. In some embodiments, the target reduction and target degradation rates are based on phenylalanine levels observed in mild PKU. In some embodiments, target reduction and target degradation rates are based on phenylalanine levels observed in mild hyperphenylalaninemia.

Treatment In Vivo

The genetically engineered bacteria of the invention may be evaluated in vivo, e.g., in an animal model. Any suitable animal model of a disease or condition associated with hyperphenylalaninemia may be used (see, e.g., Sarkissian et al., 1999). In some embodiments, the animal model is a mouse model of PKU. In certain embodiments, the mouse model of PKU is an PAH mutant BTBR mouse (BTBR-Pah$^{enu2}$, Jackson Laboratories). In these embodiments, the mouse model contains a chemically (ENU)-induced homozygous missense mutation (T835C) in exon 7 of the Pah gene, which results in a phenylalanine to serine substitution at amino acid 263 (F263S). This residue is located in the active site of the PAH enzyme, as shown by crystal structure analysis, and results in the complete loss of PAH activity. On normal diets, these mutant mice demonstrate a 10- to 20-fold increase in serum phenylalanine levels compared to unaffected controls. The genetically engineered bacteria of the invention may be administered to the animal, e.g., by oral gavage, and treatment efficacy is determined, e.g., by measuring blood phenylalanine and/or cinnamate before and after treatment. In animal models, it is noted that residence time of the genetically engineered bacteria within the GI tract may be shorter than residence time in humans. The animal may be sacrificed, and tissue samples may be collected and analyzed.

In some embodiments, pharmacokinetics and pharmacodynamic studies may be conducted in non-human primates to determine any potential toxicities arising from administration of the genetically engineered bacteria. the pharmacokinetics and pharmacodynamics of the genetically engineered bacteria. Non-limiting examples of such studies are described in Examples 30 and 31.

In some embodiments, the genetically engineered bacteria expressing LAAD can be specifically detected in the feces and differentiated from other *E. coli* strains. A Phenylalanine Deaminase Test "Phenylalanine Agar Slant" can be used for this purpose. Phenylalanine agar used to determine whether the microbe can use phenylalanine and convert it to phenyl pyruvate. When the test chemicals are added to the tube containing the sample on the phenylalanine agar, phenylpyruvate is converted to a green compound, indicating a positive test. Wild type *E. coli* does not produce phenylpyruvate, since they do not encode an enzyme, which can produce phenylpyruvate from phenylalanine, allowing differentiation from other *E. coli* strains. The genetically engineered bacteria can be differentiated from other bacterial species which are able to produce phenylpyruvate by PCR-based tests known in the art. For example, species specific sequences can be amplified. For example, universal PCR that amplifies conserved regions in various bacteria is ideal to detect any pathogen in screening of specimens. For this purpose, the conserved region of the 16S rRNA gene can be used as a target gene for the universal PCR; the 16S rRNA gene contains species-specific regions by which a large number of bacterial species can be differentiated.

In some embodiments, the Phenylalanine Deaminase Test can be used to detect the genetically engineered bacteria in a feces sample. In some embodiments, PCR-based tests can be conducted to differentiate the genetically engineered bacteria from other bacterial species.

Screening Methods

In some embodiments, of the disclosure a genetically engineered strain may be improved upon by using screening and selection methods, e.g., to increase PME enzymatic activity or to increase the ability of a strain to take up phenylalanine. In some embodiments, the screen serves to generate a bacterial strain with improved PME activity. In some embodiments, the screen serves to generate a bacterial strain which has improved phenylalanine uptake ability. In some embodiments, the screen may identify a bacterial strain with both improved PME activity and enhanced substrate import. Non-limiting examples of methods of screening which can be used are described herein.

Generation of Bacterial Strains with Enhance Ability to Transport Biomolecules

Due to their ease of culture, short generation times, very high population densities and small genomes, microbes can be evolved to unique phenotypes in abbreviated timescales. Adaptive laboratory evolution (ALE) is the process of passaging microbes under selective pressure to evolve a strain with a preferred phenotype. Most commonly, this is applied to increase utilization of carbon/energy sources or adapting a strain to environmental stresses (e.g., temperature, pH), whereby mutant strains more capable of growth on the carbon substrate or under stress will outcompete the less adapted strains in the population and will eventually come to dominate the population.

This same process can be extended to any essential metabolite by creating an auxotroph. An auxotroph is a strain incapable of synthesizing an essential metabolite and must therefore have the metabolite provided in the media to grow. In this scenario, by making an auxotroph and passaging it on decreasing amounts of the metabolite, the resulting dominant strains should be more capable of obtaining and incorporating this essential metabolite.

For example, if the biosynthetic pathway for producing an amino acid is disrupted a strain capable of high-affinity capture of said amino acid can be evolved via ALE. First, the strain is grown in varying concentrations of the auxotrophic amino acid, until a minimum concentration to support growth is established. The strain is then passaged at that concentration, and diluted into lowering concentrations of the amino acid at regular intervals. Over time, cells that are most competitive for the amino acid—at growth-limiting concentrations—will come to dominate the population. These strains will likely have mutations in their amino acid-transporters resulting in increased ability to import the essential and limiting amino acid.

Similarly, by using an auxotroph that cannot use an upstream metabolite to form an amino acid, a strain can be evolved that not only can more efficiently import the upstream metabolite, but also convert the metabolite into the essential downstream metabolite. These strains will also evolve mutations to increase import of the upstream metabolite, but may also contain mutations which increase expression or reaction kinetics of downstream enzymes, or that reduce competitive substrate utilization pathways.

In the previous examples, a metabolite innate to the microbe was made essential via mutational auxotrophy and selection was applied with growth-limiting supplementation of the endogenous metabolite. However, phenotypes capable of consuming non-native compounds can be evolved by tying their consumption to the production of an essential compound. For example, if a gene from a different organism is isolated which can produce an essential compound or a precursor to an essential compound this gene can be recombinantly introduced and expressed in the heterologous host. This new host strain will now have the ability to synthesize an essential nutrient from a previously non-metabolizable substrate. Hereby, a similar ALE process can be applied by creating an auxotroph incapable of converting an immediately downstream metabolite and selecting in growth-limiting amounts of the non-native compound with concurrent expression of the recombinant enzyme. This will result in mutations in the transport of the non-native substrate, expression and activity of the heterologous enzyme and expression and activity of downstream native enzymes. It should be emphasized that the key requirement in this process is the ability to tether the consumption of the non-native metabolite to the production of a metabolite essential to growth.

Once the basis of the selection mechanism is established and minimum levels of supplementation have been established, the actual ALE experimentation can proceed. Throughout this process several parameters must be vigilantly monitored. It is important that the cultures are maintained in an exponential growth phase and not allowed to reach saturation/stationary phase. This means that growth rates must be check during each passaging and subsequent dilutions adjusted accordingly. If growth rate improves to such a degree that dilutions become large, then the concentration of auxotrophic supplementation should be decreased such that growth rate is slowed, selection pressure is increased and dilutions are not so severe as to heavily bias subpopulations during passaging. In addition, at regular intervals cells should be diluted, grown on solid media and individual clones tested to confirm growth rate phenotypes observed in the ALE cultures.

Predicting when to halt the stop the ALE experiment also requires vigilance. As the success of directing evolution is tied directly to the number of mutations "screened" throughout the experiment and mutations are generally a function of errors during DNA replication, the cumulative cell divisions (CCD) acts as a proxy for total mutants which have been screened. Previous studies have shown that beneficial phenotypes for growth on different carbon sources can be isolated in about $10^{11.2}$ CCD$^1$. This rate can be accelerated by the addition of chemical mutagens to the cultures—such as N-methyl-N-nitro-N-nitrosoguanidine (NTG)—which causes increased DNA replication errors. However, when continued passaging leads to marginal or no improvement in growth rate the population has converged to some fitness maximum and the ALE experiment can be halted.

At the conclusion of the ALE experiment, the cells should be diluted, isolated on solid media and assayed for growth phenotypes matching that of the culture flask. Best performers from those selected are then prepped for genomic DNA and sent for whole genome sequencing. Sequencing with reveal mutations occurring around the genome capable of providing improved phenotypes, but will also contain silent mutations (those which provide no benefit but do not detract from desired phenotype). In cultures evolved in the presence of NTG or other chemical mutagen, there will be significantly more silent, background mutations. If satisfied with the best performing strain in its current state, the user can proceed to application with that strain. Otherwise the contributing mutations can be deconvoluted from the evolved strain by reintroducing the mutations to the parent strain by genome engineering techniques. See Lee, D.-H., Feist, A. M., Barrett, C. L. & Palsson, B. Ø. Cumulative Number of Cell Divisions as a Meaningful Timescale for Adaptive Laboratory Evolution of *Escherichia coli*. PLoS ONE 6, e26172 (2011).

In some embodiments, the ALE method can be used to identify genetically engineered bacteria with improved phenylalanine uptake.

Specific Screen to Improve PME Activity

Screens using genetic selection are conducted to improve phenylalanine consumption in the genetically engineered bacteria. Toxic phenylalanine analogs exert their mechanism of action (MOA) by being incorporated into cellular protein, causing cell death. These compounds, such as paralog p-fluoro-DL-phenylalanine and ortholog o-fluoro-DL-phenylalanine have utility in an untargeted approach to select PAL enzymes with increased activity. Assuming that these toxic compounds can be metabolized by PAL into a non-toxic metabolite, rather than being incorporated into cellular protein, genetically engineered bacteria which have improved phenylalanine degradation activity can tolerate higher levels of these compounds, and can be screened for and selected on this basis.

REFERENCES

Al Hafid N, Christodoulou J. Phenylketonuria: a review of current and future treatments. Transl Pediatr. 2015 October; 4(4):304-317. PMID: 26835392;

Altenhoefer et al. The probiotic *Escherichia coli* strain Nissle 1917 interferes with invasion of human intestinal epithelial cells by different enteroinvasive bacterial pathogens. FEMS Immunol Med Microbiol. 2004 Apr. 9; 40(3):223-229. PMID: 15039098;

Andersen et al. Uracil uptake in *Escherichia coli* K-12: isolation of uraA mutants and cloning of the gene. J Bacteriol. 1995 April; 177(8):2008-2013. PMID: 7721693;

Arai et al. Expression of the nir and nor genes for denitrification of *Pseudomonas aeruginosa* requires a novel CRP/FNR-related transcriptional regulator, DNR, in addition to ANR. FEBS Lett. 1995 Aug. 28; 371(1):73-76. PMID: 7664887;

Arthur et al. Intestinal inflammation targets cancer-inducing activity of the microbiota. Science. 2012 Oct. 5; 338 (6103):120-123. PMID: 22903521;

Callura et al. Tracking, Tuning and terminating microbial physiology using synthetic riboregulators. Proc Natl Acad Sci USA. 2010; 27(36):15898-15903. PMID: 20713708;

Castiglione et al. The transcription factor DNR from *Pseudomonas aeruginosa* specifically requires nitric oxide and haem for the activation of a target promoter in *Escherichia coli*. Microbiology. 2009 September; 155(Pt 9):2838-2844. PMID: 19477902;

Chang, ed. (2007) "Use of Enzyme Artificial Cells for Genetic Enzyme Defects." In Artificial Cells: Biotechnology, Nanomedicine, Regenerative Medicine, Blood Substitutes, Bioencapsulation, and Cell/Stem Cell Therapy. World Scientific Publishing, pp. 147-159;

Clarkson et al. Diaminopimelic acid and lysine auxotrophs of *Pseudomonas aeruginosa* 8602. J Gen Microbiol. 1971 May; 66(2):161-169. PMID: 4999073;

Cuevas-Ramos et al. *Escherichia coli* induces DNA damage in vivo and triggers genomic instability in mammalian cells. Proc Natl Acad Sci USA. 2010 Jun. 22; 107(25): 11537-11542. PMID: 20534522;

Danino et al. Programmable probiotics for detection of cancer in urine. Sci Transl Med. 2015 May 27; 7(289): 289ra84. PMID: 26019220;

Deutscher. The mechanisms of carbon catabolite repression in bacteria. Curr Opin Microbiol. 2008 April; 11(2):87-93. PMID: 18359269;

Dinleyici et al. *Saccharomyces boulardii* CNCM 1-745 in different clinical conditions. Expert Opin Biol Ther. 2014 November; 14(11):1593-1609. PMID: 24995675;

Dobbelaere et al. Evaluation of nutritional status and pathophysiology of growth retardation in patients with phenylketonuria. J Inherit Metab Dis. 2003; 26(1):1-11. PMID: 12872834;

Eiglmeier et al. Molecular genetic analysis of FNR-dependent promoters. Mol Microbiol. 1989 July; 3(7):869-878. PMID: 2677602;

Estrem et al. Identification of an UP element consensus sequence for bacterial promoters. Proc Natl Acad Sci USA. 1998 Aug. 18; 95(17):9761-9766. PMID: 9707549;

Galimand et al. Positive FNR-like control of anaerobic arginine degradation and nitrate respiration in *Pseudomonas aeruginosa*. J Bacteriol. 1991 March; 173(5):1598-1606. PMID: 1900277;

Gardner et al. Construction of a genetic toggle switch in *Escherichia coli*. Nature. 2000; 403:339-342. PMID: 10659857;

Gerdes et al. Essential genes on metabolic maps. Curr Opin Biotechnol. 2006 October; 17(5):448-456. PMID: 16978855;

Gilbert et al. Molecular cloning of the phenylalanine ammonia lyase gene from *Rhodosporidium toruloides* in *Escherichia coli* K-12. J Bacteriol. 1985 January; 161(1): 314-320. PMID: 2981805;

Görke B, Stülke J. Carbon catabolite repression in bacteria: many ways to make the most out of nutrients. Nat Rev Microbiol. 2008 August; 6(8):613-624. PMID: 18628769;

Hasegawa et al. Activation of a consensus FNR-dependent promoter by DNR of *Pseudomonas aeruginosa* in response to nitrite. FEMS Microbiol Lett. 1998 Sep. 15; 166(2):213-217. PMID: 9770276;

Hoeks et al. Adult issues in phenylketonuria. Neth J Med. 2009 January; 67(1):2-7. PMID: 19155540;

Hoeren et al. Sequence and expression of the gene encoding the respiratory nitrous-oxide reductase from *Paracoccus denitrificans*. Eur J Biochem. 1993 Nov. 15; 218(1):49-57. PMID: 8243476;

Hosseini et al. Propionate as a health-promoting microbial metabolite in the human gut. Nutr Rev. 2011 May; 69(5): 245-258. PMID: 21521227;

Isabella et al. Deep sequencing-based analysis of the anaerobic stimulon in *Neisseria gonorrhoeae*. BMC Genomics. 2011 Jan. 20; 12:51. PMID: 21251255;

Ivanovska et al. Pediatric drug formulations: a review of challenges and progress. Pediatrics. 2014 August; 134(2): 361-372. PMID: 25022739;Kobe et al. Regulation and crystallization of phosphorylated and dephosphorylated forms of truncated dimeric phenylalanine hydroxylase. Protein Sci. 1997 June; 6(6):1352-1357. PMID: 9194198;

Kwok et al. Nucleotide sequence of a full-length complementary DNA clone and amino acid sequence of human phenylalanine hydroxylase. Biochemistry 1985 Jan. 29; 24(3):556-561. PMID: 2986678;

Leonard J V (2006). Disorders of the urea cycle and related enzymes. *Inborn Metabolic Diseases*, 4$^{th}$ ed (pp. 263-272). Springer Medizin Verlag Heidelberg;

Longo et al. Phase 1 Trial of Subcutaneous rAvPAL-PEG in Subjects with Phenylketonuria. Lancet. 2014 Jul. 5; 384 (9937):37-44;

Lopez G, Anderson J C. Synthetic Auxotrophs with Ligand-Dependent Essential Genes for a BL21(DE3) Biosafety Strain. ACS Synth Biol. 2015 Dec. 18; 4(12):1279-1286. PMID: 26072987;

Macleod et al. Nutritional Management of Phenylketonuria. Ann Nestle Eng. 2010 June; 68(2):58-69. PMID: 22475869;

Meadow et al. Biosynthesis of diaminopimelic acid and lysine in *Escherichia coli*. Biochem J. 1959 July; 72(3): 396-400. PMID: 16748796;

Miller (1972) Experiments in Molecular Genetics. Cold Spring Harbor Laboratory Press, Cold Spring Harbor, N.Y.;

Moffitt et al. Discovery of two cyanobacterial phenylalanine ammonia lyases: kinetic and structural characterization. Biochemistry. 2007 Jan. 30; 46(4):1004-1012. PMID: 17240984;

Moore et al. Regulation of FNR dimerization by subunit charge repulsion. J Biol Chem. 2006 Nov. 3; 281(44): 33268-33275. PMID: 16959764;

Nougayrede et al. *Escherichia coli* induces DNA double-strand breaks in eukaryotic cells. Science. 2006 Aug. 11; 313(5788):848-51. PMID: 16902142;

Olier et al. Genotoxicity of *Escherichia coli* Nissle 1917 strain cannot be dissociated from its probiotic activity. Gut Microbes. 2012 November-December; 3(6):501-509. PMID: 22895085;

Pi et al. Cloning and sequencing of the pheP gene, which encodes the phenylalanine-specific transport system of *Escherichia coli*. J Bacteriol. 1991 June; 173(12):3622-3629. PMID: 1711024;

Pi et al. Topology of the phenylalanine-specific permease of *Escherichia coli*. J Bacteriol. 1996 May; 178(9):2650-2655. PMID: 8626334;

Pi et al. Functional consequences of changing proline residues in the phenylalanine-specific permease of *Escherichia coli*. J Bacteriol. 1998 November; 180(21):5515-5519. PMID: 9791098;

Purcell et al. Towards a whole-cell modeling approach for synthetic biology. Chaos. 2013 June; 23(2):025112. PMID: 23822510;

Ray et al. The effects of mutation of the anr gene on the aerobic respiratory chain of *Pseudomonas aeruginosa*. FEMS Microbiol Lett. 1997 Nov. 15; 156(2):227-232. PMID: 9513270;

Reister et al. Complete genome sequence of the Gram-negative probiotic *Escherichia coli* strain Nissle 1917. J Biotechnol. 2014 Oct. 10; 187:106-107. PMID: 25093936;

Rembacken et al. Non-pathogenic *Escherichia coli* versus mesalazine for the treatment of ulcerative colitis: a randomised trial. Lancet. 1999 Aug. 21; 354(9179):635-639. PMID: 10466665;

Remington's Pharmaceutical Sciences (2012), 22$^{nd}$ ed. Mack Publishing Co, Easton, Pa.

Salmon et al. Global gene expression profiling in *Escherichia coli* K12. The effects of oxygen availability and FNR. J Biol Chem. 2003 Aug. 8; 278(32):29837-29855. PMID: 12754220;

Sarkissian et al. A different approach to treatment of phenylketonuria: phenylalanine degradation with recombinant phenylalanine ammonia lyase. Proc Natl Acad Sci USA. 1999 Mar. 2; 96(5):2339-2344. PMID: 10051643;

Sat et al. The *Escherichia coli* mazEF suicide module mediates thymineless death. J Bacteriol. 2003 March; 185(6):1803-1807. PMID: 12618443;

Sawers. Identification and molecular characterization of a transcriptional regulator from *Pseudomonas aeruginosa* PAO1 exhibiting structural and functional similarity to the FNR protein of *Escherichia coli*. Mol Microbiol. 1991 June; 5(6):1469-1481. PMID: 1787797;

Schultz. Clinical use of *E. coli* Nissle 1917 in inflammatory bowel disease. Inflamm Bowel Dis. 2008 July; 14(7): 1012-1018. PMID: 18240278;

Sonnenborn et al. The non-pathogenic *Escherichia coli* strain Nissle 1917—features of a versatile probiotic. Microbial Ecology in Health and Disease. 2009; 21:122-158;

Trunk et al. Anaerobic adaptation in *Pseudomonas aeruginosa*: definition of the Anr and Dnr regulons. Environ Microbiol. 2010 June; 12(6):1719-1733. PMID: 20553552;

Ukena et al. Probiotic *Escherichia coli* Nissle 1917 inhibits leaky gut by enhancing mucosal integrity. PLoS One. 2007 Dec. 12; 2(12):e1308. PMID: 18074031;

Unden et al. Alternative respiratory pathways of *Escherichia coli*: energetics and transcriptional regulation in response to electron acceptors. Biochim Biophys Acta. 1997 Jul. 4; 1320(3):217-234. PMID: 9230919;

Vockley et al. Phenylalanine hydroxylase deficiency: diagnosis and management guideline. Genet Med. 2014 February; 16(2):188-200. PMID: 24385074;

Wanner et al. The phenylalanine ammonia-lyase gene family in *Arabidopsis thaliana*. Plant Mol Biol. 1995 January; 27(2):327-338. PMID: 7888622;

Williams et al. The gene stlA encodes a phenylalanine ammonia-lyase that is involved in the production of a stilbene antibiotic in *Photorhabdus luminescens* TT01. Microbiology. 2005 August; 151(Pt 8):2543-2550. PMID: 16079333.

Winteler et al. The homologous regulators ANR of *Pseudomonas aeruginosa* and FNR of *Escherichia coli* have overlapping but distinct specificities for anaerobically inducible promoters. Microbiology. 1996 March; 142 (Pt 3):685-693. PMID: 8868444;

Wright et al. GeneGuard: A Modular Plasmid System Designed for Biosafety. ACS Synth Biol. 2015 Mar. 20; 4(3):307-316. PMID: 24847673;

Wu et al. Direct regulation of the natural competence regulator gene tfoX by cyclic AMP (cAMP) and cAMP receptor protein in Vibrios. Sci Rep. 2015 Oct. 7; 5:14921. PMID: 26442598;

Xiang L, Moore B S. Biochemical characterization of a prokaryotic phenylalanine ammonia lyase. J Bacteriol. 2005 June; 187(12):4286-4289. PMID: 15937191;

Zhang R, Lin Y. DEG 5.0, a database of essential genes in both prokaryotes and eukaryotes. Nucleic Acids Res. 2009 January; 37(Database issue):D455-D458. PMID: 18974178;

Zimmermann et al. Anaerobic growth and cyanide synthesis of *Pseudomonas aeruginosa* depend on anr, a regulatory gene homologous with fnr of *Escherichia coli*. Mol Microbiol. 1991 June; 5(6):1483-1490. PMID: 1787798.

EXAMPLES

The following examples provide illustrative embodiments of the disclosure. One of ordinary skill in the art will recognize the numerous modifications and variations that may be performed without altering the spirit or scope of the disclosure. Such modifications and variations are encompassed within the scope of the disclosure. The Examples do not in any way limit the disclosure.

Example 1

Construction of PAL Plasmids

To facilitate inducible production of PAL in *Escherichia coli* Nissle, the PAL gene of *Anabaena variabilis* ("PAL1") or *Photorhabdus luminescens* ("PAL3"), as well as transcriptional and translational elements, were synthesized (Gen9, Cambridge, Mass.) and cloned into vector pBR322. The PAL gene was placed under the control of an inducible promoter. Low-copy and high-copy plasmids were generated for each of PAL1 and PAL3 under the control of an inducible FNR promoter or a Tet promoter. Exemplary FNR promoters are shown in Table 3. Organization and nucleotide sequences of these constructs are shown in FIGS. 6-9. However, as noted above, other promoters may be used to drive expression of the PAL gene, other PAL genes may be used, and other phenylalanine metabolism-regulating genes may be used.

Example 2

Transforming *E. Coli*

Each of the plasmids described herein was transformed into *E. coli* Nissle for the studies described herein according to the following steps. All tubes, solutions, and cuvettes were pre-chilled to 4° C. An overnight culture of *E. coli* Nissle was diluted 1:100 in 5 mL of lysogeny broth (LB) containing ampicillin and grown until it reached an $OD_{600}$ of 0.4-0.6. The *E. coli* cells were then centrifuged at 2,000 rpm for 5 min at 4° C., the supernatant was removed, and the cells were resuspended in 1 mL of 4° C. water. The *E. coli* were again centrifuged at 2,000 rpm for 5 min at 4° C., the supernatant was removed, and the cells were resuspended in 0.5 mL of 4° C. water. The *E. coli* were again centrifuged at 2,000 rpm for 5 min at 4° C., the supernatant was removed, and the cells were finally resuspended in 0.1 mL of 4° C. water. The electroporator was set to 2.5 kV. Plasmid (0.5 µg) was added to the cells, mixed by pipetting, and pipetted into a sterile, chilled cuvette. The dry cuvette was placed into the sample chamber, and the electric pulse was applied. One mL of room-temperature SOC media was added immediately, and the mixture was transferred to a culture tube and incubated at 37° C. for 1 hr. The cells were spread out on an LB plate containing ampicillin and incubated overnight.

Example 3

Comparison of Phenylalanine Metabolism between High-copy and Low Copy Plasmids Expressing PAL1 and PAL2

Genetically engineered bacteria comprising the same PAL gene, either PAL3 on a low-copy plasmid or high copy plasmid (SYN-PKU101 and SYN-PKU102) or PAL3 on a low-copy plasmid or a high copy plasmid (SYN-PKU201 and SYN-PKU202) were assayed for phenylalanine metabolism in vitro.

Engineered bacteria were induced with anhydrous tetracycline (ATC), and then grown in culture medium supplemented with 4 mM (660,000 ng/mL) of phenylalanine for 2 hours. Samples were removed at 0 hrs, 4 hrs, and 23 hrs, and phenylalanine (FIG. 15A) and trans-cinnamic acid(TCA) (FIG. 15B) concentrations were determined by mass spectrometry as described in Examples 24-26.

High copy plasmids and low copy plasmid strains were found to metabolize and reduce phenylalanine to similar levels (FIG. 15). A greater reduction in phenylalanine levels and increase in TCA levels was observed in the strains expressing PAL3.

Example 4

Phenylalanine Transporter—Integration of PheP into the Bacterial Chromosome

In some embodiments, it may be advantageous to increase phenylalanine transport into the cell, thereby enhancing phenylalanine metabolism. Therefore, a second copy of the native high affinity phenylalanine transporter, PheP, driven by an inducible promoter, was inserted into the Nissle genome through homologous recombination. Organization of the construct is shown in FIG. 11. The pheP gene was placed downstream of the $P_{tet}$ promoter, and the tetracycline repressor, TetR, was divergently transcribed (see, e.g., FIG. 11). This sequence was synthesized by Genewiz (Cambridge, Mass.). To create a vector capable of integrating the synthesized TetR-PheP construct into the chromosome, Gibson assembly was first used to add 1000 bp sequences of DNA homologous to the Nissle lacZ locus into the R6K origin plasmid pKD3. This targets DNA cloned between these homology arms to be integrated into the lacZ locus in the Nissle genome (FIG. 10). Gibson assembly was used to clone the TetR-PheP fragment between these arms. PCR was used to amplify the region from this plasmid containing the entire sequence of the homology arms, as well as the pheP sequence between them. This PCR fragment was used to transform electrocompetent Nissle-pKD46, a strain that contains a temperature-sensitive plasmid encoding the lambda red recombinase genes. After transformation, cells were grown for 2 hrs before plating on chloramphenicol at 20 µg/mL at 37° C. Growth at 37° C. cures the pKD46 plasmid. Transformants containing anhydrous tetracycline (ATC)-inducible pheP were lac-minus (lac-) and chloramphenicol resistant.

Example 5

Effect of the Phenylalanine Transporter on Phenylalanine Degradation

To determine the effect of the phenylalanine transporter on phenylalanine degradation,
phenylalanine degradation and trans-cinnamate accumulation achieved by genetically engineered bacteria expressing PAL1 or PAL3 on low-copy (LC) or high-copy (HC) plasmids in the presence or absence of a copy of pheP driven by the Tet promoter integrated into the chromosome was assessed.

For in vitro studies, all incubations were performed at 37° C. Cultures of *E. coli* Nissle transformed with a plasmid comprising the PAL gene driven by the Tet promoter were grown overnight and then diluted 1:100 in LB. The cells were grown with shaking (200 rpm) to early log phase. Anhydrous tetracycline (ATC) was added to cultures at a concentration of 100 ng/mL to induce expression of PAL, and bacteria were grown for another 2 hrs. Bacteria were then pelleted, washed, and resuspended in minimal media, and supplemented with 4 mM phenylalanine. Aliquots were removed at 0 hrs, 2 hrs, and 4 hrs for phenylalanine quantification (FIG. 16A), and at 2 hrs and 4 hrs for cinnamate quantification (FIG. 16B), by mass spectrometry, as described in Examples 24-26. As shown in FIG. 16, expression of pheP in conjunction with PAL significantly enhances the degradation of phenylalanine as compared to PAL alone or pheP alone. Notably, the additional copy of pheP permitted the complete degradation of phenylalanine (4 mM) in 4 hrs (FIG. 16A). FIG. 16B depicts cinnamate levels in samples at 2 hrs and 4 hrs post-induction. Since cinnamate production is directly correlated with phenylalanine degradation, these data suggest that phenylalanine disappearance is due to phenylalanine catabolism, and that cinnamate may be used as an alternative biomarker for strain activity. PheP overexpression improves phenylalanine metabolism in engineered bacteria.

In conclusion, in conjunction with pheP, even low-copy PAL-expressing plasmids are capable of almost completely eliminating phenylalanine from a test sample (FIGS. 16A and 16B). Furthermore, without wishing to be bound by theory, in some embodiments, that incorporate pheP, there may be additional advantages to using a low-copy PAL-expressing plasmid in conjunction in order to enhance the stability of PAL expression while maintaining high phenyl-alanine metabolism, and to reduce negative selection pressure on the transformed bacterium. In alternate embodiments, the phenylalanine transporter is used in conjunction with a high-copy PAL-expressing plasmid.

Example 6

FNR Promoter Activity

Figure 18:
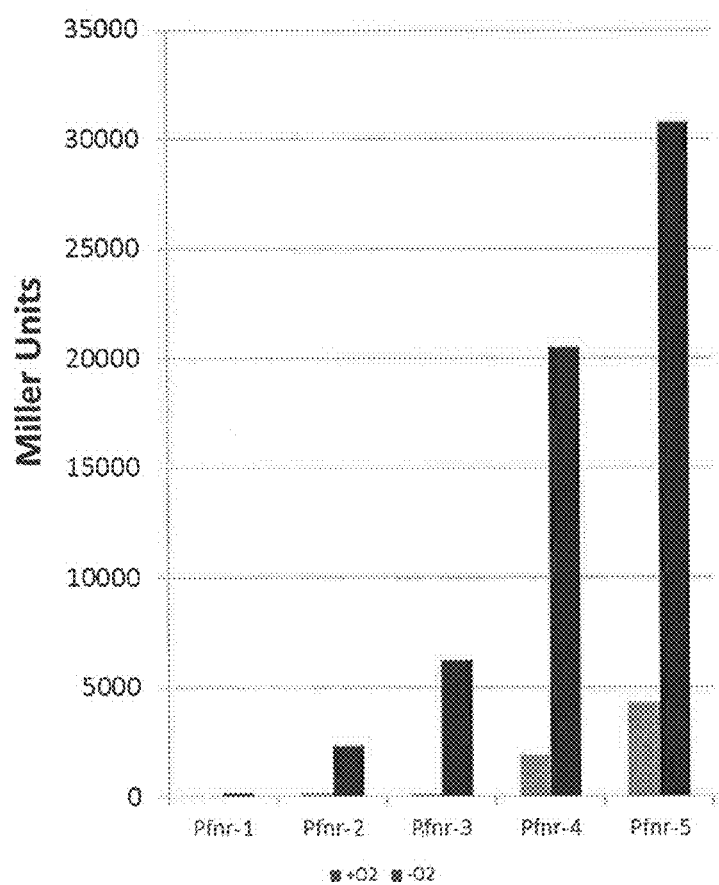
FIG. 18 depicts β-galactosidase levels in samples comprising bacteria harboring a low-copy plasmid expressing lacZ from an FNR-responsive promoter selected from the exemplary FNR promoters shown Table 3 (Pfnr1-5). Different FNR-responsive promoters were used to create a library of anaerobic-inducible reporters with a variety of expression levels and dynamic ranges. These promoters included strong ribosome binding sites. Bacterial cultures were grown in either aerobic ($+O_2$) or anaerobic conditions ($-O_2$). Samples were removed at 4 hrs and the promoter activity based on β-galactosidase levels was analyzed by performing standard β-galactosidase colorimetric assays.

In order to measure the promoter activity of different FNR promoters, the lacZ gene, as well as transcriptional and translational elements, were synthesized (Gen9, Cambridge, Mass.) and cloned into vector pBR322. The lacZ gene was placed under the control of any of the exemplary FNR promoter sequences disclosed in Table 3. The nucleotide sequences of these constructs are shown in Tables 21-28 (SEQ ID NOs 31-38). However, as noted above, the lacZ gene may be driven by other inducible promoters in order to analyze activities of those promoters, and other genes may be used in place of the lacZ gene as a readout for promoter activity. Alternatively, beta-galactosidase may be used as a reporter, exemplary results are shown in FIG. 18.

Table 21 shows the nucleotide sequence of an exemplary construct comprising a gene encoding lacZ, and an exemplary FNR promoter, $P_{fnr1}$ (SEQ ID NO: 3). The construct comprises a translational fusion of the Nissle nirB1 gene and the lacZ gene, in which the translational fusions are fused in frame to the $8^{th}$ codon of the lacZ coding region. The $P_{fnr1}$ sequence is bolded lower case, and the predicted ribosome binding site within the promoter is underlined. The lacZ sequence is underlined upper case. ATG site is bolded upper case, and the cloning sites used to synthesize the construct are shown in regular upper case.

Table 22 shows the nucleotide sequence of an exemplary construct comprising a gene encoding lacZ, and an exemplary FNR promoter, $P_{fnr2}$ (SEQ ID NO: 6). The construct comprises a translational fusion of the Nissle ydfZ gene and the lacZ gene, in which the translational fusions are fused in frame to the $8^{th}$ codon of the lacZ coding region. The $P_{fnr2}$ sequence is bolded lower case, and the predicted ribosome binding site within the promoter is underlined. The lacZ sequence is underlined upper case. ATG site is bolded upper case, and the cloning sites used to synthesize the construct are shown in regular upper case.

Table 23 shows the nucleotide sequence of an exemplary construct comprising a gene encoding lacZ, and an exemplary FNR promoter, $P_{fnr3}$ (SEQ ID NO: 7). The construct comprises a transcriptional fusion of the Nissle nirB gene and the lacZ gene, in which the transcriptional fusions use only the promoter region fused to a strong ribosomal binding site. The $P_{fnr3}$ sequence is bolded lower case, and the predicted ribosome binding site within the promoter is underlined. The lacZ sequence is underlined upper case. ATG site is bolded upper case, and the cloning sites used to synthesize the construct are shown in regular upper case.

Table 24 shows the nucleotide sequence of an exemplary construct comprising a gene encoding lacZ, and an exemplary FNR promoter, $P_{fnr4}$ (SEQ ID NO: 8). The construct comprises a transcriptional fusion of the Nissle ydfZ gene and the lacZ gene. The $P_{fnr4}$ sequence is bolded lower case, and the predicted ribosome binding site within the promoter is underlined. The lacZ sequence is underlined upper case. ATG site is bolded upper case, and the cloning sites used to synthesize the construct are shown in regular upper case.

Table 25 shows the nucleotide sequence of an exemplary construct comprising a gene encoding lacZ, and an exemplary FNR promoter, PfnrS (SEQ ID NO: 9). The construct comprises a transcriptional fusion of the anaerobically induced small RNA gene, fnrS1, fused to lacZ. The P$_{fnr}$ sequence is bolded lower case, and the predicted ribosome binding site within the promoter is underlined. The lacZ sequence is underlined upper case. ATG site is bolded upper case, and the cloning sites used to synthesize the construct are shown in regular upper case.

Table 26 shows the nucleotide sequence of an exemplary construct comprising a gene encoding PAL3, and an exemplary FNR promoter, P$_{fnr3}$ (SEQ ID NO: 7). The construct comprises a transcriptional fusion of the Nissle nirB gene and the PAL3 gene, in which the transcriptional fusions use only the promoter region fused to a strong ribosomal binding site. The P$_{fnr3}$ sequence is bolded lower case, and the predicted ribosome binding site within the promoter is underlined. The PAL3 sequence is underlined upper case. ATG site is bolded upper case, and the cloning sites used to synthesize the construct are shown in regular upper case.

Table 27 shows the nucleotide sequences of an exemplary construct comprising a gene encoding PAL3, and an exemplary FNR promoter, P$_{fnr4}$ (SEQ ID NO: 8). The construct comprises a transcriptional fusion of the Nissle ydfZ gene and the PAL3 gene. The P$_{fnr4}$ sequence is bolded lower case, and the predicted ribosome binding site within the promoter is underlined. The PAL3 sequence is underlined upper case. ATG site is bolded upper case, and the cloning sites used to synthesize the construct are shown in regular upper case.

Table 28 shows the nucleotide sequences of an exemplary construct comprising a gene encoding PAL3, and an exemplary FNR promoter, P$_{fnrs}$ (SEQ ID NO: 9). The construct comprises a transcriptional fusion of the anaerobically induced small RNA gene, fnrS1, fused to PAL3. The Pfnrs sequence is bolded lower case, and the predicted ribosome binding site within the promoter is underlined. The PAL3 sequence is underlined upper case. ATG site is bolded upper case, and the cloning sites used to synthesize the construct are shown in regular upper case.

TABLE 21

Nucleotide sequences of Pfnr1-lacZ construct, low-copy (SEQ ID NO: 31)

GGTACCgtcagcataacaccctgacctctcattaattgttcatgccgggcggcactatc gtcgtccggccttttcctctcttactctgctacgtacatctatttctataaatccgttc aatttgtctgtttttgcacaaacatgaaatatcagacaattccgtgacttaagaaaat ttatacaaatcagcaatataccccttaaggagtatataaaggtgaatttgatttacatc aataagcggggttgctgaatcgttaaggtaggcggtaatagaaaagaaatcgaggcaaa aATGagcaaagtcagactcgcaattatGGATCCTCTGGCCGTCGTATTACAACGTCGTG

ACTGGGAAAACCCTGGCGTTACCCAACTTAATCGCCTTGCGGCACATCCCCCTTTCGCC

AGCTGGCGTAATAGCGAAGAGGCCCGCACCGATCGCCCTTCCCAACAGTTGCGCAGCCT

GAATGGCGAATGGCGCTTTGCCTGGTTTCCGGCACCAGAAGCGGTGCCGGAAAGCTGGC

TGGAGTGCGATCTTCCTGACGCCGATACTGTCGTCGTCCCCTCAAACTGGCAGATGCAC

GGTTACGATGCGCCTATCTACACCAACGTGACCTATCCCATTACGGTCAATCCGCCGTT

TGTTCCCGCGGAGAATCCGACAGGTTGTTACTCGCTCACATTTAATATTGATGAAAGCT

GGCTACAGGAAGGCCAGACGCGAATTATTTTTGATGGCGTTAACTCGGCGTTTCATCTG

TGGTGCAACGGGCGCTGGGTCGGTTACGGCCAGGACAGCCGTTTGCCGTCTGAATTTGA

CCTGAGCGCATTTTTACGCGCCGGAGAAAACCGCCTCGCGGTGATGGTGCTGCGCTGGA

GTGACGGCAGTTATCTGGAAGATCAGGATATGTGGCGGATGAGCGGCATTTTCCGTGAC

GTCTCGTTGCTGCATAAACCGACCACGCAAATCAGCGATTTCCAAGTTACCACTCTCTT

TAATGATGATTTCAGCCGCGCGGTACTGGAGGCAGAAGTTCAGATGTACGGCGAGCTGC

GCGATGAACTGCGGGTGACGGTTTCTTTGTGGCAGGGTGAAACGCAGGTCGCCAGCGGC

ACCGCGCCTTTCGGCGGTGAAATTATCGATGAGCGTGGCGGTTATGCCGATCGCGTCAC

ACTACGCCTGAACGTTGAAAATCCGGAACTGTGGAGCGCCGAAATCCCGAATCTCTATC

GTGCAGTGGTTGAACTGCACACCGCCGACGGCACGCTGATTGAAGCAGAAGCCTGCGAC

GTCGGTTTCCGCGAGGTGCGGATTGAAAATGGTCTGCTGCTGCTGAACGGCAAGCCGTT

GCTGATTCGCGGCGTTAACCGTCACGAGCATCATCCTCTGCATGGTCAGGTCATGGATG

AGCAGACGATGGTGCAGGATATCCTGCTGATGAAGCAGAACAACTTTAACGCCGTGCGC

TGTTCGCATTATCCGAACCATCCGCTGTGGTACACGCTGTGCGACCGCTACGGCCTGTA

TGTGGTGGATGAAGCCAATATTGAAACCCACGGCATGGTGCCAATGAATCGTCTGACCG

TABLE 21-continued

Nucleotide sequences of Pfnr1-lacZ construct, low-copy (SEQ ID NO: 31)

ATGATCCGCGCTGGCTACCCGCGATGAGCGAACGCGTAACGCGGATGGTGCAGCGCGAT

CGTAATCACCCGAGTGTGATCATCTGGTCGCTGGGGAATGAATCAGGCCACGGCGCTAA

TCACGACGCGCTGTATCGCTGGATCAAATCTGTCGATCCTTCCCGCCCGGTACAGTATG

AAGGCGGCGGAGCCGACACCACGGCCACCGATATTATTTGCCCGATGTACGCGCGCGTG

GATGAAGACCAGCCCTTCCCGGCGGTGCCGAAATGGTCCATCAAAAAATGGCTTTCGCT

GCCTGGAGAAATGCGCCCGCTGATCCTTTGCGAATATGCCCACGCGATGGGTAACAGTC

TTGGCGGCTTCGCTAAATACTGGCAGGCGTTTCGTCAGTACCCCCGTTTACAGGGCGGC

TTCGTCTGGGACTGGGTGGATCAGTCGCTGATTAAATATGATGAAAACGGCAACCCGTG

GTCGGCTTACGGCGGTGATTTTGGCGATACGCCGAACGATCGCCAGTTCTGTATGAACG

GTCTGGTCTTTGCCGACCGCACGCCGCATCCGGCGCTGACGGAAGCAAAACACCAACAG

CAGTATTTCCAGTTCCGTTTATCCGGGCGAACCATCGAAGTGACCAGCGAATACCTGTT

CCGTCATAGCGATAACGAGTTCCTGCACTGGATGGTGGCACTGGATGGCAAGCCGCTGG

CAAGCGGTGAAGTGCCTCTGGATGTTGGCCCGCAAGGTAAGCAGTTGATTGAACTGCCT

GAACTGCCGCAGCCGGAGAGCGCCGGACAACTCTGGCTAACGGTACGCGTAGTGCAACC

AAACGCGACCGCATGGTCAGAAGCCGGACACATCAGCGCCTGGCAGCAATGGCGTCTGG

CGGAAAACCTCAGCGTGACACTCCCCTCCGCGTCCCACGCCATCCCTCAACTGACCACC

AGCGGAACGGATTTTTGCATCGAGCTGGGTAATAAGCGTTGGCAATTTAACCGCCAGTC

AGGCTTTCTTTCACAGATGTGGATTGGCGATGAAAAACAACTGCTGACCCCGCTGCGCG

ATCAGTTCACCCGTGCGCCGCTGGATAACGACATTGGCGTAAGTGAAGCGACCCGCATT

GACCCTAACGCCTGGGTCGAACGCTGGAAGGCGGCGGGCCATTACCAGGCCGAAGCGGC

GTTGTTGCAGTGCACGGCAGATACACTTGCCGACGCGGTGCTGATTACAACCGCCCACG

CGTGGCAGCATCAGGGGAAAACCTTATTTATCAGCCGGAAAACCTACCGGATTGATGGG

CACGGTGAGATGGTCATCAATGTGGATGTTGCGGTGGCAAGCGATACACCGCATCCGGC

GCGGATTGGCCTGACCTGCCAGCTGGCGCAGGTCTCAGAGCGGGTAAACTGGCTCGGCC

TGGGGCCGCAAGAAAACTATCCCGACCGCCTTACTGCAGCCTGTTTTGACCGCTGGGAT

CTGCCATTGTCAGACATGTATACCCCGTACGTCTTCCCGAGCGAAAACGGTCTGCGCTG

CGGGACGCGCGAATTGAATTATGGCCCACACCAGTGGCGCGGCGACTTCCAGTTCAACA

TCAGCCGCTACAGCCAACAACAACTGATGGAAACCAGCCATCGCCATCTGCTGCACGCG

GAAGAAGGCACATGGCTGAATATCGACGGTTTCCATATGGGGATTGGTGGCGACGACTC

CTGGAGCCCGTCAGTATCGGCGGAATTCCAGCTGAGCGCCGGTCGCTACCATTACCAGT

TGGTCTGGTGTCAAAAATAA

TABLE 22

Nucleotide sequences of Pfnr2-lacZ construct, low-copy (SEQ ID NO: 32)

GGTACCcatttcctctcatcccatccggggtgagagtcttttcccccgacttatggctc atgcatgcatcaaaaaagatgtgagcttgatcaaaaacaaaaaatatttcactcgacag gagtatttatattgcgcccgttacgtgggcttcgactgtaaatcagaaaggagaaaaca cctATGacgacctacgatcgGGATCCTCTGGCCGTCGTATTACAACGTCGTGACTGGGA

AAACCCTGGCGTTACCCAACTTAATCGCCTTGCGGCACATCCCCCTTTCGCCAGCTGGC

TABLE 22-continued

Nucleotide sequences of Pfnr2-lacZ construct, low-copy (SEQ ID NO: 32)

GTAATAGCGAAGAGGCCCGCACCGATCGCCCTTCCCAACAGTTGCGCAGCCTGAATGGC

GAATGGCGCTTTGCCTGGTTTCCGGCACCAGAAGCGGTGCCGGAAAGCTGGCTGGAGTG

CGATCTTCCTGACGCCGATACTGTCGTCGTCCCCTCAAACTGGCAGATGCACGGTTACG

ATGCGCCTATCTACACCAACGTGACCTATCCCATTACGGTCAATCCGCCGTTTGTTCCC

GCGGAGAATCCGACAGGTTGTTACTCGCTCACATTTAATATTGATGAAAGCTGGCTACA

GGAAGGCCAGACGCGAATTATTTTTGATGGCGTTAACTCGGCGTTTCATCTGTGGTGCA

ACGGGCGCTGGGTCGGTTACGGCCAGGACAGCCGTTTGCCGTCTGAATTTGACCTGAGC

GCATTTTTACGCGCCGGAGAAAACCGCCTCGCGGTGATGGTGCTGCGCTGGAGTGACGG

CAGTTATCTGGAAGATCAGGATATGTGGCGGATGAGCGGCATTTTCCGTGACGTCTCGT

TGCTGCATAAACCGACCACGCAAATCAGCGATTTCCAAGTTACCACTCTCTTTAATGAT

GATTTCAGCCGCGCGGTACTGGAGGCAGAAGTTCAGATGTACGGCGAGCTGCGCGATGA

ACTGCGGGTGACGGTTTCTTTGTGGCAGGGTGAAACGCAGGTCGCCAGCGGCACCGCGC

CTTTCGGCGGTGAAATTATCGATGAGCGTGGCGGTTATGCCGATCGCGTCACACTACGC

CTGAACGTTGAAAATCCGGAACTGTGGAGCGCCGAAATCCCGAATCTCTATCGTGCAGT

GGTTGAACTGCACACCGCCGACGGCACGCTGATTGAAGCAGAAGCCTGCGACGTCGGTT

TCCGCGAGGTGCGGATTGAAAATGGTCTGCTGCTGCTGAACGGCAAGCCGTTGCTGATT

CGCGGCGTTAACCGTCACGAGCATCATCCTCTGCATGGTCAGGTCATGGATGAGCAGAC

GATGGTGCAGGATATCCTGCTGATGAAGCAGAACAACTTTAACGCCGTGCGCTGTTCGC

ATTATCCGAACCATCCGCTGTGGTACACGCTGTGCGACCGCTACGGCCTGTATGTGGTG

GATGAAGCCAATATTGAAACCCACGGCATGGTGCCAATGAATCGTCTGACCGATGATCC

GCGCTGGCTACCCGCGATGAGCGAACGCGTAACGCGGATGGTGCAGCGCGATCGTAATC

ACCCGAGTGTGATCATCTGGTCGCTGGGGAATGAATCAGGCCACGGCGCTAATCACGAC

GCGCTGTATCGCTGGATCAAATCTGTCGATCCTTCCCGCCCGGTACAGTATGAAGGCGG

CGGAGCCGACACCACGGCCACCGATATTATTTGCCCGATGTACGCGCGCGTGGATGAAG

ACCAGCCCTTCCCGGCGGTGCCGAAATGGTCCATCAAAAAATGGCTTTCGCTGCCTGGA

GAAATGCGCCCGCTGATCCTTTGCGAATATGCCCACGCGATGGGTAACAGTCTTGGCGG

CTTCGCTAAATACTGGCAGGCGTTTCGTCAGTACCCCCGTTTACAGGGCGGCTTCGTCT

GGGACTGGGTGGATCAGTCGCTGATTAAATATGATGAAAACGGCAACCCGTGGTCGGCT

TACGGCGGTGATTTTGGCGATACGCCGAACGATCGCCAGTTCTGTATGAACGGTCTGGT

CTTTGCCGACCGCACGCCGCATCCGGCGCTGACGGAAGCAAAACACCAACAGCAGTATT

TCCAGTTCCGTTTATCCGGGCGAACCATCGAAGTGACCAGCGAATACCTGTTCCGTCAT

AGCGATAACGAGTTCCTGCACTGGATGGTGGCACTGGATGGCAAGCCGCTGGCAAGCGG

TGAAGTGCCTCTGGATGTTGGCCCGCAAGGTAAGCAGTTGATTGAACTGCCTGAACTGC

CGCAGCCGGAGAGCGCCGGACAACTCTGGCTAACGGTACGCGTAGTGCAACCAAACGCG

ACCGCATGGTCAGAAGCCGGACACATCAGCGCCTGGCAGCAATGGCGTCTGGCGGAAAA

CCTCAGCGTGACACTCCCCTCCGCGTCCCACGCCATCCCTCAACTGACCACCAGCGGAA

CGGATTTTTGCATCGAGCTGGGTAATAAGCGTTGGCAATTTAACCGCCAGTCAGGCTTT

CTTTCACAGATGTGGATTGGCGATGAAAAACAACTGCTGACCCCGCTGCGCGATCAGTT

CACCCGTGCGCCGCTGGATAACGACATTGGCGTAAGTGAAGCGACCCGCATTGACCCTA

TABLE 22-continued

Nucleotide sequences of Pfnr2-lacZ construct, low-copy (SEQ ID NO: 32)

ACGCCTGGGTCGAACGCTGGAAGGCGGCGGGCCATTACCAGGCCGAAGCGGCGTTGTTG

CAGTGCACGGCAGATACACTTGCCGACGCGGTGCTGATTACAACCGCCCACGCGTGGCA

GCATCAGGGGAAAACCTTATTTATCAGCCGGAAAACCTACCGGATTGATGGGCACGGTG

AGATGGTCATCAATGTGGATGTTGCGGTGGCAAGCGATACACCGCATCCGGCGCGGATT

GGCCTGACCTGCCAGCTGGCGCAGGTCTCAGAGCGGGTAAACTGGCTCGGCCTGGGGCC

GCAAGAAAACTATCCCGACCGCCTTACTGCAGCCTGTTTTGACCGCTGGGATCTGCCAT

TGTCAGACATGTATACCCCGTACGTCTTCCCGAGCGAAAACGGTCTGCGCTGCGGGACG

CGCGAATTGAATTATGGCCCACACCAGTGGCGCGGCGACTTCCAGTTCAACATCAGCCG

CTACAGCCAACAACAACTGATGGAAACCAGCCATCGCCATCTGCTGCACGCGGAAGAAG

GCACATGGCTGAATATCGACGGTTTCCATATGGGGATTGGTGGCGACGACTCCTGGAGC

CCGTCAGTATCGGCGGAATTCCAGCTGAGCGCCGGTCGCTACCATTACCAGTTGGTCTG

GTGTCAAAAATAA

TABLE 23

Nucleotide sequences of Pfnr3-lacZ construct, low-copy (SEQ ID NO: 33)

GGTACCgtcagcataacaccctgacctctcattaattgttcatgccgggcggcactatc gtcgtccggccttttcctctcttactctgctacgtacatctatttctataaatccgttc aatttgtctgtttttttgcacaaacatgaaatatcagacaattccgtgacttaagaaaat ttatacaaatcagcaatatacccttaaggagtatataaaggtgaatttgatttacatc aataagcggggttgctgaatcgttaaGGATCCctctagaaataattttgtttaacttta agaaggagatatacatATGACTATGATTACGGATTCTCTGGCCGTCGTATTACAACGTC

GTGACTGGGAAAACCCTGGCGTTACCCAACTTAATCGCCTTGCGGCACATCCCCCTTTC

GCCAGCTGGCGTAATAGCGAAGAGGCCCGCACCGATCGCCCTTCCCAACAGTTGCGCAG

CCTGAATGGCGAATGGCGCTTTGCCTGGTTTCCGGCACCAGAAGCGGTGCCGGAAAGCT

GGCTGGAGTGCGATCTTCCTGACGCCGATACTGTCGTCGTCCCCTCAAACTGGCAGATG

CACGGTTACGATGCGCCTATCTACACCAACGTGACCTATCCCATTACGGTCAATCCGCC

GTTTGTTCCCGCGGAGAATCCGACAGGTTGTTACTCGCTCACATTTAATATTGATGAAA

GCTGGCTACAGGAAGGCCAGACGCGAATTATTTTTGATGGCGTTAACTCGGCGTTTCAT

CTGTGGTGCAACGGGCGCTGGGTCGGTTACGGCCAGGACAGCCGTTTGCCGTCTGAATT

TGACCTGAGCGCATTTTTACGCGCCGGAGAAAACCGCCTCGCGGTGATGGTGCTGCGCT

GGAGTGACGGCAGTTATCTGGAAGATCAGGATATGTGGCGGATGAGCGGCATTTTCCGT

GACGTCTCGTTGCTGCATAAACCGACCACGCAAATCAGCGATTTCCAAGTTACCACTCT

CTTTAATGATGATTTCAGCCGCGCGGTACTGGAGGCAGAAGTTCAGATGTACGGCGAGC

TGCGCGATGAACTGCGGGTGACGGTTTCTTTGTGGCAGGGTGAAACGCAGGTCGCCAGC

GGCACCGCGCCTTTCGGCGGTGAAATTATCGATGAGCGTGGCGGTTATGCCGATCGCGT

CACACTACGCCTGAACGTTGAAAATCCGGAACTGTGGAGCGCCGAAATCCCGAATCTCT

ATCGTGCAGTGGTTGAACTGCACACCGCCGACGGCACGCTGATTGAAGCAGAAGCCTGC

GACGTCGGTTTCCGCGAGGTGCGGATTGAAAATGGTCTGCTGCTGCTGAACGGCAAGCC

TABLE 23-continued

Nucleotide sequences of Pfnr3-lacZ construct, low-copy (SEQ ID NO: 33)

GTTGCTGATTCGCGGCGTTAACCGTCACGAGCATCATCCTCTGCATGGTCAGGTCATGG
ATGAGCAGACGATGGTGCAGGATATCCTGCTGATGAAGCAGAACAACTTTAACGCCGTG
CGCTGTTCGCATTATCCGAACCATCCGCTGTGGTACACGCTGTGCGACCGCTACGGCCT
GTATGTGGTGGATGAAGCCAATATTGAAACCCACGGCATGGTGCCAATGAATCGTCTGA
CCGATGATCCGCGCTGGCTACCCGCGATGAGCGAACGCGTAACGCGGATGGTGCAGCGC
GATCGTAATCACCCGAGTGTGATCATCTGGTCGCTGGGGAATGAATCAGGCCACGGCGC
TAATCACGACGCGCTGTATCGCTGGATCAAATCTGTCGATCCTTCCCGCCCGGTACAGT
ATGAAGGCGGCGGAGCCGACACCACGGCCACCGATATTATTTGCCCGATGTACGCGCGC
GTGGATGAAGACCAGCCCTTCCCGGCGGTGCCGAAATGGTCCATCAAAAAATGGCTTTC
GCTGCCTGGAGAAATGCGCCCGCTGATCCTTTGCGAATATGCCCACGCGATGGGTAACA
GTCTTGGCGGCTTCGCTAAATACTGGCAGGCGTTTCGTCAGTACCCCCGTTTACAGGGC
GGCTTCGTCTGGGACTGGGTGGATCAGTCGCTGATTAAATATGATGAAAACGGCAACCC
GTGGTCGGCTTACGGCGGTGATTTTGGCGATACGCCGAACGATCGCCAGTTCTGTATGA
ACGGTCTGGTCTTTGCCGACCGCACGCCGCATCCGGCGCTGACGGAAGCAAAACACCAA
CAGCAGTATTTCCAGTTCCGTTTATCCGGGCGAACCATCGAAGTGACCAGCGAATACCT
GTTCCGTCATAGCGATAACGAGTTCCTGCACTGGATGGTGGCACTGGATGGCAAGCCGC
TGGCAAGCGGTGAAGTGCCTCTGGATGTTGGCCCGCAAGGTAAGCAGTTGATTGAACTG
CCTGAACTGCCGCAGCCGGAGAGCGCCGGACAACTCTGGCTAACGGTACGCGTAGTGCA
ACCAAACGCGACCGCATGGTCAGAAGCCGGACACATCAGCGCCTGGCAGCAATGGCGTC
TGGCGGAAAACCTCAGCGTGACACTCCCCTCCGCGTCCCACGCCATCCCTCAACTGACC
ACCAGCGGAACGGATTTTTGCATCGAGCTGGGTAATAAGCGTTGGCAATTTAACCGCCA
GTCAGGCTTTCTTTCACAGATGTGGATTGGCGATGAAAAACAACTGCTGACCCCGCTGC
GCGATCAGTTCACCCGTGCGCCGCTGGATAACGACATTGGCGTAAGTGAAGCGACCCGC
ATTGACCCTAACGCCTGGGTCGAACGCTGGAAGGCGGCGGGCCATTACCAGGCCGAAGC
GGCGTTGTTGCAGTGCACGGCAGATACACTTGCCGACGCGGTGCTGATTACAACCGCCC
ACGCGTGGCAGCATCAGGGGAAAACCTTATTTATCAGCCGGAAAACCTACCGGATTGAT
GGGCACGGTGAGATGGTCATCAATGTGGATGTTGCGGTGGCAAGCGATACACCGCATCC
GGCGCGGATTGGCCTGACCTGCCAGCTGGCGCAGGTCTCAGAGCGGGTAAACTGGCTCG
GCCTGGGGCCGCAAGAAAACTATCCCGACCGCCTTACTGCAGCCTGTTTTGACCGCTGG
GATCTGCCATTGTCAGACATGTATACCCCGTACGTCTTCCCGAGCGAAAACGGTCTGCG
CTGCGGGACGCGCGAATTGAATTATGGCCCACACCAGTGGCGCGGCGACTTCCAGTTCA
ACATCAGCCGCTACAGCCAACAACAACTGATGGAAACCAGCCATCGCCATCTGCTGCAC
GCGGAAGAAGGCACATGGCTGAATATCGACGGTTTCCATATGGGGATTGGTGGCGACGA
CTCCTGGAGCCCGTCAGTATCGGCGGAATTCCAGCTGAGCGCCGGTCGCTACCATTACC
AGTTGGTCTGGTGTCAAAAATAA

TABLE 24

Nucleotide sequences of Pfnr4-lacZ construct, low-copy (SEQ ID NO: 34)

GGTACCcatttcctctcatcccatccggggtgagagtcttttcccccgacttatggctc atgcatgcatcaaaaaagatgtgagcttgatcaaaaacaaaaaatatttcactcgacag gagtatttatattgcgcccGGATCCctctagaaataattttgtttaactttaagaagga gatatacatATGACTATGATTACGGATTCTCTGGCCGTCGTATTACAACGTCGTGACTG

GGAAAACCCTGGCGTTACCCAACTTAATCGCCTTGCGGCACATCCCCCTTTCGCCAGCT

GGCGTAATAGCGAAGAGGCCCGCACCGATCGCCCTTCCCAACAGTTGCGCAGCCTGAAT

GGCGAATGGCGCTTTGCCTGGTTTCCGGCACCAGAAGCGGTGCCGGAAAGCTGGCTGGA

GTGCGATCTTCCTGACGCCGATACTGTCGTCGTCCCCTCAAACTGGCAGATGCACGGTT

ACGATGCGCCTATCTACACCAACGTGACCTATCCCATTACGGTCAATCCGCCGTTTGTT

CCCGCGGAGAATCCGACAGGTTGTTACTCGCTCACATTTAATATTGATGAAAGCTGGCT

ACAGGAAGGCCAGACGCGAATTATTTTTGATGGCGTTAACTCGGCGTTTCATCTGTGGT

GCAACGGGCGCTGGGTCGGTTACGGCCAGGACAGCCGTTTGCCGTCTGAATTTGACCTG

AGCGCATTTTTACGCGCCGGAGAAAACCGCCTCGCGGTGATGGTGCTGCGCTGGAGTGA

CGGCAGTTATCTGGAAGATCAGGATATGTGGCGGATGAGCGGCATTTTCCGTGACGTCT

CGTTGCTGCATAAACCGACCACGCAAATCAGCGATTTCCAAGTTACCACTCTCTTTAAT

GATGATTTCAGCCGCGCGGTACTGGAGGCAGAAGTTCAGATGTACGGCGAGCTGCGCGA

TGAACTGCGGGTGACGGTTTCTTTGTGGCAGGGTGAAACGCAGGTCGCCAGCGGCACCG

CGCCTTTCGGCGGTGAAATTATCGATGAGCGTGGCGGTTATGCCGATCGCGTCACACTA

CGCCTGAACGTTGAAAATCCGGAACTGTGGAGCGCCGAAATCCCGAATCTCTATCGTGC

AGTGGTTGAACTGCACACCGCCGACGGCACGCTGATTGAAGCAGAAGCCTGCGACGTCG

GTTTCCGCGAGGTGCGGATTGAAAATGGTCTGCTGCTGCTGAACGGCAAGCCGTTGCTG

ATTCGCGGCGTTAACCGTCACGAGCATCATCCTCTGCATGGTCAGGTCATGGATGAGCA

GACGATGGTGCAGGATATCCTGCTGATGAAGCAGAACAACTTTAACGCCGTGCGCTGTT

CGCATTATCCGAACCATCCGCTGTGGTACACGCTGTGCGACCGCTACGGCCTGTATGTG

GTGGATGAAGCCAATATTGAAACCCACGGCATGGTGCCAATGAATCGTCTGACCGATGA

TCCGCGCTGGCTACCCGCGATGAGCGAACGCGTAACGCGGATGGTGCAGCGCGATCGTA

ATCACCCGAGTGTGATCATCTGGTCGCTGGGGAATGAATCAGGCCACGGCGCTAATCAC

GACGCGCTGTATCGCTGGATCAAATCTGTCGATCCTTCCCGCCCGGTACAGTATGAAGG

CGGCGGAGCCGACACCACGGCCACCGATATTATTTGCCCGATGTACGCGCGCGTGGATG

AAGACCAGCCCTTCCCGGCGGTGCCGAAATGGTCCATCAAAAAATGGCTTTCGCTGCCT

GGAGAAATGCGCCCGCTGATCCTTTGCGAATATGCCCACGCGATGGGTAACAGTCTTGG

CGGCTTCGCTAAATACTGGCAGGCGTTTCGTCAGTACCCCCGTTTACAGGGCGGCTTCG

TCTGGGACTGGGTGGATCAGTCGCTGATTAAATATGATGAAAACGGCAACCCGTGGTCG

GCTTACGGCGGTGATTTTGGCGATACGCCGAACGATCGCCAGTTCTGTATGAACGGTCT

GGTCTTTGCCGACCGCACGCCGCATCCGGCGCTGACGGAAGCAAAACACCAACAGCAGT

ATTTCCAGTTCCGTTTATCCGGGCGAACCATCGAAGTGACCAGCGAATACCTGTTCCGT

CATAGCGATAACGAGTTCCTGCACTGGATGGTGGCACTGGATGGCAAGCCGCTGGCAAG

CGGTGAAGTGCCTCTGGATGTTGGCCCGCAAGGTAAGCAGTTGATTGAACTGCCTGAAC

TGCCGCAGCCGGAGAGCGCCGGACAACTCTGGCTAACGGTACGCGTAGTGCAACCAAAC

TABLE 24-continued

Nucleotide sequences of Pfnr4-lacZ construct, low-copy (SEQ ID NO: 34)

GCGACCGCATGGTCAGAAGCCGGACACATCAGCGCCTGGCAGCAATGGCGTCTGGCGGA

AAACCTCAGCGTGACACTCCCCTCCGCGTCCCACGCCATCCCTCAACTGACCACCAGCG

GAACGGATTTTTGCATCGAGCTGGGTAATAAGCGTTGGCAATTTAACCGCCAGTCAGGC

TTTCTTTCACAGATGTGGATTGGCGATGAAAAACAACTGCTGACCCCGCTGCGCGATCA

GTTCACCCGTGCGCCGCTGGATAACGACATTGGCGTAAGTGAAGCGACCCGCATTGACC

CTAACGCCTGGGTCGAACGCTGGAAGGCGGCGGGCCATTACCAGGCCGAAGCGGCGTTG

TTGCAGTGCACGGCAGATACACTTGCCGACGCGGTGCTGATTACAACCGCCCACGCGTG

GCAGCATCAGGGGAAAACCTTATTTATCAGCCGGAAAACCTACCGGATTGATGGGCACG

GTGAGATGGTCATCAATGTGGATGTTGCGGTGGCAAGCGATACACCGCATCCGGCGCGG

ATTGGCCTGACCTGCCAGCTGGCGCAGGTCTCAGAGCGGGTAAACTGGCTCGGCCTGGG

GCCGCAAGAAAACTATCCCGACCGCCTTACTGCAGCCTGTTTTGACCGCTGGGATCTGC

CATTGTCAGACATGTATACCCCGTACGTCTTCCCGAGCGAAAACGGTCTGCGCTGCGGG

ACGCGCGAATTGAATTATGGCCCACACCAGTGGCGCGGCGACTTCCAGTTCAACATCAG

CCGCTACAGCCAACAACAACTGATGGAAACCAGCCATCGCCATCTGCTGCACGCGGAAG

AAGGCACATGGCTGAATATCGACGGTTTCCATATGGGGATTGGTGGCGACGACTCCTGG

AGCCCGTCAGTATCGGCGGAATTCCAGCTGAGCGCCGGTCGCTACCATTACCAGTTGGT

CTGGTGTCAAAAATAA

TABLE 25

Nucleotide sequences of Pfnrs-lacZ construct, low-copy (SEQ ID NO: 35)

GGTACCagttgttcttattggtggtgttgctttatggttgcatcgtagtaaatggttgt aacaaaagcaattttccggctgtctgtatacaaaaacgccgtaaagtttgagcgaagt caataaactctctacccattcagggcaatatctctcttGGATCCctctagaaataattt tgtttaactttaagaaggagatatacatATGCTATGATTACGGATTCTCTGGCCGTCGT

ATTACAACGTCGTGACTGGGAAAACCCTGGCGTTACCCAACTTAATCGCCTTGCGGCAC

ATCCCCCTTTCGCCAGCTGGCGTAATAGCGAAGAGGCCCGCACCGATCGCCCTTCCCAA

CAGTTGCGCAGCCTGAATGGCGAATGGCGCTTTGCCTGGTTTCCGGCACCAGAAGCGGT

GCCGGAAAGCTGGCTGGAGTGCGATCTTCCTGACGCCGATACTGTCGTCGTCCCCTCAA

ACTGGCAGATGCACGGTTACGATGCGCCTATCTACACCAACGTGACCTATCCCATTACG

GTCAATCCGCCGTTTGTTCCCGCGGAGAATCCGACAGGTTGTTACTGCTCACATTTAA

TATTGATGAAAGCTGGCTACAGGAAGGCCAGACGCGAATTATTTTTGATGGCGTTAACT

CGGCGTTTCATCTGTGGTGCAACGGGCGCTGGGTCGGTTACGGCCAGGACAGCCGTTTG

CCGTCTGAATTTGACCTGAGCGCATTTTTACGCGCCGGAGAAAACCGCCTCGCGGTGAT

GGTGCTGCGCTGGAGTGACGGCAGTTATCTGGAAGATCAGGATATGTGGCGGATGAGCG

GCATTTTCCGTGACGTCTCGTTGCTGCATAAACCGACCACGCAAATCAGCGATTTCCAA

GTTACCACTCTCTTTAATGATGATTTCAGCCGCGCGGTACTGGAGGCAGAAGTTCAGAT

GTACGGCGAGCTGCGCGATGAACTGCGGGTGACGGTTTCTTTGTGGCAGGGTGAAACGC

AGGTCGCCAGCGGCACCGCGCCTTTCGGCGGTGAAATTATCGATGAGCGTGGCGGTTAT

GCCGATCGCGTCACACTACGCCTGAACGTTGAAAATCCGGAACTGTGGAGCGCCGAAAT

TABLE 25-continued

Nucleotide sequences of Pfnrs-lacZ construct, low-copy (SEQ ID NO: 35)

CCCGAATCTCTATCGTGCAGTGGTTGAACTGCACACCGCCGACGGCACGCTGATTGAAG

CAGAAGCCTGCGACGTCGGTTTCCGCGAGGTGCGGATTGAAAATGGTCTGCTGCTGCTG

AACGGCAAGCCGTTGCTGATTCGCGGCGTTAACCGTCACGAGCATCATCCTCTGCATGG

TCAGGTCATGGATGAGCAGACGATGGTGCAGGATATCCTGCTGATGAAGCAGAACAACT

TTAACGCCGTGCGCTGTTCGCATTATCCGAACCATCCGCTGTGGTACACGCTGTGCGAC

CGCTACGGCCTGTATGTGGTGGATGAAGCCAATATTGAAACCCACGGCATGGTGCCAAT

GAATCGTCTGACCGATGATCCGCGCTGGCTACCCGCGATGAGCGAACGCGTAACGCGGA

TGGTGCAGCGCGATCGTAATCACCCGAGTGTGATCATCTGGTCGCTGGGGAATGAATCA

GGCCACGGCGCTAATCACGACGCGCTGTATCGCTGGATCAAATCTGTCGATCCTTCCCG

CCCGGTACAGTATGAAGGCGGCGGAGCCGACACCACGGCCACCGATATTATTTGCCCGA

TGTACGCGCGCGTGGATGAAGACCAGCCCTTCCCGGCGGTGCCGAAATGGTCCATCAAA

AAATGGCTTTCGCTGCCTGGAGAAATGCGCCCGCTGATCCTTTGCGAATATGCCCACGC

GATGGGTAACAGTCTTGGCGGCTTCGCTAAATACTGGCAGGCGTTTCGTCAGTACCCCC

GTTTACAGGGCGGCTTCGTCTGGGACTGGGTGGATCAGTCGCTGATTAAATATGATGAA

AACGGCAACCCGTGGTCGGCTTACGGCGGTGATTTTGGCGATACGCCGAACGATCGCCA

GTTCTGTATGAACGGTCTGGTCTTTGCCGACCGCACGCCGCATCCGGCGCTGACGGAAG

CAAAACACCAACAGCAGTATTTCCAGTTCCGTTTATCCGGGCGAACCATCGAAGTGACC

AGCGAATACCTGTTCCGTCATAGCGATAACGAGTTCCTGCACTGGATGGTGGCACTGGA

TGGCAAGCCGCTGGCAAGCGGTGAAGTGCCTCTGGATGTTGGCCCGCAAGGTAAGCAGT

TGATTGAACTGCCTGAACTGCCGCAGCCGGAGAGCGCCGGACAACTCTGGCTAACGGTA

CGCGTAGTGCAACCAAACGCGACCGCATGGTCAGAAGCCGGACACATCAGCGCCTGGCA

GCAATGGCGTCTGGCGGAAAACCTCAGCGTGACACTCCCCTCCGCGTCCCACGCCATCC

CTCAACTGACCACCAGCGGAACGGATTTTTGCATCGAGCTGGGTAATAAGCGTTGGCAA

TTTAACCGCCAGTCAGGCTTTCTTTCACAGATGTGGATTGGCGATGAAAAACAACTGCT

GACCCCGCTGCGCGATCAGTTCACCCGTGCGCCGCTGGATAACGACATTGGCGTAAGTG

AAGCGACCCGCATTGACCCTAACGCCTGGGTCGAACGCTGGAAGGCGGCGGGCCATTAC

CAGGCCGAAGCGGCGTTGTTGCAGTGCACGGCAGATACACTTGCCGACGCGGTGCTGAT

TACAACCGCCCACGCGTGGCAGCATCAGGGGAAAACCTTATTTATCAGCCGGAAAACCT

ACCGGATTGATGGGCACGGTGAGATGGTCATCAATGTGGATGTTGCGGTGGCAAGCGAT

ACACCGCATCCGGCGCGGATTGGCCTGACCTGCCAGCTGGCGCAGGTCTCAGAGCGGGT

AAACTGGCTCGGCCTGGGGCCGCAAGAAAACTATCCCGACCGCCTTACTGCAGCCTGTT

TTGACCGCTGGGATCTGCCATTGTCAGACATGTATACCCCGTACGTCTTCCCGAGCGAA

AACGGTCTGCGCTGCGGGACGCGCGAATTGAATTATGGCCCACACCAGTGGCGCGGCGA

CTTCCAGTTCAACATCAGCCGCTACAGCCAACAACAACTGATGGAAACCAGCCATCGCC

ATCTGCTGCACGCGGAAGAAGGCACATGGCTGAATATCGACGGTTTCCATATGGGGATT

GGTGGCGACGACTCCTGGAGCCCGTCAGTATCGGCGGAATTCCAGCTGAGCGCCGGTCG

CTACCATTACCAGTTGGTCTGGTGTCAAAAATAA

TABLE 26

Nucleotide sequences of Pfnr3-PAL3 construct, low-copy (SEQ ID NO: 36)

GGTACCgtcagcataacaccctgacctctcattaattgttcatgccgggcggcactatc gtcgtccggccttttcctctcttactctgctacgtacatctatttctataaatccgttc aatttgtctgttttttgcacaaacatgaaatatcagacaattccgtgacttaagaaaat ttatacaaatcagcaatataccccttaaggagtatataaaggtgaatttgatttacatc aataagcggggttgctgaatcgttaaGGATCCctctagaaataattttgtttaacttta agaaggagatatacatATGAAAGCTAAAGATGTTCAGCCAACCATTATTATTAATAAAA

ATGGCCTTATCTCTTTGGAGATATCTATGACATTGCGATAAACAAAAAAAAAGTAGAA

ATATCAACGGAGATCACTGAACTTTTGACGCATGGTCGTGAAAAATTAGAGGAAAATT

AAATTCAGGAGAGGTTATATATGGAATCAATACAGGATTTGGAGGGAATGCCAATTTAG

TTGTGCCATTTGAGAAAATCGCAGAGCATCAGCAAAATCTGTTAACTTTTCTTTCTGCT

GGTACTGGGGACTATATGTCCAAACCTTGTATTAAAGCGTCACAATTTACTATGTTACT

TTCTGTTTGCAAAGGTTGGTCTGCAACCAGACCAATTGTCGCTCAAGCAATTGTTGATC

ATATTAATCATGACATTGTTCCTCTGGTTCCTCGCTATGGCTCAGTGGGTGCAAGCGGT

GATTTAATTCCTTTATCTTATATTGCACGAGCATTATGTGGTATCGGCAAAGTTTATTA

TATGGGCGCAGAAATTGACGCTGCTGAAGCAATTAAACGTGCAGGGTTGACACCATTAT

CGTTAAAAGCCAAAGAAGGTCTTGCTCTGATTAACGGCACCCGGGTAATGTCAGGAATC

AGTGCAATCACCGTCATTAAACTGGAAAAACTATTTAAAGCCTCAATTTCTGCGATTGC

CCTTGCTGTTGAAGCATTACTTGCATCTCATGAACATTATGATGCCCGGATTCAACAAG

TAAAAAATCATCCTGGTCAAAACGCGGTGGCAAGTGCATTGCGTAATTTATTGGCAGGT

TCAACGCAGGTTAATCTATTATCTGGGGTTAAAGAACAAGCCAATAAAGCTTGTCGTCA

TCAAGAAATTACCCAACTAAATGATACCTTACAGGAAGTTTATTCAATTCGCTGTGCAC

CACAAGTATTAGGTATAGTGCCAGAATCTTTAGCTACCGCTCGGAAAATATTGGAACGG

GAAGTTATCTCAGCTAATGATAATCCATTGATAGATCCAGAAAATGGCGATGTTCTACA

CGGTGGAAATTTTATGGGGCAATATGTCGCCCGAACAATGGATGCATTAAAACTGGATA

TTGCTTTAATTGCCAATCATCTTCACGCCATTGTGGCTCTTATGATGGATAACCGTTTC

TCTCGTGGATTACCTAATTCACTGAGTCCGACACCCGGCATGTATCAAGGTTTTAAAGG

CGTCCAACTTTCTCAAACCGCTTTAGTTGCTGCAATTCGCCATGATTGTGCTGCATCAG

GTATTCATACCCTCGCCACAGAACAATACAATCAAGATATTGTCAGTTTAGGTCTGCAT

GCCGCTCAAGATGTTTTAGAGATGGAGCAGAAATTACGCAATATTGTTTCAATGACAAT

TCTGGTAGTTTGTCAGGCCATTCATCTTCGCGGCAATATTAGTGAAATTGCGCCTGAAA

CTGCTAAATTTTACCATGCAGTACGCGAAATCAGTTCTCCTTTGATCACTGATCGTGCG

TTGGATGAAGATATAATCCGCATTGCGGATGCAATTATTAATGATCAACTTCCTCTGCC

AGAAATCATGCTGGAAGAATAA

TABLE 27

Nucleotide sequences of Pfnr4-PAL3 construct, low-copy (SEQ ID NO: 37)

GGTACCcatttcctctcatcccatccggggtgagagtcttttcccccgacttatggctc atgcatgcatcaaaaaagatgtgagcttgatcaaaaacaaaaaatatttcactcgacag gagtatttatattgcgcccGGATCCctctagaaataattttgtttaactttaagaagga TABLE 27-continued Nucleotide sequences of Pfnr4-PAL3 construct, low-copy (SEQ ID NO: 37)

gatatacatATGAAAGCTAAAGATGTTCAGCCAACCATTATTATTAATAAAAATGGCCT
TATCTCTTTGGAAGATATCTATGACATTGCGATAAAACAAAAAAAAGTAGAAATATCAA
CGGAGATCACTGAACTTTTGACGCATGGTCGTGAAAAATTAGAGGAAAAATTAAATTCA
GGAGAGGTTATATATGGAATCAATACAGGATTTGGAGGGAATGCCAATTTAGTTGTGCC
ATTTGAGAAAATCGCAGAGCATCAGCAAAATCTGTTAACTTTTCTTTCTGCTGGTACTG
GGGACTATATGTCCAAACCTTGTATTAAAGCGTCACAATTTACTATGTTACTTTCTGTT
TGCAAAGGTTGGTCTGCAACCAGACCAATTGTCGCTCAAGCAATTGTTGATCATATTAA
TCATGACATTGTTCCTCTGGTTCCTCGCTATGGCTCAGTGGGTGCAAGCGGTGATTTAA
TTCCTTTATCTTATATTGCACGAGCATTATGTGGTATCGGCAAAGTTTATTATATGGGC
GCAGAAATTGACGCTGCTGAAGCAATTAAACGTGCAGGGTTGACACCATTATCGTTAAA
AGCCAAAGAAGGTCTTGCTCTGATTAACGGCACCCGGGTAATGTCAGGAATCAGTGCAA
TCACCGTCATTAAACTGGAAAAACTATTTAAAGCCTCAATTTCTGCGATTGCCCTTGCT
GTTGAAGCATTACTTGCATCTCATGAACATTATGATGCCCGGATTCAACAAGTAAAAAA
TCATCCTGGTCAAAACGCGGTGGCAAGTGCATTGCGTAATTTATTGGCAGGTTCAACGC
AGGTTAATCTATTATCTGGGGTTAAAGAACAAGCCAATAAAGCTTGTCGTCATCAAGAA
ATTACCCAACTAAATGATACCTTACAGGAAGTTTATTCAATTCGCTGTGCACCACAAGT
ATTAGGTATAGTGCCAGAATCTTTAGCTACCGCTCGGAAAATATTGGAACGGGAAGTTA
TCTCAGCTAATGATAATCCATTGATAGATCCAGAAAATGGCGATGTTCTACACGGTGGA
AATTTTATGGGGCAATATGTCGCCCGAACAATGGATGCATTAAAACTGGATATTGCTTT
AATTGCCAATCATCTTCACGCCATTGTGGCTCTTATGATGGATAACCGTTTCTCTCGTG
GATTACCTAATTCACTGAGTCCGACACCCGGCATGTATCAAGGTTTTAAAGGCGTCCAA
CTTTCTCAAACCGCTTTAGTTGCTGCAATTCGCCATGATTGTGCTGCATCAGGTATTCA
TACCCTCGCCACAGAACAATACAATCAAGATATTGTCAGTTTAGGTCTGCATGCCGCTC
AAGATGTTTTAGAGATGGAGCAGAAATTACGCAATATTGTTTCAATGACAATTCTGGTA
GTTTGTCAGGCCATTCATCTTCGCGGCAATATTAGTGAAATTGCGCCTGAAACTGCTAA
ATTTTACCATGCAGTACGCGAAATCAGTTCTCCTTTGATCACTGATCGTGCGTTGGATG
AAGATATAATCCGCATTGCGGATGCAATTATTAATGATCAACTTCCTCTGCCAGAAATC
ATGCTGGAAGAATAA

TABLE 28

Nucleotide sequences of PfnrS-PAL3 construct, low-copy (SEQ ID NO: 38)

GGTACCagttgttcttattggtggtgttgctttatggttgcatcgtagtaaatggttgt
aacaaaagcaattttccggctgtctgtatacaaaaacgccgtaaagtttgagcgaagt
caataaactctctacccattcagggcaatatctctcttGGATCCctctagaaataattt
tgtttaactttaagaaggagatatacatATGAAAGCTAAAGATGTTCAGCCAACCATTA
TTATTAATAAAAATGGCCTTATCTCTTTGGAAGATATCTATGACATTGCGATAAAACAA
AAAAAAGTAGAAATATCAACGGAGATCACTGAACTTTTGACGCATGGTCGTGAAAAATT
AGAGGAAAAATTAAATTCAGGAGAGGTTATATATGGAATCAATACAGGATTTGGAGGGA TABLE 28-continued Nucleotide sequences of PfnrS-PAL3 construct, low-copy (SEQ ID NO: 38)

ATGCCAATTTAGTTGTGCCATTTGAGAAAATCGCAGAGCATCAGCAAAATCTGTTAACT

TTTCTTTCTGCTGGTACTGGGGACTATATGTCCAAACCTTGTATTAAAGCGTCACAATT

TACTATGTTACTTTCTGTTTGCAAAGGTTGGTCTGCAACCAGACCAATTGTCGCTCAAG

CAATTGTTGATCATATTAATCATGACATTGTTCCTCTGGTTCCTCGCTATGGCTCAGTG

GGTGCAAGCGGTGATTTAATTCCTTTATCTTATATTGCACGAGCATTATGTGGTATCGG

CAAAGTTTATTATATGGGCGCAGAAATTGACGCTGCTGAAGCAATTAAACGTGCAGGGT

TGACACCATTATCGTTAAAAGCCAAAGAAGGTCTTGCTCTGATTAACGGCACCCGGGTA

ATGTCAGGAATCAGTGCAATCACCGTCATTAAACTGGAAAAACTATTTAAAGCCTCAAT

TTCTGCGATTGCCCTTGCTGTTGAAGCATTACTTGCATCTCATGAACATTATGATGCCC

GGATTCAACAAGTAAAAAATCATCCTGGTCAAAACGCGGTGGCAAGTGCATTGCGTAAT

TTATTGGCAGGTTCAACGCAGGTTAATCTATTATCTGGGGTTAAAGAACAAGCCAATAA

AGCTTGTCGTCATCAAGAAATTACCCAACTAAATGATACCTTACAGGAAGTTTATTCAA

TTCGCTGTGCACCACAAGTATTAGGTATAGTGCCAGAATCTTTAGCTACCGCTCGGAAA

ATATTGGAACGGGAAGTTATCTCAGCTAATGATAATCCATTGATAGATCCAGAAAATGG

CGATGTTCTACACGGTGGAAATTTTATGGGGCAATATGTCGCCCGAACAATGGATGCAT

TAAAACTGGATATTGCTTTAATTGCCAATCATCTTCACGCCATTGTGGCTCTTATGATG

GATAACCGTTTCTCTCGTGGATTACCTAATTCACTGAGTCCGACACCCGGCATGTATCA

AGGTTTTAAAGGCGTCCAACTTTCTCAAACCGCTTTAGTTGCTGCAATTCGCCATGATT

GTGCTGCATCAGGTATTCATACCCTCGCCACAGAACAATACAATCAAGATATTGTCAGT

TTAGGTCTGCATGCCGCTCAAGATGTTTTAGAGATGGAGCAGAAATTACGCAATATTGT

TTCAATGACAATTCTGGTAGTTTGTCAGGCCATTCATCTTCGCGGCAATATTAGTGAAA

TTGCGCCTGAAACTGCTAAATTTTACCATGCAGTACGCGAAATCAGTTCTCCTTTGATC

ACTGATCGTGCGTTGGATGAAGATATAATCCGCATTGCGGATGCAATTATTAATGATCA

ACTTCCTCTGCCAGAAATCATGCTGGAAGAATAA

Each of the plasmids was transformed into *E. coli* Nissle, as described above. Cultures of transformed *E. coli* Nissle were grown overnight and then diluted 1:200 in LB. The cells were grown with shaking at 250 rpm either aerobically or anaerobically in a Coy anaerobic chamber supplied with 90% $N_2$, 5% $CO_2$, and 5% $H_2$. After 4-6 hrs of incubation, samples were collected, and promoter activity was analyzed by performing β-galactosidase assays (Miller, 1972). As shown in FIG. 20, the activities of the FNR promoters were greatly enhanced under anaerobic conditions compared to aerobic conditions.

Example 7

Measuring the Activity of an FNR Promoter

Figure 19A:
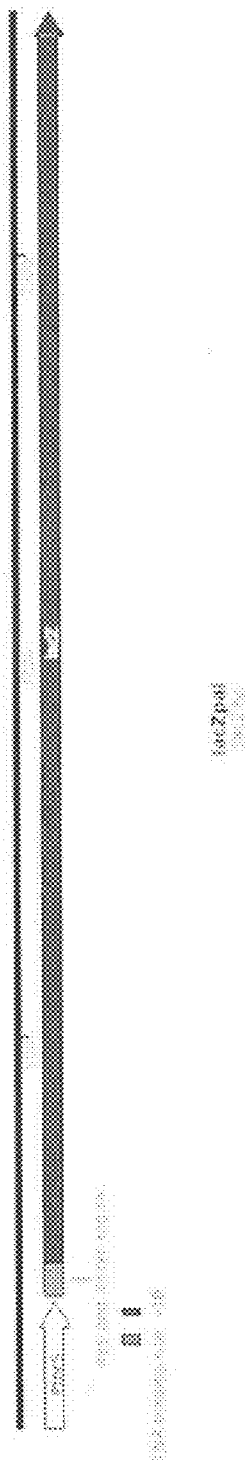
FIG. 19A depicts a schematic representation of the lacZ gene under the control of an exemplary FNR promoter ($P_{fnrS}$). LacZ encodes the β-galactosidase enzyme and is a common reporter gene in bacteria.
Figure 19B:
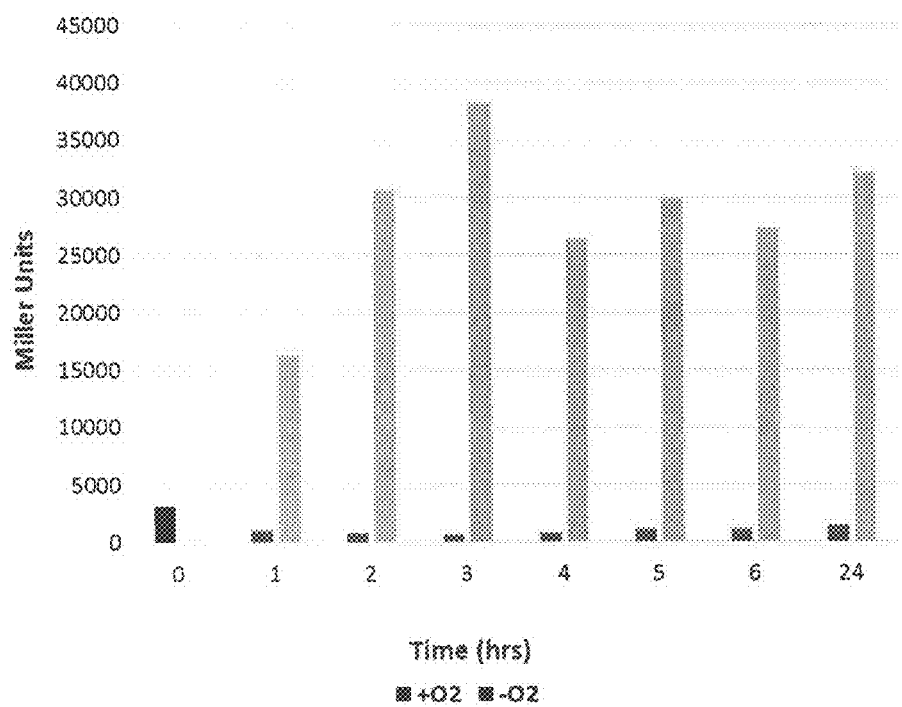
FIG. 19B depicts FNR promoter activity as a function of β-galactosidase activity in SYN-PKU304. SYN-PKU304, an engineered bacterial strain harboring a low-copy fnrS-lacZ fusion gene, was grown in the presence or absence of oxygen. Values for standard β-galactosidase colorimetric assays are expressed in Miller units (Miller, 1972). These data suggest that the fnrS promoter begins to drive high-level gene expression within 1 hr. under anaerobic conditions.
Figure 19C:
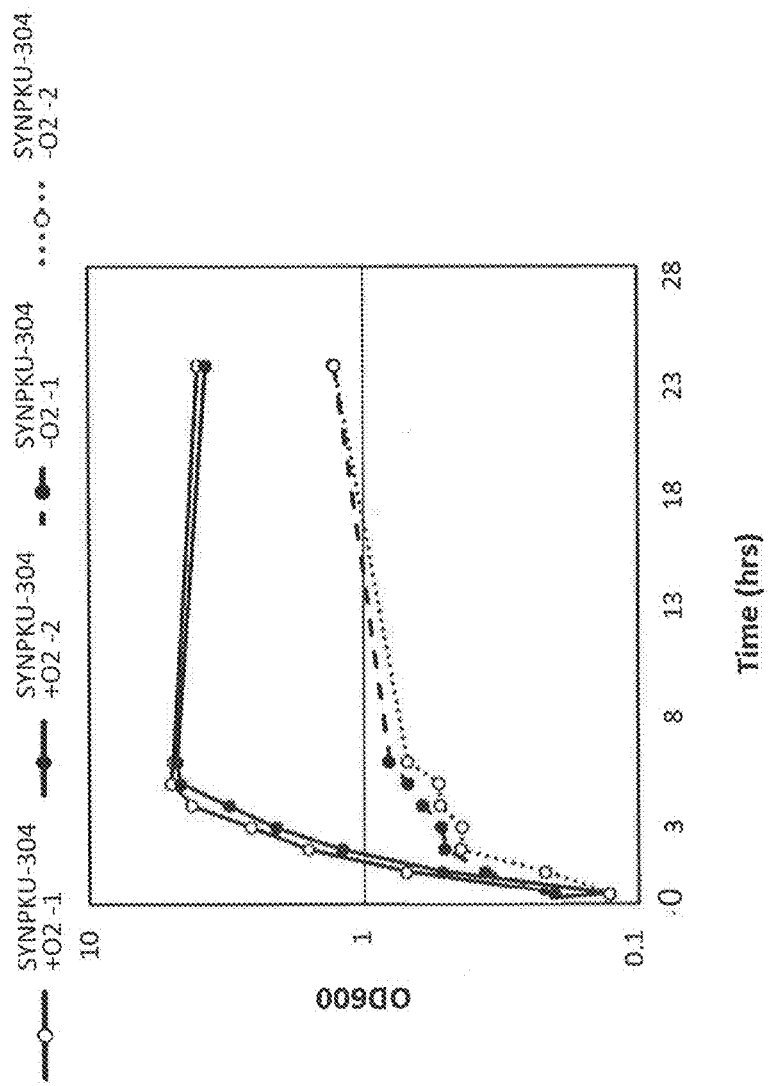
FIG. 19C depicts the growth of bacterial cell cultures expressing lacZ over time, both in the presence and absence of oxygen.

To determine the kinetics of FNR promoter-driven gene expression, *E. coli* strains harboring a low-copy fnrS-lacZ fusion gene (FIG. 19A) were grown aerobically with shaking at 250 rpm. Cultures were split after 1 hr., and then incubated either aerobically or anaerobically in a Coy anaerobic chamber (supplying 90% $N_2$, 5% $CO_2$, and 5% $H_2$) at 37° C. Promoter activity was measured as a function of β-galactosidase activity using a standard colorimetric assay (Miller, 1972). FIG. 19B demonstrates that the fnrS promoter begins to drive high-level gene expression within 1 hr. under anaerobic conditions. Growth curves of bacterial cell cultures expressing lacZ are shown in FIG. 19C, both in the presence and absence of oxygen.

Example 8

Production of PAL from FNR Promoter in Recombinant *E. Coli*

Figure 20A:
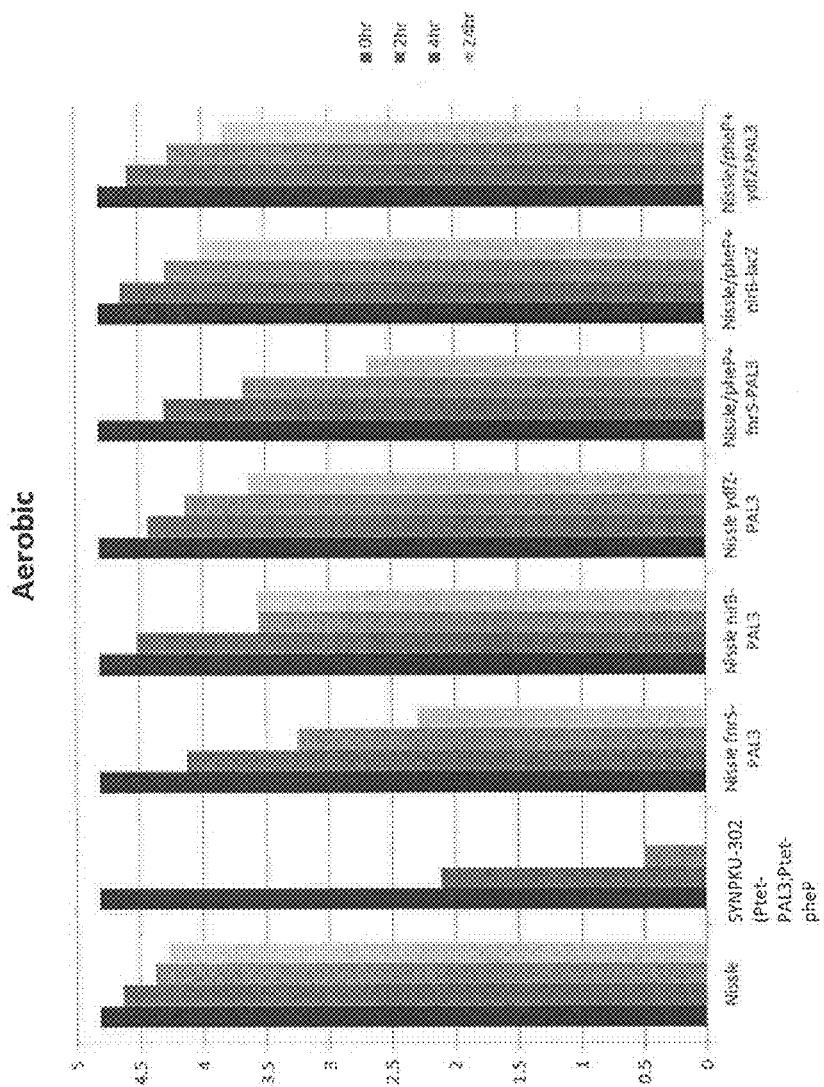
FIGS. 20A and 20B depict phenylalanine levels produced under aerobic (FIG. 20A) or anaerobic conditions (FIG. 20B) in samples of wild-type Nissle, samples of bacteria comprising a low-copy plasmid expressing PAL3 from the Tet promoter or exemplary FNR promoters, or further comprising a copy of pheP driven by the Tet promoter and integrated into the chromosome. Samples were incubated in culture medium supplemented with ATC and 4 mM (660,000 ng/mL) of phenylalanine. Samples were removed at 0 hrs, 2 hrs, 4 hrs, and 24 hrs. Phenylalanine concentration was determined by mass spectrometry. These data suggest that the FNR-responsive fnrS promoter is as effective at activating PAL3 expression as a tetracycline-inducible promoter under anaerobic conditions.
Figure 20B:
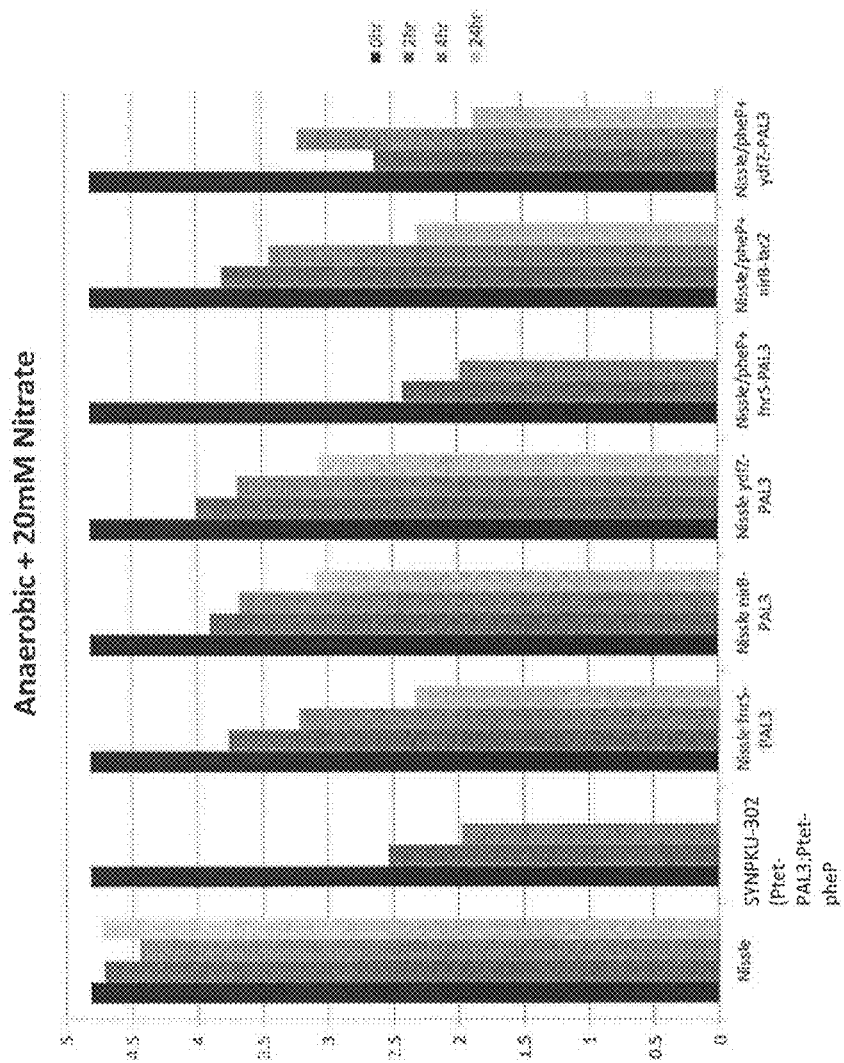

Cultures of *E. coli* Nissle transformed with a plasmid comprising the PAL gene driven by any of the exemplary FNR promoters were grown overnight and then diluted 1:200 in LB. The bacterial cells may further comprise the pheP gene driven by the Tet promoter and incorporated into the chromosome. ATC was added to cultures at a concentration of 100 ng/mL to induce expression of pheP, and the cells were grown with shaking at 250 rpm either aerobically or anaerobically in a Coy anaerobic chamber supplied with 90% $N_2$, 5% $CO_2$, and 5% $H_2$. After 4 hrs of incubation, cells were pelleted down, washed, and resuspended in M9 minimal medium supplemented with 0.5% glucose and 4 mM phenylalanine. Aliquots were collected at 0 hrs, 2 hrs, 4 hrs, and 24 hrs for phenylalanine quantification (FIG. 20). As shown in FIG. 20B, the genetically engineered bacteria expressing PAL3 driven by the FNR promoter are more efficient at removing phenylalanine from culture medium under anaerobic conditions, compared to aerobic conditions (FIG. 20A). The expression of pheP in conjunction with PAL3 further decreased levels of phenylalanine.

Example 9

Phenylalanine Degradation in Recombinant *E. Coli* with and without pheP Overexpression The SYN-PKU304 and SYN-PKU305 strains contain low-copy plasmids harboring the PAL3 gene, and a copy of pheP integrated at the lacZ locus. The SYN-PKU308 and SYN-PKU307 strains also contain low-copy plasmids harboring the PAL3 gene, but lack a copy of pheP integrated at the lacZ locus. In all four strains, expression of PAL3 and pheP (when applicable) is controlled by an oxygen level-dependent promoter.

To determine rates of phenylalanine degradation in engineered *E. coli* Nissle with and without pheP on the chromosome, overnight cultures of SYN-PKU304 and SYN-PKU307 were diluted 1:100 in LB containing ampicillin, and overnight cultures of SYN-PKU308 and SYN-PKU305 were diluted 1:100 in LB containing kanamycin. All strains were grown for 1.5 hrs before cultures were placed in a Coy anaerobic chamber supplying 90% $N_2$, 5% $CO_2$, and 5% $H_2$. After 4 hrs of induction, bacteria were pelleted, washed in PBS, and resuspended in 1 mL of assay buffer. Assay buffer contained M9 minimal media supplemented with 0.5% glucose, 8.4% sodium bicarbonate, and 4 mM of phenylalanine.

Figure 21:
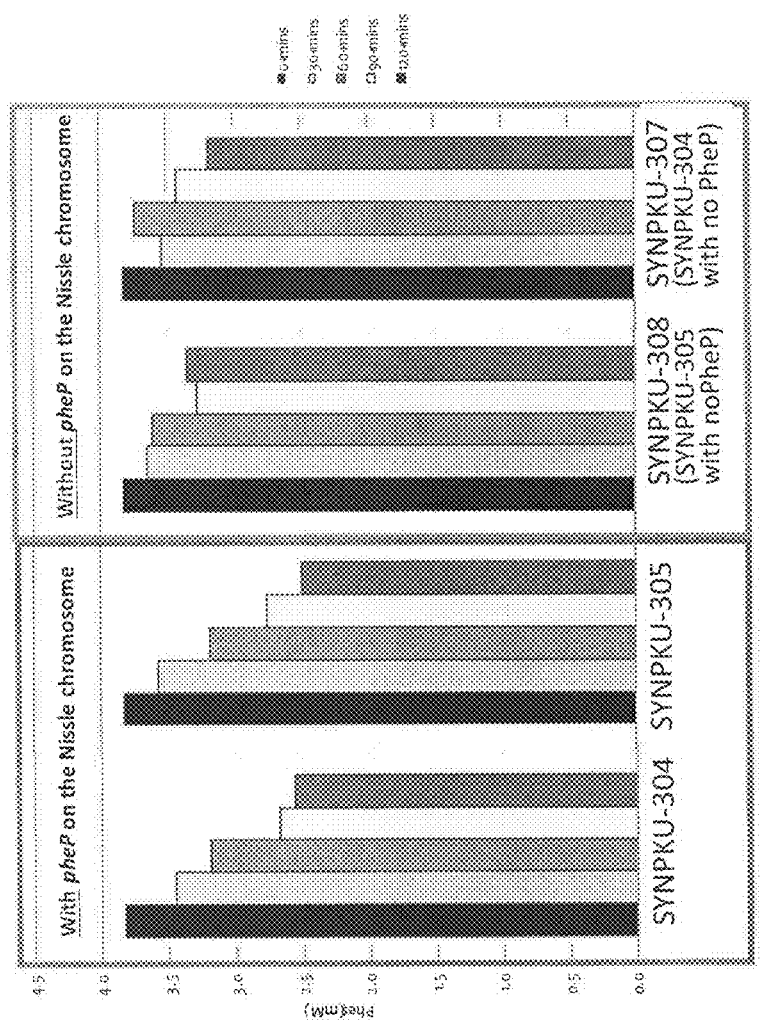
FIG. 21 depicts phenylalanine concentrations in cultures of synthetic probiotic strains, with and without an additional copy of pheP inserted on the chromosome. After 1.5 hrs of growth, cultures were placed in Coy anaerobic chamber supplying 90% $N_2$, 5% $CO_2$, and 5% $H_2$. After 4 hrs of induction, bacteria were resuspended in assay buffer containing 4 mM phenylalanine. Aliquots were removed from cell assays every 30 min for 3 hrs for phenylalanine quantification by mass spectrometry. Phenylalanine degradation rates in strains comprising an additional copy of pheP (SYN-PKU304 and SYN-PKU305; left) were higher than strains lacking an additional copy of pheP (SYN-PKU308 and SYN-PKU307; right).

For the activity assay, starting counts of colony-forming units (cfu) were quantified using serial dilution and plating. Aliquots were removed from each cell assay every 30 min for 3 hrs for phenylalanine quantification by mass spectrometry. Specifically, 150 µL of bacterial cells were pelleted and the supernatant was harvested for LC-MS analysis, with assay media without cells used as the zero-time point. FIG. 21 shows the observed phenylalanine degradation for strains with pheP on the chromosome (SYN-PKU304 and SYN-PKU305; left), as well as strains lacking pheP on the chromosome (SYN-PKU308 and SYN-PKU307; right). These data show that pheP overexpression is important in order to increase rates of phenylalanine degradation in synthetic probiotics.

Example 10

Activity of Strains with Single and Multiple Chromosomal PAL3 Insertions

To assess the effect of insertion site and number of insertions on the activity of the genetically engineered bacteria, in vitro activity of strains with different single insertions of PAL3 at various chromosomal locations and with multiple PAL3 insertions was measured.

Figure 22:
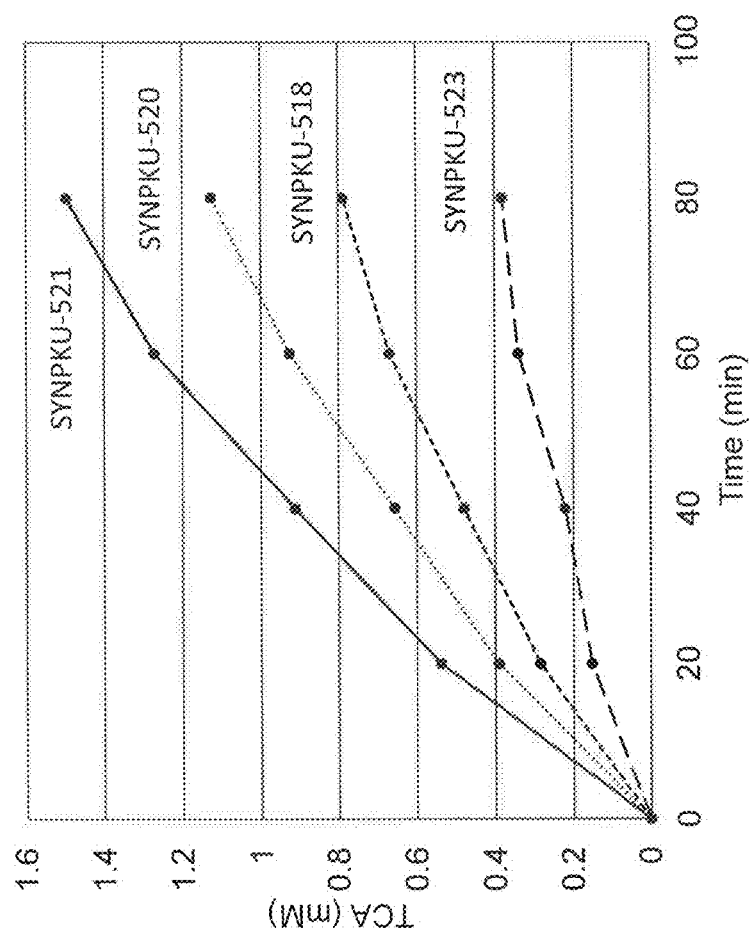
FIG. 22 depicts trans-cinnamate concentrations (PAL activity) for strains comprising single PAL3 insertions at various locations on the chromosome.
Figure 23:
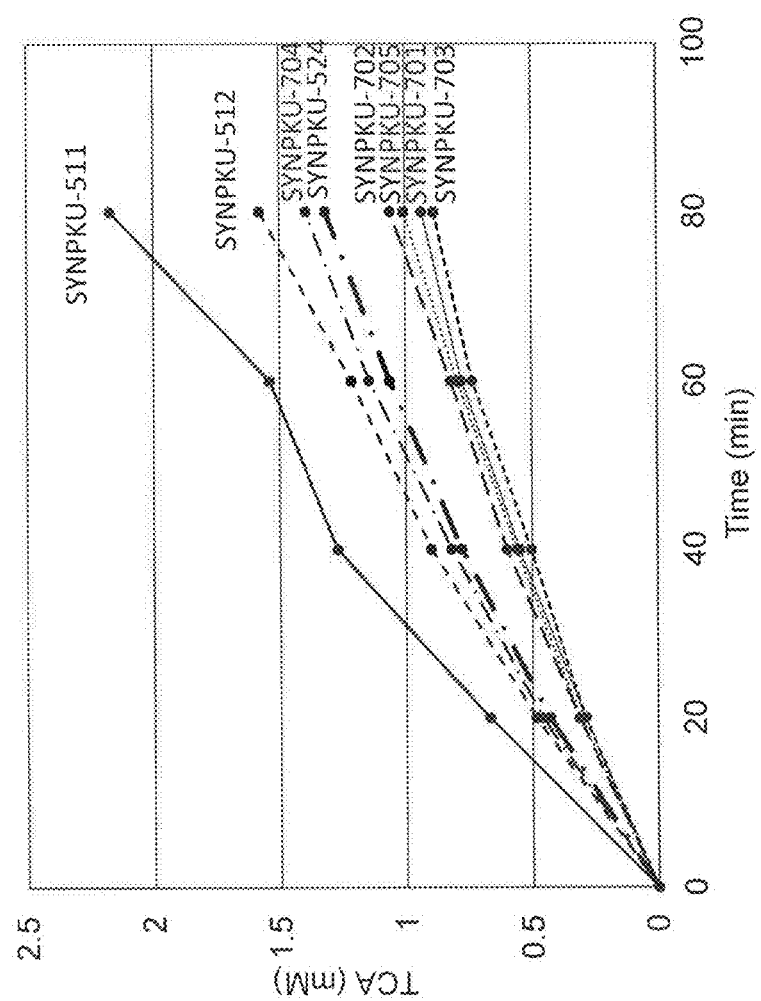
FIG. 23 depicts trans-cinnamate concentrations (PAL activity) for strains comprising multiple PAL3 insertions at various locations on the chromosome.

Cells were grown overnight in LB and diluted 1:100. After 1.5 hrs of growth, cultures were placed in Coy anaerobic chamber supplying 90% $N_2$, 5% $CO_2$, and 5% $H_2$. After 4 hrs of induction, bacteria were resuspended in assay buffer containing 50 mM phenylalanine. Aliquots were removed from cell assays every 20 min for 1.5 hrs for trans-cinnamate quantification by absorbance at 290 nm. Results are shown in FIGS. 22 and 23 and Table 39 and Table 40. FIG. 22 depicts trans-cinnamate concentrations (PAL activity) for strains comprising single PAL3 insertions at various locations on the chromosome. FIG. 23 depicts trans-cinnamate concentrations (PAL activity) for strains comprising multiple PAL3 insertions at various locations on the chromosome.

TABLE 39

Activity of various strains comprising a single PAL3 chromosomal insertion at various sites

| Insertion: | Strain: | rate (umol/hr./1e9 cells): |
|---|---|---|
| agaI/rsmI | SYN-PKU520 | 1.97 |
| yicS/nepI | SYN-PKU521 | 2.44 |
| cea | SYN-PKU522 | ND |
| malEK | SYN-PKU518 | 1.66 |
| malPT | SYN-PKU523 | 0.47 |

TABLE 40

In vitro activity of various strains comprising one or more chromosomal PAL3 insertions

| Genotypes: | Strain | Rate (umol/hr./1e9 cells) |
|---|---|---|
| agaI:PAL, cea:PAL, matPT:PAL, malEK:PAL, lacZ:pheP, thyA- | SYN-PKU512 | 6.76 |
| agaI:PAL, yicS:PAL, cea:PAL, matPT:PAL, malEK:PAL, lacZ:pheP, thyA- | SYN-PKU511 | 7.65 |
| malPT:PAL, malEK:PAL, lacZ:pheP | SYN-PKU524 | 2.89 |
| malEK:PAL, lacZ:pheP, ara-LAAD | SYN-PKU702 | 1.53 |
| malPT:PAL, malEK:PAL, lacZ:pheP, ara-LAAD | SYN-PKU701 | 2.65 |
| malPT:PAL, malEK:PAL, lacZ:pheP, agaI:pheP, ara-LAAD | SYN-PKU703 | 3.14 |
| yicS:PAL, malPT:PAL, malEK:PAL lacZ:pheP, ara-LAAD | SYN-PKU704 | 3.47 |
| yicS:PAL, malPT:PAL, malEK:PAL, lacZ:pheP, agaI:pheP, ara-LAAD | SYN-PKU705 | 3.74 |

Example 11

Activity of a Strain with Five Chromosomal Copies of PAL3

The activity of a strain SYN-PKU511, a strain comprising five integrated copies of an anaerobically (FNR) controlled PAL3 and an anaerobically controlled pheP integrated in the lacZ locus, was assessed.

Figure 24:
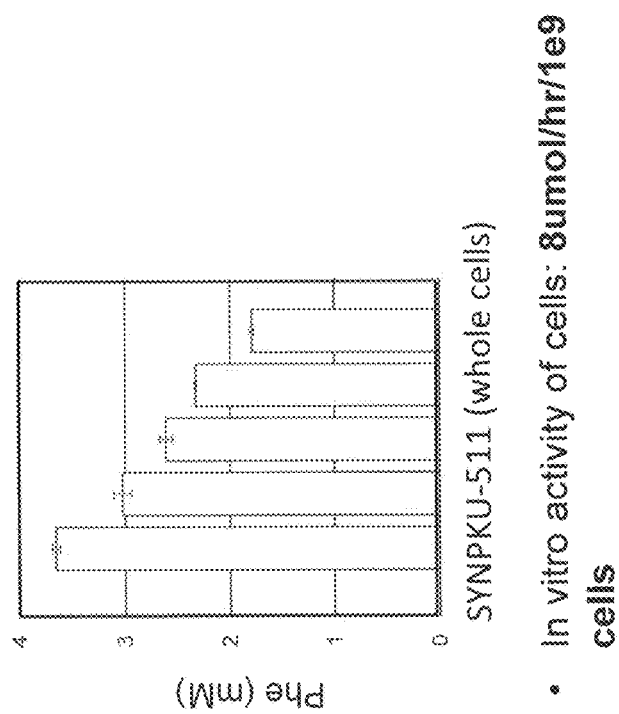
FIG. 24 depicts phenylalanine concentrations in cultures of synthetic probiotic strain SYN-PKU511 over time. After 2.5 hrs of growth, cultures were placed in Coy anaerobic chamber supplying 90% N2, 5% CO2, and 5% H2. After 3.5 hrs of induction in phenylalanine containing medium, whole cell extracts were prepared every 30 min for 3 hrs and phenylalanine was quantified by mass spectrometry. SYN-PKU511 comprises 5 integrated copies of an anaerobically (FNR) controlled gene encoding phenylalanine ammonia lyase (PAL) at 5 chromosomal locations and an anaerobically controlled gene encoding a high affinity Phe transporter (pheP) integrated in the lacZ locus.

The genetically engineered bacteria were grown overnight, diluted and allowed to grow for another 2.5 hours. Cultures were then placed in Coy anaerobic chamber supplying 90% N2, 5% CO2, and 5% H2. After 3.5 hrs of induction in phenylalanine containing medium (4 mM phenylalanine), whole cell extracts were prepared every 30 min for 3 hrs and phenylalanine was quantified by mass spectrometry. Results are shown in FIG. 24. The in vitro activity of the cells was 8 umol/hr./1e9 cells. Phenylalanine levels drop to about half of the original levels after 2 hours.

Example 12

Activity of a Strain Expressing LAAD

To assess whether LAAD expression can be used as an alternative, additional or complementary phenylalanine degradation means to PAL3, the ability of genetically engineered strain SYN-PKU401, which contains a high copy plasmid expressing LAAD driven by a Tet-inducible promoter, was measured at various cell concentrations and at varying oxygen levels.

Overnight cultures of SYN-PKU401 were diluted 1:100 and grown to early log phase before induction with ATC (100 ng/ml) for 2 hours. Cells were spun down and incubated as follows.

Cells (1 ml) were incubated aerobically in a 14 ml culture tube, shaking at 250 rpm (FIGS. 25A and B). For microaerobic conditions, cells (1 ml) were incubated in a 1.7 ml conical tube without shaking. Cells were incubated anaerobically in a Coy anaerobic chamber supplying 90% N2, 5% CO2, and 5% H2 (FIG. 25B). Aliquots were removed from cell assays every 30 min for 2 hrs for phenylalanine quantification by mass spectrometry, and results are shown in FIGS. 25A and 25B. FIG. 25A shows cell concentration dependent aerobic activity. The activity in aerobic conditions is ~50 umol/hr./1e9cells, and some activity is retained under microaerobic conditions, which may allow for activity in environments with oxygen concentrations less than ambient air. The activity of SYN-PKU401 under microaerobic conditions is comparable to SYN-PKU304 under anaerobic conditions, however, activity seems to be dependent on cell density.

Table 41 and Table 42 contain LAAD constructs of interest. Table 41 shows the sequence of an exemplary construct comprising a gene encoding LAAD from *Proteus mirabilis* and a Tet repressor gene and a Tet promoter sequence and RBS and leader region, on a plasmid SEQ ID NO: 39, with the LAAD sequence underlined the TetR sequence in italics and the Tet promoter sequence bolded and the RBS and leader region underlined and italics. Table 42 shows the sequence of an exemplary construct comprising a gene encoding araC and a gene encoding LAAD from *Proteus mirabilis* and an arabinose inducible promoter (ParaBAD) sequence for chromosomal insertion into the endogenous arabinose operon (SEQ ID NO: 40), with the araC sequence underlined and the ParaBAD promoter sequence bolded and the LAAD sequence in italics and the RBS and leader region underlined and in italics.

In some embodiments, genetically engineered bacteria comprise a nucleic acid sequence that is at least about 80%, at least about 85%, at least about 90%, at least about 95%, or at least about 99% homologous to the DNA sequence of SEQ ID NO: 20-42, or a functional fragment thereof.

TABLE 41

LAAD driven by a Tet inducible promoter on a plasmid
Nucleotide sequences of TetR-LAAD plasmid construct (SEQ ID NO: 39)

*Ttaagacccactttcacatttaagttgttttctaatccgcatatgatcaattcaaggc*

*cgaataagaaggctggctctgcaccttggtgatcaaataattcgatagcttgtcgtaat*

*aatggcggcatactatcagtagtaggtgtttcccttcttctttagcgacttgatgctc*

*ttgatcttccaatacgcaacctaaagtaaaatgccccacagcgctgagtgcatataatg*

*cattctctagtgaaaaaccttgttggcataaaaaggctaattgattttcgagagtttca*

*tactgttttctgtaggccgtgtacctaaatgtacttttgctccatcgcgatgacttag*

*taaagcacatctaaaacttttagcgttattacgtaaaaaatcttgccagctttcccctt*

*ctaaagggcaaaagtgagtatggtgcctatctaacatctcaatggctaaggcgtcgagc*

*aaagcccgcttattttttacatgccaatacaatgtaggctgctctacacctagcttctg*

*ggcgagtttacgggttgttaaaccttcgattccgacctcattaagcagctctaatgcgc*

*tgttaatcactttacttttatctaatctagacatcattaattcctaattttt*gttgaca ctctatcattgatagagttatttaccactccctatcagtgatagagaaaagtgaa<u>ctc</u>

<u>tagaaataattttgtttaactttaagaaggagatatacatatgaacatttcaaggagaa</u>

<u>agctacttttaggtgttggtgctgcgggcgttttagcaggtggtgcggctttagttcca</u>

<u>atggttcgccgtgacggcaaatttgtggaagctaaatcaagagcatcatttgttgaagg</u>

<u>tacgcaagggctcttcctaaagaagcagatgtagtgattattggtgccggtattcaag</u>

<u>ggatcatgaccgctattaaccttgctgaacgtggtatgagtgtcactatcttagaaaag</u>

<u>ggtcagattgccggtgagcaatcaggccgtgcatacagccaaattattagttaccaaac</u>

<u>atcgccagaaatcttcccattacaccattatgggaaaatattatggcgtggcatgaatg</u>

<u>agaaaattggtgcggataccagttatcgtactcaaggtcgtgtagaagcgctggcagat</u>

<u>gaaaaagcattagataaagctcaagcgtggatcaaaacagctaaagaagcggcaggttt</u>

TABLE 41-continued

LAAD driven by a Tet inducible promoter on a plasmid
Nucleotide sequences of TetR-LAAD plasmid construct (SEQ ID NO: 39)

tgatacaccattaaatactcgcatcattaaaggtgaagagctatcaaatcgcttagtcg gtgctcaaacgccatggactgttgctgcatttgaagaagattcaggctctgttgatcct gaaacaggcacacctgcactcgctcgttatgccaaacaaatcggtgtgaaaatttatac caactgtgcagtaagaggtattgaaactgcgggtggtaaaatctctgatgtggtgagtg agaaagggcgattaaaacgtctcaagttgtactcgctggggtatctggtcgcgttta tttatgggcaatatgggtattgatatcccaacgctcaatgtatatctatcacaacaacg tgtctcaggggttcctggtgcaccacgtggtaatgtgcatttacctaatggtattcatt tccgcgaacaagcggatggtacttatgccgttgcaccacgtatctttacgagttcaata gtcaaagatagcttcctgctagggcctaaatttatgcacttattaggtggcggagagtt accgttggaattctctattggtgaagatctatttaattcatttaaaatgccgacctctt ggaatttagatgaaaaaacaccattcgaacaattccgagttgccacggcaacacaaaat acgcaacacttagatgctgttttccaaagaatgaaaacagaattcccagtatttgaaaa atcagaagttgttgaacgttggggtgccgttgtgagtccaacatttgatgaattaccta tcatttctgaggtcaaagaatacccaggcttagtgattaacacggcaacagtgtgggt atgacagaaggcccggcagcgggtgaagtgaccgctgatattgtcatgggcaagaaacc tgttattgatccaacgccgtttagtttggatcgttttaagaagtaa

TABLE 42

LAAD sequence driven by the AraBAD promoter for insertion
into the Ara operon
Nucleotide sequences of AraC-ARABAD promoter-LAAD construct (SEQ ID NO: 40)

Ttattcacaacctgccctaaactcgctcggactcgccccggtgcattttttaaatactc gcgagaaatagagttgatcgtcaaaaccgacattgcgaccgacggtggcgataggcatc cgggtggtgctcaaaagcagcttcgcctgactgatgcgctggtcctcgcgccagcttaa tacgctaatccctaactgctggcggaacaaatgcgacagacgcgacggcgacaggcaga catgctgtgcgacgctggcgatatcaaaattactgtctgccaggtgatcgctgatgtac tgacaagcctcgcgtacccgattatccatcggtggatggagcgactcgttaatcgcttc catgcgccgcagtaacaattgctcaagcagatttatcgccagcaattccgaatagcgcc cttccccttgtccggcattaatgatttgcccaaacaggtcgctgaaatgcggctggtgc gcttcatccgggcgaaagaaaccggtattggcaaatatcgacggccagttaagccattc atgccagtaggcgcgcggacgaaagtaaacccactggtgataccattcgtgagcctccg gatgacgaccgtagtgatgaatctctccaggcgggaacagcaaaatatcacccggtcgg cagacaaattctcgtccctgattttcaccacccctgaccgcgaatggtgagattgag aatataacctttcattcccagcggtcggtcgataaaaaaatcgagataaccgttggcct caatcggcgttaaaccgccaccagatgggcgttaaacgagtatcccggcagcagggga tcattttgcgcttcagccatacttttcatactcccgccattcagagaagaaaccaattg tccatattgcatcagacattgccgtcactgcgtcttttactggctcttctcgctaaccc aaccggtaacccgcttattaaaagcattctgtaacaaagcgggaccaaagccatgaca TABLE 42-continued LAAD sequence driven by the AraBAD promoter for insertion
into the Ara operon
Nucleotide sequences of AraC-ARABAD promoter-LAAD construct (SEQ ID NO: 40)

aaaacgcgtaacaaaagtgtctataatcacggcagaaaagtccacattgattatttgca cggcgtcacactttgctatgccatagcattttatccataagattagcggatccagcct gacgcttttttcgcaactctctactgtttctccatAc*ctctagaaataattttgttta*

*actttaagaaggagatatacat*atgaacatttcaaggagaaagctacttttaggtgttg gtgctgcgggcgttttagcaggtggtgcggctttagttccaatggttcgccgtgacggc aaatttgtggaagctaaatcaagagcatcatttgttgaaggtacgcaaggggctcttcc taaagaagcagatgtagtgattattggtgccggtattcaagggatcatgaccgctatta accttgctgaacgtggtatgagtgtcactatcttagaaaagggtcagattgccggtgag caatcaggccgtgcatacagccaaattattagttaccaaacatcgccagaaatcttccc attacaccattatgggaaatattatggcgtggcatgaatgagaaaattggtgcggata ccagttatcgtactcaaggtcgtgtagaagcgctggcagatgaaaaagcattagataaa gctcaagcgtggatcaaaacagctaaagaagcggcaggttttgatacaccattaaatac tcgcatcattaaaggtgaagagctatcaaatcgcttagtcggtgctcaaacgccatgga ctgttgctgcatttgaagaagattcaggctctgttgatcctgaaacaggcacacctgca ctcgctcgttatgccaaacaaatcggtgtgaaaatttataccaactgtgcagtaagagg tattgaaactgcgggtggtaaaatctctgatgtggtgagtgagaaagggggcgattaaaa cgtctcaagttgtactcgctgggggtatctggtcgcgtttatttatgggcaatatgggt attgatatcccaacgctcaatgtatatctatcacaacaacgtgtctcaggggttcctgg tgcaccacgtggtaatgtgcatttacctaatggtattcatttccgcgaacaagcggatg gtacttatgccgttgcaccacgtatctttacgagttcaatagtcaaagatagcttcctg ctagggcctaaatttatgcacttattaggtggcggagagttaccgttggaattctctat tggtgaagatctatttaattcatttaaaatgccgacctcttggaatttagatgaaaaaa caccattcgaacaattccgagttgccacggcaacacaaaatacgcaacacttagatgct gttttccaaagaatgaaaacagaattcccagtatttgaaaaatcagaagttgttgaacg ttgggggtgccgttgtgagtccaacatttgatgaattacctatcatttctgaggtcaaag aatacccaggcttagtgattaacacggcaacagtgtggggtatgacagaaggcccggca gcgggtgaagtgaccgctgatattgtcatgggcaagaaacctgttattgatccaacgcc gtttagtttggatcgttttaagaagtaa Example 13

Efficacy of PAL-expressing Bacteria in a Mouse Model of PKU

For in vivo studies, BTBR-Pah$^{enu2}$ mice were obtained from Jackson Laboratory and bred to homozygosity for use as a model of PKU. Bacteria harboring a low-copy pSC101 origin plasmid expressing PAL3 from the Tet promoter, as well as a copy of pheP driven by the Tet promoter integrated into the genome (SYN-PKU302), were grown. SYN-PKU1 was induced by ATC for 2 hrs prior to administration. Bacteria were resuspended in phosphate buffered saline (PBS) and $10^9$ ATC-induced SYN-PKU302 or control Nissle bacteria were administered to mice by oral gavage.

At the beginning of the study, mice were given water that was supplemented with 100 micrograms/mL ATC and 5% sucrose. Mice were fasted by removing chow overnight (10 hrs), and blood samples were collected by mandibular bleeding the next morning in order to determine baseline phenylalanine levels. Blood samples were collected in heparinized tubes and spun at 2G for 20 min to produce plasma, which was then removed and stored at −80° C. Mice were given chow again, and were gavaged after 1 hr. with 100 μL ($5 \times 10^9$ CFU) of bacteria that had previously been induced for 2 hrs with ATC. Mice were put back on chow for 2 hrs. Plasma samples were prepared as described above.

Figures 26A, 26B:
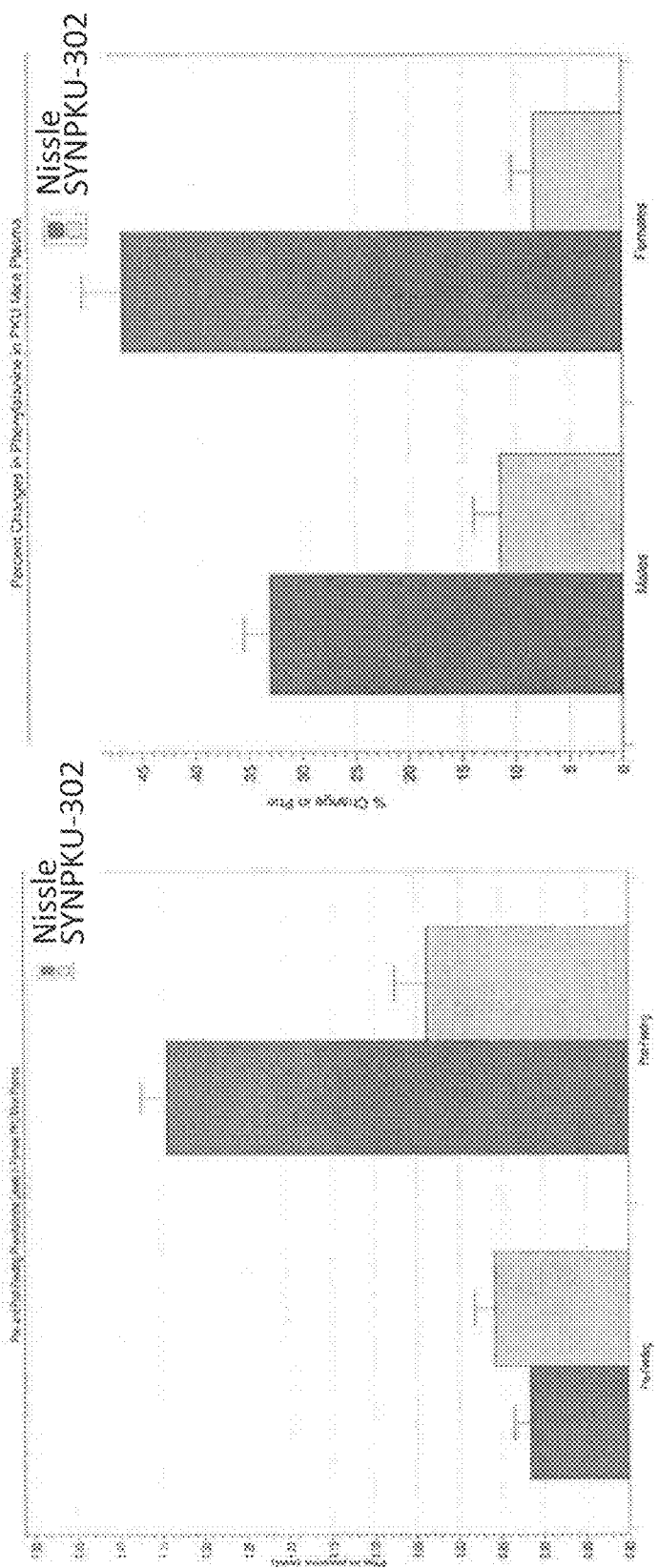
FIG. 26A shows phenylalanine concentrations before and after feeding in an in vivo mouse model of PKU. At the beginning of the study, homozygous BTBR-Pah$^{enu2}$ mice were given water supplemented with 100 micrograms/mL ATC and 5% sucrose. Mice were fasted by removing chow overnight (10 hrs), and blood samples were collected by mandibular bleeding the next morning in order to determine baseline phenylalanine levels. Mice were given chow again, gavaged with 100 microliters ($5 \times 10^9$ CFU) of bacteria (SYN-PKU302 or control Nissle) after 1 hr., and allowed to feed for another 2 hrs. Serum phenylalanine concentrations were determined 2 hrs post-gavage.
FIG. 26B shows the percent (%) change in blood phenylalanine concentrations before and after feeding as a male or female group average ($p<0.01$).

FIG. 26A shows phenylalanine levels before and after feeding, and FIG. 26B shows the percent (%) change in blood phenylalanine levels before and after feeding as a male or female group average (p<0.01). As shown in FIG. 26, PKU mice treated with SYN-PKU1 exhibit a significantly reduced post-feeding rise in serum phenylalanine levels compared to controls.

Example 14

Efficacy of PAL-expressing Bacteria Following Subcutaneous Phenylalanine Challenge Streptomycin-resistant *E. coli* Nissle (SYN-PKU901) was grown from frozen stocks to a density of $10^{10}$ cells/mL. Bacteria containing a copy of pheP under the control of a Tet promoter integrated into the lacZ locus, as well as a high-copy plasmid expressing PAL3 under the control of a Tet promoter (SYN-PKU303) were grown to an $A_{600}$ of 0.25 and then induced by ATC (100 ng/mL) for 4 hrs. Bacteria were centrifuged, washed, and resuspended in bicarbonate buffer at density of $1\times10^{10}$ cells/mL before freezing at $-80°$ C.

Beginning at least 3 days prior to the study (i.e., Days −6 to −3), homozygous BTBR-Pah$^{enu2}$ mice (approx. 6-12 weeks of age) were maintained on phenylalanine-free chow and water that was supplemented with 0.5 grams/L phenylalanine. On Day 1, mice were randomized into treatment groups and blood samples were collected by sub-mandibular skin puncture to determine baseline phenylalanine levels. Mice were also weighed to determine the average weight for each group. Mice were then administered single dose of phenylalanine by subcutaneous injection at 0.1 mg per gram body weight, according to the average group weight. At 30 and 90 min post-injection, 200 µL of $H_2O$ (n=30), SYN-PKU901 (n=33), or SYN-PKU303 (n=34) were administered to mice by oral gavage. Blood samples were collected at 2 hrs and 4 hrs following phenylalanine challenge, and phenylalanine levels in the blood were measured using mass spectrometry.

Figure 27A:
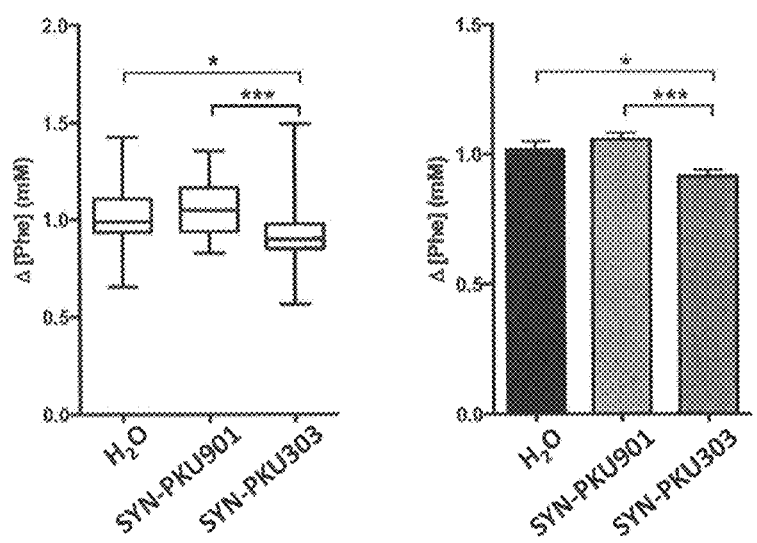
FIGS. 27A and 27B depict blood phenylalanine concentrations relative to baseline following subcutaneous phenylalanine challenge in an in vivo mouse model of PKU. Mice were orally gavaged with 200 μL of $H_2O$ (n=30), SYN-PKU901 (n=33), or SYN-PKU303 (n=34) at 30 and 90 minutes post-phenylalanine injection (0.1 mg/gram of average group body weight).
Figure 27B:
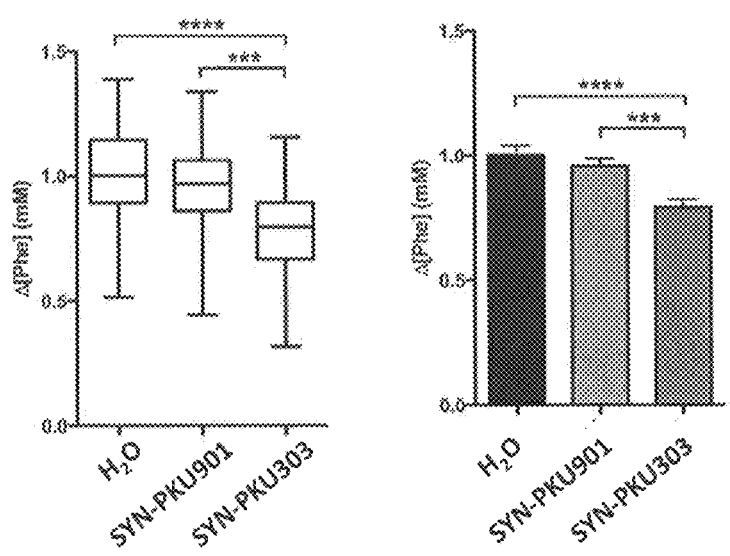
Figure 28:
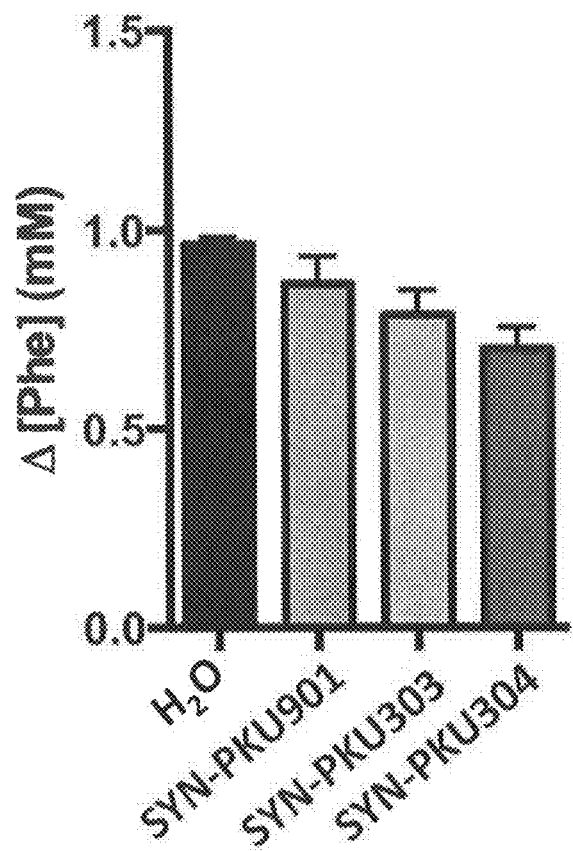
FIG. 28 depicts blood phenylalanine concentrations relative to baseline following subcutaneous phenylalanine challenge in an in vivo mouse model of PKU. Mice were orally gavaged with 200 μL of $H_2O$ (n=30), SYN-PKU901 (n=33), SYN-PKU303 (n=34), or SYN-PKU304 (n=34) at 30 and 90 minutes post-phenylalanine injection (0.1 mg/gram of average group body weight).
Figures 29A, 29B:
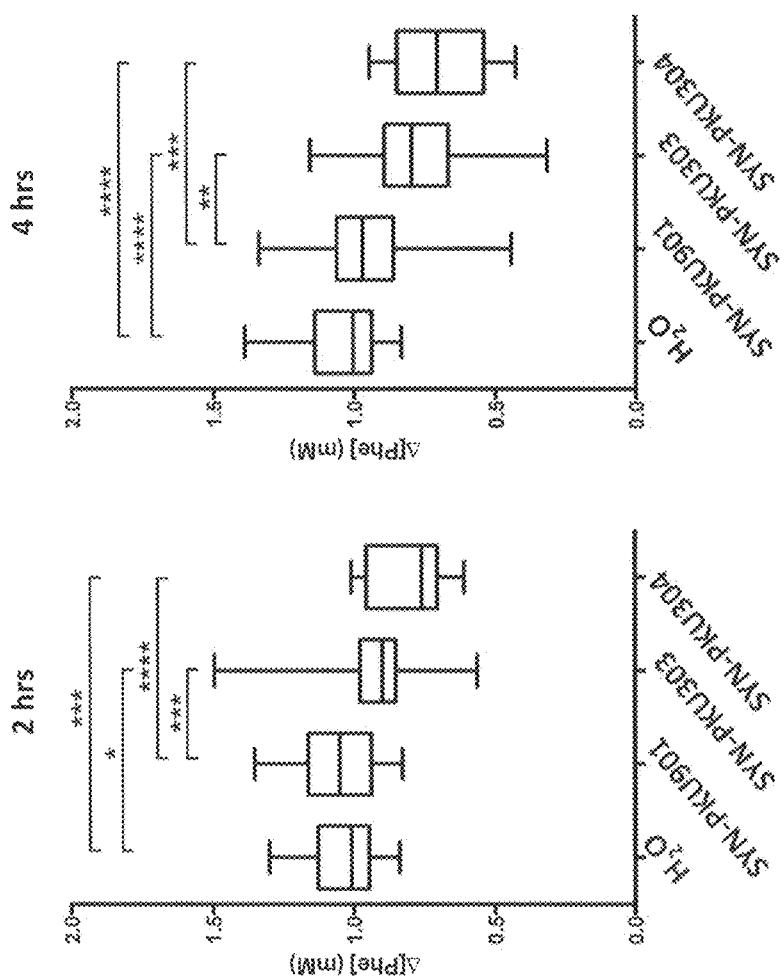
FIGS. 29A and 29B depict blood phenylalanine concentrations relative to baseline following subcutaneous phenylalanine challenge in an in vivo mouse model of PKU. Mice were orally gavaged with H2O, SYN-PKU901, SYN-PKU303, or SYN-PKU304 at 30 and 90 minutes post-phenylalanine injection (0.1 mg/gram of average group body weight).

FIG. 27 shows phenylalanine blood concentrations relative to baseline concentrations at 2 hrs (FIG. 27A) and 4 hrs (FIG. 27B) post-phenylalanine injection. These data suggest that subcutaneous injection of phenylalanine causes hyperphenylalanemia in homozygous enu2/enu2 mice, and that oral administration of SYN-PKU303 significantly reduces blood phenylalanine levels following phenylalanine challenge, compared to control groups (p<0.00001 at 4 hrs). Moreover, these results confirm that the orally-administered engineered bacteria, and not the non-engineered Nissle parent, can significantly impact blood-phenylalanine levels independent of dietary exposure. Thus, a PKU-specific probiotic may not need to be co-administered in conjunction with diet.

Example 15

Dose-response Activity of PAL-expressing Bacteria on Systemic Phenylalanine

Streptomycin-resistant *E. coli* Nissle (SYN-PKU901) were grown from frozen stocks to a density of $10^{10}$ cells/mL. Bacteria containing a copy of pheP under the control of a $P_{fnrS}$ promoter integrated into the lacZ locus, as well as a low-copy plasmid expressing PAL3 under the control of a $P_{fnrS}$ promoter (SYN-PKU304) were grown to an $A_{600}$ of 0.25 and then induced anaerobically by purging the bacterial fermenter with nitrogen for 4 hrs. Bacteria were centrifuged, washed, and resuspended in bicarbonate buffer at density of $5\times10^9$ cells/mL before freezing at $-80°$ C.

Beginning at least 3 days prior to the study (i.e., Days −6 to −3), mice were maintained on phenylalanine-free chow and water that was supplemented with 0.5 grams/L phenylalanine. On Day 1, mice were randomized into treatment groups and blood samples were collected by sub-mandibular skin puncture to determine baseline phenylalanine levels. Mice were also weighed to determine the average weight for each group. Mice were then administered single dose of phenylalanine by subcutaneous injection at 0.1 mg per gram body weight, according to the average group weight. At 30 and 90 min post-injection, 200 µL of $H_2O$ (n=12), 200 µL of SYN-PKU901 (n=12), or 100 µL, 200 µL, or 400 µL of SYN-PKU304 (n=12 in each dose group) were administered to mice by oral gavage. Blood samples were collected at 2 hrs and 4 hrs following phenylalanine challenge, and phenylalanine levels in the blood were measured using mass spectrometry.

Figures 30A, 30B:
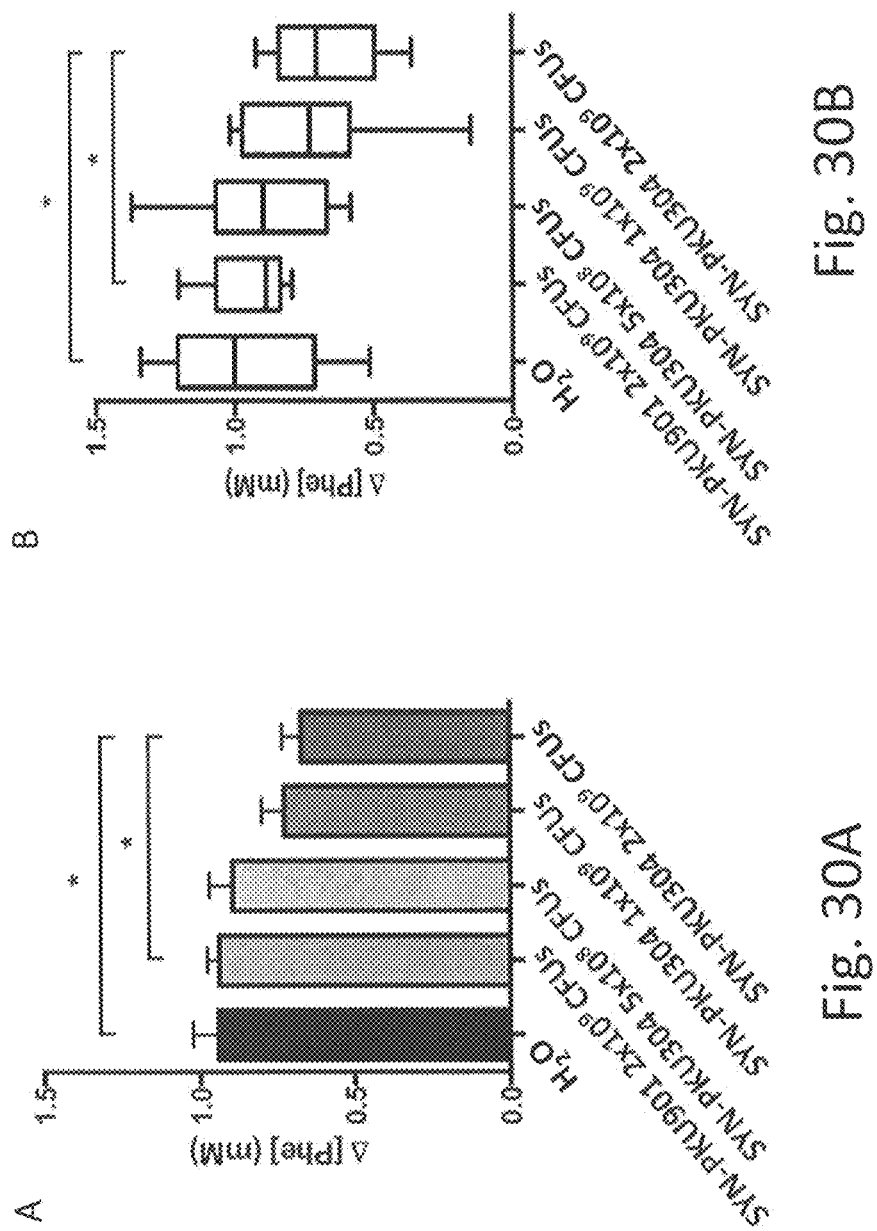
FIGS. 30A and 30B depict blood phenylalanine concentrations relative to baseline following subcutaneous phenylalanine challenge in an in vivo mouse model of PKU. Mice were orally gavaged with 200 µL of H2O (n=12), 200 µL of SYN-PKU901 (n=12), or 100, 200, or 400 µL of SYN-PKU304 (n=12 in each dose group) at 30 and 90 minutes post-phenylalanine injection (0.1 mg/gram of average group body weight).
Figure 32A:
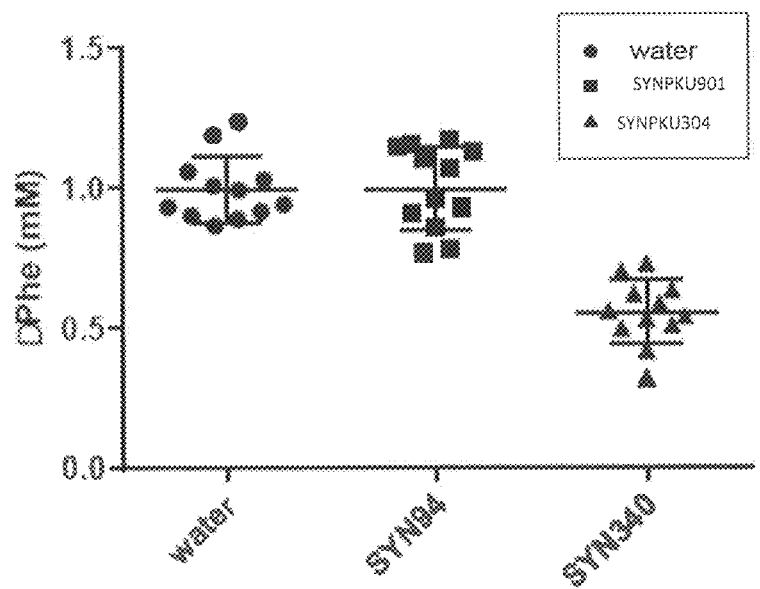
FIGS. 32A, 32B, 32C, 32D, 32E, and 32F depict blood phenylalanine concentrations relative to baseline and concentrations of phenylalanine (FIG. 32A), and absolute values of phenylalanine and PKU specific and PAL specific metabolites (FIGS. 32B, 32C, 32D, 32E, and 32F) following subcutaneous phenylalanine challenge in an in vivo mouse model of PKU. Mice were orally gavaged with a total of 800 µL of H2O (n=12), SYN-PKU901 (n=12), or 800 µL of SYN-PKU304 (n=12) (2.9e10 cfu/mouse) at 30 and 90 minutes post-phenylalanine injection.
Figure 32B:
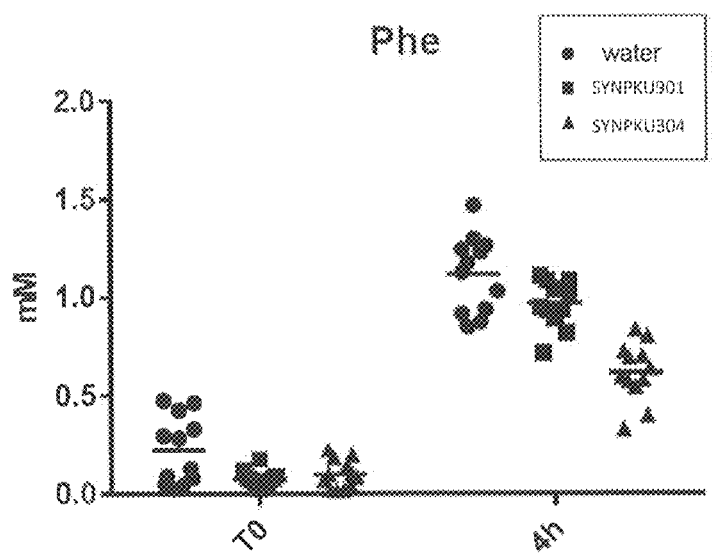
Figure 32C:
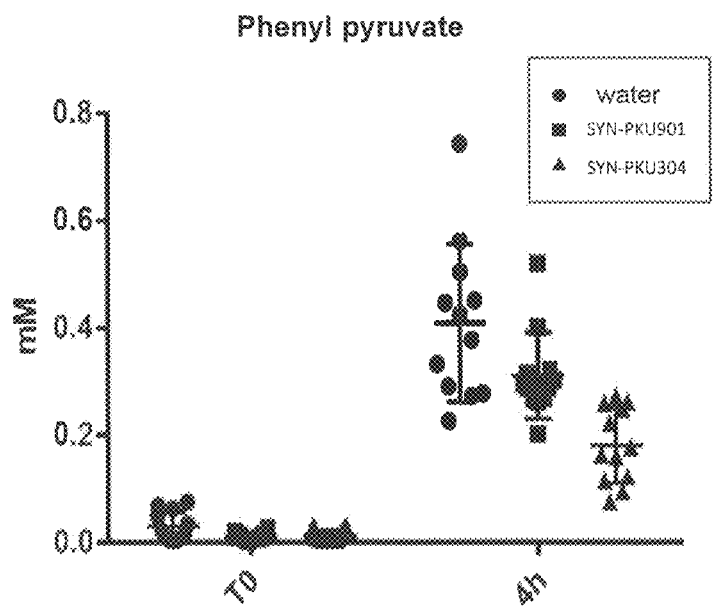
Figure 32D:
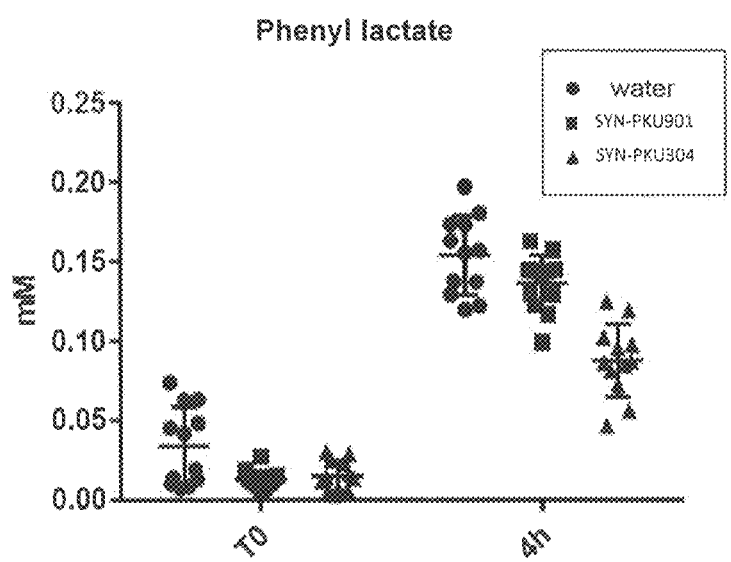
Figure 32E:
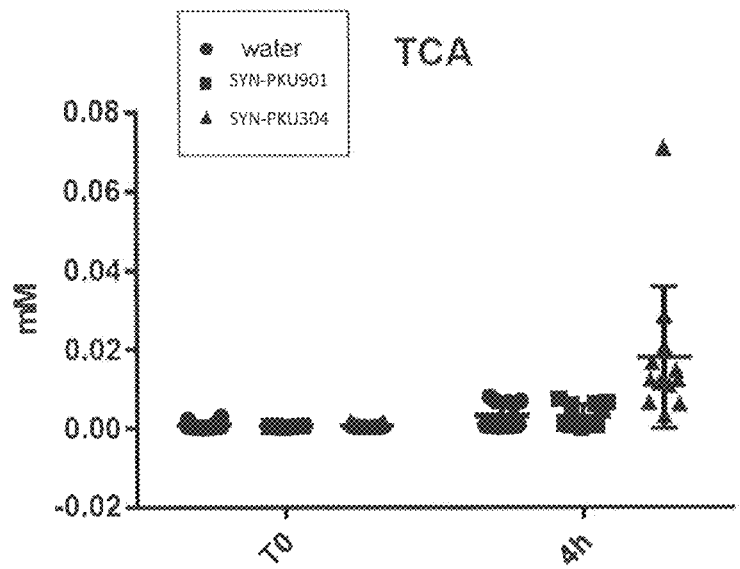
Figure 32F:
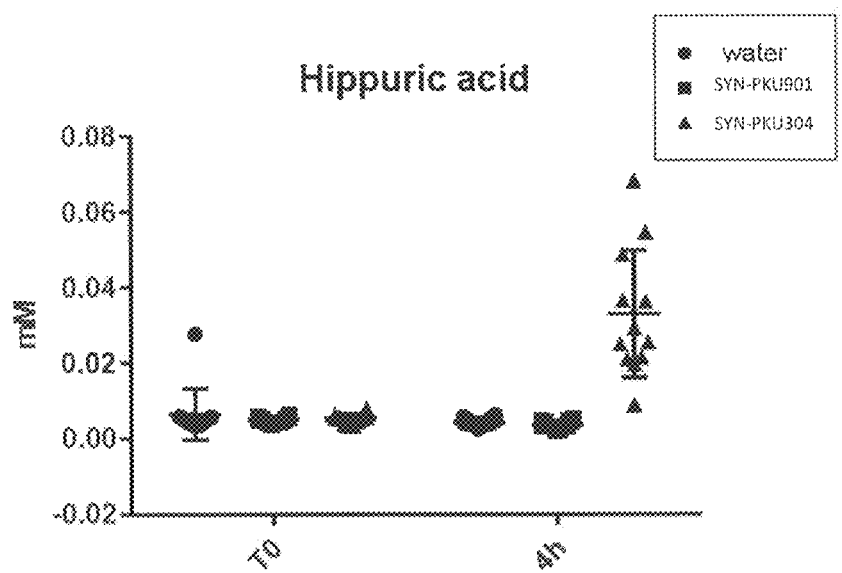

FIG. 30 shows phenylalanine blood concentrations relative to baseline concentrations post-phenylalanine injection. These data demonstrate a dose-dependent decrease in blood phenylalanine levels in SYN-PKU304-treated mice compared to mock treatment ($H_2O$) or administration of the parental strain (SYN-PKU901), following subcutaneous injection of phenylalanine (* 30% decrease; p<0.05).

Example 16

Phenylalanine Degradation Activity In Vivo (PAL)

To compare the correlation between in vivo and in vitro phenylalanine activity, SYN-PKU304(containing a low copy plasmin expressing PAL3 with a chromosomal insertion of PfnrS-pheP at the LacZ locus, was compared to SYN-PKU901, a control Nissle strain with streptomycin resistance in vivo).

Beginning at least 3 days prior to the study (i.e., Days −6 to −3), homozygous BTBR-Pah$^{enu2}$ mice (approx. 6-12 weeks of age) were maintained on phenylalanine-free chow and water that was supplemented with 0.5 grams/L phenylalanine. On Day 1, mice were randomized into treatment groups and blood samples were collected by sub-mandibular skin puncture to determine baseline phenylalanine levels. Mice were also weighed to determine the average weight for each group. Mice were then administered single dose of phenylalanine by subcutaneous injection at 0.1 mg per gram body weight, according to the average group weight. At 30 and 90 min post-injection, the bacteria were administered to mice by oral gavage.

To prepare the cells, cells were diluted 1:100 in LB (2 L), grown for 1.5 h aerobically, then shifted to the anaerobe chamber for 4 hours. Prior to administration, cells were concentrated 200× and frozen (15% glycerol, 2 g/L glucose, in PBS). Cells were thawed on ice, and 4e10 cfu/mL and mixed 9:1 in 1M bicarbonate. Each mouse gavaged 800uL total, or 2.9e10 cfu/mouse.

Blood samples were collected at 2 hrs and 4 hrs following phenylalanine challenge, and phenylalanine levels in the blood were measured using mass spectrometry, and the change in Phenylalanine concentration per hour was calculated. Results are shown in FIG. 32. The total metabolic activity measured was 81.2 umol/hr. and the total reduction in change in phenylalanine was 45% (P<0.05). These same cells showed an in vitro activity of 2.8 umol/hr./1e9 cells.

Additionally, various metabolites were measured to determine whether secondary metabolites can be used as an additional parameter to assess the rate of phenylalanine consumption of the engineered bacteria. When PAH activity is reduced in PKU, the accumulated phenylalanine is converted into PKU specific metabolites phenylpyruvate, which can be further converted into phenyllactic acid. In the presence of the genetically engineered bacteria, phenylalanine is converted by PAL to PAL specific metabolites trans-cinnamic acid, which then can be further converted by liver enzymes to hippuric acid (FIG. 32). Blood samples were analyzed for phenylpyruvate, phenyllactate, trans-cinnamic acid, and hippuric acid as described in Example 24-26. Results are shown in FIGS. 32C, 32D, 32E, and 32F and are consistent with the phenylalanine degradation shown in FIGS. 32A and 32B. For SYN-PKU304, PAL specific metabolites are detected at 4 hours, and moreover, lower levels of PKU specific metabolites are observed as compared to SYN-PKU901, indicating that PAL phenylalanine degradation may cause a shift away from PKU specific metabolites in favor or PAL specific metabolites.

Example 17

Phenylalanine Degradation Activity In Vivo (PAL)

SYN-PKU517 (comprising 2 chromosomal insertions of PAL (2XfnrS-PAL (malEK, malPT)), and a chromosomal insertion of pheP (fnrS-pheP (lacZ)), thyA auxotrophy (kan/cm)) was compared to SYN-PKU901.

Mice were maintained, fed, and administered phenylalanine as described above. To prepare the bacterial cells for gavage, cells were diluted 1:100 in LB (2 L), grown for 1.5 h aerobically, then shifted to the anaerobe chamber for 4 hours. Prior to administration, cells were concentrated 200× and frozen (15% glycerol, 2 g/L glucose, in PBS). Cells were thawed on ice, and 4e10 cfu/mL was mixed 9:1 in 1M bicarbonate. Each mouse gavaged 800uL total, or 3.6e10 cfu/mouse.

Figure 33A:
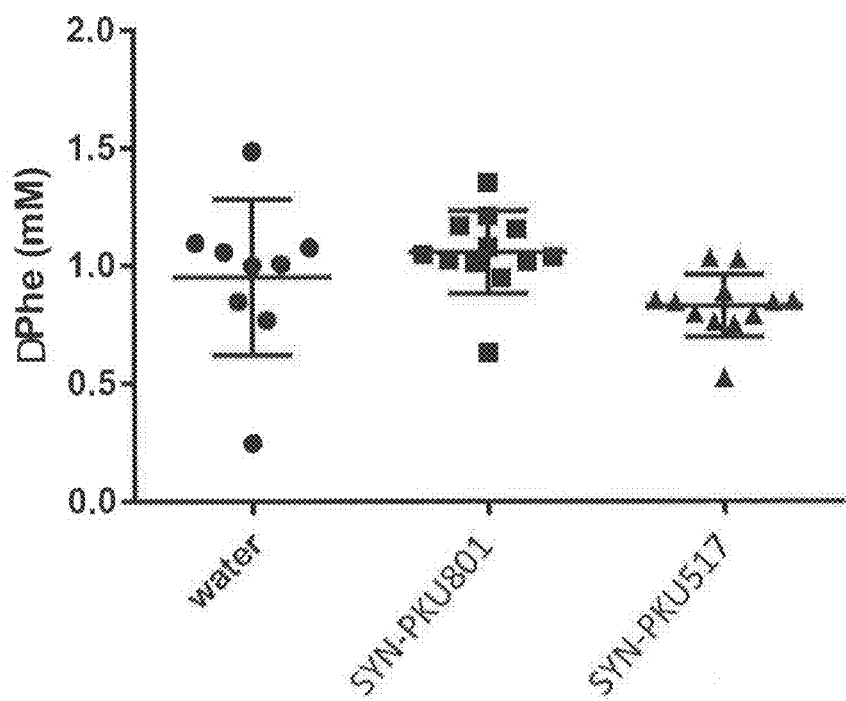
FIGS. 33A, 33B, 33C, 33D, 33E, and 33F depict blood phenylalanine concentrations relative to baseline and concentrations of phenylalanine (FIG. 33A), and absolute values of phenylalanine and PKU specific and PAL specific metabolites (FIGS. 33B, 33C, 33D, 33E, and 33F) following subcutaneous phenylalanine challenge in an in vivo mouse model of PKU. Mice were orally gavaged with a total of 800 µL of H2O (n=9]), SYN-PKU801 (n=12), or 800 µL of SYN-PKU517 (n=12) (3.6e10 cfu/mouse) at 30 and 90 minutes post-phenylalanine injection.
Figure 33B:
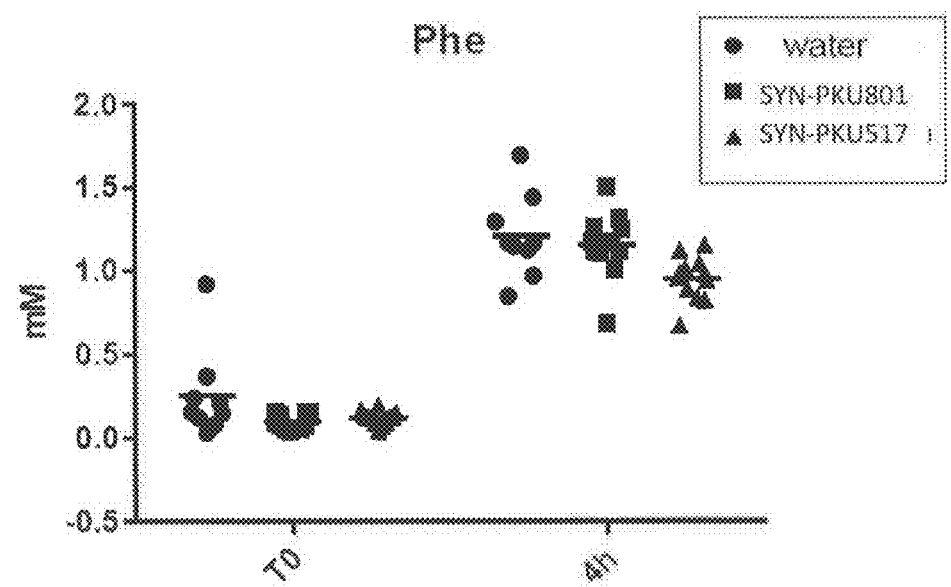
Figure 33C:
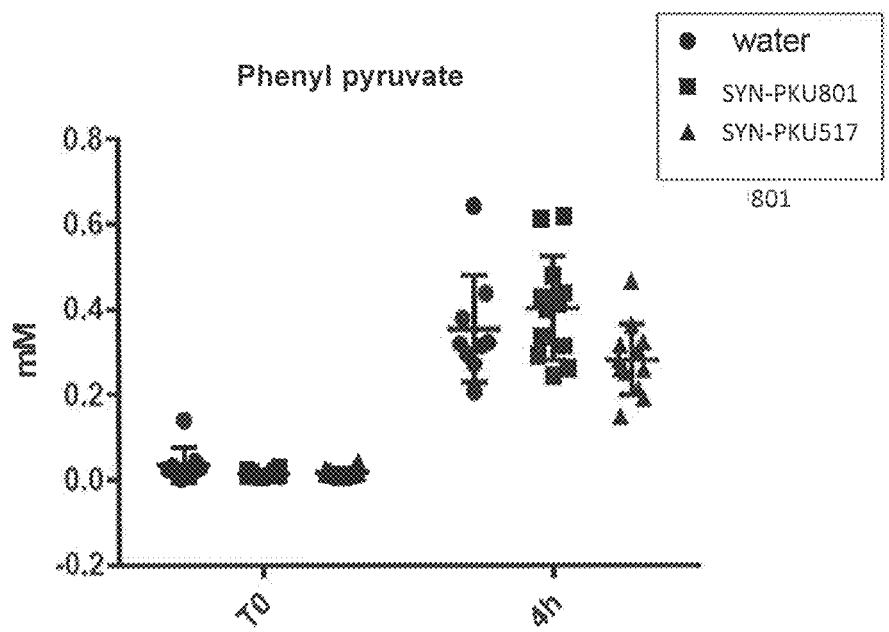
Figure 33D:
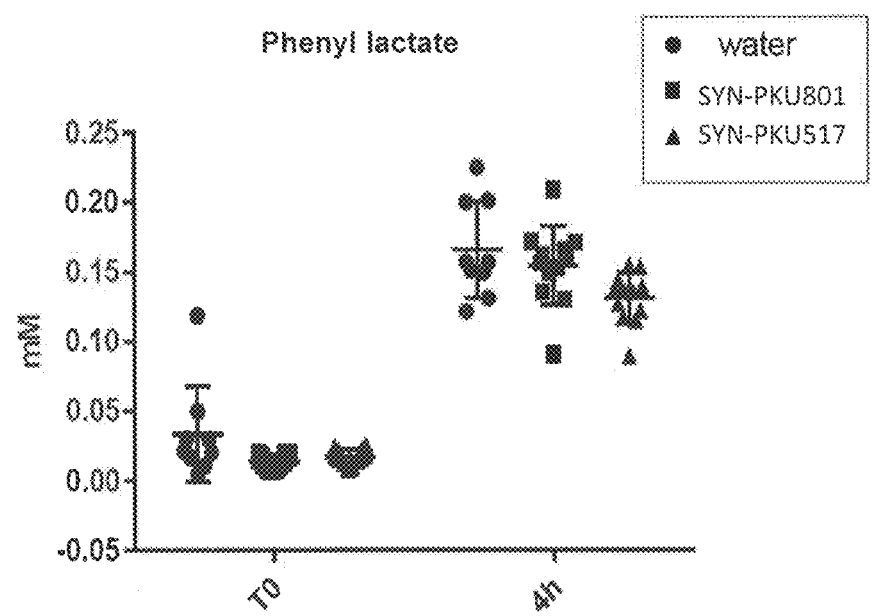
Figure 33E:
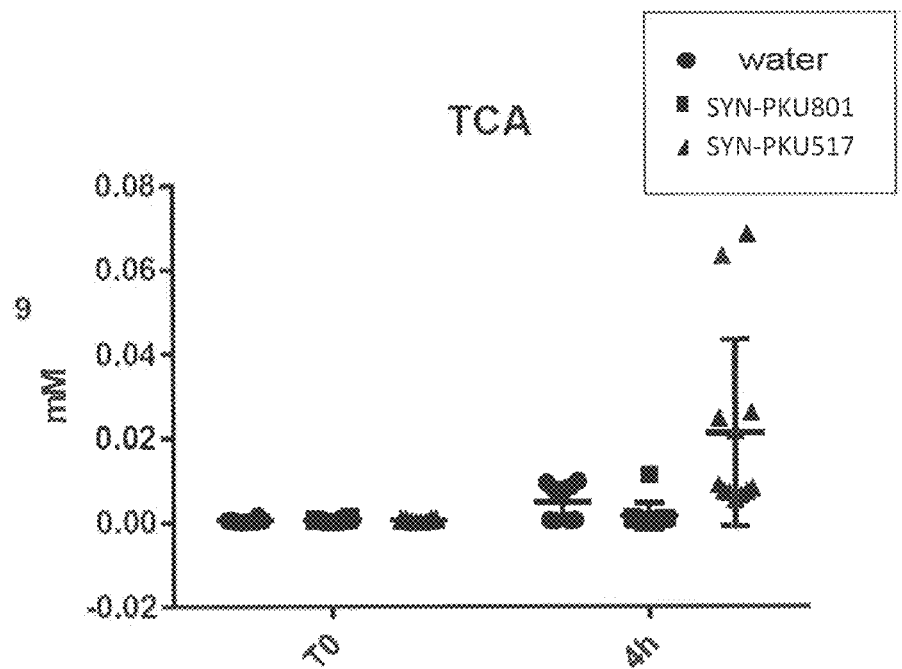
Figure 33F:
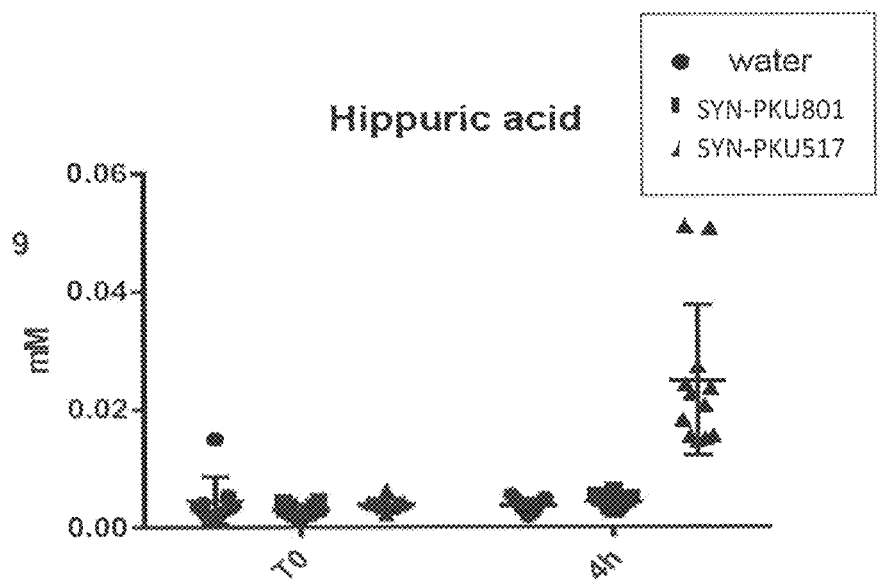

As described above, blood samples were collected, and the change in phenylalanine concentration as compared to baseline was calculated. Results are shown in FIGS. 33A and 33B. The total metabolic activity measured was 39.6 umol/hr. and the total reduction in change in phenylalanine was 17% ($P<0.05$). These same cells showed an in vitro activity of 1.1 umol/hr./1e9 cells.

Absolute levels of phenylalanine and of PKU and PAL metabolites are shown in FIGS. 33C, 33D, 33E, and 33F and are consistent with the phenylalanine degradation shown in FIGS. 33A and 33B. For SYN-PKU517, PAL specific metabolites were detected at 4 hours, and moreover, lower levels of PKU specific metabolites were observed as compared to SYN-PKU901, indicating that PAL phenylalanine degradation may cause a shift away from PKU specific metabolites in favor or PAL specific metabolites.

In some embodiments, urine is collected at predetermined time points, and analyzed for phenylalanine levels and levels of PAL and PKU metabolites.

Example 18

Phenylalanine Degradation Activity In Vivo (PAL)

SYN-PKU705 (comprising 3 chromosomal insertions of PAL (3XfnrS-PAL (malEK, malPT, yicS/nepl)), and 2 chromosomal insertions of pheP (2XfnrS-pheP (lacZ, agal/rsml)), and LAAD (driven by the ParaBAD promoter integrated within the endogenous arabinose operon) was compared to SYN-PKU901.

Figure 34A:
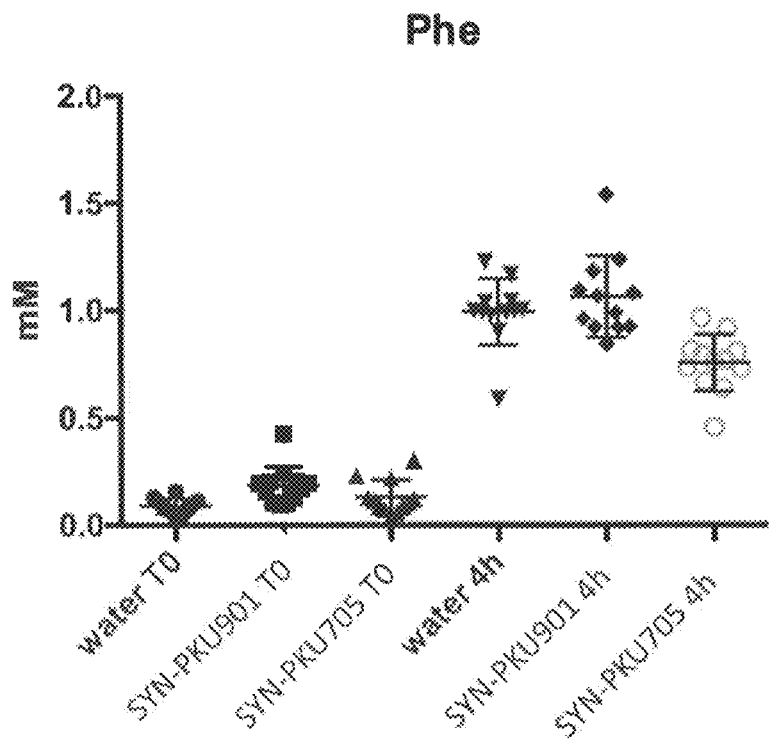
FIGS. 34A, 34B, 34C, 34D, 34E, and 34F depict blood phenylalanine concentrations relative to baseline and concentrations of phenylalanine (FIG. 34A), and absolute values of phenylalanine and PKU specific and PAL specific metabolites (FIGS. 34B, 34C, 34D, 34E, and 34F) following subcutaneous phenylalanine challenge in an in vivo mouse model of PKU. Mice were orally gavaged with a total of 800 µL of H2O (n=12), SYN-PKU901 (n=12), or 800 µL of SYN-PKU705 (n=12) (3.6e10 cfu/mouse) at 30 and 90 minutes post-phenylalanine injection.

Mice were maintained, fed, and administered phenylalanine as described above. To prepare the bacterial cells for gavage, cells were diluted 1:100 in LB (2 L), grown for 1.5 h aerobically, then shifted to the anaerobe chamber for 4 hours. Prior to administration, cells were concentrated 200× and frozen (15% glycerol, 2 g/L glucose, in PBS). Cells were thawed on ice, and 5e10 cfu/mL was mixed 9:1 in 1M bicarbonate. Each mouse gavaged 800uL total, or 3.6e10 cfu/mouse. Note: Though this strain contains the LAAD gene, it was not induced in this study As described above, blood samples were collected, and the change in phenylalanine concentration as compared to baseline was calculated. Results are shown in FIG. 34A. The total metabolic activity measured was 133.2 umol/hr. and the total reduction in change in phenylalanine was 30% ($P<0.05$). These same cells showed an in vitro activity of 3.7 umol/hr./1e9 cells.

Figure 34B:
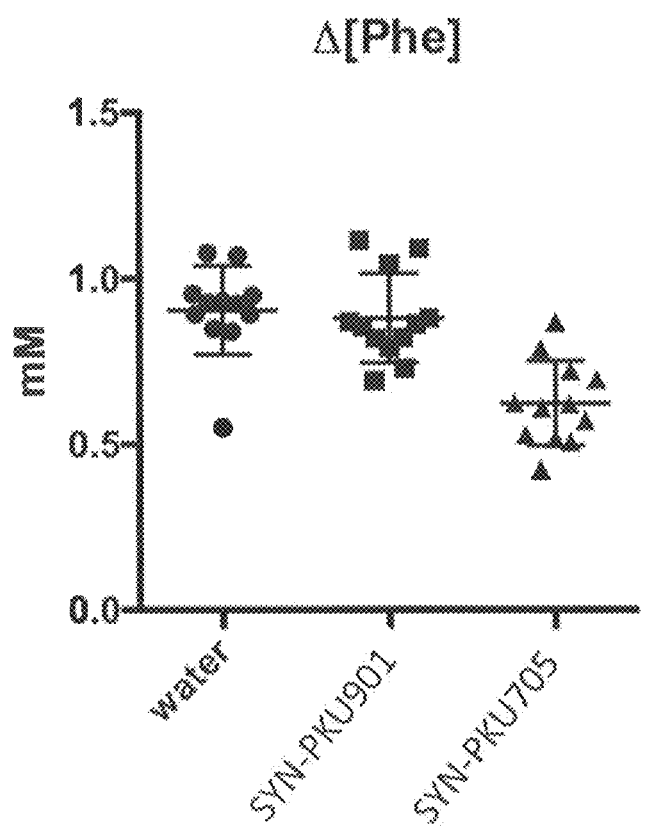
Figure 34C:
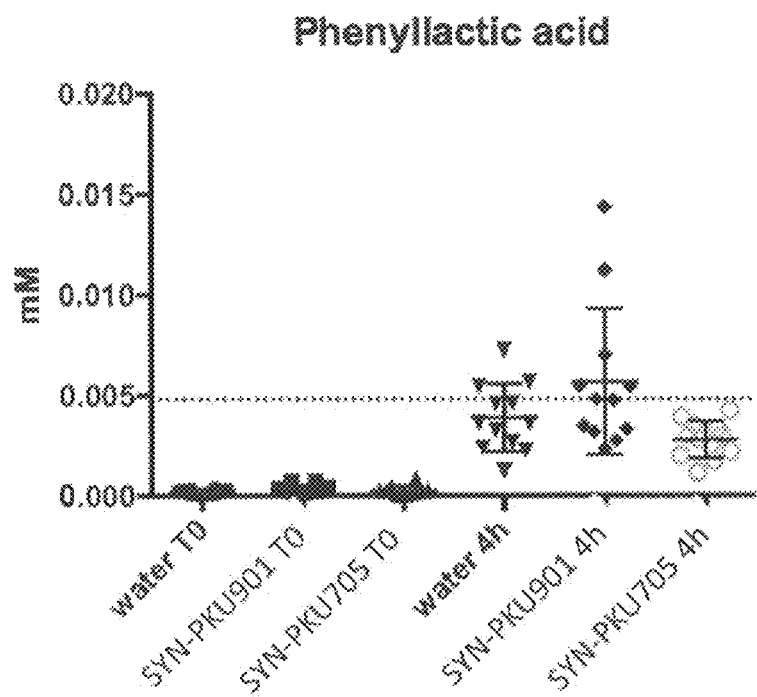
Figure 34D:
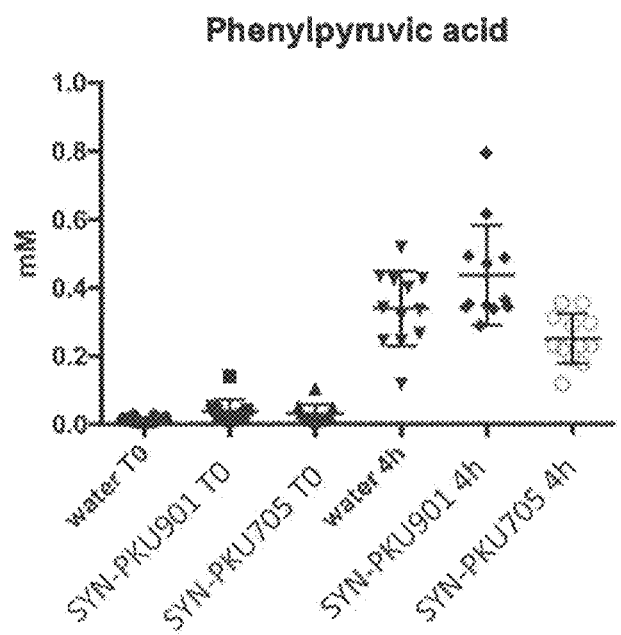
Figure 34E:
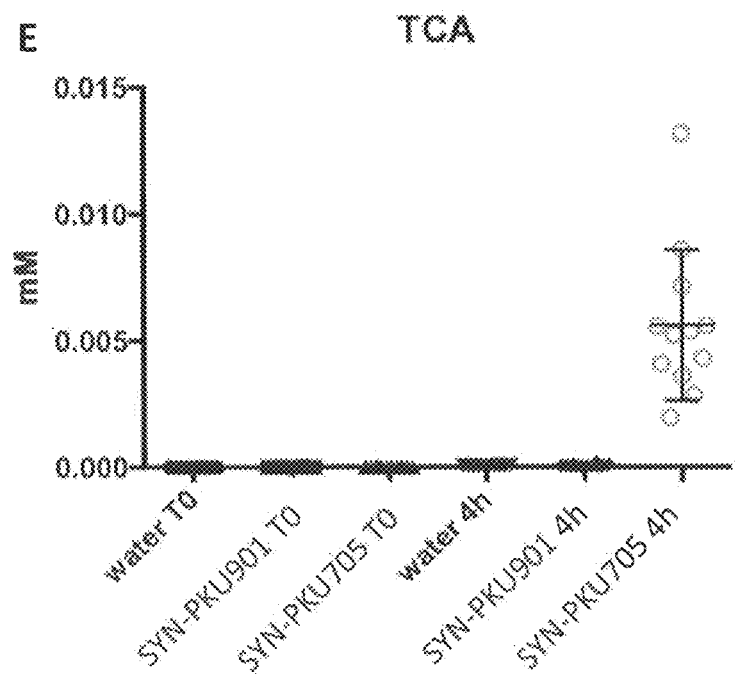
Figure 34F:
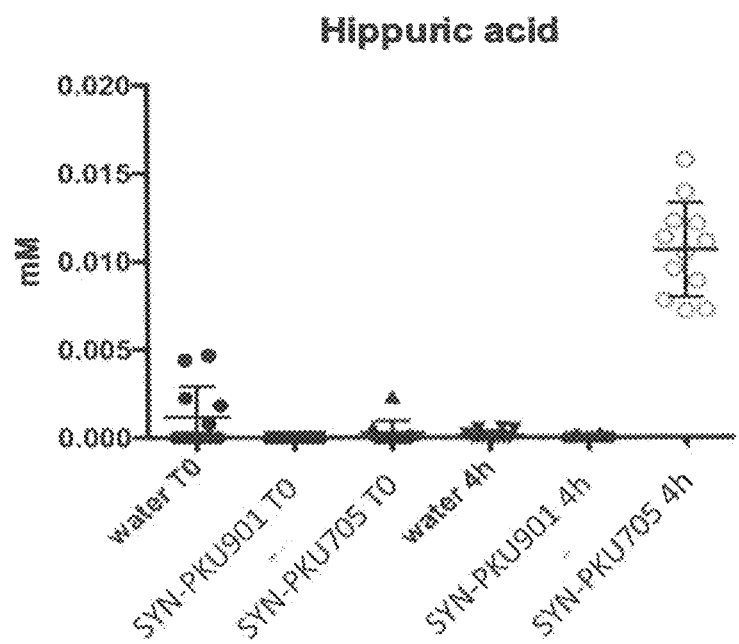

Absolute levels of phenylalanine and of PKU and PAL metabolites are shown in FIGS. 34C, 34D, 34E, and 34F and are consistent with the phenylalanine degradation shown in FIGS. 34A and 34B. PAL specific metabolites were detected at 4 hours, and moreover, lower levels of PKU specific metabolites were observed as compared to SYN-PKU901, indicating that PAL phenylalanine degradation may cause a shift away from PKU specific metabolites in favor or PAL specific metabolites. total metabolic activity measured activity was greater than the total metabolic activity measured of the PAL3 plasmid-based strain SYN-PKU304 and the total reduction in phenylalanine approached that of SYN-PKU304 (30% as compared to 45%).

In some embodiments, urine is collected at predetermined time points, and analyzed for phenylalanine levels and levels of PAL and PKU metabolites.

Example 19

Phenylalanine Degradation Activity In Vivo (PAL) LAAD

The suitability of *P. proteus* LAAD for phenylalanine degradation by the genetically engineered bacteria is further assessed in vivo. Bacterial strain SYN-PKU401 (comprising a high copy plasmid comprising LAAD driven by a Tet-inducible promoter is compared to SYN-PKU901.

Mice are maintained, fed, and administered phenylalanine as described above. To prepare the bacterial cells for gavage, cells are diluted 1:100 in LB (2 L), grown for 1.5 h aerobically, then ATC is added and the cells are grown for another 2 hours. Prior to administration, cells are concentrated 200× and frozen for storage. Cells are thawed on ice, and resuspended. Cells are mixed 9:1 in 1M bicarbonate. Each mouse is gavaged four times with 800uL total volume, or with a total of bacteria ranging from $2 \times 10^9$ to $1 \times 10^{10}$. Blood samples are collected from the mice described in the previous examples and are analyzed for phenylalanine, phenylpyruvate, phenyllactate, trans-cinnamic acid, and hippuric acid levels. Total reduction in phenylalanine and total metabolic activity are calculated.

Example 20

Effect of pH on Phenylalanine Degradation in Recombinant *E. Coli*

Figure 39A:
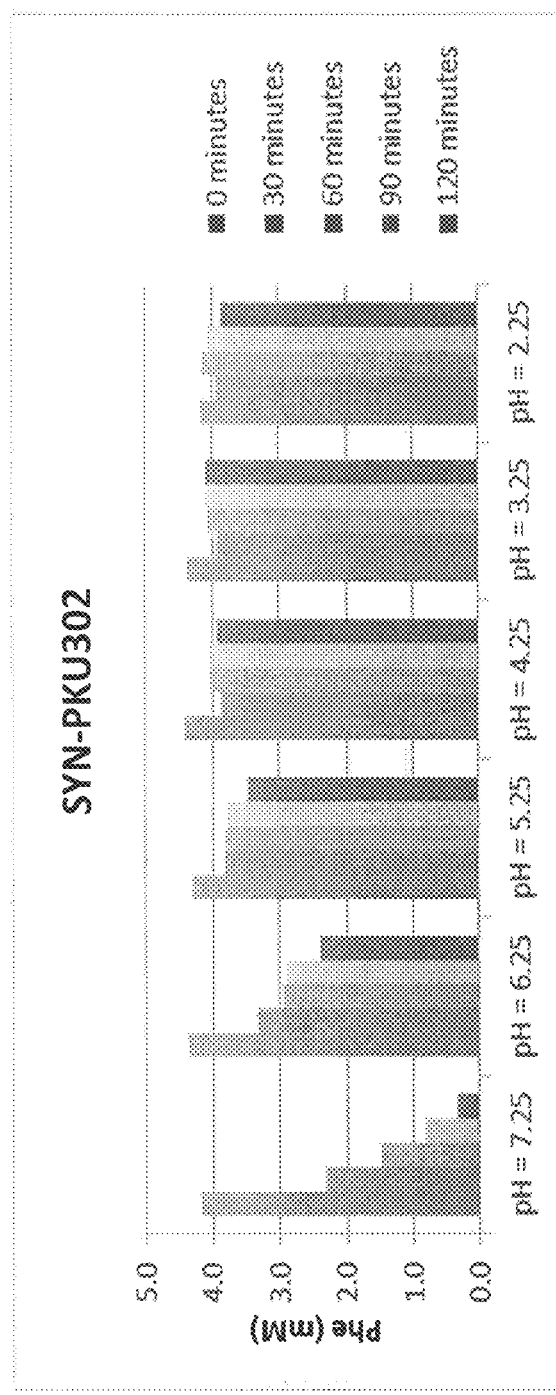
FIGS. 39A and 39B depict phenylalanine concentrations in SYN-PKU302 cultures over time. After 1.5 hrs of growth, ATC was added to cultures of SYN-PKU302, and SYN-PKU304 cultures were placed in Coy anaerobic chamber supplying 90% $N_2$, 5% $CO_2$, and 5% $H_2$. After 4 hrs of induction, bacteria were resuspended in assay buffer containing 4 mM phenylalanine and at different pH (pH range 7.25-2.25). Aliquots were removed from cell assays every 30 min for 2 hrs for phenylalanine quantification by mass spectrometry. Phenylalanine degradation rates decreased as pH of the assay buffer decreased in both strains, SYN-PKU302 (FIG. 39A) and SYN-PKU304 (FIG. 39B).
Figure 39B:
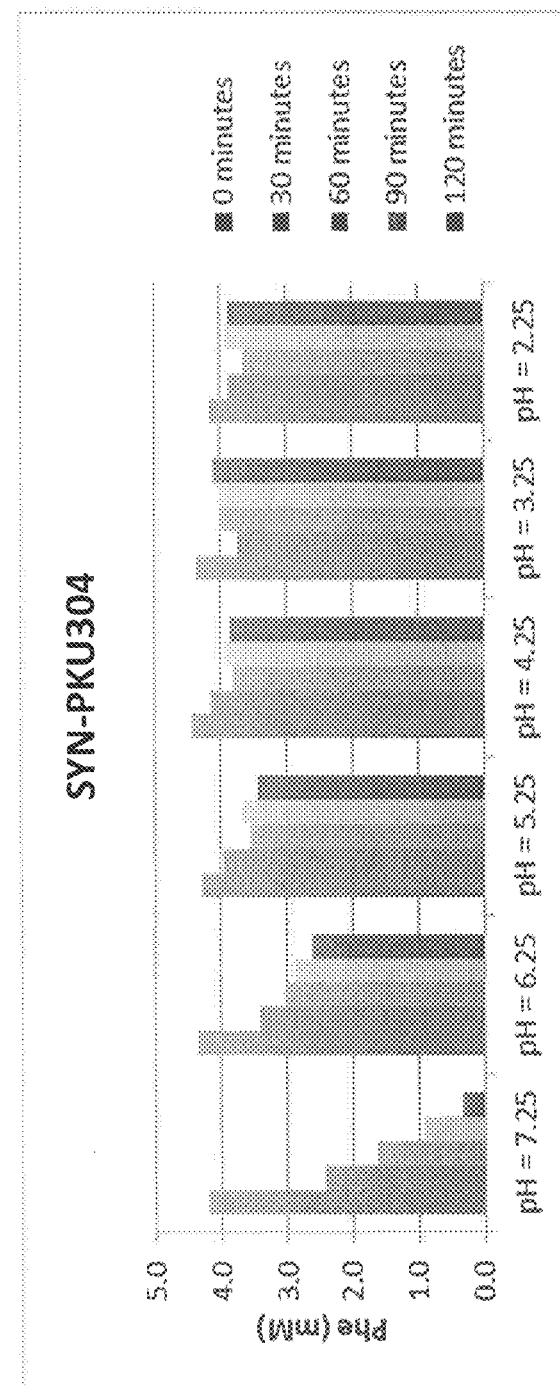
Figure 40:
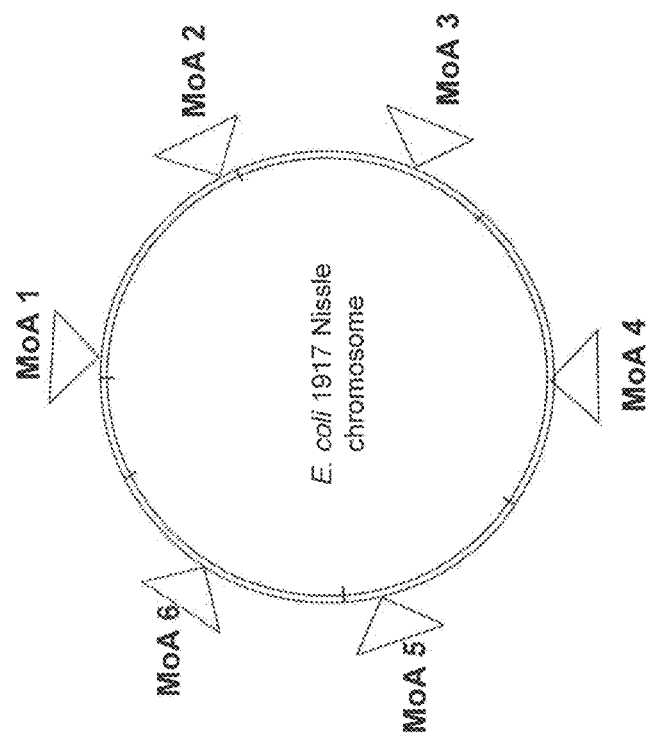
FIG. 40 depicts an exemplary schematic of the E. coli 1917 Nissle chromosome comprising multiple mechanisms of action (MoAs).

To determine whether the rates of phenylalanine degradation in SYN-PKU304 and SYN-PKU302 are affected by low pH, overnight cultures of both strains were diluted 1:100 in LB and grown with shaking (250 rpm) at 37° C. After 1.5 hrs of growth, ATC (100 ng/mL) was added to cultures of SYN-PKU302, and SYN-PKU304 cultures were placed in a Coy anaerobic chamber (supplying 90% $N_2$, 5% $CO_2$, and 5% $H_2$). After 4 hrs of induction, bacteria were pelleted, washed in PBS, and resuspended in assay buffer (M9 minimal media with 0.5% glucose, 8.4% sodium bicarbonate, and 4 mM Phe) to a concentration of 5e9 cells/mL. Assay buffer was prepared with incrementally decreasing values of pH, ranging from 7.25-2.25, using 1M HCl. Aliquots were removed from the cell assay every 30 min for 2 hrs for phenylalanine quantification by mass spectrometry. As shown in FIG. 39, phenylalanine degradation rates decreased as pH of the assay buffer decreased in both strains, SYN-PKU302 (FIG. 39A) and SYN-PKU304 (FIG. 39B).

Example 21

Degradation of Dipeptides and Tripeptides

Overnight strains of SYN-PKU304, and SYN-PKU705 were diluted 1:100 and grown to early log before shifting to anaerobic conditions for induction of PAL and pheP. One culture of SYN-PKU705 was also induced with arabinose to induce the LAAD protein. The focus of this study was to determine if PKU strains could degrade Phe when sequestered in the form of di and tripeptides. After strain induction Cells were spun down and resuspended in assay buffer containing M9 minimal media, 0.5% glucose, 50 mM MOPS, and 50 mM of Phe or Phe-containing di- or tripeptide. Supernatant samples were removed every 20 minutes for a total of 80 minutes, and supernatant was analyzed on a UV-Vis spectrophotometer to measure absorbance at 290 nm (the absorption peak for trans-cinnamic acid). Results are shown in Table 43 indicated that PKU strains were capable of degrading Phe rapidly even in the form of di- and tri-peptides.

TABLE 43

Dipeptide and Tripeptide Degradation Rates

| | Rate (umol TCA produced/hr./1e9 cfu) | | | | | |
|---|---|---|---|---|---|---|
| | Phe | Phe-Val | Phe-Ala | Gly-Phe | Phe-Pro | Phe-Gly-Gly |
| SYN-PKU304 | 4.1 | 3.9 | 3.5 | 1.7 | 1.1 | 2.0 |
| SYN-PKU705 | 6.9 | 5.8 | 5.0 | 4.1 | 1.3 | 4.5 |
| SYN-PKU705 +ara | 4.8 | 5.8 | 4.2 | 2.0 | 1.4 | 3.3 |

Example 22

Engineering Bacterial Strains Using Chromosomal Insertions

Bacterial strains, in which the pheP and/or PAL3 genes are integrated directly into the *E. coli* Nissle genome under the control of an FNR-responsive promoter, were constructed. The methods described below may be used for engineering bacterial strains comprising chromosomal insertions (e.g., SYN-PKU902 and/or any of the integrated strains listed in Table 14.

The SYN-PKU902 strain (lacZ::$P_{fnrS}$-PAL3-pheP) contains a copy of PAL3 and a copy of pheP integrated at the lacZ locus, with both genes operatively linked to a single fnrS promoter and co-transcribed in a bicistronic message (FIG. 41). Table 21 shows the sequence of an exemplary construct in which the PAL3 and pheP genes are co-transcribed under the control of an exemplary FNR promoter (SEQ ID NO: 31), with the FNR promoter sequence bolded, the PAL3 sequence boxed, the pheP sequence underlined, and ribosomal binding sites highlighted.

To create a vector capable of integrating the $P_{fnrS}$-PAL3-pheP sequence into the chromosome, Gibson assembly was used to add 1000 bp sequences of DNA homologous to the Nissle lacZ locus to both sides of a flippase recombination target (FRT) site-flanked chloramphenicol resistance ($cm^R$) cassette on a knock-in knock-out (KIKO) plasmid. Gibson assembly was then used to clone the $P_{fnrS}$-PAL3-pheP DNA sequence between these homology arms, adjacent to the FRT-$cm^R$-FRT site. Successful insertion of the fragment was validated by sequencing. PCR was used to amplify the entire lacZ::FRT-$cm^R$-FRT:: $P_{fnrS}$-PAL3-pheP::lacZ region. This knock-in PCR fragment was used to transform an electrocompetent Nissle strain that contains a temperature-sensitive plasmid encoding the lambda red recombinase genes. After transformation, cells were grown for 2 hrs at 37° C. Growth at 37° C. cured the temperature-sensitive plasmid. Transformants with successful chromosomal integration of the fragment were selected on chloramphenicol at 20 µg/mL.

The SYN-PKU501 strain (malPT::$P_{fnrS}$-PAL3, lacZ::$P_{fnrS}$-pheP) contains a copy of PAL3 integrated at the malP/T locus, and a copy of pheP integrated at the lacZ locus, with both genes operatively linked to separate fnrS promoters (see Table 28; SEQ ID NO: 38). The SYN-PKU502 strain (malPT::$P_{fnrS}$-PAL3, lacZ::$P_{fnrS}$-PAL3-pheP) contains a copy of PAL3 integrated at the malP IT locus under the control of an fnrS promoter (see Table 28; SEQ ID NO: 38), as well as a PAL3-pheP construct integrated at the lacZ locus, wherein both genes at the lacZ locus are operatively linked to a single fnrS promoter and co-transcribed in a bicistronic message (see Table 21; SEQ ID NO: 31).

To create a vector capable of integrating the $P_{fnrS}$-PAL3 sequence (SEQ ID NO: 38) into the *E. coli* Nissle chromosome in SYN-PKU501 and SYN-PKU502, Gibson assembly was used to add 1000 bp sequences of DNA homologous to the Nissle malP and malT loci on either side of an FRT site-flanked kanamycin resistance ($kn^R$) cassette on a KIKO plasmid. Gibson assembly was then used to clone the $P_{fnrS}$-PAL3 DNA sequence between these homology arms, adjacent to the FRT-$kn^R$-FRT site. Successful insertion of the fragment was validated by sequencing. PCR was used to amplify the entire ma/P::FRT-$kn^R$-FRT:: $P_{fnrS}$-PAL3::malT region. This knock-in PCR fragment was used to transform an electrocompetent Nissle strain already containing $P_{fnrS}$-pheP or bicistronic $P_{fnrS}$-PAL3-pheP in the lacZ locus, and expressing the lambda red recombinase genes. After transformation, cells were grown for 2 hrs at 37° C. Transformants with successful integration of the fragment were selected on kanamycin at 50 µg/mL. These same methods may be used to create a vector capable of integrating the $P_{fnrS}$-PAL3 sequence (SEQ ID NO: 38) at the malE/K insertion site in SYN-PKU506 and SYN-PKU507.

Figure 42A:
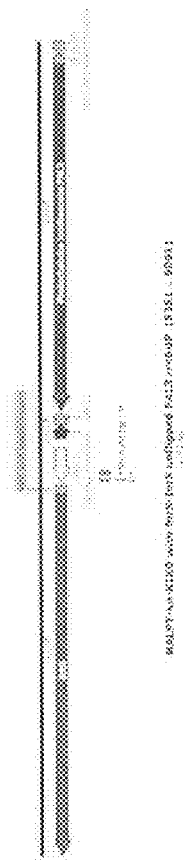
FIGS. 42A and 42B depict the gene organization of an exemplary construct in which the Int5 recombinase gene is operably linked to an exemplary FNR promoter ($P_{fnrS}$), and the PAL3 gene is operably linked to a strong constitutive promoter.
Figure 42B:
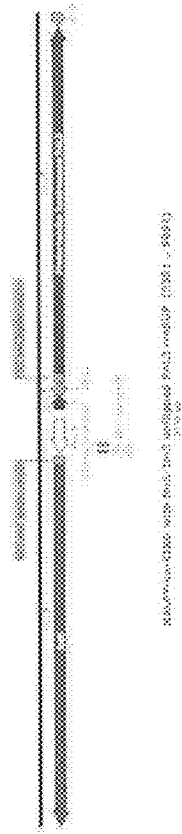
Figure 43A:
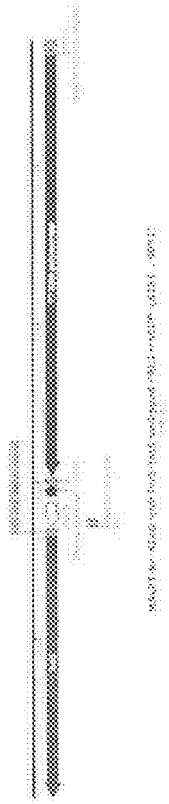
FIGS. 43A, 43B, and 43C depict the gene organization of an exemplary construct in which the Int5 recombinase gene is operably linked to an FNR promoter ($P_{fnrS}$), and the gene encoding T7 RNA polymerase is flanked by recombinase sites and operably linked to a strong constitutive promoter.
Figure 43B:
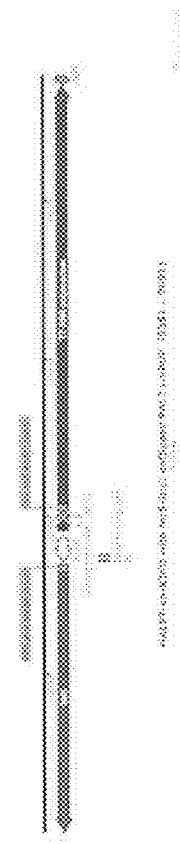
Figure 43C:
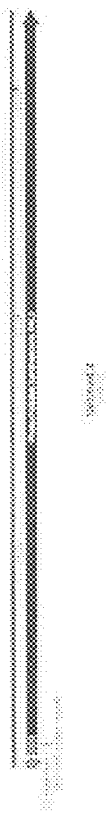
Figure 44A:
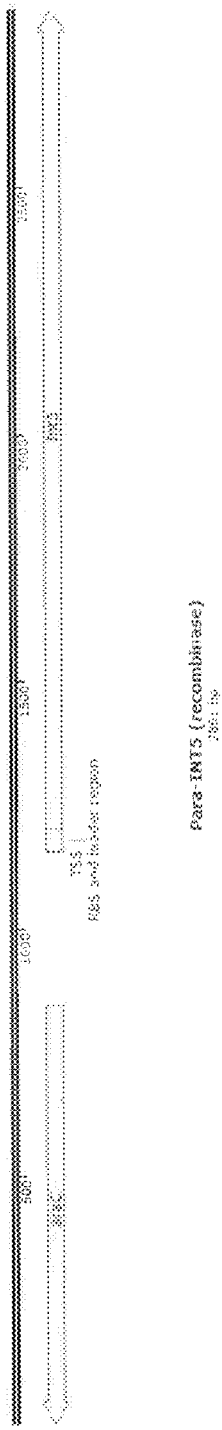
FIGS. 44A, 44B, and 44C depict the gene organization of an exemplary construct in which the Int5 recombinase gene is operably linked to an ParaBAD promoter ($P_{araBAD}$), and the gene encoding T7 RNA polymerase is flanked by recombinase sites and operably linked to a strong constitutive promoter.
Figure 44B:
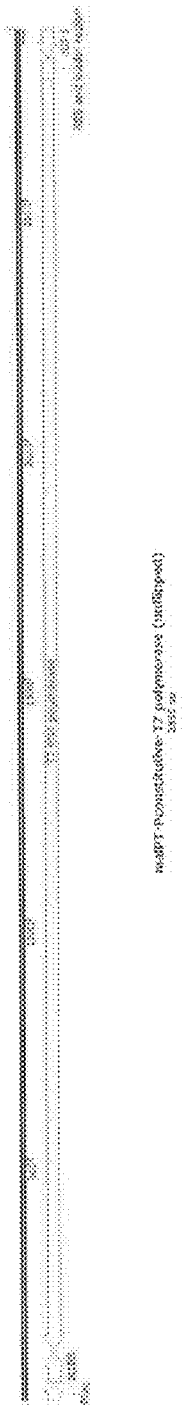
Figure 44C:
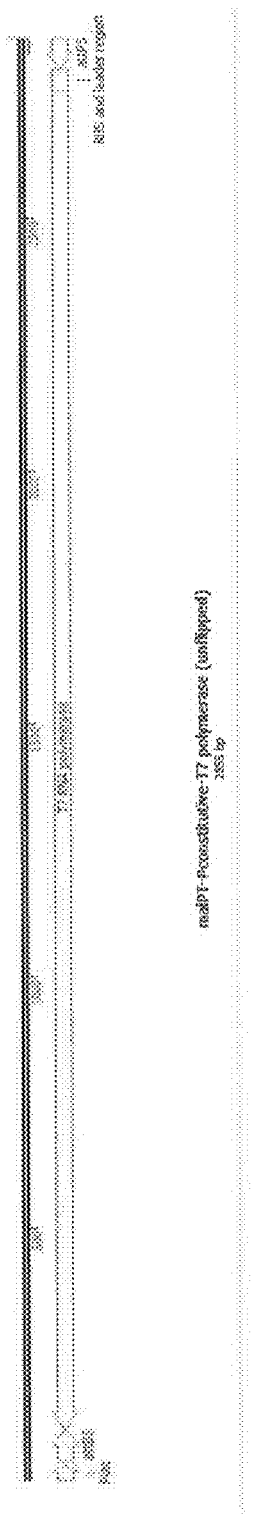
Figure 45B:
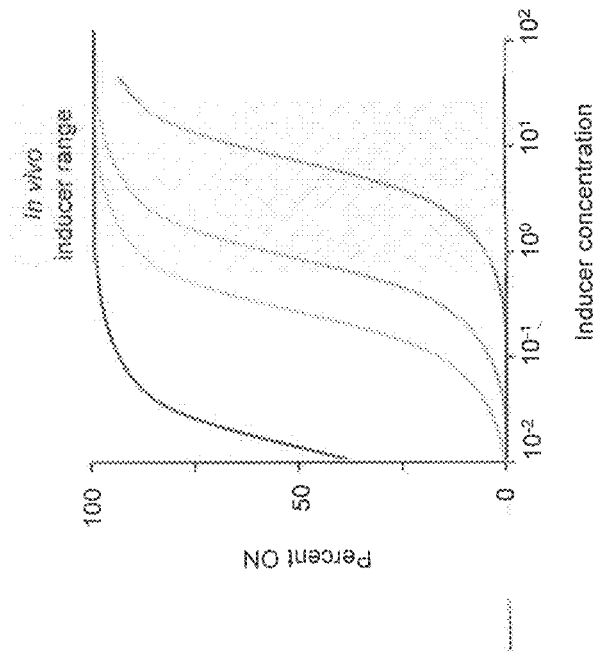
FIG. 45B depicts the relationship between the concentration of an inducer and the percentage of PAL3-containing constructs in the ON orientation. The shaded area shows the predicted efficacy range of the inducer in vivo.
Figure 45A:
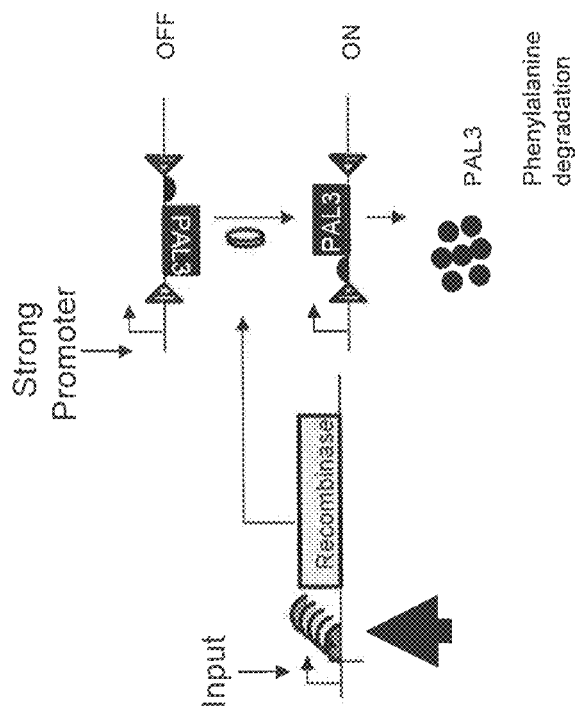
FIG. 45A depicts a schematic of a recombinase-based switch to activate PAL3 expression using different inducible promoters and ribosome binding sites. Recombinase expression causes recombinatorial flipping of the PAL3 gene to the ON orientation, leading to the production of PAL3 and to the degradation of phenylalanine. In some embodiments, recombinase-based switches are tuned to respond to specific levels of an inducer.
Figure 46A:
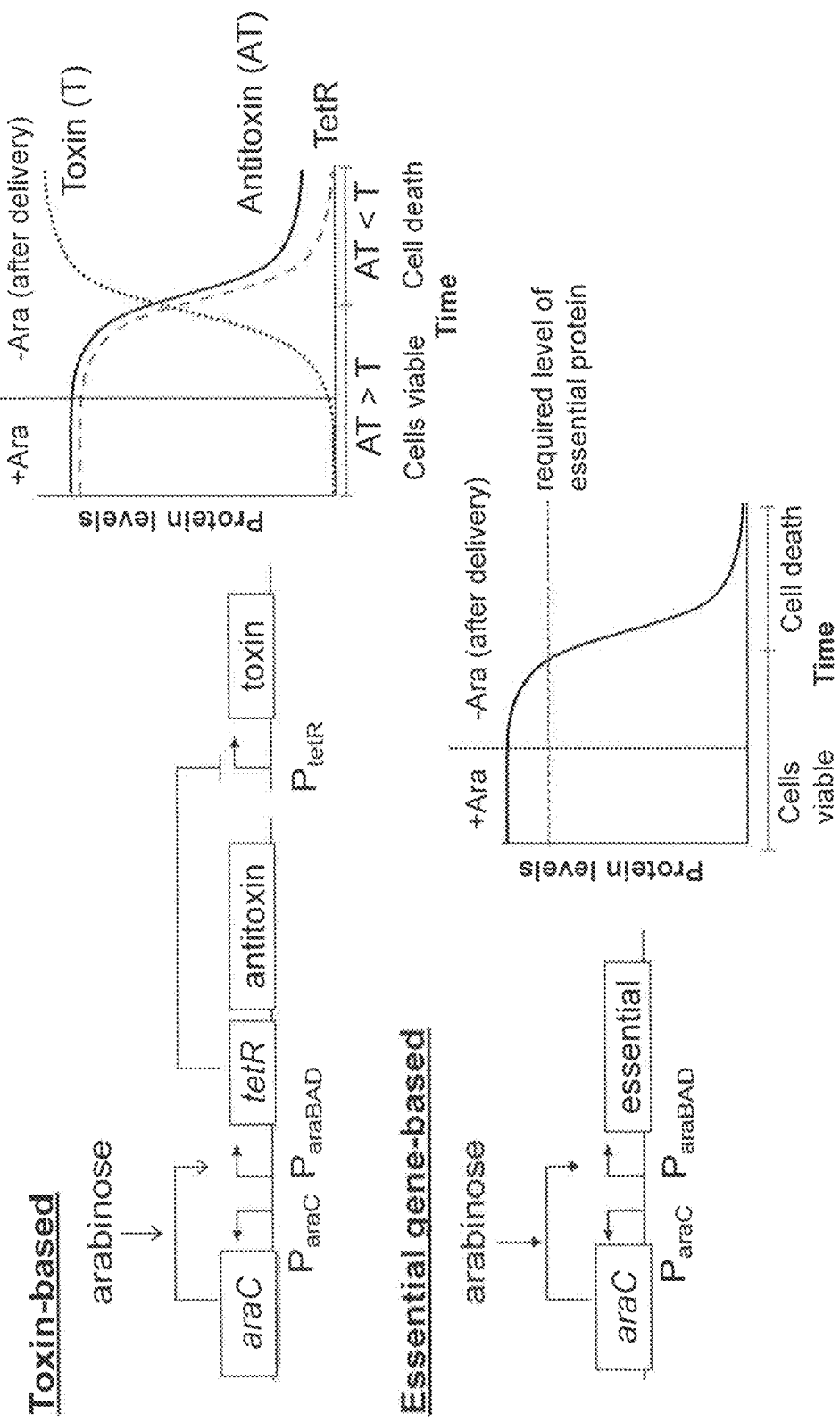
FIG. 46A depicts another non-limiting embodiment of the disclosure, wherein the expression of a heterologous gene is activated by an exogenous environmental signal. In the absence of arabinose, the AraC transcription factor adopts a conformation that represses transcription. In the presence of arabinose, the AraC transcription factor undergoes a conformational change that allows it to bind to and activate the ParaBAD promoter ($P_{araBAD}$), which induces expression of the Tet repressor (TetR) and an anti-toxin. The anti-toxin builds up in the recombinant bacterial cell, while TetR prevents expression of a toxin (which is under the control of a promoter having a TetR binding site). However, when arabinose is not present, both the anti-toxin and TetR are not expressed. Since TetR is not present to repress expression of the toxin, the toxin is expressed and kills the cell.
Figure 46B:
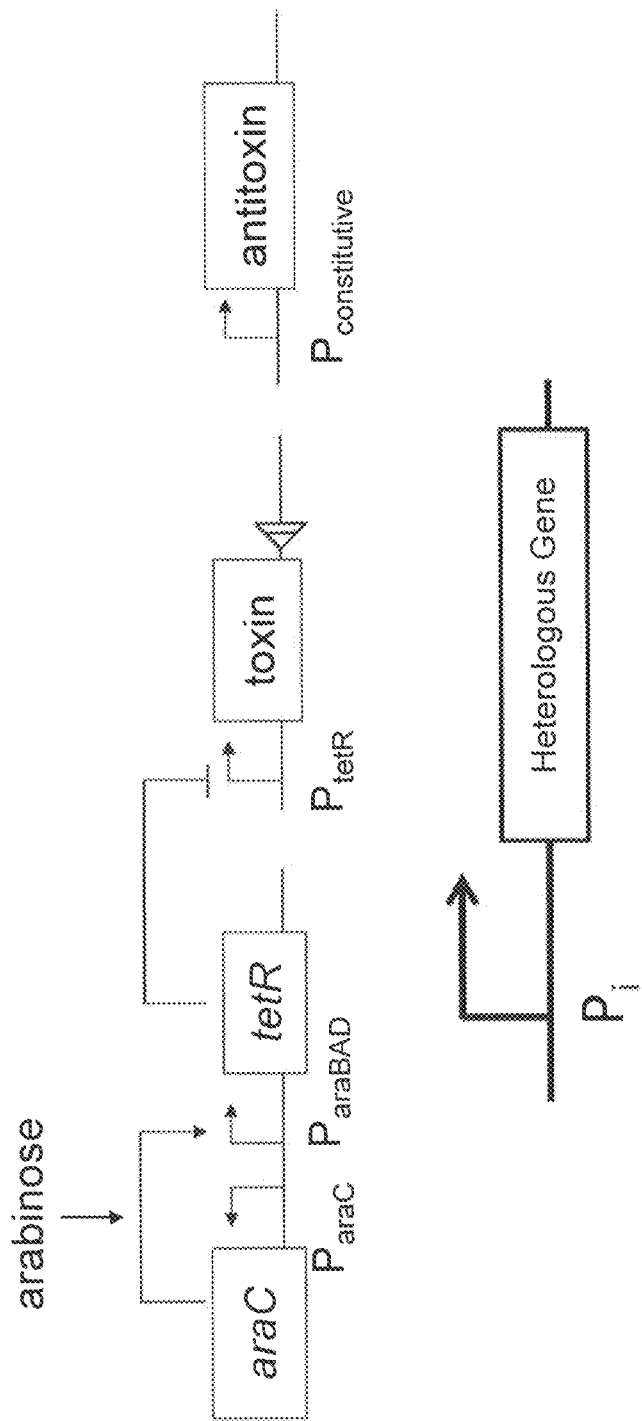
FIG. 46B depicts a non-limiting embodiment of the disclosure, where an anti-toxin is expressed from a constitutive promoter, and expression of a heterologous gene is activated by an exogenous environmental signal. In the absence of arabinose, the AraC transcription factor adopts a conformation that represses transcription. In the presence of arabinose, the AraC transcription factor undergoes a conformational change that allows it to bind to and activate the araBAD promoter, which induces expression of TetR, thus preventing expression of a toxin. However, when arabinose is not present, TetR is not expressed, and the toxin is expressed, eventually overcoming the anti-toxin and killing the cell. The constitutive promoter regulating expression of the anti-toxin should be a weaker promoter than the promoter driving expression of the toxin. The araC gene is under the control of a constitutive promoter in this circuit.
Figure 46C:
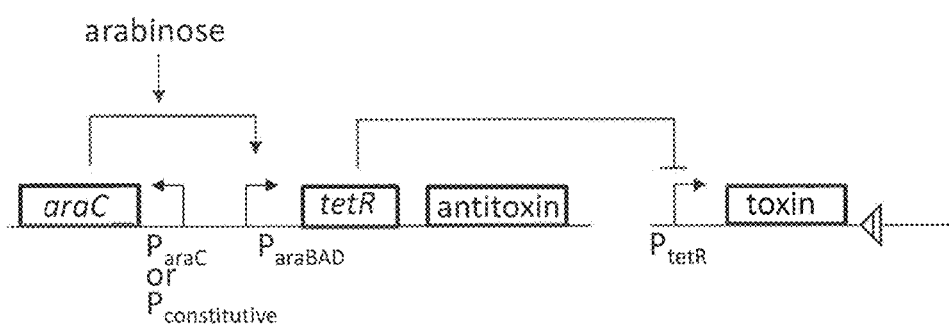
FIG. 46C depicts another non-limiting embodiment of the disclosure, wherein the expression of a heterologous gene is activated by an exogenous environmental signal. In the absence of arabinose, the AraC transcription factor adopts a conformation that represses transcription. In the presence of arabinose, the AraC transcription factor undergoes a conformational change that allows it to bind to and activate the araBAD promoter, which induces expression of the Tet repressor (TetR) and an anti-toxin. The anti-toxin builds up in the recombinant bacterial cell, while TetR prevents expression of a toxin (which is under the control of a promoter having a TetR binding site). However, when arabinose is not present, both the anti-toxin and TetR are not expressed. Since TetR is not present to repress expression of the toxin, the toxin is expressed and kills the cell. The araC gene is either under the control of a constitutive promoter or an inducible promoter (e.g., AraC promoter) in this circuit.
Figure 47:
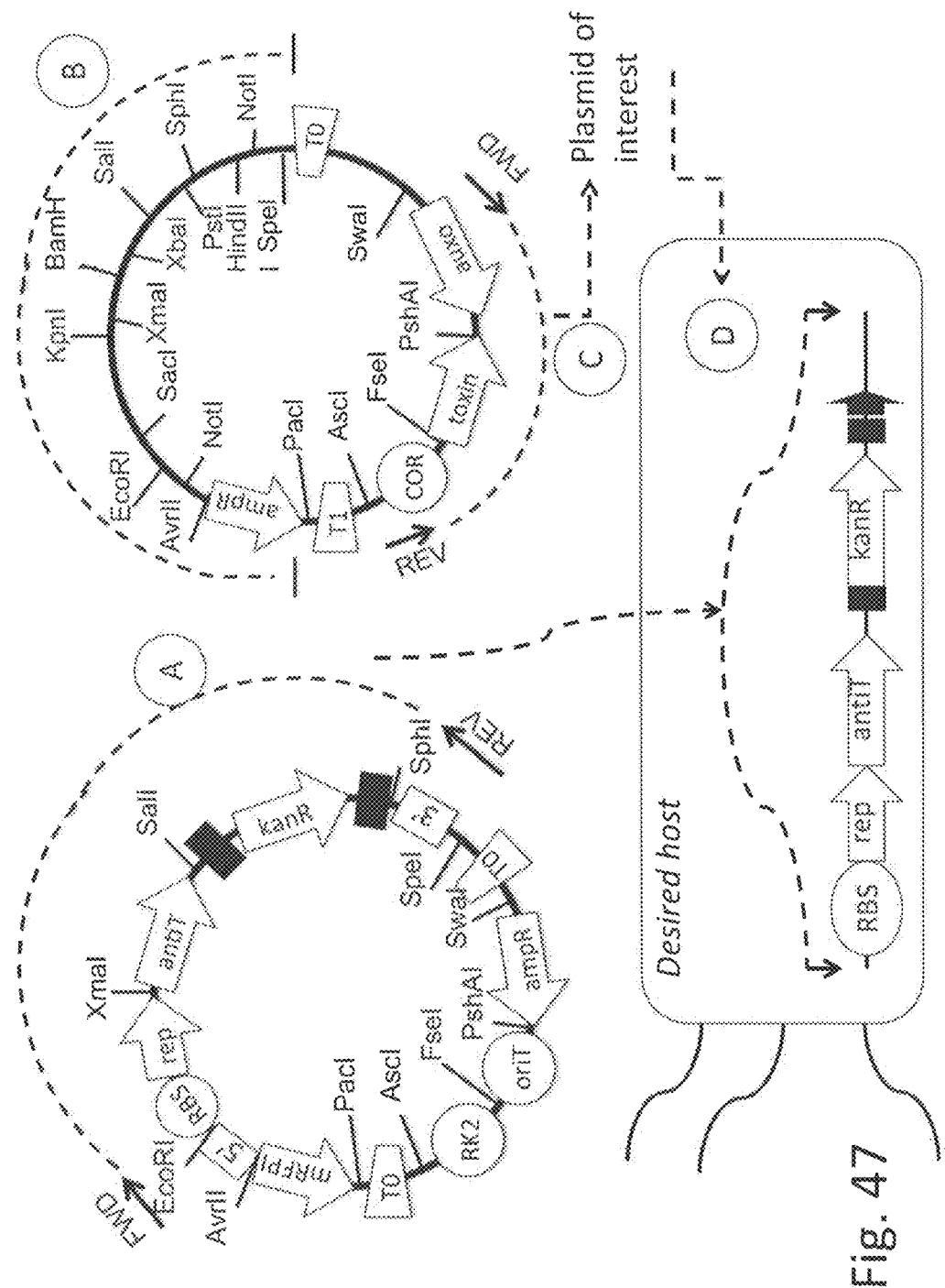
FIG. 47 depicts the use of GeneGuards as an engineered safety component. All engineered DNA is present on a plasmid which can be conditionally destroyed. See, e.g., Wright et al., 2015.
Figure 48A:
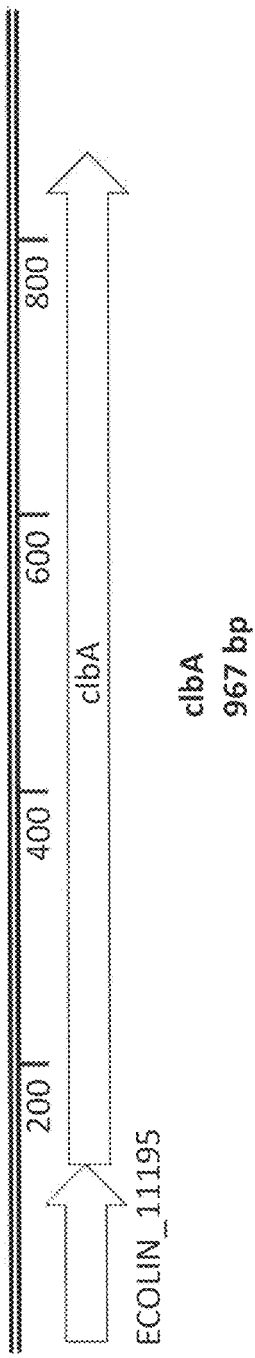
FIG. 48A depicts a schematic diagram of a wild-type clbA construct.
Figure 48B:
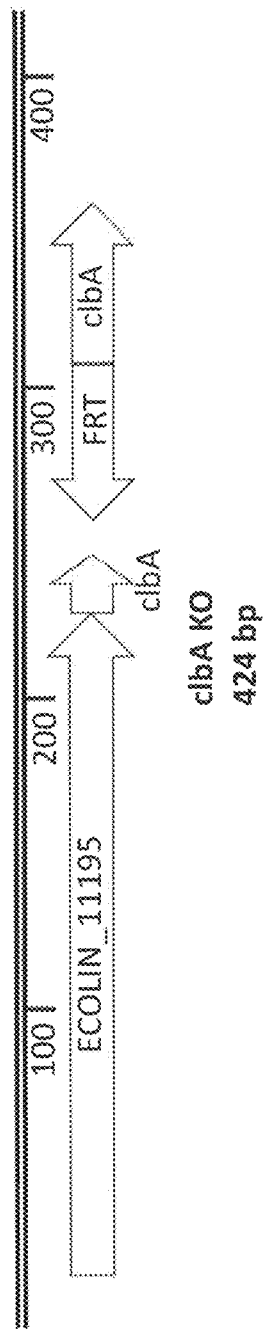
FIG. 48B depicts a schematic diagram of a clbA knockout construct.
Figure 50:
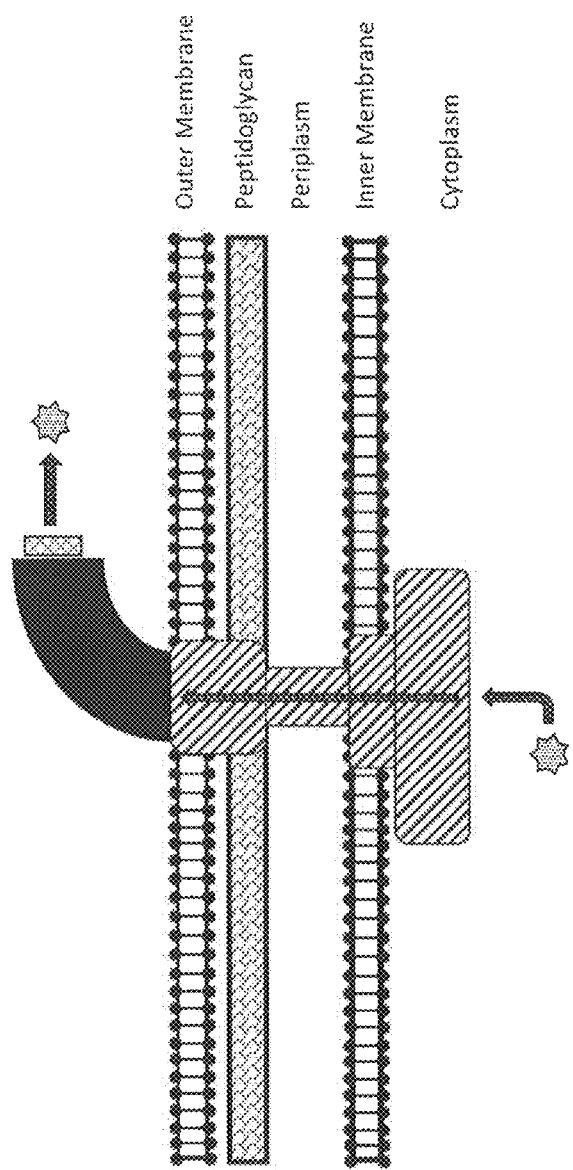
FIG. 50 depicts a schematic of a secretion system based on the flagellar type III secretion in which a modified flagellum is used to secrete a therapeutic peptide of interest by recombinantly fusing the peptide to an N-terminal flagellar secretion signal of a native flagellar component so that the intracellularly expressed chimeric peptide can be mobilized across the inner and outer membranes into the surrounding host environment.
Figure 51:
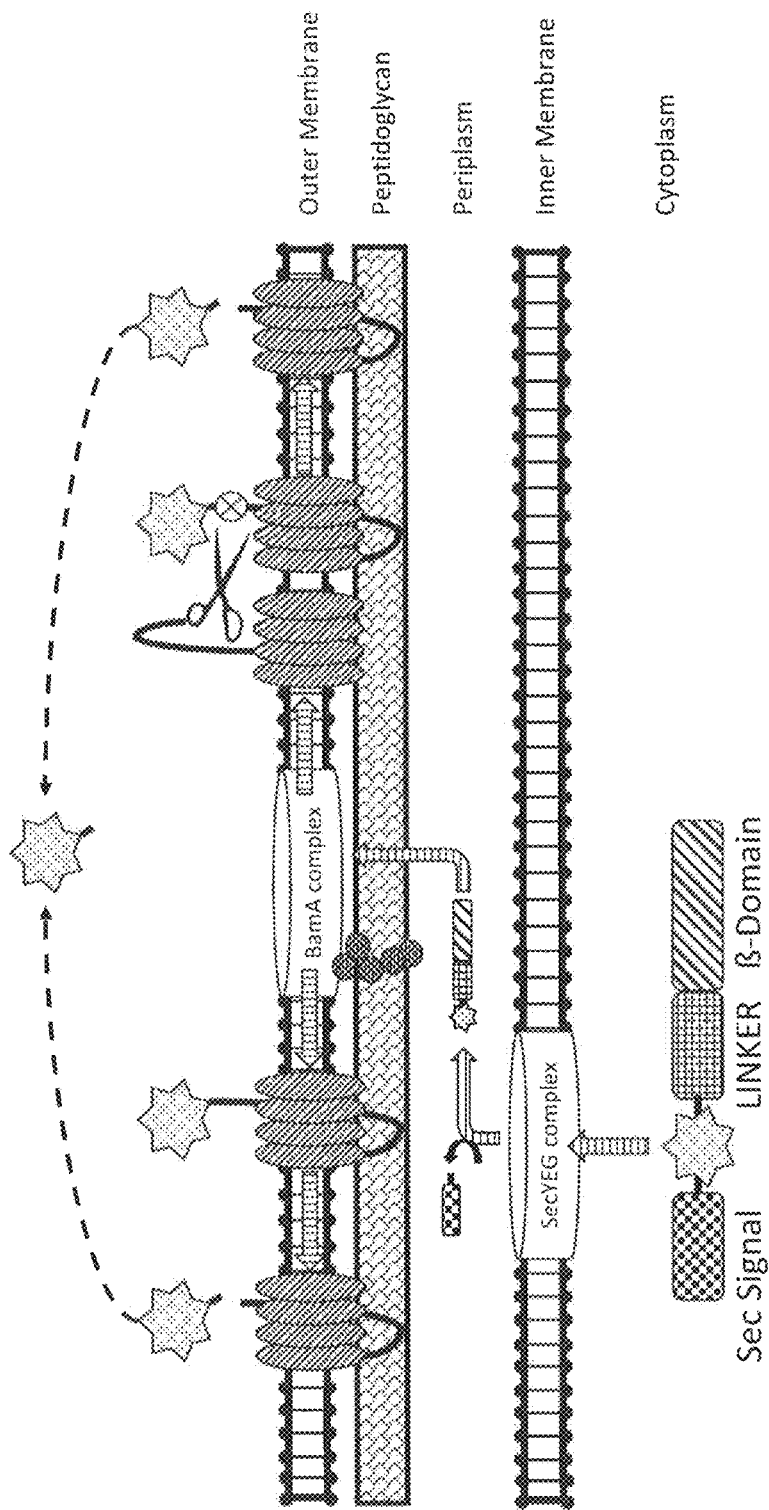
FIG. 51 depicts a schematic of a type V secretion system for the extracellular production of recombinant proteins in which a therapeutic peptide (star) can be fused to an N-terminal secretion signal, a linker and the beta-domain of an auto-secreter. In this system, the N-terminal signal sequence directs the protein to the SecA-YEG machinery, which moves the protein across the inner membrane into the periplasm, followed by subsequent cleavage of the signal sequence. The beta-domain is recruited to the Bam complex where the beta-domain is folded and inserted into the outer membrane as a beta-barrel structure. The therapeutic peptide is then threaded through the hollow pore of the beta-barrel structure ahead of the linker sequence. The therapeutic peptide is freed from the linker system by an autocatalytic cleavage or by targeting of a membrane-associated peptidase (scissors) to a complementary protease cut site in the linker.
Figure 52:
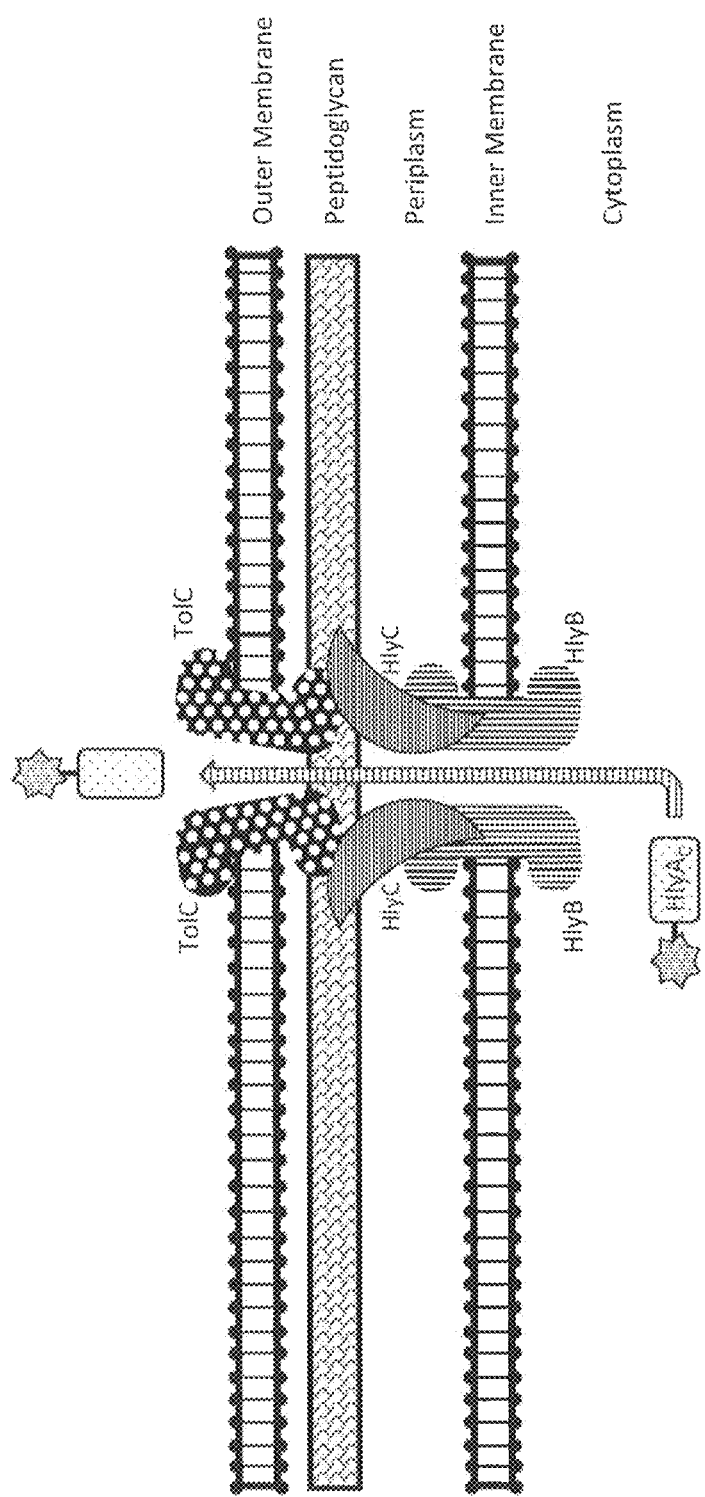
FIG. 52 depicts a schematic of a type I secretion system, which translocates a passenger peptide directly from the cytoplasm to the extracellular space using HlyB (an ATP-binding cassette secreter; HlyD (a membrane fusion protein); and TolC (an outer membrane protein) which form a channel through both the inner and outer membranes. The secretion signal-containing C-terminal portion of HlyA is fused to the C-terminal portion of a therapeutic peptide (star) to mediate secretion of this peptide.
Figure 53:
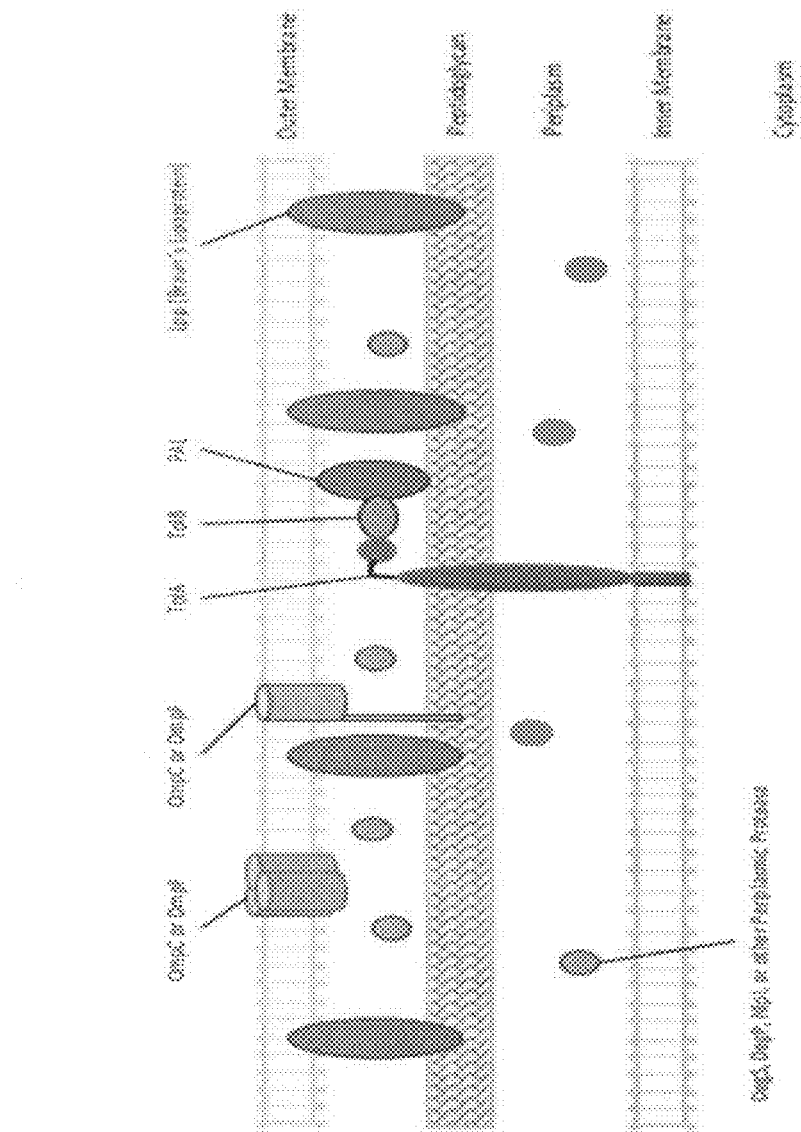
FIG. 53 depicts a schematic of the outer and inner membranes of a gram-negative bacterium, and several deletion targets for generating a leaky or destabilized outer membrane, thereby facilitating the translocation of a therapeutic polypeptides to the extracellular space, e.g., therapeutic polypeptides of eukaryotic origin containing disulphide bonds. Deactivating mutations of one or more genes encoding a protein that tethers the outer membrane to the peptidoglycan skeleton, e.g., lpp, ompC, ompA, ompF, tolA, tolB, pal, and/or one or more genes encoding a periplasmic protease, e.g., degS, degP, nlpl, generates a leaky phenotype. Combinations of mutations may synergistically enhance the leaky phenotype.
Figure 54:
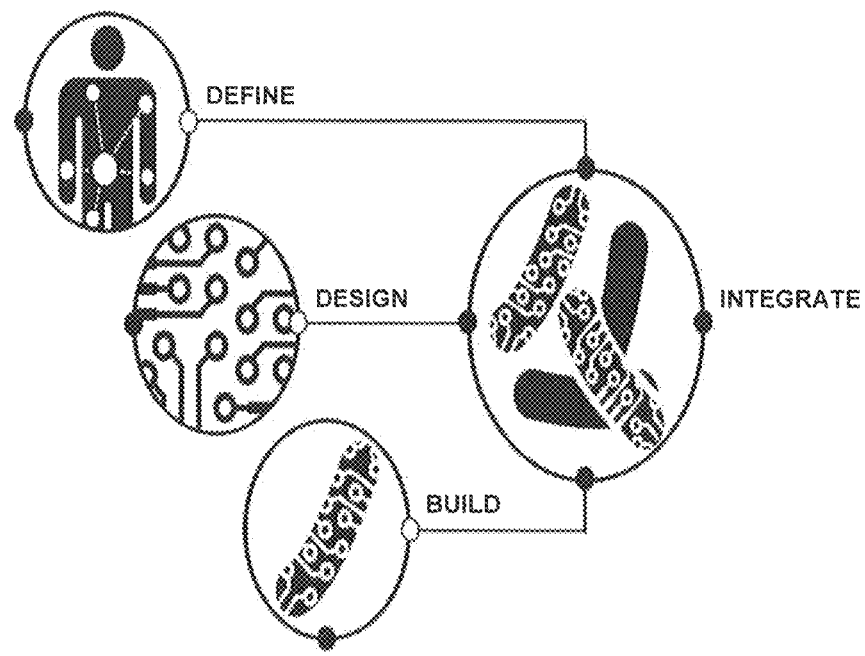
FIG. 54 depicts a schematic of non-limiting processes for designing and producing the genetically engineered bacteria of the present disclosure.
Figure 55:
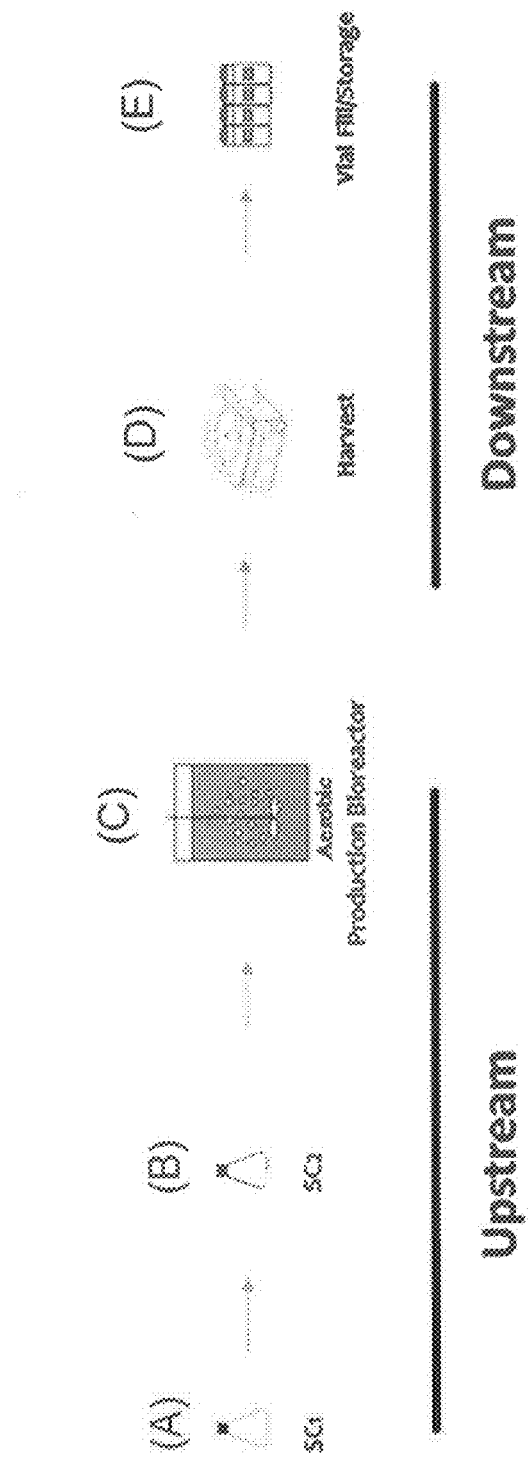
FIG. 55 depicts a schematic of non-limiting manufacturing processes for upstream and downstream production of the genetically engineered bacteria of the present disclosure.

In some embodiments, recombinase-based switches may be used to activate PAL3 expression. The SYN-PKU601 strain (malPT::$P_{fnrS}$-Int5, rrnBUP-PAL3; lacZ::$P_{fnrS}$-pheP) contains the Int5 recombinase operably linked to a $P_{fnrS}$ promoter, as well as a copy of PAL3 under the control of a strong constitutive promoter, integrated at the mal/T locus (FIG. 42). Table 45 shows the sequence of an exemplary $P_{fnrS}$-Int5, rrnBUP-PAL3 construct (SEQ ID NO: 42), wherein $P_{fnrS}$, Int5, and PAL3 are in reverse orientation. The Int5 sequence is bolded, the $P_{fnrS}$ sequence is boxed, the PAL3 sequence is underlined, and recombinase sites are bolded and underlined. Ribosomal binding sites are highlighted, and the rrnBUP constitutive promoter sequence is boxed. The UP element-containing *E. coli* rrnBUP promoter was selected to yield high PAL3 expression (Estrem et al., 1998), although any strong promoter may be used. SYN-PKU601 also contains a copy of pheP integrated at the lacZ locus.

To construct the SYN-PKU601 strain, the $P_{fnrS}$-driven Int5 gene and the rrnBUP-driven, recombinase site-flanked PAL3 gene sequences were synthesized by Genewiz (Cambridge, Mass.). Gibson assembly was used to add 1000 bp sequences of DNA homologous to the Nissle malP and malT loci on either side of the $P_{fnrS}$-Int5, rrnBUP-PAL3 DNA sequence and to clone this sequence between the homology arms. Successful insertion of the fragment into a KIKO plasmid was validated by sequencing. PCR was used to amplify the entire $P_{fnrS}$-Int5, rrnBUP-PAL3 region. This knock-in PCR fragment was used to transform an electrocompetent Nissle strain already containing $P_{fnrS}$-pheP in the lacZ locus, and expressing the lambda red recombinase genes. After transformation, cells were grown for 2 hrs at 37° C. Transformants with successful integration of the $P_{fnrS}$-PAL3 fragment at the malPT intergenic region were selected on kanamycin at 50 pg/mL. This strategy may also be used to construct a recombinase-based strain requiring T7 polymerase activity for PAL3 expression (FIG. 43). [Table 46 shows the sequence of an exemplary $P_{fnrS}$-Int5, rrnBUP-T7 construct (SEQ ID NO: 43), wherein $P_{fnrS}$, Int5, and the T7 polymerase gene are in reverse orientation. The Int5 sequence is bolded, the $P_{fnrS}$ sequence is boxed, the T7 polymerase sequence is underlined, and recombinase sites are bolded and underlined. Ribosomal binding sites are highlighted, and the rrnBUP constitutive promoter sequence is boxed, boxed Table 44 shows the sequence of an exemplary $P_{T7}$-PAL3 construct, with the $P_{T7}$ sequence highlighted, the ribosome binding site underlined, and the PAL3 sequence bolded.

TABLE 44

Nucleotide sequences of FNR promoter-PAL3-pheP construct (SEQ ID NO: 41)

ggtaccAGTTGTTCTTATTGGTGGTGTTGCTTTATGGTTGCATCGTAGTA
AATGGTTGTAACAAAAGCAATTTTTCCGGCTGTCTGTATACAAAAACGCC
GCAAAGTTTGAGCGAAGTCAATAAACTCTCTACCCATTCAGGGCAATATC TCTCTTggatccaaagtgaactctagaaataattttgtttaactttaaga aggagatatacatATGAAAGCTAAAGATGTTCAGCCAACCATTATTATTA

ATAAAAATGGCCTTATCTCTTTGGAAGATATCTATGACATTGCGATAAAA

CAAAAAAAGTAGAAATATCAACGGAGATCACTGAACTTTTGACGCATGG

TCGTGAAAAATTAGAGGAAAAATTAAATTCAGGAGAGGTTATATATGGAA

TCAATACAGGATTTGGAGGGAATGCCAATTTAGTTGTGCCATTTGAGAAA

ATCGCAGAGCATCAGCAAAATCTGTTAACTTTTCTTTCTGCTGGTACTGG

TABLE 44-continued

Nucleotide sequences of FNR promoter-PAL3-pheP construct (SEQ ID NO: 41)

GGACTATATGTCCAAACCTTGTATTAAAGCGTCACAATTTACTATGTTAC

TTTCTGTTTGCAAAGGTTGGTCTGCAACCAGACCAATTGTCGCTCAAGCA

ATTGTTGATCATATTAATCATGACATTGTTCCTCTGGTTCCTCGCTATGG

CTCAGTGGGTGCAAGCGGTGATTTAATTCCTTTATCTTATATTGCACGAG

CATTATGTGGTATCGGCAAAGTTTATTTATATGGGCGCAGAAATTGACGCT

GCTGAAGCAATTAAACGTGCAGGGTTGACACCATTATCGTTAAAAGCCAA

AGAAGGTCTTGCTCTGATTAACGGCACCCGGGTAATGTCAGGAATCAGTG

ATTGCCCTTGCTGTTGAAGCATTACTTGCATCTCATGAACATTATGATGC

CCGGATTCAACAAGTAAAAAATCATCCTGGTCAAAACGCGGTGGCAAGTG

CATTGCGTAATTTATTGGCAGGTTCAACGCAGGTTAATCTATTATCTGGG

GTTAAAGAACAAGCCAATAAAGCTTGTCGTCATCAAGAAATTACCCAACT

AAATGATACCTTACAGGAAGTTTATTCAATTCGCTGTGCACCACAAGTAT

TAGGTATAGTGCCAGAATCTTTAGCTACCGCTCGGAAAATATTGGAACGG

GAAGTTATCTCAGCTAATGATAATCCATTGATAGATCCAGAAAATGGCGA

TGTTCTACACGGTGGAAATTTTATGGGGCAATATGTCGCCCGAACAATGG

ATGCATTAAAACTGGATATTGCTTTAATTGCCAATCATCTTCACGCCATT

GTGGCTCTTATGATGGATAACCGTTTCTCTCGTGGATTACCTAATTCACT

GAGTCCGACACCCGGCATGTATCAAGGTTTTAAAGGCGTCCAACTTTCTC

AAACCGCTTTAGTTGCTGCAATTCGCCATGATTGTGCTGCATCAGGTATT

CATACCCTCGCCACAGAACAATACAATCAAGATATTGTCAGTTTAGGTCT

GCATGCCGCTCAAGATGTTTTAGAGATGGAGCAGAAATTACGCAATATTG

TTTCAATGACAATTCTGGTAGTTTGTCAGGCCATTCATCTTCGCGGCAAT

ATTAGTGAAATTGCGCCTGAAACTGCTAAATTTTACCATGCAGTACGCGA

AATCAGTTCTCCTTTGATCACTGATCGTGCGTTGGATGAAGATATAATCC

GCATTGCGGATGCAATTATTAATGATCAACTTCCTCTGCCAGAAATCATG

CTGGAAGAATAAaggaaggagatatacatgAAAAACGCGTCAACCGTA

TCGGAAGATACTGCGTCGAATCAAGAGCCGACGCTTCATCGCGGATTACA
TAACCGTCATATTCAACTGATTGCGTTGGGTGGCGCAATTGGTACTGGTC
TGTTTCTTGGCATTGGCCCGGCGATTCAGATGGCGGGTCCGGCTGTATTG

TABLE 44-continued

Nucleotide sequences of FNR promoter-PAL3-pheP construct (SEQ ID NO: 41)

CTGGGCTACGGCGTCGCCGGGATCATCGCTTTCCTGATTATGCGCCAGCT
TGGCGAAATGGTGGTTGAGGAGCCGGTATCCGGTTCATTTGCCCACTTTG
CCTATAAATACTGGGGACCGTTTGCGGGCTTCCTCTCTGGCTGGAACTAC
TGGGTAATGTTCGTGCTGGTGGGAATGGCAGAGCTGACCGCTGCGGGCAT
CTATATGCAGTACTGGTTCCCGGATGTTCCAACGTGGATTTGGGCTGCCG
CCTTCTTTATTATCATCAACGCCGTTAACCTGGTGAACGTGCGCTTATAT
GGCGAAACCGAGTTCTGGTTTGCGTTGATTAAAGTGCTGGCAATCATCGG
TATGATCGGCTTTGGCCTGTGGCTGCTGTTTTCTGGTCACGGCGGCGAGA
AAGCCAGTATCGACAACCTCTGGCGCTACGGTGGTTTCTTCGCCACCGGC
TGGAATGGGCTGATTTTGTCGCTGGCGGTAATTATGTTCTCCTTCGGCGG
TCTGGAGCTGATTGGGATTACTGCCGCTGAAGCGCGCGATCCGGAAAAAA
GCATTCCAAAAGCGGTAAATCAGGTGGTGTATCGCATCCTGCTGTTTTAC
ATCGGTTCACTGGTGGTTTTACTGGCGCTCTATCCGTGGGTGGAAGTGAA
ATCCAACAGTAGCCCGTTTGTGATGATTTTCCATAATCTCGACAGCAACG
TGGTAGCTTCTGCGCTGAACTTCGTCATTCTGGTAGCATCGCTGTCAGTG
TATAACAGCGGGGTTTACTCTAACAGCCGCATGCTGTTTTGGCCTTTCTGT
GCAGGGTAATGCGCCGAAGTTTTTGACTCGCGTCAGCCGTCGCGGTGTGC
CGATTAACTCGCTGATGCTTTCCGGAGCGATCACTTCGCTGGTGGTGTTA
ATCAACTATCTGCTGCCGCAAAAAGCGTTTGGTCTGCTGATGGCGCTGGT
GGTAGCAACGCTGCTGTTGAACTGGATTATGATCTGTCTGGCGCATCTGC
GTTTTCGTGCAGCGATGCGACGTCAGGGGCGTGAAACACAGTTTAAGGCG
CTGCTCTATCCGTTCGGCAACTATCTCTGCATTGCCTTCCTCGGCATGAT
TTTGCTGCTGATGTGCACGATGGATGATATGCGCTTGTCAGCGATCCTGC
TGCCGGTGTGGATTGTATTCCTGTTTATGGCATTTAAAACGCTGCGTCGG
AAAtaa

TABLE 45

Nucleotide sequences of FNR promoter-Int5, rrnBUP-PAL3 construct (SEQ ID NO: 42)

ttaggtacgggctgcccatttgattttaacgcgttcatcaccatcaaacg
gacgaccacgctggcttttgcaacccaaatttcatcgatgcaggtatca
ataattgcattacgcatggtcggggttgcacgcagccacagttcttcata
atcgctgctatcaacaatccagctaacatcaactgctgcgcttgcgctgc
tttcgctaactgcatctttggctgcctgcagggtgctcagtgcttcttga
tatgcaggggcaaaaaactgttctgccggaccatcataaacaccattctg
acgatcacgcagcaggcgacccagatttttttcggcttcacgaactgcgg
cttttgcatactttttcatcttcgcttgcctgcggatgggtcagtgctgcc
cagcgatctgcaactgcaataacaaacggatcatccggttcgcttgctgc
taattttgctgcccaacgaaatgcaacatattcttcaacgcttttacgtg
caacataggtcggtgccggacaacccacccttttcacactgctacgccaacaa
cgataaccattaccgctatagctacagctaccaccacaacccggacaacg
catacgaccgctcagcagatgtttgcgacgggtatcatgatcgctaccat
ccagcggaacaccaacaccatcttcacctttaacggctgcttttgcggct
tcttgttcttcatcggtcaccagcggaggaccatgcataacgctaacacg
tttaccttcaccgttataaaaggtcagacgacgctgtttaccatcctgac
gacctgtggctgccaaacccgcatatgccggattctgaatcatatcacgc
acggtaactgcaatccacggaccaccggtcgggctcggaatttcacgggt
attcattgcatgtgcggtgcctgcatagctcagacgatcggtaaccggca
gggtaaaaaccagacgggctgcttctgctttggtcagaccatcaggacca
cccgcatcttcatcatctgctgccagtttacgttcatcatattcatcacc
ctcttcatcactaacggtaaccagaacaacacgcagaccatacggtgcac
gggcattaaccattcaccattttcacgctgatgtgctttggtatcacga
acacgttcgctcagttttttctgcttcttcgcgtgcttcttctgcacgacg
aatcagttcaccgcgatcacgtttattggtgctatccagaaccggacgac
cggtatcttcatcccaaccaaacagcagacgacgaggcataccatcttcc
ggttcgataattttcagaattgcaccggcaccaccacgatcccaacgatc
cagacgataacaccacagtgcaccaacttcaccgctttccagggcttca
gtgctttgctctgatcatcacgtgcttttacctttacgaaaacggcttgcg
ctaccaacttctttccaaacatgacgaacctgcatacccagcagtgctgc
aactttacgacccagggtttcttgtgctgcaatgctaatttcttgtttac
gacgctgacctgcacccatttgcacggcttttaactgctttgcttttacga
caaaacaggtcaatcagacctgcaggatccggaccggtttcggtggtcat
accaggcat atgtatatctccttcttaaagttaaacaaaattattctag
agttcactttggatcc AAGAGAGATATTGCCCTGAATGGGTAGAGAGTTT
ATTGACTTCGCTCAAACTTTTGCGGCGTTTTGTATACAGACAGCCGGAAA

TABLE 45-continued

Nucleotide sequences of FNR promoter-Int5, rrnBUP-PAL3 construct (SEQ ID NO: 42)

AATTGCTTTTGTTACAACCATTTACTACGATGCAACCATAAAGCAACACC

ACCAATAAGAACAACTggtacc GGATATTCATATGGACCATGGCAGCTAG

CCCTGCAGGGTGCAC TCAGAAAATTATTTTAAATTTCCTCTTGTCAGGCC
GGAATAACTCCCTATAATGCGCCACCAC gagcgccggatcagggagtgga
cggcctgggagcgctacacgctgtggctgcggtcggtgcTTATTCTTCCA
GCATGATTTCTGGCAGAGGAAGTTGATCATTAATAATTGCATCCGCAATG
CGGATTATATCTTCATCCAACGCACGATCAGTGATCAAAGGAGAACTGAT
TTCGCGTACTGCATGGTAAAATTTAGCAGTTTCAGGCGCAATTTCACTAA
TATTGCCGCGAAGATGATGGCCTGACAAACTACCAGAATTGTCATTGAAA
CAATATTGCGTAATTTCTGCTCCATCTCTAAAACATCTTGAGCGGCATGC
AGACCTAAACTGACAATATCTTGATTGTATTGTTCTGTGGCGAGGGTATG
AATACCTGATGCAGCACAATCATGGCGAATTGCAGCAACTAAAGCGGTTT
GAGAAAGTTGGACGCCTTTAAAACCTTGATACATGCCGGGTGTCGGACTC
AGTGAATTAGGTAATCCACGAGAGAAACGGTTATCCATCATAAGAGCCAC
AATGGCGTGAAGATGATTGGCAATTAAAGCAATATCCAGTTTTAATGCAT
CCATTGTTCGGGCGACATATTGCCCCATAAAATTTCCACCGTGTAGAACA
TCGCCATTTTCTGGATCTATCAATGGATTATCATTAGCTGAGATAACTTC
CCGTTCCAATATTTTCCGAGCGGTAGCTAAAGATTCTGGCACTATACCTA
ATACTTGTGGTGCACAGCGAATTGAATAAACTTCCTGTAAGGTATCATTT
AGTTGGGTAATTTCTTGATGACGACAAGCTTTATTGGCTTGTTCTTTAAC
CCCAGATAATAGATTAACCTGCGTTGAACCTGCCAATAAATTACGCAATG
CACTTGCCACCGCGTTTTGACCAGGATGATTTTTTACTTGTTGAATCCGG
GCATCATAATGTTCATGAGATGCAAGTAATGCTTCAACAGCAAGGGCAAT
CGCAGAAATTGAGGCTTTAAATAGTTTTTCCAGTTTAATGACGGTGATTG
CACTGATTCCTGACATTACCCGGGTGCCGTTAATCAGAGCAAGACCTTCT
TTGGCTTTTAACGATAATGGTGTCAACCCTGCACGTTTAATTGCTTCAGC
AGCGTCAATTTCTGCGCCCATATAATAAACTTTGCCGATACCACATAATG
CTCGTGCAATATAAGATAAAGGAATTAAATCACCGCTTGCACCCACTGAG
CCATAGCGAGGAACCAGAGGAACAATGTCATGATTAATATGATCAACAAT
TGCTTGAGCGACAATTGGTCTGGTTGCAGACCAACCTTTGCAAACAGAAA
GTAACATAGTAAATTTGTGACGTTTAATACAAGGTTTGGACATATAGTCC
CCAGTACCAGCAGAAAGAAAGTTAACAGATTTTGCTGATGCTCTGCGAT
TTTCTCAAATGGCACAACTAAATTGGCATTCCCTCCAAATCCTGTATTGA
TTCCATATATAACCTCTCCTGAATTTAATTTTTCCTCTAATTTTTCACGA
CCATGCGTCAAAAGTTCAGTGATCTCCGTTGATATTCTACTTTTTTTTG
TTTTATCGCAATGTCATAGATATCTTCCAAAGAGATAAGGCCATTTTTAT TAATAATAATGGTTGGCTGAACATCTTTAGCTTTCAT atgtatatctcct
tcttaaagttaaacaaaattattctagag cagatcagggtgcgcaagtt gtcaacgctcccaggagagttatcgacttgcgtattaggg

TABLE 46

Nucleotide sequences of FNR promoter-Int5, rrnBUP-T7 construct (SEQ ID NO: 43)

ttaggtacgggctgcccatttgattttaacgcgttcatcaccatcaaacg
gacgaccacgctggcttttgcaacccaaatttcatcgatgcaggtatca
ataattgcattacgcatggtcggggttgcacgcagccacagttcttcata
atcgctgctatcaacaatccagctaacatcaactgctgcgcttgcgctgc
tttcgctaactgcatctttggctgcctgcagggtgctcagtgcttcttga
tatgcaggggcaaaaaactgttctgccggaccatcataaacaccattctg
acgatcacgcagcaggcgacccagatttttttcggcttcacgaactgcgg
cttttgcatactttttcatcttcgcttgcctgcggatgggtcagtgctgcc
cagcgatctgcaactgcaataacaaacggatcatccggttcgcttgctgc
taattttgctgcccaacgaaatgcaacatattcttcaacgcttttacgtg
caacataggtcggtgccggacaacccacccttcacactgctacgccaacaa
cgataaccattaccgctatagctacagctaccaccacaacccggacaacg
catacgaccgctcagcagatgtttgcgacgggtatcatgatcgctaccat
ccagcggaacaccaacaccatcttcacctttaacggctgcttttgcggct
tcttgttcttcatcggtcaccagcggaggaccatgcataacgctaacacg
tttaccttcaccgttataaaaggtcagacgacgctgtttaccatcctgac
gacctgtggctgccaaacccgcatatgccggattctgaatcatatcacgc
acggtaactgcaatccacggaccaccggtcgggctcggaatttcacgggt
attcattgcatgtgcggtgcctgcatagctcagacgatcggtaaccggca
gggtaaaaaccagacgggctgcttctgctttggtcagaccatcaggacca
cccgcatcttcatcatctgctgccagtttacgttcatcatattcatcacc TABLE 46-continued Nucleotide sequences of FNR promoter-Int5,
rrnBUP-T7 construct (SEQ ID NO: 43)

ctcttcatcactaacggtaaccagaacaacacgcagaccatacggtgcac
gggcattaacccattcaccattttcacgctgatgtgctttggtatcacga
acacgttcgctcagtttttctgcttcttcgcgtgcttcttctgcacgacg
aatcagttcaccgcgatcacgtttattggtgctatccagaaccggacgac
cggtatcttcatcccaaccaaacagcagacgacgaggcataccatcttcc
ggttcgataattttcagaattgcaccggcaccaccacgatcccaacgatc
cagacgataacaccacagtgcaccaacttcaccgctttccagggctttca
gtgctttgctctgatcatcacgtgctttacctttacgaaaacggcttgcg
ctaccaacttctttccaaacatgacgaacctgcatacccagcagtgctgc
aactttacgacccagggtttcttgtgctgcaatgctaattctttgtttac
gacgctgacctgcaccatttgcacggcttttaactgctttgcttttacga
caaaacaggtcaatcagacctgcaggatccggaccggtttcggtggtcat accaggcat <span style="background-color:lightgray">atgtatatctccttcttaaagttaaacaaaattatttctag</span>

<span style="background-color:lightgray">agttcactttggatcg</span> AAGAGAGATATTGCCCTGAATGGGTAGAGAGTTT

ATTGACTTCGCTCAAACTTTGCGGCGTTTTTGTATACAGACAGCCGGAAA

ACCAATAAGAACAACT ggtacc GGATATTCATATGGACCATGGCAGCTAG

CCCTGCAGGGTGCAC TCAGAAAATTATTTTAAATTTCCTCTTGTCAGGCC
GGAATAACTCCCTATAATGCGCCACCAC gagcgccggatcagggagtgg
acggcctgggagcgctacacgctgtggctgcggtcggtgcttacgcgaac
gcgaagtccgactctaagatgtcacggaggttcaagttaccttttagccgg
aagtgctggcatttttgtccaattgagactcgtgcaactggtcagcgaact
ggtcgtagaaatcagccagtacatcacaagactcatatgtgtcaaccata
gtttcgcgcactgctttgaacaggttcgcagcgtcagccggaatggtacc
gaaggagtcgtgaatcagtgcaaaagattcgattccgtacttctcgtgtg
cccacactacagtcttacgaaggtggctaccgtcttggctgtgtacaaag
ttaggagcgataccagactcctgtttgtgtgcatcaatctcgctatcttt
gttggtgttaatggtaggctgtaagcggaactgaccgaggaacatcaggt
tcaagccgctctgaataggcttcttgtattcctgccacacagggaaacca
tcaggagttacccaatgcaacgcaacgcttgcgaagaatctctccagt
cttcttatctttgacctcagcagcagcagcttagcagcagacttaagcc
agttcattgcttcaaccgcagctaccaccgtcacgctcacagattcccaa
atcagcttagccatgtatccagcagcctgattcggctgagtgaacatcag
acccttgccggaatcaatagctggctgaatggtatcttccagcacttgtt
gacggaagccgaactctttggacccgtaagccagcgtcatgactgaacgt
ttagtcacactgcgagtaacaccgtaagccagccattgaccagcagtgc
cttagtgcccagcttgactttctcagagatttcaccagtgttctcatcgg
tcacggtaactacttcgttatcggtcccattgattgcgtctgcttgtaga
atctcgttgactttcttagcaacaatcccgtagatgtcctgaacggtttc
actaggaagcaagttaaccgcgcgaccaccaccaccctcatctcggagcatcg
cggagaagtgctggatgccgaggcaagacccgtcaaacgccagcggaagg
gagcagttatagctcaggccgtggtgctgtaccccagcgtactcaaagca
gaacgcaaggaagcagaacggagaatcttgctcagcccaccaagtgttct
ccagtggagacttagcgcaagccatgatgttctcgtggttttcctcaatg
aacttgatgcgctcagggaacggaaccttatcgacacccgcacagtttgc
accgtggattttcagccagtagtaaccttccttaccgattggtttacctt
tcgccagcgtaagcagtccttttggtcatatcgttaccttgcgggttgaac
attgacacagcgtaaacacgaccgcgccagtccatgttgtaaggggaacca
gatggccttatggttagcaaacttattggcttgctcaagcatgaactcaa
ggctgatacggcgagcttgcgagcctgtccttgcggtacacagcagg
gcagcacgtttccacgcggtgagagcctcaggattcatgtcgatgtcttc
cggtttcatcgggagttcttcacgctcaatcgcagggatgtcctcgaccg
gacaatgcttccacttggtgattacgttggcgaccgctaggacttcttg
ttgattttccatgcggtgttttgcgcaatgttaatcgcttttgtacacctc
aggcatgtaaacgtcttcgtgacgcatcagtgctttcttactgtgagtac
gcaccagcgccagaggacgacgaccgtagcccaatagccaccaccagta
atgccagtccacggcttaggaggaactacgcaaggttggaacatcggaga
gatgccagccagcgcacctgcaggtgctgcgatagcctcagcgtattcag
gtgcgagttcgatagtctcagagtcttgacctactacgccagcattttgg
cggtgtaagctaaccattccggttgactcaatgagcatctcgatgcagcg
tactcctacatgaatagagtcttccttatgccacgaagaccacgcctcgc
caccgagtagaccttagagagcatgtcagcctcgacaacttgcataaat
gctttcttgtagacgtgccctacgcgcttgttgagttgttcctcaacgtt
tttcttgaagtgcttagcttcaaggtcacggatacgaccgaagcgagcct
cgtcctcaatgccgaccgattgcgcttgctacgacctgaacggttgta
ttgtcagcactggttaggcaagccagagtggtcttaatggtgatgtacgc
tacggcttccggcttgatttcttgcaggaactggaaggctgtcgggcgct
tgccgcgcttagctttcacttcctcaaaccagtcgttgatgcgtgcaatc
atcttagggagtagggtagtgatgagagggcttggcggcagcgttatccgc TABLE 46-continued Nucleotide sequences of FNR promoter-Int5,
rrnBUP-T7 construct (SEQ ID NO: 43)

aacctcaccagctttaagttgacgctcaaacatcttgcggaagcgtgctt cacccatctcgtaagactcatgctcaagggccaactgttcgcgagctaaa cgctcaccgtaatggtcagccagagtgttgaacgggatagcagccagttc gatgtcagagaagtcgttcttagcgatgttaatcgtgttcat <span style="background-color:lightgray">atgtatat</span>

<span style="background-color:lightgray">ctccttcttaaagttaaacaaaattattctagag</span>cagatcagggtgcgca agttgtcaacgctcccaggagagttatcgacttgcgtattaggg

TABLE 47

Nucleotide sequences of T7 promoter-PAL3 construct
(SEQ ID NO: 44)

<span style="background-color:lightgray">taatacgactcactatagggag</span>aaagtgaactctagaaataattttgttt aactttaagaaggagatatacatATGAAAGCTAAAGATGTTCAGCCAACC
ATTATTATTAATAAAAATGGCCTTATCTCTTTGGAAGATATCTATGACAT
TGCGATAAAACAAAAAAAAGTAGAAATATCAACGGAGATCACTGAACTTT
TGACGCATGGTCGTGAAAAATTAGAGGAAAAATTAAATTCAGGAGAGGTT
ATATATGGAATCAATACAGGATTTGGAGGGAATGCCAATTTAGTTGTGCC
ATTTGAGAAAATCGCAGAGCATCAGCAAAATCTGTTAACTTTTCTTTCTG
CTGGTACTGGGGACTATATGTCCAAACCTTGTATTAAAGCGTCACAATTT
ACTATGTTACTTTCTGTTTGCAAAGGTTGGTCTGCAACCAGACCAATTGT
CGCTCAAGCAATTGTTGATCATATTAATCATGACATTGTTCCTCTGGTTC
CTCGCTATGGCTCAGTGGGTGCAAGCGGTGATTTAATTCCTTTATCTTAT
ATTGCACGAGCATTATGTGGTATCGGCAAAGTTTATTATATGGGCGCAGA
AATTGACGCTGCTGAAGCAATTAAACGTGCAGGGTTGACACCATTATCGT
TAAAAGCCAAAGAAGGTCTTGCTCTGATTAACGGCACCCGGGTAATGTCA
GGAATCAGTGCAATCACCGTCATTAAACTGGAAAAACTATTTAAAGCCTC
AATTTCTGCGATTGCCCTTGCTGTTGAAGCATTACTTGCATCTCATGAAC
ATTATGATGCCCGGATTCAACAAGTAAAAAATCATCCTGGTCAAAACGCG
GTGGCAAGTGCATTGCGTAATTTATTGGCAGGTTCAACGCAGGTTAATCT
ATTATCTGGGGTTAAAGAACAAGCCAATAAAGCTTGTCGTCATCAAGAAA
TTACCCAACTAAATGATACCTTACAGGAAGTTTATTCAATTCGCTGTGCA
CCACAAGTATTAGGTATAGTGCCAGAATCTTTAGCTACCGCTCGGAAAAT
ATTGGAACGGGAAGTTATCTCAGCTAATGATAATCCATTGATAGATCCAG
AAAATGGCGATGTTCTACACGGTGGAAATTTTATGGGGCAATATGTCGCC
CGAACAATGGATGCATTAAAACTGGATATTGCTTTAATTGCCAATCATCT
TCACGCCATTGTGGCTCTTATGATGGATAACCGTTTCTCTCGTGGATTAC
CTAATTCACTGAGTCCGACACCCGGCATGTATCAAGGTTTTAAAGGCGTC
CAACTTTCTCAAACCGCTTTAGTTGCTGCAATTCGCCATGATTGTGCTGC
ATCAGGTATTCATACCCTGCGACAGAAACAATCAATCAAGATATTGTCA
GTTTAGGTCTGCATGCCGCTCAAGATGTTTTAGAGATGGAGCAGAAATTA
CGCAATATTGTTTCAATGACAATTCTGGTAGTTTGTCAGGCCATTCATCT
TCGCGGCAATATTAGTGAAATTGCGCCTGAAACTGCTAAATTTTACCATG
CAGTACGCGAAATCAGTTCTCCTTTGATCACTGATCGTGCGTTGGATGAA
GATATAATCCGCATTGCGGATGCAATTATTAATGATCAACTTCCTCTGCC
AGAAATCATGCTGGAAGAATAA To construct the SYN-PKU602 strain comprising $P_{ARA}$-Int5 construct, $P_{T7}$-PAL3 construct, and $P_{LAC}$-T7 polymerase construct (FIG. 44), Gibson assembly was used essentially as described above.

Table 48 shows the sequence of an exemplary $P_{ARA}$-Int5 construct (SEQ ID NO: 45), for integration at the Ara locus. The Int5 sequence is bolded, the $P_{ara}$ sequence containing TSS and RBS sites is underlined, and AraC sequence is in italics.

TABLE 48

Nucleotide Sequence of P_{ARA}-Int5 construct; SEQ ID NO: 45

*TTATTCACAACCTGCCCTAAACTCGCTCGGACTCGCCCCGGTGCATTTTTTAAATACTC*

*GCGAGAAATAGAGTTGATCGTCAAAACCGACATTGCGACCGACGGTGGCGATAGGCATC*

*CGGGTGGTGCTCAAAAGCAGCTTCGCCTGACTGATGCGCTGGTCCTCGCGCCAGCTTAA*

*TACGCTAATCCCTAACTGCTGGCGGAACAAATGCGACAGACGCGACGGCGACAGGCAGA*

*CATGCTGTGCGACGCTGGCGATATCAAAATTACTGTCTGCCAGGTGATCGCTGATGTAC*

*TGACAAGCCTCGCGTACCCGATTATCCATCGGTGGATGGAGCGACTCGTTAATCGCTTC*

*CATGCGCCGCAGTAACAATTGCTCAAGCAGATTTATCGCCAGCAATTCCGAATAGCGCC*

*CTTCCCCTTGTCCGGCATTAATGATTTGCCCAAACAGGTCGCTGAAATGCGGCTGGTGC*

*GCTTCATCCGGGCGAAAGAAACCGGTATTGGCAAATATCGACGGCCAGTTAAGCCATTC*

*ATGCCAGTAGGCGCGCGGACGAAAGTAAACCCACTGGTGATACCATTCGTGAGCCTCCG*

*GATGACGACCGTAGTGATGAATCTCTCCAGGCGGGAACAGCAAAATATCACCCGGTCGG*

*CAGACAAATTCTCGTCCCTGATTTTTCACCACCCCCTGACCGCGAATGGTGAGATTGAG*

*AATATAACCTTTCATTCCCAGCGGTCGGTCGATAAAAAAATCGAGATAACCGTTGGCCT*

*CAATCGGCGTTAAACCCGCCACCAGATGGGCGTTAAACGAGTATCCCGGCAGCAGGGGA*

*TCATTTTGCGCTTCAGCCAT<u>ACTTTTCATACTCCCGCCATTCAGAGAAGAAACCAATTG</u>*

<u>TCCATATTGCATCAGACATTGCCGTCACTGCGTCTTTTACTGGCTCTTCTCGCTAACCC</u>

<u>AACCGGTAACCCCGCTTATTAAAAGCATTCTGTAACAAAGCGGGACCAAAGCCATGACA</u>

<u>AAAACGCGTAACAAAAGTGTCTATAATCACGGCAGAAAAGTCCACATTGATTATTTGCA</u>

<u>CGGCGTCACACTTTGCTATGCCATAGCATTTTTATCCATAAGATTAGCGGATCCAGCCT</u>

<u>GACGCTTTTTTCGCAACTCTCTACTGTTTCTCCATACCTCTAGAAATAATTTTGTTTA</u>

<u>ACTTTAAGAAGGAGATATACAT</u>ATGCCTGGTATGACCACCGAAACCGGTCCGGATCCTG

CAGGTCTGATTGACCTGTTTTGTCGTAAAAGCAAAGCAGTTAAAAGCCGTGCAAATGGT

GCAGGTCAGCGTCGTAAACAAGAAATTAGCATTGCAGCACAAGAAACCCTGGGTCGTAA

AGTTGCAGCACTGCTGGGTATGCAGGTTCGTCATGTTTGGAAAGAAGTTGGTAGCGCAA

GCCGTTTTCGTAAAGGTAAAGCACGTGATGATCAGAGCAAAGCACTGAAAGCCCTGGAA

AGCGGTGAAGTTGGTGCACTGTGGTGTTATCGTCTGGATCGTTGGGATCGTGGTGGTGC

CGGTGCAATTCTGAAAATTATCGAACCGGAAGATGGTATGCCTCGTCGTCTGCTGTTTG

GTTGGGATGAAGATACCGGTCGTCCGGTTCTGGATAGCACCAATAAACGTGATCGCGGT

GAACTGATTCGTCGTGCAGAAGAAGCACGCGAAGAAGCAGAAAAACTGAGCGAACGTGT

TCGTGATACCAAAGCACATCAGCGTGAAAATGGTGAATGGGTTAATGCCCGTGCACCGT

ATGGTCTGCGTGTTGTTCTGGTTACCGTTAGTGATGAAGAGGGTGATGAATATGATGAA

CGTAAACTGGCAGCAGATGATGAAGATGCGGGTGGTCCTGATGGTCTGACCAAAGCAGA

AGCAGCCCGTCTGGTTTTTACCCTGCCGGTTACCGATCGTCTGAGCTATGCAGGCACCG

CACATGCAATGAATACCCGTGAAATTCCGAGCCCGACCGGTGGTCCGTGGATTGCAGTT

ACCGTGCGTGATATGATTCAGAATCCGGCATATGCGGGTTGGCAGACCACAGGTCGTCA

GGATGGTAAACAGCGTCGTCTGACCTTTTATAACGGTGAAGGTAAACGTGTTAGCGTTA

TGCATGGTCCTCCGCTGGTGACCGATGAAGAACAAGAAGCCGCAAAAGCAGCCGTTAAA

GGTGAAGATGGTGTTGGTGTTCCGCTGGATGGTAGCGATCATGATACCCGTCGCAAACA

TCTGCTGAGCGGTCGTATGCGTTGTCCGGGTTGTGGTGGTAGCTGTAGCTATAGCGGTA

TABLE 48-continued

Nucleotide Sequence of P<sub>ARA</sub>-Int5 construct; SEQ ID NO: 45

```
ATGGTTATCGTTGTTGGCGTAGCAGTGTGAAAGGTGGTTGTCCGGCACCGACCTATGTT
GCACGTAAAAGCGTTGAAGAATATGTTGCATTTCGTTGGGCAGCAAAATTAGCAGCAAG
CGAACCGGATGATCCGTTTGTTATTGCAGTTGCAGATCGCTGGGCAGCACTGACCCATC
CGCAGGCAAGCGAAGATGAAAAGTATGCAAAAGCCGCAGTTCGTGAAGCCGAAAAAAAT
CTGGGTCGCCTGCTGCGTGATCGTCAGAATGGTGTTTATGATGGTCCGGCAGAACAGTT
TTTTGCCCCTGCATATCAAGAAGCACTGAGCACCCTGCAGGCAGCCAAAGATGCAGTTA
GCGAAAGCAGCGCAAGCGCAGCAGTTGATGTTAGCTGGATTGTTGATAGCAGCGATTAT
GAAGAACTGTGGCTGCGTGCAACCCCGACCATGCGTAATGCAATTATTGATACCTGCAT
CGATGAAATTTGGGTTGCAAAAGGCCAGCGTGGTCGTCCGTTTGATGGTGATGAACGCG
TTAAAATCAAATGGGCAGCCCGTACCTAA
```

Example 23

Generation of DeltaThyA

An auxotrophic mutation causes bacteria to die in the absence of an exogenously added nutrient essential for survival or growth because they lack the gene(s) necessary to produce that essential nutrient. In order to generate genetically engineered bacteria with an auxotrophic modification, the thyA, a gene essential for oligonucleotide synthesis was deleted. Deletion of the thyA gene in *E. coli* Nissle yields a strain that cannot form a colony on LB plates unless they are supplemented with thymidine.

A thyA::cam PCR fragment was amplified using 3 rounds of PCR as follows. Sequences of the primers used at a 100 um concentration are found in Table 49.

For the first PCR round, 4×50 ul PCR reactions containing 1 ng pKD3 as template, 25 ul 2×phusion, 0.2 ul primer SR36 and SR38, and either 0, 0.2, 0.4 or 0.6 ul DMSO were brought up to 50 ul volume with nuclease free water and amplified under the following cycle conditions:
step1: 98 c for 30 s
step2: 98 c for 10 s
step3: 55 c for 15 s
step4: 72 c for 20 s
repeat step 2-4 for 30 cycles
step5: 72 c for 5 min Subsequently, 5 ul of each PCR reaction was run on an agarose gel to confirm PCR product of the appropriate size. The PCR product was purified from the remaining PCR reaction using a Zymoclean gel DNA recovery kit according to the manufacturer's instructions and eluted in 30 ul nuclease free water.

For the second round of PCR, 1 ul purified PCR product from round 1 was used as template, in 4×50 ul PCR reactions as described above except with 0.2 ul of primers SR33 and

TABLE 49

Primer Sequences

| Name | Sequence | Description | SEQ ID NO |
|---|---|---|---|
| SR36 | tagaactgatgcaaaaagtgctcgacgaaggcacacagaTGTGTAGGCTGGAGCTGCTTC | Round 1: binds on pKD3 | SEQ ID NO: 46 |
| SR38 | gtttcgtaattagatagccaccggcgctttaatgcccggaCATATGAATATCCTCCTTAG | Round 1: binds on pKD3 | SEQ ID NO: 47 |
| SR33 | caacacgtttcctgaggaaccatgaaacagtatttagaactgatgcaaaaag | Round 2: binds to round 1 PCR product | SEQ ID NO: 48 |
| SR34 | cgcacactggcgtcggctctggcaggatgtttcgtaattagatagc | Round 2: binds to round 1 PCR product | SEQ ID NO: 49 |
| SR43 | atatcgtcgcagcccacagcaacacgtttcctgagg | Round 3: binds to round 2 PCR product | SEQ ID NO: 50 |
| SR44 | aagaatttaacggagggcaaaaaaaaccgacgcacactggcgtcggc | Round 3: binds to round 2 PCR product | SEQ ID NO: 51 |

SR34. Cycle conditions were the same as noted above for the first PCR reaction. The PCR product run on an agarose gel to verify amplification, purified, and eluted in 30 ul as described above.

For the third round of PCR, 1 ul of purified PCR product from round 2 was used as template in 4×50 ul PCR reactions as described except with primer SR43 and SR44. Cycle conditions were the same as described for rounds 1 and 2. Amplification was verified, the PCR product purified, and eluted as described above. The concentration and purity was measured using a spectrophotometer. The resulting linear DNA fragment, which contains 92 bp homologous to upstream of thyA, the chloramphenicol cassette flanked by frt sites, and 98 bp homologous to downstream of the thyA gene, was transformed into a E. coli Nissle 1917 strain containing pKD46 grown for recombineering. Following electroporation, 1 ml SOC medium containing 3 mM thymidine was added, and cells were allowed to recover at 37 C for 2 h with shaking. Cells were then pelleted at 10,000×g for 1 minute, the supernatant was discarded, and the cell pellet was resuspended in 100 ul LB containing 3 mM thymidine and spread on LB agar plates containing 3 mM thy and 20 ug/ml chloramphenicol. Cells were incubated at 37 C overnight. Colonies that appeared on LB plates were restreaked. +cam 20 ug/ml+or −thy 3 mM. (thyA auxotrophs will only grow in media supplemented with thy 3 mM).

Next, the antibiotic resistance was removed with pCP20 transformation. pCP20 has the yeast Flp recombinase gene, FLP, chloramphenicol and ampicillin resistant genes, and temperature sensitive replication. Bacteria were grown in LB media containing the selecting antibiotic at 37° C. until OD600=0.4-0.6. 1 mL of cells were washed as follows: cells were pelleted at 16,000×g for 1 minute. The supernatant was discarded and the pellet was resuspended in 1 mL ice-cold 10% glycerol. This wash step was repeated 3× times. The final pellet was resuspended in 70 ul ice-cold 10% glycerol. Next, cells were electroporated with 1 ng pCP20 plasmid DNA, and 1 mL SOC supplemented with 3 mM thymidine was immediately added to the cuvette. Cells were resuspended and transferred to a culture tube and grown at 30° C. for 1 hours. Cells were then pelleted at 10,000×g for 1 minute, the supernatant was discarded, and the cell pellet was resuspended in 100 ul LB containing 3 mM thymidine and spread on LB agar plates containing 3 mM thy and 100 ug/ml carbenicillin and grown at 30° C. for 16-24 hours. Next, transformants were colony purified non-selectively (no antibiotics) at 42° C.

To test the colony-purified transformants, a colony was picked from the 42° C. plate with a pipette tip and resuspended in 10 μL LB. 3 μL of the cell suspension was pipetted onto a set of 3 plates: Cam, (37° C.; tests for the presence/absence of CamR gene in the genome of the host strain), Amp, (30° C., tests for the presence/absence of AmpR from the pCP20 plasmid) and LB only (desired cells that have lost the chloramphenicol cassette and the pCP20 plasmid), 37° C. Colonies were considered cured if there is no growth in neither the Cam or Amp plate, picked, and re-streaked on an LB plate to get single colonies, and grown overnight at 37° C.

Example 24

Phenylalanine Quantification (Dansyl-chloride Derivatization)

For in vitro and in vivo assays described herein, which assess the ability of the genetically engineered bacteria to degrade phenylalanine and which require quantification of phenylalanine levels in the sample, a dansyl-chloride derivatization protocol was employed as follows.

Sample Preparation

Phenylalanine standards (1000, 500, 250, 100, 20, 4 and 0.8 μg/mL in water) were prepared. On ice, 10μL of sample was pipetted into a V-bottom polypropylene 96-well plate, and 190 μL of 60% acetonitrile with lug/mL of L-Phenyl-$d_5$-alanine internal standard was added. The plate was heat sealed, mixed well, and centrifuged at 4000 rpm for 5 min. Next, 5μL of diluted samples were added to 95 μL of derivatization mix (85 μL 10 mM NaHCO$_3$ pH 9.7 and 10 μL 10 mg/mL dansyl-chloride (diluted in acetonitrile)) in a V-bottom 96-well polypropylene plate, and the plate was heat-sealed and mixed well. The samples were incubated at 60° C. for 45 min for derivatization and then centrifuged at 4000 rpm for 5 minutes. Next, 20 μL of the derivatized samples were added to 180μL of water with 0.1% formic acid in a round-bottom 96-well plate, plates were heat-sealed and mixed well.

LC-MS/MS Method

Phenylalanine was measured by liquid chromatography coupled to tandem mass spectrometry (LC-MS/MS) using a Thermo TSQ Quantum Max triple quadrupole mass spectrometer. HPLC Method details are described in Table 50 and Table 51. Tandem Mass Spectrometry details are described in Table 52.

TABLE 50

| HPLC Method Details | |
|---|---|
| Column | Luna C18(2) column, 5 μm (50 × 2.1mm) |
| Mobile Phase A | 100% H2O, 0.1% Formic Acid |
| Mobile Phase B | 100% ACN, 0.1% Formic Acid |
| Injection volume | 10uL |

TABLE 51

| HPLC Method Details | | | |
|---|---|---|---|
| Total Time (mm) | Flow Rate (μL/min) | A% | B% |
| 0 | 400 | 90 | 10 |
| 0.5 | 400 | 90 | 10 |
| 0.6 | 400 | 10 | 90 |
| 2 | 400 | 10 | 90 |
| 2.01 | 400 | 90 | 10 |
| 3 | 400 | 90 | 10 |

TABLE 52

| Tandem Mass Spectrometry Details | |
|---|---|
| Ion Source | HESI-II |
| Polarity | Positive |
| SRM transitions | |
| L-Phenylalanine | 399.1/170.1 |
| L-Phenyl-d5-alanine | 404.1/170.1 |

Example 25

Trans-cinnamic Acid Quantification (Trifluoroethylamine Derivatization)

For in vitro and in vivo assays described herein, which assess the ability of the genetically engineered bacteria to degrade phenylalanine and which require quantification of Trans-cinnamic acid levels in the sample, a trifluoroethylamine derivatization protocol was employed as follows.

Sample Preparation

Trans-cinnamic acid standard (500, 250, 100, 20, 4 and 0.8 µg/mL in water) were prepared. On ice, 10 µL of sample was pipetted into a V-bottom polypropylene 96-well plate. Next, 30 µL of 80% acetonitrile with 2 ug/mL of trans-cinnamic acid-d7 internal standard was added, and the plate was heat sealed, mixed well, and centrifuged at 4000 rpm for 5 minutes. Next, 20 µL of diluted samples were added to 180 µL of 10 mM MES pH4, 20 mM N-(3-Dimethylaminopropyl)-N'-ethylcarbodiimide (EDC), 20 mM trifluoroethylamine in a round-bottom 96-well polypropylene plate. The plate was heat-sealed, mixed well, and samples were incubated at room temperature for 1 hour.

LC-MS/MS Method

Trans-cinnamic acid was measured by liquid chromatography coupled to tandem mass spectrometry (LC-MS/MS) using a Thermo TSQ Quantum Max triple quadrupole mass spectrometer. HPLC Method details are described in Table 53 and Table 54. Tandem Mass Spectrometry details are described in Table 55.

TABLE 53

HPLC Method Details

| Column | Thermo Aquasil C18 column, 5 µm (50 × 2.1 mm) |
|---|---|
| Mobile Phase A | 100% H2O, 0.1% Formic Acid |
| Mobile Phase B | 100% ACN, 0.1% Formic Acid |
| Injection volume | 10uL |

TABLE 54

HPLC Method Details

| Total Time (min) | Flow Rate (µL/min) | A% | B% |
|---|---|---|---|
| 0 | 500 | 100 | 0 |
| 1 | 500 | 100 | 0 |
| 2 | 500 | 10 | 90 |
| 4 | 500 | 10 | 90 |
| 4.01 | 500 | 100 | 0 |
| 5 | 500 | 100 | 0 |

TABLE 55

Tandem Mass Spectrometry Details

| Ion Source: | HESI-II |
|---|---|
| Polarity | Positive |
| SRM transitions | |
| Trans-cinnamic acid: | 230.1/131.1 |
| Trans-cinnamic acid-d7 | 237.1/137.2 |

Example 26

Phenylalanine, Trans-cinnamic Acid, Phenylacetic Acid, Phenylpyruvic Acid, Phenyllactic Acid, Hippuric Acid and Benzoic Acid Quantification (2-Hydrazinoquinoline Derivatization)

For in vitro and in vivo assays described herein, which assess the ability of the genetically engineered bacteria to degrade phenylalanine and which require quantification of phenylalanine, trans-cinnamic acid, phenylacetic acid, phenylpyruvic acid, phenyllactic acid, hippuric acid, and benzoic acid levels in the sample, a 2-Hydrazinoquinoline derivatization protocol was employed as follows Sample Preparation Standard solutions containing 250, 100, 20, 4, 0.8, 0.16 and 0.032 µg/mL of each standard in water were prepared. On ice, 10 µL of sample was pipetted into a V-bottom polypropylene 96-well plate, and 90 µL of the derivatizing solution containing 50 mM of 2-Hydrazinoquinoline (2-HQ), dipyridyl disulfide, and triphenylphospine in acetonitrile with lug/mL of L-Phenyl-$d_5$-alanine, lug/mL of hippuric acid-d5 and 0.25 ug/mL trans-cinnamic acid-d7 internal standards was added. The plate was heat-sealed, mixed well, and samples were incubated at 60° C. for 1 hour for derivatization, and then centrifuged at 4000 rpm for 5 min. In a round-bottom 96-well plate, 20 µL of the derivatized samples were added to 180µL of water with 0.1% formic acid. Plates were heat-sealed and mixed well.

LC-MS/MS Method

Metabolites derivatized by 2-HQ were measured by liquid chromatography coupled to tandem mass spectrometry (LC-MS/MS) using a Thermo TSQ Quantum Max triple quadrupole mass spectrometer. HPLC details are described in Table 56 and Table 57. Tandem Mass Spectrometry details are described in Table 58.

TABLE 56

HPLC Method Details

| Column | Luna C18(2) column, 3 µm (150 × 2.1 mm) |
|---|---|
| Mobile Phase A | 100% H2O, 0.1% Formic Acid |
| Mobile Phase B | 100% ACN, 0.1% Formic Acid |
| Injection volume | 10uL |

TABLE 57

HPLC Method Details

| Total Time (min) | Flow Rate (µL/min) | A% | B% |
|---|---|---|---|
| 0 | 500 | 90 | 10 |
| 0.5 | 500 | 90 | 10 |
| 2 | 500 | 10 | 90 |
| 4 | 500 | 10 | 90 |
| 4.01 | 500 | 90 | 10 |
| 4.25 | 500 | 90 | 10 |

TABLE 58

| Tandem Mass Spectrometry Details | |
|---|---|
| Ion Source | HESI-II |
| Polarity | Positive |
| SRM transitions | |
| L-Phenylalanine: | 307.1/186.1 |
| L-Phenyld5-alanine | 312.1/186 |
| Trans-cinnamic acid | 290.05/131.1 |
| Trans-cinnamic acid-d7 | 297.05/138.1 |
| Hippuric acid | 321.1/160.1 |
| Hippuric acid-d5 | 326/160 |
| Phenylacetic acid | 278.05/160.1 |
| Phenyllactic acid | 308.05/144.1 |
| Benzoic acid | 264.05/105.1 |
| Phenylpyruvate | 306.05/260.1 |

Example 27

Relative Efficacy of Chromosomal Insertion and Plasmid-bearing Strains

To compare the rate of phenylalanine degradation between engineered bacterial strains with chromosomal insertions and those harboring plasmids, overnight cultures were diluted 1:100 in LB and grown with shaking (250 rpm) at 37° C. After 1.5 hrs of growth, cultures were placed in a Coy anaerobic chamber supplying 90% $N_2$, 5% $CO_2$, 5% $H_2$. After 4 hrs of induction, bacteria were pelleted, washed in PBS, and resuspended in assay buffer (M9 minimal media with 0.5% glucose, 8.4% sodium bicarbonate, and 4 mM Phe). Rates of phenylalanine degradation (i.e., disappearance from the assay solution) or cinnamate accumulation from 30 to 90 min were normalized to 1e9 cells. Table 59 shows the normalized rates for all strains and describes genotypes and the activities of non-limiting examples of engineered plasmid-bearing strains and engineered strains comprising chromosomal insertions.

TABLE 59

Genotype and Activity of engineered plasmid-bearing strains and engineered strains comprising chromosomal insertions.

| Strain Name | Genotype | PAL Activity (umol/hr./10A 9 cells) | LAAD activity (umol/hr./1 01\9 cells) |
|---|---|---|---|
| Plasmid -based strains | | | |
| SYN-PKU101 | Low copy pSC101-Ptet::PAL1, ampicillin resistant | ND | NA |
| SYN-PKU102 | High copy pColEl-Ptet::PALI, ampicillin resistant, | ND | NA |
| SYN-PKU201 | Low copy pSC101-Ptet::PAL3, ampicillin resistant | ND | NA |
| SYN-PKU202 | High copy pColE1-Ptet::PAL3, ampicillin resistant, | ND | NA |
| SYN-PKU203 | lacZ::Ptet-pheP::cam | 0 | NA |
| SYN-PKU401 | Low copy pSC101-Ptet::PAL1, ampicillin resistant, chromosomal lacZ::Ptet-pheP::cam | 1.1 | NA |
| SYN-PKU402 | High copy pColEl-Ptet::PAL1, ampicillin resistant, chromosomal lacZ::Ptet-pheP::cam | 0.8 | NA |
| SYN-PKU302 | Low Copy pSC101-Ptet::PAL3, ampicillin resistant; chromosomal lacZ::Ptet-pheP::cam | 2.2 | NA |
| SYN-PKU303 | High copy pColE1-Ptet::PAL3, ampicillin resistant, chromosomal lacZ::Ptet-pheP::cam | 7.1 | NA |
| SYN-PKU304 | Low Copy pSC101-PfnrS::PAL3, ampicillin resistant; chromosomal lacZ::PfnrS-pheP::cam | 3 | NA |
| SYN-PKU305 | Low Copy pSC101-PfnrS::PAL3, kanamycin resistant; chromosomal lacZ::PfnrS-pheP::cam | 3 | NA |
| SYN-PKU306 | Low Copy pSC101-PfnrS::PAL3, kanamycin resistant; thyA | 0.3 | NA |
| SYN-PKU307 | Low Copy pSC101-PfnrS::PAL3, ampicillin resistant; | 0.3 | NA |
| SYN-PKU308 | Low Copy pSC101-PfnrS::PAL3, kanamycin resistant; | 0.3 | NA |
| SYN-PKU401 | High Copy pUC57-Ptet::LAAD; kanamycin resistant | NA | 50 ($^+O_2$),0 ($^-O_2$) |
| Integrated strains | | | |
| SYN-PKU501 | malPT:: PfnrS::PAL3::kan | 0.3 | NA |
| SYN-PKU502 | malPT:: PfnrS::PAL3::kan; bicistronic lacZ:: PfnrS::PAL3-pheP::cam | ND | NA |
| SYN-PKU503 | malEK::PfnrS::PAL3::cam | 0.3 | NA |
| SYN-PKU504 | agaI/rsmI::PfnrS::PAL3 | 0.3 | NA |
| SYN-PKU505 | cea::PfnrS::PAL3 | 0.3 | NA |

TABLE 59-continued

Genotype and Activity of engineered plasmid-bearing strains and engineered strains comprising chromosomal insertions.

| Strain Name | Genotype | PAL Activity (umol/hr./10A 9 cells) | LAAD activity (umol/hr./1 01\9 cells) |
|---|---|---|---|
| SYN-PKU506 | malEK::PfnrS::PAL3; agaI/rsmI::PfnrS::PAL3; cea::PfnrS::PAL3 | 0.7 | NA |
| SYN-PKU507 | malEK:: PfnrS::PAL3; agaI/rsmI::PfnrS::PAL3; cea::PfnrS::PAL3;lacZ::Pfnr-pheP::cam | 5.2 | NA |
| SYN-PKU508 | malEK::PfnrS::PAL3; pheA auxotroph | 0.4 | NA |
| SYN-PKU509 | malEK::PfnrS::PAL3; agaI/rsmI::PfnrS::PAL3; cea::PfnrS::PAL3; lacZ::Pfnr-pheP::cam | 4.9 | NA |
| SYN-PKU601 | malPT::PfnrS-INT5::kan, rrnBUP - [PAL3]; lacZ::Pfnr-pheP::cam (recombinase based strain) | 0.9 | NA |
| SYN-PKU510 | malEK::PfnrS::PAL3; agaI/rsmI::PfnrS::PAL3; cea::PfnrS::PAL3; | 0.6 | NA |
| SYN-PKU511 | malEK:: PfnrS::PAL3; agaI/rsmI::PfnrS::PAL3; cea::PfnrS::PAL3; yicS/nepl::PfnrS-PAL3::kan; malPT::PfnrS::PAL3; lacZ::Pfnr-pheP; Δ thyA | 7.7 | NA |
| SYN-PKU204 | lacZ::Pfnr-pheP::cam | ND | NA |
| SYN-PKU512 | malEK::PfnrS::PAL3; agaI/rsmI::PfnrS::PAL3; cea::PfnrS::PAL3; malPT::PfnrS::PAL3; lacZ::Pfnr-pheP::cam; Δ thyA | 6.7 | NA |
| SYN-PKU513 | malEK:: PfnrS::PAL3; agaI/rsmI::PfnrS::PAL3; cea::PfnrS::PAL3; lacZ::Pfnr-pheP; ΔthyA | 4.9 | NA |
| SYN-PKU514 | malEK:: PfnrS::PAL3; agaI/rsmI::PfnrS::PAL3; cea::PfnrS::PAL3; malPT::PfnrS::PAL3; ΔthyA | 0.8 | NA |
| SYN-PKU515 | malEK:: PfnrS::PAL3; agaI/rsmI::PfnrS::PAL3; cea::PfnrS::PAL3; Δ thyA | 0.7 | NA |
| SYN-PKU516 | agaI/rsmI::PfnrS::PAL3::kan | 0.3 | NA |
| SYN-PKU517 | malEK:: PfnrS::PAL3::cam; malPT::PfnrS::P AL3 ::kan; lacZ::PfnrS-pheP; ΔthyA | 2.9 | NA |
| SYN-PKU518 | malEK-PfnrS::PAL3::cam; PfnrS::pheP::kan | 1.7 | NA |
| SYN-PKU519 | ParaBC-PAL3::cam;PfnrS-pheP::kan | 1.3 | NA |
| SYN-PKU520 | agaI/rsmI::PfnrS::PAL3::kan;PfnrS-PheP::cam | 2.0 | NA |
| SYN-PKU801 | ΔargR; thyA::cam | ND | NA |
| SYN-PKU701 | ParaBC-LAAD::cam;malEK-PfnrS-PAL3; malPT::PfnrS-PAL3::kan; PfnrS-PheP | 2.7 | 28 ($^+O_2$),0 ($^-O_2$) |
| SYN-PKU521 | yicS/nepl::PfnrS-PAL3::kan; lacZ::Pfnr-pheP::cam | 2.4 | NA |
| SYN-PKU522 | cea::PfnrS-PAL3::kan; lacZ::Pfnr-pheP::cam | ND | NA |
| SYN-PKU523 | malPT::PfnrS-PAL3::kan; lacZ::Pfnr-pheP::cam | 0.5 | NA |
| SYN-PKU524 | malEK:: PfnrS::PAL3; malPT::PfnrS::PAL3; lacZ::Pfnr-pheP | 2.9 | NA |
| SYN-PKU702 | malEK:: PfnrS::PAL3; lacZ::Pfnr-pheP; Para::LAAD | 1.5 | ND |
| SYN-PKU703 | malEK:: PfnrS::PAL3; malPT::PfnrS::PAL3; lacZ::Pfnr-pheP; agaI/rsmI::PfnrS::pheP; Para. :LAAD | 3.1 | ND |
| SYN-PKU704 | malEK:: PfnrS::PAL3; malPT::PfnrS::PAL3; yicS/nepI::PfnrS-PAL3; lacZ::Pfnr-pheP; Para. :LAAD | 3.5 | ND |
| SYN-PKU705 | malEK:: PfnrS::PAL3; malPT::PfnrS::PAL3;yicS/nepL:PfnrS-PAL3::kan;lacZ::Pfnr-pheP; agaI/rsmf:PfnrS::phePPara.:LAAD | 3.7 | ND |

TABLE 59-continued

Genotype and Activity of engineered plasmid-bearing strains and engineered strains comprising chromosomal insertions.

| Strain Name | Genotype | PAL Activity (umol/hr./10A 9 cells) | LAAD activity (umol/hr./1 01\9 cells) |
|---|---|---|---|
| SYN-PKU602 | malEK::PT7::PAL3;Para.:INT5::cam (recombinase);lacZ::Pfnr-pheP; malPT::Pconstitutive::T7 polymerase (unflipped); | 2.4 | NA |
| SYN-PKU901 | Nissle with streptomycin resistance | NA | NA |

Example 28

Screening for Improved Phe Consumption

Screens using genetic selection are conducted to improve phenylalanine consumption in the genetically engineered bacteria. Toxic phenylalanine analogs exert their mechanism of action (MOA) by being incorporated into cellular protein, causing cell death. These compounds were evaluated for their utility in an untargeted approach to select PAL enzymes with increased activity. Assuming that these toxic compounds can be metabolized by PAL into a non-toxic metabolite, rather than being incorporated into cellular protein, genetically engineered bacteria which have improved phenylalanine degradation activity can tolerate higher levels of these compounds, and can be screened for and selected on this basis.

Figure 35:
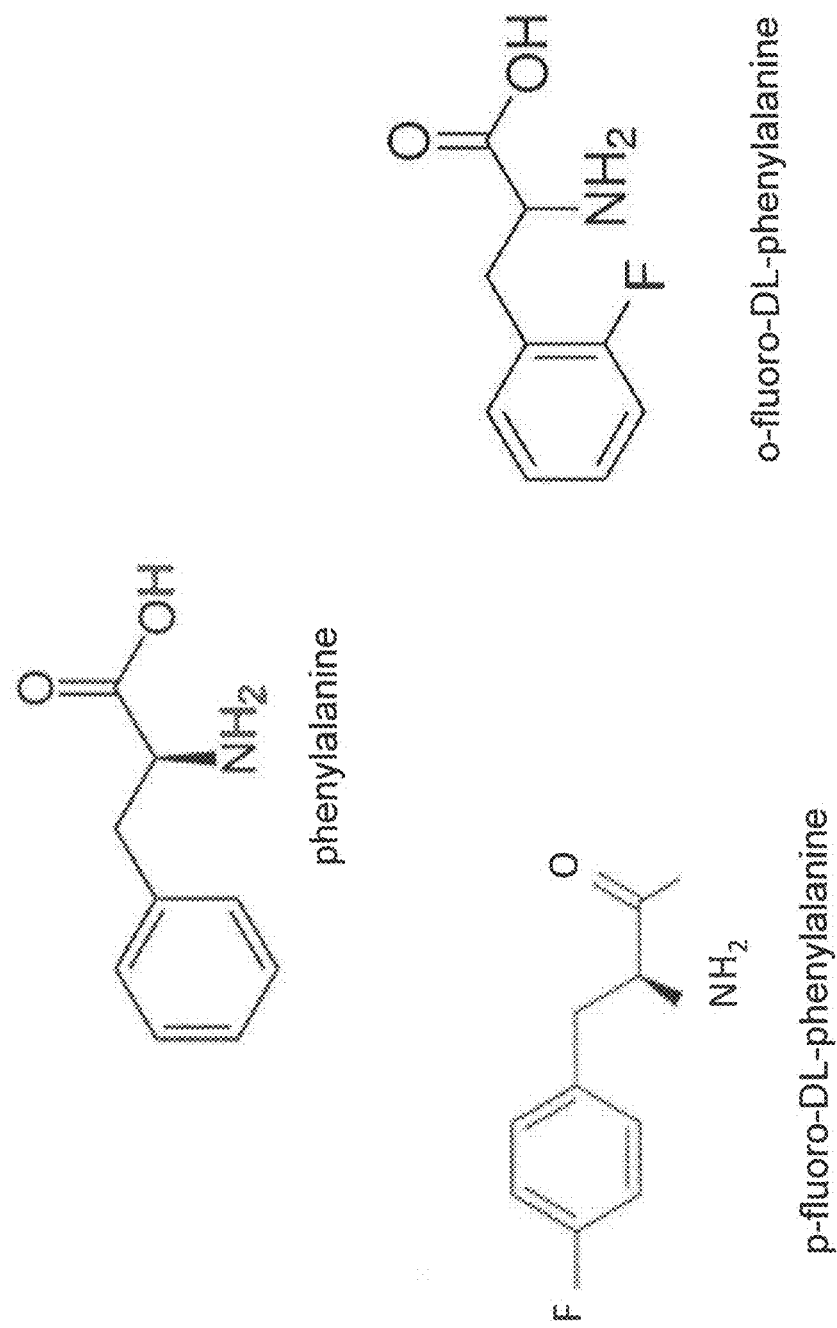
FIG. 35 depicts phenylalanine and 2 toxic analogs, p-fluoro-DL-phenylalanine, and o-fluoro-DL-phenylalanine, which are useful for an untargeted approach to select PAL enzymes with increased activity. P-fluoro-DL-phenylalanine, and o-fluoro-DL-phenylalanine are incorporated into cellular protein in the place of phenylalanine, resulting in cell death. Since these compounds are readily taken up by PheP, and can act as a substrate for PAL as shown below, they can be employed in genetic selection and screening for the identification of strains with improved Phe consumption activity. Mutations allowing more efficient PAL metabolism may prevent the incorporation of the phenylalanine analog into cellular protein, therefore allowing growth under higher concentrations of the analog.

Various genetically engineered bacterial strains as well as control Nissle were treated with two analogs, p-fluoro-DL-minimum phenylalanine and o-fluoro-DL-phenylalanine (FIG. 35) at increasing concentrations. Minimum inhibitory concentration (MIC) was determined and the fold change relative to the wild type Nissle was determined. Results are shown in Table 60.

These results indicate that the para-analog appear to be taken up readily by pheP and are potentially a substrate of PAL, and that the ortholog appears to be taken up readily by pheP and is potentially a substrate of PAL. As a result, these compounds have utility for screening for PAL enzymes with greater activity.

TABLE 60

MIC and Fold Change Relative to WT for various strains

| MIC (ug/mL) | fold change (WT) | Strain |
|---|---|---|
| | | para-fluoro-Phe |
| 1250 | 1 | Wild Type Nissle |
| <2.4 | >↓520X | SYN-PKU203 (Ptet::pheP chr.) |
| 2500 | ↑2X | SYN-PKU202 (Ptet-PAL3 high copy) |
| 19.5 | ↓64X | SYN-PKU302 (Ptet-PAL low copy + Ptet-pheP chr.) |
| 39 | ↓32X | SYN-PKU303 (Ptet-PAL high copy + Ptet-pheP chr.) |
| | | ortho-fluoro-Phe |
| 62.5 | 1 | Wild Type Nissle |
| 1 | ↓64X | SYN-PKU203 (Ptet::pheP chr.) |
| 250 | ↑4X | SYN-PKU202 (Ptet-PAL3 high copy) |
| 31.3 | ↓2X | SYN-PKU302 (Ptet-PAL low copy + Ptet-pheP chr.) |
| 15.6 | ↓4X | SYN-PKU303 (Ptet-PAL high copy + Ptet-pheP chr.) |

Example 29

Repeat-Dose Pharmacokinetic and Pharmacodynamic Study of Genetically Engineered Bacteria Following Daily Nasogastric Gavage Dose Administration for 28-days in Cynomolgus Monkeys (Non-GLP)

To evaluate any potential toxicities arising from administration of the genetically engineered bacteria or E. coli Nissle alone, the pharmacokinetics and pharmacodynamics of the genetically engineered bacteria and an E. coli Nissle are studied following daily nasogastric gavage (NG) dose administration for 28-days to female cynomolgus monkeys. Cynomolgus monkeys is selected because this species is closely related, both phylogenetically and physiologically, to humans and is a species commonly used for nonclinical toxicity evaluations. The genetically engineered bacteria are administered by nasal gastric gavage, consistent with the proposed route of administration in humans. Animals overall well-being (clinical observations), weight clinical pathology (serum chemistry, hematology, and coagulation) are tracked. Plasma is analyzed for ammonia levels, and fecal samples examined for bacterial load.

The genetically engineered strain comprises one or more copies of PAL3 integrated into the chromosome and one or more copies of PheP integrated into the chromosome, each of which are under the control of an FNRS promoter. In some embodiments, the genetically engineered strain also comprises one or more copies of LAAD, driven by an arabinose inducible promoter, e.g., ParaBAD. In some embodiments, the strain further comprises a auxotrophy mutation, e.g., deltaThyA. In some embodiments, the genetically engineered bacteria further comprise an antibiotic resistance, e.g., kanamycin. In some embodiments, the genetically engineered bacteria do not comprise an auxotrophy mutation. In some embodiments, the genetically engineered bacteria do not comprise an antibiotic resistance.

Materials, Animals and Dosing Regimen

The study is conducted in compliance with nonclinical Laboratory Studies Good Laboratory Practice Regulations issued by the U.S. Food and Drug Administration (Title 21 of the Code of Federal Regulations, Part 58; effective Jun. 20, 1979) and the OECD Principles on Good Laboratory Practice (C [97]186/Final; effective 1997). The animals are individually housed based on the recommendations set forth in the Guide for the Care and Use of Laboratory Animals (National Research Council 2011).

Animals used in the study are Female Purpose-bred, non-naive cynomolgus monkey (*Macaca fascicularis*) with 3 to 6 kg (at initial physical exam) 3 to 8 years (at initial physical exam) of age (SNBL USA stock, Origin: Cambodia).

For the duration of the study, animals are offered PMI LabDiet® Fiber-Plus® Monkey Diet 5049 biscuits twice daily. Animal are fasted for at least 2 hours prior to dose administration and fed within 1-hour post dose. Animals also are fasted as required by specific procedures (e.g., prior to blood draws for serum chemistry, fecal collection). The diet is routinely analyzed for contaminants and found to be within manufacturer's specifications. No contaminants are expected to be present at levels that would interfere with the outcome of the study. Food analysis records are maintained in the testing facility records.

Fresh drinking water is provided ad libitum to all animals. The water is routinely analyzed for contaminants. No contaminants are present at levels that would interfere with the outcome of the study. Animals are given fruits, vegetables, other dietary supplements, and cage enrichment devices throughout the course of the study.

Previously quarantined animals are acclimated to the study room for 7 days prior to initiation of dosing (day 1). The last dosing occurs on day 28. A stratified randomization scheme incorporating body weights is used to assign animals to study groups. Animals are assigned to groups and treated as indicated in Table 61.

TABLE 61

Group Assignments

| Group | Test/Control Articles | Dose Level (cfu/Animal) | Dose Conc. (cfu/mL) | Volume (mL Animal) | Bicarb. Conc. (M) | Flu Volume (mL/Animal) | Number of Females |
|---|---|---|---|---|---|---|---|
| 1 | Control Article | 0 | 0 | 10 | 0.36 | 5 | 3 |
| 2 | E coli Nissle | $1 \times 10^9$ | $1 \times 10^9$ | 1 | 0.12 | 14 | 3 |
| 3 | E coli Nissle | $1 \times 10^{12}$ | $1 \times 10^{11}$ | 10 | 0.36 | 5 | 3 |
| 4 | Genetically engineered bacteria | $1 \times 10^9$ | $1 \times 10^9$ | 1 | 0.12 | 14 | 3 |
| 5 | Genetically engineered bacteria | $1 \times 10^{12}$ | $1 \times 10^{11}$ | 10 | 0.36 | 5 | 3 |

Nissle control and genetically engineered bacterial stocks are prepared at 1×109 cfu/mL and 1×1011 cfu/mL in 15% glycerol in 1× PBS with 2.2% glucose and 3 mM thymidine and are kept at 86 to −60° C. (see Table 61). PBS made in 20% glycerol with sodium bicarbonate is used as a control vehicle. Carbonate concentration is 0.36M and 0.12M for sodium bicarbonate (see table XXX). On the day of each dosing, bacteria and vehicle control are removed from the freezer and put on ice and thawed and placed on ice until dosing.

Animals are dosed at 0, 1×10$^9$, or 1×10$^{12}$ cfu/animal. All animals are dosed via nasal gastric gavage (NG) followed by control/vehicle flush once daily for 28-days. The concentration of bicarbonate and volume for each group is specified in Table YYY. Vials are inverted at least 3 times prior to drawing the dose in the syringe. The dose site and dose time (end of flush time) is recorded.

Analysis

Overall condition: Clinical observations are performed twice daily beginning on the second day of acclamation for each animal. The first observation is in the AM, prior to room cleaning. The second observation is no sooner than 4 hours after the AM observation. During the dosing phase, the second observation is performed 4 hour (±10 minutes) post dose administration. Additional clinical observations are performed, as necessary.

Weight: Each animal is weighed on Day −6, 1, 8, 15, 22, and 29 prior to the first feeding and also prior to dose administration. Additional body weights are taken as needed if necessary.

Blood Collection: Blood is collected from a peripheral vein of restrained, conscious animals. Whenever possible, blood is collected via a single draw and then divided appropriately. Specimen collection frequency is summarized in Table 62.

TABLE 62

Specimen collection frequency

| Time Point | Hematology | Coagulation | Serum Chemistry | Plasma Sample (on ice) | Fecal sample (on ice) |
|---|---|---|---|---|---|
| Acclimation Week 1 | 1x | 1x | 1x | 1x | 1x |
| Dosing | Day 2 (Predose) | Day 2 (Predose) | Day 2 (Predose) | Days 2 and 7 | Days 2 and 7 |
| Dosing | Day 14 (Predose) | Day 14 (Predose) | Day 14 (Predose) | Day 14 (Predose) | Day 14-20 |
| Dosing | — | — | — | — | Day 21-27- |
| Dosing | — | — | — | Day 28 (Predose) | Day 28-30 |
| Dosing Weeks | Day 30 | Day 30 | Day 30 | Day 30 | Day 35, 40 |

— = Not applicable
x = Number of times procedure performed within the week

Hematology: Approximately 1.3 mL of blood is tested in 2 mL K2EDTA tubes using an Advia automated analyzer. Parameters measured are White Blood Cells, Red Blood Cells, Hemoglobin, Hematocrit, Mean Corpuscular Volume, Mean Corpuscular Hemoglobin, Mean Corpuscular Hemoglobin Concentration, Red Cell Distribution Width, Platelets, Mean Platelet Volume, Differential leukocyte count (absolute): Neutrophils Absolute Lymphocytes Absolute Monocytes Absolute Eosinophils Absolute, Basophils Absolute Reticulocyte Percent, and Reticulocyte Absolute Count.

Coagulation: Approximately 1.3 mL of blood is tested in 1.8 mL 3.2% sodium citrate tubes. The following Coagulation parameters are determined using a STACompact automated analyzer: Activated Partial Thromboplastin Time, Fibrinogen, and Prothrombin Time. Sodium citrate-treated plasma is stored at −60 to −86° C. prior to analysis and discarded after analysis.

Serum Chemistry: Animals are fasted for 4 hours prior to removal of sample. The following parameters are tested in approximately 1 mL of blood in 4 mL serum separator tubes using a AU680 analyzer: Albumin, Alkaline Phosphatase, Alanine Aminotransferase Aspartate Aminotransferase, Total Bilirubin, Calcium, Total Cholesterol, Creatine Kinase, Creatinine, Glucose, Inorganic Phosphorus, Total Protein, Triglyceride, Sodium, Potassium, Chloride Globulin, Albumin/Globulin Ratio, Blood Urea Nitrogen, and Gamma Glutamyltransferase.

Residual serum is stored at −60 to −86° C. and disposed of prior to study finalization.

Plasma Samples: Animals are fasted for 4 hours prior to removal of the sample. Blood samples are collected from the femoral vein at the target time points listed in Table YYY. After aliquotting the target volume of blood in the blood tube, approximately 0.05 mL of mineral oil is added covering the surface of blood. Tubes are not inverted and placed on a rack and wet ice. Blood sample collection dates and times were recorded. The minimum sample volume is 1 ml of blood collected in a 2 ml lithium heparin tube. Within 15 minutes of collection, the samples are centrifuged at 2 to 8° C. to obtain plasma. Plasma is transferred to a vial and stored at −60 to −86° C. Specimens are stored on dry ice prior to analysis. Analysis of specimens is conducted using a blood ammonia analyzer instrument.

Phenylalanine, trans-cinnamic acid, and hippuric acid is measured by liquid chromatography coupled to tandem mass spectrometry (LC-MS/MS) using a Thermo TSQ Quantum Max triple quadrupole mass spectrometer.

Fecal Sample Collection: Two fecal samples per animal are collected at the target time points listed in Table YYY. Sample collection dates and times are recorded. 50 mL falcon tube with approximately 5 mL PBS are used as the container (If feces is liquid, no PBS is added). To get the fecal sample weight, pre- and post-sampling weight of container was taken. Samples are collected from the bottom of the cage from each animal. To get fresh and un-contaminated samples, remaining food is removed and the cage pan was cleaned and squeegeed to remove debris and/or water before the collection. Sample is put on wet ice immediately after the collection. Samples are stored at −20 to −15° C. until analysis. Analysis of specimens is conducted using a PCR analytical method.

Example 30

4-Week Toxicity Study in Cynomolgus Monkeys with a 4-Week Recovery (GLP)

To evaluate any potential toxicities arising from administration of the genetically engineered bacteria, the pharmacokinetics and pharmacodynamics of the genetically engineered bacteria is studied following daily nasogastric gavage (NG) dose administration for 28-days to female cynomolgus monkeys under GLP conditions.

The genetically engineered strain comprises one or more copies of PAL3 integrated into the chromosome and one or more copies of PheP integrated into the chromosome, each of which are under the control of an FNRS promoter. In some embodiments, the genetically engineered strain also comprises one or more copies of LAAD, driven by and arabinose inducible promoter, e.g., ParaBAD. In some embodiments, the strains further comprise a auxotrophy mutation, e.g., deltaThyA. In some embodiments, the genetically engineered bacteria further comprise an antibiotic resistance, e.g., kanamycin. In some embodiments, the genetically engineered bacteria do not comprise an auxotrophy mutation. In some embodiments, the genetically engineered bacteria do not comprise an antibiotic resistance.

The study is conducted in compliance with nonclinical Laboratory Studies Good Laboratory Practice Regulations issued by the U.S. Food and Drug Administration (Title 21 of the Code of Federal Regulations, Part 58; effective Jun. 20, 1979) and the OECD Principles on Good Laboratory Practice (C[97]186/Final; effective 1997). The animals are individually housed based on the recommendations set forth in the Guide for the Care and Use of Laboratory Animals (National Research Council 2011).

Animals are administered the genetically engineered bacteria or control vehicle essentially as described in Example 29, except that all materials are manufactured under GMP standards. Dosing is tabulated in Table 63. Additionally, animals are acclimated for 14 days and the dosing period is daily for 28 days followed by a recovery period of 28 days. Additionally, animals are euthanized at the end of the study to conduct histological analysis.

TABLE 63

| Dosing Period and Regimen | |
|---|---|
| ACCLIMATION | 14 days |
| TEST ARTICLE PREP | Daily |
| DOSING PERIOD | Daily for 28 days |
| RECOVERY PERIOD | 28 days |
| REGULATIONS | FDA GLP |

| GROUP | TEST ARTICLE | DOSE LEVEL | DOSE ROUTE | NUMBER OF ANIMALS | |
|---|---|---|---|---|---|
| | | | | MALES (♂) | FEMALES (♀) |
| 1 | Vehicle | 0 | NG | $3^a + 2^b$ | $3^a + 2^b$ |
| 2 | Genetically engineered bacteria | $1 \times 10^9$ | NG | $3^a$ | $3^a$ |
| 3 | Genetically engineered bacteria | $1 \times 10^{10}$ | NG | $3^a$ | $3^a$ |
| 4 | Genetically engineered bacteria | $1 \times 10^{11}$ | NG | $3^a + 2^b$ | $3^a + 2^b$ |

[a]Terminal Necropsy, Day 29
[b]Recovery Necropsy, Day 56

Study Analysis is conducted as described in Table 64. Hematology, Coagulation, Serum Chemistry and Plasma Samples parameters are essentially as described in Example 30, and are analyzed using the methods described in Example 30. Collection and analysis of fecal samples is essentially conducted as described in Example 30.

TABLE 64

| Study Analysis | |
|---|---|
| PROCEDURE | TIME POINTS |
| DOSE CONCENTRATION ANALYSIS | Day 1 and Day 28 |
| CLINICAL OBSERVATIONS | Twice Daily (cageside observations) |
| FOOD CONSUMPTION | Daily (qualitative) |
| BODY WEIGHTS | Weekly |
| OPHTHALMOLOGY | Once during acclimation, Week 4, and Week 8 |
| ECGs/HR/BP | Once during acclimation, Week 4, and Week 8 |

TABLE 64-continued

Study Analysis

| PROCEDURE | TIME POINTS |
|---|---|
| HEMATOLOGY | Twice during acclimation, Day 2 (pre-dose), Day 15 (pre-dose), Day 29, Day 42, and Day 56 |
| COAGULATION | Twice during acclimation, Day 2 (pre-dose), Day 15 (pre-dose), Day 29, Day 42, and Day 56 |
| SERUM CHEMISTRY | Twice during acclimation, Day 2 (pre-dose), Day 15 (pre-dose), Day 29, Day 42, and Day 56 |
| BODY (RECTAL) TEMPERATURE | Twice during acclimation (with at least 7 days between measurements); once weekly during dosing (~6 hrs post-dose), and Weeks 5 and 8 |
| STOOL SAMPLE COLLECTION (BACTERIAL CULTURE) | Once during acclimation, prior to dosing on Days 2, 7, and 14, Day 29, Day 33, and Week 8 Rectal/Fecal swabs are collected via cotton tip applicator; the cotton part of the swab is transferred to a tube with an appropriate broth/media and immediately put on wet ice. Fecal samples are stored at 2 to 8° C. until time of analysis. |
| CYTOKINE BLOOD COLLECTIONS | Once during acclimation, Days 1, 3, 7, 14 and 28 (6 hrs post-dose), and Day 56 |
| ARCHIVE BLOOD SAMPLE COLLECTION (SAMPLE TO BE HELD FOR POSSIBLE ANALYSIS) | Once during acclimation, Days 1, 3, 7, 14 and 28 (6 hrs post-dose), and Day 56; Blood samples are processed to serum; samples are stored frozen. |
| NECROPSY & TISSUE COLLECTION | All animals (e.g., colon, intestine, cecum, liver, spleen) |
| ORGAN WEIGHTS | All animals |
| TISSUE COLLECTION FOR PK/PD ASSESSMENT | All animals |
| HISTOPATHOLOGY | All animals |
| STATISTICAL ANALYSIS | Comparative (Anova/Bartletts) |

Example 31

Genetically Engineered Bacteria with HlyA Tag for Secretion of PMEs

Constructs for secretion of PMEs were generated as shown in Table 65. This sequences are subsequently tagged, e.g., with a HIS tag, e.g., inserted before the C terminal secretion sequence. E. coli are transformed with the constructs on a low-copy plasmid. Secreted PMEs are isolated from the media using affinity chromatography (His-Tag). PME molecular weight is confirmed by western blot. Activity of the purified enzyme is tested in an in vitro assay in a phenylalanine-containing buffer. Metabolites are measured over time as described in Examples 24-26.

TABLE 65

Secretion Sequences

| SEQ ID NO | Description | Sequence |
|---|---|---|
| SEQ ID NO: 52 | HylA Secretion tag | LNPLINEISKIISAAGNFDVKEERAAASL LQLSGNASDFSYGRNSITLTASA |
| SEQ ID NO: 53 | PAL (upper case) expressed as fusion protein with the 53 amino acids of the C termini of alpha-hemolysin (hlyA) of E. coli CFT073 (lower case). | MKAKDVQPTIIINKNGLISLEDIYDIAIK QKKVEISTEITELLTHGREKLEEKLNSGE VIYGINTGFGGNANLVVPFEKIAEHQQNL LTFLSAGTGDYMSKPCIKASQFTMLLSVC KGWSATRPIVAQAIVDHINHDIVPLVPRY GSVGASGDLIPLSYIARALCGIGKVYYMG AEIDAAEAIKRAGLTPLSLKAKEGLALIN GTRVMSGISAITVIKLEKLFKASISAIAL AVEALLASHEHYDARIQQVKNHPGQNAVA SALRNLLAGSTQVNLLSGVKEQANKACRH QEITQLNDTLQEVYSIRCAPQVLGIVPES LATARKILEREVISANDNPLIDPENGDVL HGGNFMGQYVARTMDALKLDIALIANHLH AIVALMMDNRFSRGLPNSLSPTPGMYQGF KGVQLSQTALVAAIRHDCAASGIHTLATE QYNQDIVSLGLHAAQDVLEMEQKLRNIVS MTILVVCQAIHLRGNISEIAPETAKFYHA VREISSPLITDRALDEDIIRIADAIINDQ LPLPEIMLEE lnplineiskiisaagnfdvkeeraaasl lqlsgnasdfsygrnsitltasa* |

TABLE 65-continued

Secretion Sequences

| SEQ ID NO | Description | Sequence |
|---|---|---|
| SEQ ID NO: 54 | LAAD (uppercase) expressed as fusion protein with the 53 amino acids of the C termini of alpha-hemolysin (hlyA) of E. coli CFT073 (lower case) | MNISRRKLLLGVGAAGVLAGGAALVPMVR RDGKFVEAKSRASFVEGTQGALPKEADVV IIGAGIQGIMTAINLAERGMSVTILEKGQ IAGEQSGRAYSQIISYQTSPEIFPLHHYG KILWRGMNEKIGADTSYRTQGRVEALADE KALDKAQAWIKTAKEAAGFDTPLNTRIIK GEELSNRLVGAQTPWTVAAFEEDSGSVDP ETGTPALARYAKQIGVKIYTNCAVRGIET AGGKISDVVSEKGAIKTSQVVLAGGIWSR LFMGNMGIDIPTLNVYLSQQRVSGVPGAP RGNVHLPNGIHFREQADGTYAVAPRIFTS SIVKDSFLLGPKFMHLLGGGELPLEFSIG EDLFNSFKMPTSWNLDEKTPFEQFRVATA TQNTQHLDAVFQRMKTEFPVFEKSEVVER WGAVVSPTFDELPIISEVKEYPGLVINTA TVWGMTEGPAAGEVTADIVMGKKPVIDPT PFSLDRFKK lnplineiskiisaagnfdvkeeraaasl lqlsgnasdfsygrnsitltasa |
| SEQ ID NO: 55 | HylA secretion signal | CTTAATCCATTAATTAATGAAATCAGCAA AATCATTTCAGCTGCAGGTAATTTTGATG TTAAAGAGGAAAGAGCTGCAGCTTCTTTA TTGCAGTTGTCCGGTAATGCCAGTGATTT TTCATATGGACGGAACTCAATAACTTTGA CAGCATCAGCATAA |
| SEQ ID NO: 56 | LAAD (bold italics) driven by ParaBAD (underlined) with C terminal HylA Secretion tag (bold) | <u>Acttttcatactcccgccattcagagaag aaaccaattgtccatattgcatcagacat tgccgtcactgcgtcttttactggctctt ctcgctaacccaaccggtaaccccgctta ttaaaagcattctgtaacaaagcgggacc aaagccatgacaaaaacgcgtaacaaaag tgtctataatcacggcagaaaa</u> *atgaacatttcaaggagaaagctactttt aggtgttggtgctgcgggcgttttagcag gtggtgcggctttagttccaatggttcgc cgtgacggcaaatttgtggaagctaaatc aagacatctattgttgaaggtacgcaag gggctcttcctaaagaagcagatgtagtg attattggtgccggtattcaagggatcat gaccgctattaaccttgctgaacgtggta tgagtgtcactatcttagaaaagggtcag attgccggtgagcaatcaggccgtgcata cagccaaattattagttaccaaacatcgc cagaaatcttcccattacaccattatggg aaaatattatggcgtggcatgaatgagaa aattggtgcggataccagttatcgtactc aaggtcgtgtagaagcgctggcagatgaa aaagcattagataaagctcaagcgtggat caaaacagctaaagaagcggcaggttttg atacaccattaaatactcgcatcattaaa ggtgaagagctatcaaatcgcttagtcgg tgctcaaacgccatggactgttgctgcat ttgaagaagattcaggctctgttgatcct gaaacaggcacacctgcactcgctcgtta tgccaaacaaatcggtgtgaaaatttata ccaactgtgcagtaagaggtattgaaact gcgggtggtaaaatctctgatgtggtgag tgagaaggggcgattaaaacgtctcaag ttgtactcgctgggggtatctggtcgcgt ttatttatgggcaatatgggtattgatat cccaacgctcaatgtatatctatcacaac aacgtgtctcaggggttcctggtgcacca cgtggtaatgtgcatttacctaatggtat tcatttccgcgaacaagcggatggtactt atgccgttgcaccacgtatctttacgagt tcaatagtcaaagatagcttcctgctagg gcctaaatttatgcacttattaggtggcg gagagttaccgttggaattctctattggt gaagatctattttaattcatttaaaatgcc gacctcttggaatttagatgaaaaaacac cattcgaacaattccgagttgccacggca acacaaaaatacgcaacacttagatgctgt tttccaaagaatgaaaacagaattcccag*

TABLE 65-continued

Secretion Sequences

| SEQ ID NO | Description | Sequence |
|---|---|---|
| | | *tatttgaaaaatcagaagttgttgaacgt* |
| | | *tggggtgccgttgtgagtccaacatttga* |
| | | *tgaattacctatcatttctgaggtcaaag* |
| | | *aatacccaggcttagtgattaacacggca* |
| | | *acagtgtggggtatgacagaaggcccggc* |
| | | *agcgggtgaagtgaccgctgatattgtca* |
| | | *tgggcaagaaacctgttattgatccaacg* |
| | | *ccgtttagtttggatcgttttaagaagta* |
| | | *a*CTTAATCCATTAATTAATGAAATCAGCA |
| | | AAATCATTTCAGCTGCAGGTAATTTTGAT |
| | | GTTAAAGAGGAAAGAGCTGCAGCTTCTTT |
| | | ATTGCAGTTGTCCGGTAATGCCAGTGATT |
| | | TTTCATATGGACGAACTCAATAACTTTG |
| | | ACAGCATCAGCATAA |
| SEQ ID NO: 57 | PfnrS-PAL3 with C terminal secretion tag. PfnrS (bolded lower case), PAL3 sequence is underlined upper case C terminal secretion tag is bold uppercase | GGTACC*agttgttcttattggtggtgttg* *ctttatggttgcatcgtagtaaatggttg* *taacaaaagcaattttccggctgtctgt* *atacaaaaacgccgtaaagtttgagcgaa* *gtcaataaactctctacccattcagggca* *atatctctctt*GGATCC*ctctagaaataa* *ttttgtttaactttaagaaggagatatac* *at*<u>ATGAAAGCTAAAGATGTTCAGCCAACC ATTATTATTAATAAAAATGGCCTTATCTC TTTGGAAGATATCTATGACATTGCGATAA AACAAAAAAAAGTAGAAATATCAACGGAG ATCACTGAACTTTTGACGCATGGTCGTGA AAAATTAGAGGAAAAATTAAATTCAGGAG AGGTTATATATGGAATCAATACAGGATTT GGAGGGAATGCCAATTTAGTTGTGCCATT TGAGAAAATCGCAGAGCATCAGCAAAATC TGTTAACTTTTCTTTCTGCTGGTACTGGG GACTATATGTCCAAACCTTGTATTAAAGC GTCACAATTTACTATGTTACTTTCTGTTT GCAAAGGTTGGTCTGCAACCAGACCAATT GTCGCTCAAGCAATTGTTGATCATATTAA TCATGACATTGTTCCTCTGGTTCCTCGCT ATGGCTCAGTGGGTGCAAGCGGTGATTTA ATTCCTTTATCTTATATTGCACGAGCATT ATGTGGTATCGGCAAAGTTTATTATATGG GCGCAGAAATTGACGCTGCTGAAGCAATT AAACGTGCAGGGTTGACACCATTATCGTT AAAAGCCAAAGAAGGTCTTGCTCTGATTA ACGGCACCCGGGTAATGTCAGGAATCAGT GCAATCACCGTCATTAAACTGGAAAAACT ATTTAAAGCCTCAATTTCTGCGATTGCCC TTGCTGTTGAAGCATTACTTGCATCTCAT GAACATTATGATGCCCGGATTCAACAAGT AAAAAATCATCCTGGTCAAAACGCGGTGG CAAGTGCATTGCGTAATTTATTGGCAGGT TCAACGCAGGTTAATCTATTATCTGGGGT TAAAGAACAAGCCAATAAAGCTTGTCGTC ATCAAGAAATTACCCAACTAAATGATACC TTACAGGAAGTTTATTCAATTCGCTGTGC ACCACAAGTATTAGGTATAGTGCCAGAAT CTTTAGCTACCGCTCGGAAAATATTGGAA CGGGAAGTTATCTCAGCTAATGATAATCC ATTGATAGATCCAGAAAATGGCGATGTTC TACACGGTGGAAATTTTATGGGGCAATAT GTCGCCCGAACAATGGATGCATTAAAACT GGATATTGCTTTAATTGCCAATCATCTTC ACGCCATTGTGGCTCTTATGATGGATAAC CGTTTCTCTCGTGGATTACCTAATTCACT GAGTCCGACACCCGGCATGTATCAAGGTT TTAAAGGCGTCAACTTTCTCAAACCGCT TTAGTTGCTGCAATTCGCCATGATTGTGC TGCATCAGGTATTCATACCCTCGCCACAG AACAATACAATCAAGATATTGTCAGTTTA GGTCTGCATGCCGCTCAAGATGTTTTAGA GATGGAGCAGAAATTACGCAATATTGTTT CAATGACAATTCTGGTAGTTTGTCAGGCC ATTCATCTTCGCGGCAATATTAGTGAAAT TGCGCCTGAAACTGCTAAATTTTACCATG CAGTACGCGAAATCAGTTCTCCTTTGATC ACTGATCGTGCGTTGGATGAAGATATAAT CCGCATTGCGGATGCAATTATTAATGATC</u> |

TABLE 65-continued

Secretion Sequences

| SEQ ID NO | Description | Sequence |
|---|---|---|
| | | AACTTCCTCTGCCAGAAATCATGCTGGAA GAATAACTTAATCCATTAATTAATGAAAT CAGCAAAATCATTTCAGCTGCAGGTAATT TTGATGTTAAAGAGGAAAGAGCTGCAGCT TCTTTATTGCAGTTGTCCGGTAATGCCAG TGATTTTTCATATGGACGGAACTCAATAA CTTTGACAGCATCAGCATAA |

TABLE 66

HlyB and HlyD protein sequences

| SEQ ID NO: 58 | HlyB protein | MDSCHKIDYGLYALEILAQYHNVSVNPEE IKHRFDTDGTGLGLTSWLLAAKSLELKVK QVKKTIDRLNFISLPALVWREDGRHFILT KVSKEANRYLIFDLEQRNPRVLEQSEFEA LYQGHIILIASRSSVTGKLAKFDFTWFIP AIIKYRKIFIETLVVSVFLQLFALITPLF FQVVMDKVLVHRGFSTLNVITVALSVVVV FEIILSGLRTYIFAHSTSRIDVELGAKLF RHLLALPISYFESRRVGDTVARVRELDQI RNFLTGQALTSVLDLLFSFIFFAVMWYYS PKLTLVILFSLPCYAAWSVFISPILRRRL DDKFSRNADNQSFLVESVTAINTIKAMAV SPQMTNIWDKQLAGYVAAGFKVTVLATIG QQGIQLIQKTVMIINLWLGAHLVISGDLS IGQLIAFNMLAGQIVAPVIRLAQIWQDFQ QVGISVTRLGDVLNSPTESYHGKLALPEI NGNITFRNIRFRYKPDSPVILDNINLSIK QGEVIGIVGRSGSGKSTLTKLIQRFYIPE NGQVLIDGHDLALADPNWLRRQVGVVLQD NVLLNRSIIDNISLANPGMSVEKVIYAAK LAGAHDFISELREGYNTIVGEQGAGLSGG QRQRIAIARALVNNPKILIFDEATSALDY ESEHIIMRNMHKICKGRTVIIIAHRLSTV KNADRIIVMEKGKIVEQGKHKELLSEPES LYSYLYQLQSD |

TABLE 66-continued

HlyB and HlyD protein sequences

| SEQ ID NO: 59 | HlyD protein | MKTWLMGFSEFLLRYKLVWSETWKIRKQL DTPVREKDENEFLPAHLELIETPVSRRPR LVAYFIMGFLVIAVILSVLGQVEIVATAN GKLTLSGRSKEIKPIENSIVKEIIVKEGE SVRKGDVLLKLTALGAEADTLKTQSSLLQ TRLEQTRYQILSRSIELNKLPELKLPDEP YFQNVSEEEVLRLTSLIKEQFSTWQNQKY QKELNLDKKRAERLTILARINRYENLSRV EKSRLDDFRSLLHKQAIAKHAVLEQENKY VEAANELRVYKSQLEQIESEILSAKEEYQ LVTQLFKNEILDKLRQTTDNIELLTLELE KNEERQQASVIRAPVSGKVQQLKVHTEGG VVTTAETLMVIVPEDDTLEVTALVQNKDI GFINVGQNAIIKVEAFPYTRYGYLVGKVK NINLDAIEDQKLGLVFNVIVSVEENDLST GNKHIPLSSGMAVTAEIKTGMRSVISYLL SPLEESVTESLHER |

Example 32

Genetically Engineered Bacteria Comprising Additional Constructs

Constructs for secretion of PMEs were generated as shown in Table 66.

TABLE 66

| Description | Sequence | SEQ ID NO |
|---|---|---|
| phenylalanine transporter [Escherichia coli str. K-12 substr. MG1655] Acc. No. NP_415108 (PheP) | MKNASTVSEDTASNQEPTLHRGLHNRHIQLIA LGGAIGTGLFLGIGPAIQMAGPAVLLGYGVAG IIAFLIMRQLGEMVVEEPVSGSFAHFAYKYWG PFAGFLSGWNYWVMFVLVGMAELTAAGIYMQY WFPDVPTWIWAAAFFIIINAVNLVNVRLYGET EFWFALIKVLAIIGMIGFGLWLLFSGHGGEKA SIDNLWRYGGFPATGWNGLILSLAVIMFSFGG LELIGITAAEARDPEKSIPKAVNQVVYRILLF YIGSLVVLLALYPWVEVKSNSSPFVMIFHNLD SNVVASALNFVILVASLSVYNSGVYSNSRMLF GLSVQGNAPKFLTRVSRRGVPINSLMLSGAIT SLVVLINYLLPQKAFGLLMALVVATLLLNWIM ICLAHLRFRAAMRRQGRETQFKALLYPFGNYL CIAFLGMILLLMCTMDDMRLSAILLPVWIVFL FMAFKTLRRK | 60 |
| aromatic amino acid transport protein AroP [Escherichia coli F11] Acc. NO: EDV65095 | MEGQQHGEQLKRGLKNRHIQLIALGGAIGTGL FLGSASVIQSAGPGIILGYAIAGFIAFLIMRQ LGEMVVEEPVAGSFSHFAYKYWGSFAGFASGW NYWVLYVLVAMAELTAVGKYIQFWYPEIPTWV SAAVFFVVINAINLTNVKVFGEMEFWFAIIKV IAVVAMIIFGAWLLFSGNGGPQASVSNLWDQG GFLPHGFTGLVMKMAIIMFSFGGGLELVGITAA EADNPEQSIPKATNQVIYRILIFYIGSLAVLL SLMPWTRVTADTSPFVLIFHELGDTFVANALN IVVLTAALSVYNSCVYCNSRMLFGLAQQGNAP KALASVDKRGVPVNTILVSALVTALCVLINYL | 61 |

TABLE 66-continued

| Description | Sequence | SEQ ID NO |
|---|---|---|
| | APESAFGLLMALVVSALVINWAMISLAHMKFR RAKQEQGVVTRFPALLYPLGNWVCLLFMAAVL VIMLMTPGMAISVYLIPVWLIVLGIGYLFKEK TAKAVKAH | |
| FNRS promoter (bold, lower case)-PheP (upper case underlined) | GGTACCagttgttcttattggtggtgttgctt tatggttgcatcgtagtaaatggttgtaacaa aagcaattttccggctgtctgtatacaaaaa cgccgtaaagtttgagcgaagtcaataaactc tctacccattcagggcaatatctctcttGGAT CCctctagaaataattttgtttaactttaaga aggagatatacat<u>ATGAAAAACGCGTCAACCG TATCGGAAGATACTGCGTCGAATCAAGAGCCG ACGCTTCATCGCGGATTACATAACCGTCATAT TCAACTGATTGCGTTGGGTGGCGCAATTGGTA CTGGTCTGTTTCTTGGCATTGGCCCGGCGATT CAGATGGCGGGTCCGGCTGTATTGCTGGGCTA CGGCGTCGCCGGGATCATCGCTTTCCTGATTA TGCGCCAGCTTGGCGAAATGGTGGTTGAGGAG CCGGTATCCGGTTCATTTGCCCACTTTGCCTA TAAATACTGGGGACCGTTTGCGGGCTTCCTCT CTGGCTGGAACTACTGGGTAATGTTCGTGCTG GTGGGAATGGCAGAGCTGACCGCTGCGGGCAT CTATATGCAGT63ACTGGTTCCCGGATGTTCC AACGTGGATTTGGGCTGCCGCCTTCTTTATTA TCATCAACGCCGTTAACCTGGTGAACGTGCGC TTATATGGCGAAACCGAGTTCTGGTTTGCGTT GATTAAAGTGCTGGCAATCATCGGTATGATCG GCTTTGGCCTGTGGCTGCTTTTGTCTGGTCAC GGCGGCGAGAAAGCCAGTATCGACAACCTCTG GCGCTACGGTGGTTTCTTCGCCACCGGCTGGA ATGGGCTGATTTTGTCGCTGGCGGTAATTATG TTCTCCTTCGGCGGTCTGGAGCTGATTGGGAT TACTGCCGCTGAAGCGCGCGATCCGGAAAAAA GCATTCCAAAAGCGGTAAATCAGGTGGTGTAT CGCATCCTGCTGTTTTACATCGGTTCACTGGT GGTTTTACTGGCGCTCTATCCGTGGGTGGAAG TGAAATCCAACAGTAGCCCGTTTGTGATGATT TTCCATAATCTCGACAGCAACGTGGTAGCTTC TGCGCTGAACTTCGTCATTCTGGTAGCATCGC TGTCAGTGTATAACAGCGGGGTTTACTCTAAC AGCCGCATGCTGTTTGGCCTTTCTGTGCAGGG TAATGCGCCGAAGTTTTTGACTCGCGTCAGCC GTCGCGGTGTGCCGATTAACTCGCTGATGCTT TCCGGAGCGATCACTTCGCTGGTGGTGTTAAT CAACTATCTGCTGCCGCAAAAAGCGTTTGGTC TGCTGATGGCGCTGGTGGTAGCAACGCTGCTG TTGAACTGGATTATGATCTGTCTGGCGCATCT GCGTTTTCGTGCAGCGATGCGACGTCAGGGGC GTGAAACACAGTTTAAGGCGCTGCTCTATCCG TTCGGCAACTATCTCTGCATTGCCTTCCTCGG CATGATTTTGCTGCTGATGTGCACGATGGATG ATATGCGCTTGTCAGCGATCCTGCTGCCGGTG TGGATTGTATTCCTGTTTATGGCATTTAAAAC GCTGCGTCGGAAATAA</u> | 62 |
| FNRS promoter (bold, lower case)-AroP (upper case underlined, codon optimized) | GGTACCagttgttcttattggtggtgttgctt tatggttgcatcgtagtaaatggttgtaacaa aagcaattttccggctgtctgtatacaaaaa cgccgtaaagtttgagcgaagtcaataaactc tctacccattcagggcaatatctctcttGGAT CCctctagaaataattttgtttaactttaaga aggagatatacat<u>ATGGAGGGGCAGCAGCATG GGGAGCAACTGAAGCGCGGGTTAAAAAATCGT CACATTCAATTAATCGCGCTGGGCGGAGCAAT TGGTACGGGATTGTTCCTGGGTTCAGCGAGCG TCATCCAATCGGCAGGTCCAGGGATCATCTTG GGATATGCGATCGCAGGCTTTATCGCTTTTCT TATTATGCGCCAATTAGGTGAGATGGTGGTCG AGGAGCCTGTAGCTGGCTCCTTCTCACATTTC GCGTACAAGTATTGGGATCCTTTGCGGGATT TGCTTCTGGTTGGAACTATTGGGTTCTTTATG TCCTGGTGGCCATGGCGGAGCTGACCGCGGTT GGAAAATATATCCAGTTCTGGTACCCCGAGAT CCCGACGTGGGTCTCAGCCGCGGTATTCTTTG TTGTTATCAATGCAATCAATTTAACCAACGTA AAAGTATTTGGTGAAATGGAGTTCTGGTTCGC</u> | 63 |

TABLE 66-continued

| Description | Sequence | SEQ ID NO |
|---|---|---|
| | GATTATCAAAGTAATTGCCGTAGTTGCTATGA<br>TTATTTTTGGGGCATGGTTGCTTTTCTCAGGA<br>AATGGCGGACCACAAGCGTCGGTTTCAAACCT<br>GTGGGATCAAGGGGGATTCCTGCCGCACGGAT<br>TTACGGGCTTGGTGATGATGATGGCTATCATT<br>ATGTTTTCTTTCGGTGGTCTTGAATTAGTGGG<br>TATTACCGCAGCAGAGGCAGATAATCCCGAAC<br>AAAGCATCCCAAAAGCTACTAACCAAGTTATT<br>TACCGTATCCTGATTTTTTATATTGGTTCTCT<br>GGCAGTCCTGCTTTCCTTAATGCCCTGGACAC<br>GTGTAACGGCCGATACATCCCCTTTTGTACTT<br>ATCTTTCACGAACTGGGAGACACGTTCGTCGC<br>CAATGCATTAAACATTGTTGTGCTGACAGCTG<br>CCTTATCTGTGTATAATAGCTGCGTTTATTGC<br>AATTCACGTATGTTATTCGGGCTTGCTCAGCA<br>GGGTAACGCGCCAAAGGCGTTGGCCTCAGTAG<br>ATAAGCGCGGAGTGCCTGTAAATACAATTTTG<br>GTCAGCGCATTAGTCACGGCTCTTTGCGTTCT<br>GATTAACTATCTGGCTCCTGAAAGCGCATTCG<br>GATTACTTATGGCCCTGGTTGTTTCCGCCCTG<br>GTTATCAATTGGGCAATGATTAGTTTGGCACA<br>TATGAAGTTCCGCCGTGCTAAACAAGAACAAG<br>GTGTCGTAACTCGTTTCCCTGCCTTATTGTAT<br>CCGCTGGGGAATTGGGTATGCCTTCTTTTTAT<br>GGCCGCAGTACTGGTAATTATGTTGATGACGC<br>CCGGCATGGCTATTAGTGTATACCTTATTCCG<br>GTATGGTTAATCGTCTTGGGTATCGGCTACTT<br>ATTTAAAGAAAAAACAGCAAAAGCCGTAAAGG<br>CTCAT | |

The invention claimed is:

1. A bacterium for metabolizing phenylalanine comprising:
   a) one or more gene(s) encoding a phenylalanine ammonia lyase (PAL), wherein the one or more gene(s) encoding the PAL is operably linked to a promoter that is not associated in nature with the one or more gene(s) encoding PAL, said promoter directly or indirectly induced under low-oxygen or anaerobic conditions; and
   b) one or more gene(s) encoding a non-native phenylalanine transporter, wherein the one or more gene(s) encoding the phenylalanine transporter is operably linked to a promoter that is not associated in nature with the one or more gene(s) encoding the phenylalanine transporter, said promoter directly or indirectly induced under low-oxygen or anaerobic conditions;
   wherein the bacterium expresses the gene(s) encoding PAL under conditions that induce the promoter operably linked to the gene(s) encoding PAL, and wherein the bacterium expresses the gene(s) encoding phenylalanine transporter under conditions that induce the promoter operably linked to the gene(s) encoding the phenylalanine transporter; and wherein the bacterium is *Escherichia coli* strain Nissle.

2. The bacterium of claim 1, wherein the promoter operably linked to the gene(s) encoding a PAL and the promoter operably linked to the gene(s) encoding a phenylalanine transporter are separate copies of the same promoter.

3. The bacterium of claim 1, wherein the promoter operably linked to the gene(s) encoding a PAL and the promoter operably linked to the gene(s) encoding the phenylalanine transporter are different promoters.

4. The bacterium of claim 1, wherein the promoter is selected from the group consisting of an FNR-responsive promoter, an ANR-responsive promoter, and a DNR-responsive promoter.

5. The bacterium of claim 1, wherein the promoter operably linked to the gene(s) encoding a PAL and/or the promoter operably linked to the gene(s) encoding a phenylalanine transporter is directly or indirectly induced by an environmental factor that is not naturally present in a mammalian gut.

6. The bacterium of claim 1, wherein the gene(s) encoding a phenylalanine transporter is located on a chromosome in the bacterium.

7. The bacterium of claim 1, wherein the gene(s) encoding a phenylalanine transporter is located on a plasmid in the bacterium.

8. The bacterium of claim 1, wherein the gene(s) encoding a PAL is located on a plasmid in the bacterium.

9. The bacterium of claim 1, wherein the gene(s) encoding a PAL is located on a chromosome in the bacterium.

10. The bacterium of claim 1, wherein the PAL is from *Anabaena variabilis* (PAL1) or from *Photorhabdus luminescens* (PAL3).

11. The bacterium of claim 1, wherein the phenylalanine transporter is PheP.

12. The bacterium of claim 1, wherein the bacterium is a probiotic bacterium.

13. The bacterium of claim 1, wherein the bacterium is an auxotroph in a gene that is complemented when the bacterium is present in a mammalian gut.

14. The bacterium of claim 13, wherein the bacterium is an auxotroph in diaminopimelic acid or an enzyme in the thymidine biosynthetic pathway.

15. A pharmaceutically acceptable composition comprising the bacterium of claim 1.

* * * * *

SEQUENCE LISTING

<160> NUMBER OF SEQ ID NOS: 66

<210> SEQ ID NO 1
<211> LENGTH: 567
<212> TYPE: PRT
<213> ORGANISM: Anabaena variabilis

<400> SEQUENCE: 1

```
Met Lys Thr Leu Ser Gln Ala Gln Ser Lys Thr Ser Gln Gln Phe
1               5                   10                  15

Ser Phe Thr Gly Asn Ser Ser Ala Asn Val Ile Ile Gly Asn Gln Lys
            20                  25                  30

Leu Thr Ile Asn Asp Val Ala Arg Val Ala Arg Asn Gly Thr Leu Val
        35                  40                  45

Ser Leu Thr Asn Asn Thr Asp Ile Leu Gln Gly Ile Gln Ala Ser Cys
    50                  55                  60

Asp Tyr Ile Asn Asn Ala Val Glu Ser Gly Glu Pro Ile Tyr Gly Val
65                  70                  75                  80

Thr Ser Gly Phe Gly Gly Met Ala Asn Val Ala Ile Ser Arg Glu Gln
                85                  90                  95

Ala Ser Glu Leu Gln Thr Asn Leu Val Trp Phe Leu Lys Thr Gly Ala
            100                 105                 110

Gly Asn Lys Leu Pro Leu Ala Asp Val Arg Ala Ala Met Leu Leu Arg
        115                 120                 125

Ala Asn Ser His Met Arg Gly Ala Ser Gly Ile Arg Leu Glu Leu Ile
    130                 135                 140

Lys Arg Met Glu Ile Phe Leu Asn Ala Gly Val Thr Pro Tyr Val Tyr
145                 150                 155                 160

Glu Phe Gly Ser Ile Gly Ala Ser Gly Asp Leu Val Pro Leu Ser Tyr
```

```
            165                 170                 175
Ile Thr Gly Ser Leu Ile Gly Leu Asp Pro Ser Phe Lys Val Asp Phe
            180                 185                 190

Asn Gly Lys Glu Met Asp Ala Pro Thr Ala Leu Arg Gln Leu Asn Leu
            195                 200                 205

Ser Pro Leu Thr Leu Pro Lys Glu Gly Leu Ala Met Met Asn Gly
210                 215                 220

Thr Ser Val Met Thr Gly Ile Ala Ala Asn Cys Val Tyr Asp Thr Gln
225                 230                 235                 240

Ile Leu Thr Ala Ile Ala Met Gly Val His Ala Leu Asp Ile Gln Ala
                245                 250                 255

Leu Asn Gly Thr Asn Gln Ser Phe His Pro Phe Ile His Asn Ser Lys
            260                 265                 270

Pro His Pro Gly Gln Leu Trp Ala Ala Asp Gln Met Ile Ser Leu Leu
            275                 280                 285

Ala Asn Ser Gln Leu Val Arg Asp Glu Leu Asp Gly Lys His Asp Tyr
            290                 295                 300

Arg Asp His Glu Leu Ile Gln Asp Arg Tyr Ser Leu Arg Cys Leu Pro
305                 310                 315                 320

Gln Tyr Leu Gly Pro Ile Val Asp Gly Ile Ser Gln Ile Ala Lys Gln
                325                 330                 335

Ile Glu Ile Glu Ile Asn Ser Val Thr Asp Asn Pro Leu Ile Asp Val
            340                 345                 350

Asp Asn Gln Ala Ser Tyr His Gly Gly Asn Phe Leu Gly Gln Tyr Val
            355                 360                 365

Gly Met Gly Met Asp His Leu Arg Tyr Tyr Ile Gly Leu Leu Ala Lys
            370                 375                 380

His Leu Asp Val Gln Ile Ala Leu Leu Ala Ser Pro Glu Phe Ser Asn
385                 390                 395                 400

Gly Leu Pro Pro Ser Leu Leu Gly Asn Arg Glu Arg Lys Val Asn Met
                405                 410                 415

Gly Leu Lys Gly Leu Gln Ile Cys Gly Asn Ser Ile Met Pro Leu Leu
            420                 425                 430

Thr Phe Tyr Gly Asn Ser Ile Ala Asp Arg Phe Pro Thr His Ala Glu
            435                 440                 445

Gln Phe Asn Gln Asn Ile Asn Ser Gln Gly Tyr Thr Ser Ala Thr Leu
            450                 455                 460

Ala Arg Arg Ser Val Asp Ile Phe Gln Asn Tyr Val Ala Ile Ala Leu
465                 470                 475                 480

Met Phe Gly Val Gln Ala Val Asp Leu Arg Thr Tyr Lys Lys Thr Gly
                485                 490                 495

His Tyr Asp Ala Arg Ala Cys Leu Ser Pro Ala Thr Glu Arg Leu Tyr
            500                 505                 510

Ser Ala Val Arg His Val Val Gly Gln Lys Pro Thr Ser Asp Arg Pro
            515                 520                 525

Tyr Ile Trp Asn Asp Asn Glu Gln Gly Leu Asp Glu His Ile Ala Arg
            530                 535                 540

Ile Ser Ala Asp Ile Ala Ala Gly Gly Val Ile Val Gln Ala Val Gln
545                 550                 555                 560

Asp Ile Leu Pro Cys Leu His
                565
```

<210> SEQ ID NO 2

<211> LENGTH: 567
<212> TYPE: PRT
<213> ORGANISM: Anabaena variabilis

<400> SEQUENCE: 2

```
Met Lys Thr Leu Ser Gln Ala Gln Ser Lys Thr Ser Ser Gln Gln Phe
1               5                   10                  15

Ser Phe Thr Gly Asn Ser Ser Ala Asn Val Ile Ile Gly Asn Gln Lys
            20                  25                  30

Leu Thr Ile Asn Asp Val Ala Arg Val Ala Arg Asn Gly Thr Leu Val
        35                  40                  45

Ser Leu Thr Asn Asn Thr Asp Ile Leu Gln Gly Ile Gln Ala Ser Cys
    50                  55                  60

Asp Tyr Ile Asn Asn Ala Val Glu Ser Gly Glu Pro Ile Tyr Gly Val
65                  70                  75                  80

Thr Ser Gly Phe Gly Gly Met Ala Asn Val Ala Ile Ser Arg Glu Gln
                85                  90                  95

Ala Ser Glu Leu Gln Thr Asn Leu Val Trp Phe Leu Lys Thr Gly Ala
            100                 105                 110

Gly Asn Lys Leu Pro Leu Ala Asp Val Arg Ala Ala Met Leu Leu Arg
        115                 120                 125

Ala Asn Ser His Met Arg Gly Ala Ser Gly Ile Arg Leu Glu Leu Ile
    130                 135                 140

Lys Arg Met Glu Ile Phe Leu Asn Ala Gly Val Thr Pro Tyr Val Tyr
145                 150                 155                 160

Glu Phe Gly Ser Ile Gly Ala Ser Gly Asp Leu Val Pro Leu Ser Tyr
                165                 170                 175

Ile Thr Gly Ser Leu Ile Gly Leu Asp Pro Ser Phe Lys Val Asp Phe
            180                 185                 190

Asn Gly Lys Glu Met Asp Ala Pro Thr Ala Leu Arg Gln Leu Asn Leu
        195                 200                 205

Ser Pro Leu Thr Leu Leu Pro Lys Glu Gly Leu Ala Met Met Asn Gly
    210                 215                 220

Thr Ser Val Met Thr Gly Ile Ala Ala Asn Cys Val Tyr Asp Thr Gln
225                 230                 235                 240

Ile Leu Thr Ala Ile Ala Met Gly Val His Ala Leu Asp Ile Gln Ala
                245                 250                 255

Leu Asn Gly Thr Asn Gln Ser Phe His Pro Phe Ile His Asn Ser Lys
            260                 265                 270

Pro His Pro Gly Gln Leu Trp Ala Ala Asp Gln Met Ile Ser Leu Leu
        275                 280                 285

Ala Asn Ser Gln Leu Val Arg Asp Glu Leu Asp Gly Lys His Asp Tyr
    290                 295                 300

Arg Asp His Glu Leu Ile Gln Asp Arg Tyr Ser Leu Arg Cys Leu Pro
305                 310                 315                 320

Gln Tyr Leu Gly Pro Ile Val Asp Gly Ile Ser Gln Ile Ala Lys Gln
                325                 330                 335

Ile Glu Ile Glu Ile Asn Ser Val Thr Asp Asn Pro Leu Ile Asp Val
            340                 345                 350

Asp Asn Gln Ala Ser Tyr His Gly Gly Asn Phe Leu Gly Gln Tyr Val
        355                 360                 365

Gly Met Gly Met Asp His Leu Arg Tyr Tyr Ile Gly Leu Leu Ala Lys
    370                 375                 380

His Leu Asp Val Gln Ile Ala Leu Leu Ala Ser Pro Glu Phe Ser Asn
```

```
385                 390                 395                 400
Gly Leu Pro Pro Ser Leu Leu Gly Asn Arg Glu Arg Lys Val Asn Met
                405                 410                 415

Gly Leu Lys Gly Leu Gln Ile Cys Gly Asn Ser Ile Met Pro Leu Leu
                420                 425                 430

Thr Phe Tyr Gly Asn Ser Ile Ala Asp Arg Phe Pro Thr His Ala Glu
                435                 440                 445

Gln Phe Asn Gln Asn Ile Asn Ser Gln Gly Tyr Thr Ser Ala Thr Leu
                450                 455                 460

Ala Arg Arg Ser Val Asp Ile Phe Gln Asn Tyr Val Ala Ile Ala Leu
465                 470                 475                 480

Met Phe Gly Val Gln Ala Val Asp Leu Arg Thr Tyr Lys Lys Thr Gly
                485                 490                 495

His Tyr Asp Ala Arg Ala Cys Leu Ser Pro Ala Thr Glu Arg Leu Tyr
                500                 505                 510

Ser Ala Val Arg His Val Val Gly Gln Lys Pro Thr Ser Asp Arg Pro
                515                 520                 525

Tyr Ile Trp Asn Asp Asn Glu Gln Gly Leu Asp Glu His Ile Ala Arg
                530                 535                 540

Ile Ser Ala Asp Ile Ala Ala Gly Gly Val Ile Val Gln Ala Val Gln
545                 550                 555                 560

Asp Ile Leu Pro Cys Leu His
                565

<210> SEQ ID NO 3
<211> LENGTH: 532
<212> TYPE: PRT
<213> ORGANISM: Photorhabdus luminescens

<400> SEQUENCE: 3

Met Lys Ala Lys Asp Val Gln Pro Thr Ile Ile Asn Lys Asn Gly
1               5                   10                  15

Leu Ile Ser Leu Glu Asp Ile Tyr Asp Ile Ala Ile Lys Gln Lys Lys
                20                  25                  30

Val Glu Ile Ser Thr Glu Ile Thr Glu Leu Leu Thr His Gly Arg Glu
                35                  40                  45

Lys Leu Glu Glu Lys Leu Asn Ser Gly Glu Val Ile Tyr Gly Ile Asn
                50                  55                  60

Thr Gly Phe Gly Gly Asn Ala Asn Leu Val Val Pro Phe Glu Lys Ile
65                  70                  75                  80

Ala Glu His Gln Gln Asn Leu Leu Thr Phe Leu Ser Ala Gly Thr Gly
                85                  90                  95

Asp Tyr Met Ser Lys Pro Cys Ile Lys Ala Ser Gln Phe Thr Met Leu
                100                 105                 110

Leu Ser Val Cys Lys Gly Trp Ser Ala Thr Arg Pro Ile Val Ala Gln
                115                 120                 125

Ala Ile Val Asp His Ile Asn His Asp Ile Val Pro Leu Val Pro Arg
                130                 135                 140

Tyr Gly Ser Val Gly Ala Ser Gly Asp Leu Ile Pro Leu Ser Tyr Ile
145                 150                 155                 160

Ala Arg Ala Leu Cys Gly Ile Gly Lys Val Tyr Tyr Met Gly Ala Glu
                165                 170                 175

Ile Asp Ala Ala Glu Ala Ile Lys Arg Ala Gly Leu Thr Pro Leu Ser
                180                 185                 190
```

```
Leu Lys Ala Lys Glu Gly Leu Ala Leu Ile Asn Gly Thr Arg Val Met
            195                 200                 205

Ser Gly Ile Ser Ala Ile Thr Val Ile Lys Leu Glu Lys Leu Phe Lys
210                 215                 220

Ala Ser Ile Ser Ala Ile Ala Leu Ala Val Glu Ala Leu Leu Ala Ser
225                 230                 235                 240

His Glu His Tyr Asp Ala Arg Ile Gln Gln Val Lys Asn His Pro Gly
            245                 250                 255

Gln Asn Ala Val Ala Ser Ala Leu Arg Asn Leu Leu Ala Gly Ser Thr
            260                 265                 270

Gln Val Asn Leu Leu Ser Gly Val Lys Glu Gln Ala Asn Lys Ala Cys
            275                 280                 285

Arg His Gln Glu Ile Thr Gln Leu Asn Asp Thr Leu Gln Glu Val Tyr
290                 295                 300

Ser Ile Arg Cys Ala Pro Gln Val Leu Gly Ile Val Pro Glu Ser Leu
305                 310                 315                 320

Ala Thr Ala Arg Lys Ile Leu Glu Arg Glu Val Ile Ser Ala Asn Asp
            325                 330                 335

Asn Pro Leu Ile Asp Pro Glu Asn Gly Asp Val Leu His Gly Gly Asn
            340                 345                 350

Phe Met Gly Gln Tyr Val Ala Arg Thr Met Asp Ala Leu Lys Leu Asp
            355                 360                 365

Ile Ala Leu Ile Ala Asn His Leu His Ala Ile Val Ala Leu Met Met
370                 375                 380

Asp Asn Arg Phe Ser Arg Gly Leu Pro Asn Ser Leu Ser Pro Thr Pro
385                 390                 395                 400

Gly Met Tyr Gln Gly Phe Lys Gly Val Gln Leu Ser Gln Thr Ala Leu
            405                 410                 415

Val Ala Ala Ile Arg His Asp Cys Ala Ala Ser Gly Ile His Thr Leu
            420                 425                 430

Ala Thr Glu Gln Tyr Asn Gln Asp Ile Val Ser Leu Gly Leu His Ala
            435                 440                 445

Ala Gln Asp Val Leu Glu Met Glu Gln Lys Leu Arg Asn Ile Val Ser
450                 455                 460

Met Thr Ile Leu Val Val Cys Gln Ala Ile His Leu Arg Gly Asn Ile
465                 470                 475                 480

Ser Glu Ile Ala Pro Glu Thr Ala Lys Phe Tyr His Ala Val Arg Glu
            485                 490                 495

Ile Ser Ser Pro Leu Ile Thr Asp Arg Ala Leu Asp Glu Asp Ile Ile
            500                 505                 510

Arg Ile Ala Asp Ala Ile Ile Asn Asp Gln Leu Pro Leu Pro Glu Ile
            515                 520                 525

Met Leu Glu Glu
530

<210> SEQ ID NO 4
<211> LENGTH: 514
<212> TYPE: PRT
<213> ORGANISM: Photorhabdus luminescens

<400> SEQUENCE: 4

Met Lys Gln Leu Thr Ile Tyr Pro Gly Lys Leu Thr Leu Asp Glu Leu
1               5                   10                  15

Arg Gln Val Tyr Leu Gln Pro Val Lys Ile Thr Leu Asp Ser Gln Ile
            20                  25                  30
```

-continued

Phe Pro Ala Ile Glu Arg Ser Val Glu Cys Val Asn Ala Ile Leu Ala
            35                  40                  45

Glu Asn Arg Thr Ala Tyr Gly Ile Asn Thr Gly Phe Gly Leu Leu Ala
 50                  55                  60

Ser Thr Arg Ile Glu Glu Asp Asn Leu Glu Lys Leu Gln Arg Ser Leu
 65                  70                  75                  80

Val Val Ser His Ala Ala Gly Val Gly Lys Ala Leu Asp Asp Asn Met
             85                  90                  95

Thr Arg Leu Ile Met Val Leu Lys Ile Asn Ser Leu Ser Arg Gly Tyr
            100                 105                 110

Ser Gly Ile Arg Leu Ala Val Ile Gln Ala Leu Ile Ala Leu Val Asn
            115                 120                 125

Ala Glu Ile Tyr Pro His Ile Pro Cys Lys Gly Ser Val Gly Ala Ser
        130                 135                 140

Gly Asp Leu Ala Pro Leu Ala His Met Ser Leu Leu Leu Gly Glu
145                 150                 155                 160

Gly Gln Ala Arg Tyr Gln Gly Glu Trp Leu Pro Ala Lys Glu Ala Leu
                165                 170                 175

Ala Lys Ala Asn Leu Gln Pro Ile Thr Leu Ala Ala Lys Glu Gly Leu
            180                 185                 190

Ala Leu Leu Asn Gly Thr Gln Val Ser Thr Ala Phe Ala Leu Arg Gly
            195                 200                 205

Leu Phe Glu Ala Glu Asp Leu Leu Ala Ala Ile Val Cys Gly Ser
        210                 215                 220

Leu Ser Val Glu Ala Ala Leu Gly Ser Arg Lys Pro Phe Asp Ala Arg
225                 230                 235                 240

Val His Val Val Arg Gly Gln Gln Gly Gln Ile Asp Val Ala Ala Leu
                245                 250                 255

Tyr Arg His Val Leu Glu Glu Ser Ser Glu Leu Ser Asp Ser His Ile
            260                 265                 270

Asn Cys Pro Lys Val Gln Asp Pro Tyr Ser Leu Arg Cys Gln Pro Gln
            275                 280                 285

Val Met Gly Ala Cys Leu Thr Gln Leu Arg His Ala Ala Asp Val Ile
            290                 295                 300

Leu Thr Glu Ala Asn Ala Val Ser Asp Asn Pro Leu Val Phe Ala Glu
305                 310                 315                 320

Gln Gly Glu Val Ile Ser Gly Gly Asn Phe His Ala Glu Pro Val Ala
                325                 330                 335

Met Ala Ser Asp Asn Leu Ala Leu Val Leu Ala Glu Ile Gly Ala Leu
            340                 345                 350

Ser Glu Arg Arg Ile Ala Leu Leu Met Asp Ser His Met Ser Gln Leu
            355                 360                 365

Pro Pro Phe Leu Val Glu Asn Gly Gly Val Asn Ser Gly Phe Met Ile
        370                 375                 380

Ala Gln Val Thr Ala Ala Ala Leu Ala Ser Glu Asn Lys Ala Leu Ala
385                 390                 395                 400

His Pro Ala Ser Val Asp Ser Leu Pro Thr Ser Ala Asn Gln Glu Asp
                405                 410                 415

His Val Ser Met Ala Pro Ala Ala Gly Arg Arg Leu Trp Glu Met Ala
            420                 425                 430

Glu Asn Thr Arg Gly Ile Leu Ala Ile Glu Trp Leu Ser Ala Cys Gln
            435                 440                 445

```
Gly Ile Asp Phe Arg Asn Gly Leu Lys Ser Ser Pro Ile Leu Glu Glu
            450                 455                 460

Ala Arg Val Ile Leu Arg Ala Lys Val Asp Tyr Tyr Asp Gln Asp Arg
465                 470                 475                 480

Phe Phe Ala Pro Asp Ile Asp Ala Ala Val Lys Leu Leu Ala Glu Gln
                485                 490                 495

His Leu Ser Ser Leu Leu Pro Ser Gly Gln Ile Leu Gln Arg Lys Asn
                500                 505                 510

Asn Arg

<210> SEQ ID NO 5
<211> LENGTH: 471
<212> TYPE: PRT
<213> ORGANISM: Proteus mirabilis

<400> SEQUENCE: 5

Met Ala Ile Ser Arg Arg Lys Phe Ile Leu Gly Gly Thr Val Val Ala
1               5                   10                  15

Val Ala Ala Gly Ala Gly Val Leu Thr Pro Met Leu Thr Arg Glu Gly
                20                  25                  30

Arg Phe Val Pro Gly Thr Pro Arg His Gly Phe Val Glu Gly Thr Gly
            35                  40                  45

Gly Pro Leu Pro Lys Gln Asp Asp Val Val Ile Gly Ala Gly Ile
50                  55                  60

Leu Gly Ile Met Thr Ala Ile Asn Leu Ala Glu Arg Gly Leu Ser Val
65                  70                  75                  80

Thr Ile Val Glu Lys Gly Asn Ile Ala Gly Gln Ser Ser Arg Phe
                85                  90                  95

Tyr Gly Gln Ala Ile Ser Tyr Lys Met Pro Asp Glu Thr Phe Leu Leu
            100                 105                 110

His His Leu Gly Lys His Arg Trp Arg Glu Met Asn Ala Lys Val Gly
        115                 120                 125

Ile Asp Thr Thr Tyr Arg Thr Gln Gly Arg Val Glu Val Pro Leu Asp
130                 135                 140

Glu Glu Asp Leu Glu Asn Val Arg Lys Trp Ile Asp Ala Lys Ser Lys
145                 150                 155                 160

Asp Val Gly Ser Asp Ile Pro Phe Arg Thr Lys Met Ile Glu Gly Ala
                165                 170                 175

Glu Leu Lys Gln Arg Leu Arg Gly Ala Thr Thr Asp Trp Lys Ile Ala
            180                 185                 190

Gly Phe Glu Glu Asp Ser Gly Ser Phe Asp Pro Glu Val Ala Thr Phe
        195                 200                 205

Val Met Ala Glu Tyr Ala Lys Lys Met Gly Ile Lys Ile Phe Thr Asn
210                 215                 220

Cys Ala Ala Arg Gly Leu Glu Thr Gln Ala Gly Val Ile Ser Asp Val
225                 230                 235                 240

Val Thr Glu Lys Gly Pro Ile Lys Thr Ser Arg Val Val Ala Gly
                245                 250                 255

Gly Val Gly Ser Arg Leu Phe Met Gln Asn Leu Asn Val Asp Val Pro
            260                 265                 270

Thr Leu Pro Ala Tyr Gln Ser Gln Leu Ile Ser Ala Ala Pro Asn
        275                 280                 285

Ala Pro Gly Gly Asn Val Ala Leu Pro Gly Gly Ile Phe Phe Arg Asp
290                 295                 300
```

Gln Ala Asp Gly Thr Tyr Ala Thr Ser Pro Arg Val Ile Val Ala Pro
305                 310                 315                 320

Val Val Lys Glu Ser Phe Thr Tyr Gly Tyr Lys Tyr Leu Pro Leu Leu
            325                 330                 335

Ala Leu Pro Asp Phe Pro Val His Ile Ser Leu Asn Glu Gln Leu Ile
            340                 345                 350

Asn Ser Phe Met Gln Ser Thr His Trp Asp Leu Asn Glu Glu Ser Pro
            355                 360                 365

Phe Glu Lys Tyr Arg Asp Met Thr Ala Leu Pro Asp Leu Pro Glu Leu
            370                 375                 380

Asn Ala Ser Leu Glu Lys Leu Lys Lys Glu Phe Pro Ala Phe Lys Glu
385                 390                 395                 400

Ser Thr Leu Ile Asp Gln Trp Ser Gly Ala Met Ala Ile Ala Pro Asp
            405                 410                 415

Glu Asn Pro Ile Ile Ser Asp Val Lys Glu Tyr Pro Gly Leu Val Ile
            420                 425                 430

Asn Thr Ala Thr Gly Trp Gly Met Thr Glu Ser Pro Val Ser Ala Glu
            435                 440                 445

Ile Thr Ala Asp Leu Leu Leu Gly Lys Lys Pro Val Leu Asp Ala Lys
450                 455                 460

Pro Phe Ser Leu Tyr Arg Phe
465             470

<210> SEQ ID NO 6
<211> LENGTH: 473
<212> TYPE: PRT
<213> ORGANISM: Proteus mirabilis

<400> SEQUENCE: 6

Met Asn Ile Ser Arg Arg Lys Leu Leu Leu Gly Val Gly Ala Ala Gly
1               5                   10                  15

Val Leu Ala Gly Gly Ala Ala Leu Val Pro Met Val Arg Arg Asp Gly
            20                  25                  30

Lys Phe Val Glu Ala Lys Ser Arg Ala Ser Phe Val Glu Gly Thr Gln
        35                  40                  45

Gly Ala Leu Pro Lys Glu Ala Asp Val Val Ile Gly Ala Gly Ile
50                  55                  60

Gln Gly Ile Met Thr Ala Ile Asn Leu Ala Glu Arg Gly Met Ser Val
65                  70                  75                  80

Thr Ile Leu Glu Lys Gly Gln Ile Ala Gly Glu Gln Ser Gly Arg Ala
            85                  90                  95

Tyr Ser Gln Ile Ile Ser Tyr Gln Thr Ser Pro Glu Ile Phe Pro Leu
            100                 105                 110

His His Tyr Gly Lys Ile Leu Trp Arg Gly Met Asn Glu Lys Ile Gly
            115                 120                 125

Ala Asp Thr Ser Tyr Arg Thr Gln Gly Arg Val Glu Ala Leu Ala Asp
            130                 135                 140

Glu Lys Ala Leu Asp Lys Ala Gln Ala Trp Ile Lys Thr Ala Lys Glu
145                 150                 155                 160

Ala Ala Gly Phe Asp Thr Pro Leu Asn Thr Arg Ile Ile Lys Gly Glu
            165                 170                 175

Glu Leu Ser Asn Arg Leu Val Gly Ala Gln Thr Pro Trp Thr Val Ala
            180                 185                 190

Ala Phe Glu Glu Asp Ser Gly Ser Val Asp Pro Glu Thr Gly Thr Pro
            195                 200                 205

Ala Leu Ala Arg Tyr Ala Lys Gln Ile Gly Val Lys Ile Tyr Thr Asn
    210                 215                 220

Cys Ala Val Arg Gly Ile Glu Thr Ala Gly Lys Ile Ser Asp Val
225                 230                 235                 240

Val Ser Glu Lys Gly Ala Ile Lys Thr Ser Gln Val Val Leu Ala Gly
                245                 250                 255

Gly Ile Trp Ser Arg Leu Phe Met Gly Asn Met Gly Ile Asp Ile Pro
            260                 265                 270

Thr Leu Asn Val Tyr Leu Ser Gln Gln Arg Val Ser Gly Val Pro Gly
        275                 280                 285

Ala Pro Arg Gly Asn Val His Leu Pro Asn Gly Ile His Phe Arg Glu
    290                 295                 300

Gln Ala Asp Gly Thr Tyr Ala Val Ala Pro Arg Ile Phe Thr Ser Ser
305                 310                 315                 320

Ile Val Lys Asp Ser Phe Leu Leu Gly Pro Lys Phe Met His Leu Leu
                325                 330                 335

Gly Gly Gly Glu Leu Pro Leu Glu Phe Ser Ile Gly Glu Asp Leu Phe
            340                 345                 350

Asn Ser Phe Lys Met Pro Thr Ser Trp Asn Leu Asp Glu Lys Thr Pro
        355                 360                 365

Phe Glu Gln Phe Arg Val Ala Thr Ala Thr Gln Asn Thr Gln His Leu
    370                 375                 380

Asp Ala Val Phe Gln Arg Met Lys Thr Glu Phe Pro Val Phe Glu Lys
385                 390                 395                 400

Ser Glu Val Val Glu Arg Trp Gly Ala Val Val Ser Pro Thr Phe Asp
                405                 410                 415

Glu Leu Pro Ile Ile Ser Glu Val Lys Glu Tyr Pro Gly Leu Val Ile
            420                 425                 430

Asn Thr Ala Thr Val Trp Gly Met Thr Glu Gly Pro Ala Ala Gly Glu
        435                 440                 445

Val Thr Ala Asp Ile Val Met Gly Lys Lys Pro Val Ile Asp Pro Thr
    450                 455                 460

Pro Phe Ser Leu Asp Arg Phe Lys Lys
465                 470

<210> SEQ ID NO 7
<211> LENGTH: 471
<212> TYPE: PRT
<213> ORGANISM: Proteus vulgaris

<400> SEQUENCE: 7

Met Ala Ile Ser Arg Arg Lys Phe Ile Ile Gly Gly Thr Val Val Ala
1               5                   10                  15

Val Ala Ala Gly Ala Gly Ile Leu Thr Pro Met Leu Thr Arg Glu Gly
                20                  25                  30

Arg Phe Val Pro Gly Thr Pro Arg His Gly Phe Val Glu Gly Thr Glu
            35                  40                  45

Gly Ala Leu Pro Lys Gln Ala Asp Val Val Val Gly Ala Gly Ile
        50                  55                  60

Leu Gly Ile Met Thr Ala Ile Asn Leu Val Glu Arg Gly Leu Ser Val
65                  70                  75                  80

Val Ile Val Glu Lys Gly Asn Ile Ala Gly Glu Gln Ser Ser Arg Phe
                85                  90                  95

Tyr Gly Gln Ala Ile Ser Tyr Lys Met Pro Asp Glu Thr Phe Leu Leu

```
               100                 105                 110
    His His Leu Gly Lys His Arg Trp Arg Glu Met Asn Ala Lys Val Gly
                    115                 120                 125
    Ile Asp Thr Thr Tyr Arg Thr Gln Gly Arg Val Glu Val Pro Leu Asp
                    130                 135                 140
    Glu Glu Asp Leu Val Asn Val Arg Lys Trp Ile Asp Glu Arg Ser Lys
    145                 150                 155                 160
    Asn Val Gly Ser Asp Ile Pro Phe Lys Thr Arg Ile Ile Glu Gly Ala
                    165                 170                 175
    Glu Leu Asn Gln Arg Leu Arg Gly Ala Thr Thr Asp Trp Lys Ile Ala
                    180                 185                 190
    Gly Phe Glu Glu Asp Ser Gly Ser Phe Asp Pro Glu Val Ala Thr Phe
                    195                 200                 205
    Val Met Ala Glu Tyr Ala Lys Lys Met Gly Val Arg Ile Tyr Thr Gln
                    210                 215                 220
    Cys Ala Ala Arg Gly Leu Glu Thr Gln Ala Gly Val Ile Ser Asp Val
    225                 230                 235                 240
    Val Thr Glu Lys Gly Ala Ile Lys Thr Ser Gln Val Val Ala Gly
                    245                 250                 255
    Gly Val Trp Ser Arg Leu Phe Met Gln Asn Leu Asn Val Asp Val Pro
                    260                 265                 270
    Thr Leu Pro Ala Tyr Gln Ser Gln Gln Leu Ile Ser Gly Ser Pro Thr
                    275                 280                 285
    Ala Pro Gly Gly Asn Val Ala Leu Pro Gly Gly Ile Phe Phe Arg Glu
                    290                 295                 300
    Gln Ala Asp Gly Thr Tyr Ala Thr Ser Pro Arg Val Ile Val Ala Pro
    305                 310                 315                 320
    Val Val Lys Glu Ser Phe Thr Tyr Gly Tyr Lys Tyr Leu Pro Leu Leu
                    325                 330                 335
    Ala Leu Pro Asp Phe Pro Val His Ile Ser Leu Asn Glu Gln Leu Ile
                    340                 345                 350
    Asn Ser Phe Met Gln Ser Thr His Trp Asn Leu Asp Glu Val Ser Pro
                    355                 360                 365
    Phe Glu Gln Phe Arg Asn Met Thr Ala Leu Pro Asp Leu Pro Glu Leu
                    370                 375                 380
    Asn Ala Ser Leu Glu Lys Leu Lys Ala Glu Phe Pro Ala Phe Lys Glu
    385                 390                 395                 400
    Ser Lys Leu Ile Asp Gln Trp Ser Gly Ala Met Ala Ile Ala Pro Asp
                    405                 410                 415
    Glu Asn Pro Ile Ile Ser Glu Val Lys Glu Tyr Pro Gly Leu Val Ile
                    420                 425                 430
    Asn Thr Ala Thr Gly Trp Gly Met Thr Glu Ser Pro Val Ser Ala Glu
                    435                 440                 445
    Leu Thr Ala Asp Leu Leu Leu Gly Lys Lys Pro Val Leu Asp Pro Lys
    450                 455                 460
    Pro Phe Ser Leu Tyr Arg Phe
    465                 470

<210> SEQ ID NO 8
<211> LENGTH: 452
<212> TYPE: PRT
<213> ORGANISM: Homo sapiens

<400> SEQUENCE: 8
```

-continued

```
Met Ser Thr Ala Val Leu Glu Asn Pro Gly Leu Gly Arg Lys Leu Ser
1               5                   10                  15

Asp Phe Gly Gln Glu Thr Ser Tyr Ile Glu Asp Asn Cys Asn Gln Asn
                20                  25                  30

Gly Ala Ile Ser Leu Ile Phe Ser Leu Lys Glu Glu Val Gly Ala Leu
            35                  40                  45

Ala Lys Val Leu Arg Leu Phe Glu Glu Asn Asp Val Asn Leu Thr His
        50                  55                  60

Ile Glu Ser Arg Pro Ser Arg Leu Lys Lys Asp Glu Tyr Glu Phe Phe
65                  70                  75                  80

Thr His Leu Asp Lys Arg Ser Leu Pro Ala Leu Thr Asn Ile Ile Lys
                85                  90                  95

Ile Leu Arg His Asp Ile Gly Ala Thr Val His Glu Leu Ser Arg Asp
                100                 105                 110

Lys Lys Lys Asp Thr Val Pro Trp Phe Pro Arg Thr Ile Gln Glu Leu
            115                 120                 125

Asp Arg Phe Ala Asn Gln Ile Leu Ser Tyr Gly Ala Glu Leu Asp Ala
        130                 135                 140

Asp His Pro Gly Phe Lys Asp Pro Val Tyr Arg Ala Arg Arg Lys Gln
145                 150                 155                 160

Phe Ala Asp Ile Ala Tyr Asn Tyr Arg His Gly Gln Pro Ile Pro Arg
                165                 170                 175

Val Glu Tyr Met Glu Glu Gly Lys Lys Thr Trp Gly Thr Val Phe Lys
                180                 185                 190

Thr Leu Lys Ser Leu Tyr Lys Thr His Ala Cys Tyr Glu Tyr Asn His
            195                 200                 205

Ile Phe Pro Leu Leu Glu Lys Tyr Cys Gly Phe His Glu Asp Asn Ile
        210                 215                 220

Pro Gln Leu Glu Asp Val Ser Gln Phe Leu Gln Thr Cys Thr Gly Phe
225                 230                 235                 240

Arg Leu Arg Pro Val Ala Gly Leu Leu Ser Ser Arg Asp Phe Leu Gly
                245                 250                 255

Gly Leu Ala Phe Arg Val Phe His Cys Thr Gln Tyr Ile Arg His Gly
                260                 265                 270

Ser Lys Pro Met Tyr Thr Pro Glu Pro Asp Ile Cys His Glu Leu Leu
            275                 280                 285

Gly His Val Pro Leu Phe Ser Asp Arg Ser Phe Ala Gln Phe Ser Gln
        290                 295                 300

Glu Ile Gly Leu Ala Ser Leu Gly Ala Pro Asp Glu Tyr Ile Glu Lys
305                 310                 315                 320

Leu Ala Thr Ile Tyr Trp Phe Thr Val Glu Phe Gly Leu Cys Lys Gln
                325                 330                 335

Gly Asp Ser Ile Lys Ala Tyr Gly Ala Gly Leu Leu Ser Ser Phe Gly
                340                 345                 350

Glu Leu Gln Tyr Cys Leu Ser Glu Lys Pro Lys Leu Leu Pro Leu Glu
            355                 360                 365

Leu Glu Lys Thr Ala Ile Gln Asn Tyr Thr Val Thr Glu Phe Gln Pro
        370                 375                 380

Leu Tyr Tyr Val Ala Glu Ser Phe Asn Asp Ala Lys Glu Lys Val Arg
385                 390                 395                 400

Asn Phe Ala Ala Thr Ile Pro Arg Pro Phe Ser Val Arg Tyr Asp Pro
                405                 410                 415

Tyr Thr Gln Arg Ile Glu Val Leu Asp Asn Thr Gln Gln Leu Lys Ile
```

```
            420             425              430
Leu Ala Asp Ser Ile Asn Ser Glu Ile Gly Ile Leu Cys Ser Ala Leu
        435                 440                 445

Gln Lys Ile Lys
    450

<210> SEQ ID NO 9
<211> LENGTH: 117
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 9
atccccatca ctcttgatgg agatcaattc cccaagctgc tagagcgtta ccttgccctt      60
aaacattagc aatgtcgatt tatcagaggg ccgacaggct cccacaggag aaaaccg       117

<210> SEQ ID NO 10
<211> LENGTH: 108
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 10
ctcttgatcg ttatcaattc ccacgctgtt tcagagcgtt accttgccct taaacattag      60
caatgtcgat ttatcagagg gccgacaggc tcccacagga gaaaaccg                 108

<210> SEQ ID NO 11
<211> LENGTH: 290
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 11
gtcagcataa caccctgacc tctcattaat tgttcatgcc gggcggcact atcgtcgtcc      60
ggccttttcc tctcttactc tgctacgtac atctatttct ataaatccgt tcaatttgtc    120
tgttttttgc acaaacatga aatatcagac aattccgtga cttaagaaaa tttatacaaa    180
tcagcaatat acccctttaag gagtatataa aggtgaattt gatttacatc aataagcggg   240
gttgctgaat cgttaaggta ggcggtaata gaaaagaaat cgaggcaaaa                290

<210> SEQ ID NO 12
<211> LENGTH: 433
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 12
cggcccgatc gttgaacata gcggtccgca ggcggcactg cttacagcaa acggtctgta      60
cgctgtcgtc tttgtgatgt gcttcctgtt aggtttcgtc agccgtcacc gtcagcataa    120
caccctgacc tctcattaat tgctcatgcc ggacggcact atcgtcgtcc ggccttttcc    180
```

```
tctcttcccc cgctacgtgc atctatttct ataaacccgc tcattttgtc tattttttgc      240
acaaacatga aatatcagac aattccgtga cttaagaaaa tttatacaaa tcagcaatat      300
acccattaag gagtatataa aggtgaattt gatttacatc aataagcggg gttgctgaat      360
cgttaaggta ggcggtaata gaaaagaaat cgaggcaaaa atgtttgttt aactttaaga      420
aggagatata cat                                                         433

<210> SEQ ID NO 13
<211> LENGTH: 290
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 13
gtcagcataa caccctgacc tctcattaat tgctcatgcc ggacggcact atcgtcgtcc       60
ggccttttcc tctcttcccc cgctacgtgc atctatttct ataaacccgc tcattttgtc      120
tattttttgc acaaacatga aatatcagac aattccgtga cttaagaaaa tttatacaaa      180
tcagcaatat acccattaag gagtatataa aggtgaattt gatttacatc aataagcggg      240
gttgctgaat cgttaaggta ggcggtaata gaaaagaaat cgaggcaaaa                 290

<210> SEQ ID NO 14
<211> LENGTH: 173
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 14
atttcctctc atcccatccg gggtgagagt cttttccccc gacttatggc tcatgcatgc       60
atcaaaaaag atgtgagctt gatcaaaaac aaaaaatatt tcactcgaca ggagtattta      120
tattgcgccc gttacgtggg cttcgactgt aaatcagaaa ggagaaaaca cct             173

<210> SEQ ID NO 15
<211> LENGTH: 305
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 15
gtcagcataa caccctgacc tctcattaat tgttcatgcc gggcggcact atcgtcgtcc       60
ggccttttcc tctcttactc tgctacgtac atctatttct ataaatccgt tcaatttgtc      120
tgttttttgc acaaacatga aatatcagac aattccgtga cttaagaaaa tttatacaaa      180
tcagcaatat accccttaag gagtatataa aggtgaattt gatttacatc aataagcggg      240
gttgctgaat cgttaaggat ccctctagaa ataattttgt ttaactttaa gaaggagata      300
tacat                                                                  305

<210> SEQ ID NO 16
<211> LENGTH: 180
<212> TYPE: DNA
```

```
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 16
catttcctct catcccatcc ggggtgagag tcttttcccc cgacttatgg ctcatgcatg      60
catcaaaaaa gatgtgagct tgatcaaaaa caaaaaatat ttcactcgac aggagtattt     120
atattgcgcc cggatccctc tagaaataat tttgtttaac tttaagaagg agatatacat     180

<210> SEQ ID NO 17
<211> LENGTH: 199
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 17
agttgttctt attggtggtg ttgctttatg gttgcatcgt agtaaatggt tgtaacaaaa      60 gcaattttc  cggctgtctg tatacaaaaa cgccgtaaag tttgagcgaa gtcaataaac     120
tctctaccca ttcagggcaa tatctctctt ggatccctct agaaataatt tgtttaact     180 ttaagaagga gatatacat                                                  199

<210> SEQ ID NO 18
<211> LENGTH: 207
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 18
agttgttctt attggtggtg ttgctttatg gttgcatcgt agtaaatggt tgtaacaaaa      60 gcaattttc  cggctgtctg tatacaaaaa cgccgcaaag tttgagcgaa gtcaataaac     120
tctctaccca ttcagggcaa tatctctctt ggatccaaag tgaactctag aaataatttt     180
gtttaacttt aagaaggaga tatacat                                         207

<210> SEQ ID NO 19
<211> LENGTH: 390
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 19
tcgtctttgt gatgtgcttc ctgttaggtt tcgtcagccg tcaccgtcag cataacaccc      60
tgacctctca ttaattgctc atgccggacg gcactatcgt cgtccggcct tttcctctct     120
tcccccgcta cgtgcatcta tttctataaa cccgctcatt ttgtctattt tttgcacaaa     180
catgaaatat cagacaattc cgtgacttaa gaaaatttat acaaatcagc aatataccca     240
ttaaggagta tataaggtg aatttgattt acatcaataa gcggggttgc tgaatcgtta     300
aggtagaaat gtgatctagt tcacatttgc ggtaatagaa aagaaatcga ggcaaaaatg     360
tttgtttaac tttaagaagg agatatacat                                      390
```

<210> SEQ ID NO 20
<211> LENGTH: 200
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 20
agttgttctt attggtggtg ttgctttatg gttgcatcgt agtaaatggt tgtaacaaaa    60 gcaattttc cggctgtctg tatacaaaaa cgccgcaaag tttgagcgaa gtcaataaac    120
tctctaccca ttcagggcaa tatctctcaa atgtgatcta gttcacattt tttgtttaac    180
tttaagaagg agatatacat                                                200

<210> SEQ ID NO 21
<211> LENGTH: 1485
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 21
ctcttgatcg ttatcaattc ccacgctgtt tcagagcgtt accttgccct taaacattag    60
caatgtcgat ttatcagagg gccgacaggc tcccacagga gaaaaccgat gaaaaacgcg    120
tcaaccgtat cggaagatac tgcgtcgaat caagagccga cgcttcatcg cggattacat    180
aaccgtcata ttcaactgat tgcgttgggt ggcgcaattg gtactggtct gtttcttggc    240
attggcccgg cgattcagat ggcgggtccg gctgtattgc tgggctacgg cgtcgccggg    300
atcatcgctt cctgattat gcgccagctt ggcgaaatgg tggttgagga gccggtatcc    360
ggttcatttg cccactttgc ctataaatac tggggaccgt ttgcgggctt cctctctggc    420
tggaactact gggtaatgtt cgtgctggtg ggaatggcag agctgaccgc tgcgggcatc    480
tatatgcagt actggttccc ggatgttcca acgtggattt gggctgccgc cttctttatt    540
atcatcaacg ccgttaacct ggtgaacgtg cgcttatatg gcgaaaccga gttctggttt    600
gcgttgatta aagtgctggc aatcatcggt atgatcggct ttggcctgtg gctgctgttt    660
tctggtcacg gcggcgagaa agccagtatc gacaacctct ggcgctacgg tggtttcttc    720
gccaccggct ggaatgggct gattttgtcg ctggcggtaa ttatgttctc cttcggcggt    780
ctggagctga ttgggattac tgccgctgaa gcgcgcgatc cggaaaaaag cattccaaaa    840
gcggtaaatc aggtggtgta tcgcatcctg ctgttttaca tcggttcact ggtggtttta    900
ctggcgctct atccgtgggt ggaagtgaaa tccaacagta gcccgtttgt gatgatttc    960 cataatctcg acagcaacgt ggtagcttct gcgctgaact tcgtcattct ggtagcatcg    1020
ctgtcagtgt ataacagcgg ggtttactct aacagccgca tgctgtttgg cctttctgtg    1080
cagggtaatg cgccgaagtt tttgactcgc gtcagccgtc gcggtgtgcc gattaactcg    1140
ctgatgcttt ccggagcgat cacttcgctg gtggtgttaa tcaactatct gctgccgcaa    1200
aaagcgtttg gtctgctgat ggcgctggtg gtagcaacgc tgctgttgaa ctggattatg    1260
atctgtctgg cgcatctgcg ttttcgtgca gcgatgcgac gtcaggggcg tgaaacacag    1320
tttaaggcgc tgctctatcc gttcggcaac tatctctgca ttgccttcct cggcatgatt    1380

```
ttgctgctga tgtgcacgat ggatgatatg cgcttgtcag cgatcctgct gccggtgtgg    1440
attgtattcc tgtttatggc atttaaaacg ctgcgtcgga aataa                    1485

<210> SEQ ID NO 22
<211> LENGTH: 4428
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 22
ctcttgatcg ttatcaattc ccacgctgtt tcagagcgtt accttgccct taaacattag     60
caatgtcgat ttatcagagg gccgacaggc tcccacagga gaaaaccgat gaaaacacta    120
tcacaggccc aatctaaaac ttcttcacag caattcagct ttaccgggaa ctcgtctgcg    180
aatgtaatta tcggcaatca aaagctgacc attaatgatg tagctcgcgt tgcccggaat    240
ggcactttgg tgtcactgac gaacaatacc gacattctgc aaggtattca agctagctgc    300
gattatatca ataacgccgt tgaatctggc gagccaatct acggggtaac aagcggtttt    360
ggtgggatgg cgaacgttgc cattagccgt gaacaggcga gcgaacttca gaccaacctc    420
gtttggttcc taaagacagg agctggtaat aagttacctc tggctgacgt aagagccgcg    480
atgctgcttc gcgctaatag tcacatgcgc ggcgccagtg tatccgtctt gagcttatc    540 aagaggatgg aaatcttcct caacgcgggt gtcacaccat atgtttatga gtttggtagt    600
atcggagcca gtggtgatct tgttcccctg agttatatta cgggttcatt gattggttta    660
gacccgtcct ttaaagtgga ttttaacggg aaagaaatgg acgccccgac cgctttacga    720
cagcttaatc tgagcccact tactttgctc cctaaagaag gtcttgccat gatgaatggc    780
acctctgtga tgactggaat tgccgcgaat tgtgtgtatg acacgcagat cctaacggcc    840
attgccatgg gtgttcacgc gttggacatt caagccctga atggtacaaa ccagtcgttt    900
catccgttta tccataattc aaaaccccat ccgggacagc tttgggctgc tgatcagatg    960
atctcactcc tggccaatag tcaactggtt cgggacgagc tcgacggcaa acatgattat   1020
cgcgatcatg agctcatcca ggaccggtat tcacttcgtt gtctcccaca atacctgggg   1080
cctatcgttg atggtatatc tcaaattgcg aagcaaattg aaattgagat caatagcgta   1140
accgacaacc cgcttatcga tgttgataat caggcctctt atcacggtgg caattttctg   1200
ggccagtatg ttggtatggg gatggatcac ctgcggtact atattgggct tctggctaaa   1260
catcttgatg tgcagattgc cttattagct tcaccagaat tttcaaatgg actgccgcca   1320
tcattgctcg gtaacagaga aaggaaagta aatatgggcc ttaagggcct tcagatatgt   1380
ggtaactcaa tcatgccccct cctgaccttt tatgggaact caattgctga tcgtttttccg   1440 acacatgctg aacagtttaa ccaaaacatt aactcacagg ctatacatc cgcgacgtta   1500 gcgcgtcggt ccgtggatat cttccagaat tatgttgcta tcgctctgat gttcggcgta   1560
caggccgttg atttgcgcac ttataaaaaa accggtcact acgatgctcg ggcttgcctg   1620
tcgcctgcca ccgagcggct ttatagcgcc gtacgtcatg ttgtgggtca gaaaccgacg   1680
tcggaccgcc cctatatttg aatgataat gaacaagggc tggatgaaca catcgcccgg   1740
atatctgccg atattccgc cggaggtgtc atcgtccagg cggtacaaga catacttcct   1800
tgcctgcatt aagcttggcg taatcatggt catagctgtt tcctgtgtga aattgttatc   1860
cgctcacaat tccacacaac atacgagccg gaagcataaa gtgtaaagcc tggggtgcct   1920
```

-continued

```
aatgagtgag ctaactcaca ttaattgcgt tgcgctcact gcccgctttc cagtcgggaa    1980
acctgtcgtg ccagctgcat taatgaatcg gccaacgcgc ggggagaggc ggtttgcgta    2040
ttgggcgctc ttccgcttcc tcgctcactg actcgctgcg ctcggtcgtt cggctgcggc    2100
gagcggtatc agctcactca aaggcggtaa tacggttatc cacagaatca ggggataacg    2160
caggaaagaa catgtgagca aaaggccagc aaaaggccag gaaccgtaaa aaggccgcgt    2220
tgctggcgtt tttccatagg ctccgccccc ctgacgagca tcacaaaaat cgacgctcaa    2280
gtcagaggtg gcgaaacccg acaggactat aaagatacca ggcgtttccc cctggaagct    2340
ccctcgtgcg ctctcctgtt ccgaccctgc cgcttaccgg atacctgtcc gcctttctcc    2400
cttcgggaag cgtggcgctt tctcatagct cacgctgtag gtatctcagt tcggtgtagg    2460
tcgttcgctc caagctgggc tgtgtgcacg aaccccccgt tcagcccgac cgctgcgcct    2520
tatccggtaa ctatcgtctt gagtccaacc cggtaagaca cgacttatcg ccactggcag    2580
cagccactgg taacaggatt agcagagcga ggtatgtagg cggtgctaca gagttcttga    2640
agtggtggcc taactacggc tacactagaa gaacagtatt tggtatctgc gctctgctga    2700
agccagttac cttcggaaaa agagttggta gctcttgatc cggcaaacaa accaccgctg    2760
gtagcggtgg tttttttgtt tgcaagcagc agattacgcg cagaaaaaaa ggatctcaag    2820
aagatccttt gatcttttct acggggtctg acgctcagtg gaacgaaaac tcacgttaag    2880
ggattttggt catgagatta tcaaaaagga tcttcaccta gatcctttta aattaaaaat    2940
gaagttttaa atcaatctaa agtatatatg agtaaacttg gtctgacagt taccaatgct    3000
taatcagtga ggcacctatc tcagcgatct gtctatttcg ttcatccata gttgcctgac    3060
tccccgtcgt gtagataact acgatacggg agggcttacc atctggcccc agtgctgcaa    3120
tgataccgcg agacccacgc tcaccggctc cagatttatc agcaataaac cagccagccg    3180
gaagggccga gcgcagaagt ggtcctgcaa ctttatccgc ctccatccag tctattaatt    3240
gttgccggga agctagagta agtagttcgc cagttaatag tttgcgcaac gttgttgcca    3300
ttgctacagg catcgtggtg tcacgctcgt cgtttggtat ggcttcattc agctccggtt    3360
cccaacgatc aaggcgagtt acatgatccc ccatgttgtg caaaaaagcg gttagctcct    3420
tcggtcctcc gatcgttgtc agaagtaagt tggccgcagt gttatcactc atggttatgg    3480
cagcactgca taattctctt actgtcatgc catccgtaag atgcttttct gtgactggtg    3540
agtactcaac caagtcattc tgagaatagt gtatgcggcg accgagttgc tcttgcccgg    3600
cgtcaatacg ggataatacc gcgccacata gcagaacttt aaaagtgctc atcattggaa    3660
aacgttcttc ggggcgaaaa ctctcaagga tcttaccgct gttgagatcc agttcgatgt    3720
aacccactcg tgcacccaac tgatcttcag catcttttac tttcaccagc gtttctgggt    3780
gagcaaaaac aggaaggcaa aatgccgcaa aaaagggaat aagggcgaca cggaaatgtt    3840
gaatactcat actcttcctt tttcaatatt attgaagcat ttatcagggt tattgtctca    3900
tgagcggata catatttgaa tgtatttaga aaaataaaca ataggggtt ccgcgcacat    3960 ttccccgaaa agtgccacct gacgtctaag aaaccattat tatcatgaca ttaacctata    4020
aaaataggcg tatcacgagg ccctttcgtc tcgcgcgttt cggtgatgac ggtgaaaacc    4080
tctgacacat gcagctcccg gagacggtca gcttgtctgt aagcggat gccgggagca    4140 gacaagcccg tcagggcgcg tcagcgggtg ttggcgggtg tcgggctgg cttaactatg    4200 cggcatcaga gcagattgta ctgagagtgc accatatgcg gtgtgaaata ccgcacagat    4260
```

```
gcgtaaggag aaaataccgc atcaggcgcc attcgccatt caggctgcgc aactgttggg    4320
aagggcgatc ggtgcgggcc tcttcgctat tacgccagct ggcgaaaggg ggatgtgctg    4380
caaggcgatt aagttgggta acgccagggt tttcccagtc acgacgtt               4428

<210> SEQ ID NO 23
<211> LENGTH: 4323
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 23
ctcttgatcg ttatcaattc ccacgctgtt tcagagcgtt accttgccct taaacattag      60
caatgtcgat ttatcagagg gccgacaggc tcccacagga gaaaaccgat gaaagctaaa     120
gatgttcagc caaccattat tattaataaa aatggcctta tctctttgga agatatctat     180
gacattgcga taaacaaaa aaaagtagaa atatcaacgg agatcactga acttttgacg     240
catggtcgtg aaaaattaga ggaaaaatta aattcaggag aggttatata tggaatcaat     300
acaggatttg gagggaatgc caatttagtt gtgccatttg agaaaatcgc agagcatcag     360
caaaatctgt taactttctt ttctgctggt actggggact atatgtccaa accttgtatt     420
aaagcgtcac aatttactat gttactttct gtttgcaaag gttggtctgc aaccagacca     480
attgtcgctc aagcaattgt tgatcatatt aatcatgaca ttgttcctct ggttcctcgc     540
tatggctcag tgggtgcaag cggtgattta attcctttat cttatattgc acgagcatta     600
tgtggtatcg gcaaagttta ttatatgggc gcagaaattg acgctgctga agcaattaaa     660
cgtgcagggt tgacaccatt atcgttaaaa gccaagaag gtcttgctct gattaacggc     720 accccgggtaa tgtcaggaat cagtgcaatc accgtcatta aactggaaaa actatttaaa     780
gcctcaattt ctgcgattgc ccttgctgtt gaagcattac ttgcatctca tgaacattat     840
gatgcccgga ttcaacaagt aaaaaatcat cctggtcaaa acgcggtggc aagtgcattg     900
cgtaatttat tggcaggttc aacgcaggtt aatctattat ctggggttaa agaacaagcc     960
aataaagctt gtcgtcatca agaaattacc caactaaatg ataccttaca ggaagtttat    1020
tcaattcgct gtgcaccaca agtattaggt atagtgccag aatctttagc taccgctcgg    1080
aaaatattgg aacgggaagt tatctcagct aatgataatc cattgataga tccagaaaat    1140
ggcgatgttc tacacggtgg aaattttatg gggcaatatg tcgcccgaac aatggatgca    1200
ttaaaactgg atattgcttt aattgccaat catcttcacg ccattgtggc tcttatgatg    1260
gataaccgtt tctctcgtgg attacctaat tcactgagtc cgacacccgg catgtatcaa    1320
ggttttaaag gcgtccaact ttctcaaacc gctttagttg ctgcaattcg ccatgattgt    1380
gctgcatcag gtattcatac cctcgccaca gaacaataca atcaagatat tgtcagttta    1440
ggtctgcatg ccgctcaaga tgttttagag atggagcaga aattacgcaa tattgtttca    1500
atgacaattc tggtagtttg tcaggccatt catcttcgcg gcaatattag tgaaattgcg    1560
cctgaaactg ctaaatttta ccatgcagta cgcgaaatca gttctccttt gatcactgat    1620
cgtgcgttgg atgaagatat aatccgcatt gcggatgcaa ttattaatga tcaacttcct    1680
ctgccagaaa tcatgctgga agaataagct tggcgtaatc atggtcatag ctgtttcctg    1740
tgtgaaattg ttatccgctc acaattccac acaacatacg agccgaaagc ataaagtgta    1800
aagcctgggg tgcctaatga gtgagctaac tcacattaat tgcgttgcgc tcactgcccg    1860
```

```
ctttccagtc gggaaacctg tcgtgccagc tgcattaatg aatcggccaa cgcgcgggga    1920
gaggcggttt gcgtattggg cgctcttccg cttcctcgct cactgactcg ctgcgctcgg    1980
tcgttcggct gcggcgagcg gtatcagctc actcaaaggc ggtaatacgg ttatccacag    2040
aatcagggga taacgcagga agaacatgt gagcaaaagg ccagcaaaag gccaggaacc     2100
gtaaaaaggc cgcgttgctg cgttttttcc ataggctccg ccccctgac gagcatcaca     2160 aaaatcgacg ctcaagtcag aggtggcgaa acccgacagg actataaaga taccaggcgt    2220
ttccccctgg aagctccctc gtgcgctctc ctgttccgac cctgccgctt accggatacc    2280
tgtccgcctt tctcccttcg ggaagcgtgg cgctttctca tagctcacgc tgtaggtatc    2340
tcagttcggt gtaggtcgtt cgctccaagc tgggctgtgt gcacgaaccc cccgttcagc    2400
ccgaccgctg cgccttatcc ggtaactatc gtcttgagtc aacccggta agacacgact    2460 tatcgccact ggcagcagcc actggtaaca ggattagcag agcgaggtat gtaggcggtg    2520
ctacagagtt cttgaagtgg tggcctaact acgctacac tagaagaaca gtatttggta    2580
tctgcgctct gctgaagcca gttaccttcg gaaaagagt tggtagctct tgatccggca    2640
aacaaaccac cgctggtagc ggtggttttt ttgtttgcaa gcagcagatt acgcgcagaa    2700
aaaaaggatc tcaagaagat cctttgatct tttctacggg gtctgacgct cagtggaacg    2760
aaaactcacg ttaagggatt ttggtcatga gattatcaaa aaggatcttc acctagatcc    2820
ttttaaatta aaaatgaagt tttaaatcaa tctaaagtat atatgagtaa acttggtctg    2880
acagttacca atgcttaatc agtgaggcac ctatctcagc gatctgtcta tttcgttcat    2940
ccatagttgc ctgactcccc gtcgtgtaga taactacgat acgggagggc ttaccatctg    3000
gccccagtgc tgcaatgata ccgcgagacc cacgctcacc ggctccagat ttatcagcaa    3060
taaaccagcc agccggaagg gccgagcgca gaagtggtcc tgcaacttta tccgcctcca    3120
tccagtctat taattgttgc cgggaagcta gagtaagtag ttcgccagtt aatagtttgc    3180
gcaacgttgt tgccattgct acaggcatcg tggtgtcacg ctcgtcgttt ggtatggctt    3240
cattcagctc cggttcccaa cgatcaaggc gagttacatg atcccccatg ttgtgcaaaa    3300
aagcggttag ctccttcggt cctccgatcg ttgtcagaag taagttggcc gcagtgttat    3360
cactcatggt tatggcagca ctgcataatt ctcttactgt catgccatcc gtaagatgct    3420
tttctgtgac tggtgagtac tcaaccaagt cattctgaga atagtgtatg cggcgaccga    3480
gttgctcttg cccggcgtca atacgggata ataccgcgcc acatagcaga actttaaaag    3540
tgctcatcat tggaaaacgt tcttcggggc gaaaactctc aaggatctta ccgctgttga    3600
gatccagttc gatgtaaccc actcgtgcac ccaactgatc ttcagcatct tttactttca    3660
ccagcgtttc tgggtgagca aaaacaggaa ggcaaaatgc cgcaaaaaag ggaataaggg    3720
cgacacggaa atgttgaata ctcatactct tcctttttca atattattga agcatttatc    3780
agggttattg tctcatgagc ggatacatat ttgaatgtat ttagaaaaat aaacaaatag    3840
gggttccgcg cacatttccc cgaaaagtgc cacctgacgt ctaagaaacc attattatca    3900
tgacattaac ctataaaaat aggcgtatca cgaggccctt tcgtctcgcg cgtttcggtg    3960
atgacggtga aaacctctga cacatgcagc tcccggagac ggtcacagct tgtctgtaag    4020
cggatgccgg gagcagacaa gcccgtcagg gcgcgtcagc gggtgttggc gggtgtcggg    4080
gctggcttaa ctatgcggca tcagagcaga ttgtactgag agtgcaccat atgcggtgtg    4140
aaataccgca cagatgcgta aggagaaaat accgcatcag gcgccattcg ccattcaggc    4200
```

```
tgcgcaactg ttgggaaggg cgatcggtgc gggcctcttc gctattacgc cagctggcga    4260 aaggggatg tgctgcaagg cgattaagtt gggtaacgcc agggttttcc cagtcacgac     4320
gtt                                                                   4323

<210> SEQ ID NO 24
<211> LENGTH: 5092
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 24
ctctagaaat aatttgttt aactttaaga aggagatata catatgaaaa cactatcaca       60
ggcccaatct aaaacttctt cacagcaatt cagctttacc gggaactcgt ctgcgaatgt     120
aattatcggc aatcaaaagc tgaccattaa tgatgtagct cgcgttgccc ggaatggcac     180
tttggtgtca ctgacgaaca ataccgacat tctgcaaggt attcaagcta gctgcgatta    240
tatcaataac gccgttgaat ctggcgagcc aatctacggg gtaacaagcg gttttggtgg    300
gatggcgaac gttgccatta gccgtgaaca ggcgagcgaa cttcagacca acctcgtttg    360
gttcctaaag acaggagctg gtaataagtt acctctggct gacgtaagag ccgcgatgct    420
gcttcgcgct aatagtcaca tgcgcggcgc cagtggtatc cgtcttgagc ttatcaagag    480
gatggaaatc ttcctcaacg cgggtgtcac accatatgtt tatgagtttg gtagtatcgg    540
agccagtggt gatcttgttc ccctgagtta tattacgggt tcattgattg gtttagaccc    600
gtcctttaaa gtggatttta cgggaaagaa aatggacgcc ccgaccgctt tacgacagct    660
taatctgagc ccacttactt tgctccctaa gaaggtctt gccatgatga atggcacctc     720
tgtgatgact ggaattgccg cgaattgtgt gtatgacacg cagatcctaa cggccattgc    780
catgggtgtt cacgcgttgg acattcaagc cctgaatgat acaaaccagt cgtttcatcc    840
gtttatccat aattcaaaac cccatccggg acagctttgg gctgctgatc agatgatctc    900
actcctggcc aatagtcaac tggttcggga cgagctcgac ggcaaacatg attatcgcga    960
tcatgagctc atccaggacc ggtattcact tcgttgtctc ccacaatacc tggggcctat   1020
cgttgatggt atatctcaaa ttgcgaagca aattgaaatt gagatcaata gcgtaaccga    1080
caacccgctt atcgatgttg ataatcaggc ctcttatcac ggtggcaatt ttctgggcca    1140
gtatgttggt atgggatgg atcacctgcg gtactatatt gggcttctgg ctaaacatct     1200
tgatgtgcag attgccttat tagcttcacc agaattttca aatggactgc cgccatcatt    1260
gctcggtaac agagaaagga agtaaatat gggccttaag ggccttcaga tatgtggtaa     1320
ctcaatcatg cccctcctga cctttatgg gaactcaatt gctgatcgtt ttccgacaca     1380
tgctgaacag tttaaccaaa acattaactc acagggctat acatccgcga cgttagcgcg    1440
tcggtccgtg gatatcttcc agaattatgt tgctatcgct ctgatgttcg gcgtacaggc    1500
cgttgatttg cgcacttata aaaaaccgg tcactacgat gctcgggctt gcctgtcgcc     1560
tgccaccgag cggctttata gcgccgtacg tcatgttgtg ggtcagaaac cgacgtcgga    1620 ccgccctat attggaatg ataatgaaca agggctggat gaacacatcg cccggatatc      1680
tgccgatatt gccgccggag gtgtcatcgt ccaggcggta caagacatac ttccttgcct    1740
gcattaagct tggcgtaatc atggtcatag ctgtttcctg tgtgaaattg ttatccgctc    1800
acaattccac acaacatacg agccggaagc ataaagtgta aagcctgggg tgcctaatga    1860
```

```
gtgagctaac tcacattaat tgcgttgcgc tcactgcccg ctttccagtc gggaaacctg   1920
tcgtgccagc tgcattaatg aatcggccaa cgcgcgggga gaggcggttt gcgtattggg   1980
cgctcttccg cttcctcgct cactgactcg ctgcgctcgg tcgttcggct gcggcgagcg   2040
gtatcagctc actcaaaggc ggtaatacgg ttatccacag aatcagggga taacgcagga   2100
aagaacatgt gagcaaaagg ccagcaaaag gccaggaacc gtaaaaaggc cgcgttgctg   2160
gcgtttttcc ataggctccg ccccctgac gagcatcaca aaaatcgacg ctcaagtcag   2220
aggtggcgaa acccgacagg actataaaga taccaggcgt ttccccctgg aagctccctc   2280
gtgcgctctc ctgttccgac cctgccgctt accggatacc tgtccgcctt ctcccttcg    2340 ggaagcgtgg cgctttctca tagctcacgc tgtaggtatc tcagttcggt gtaggtcgtt   2400
cgctccaagc tgggctgtgt gcacgaaccc cccgttcagc ccgaccgctg cgccttatcc   2460
ggtaactatc gtcttgagtc caacccggta agacacgact tatcgccact ggcagcagcc   2520
actggtaaca ggattagcag agcgaggtat gtaggcggtg ctacagagtt cttgaagtgg   2580
tggcctaact acggctacac tagaagaaca gtatttggta tctgcgctct gctgaagcca   2640
gttaccttcg gaaaaagagt tggtagctct tgatccggca acaaaccac cgctggtagc    2700 ggtggttttt ttgtttgcaa gcagcagatt acgcgcagaa aaaaggatc tcaagaagat    2760 cctttgatct tttctacggg gtctgacgct cagtggaacg aaaactcacg ttaagggatt   2820
ttggtcatga gattatcaaa aaggatcttc acctagatcc ttttaaatta aaatgaagt    2880 tttaaatcaa tctaaagtat atatgagtaa acttggtctg acagttacca atgcttaatc   2940
agtgaggcac ctatctcagc gatctgtcta tttcgttcat ccatagttgc ctgactcccc   3000
gtcgtgtaga taactacgat acgggagggc ttaccatctg gccccagtgc tgcaatgata   3060
ccgcgagacc cacgctcacc ggctccagat ttatcagcaa taaaccagcc agccggaagg   3120
gccgagcgca gaagtggtcc tgcaacttta tccgcctcca tccagtctat taattgttgc   3180
cgggaagcta gagtaagtag ttcgccagtt aatagtttgc gcaacgttgt tgccattgct   3240
acaggcatcg tggtgtcacg ctcgtcgttt ggtatggctt cattcagctc cggttcccaa   3300
cgatcaaggc gagttacatg atcccccatg ttgtgcaaaa aagcggttag ctccttcggt   3360
cctccgatcg ttgtcagaag taagttggcc gcagtgttat cactcatggt tatggcagca   3420
ctgcataatt ctcttactgt catgccatcc gtaagatgct tttctgtgac tggtgagtac   3480
tcaaccaagt cattctgaga atagtgtatg cggcgaccga gttgctcttg cccggcgtca   3540
atacgggata taccgcgcc acatagcaga actttaaaag tgctcatcat tggaaaacgt    3600 tcttcgggc gaaaactctc aaggatctta ccgctgttga tccagttc gatgtaaccc     3660 actcgtgcac ccaactgatc ttcagcatct tttactttca ccagcgtttc tgggtgagca   3720
aaaacaggaa ggcaaaatgc cgcaaaaaag ggaataaggg cgacacggaa atgttgaata   3780
ctcatactct ccttttttca atattattga agcatttatc agggttattg tctcatgagc   3840
ggatacatat ttgaatgtat ttagaaaaat aaacaaatag gggttccgcg cacatttccc   3900
cgaaaagtgc cacctgacgt ctaagaaacc attattatca tgacattaac ctataaaaat   3960
aggcgtatca cgaggccctt tcgtctcgcg cgtttcggtg atgacggtga aaacctctga   4020
cacatgcagc tcccggagac ggtcacagct tgtctgtaag cggatgccgg gagcagacaa   4080
gcccgtcagg gcgcgtcagc gggtgttggc gggtgtcggg gctggcttaa ctatgcggca   4140
tcagagcaga ttgtactgag agtgcaccat atgcggtgtg aaataccgca cagatgcgta   4200
```

```
aggagaaaat accgcatcag gcgccattcg ccattcaggc tgcgcaactg ttgggaaggg      4260
cgatcggtgc gggcctcttc gctattacgc cagctggcga aaggggggatg tgctgcaagg     4320 cgattaagtt gggtaacgcc agggttttcc cagtcacgac gttgtaaaac gacggccagt     4380
gaattcgtta agacccactt tcacatttaa gttgttttc taatccgcat atgatcaatt      4440
caaggccgaa taagaaggct ggctctgcac cttggtgatc aaataattcg atagcttgtc     4500
gtaataatgg cggcatacta tcagtagtag gtgtttccct ttcttcttta gcgacttgat    4560
gctcttgatc ttccaatacg caacctaaag taaaatgccc cacagcgctg agtgcatata    4620
atgcattctc tagtgaaaaa ccttgttggc ataaaaaggc taattgattt tcgagagttt    4680
catactgttt ttctgtaggc cgtgtaccta aatgtacttt tgctccatcg cgatgactta    4740
gtaaagcaca tctaaaactt ttagcgttat tacgtaaaaa atcttgccag ctttcccctt    4800
ctaaagggca aaagtgagta tggtgcctat ctaacatctc aatggctaag gcgtcgagca    4860
aagcccgctt atttttaca tgccaataca atgtaggctg ctctacacct agcttctggg     4920
cgagtttacg ggttgttaaa ccttcgattc cgacctcatt aagcagctct aatgcgctgt    4980
taatcacttt acttttatct aatctagaca tcattaattc ctaattttg ttgacactct     5040 atcattgata gagttatttt accactccct atcagtgata gagaaaagtg aa            5092

<210> SEQ ID NO 25
<211> LENGTH: 4987
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 25
ctctagaaat aattttgttt aactttaaga aggagatata catatgaaag ctaaagatgt       60
tcagccaacc attattatta ataaaaatgg ccttatctct ttggaagata tctatgacat     120
tgcgataaaa caaaaaaaag tagaaatatc aacggagatc actgaacttt tgacgcatgg     180
tcgtgaaaaa ttagaggaaa aattaaattc aggagaggtt atatatgaa tcaatacagg      240 atttggaggg aatgccaatt tagttgtgcc atttgagaaa atcgcagagc atcagcaaaa     300
tctgttaact tttcttctg ctggtactgg ggactatatg tccaaacctt gtattaaagc     360
gtcacaattt actatgttac tttctgtttg caaaggttgg tctgcaacca gaccaattgt     420
cgctcaagca attgttgatc atattaatca tgacattgtt cctctggttc ctcgctatgg    480
ctcagtgggt gcaagcggtg atttaattcc tttatcttat attgcacgag cattatgtgg    540
tatcggcaaa gttattatata tgggcgcaga aattgacgct gctgaagcaa ttaaacgtgc    600
agggttgaca ccattatcgt taaaagccaa agaaggtctt gctctgatta acggcacccg    660
ggtaatgtca ggaatcagtg caatcaccgt cattaaactg gaaaaactat ttaaagcctc    720
aatttctgcg attgcccttg ctgttgaagc attacttgca tctcatgaac attatgatgc    780
ccggattcaa caagtaaaaa atcatcctgg tcaaacgcg gtggcaagtg cattgcgtaa    840
tttattggca ggttcaacgc aggttaatct attatctggg gttaaagaac aagccaataa    900
agcttgtcgt catcaagaaa ttacccaact aaatgatacc ttacaggaag tttattcaat    960
tcgctgtgca ccacaagtat taggtatagt gccagaatct ttagctaccg ctcggaaaat    1020
attggaacgg gaagttatct cagctaatga taatccattg atagatccag aaaatgcgca    1080
tgttctacac ggtggaaatt ttatggggca atatgtcgcc cgaacaatgg atgcattaaa    1140
```

```
actggatatt gctttaattg ccaatcatct tcacgccatt gtggctctta tgatggataa   1200
ccgtttctct cgtggattac ctaattcact gagtccgaca cccggcatgt atcaaggttt   1260
taaaggcgtc caactttctc aaaccgcttt agttgctgca attcgccatg attgtgctgc   1320
atcaggtatt cataccctcg ccacagaaca atacaatcaa gatattgtca gtttaggtct   1380
gcatgccgct caagatgttt tagagatgga gcagaaatta cgcaatattg tttcaatgac   1440
aattctggta gtttgtcagg ccattcatct tcgcggcaat attagtgaaa ttgcgcctga   1500
aactgctaaa ttttaccatg cagtacgcga aatcagttct cctttgatca ctgatcgtgc   1560
gttggatgaa gatataatcc gcattgcgga tgcaattatt aatgatcaac ttcctctgcc   1620
agaaatcatg ctggaagaat aagcttggcg taatcatggt catagctgtt tcctgtgtga   1680
aattgttatc cgctcacaat tccacacaac atacgagccg gaagcataaa gtgtaaagcc   1740
tggggtgcct aatgagtgag ctaactcaca ttaattgcgt tgcgctcact gcccgctttc   1800
cagtcgggaa acctgtcgtg ccagctgcat taatgaatcg gccaacgcgc ggggagaggc   1860
ggtttgcgta ttgggcgctc ttccgcttcc tcgctcactg actcgctgcg ctcggtcgtt   1920
cggctgcggc gagcggtatc agctcactca aaggcggtaa tacggttatc cacagaatca   1980
ggggataacg caggaaagaa catgtgagca aaaggccagc aaaaggccag gaaccgtaaa   2040
aaggccgcgt tgctggcgtt tttccatagg ctccgccccc ctgacgagca tcacaaaaat   2100
cgacgctcaa gtcagaggtg gcgaaacccg acaggactat aaagatacca ggcgtttccc   2160
cctggaagct ccctcgtgcg ctctcctgtt ccgaccctgc cgcttaccgg atacctgtcc   2220
gcctttctcc cttcgggaag cgtggcgctt tctcatagct cacgctgtag gtatctcagt   2280
tcggtgtagg tcgttcgctc caagctgggc tgtgtgcacg aacccccagt tcagcccgac   2340
cgctgcgcct tatccggtaa ctatcgtctt gagtccaacc cggtaagaca cgacttatcg   2400
ccactggcag cagccactgg taacaggatt agcagagcga ggtatgtagg cggtgctaca   2460
gagttcttga agtggtggcc taactacggc tacactagaa gaacagtatt tggtatctgc   2520
gctctgctga agccagttac cttcggaaaa agagttggta gctcttgatc cggcaaacaa   2580
accaccgctg gtagcggtgg tttttttgtt tgcaagcagc agattacgcg cagaaaaaaa   2640
ggatctcaag aagatccttt gatcttttct acggggtctg acgctcagtg gaacgaaaac   2700
tcacgttaag ggattttggt catgagatta tcaaaaagga tcttcaccta gatcctttta   2760
aattaaaaat gaagttttaa atcaatctaa agtatatatg agtaaacttg gtctgacagt   2820
taccaatgct taatcagtga ggcacctatc tcagcgatct gtctatttcg ttcatccata   2880
gttgcctgac tccccgtcgt gtagataact acgatacggg agggcttacc atctggcccc   2940
agtgctgcaa tgataccgcg agacccacgc tcaccggctc cagatttatc agcaataaac   3000
cagccagccg gaagggccga gcgcagaagt ggtcctgcaa ctttatccgc ctccatccag   3060
tctattaatt gttgccggga agctagagta agtagttcgc cagttaatag tttgcgcaac   3120
gttgttgcca ttgctacagg catcgtggtg tcacgctcgt cgtttggtat ggcttcattc   3180
agctccggtt cccaacgatc aaggcgagtt acatgatccc ccatgttgtg caaaaaagcg   3240
gttagctcct tcggtcctcc gatcgttgtc agaagtaagt tggccgcagt gttatcactc   3300
atggttatgg cagcactgca taattctctt actgtcatgc catccgtaag atgcttttct   3360
gtgactggtg agtactcaac caagtcattc tgagaatagt gtatgcggcg accgagttgc   3420
tcttgcccgg cgtcaatacg ggataatacc gcgccacata gcagaacttt aaaagtgctc   3480
```

```
atcattggaa aacgttcttc ggggcgaaaa ctctcaagga tcttaccgct gttgagatcc    3540
agttcgatgt aacccactcg tgcacccaac tgatcttcag catctttac tttcaccagc     3600 gtttctgggt gagcaaaaac aggaaggcaa aatgccgcaa aaaagggaat aagggcgaca    3660
cggaaatgtt gaatactcat actcttcctt tttcaatatt attgaagcat ttatcagggt    3720
tattgtctca tgagcggata catatttgaa tgtatttaga aaaataaaca aataggggtt    3780
ccgcgcacat ttccccgaaa agtgccacct gacgtctaag aaaccattat tatcatgaca    3840
ttaacctata aaataggcg tatcacgagg cccttttcgtc tcgcgcgttt cggtgatgac     3900
ggtgaaaacc tctgacacat gcagctcccg gagacggtca cagcttgtct gtaagcggat    3960
gccgggagca gacaagcccg tcaggcgcg tcagcgggtg ttggcgggtg tcgggctgg      4020 cttaactatg cggcatcaga gcagattgta ctgagagtgc accatatgcg gtgtgaaata    4080
ccgcacagat gcgtaaggag aaaataccgc atcaggcgcc attcgccatt caggctgcgc    4140
aactgttggg aagggcgatc ggtgcgggcc tcttcgctat tacgccagct ggcgaaaggg    4200
ggatgtgctg caaggcgatt aagttgggta acgccagggt tttcccagtc acgacgttgt    4260
aaaacgacgg ccagtgaatt cgttaagacc cactttcaca tttaagttgt ttttctaatc    4320
cgcatatgat caattcaagg ccgaataaga aggctggctc tgcaccttgg tgatcaaata    4380
attcgatagc ttgtcgtaat aatggcggca tactatcagt agtaggtgtt tccctttctt    4440
ctttagcgac ttgatgctct tgatcttcca atacgcaacc taaagtaaaa tgccccacag    4500
cgctgagtgc atataatgca ttctctagtg aaaaaccttg ttggcataaa aaggctaatt    4560
gattttcgag agtttcatac tgttttttctg taggccgtgt acctaaatgt acttttgctc    4620
catcgcgatg acttagtaaa gcacatctaa aacttttagc gttattacgt aaaaaatctt    4680
gccagctttc cccttctaaa gggcaaaagt gagtatggtg cctatctaac atctcaatgg    4740
ctaaggcgtc gagcaaagcc cgcttatttt ttacatgcca atacaatgta ggctgctcta    4800
cacctagctt ctgggcgagt ttacgggttg ttaaaccttc gattccgacc tcattaagca    4860
gctctaatgc gctgttaatc actttacttt tatctaatct agacatcatt aattcctaat    4920
ttttgttgac actctatcat tgatagagtt attttaccac tccctatcag tgatagagaa    4980
aagtgaa                                                              4987
```

<210> SEQ ID NO 26
<211> LENGTH: 5962
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 26

```
ctcttgatcg ttatcaattc ccacgctgtt tcagagcgtt accttgccct taaacattag     60
caatgtcgat ttatcagagg gccgacaggc tcccacagga gaaaaccgat gaaaacacta    120
tcacaggccc aatctaaaac ttcttcacag caattcagct ttaccgggaa ctcgtctgcg    180
aatgtaatta tcggcaatca aaagctgacc attaatgatg tagctcgcgt tgcccggaat    240
ggcactttgg tgtcactgac gaacaatacc gacattctgc aaggtattca agctagctgc    300
gattatatca ataacgccgt tgaatctggc gagccaatct acggggtaac aagcggtttt    360
ggtgggatgg cgaacgttgc cattagccgt gaacaggcga gcgaacttca gaccaacctc    420
gtttggttcc taaagacagg agctggtaat aagttacctc tggctgacgt aagagccgcg    480
```

```
atgctgcttc gcgctaatag tcacatgcgc ggcgccagtg gtatccgtct tgagcttatc    540
aagaggatgg aaatcttcct caacgcgggt gtcacaccat atgtttatga gtttggtagt    600
atcggagcca gtggtgatct tgttcccctg agttatatta cgggttcatt gattggttta    660
gacccgtcct ttaaagtgga ttttaacggg aagaaatgg acgccccgac cgctttacga     720
cagcttaatc tgagcccact tactttgctc cctaaagaag gtcttgccat gatgaatggc    780
acctctgtga tgactggaat tgccgcgaat tgtgtgtatg acacgcagat cctaacggcc    840
attgccatgg gtgttcacgc gttggacatt caagccctga tggtacaaa ccagtcgttt     900 catccgttta tccataattc aaaacccat ccgggacagc tttgggctgc tgatcagatg     960
atctcactcc tggccaatag tcaactggtt cgggacgagc tcgacggcaa acatgattat    1020
cgcgatcatg agctcatcca ggaccggtat tcacttcgtt gtctcccaca tacctgggg     1080 cctatcgttg atggtatatc tcaaattgcg aagcaaattg aaattgagat caatagcgta    1140
accgacaacc cgcttatcga tgttgataat caggcctctt atcacggtgg caattttctg    1200
ggccagtatg ttggtatggg gatggatcac ctgcggtact atattgggct tctggctaaa    1260
catcttgatg tgcagattgc cttattagct tcaccagaat tttcaaatgg actgccgcca    1320
tcattgctcg gtaacagaga aggaaagta aatatgggcc ttaagggcct tcagatatgt     1380
ggtaactcaa tcatgcccct cctgaccttt tatgggaact caattgctga tcgttttccg    1440
acacatgctg aacagtttaa ccaaaacatt aactcacagg gctatacatc cgcgacgtta    1500
gcgcgtcggt ccgtggatat cttccagaat tatgttgcta tcgctctgat gttcggcgta    1560
caggccgttg atttgcgcac ttataaaaaa accggtcact acgatgctcg ggcttgcctg    1620
tcgcctgcca ccgagcggct ttatagcgcc gtacgtcatg ttgtgggtca gaaaccgacg    1680
tcggaccgcc cctatatttg gaatgataat gaacaagggc tggatgaaca catcgcccgg    1740
atatctgccg atattgccgc cggaggtgtc atcgtccagg cggtacaaga catacttcct    1800
tgcctgcatt aagcttggcg taatcatggt catagctgtt tcctgtgtga aattgttatc    1860
cgctcacaat tccacacaac atacgagccg gaagcataaa gtgtaaagcc tggggtgcct    1920
aatgagtgag ctaactcaca ttaattgcgt tgcgctcact gcccgctttc cagtcggaa     1980 acctgtcgtg ccagctgcat taatgaatcg gccaacgcgc ggggagaggc ggtttgcgta    2040
ttgggcgctc ttccgcttcc tcgctcactg actcgctgcg ctcggtcgtt cggctgcggc    2100
gagcggtatc agctcactca aaggcggtag tacgggtttt gctgcccgca acgggctgt     2160 tctggtgttg ctagtttgtt atcagaatcg cagatccggc ttcaggtttg ccggctgaaa    2220
gcgctatttc ttccagaatt gccatgattt tttccccacg ggaggcgtca ctggctcccg    2280
tgttgtcggc agctttgatt cgataagcag catcgcctgt tcaggctgt  ctatgtgtga    2340 ctgttgagct gtaacaagtt gtctcaggtg ttcaatttca tgttctagtt gctttgtttt    2400
actggtttca cctgttctat taggtgttac atgctgttca tctgttacat tgtcgatctg    2460
ttcatggtga acagctttaa atgcaccaaa aactcgtaaa agctctgatg tatctatctt    2520
ttttacaccg ttttcatctg tgcatatgga cagttttccc tttgatatct aacggtgaac    2580
agttgttcta cttttgtttg ttagtcttga tgcttcactg atagatacaa gagccataag    2640
aacctcagat ccttccgtat ttagccagta tgttctctag tgtggttcgt tgttttttgcg   2700 tgagccatga gaacgaacca ttgagatcat gcttactttg catgtcactc aaaaattttg    2760
cctcaaaact ggtgagctga attttgcag ttaaagcatc gtgtagtgtt tttcttagtc     2820
```

```
cgttacgtag gtaggaatct gatgtaatgg ttgttggtat tttgtcacca ttcatttta    2880 tctggttgtt ctcaagttcg gttacgagat ccatttgtct atctagttca acttggaaaa    2940
tcaacgtatc agtcgggcgg cctcgcttat caaccaccaa tttcatattg ctgtaagtgt    3000
ttaaatcttt acttattggt ttcaaaaccc attggttaag cctttaaac tcatggtagt     3060 tattttcaag cattaacatg aacttaaatt catcaaggct aatctctata tttgccttgt    3120
gagttttctt ttgtgttagt tcttttaata accactcata aatcctcata gagtatttgt    3180
tttcaaaaga cttaacatgt tccagattat attttatgaa ttttttttaac tggaaaagat   3240 aaggcaatat ctcttcacta aaaactaatt ctaattttc gcttgagaac ttggcatagt     3300
ttgtccactg gaaaatctca agcctttaa ccaaggatt cctgatttcc acagttctcg      3360
tcatcagctc tctggttgct ttagctaata caccataagc attttcccta ctgatgttca    3420
tcatctgagc gtattggtta taagtgaacg ataccgtccg ttctttcctt gtagggtttt    3480
caatcgtggg gttgagtagt gccacacagc ataaaattag cttggtttca tgctccgtta    3540
agtcatagcg actaatcgct agttcatttg ctttgaaaac aactaattca gacatacatc    3600
tcaattggtc taggtgattt taatcactat accaattgag atgggctagt caatgataat    3660
tactagtcct tttcctttga gttgtgggta tctgtaaatt ctgctagacc tttgctggaa    3720
aacttgtaaa ttctgctaga ccctctgtaa attccgctag acctttgtgt gttttttttg    3780
tttatattca agtggttata atttatgaa taaagaaaga ataaaaaaag ataaaaagaa      3840
tagatcccag ccctgtgtat aactcactac tttagtcagt tccgcagtat tacaaaagga    3900
tgtcgcaaac gctgtttgct cctctacaaa acagacctta aaaccctaaa ggcttaagta    3960
gcaccctcgc aagctcgggc aaatcgctga atattccttt tgtctccgac catcaggcac    4020
ctgagtcgct gtcttttcg tgacattcag ttcgctgcgc tcacggctct ggcagtgaat     4080
gggggtaaat ggcactacag gcgccttta tggattcatg caaggaaact acccataata     4140
caagaaaagc ccgtcacggg cttcagggg cgttttatgg cgggtctgct atgtggtgct      4200
atctgacttt ttgctgttca gcagttcctg ccctctgatt ttccagtctg accacttcgg    4260
attatcccgt gacaggtcat tcagactggc taatgcaccc agtaaggcag cggtatcatc    4320
aacaggctta cccgtcttac tgtctttct acggggtctg acgctcagtg aacgaaaac       4380 tcacgttaag ggattttggt catgagatta tcaaaaagga tcttcaccta gatccttta     4440 aattaaaaat gaagttttaa atcaatctaa agtatatatg agtaaacttg gtctgacagt    4500
taccaatgct taatcagtga ggcacctatc tcagcgatct gtctatttcg ttcatccata    4560
gttgcctgac tccccgtcgt gtagataact acgatacggg agggcttacc atctggcccc   4620
agtgctgcaa tgataccgcg agacccacgc tcaccggctc cagatttatc agcaataaac   4680
cagccagccg gaagggccga gcgcagaagt ggtcctgcaa ctttatccgc ctccatccag    4740
tctattaatt gttgccggga agctagagta agtagttcgc cagttaatag tttgcgcaac    4800
gttgttgcca ttgctacagg catcgtggtg tcacgctcgt cgtttggtat ggcttcattc    4860
agctccggtt cccaacgatc aaggcgagtt acatgatccc ccatgttgtg caaaaaagcg    4920
gttagctcct tcggtcctcc gatcgttgtc agaagtaagt tggccgcagt gttatcactc    4980
atggttatgg cagcactgca taattctctt actgtcatgc catccgtaag atgcttttct    5040
gtgactggtg agtactcaac caagtcattc tgagaatagt gtatgcggcg accgagttgc   5100
tcttgcccgg cgtcaatacg ggataatacc gcgccacata gcagaacttt aaaagtgctc   5160
atcattggaa aacgttcttc ggggcgaaaa ctctcaagga tcttaccgct gttgagatcc   5220
```

```
agttcgatgt aacccactcg tgcacccaac tgatcttcag catcttttac tttcaccagc    5280
gtttctgggt gagcaaaaac aggaaggcaa aatgccgcaa aaaagggaat aagggcgaca    5340
cggaaatgtt gaatactcat actcttcctt tttcaatatt attgaagcat ttatcagggt    5400
tattgtctca tgagcggata catatttgaa tgtatttaga aaaataaaca aatagggatt    5460
ccgcgcacat ttccccgaaa agtgccacct gacgtctaag aaaccattat tatcatgaca    5520
ttaacctata aaataggcg tatcacgagg cccttcgtc tcgcgcgttt cggtgatgac       5580
ggtgaaaacc tctgacacat gcagctccg gagacggtca cagcttgtct gtaagcggat      5640
gccgggagca gacaagcccg tcaggcgcg tcagcgggtg ttggcgggtg tcggggctgg      5700
cttaactatg cggcatcaga gcagattgta ctgagagtgc accatatgcg gtgtgaaata    5760
ccgcacagat gcgtaaggag aaaataccgc atcaggcgcc attcgccatt caggctgcgc    5820
aactgttggg aagggcgatc ggtgcgggcc tcttcgctat tacgccagct ggcgaaaggg    5880
ggatgtgctg caaggcgatt aagttgggta acgccagggt tttcccagtc acgacgttgt    5940
aaaacgacgg ccagtgaatt cg                                             5962

<210> SEQ ID NO 27
<211> LENGTH: 5857
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 27
ctcttgatcg ttatcaattc ccacgctgtt tcagagcgtt accttgccct taaacattag      60
caatgtcgat ttatcagagg gccgacaggc tcccacagga gaaaaccgat gaaagctaaa     120
gatgttcagc caaccattat tattaataaa aatggcctta tctctttgga agatatctat     180
gacattgcga taaaacaaaa aaaagtagaa atatcaacgg agatcactga acttttgacg     240
catggtcgtg aaaaattaga ggaaaaatta aattcaggag aggttatata tggaatcaat     300
acaggatttg gagggaatgc caatttagtt gtgccatttg agaaaatcgc agagcatcag     360
caaaatctgt taacttttct ttctgctggt actggggact atatgtccaa accttgtatt     420
aaagcgtcac aatttactat gttactttct gtttgcaaag gttggtctgc aaccagacca     480
attgtcgctc aagcaattgt tgatcatatt aatcatgaca ttgttcctct ggttcctcgc     540
tatggctcag tgggtgcaag cggtgattta attcctttat cttatattgc acgagcatta    600
tgtggtatcg gcaaagtta ttatatgggc gcagaaattg acgctgctga agcaattaaa     660 cgtgcaggt gacaccatt atcgttaaaa gccaaagaag gtcttgctct gattaacggc      720
acccgggtaa tgtcaggaat cagtgcaatc accgtcatta actggaaaa actatttaaa     780 gcctcaattt ctgcgattgc ccttgctgtt gaagcattac ttgcatctca tgaacattat    840
gatgcccgga ttcaacaagt aaaaaatcat cctggtcaaa acgcggtggc aagtgcattg    900
cgtaatttat tggcaggttc aacgcaggtt aatctattat ctgggggttaa agaacaagcc    960 aataaagctt gtcgtcatca agaaattacc caactaaatg ataccttaca ggaagtttat    1020
tcaattcgct gtgcaccaca agtattaggt atagtgccag aatctttagc taccgctcgg   1080
aaaatattgg aacgggaagt tatctcagct aatgataatc cattgataga tccagaaaat   1140
ggcgatgttc tacacggtgg aaattttatg gggcaatatg tcgcccgaac aatggatgca   1200
```

```
ttaaaactgg atattgcttt aattgccaat catcttcacg ccattgtggc tcttatgatg   1260
gataaccgtt tctctcgtgg attacctaat tcactgagtc cgacacccgg catgtatcaa   1320
ggttttaaag gcgtccaact ttctcaaacc gctttagttg ctgcaattcg ccatgattgt   1380
gctgcatcag gtattcatac cctcgccaca gaacaataca atcaagatat tgtcagttta   1440
ggtctgcatg ccgctcaaga tgttttagag atggagcaga aattacgcaa tattgtttca   1500
atgacaattc tggtagtttg tcaggccatt catcttcgcg gcaatattag tgaaattgcg   1560
cctgaaactg ctaaattta ccatgcagta cgcgaaatca gttctccttt gatcactgat   1620
cgtgcgttgg atgaagatat aatccgcatt gcggatgcaa ttattaatga tcaacttcct   1680
ctgccagaaa tcatgctgga agaataagct tggcgtaatc atggtcatag ctgtttcctg   1740
tgtgaaattg ttatccgctc acaattccac acaacatacg agccggaagc ataaagtgta   1800
aagcctgggg tgcctaatga gtgagctaac tcacattaat tgcgttgcgc tcactgcccg   1860
ctttccagtc gggaaacctg tcgtgccagc tgcattaatg aatcggccaa cgcgcgggga   1920
gaggcggttt gcgtattggg cgctcttccg cttcctcgct cactgactcg ctgcgctcgg   1980
tcgttcggct gcggcgagcg gtatcagctc actcaaaggc ggtagtacgg ttttgctgc    2040 ccgcaaacgg gctgttctgg tgttgctagt ttgttatcag aatcgcagat ccggcttcag   2100
gtttgccggc tgaaagcgct atttcttcca gaattgccat gattttttcc ccacgggagg   2160
cgtcactggc tcccgtgttg tcggcagctt tgattcgata agcagcatcg cctgtttcag   2220
gctgtctatg tgtgactgtt gagctgtaac aagttgtctc aggtgttcaa tttcatgttc   2280
tagttgcttt gttttactgg tttcacctgt tctattaggt gttacatgct gttcatctgt   2340
tacattgtcg atctgttcat ggtgaacagc tttaaatgca ccaaaaactc gtaaaagctc   2400
tgatgtatct atctttttta caccgttttc atctgtgcat atggacagtt ttccctttga   2460
tatctaacgg tgaacagttg ttctactttt gtttgttagt cttgatgctt cactgataga   2520
tacaagagcc ataagaacct cagatccttc cgtatttagc cagtatgttc tctagtgtgg   2580
ttcgttgttt ttgcgtgagc catgagaacg aaccattgag atcatgctta ctttgcatgt   2640
cactcaaaaa ttttgcctca aaactggtga gctgaatttt tgcagttaaa gcatcgtgta   2700 gtgttttct tagtccgtta cgtaggtagg aatctgatgt aatggttgtt ggtattttgt    2760
caccattcat ttttatctgg ttgttctcaa gttcggttac gagatccatt tgtctatcta   2820
gttcaacttg gaaaatcaac gtatcagtcg ggcggcctcg cttatcaacc accaatttca   2880
tattgctgta agtgtttaaa tctttactta ttggtttcaa aacccattgg ttaagccttt   2940
taaactcatg gtagttattt tcaagcatta acatgaactt aaattcatca aggctaatct   3000
ctatatttgc cttgtgagtt ttcttttgtg ttagttcttt taataaccac tcataaatcc   3060
tcatagagta tttgttttca aaagacttaa catgttccag attatatttt atgaattttt   3120
ttaactggaa aagataaggc aatatctctt cactaaaaac taattctaat ttttcgcttg   3180
agaacttggc atagtttgtc cactggaaaa tctcaaagcc tttaaccaaa ggattcctga   3240
tttccacagt tctcgtcatc agctctctgg ttgctttagc taatacacca taagcatttt   3300
ccctactgat gttcatcatc tgagcgtatt ggttataagt gaacgatacc gtccgttctt   3360
tccttgtagg gttttcaatc gtggggttga gtagtgccac acagcataaa attagcttgg   3420
tttcatgctc cgttaagtca tagcgactaa tcgctagttc atttgctttg aaaacaacta   3480
attcagacat acatctcaat tggtctaggt gattttaatc actataccaa ttgagatggg   3540
ctagtcaatg ataattacta gtccttttcc tttgagttgt gggtatctgt aaattctgct   3600
```

```
agacctttgc tggaaaactt gtaaattctg ctagaccctc tgtaaattcc gctagacctt    3660
tgtgtgtttt ttttgtttat attcaagtgg ttataattta tagaataaag aaagaataaa    3720
aaaagataaa aagaatagat cccagccctg tgtataactc actactttag tcagttccgc    3780
agtattacaa aaggatgtcg caaacgctgt ttgctcctct acaaaacaga ccttaaaacc    3840
ctaaaggctt aagtagcacc ctcgcaagct cgggcaaatc gctgaatatt cctttgtct    3900
ccgaccatca ggcacctgag tcgctgtctt tttcgtgaca ttcagttcgc tgcgctcacg    3960
gctctggcag tgaatggggg taaatggcac tacaggcgcc ttttatggat tcatgcaagg    4020
aaactaccca taatacaaga aaagcccgtc acgggcttct cagggcgttt tatggcgggt    4080
ctgctatgtg gtgctatctg actttttgct gttcagcagt tcctgccctc tgattttcca    4140
gtctgaccac ttcggattat cccgtgacag gtcattcaga ctggctaatg cacccagtaa    4200
ggcagcggta tcatcaacag gcttacccgt cttactgtct tttctacggg gtctgacgct    4260
cagtggaacg aaaactcacg ttaagggatt ttggtcatga gattatcaaa aaggatcttc    4320
acctagatcc ttttaaatta aaaatgaagt tttaaatcaa tctaaagtat atatgagtaa    4380
acttggtctg acagttacca atgcttaatc agtgaggcac ctatctcagc gatctgtcta    4440
tttcgttcat ccatagttgc ctgactcccc gtcgtgtaga taactacgat acgggagggc    4500
ttaccatctg gccccagtgc tgcaatgata ccgcgagacc cacgctcacc ggctccagat    4560
ttatcagcaa taaaccagcc agccggaagg gccgagcgca gaagtggtcc tgcaacttta    4620
tccgcctcca tccagtctat taattgttgc cgggaagcta gagtaagtag ttcgccagtt    4680
aatagtttgc gcaacgttgt tgccattgct acaggcatcg tggtgtcacg ctcgtcgttt    4740
ggtatggctt cattcagctc cggttcccaa cgatcaaggc gagttacatg atcccccatg    4800
ttgtgcaaaa aagcggttag ctccttcggt cctccgatcg ttgtcagaag taagttggcc    4860
gcagtgttat cactcatggt tatggcagca ctgcataatt ctcttactgt catgccatcc    4920
gtaagatgct tttctgtgac tggtgagtac tcaaccaagt cattctgaga atagtgtatg    4980
cggcgaccga gttgctcttg cccggcgtca atacgggata ataccgcgcc acatagcaga    5040
actttaaaag tgctcatcat tggaaaacgt tcttcggggc gaaaactctc aaggatctta    5100
ccgctgttga gatccagttc gatgtaaccc actcgtgcac ccaactgatc ttcagcatct    5160
tttactttca ccagcgtttc tgggtgagca aaaacaggaa ggcaaaatgc cgcaaaaaag    5220
ggaataaggg cgacacggaa atgttgaata ctcatactct tcctttttca atattattga    5280
agcatttatc agggttattg tctcatgagc ggatacatat ttgaatgtat ttagaaaaat    5340
aaacaaatag gggttccgcg cacatttccc cgaaaagtgc cacctgacgt ctaagaaacc    5400
attattatca tgacattaac ctataaaaat aggcgtatca cgaggccctt tcgtctcgcg    5460
cgtttcggtg atgacggtga aaacctctga cacatgcagc tcccggagac ggtcacagct    5520
tgtctgtaag cggatgccgg gagcagacaa gcccgtcagg gcgcgtcagc gggtgttggc    5580
gggtgtcggg gctggcttaa ctatgcggca tcagagcaga ttgtactgag agtgcaccat    5640
atgcggtgtg aaataccgca cagatgcgta aggagaaaat accgcatcag gcgccattcg    5700
ccattcaggc tgcgcaactg ttgggaaggg cgatcggtgc gggcctcttc gctattacgc    5760
cagctggcga aggggggatg tgctgcaagg cgattaagtt gggtaacgcc agggttttcc    5820
cagtcacgac gttgtaaaac gacggccagt gaattcg                            5857
```

<210> SEQ ID NO 28

<211> LENGTH: 6602
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 28

| | |
|---|---:|
| accactccct atcagtgata gagaaaagtg aactctagaa ataattttgt ttaactttaa | 60 |
| gaaggagata tacatatgaa aacactatca caggcccaat ctaaaacttc ttcacagcaa | 120 |
| ttcagcttta ccgggaactc gtctgcgaat gtaattatcg gcaatcaaaa gctgaccatt | 180 |
| aatgatgtag ctcgcgttgc ccggaatggc actttggtgt cactgacgaa caataccgac | 240 |
| attctgcaag gtattcaagc tagctgcgat tatatcaata cgccgttga atctggcgag | 300 |
| ccaatctacg gggtaacaag cggttttggt gggatggcga acgttgccat tagccgtgaa | 360 |
| caggcgagcg aacttcagac caacctcgtt tggttcctaa agacaggagc tggtaataag | 420 |
| ttacctctgg ctgacgtaag agccgcgatg ctgcttcgcg ctaatagtca catgcgcggc | 480 |
| gccagtggta tccgtcttga gcttatcaag aggatggaaa tcttcctcaa cgcgggtgtc | 540 |
| acaccatatg tttatgagtt tggtagtatc ggagccagtg gtgatcttgt tcccctgagt | 600 |
| tatattacgg gttcattgat tggtttagac ccgtccttta agtggatttt aacgggaaa | 660 |
| gaaatggacg ccccgaccgc tttacgacag cttaatctga gcccacttac tttgctccct | 720 |
| aaagaaggtc ttgccatgat gaatggcacc tctgtgatga ctggaattgc gcgaattgt | 780 |
| gtgtatgaca cgcagatcct aacggccatt gccatgggtg ttcacgcgtt ggacattcaa | 840 |
| gccctgaatg gtacaaacca gtcgtttcat ccgtttatcc ataattcaaa accccatccg | 900 |
| ggacagcttt gggctgctga tcagatgatc tcactcctgg ccaatagtca actggttcgg | 960 |
| gacgagctcg acggcaaaca tgattatcgc gatcatgagc tcatccagga ccggtattca | 1020 |
| cttcgttgtc tcccacaata cctggggcct atcgttgatg gtatatctca aattgcgaag | 1080 |
| caaattgaaa ttgagatcaa tagcgtaacc gacaacccgc ttatcgatgt tgataatcag | 1140 |
| gcctcttatc acggtggcaa ttttctgggc cagtatgttg gtatggggat ggatcacctg | 1200 |
| cggtactata ttgggcttct ggctaaacat cttgatgtgc agattgcctt attagcttca | 1260 |
| ccagaatttt caaatggact gccgccatca ttgctcggta acagagaaag gaaagtaaat | 1320 |
| atgggcctta agggccttca gatatgtggt aactcaatca tgccctcct gacctttat | 1380 |
| gggaactcaa ttgctgatcg ttttccgaca catgctgaac agtttaaccca aaacattaac | 1440 |
| tcacagggct atacatccgc gacgttagcg cgtcggtccg tggatatctt ccagaattat | 1500 |
| gttgctatcg ctctgatgtt cggcgtacag gccgttgatt tgcgcactta taaaaaaacc | 1560 |
| ggtcactacg atgctcgggc ttgcctgtcg cctgccaccg agcggcttta tagcgccgta | 1620 |
| cgtcatgttg tgggtcagaa accgacgtcg gaccgcccct atatttggaa tgataatgaa | 1680 |
| caagggctgg atgaacacat cgcccggata tctgccgata ttgccgccgg aggtgtcatc | 1740 |
| gtccaggcgg tacaagacat acttccttgc ctgcattaag cttggcgtaa tcatggtcat | 1800 |
| agctgtttcc tgtgtgaaat tgttatccgc tcacaattcc acacaacata cgagccggaa | 1860 |
| gcataaagtg taaagcctgg ggtgcctaat gagtgagcta actcacatta ttgcgttgc | 1920 |
| gctcactgcc cgctttccag tcgggaaacc tgtcgtgcca gctgcattaa tgaatcggcc | 1980 |
| aacgcgcggg gagaggcggt ttgcgtattg ggcgctcttc cgcttcctcg ctcactgact | 2040 |
| cgctgcgctc ggtcgttcgg ctgcggcgag cggtatcagc tcactcaaag gcggtagtac | 2100 |

```
gggttttgct gcccgcaaac gggctgttct ggtgttgcta gtttgttatc agaatcgcag    2160
atccggcttc aggtttgccg gctgaaagcg ctatttcttc cagaattgcc atgatttttt    2220
ccccacggga ggcgtcactg gctcccgtgt tgtcggcagc tttgattcga taagcagcat    2280
cgcctgtttc aggctgtcta tgtgtgactg ttgagctgta acaagttgtc tcaggtgttc    2340
aatttcatgt tctagttgct ttgttttact ggtttcacct gttctattag gtgttacatg    2400
ctgttcatct gttacattgt cgatctgttc atggtgaaca gctttaaatg caccaaaaac    2460
tcgtaaaagc tctgatgtat ctatcttttt tacaccgttt tcatctgtgc atatggacag    2520 ttttccctttt gatatctaac ggtgaacagt tgttctactt ttgttttgtta gtcttgatgc    2580 ttcactgata gatacaagag ccataagaac ctcagatcct tccgtattta gccagtatgt    2640
tctctagtgt ggttcgttgt ttttgcgtga gccatgagaa cgaaccattg agatcatgct    2700
tactttgcat gtcactcaaa aattttgcct caaaactggt gagctgaatt tttgcagtta    2760
aagcatcgtg tagtgttttt cttagtccgt tacgtaggta ggaatctgat gtaatggttg    2820
ttggtatttt gtcaccattc atttttatct ggttgttctc aagttcggtt acgagatcca    2880
tttgtctatc tagttcaact tggaaaatca acgtatcagt cgggcggcct cgcttatcaa    2940
ccaccaattt catattgctg taagtgttta aatctttact tattggtttc aaaacccatt    3000
ggttaagcct tttaaactca tggtagttat tttcaagcat taacatgaac ttaaattcat    3060
caaggctaat ctctatattt gccttgtgag ttttcttttg tgttagttct tttaataacc    3120
actcataaat cctcatagag tatttgttttt caaaagactt aacatgttcc agattatatt    3180
ttatgaattt ttttaactgg aaaagataag gcaatatctc ttcactaaaa actaattcta    3240 attttttcgct tgagaacttg gcatagtttg tccactggaa aatctcaaag cctttaacca    3300
aaggattcct gatttccaca gttctcgtca tcagctctct ggttgcttta gctaatacac    3360
cataagcatt tttccctactg atgttcatca tctgagcgta ttggttataa gtgaacgata    3420
ccgtccgttc tttccttgta gggttttcaa tcgtggggtt gagtagtgcc acacagcata    3480
aaattagctt ggtttcatgc tccgttaagt catagcgact aatcgctagt tcatttgctt    3540
tgaaaacaac taattcagac atacatctca attggtctag gtgattttaa tcactatacc    3600
aattgagatg ggctagtcaa tgataattac tagtcctttt cctttgagtt gtgggtatct    3660
gtaaattctg ctagacctttt gctggaaaac ttgtaaattc tgctagaccc tctgtaaatt    3720
ccgctagacc tttgtgtgtt ttttttgttt atattcaagt ggttataatt tatagaataa    3780
agaaagaata aaaaaagata aaagaatag atcccagccc tgtgtataac tcactactttt    3840 agtcagttcc gcagtattac aaaaggatgt cgcaaacgct gtttgctcct ctacaaaaca    3900
gaccttaaaa ccctaaaggc ttaagtagca ccctcgcaag ctcgggcaaa tcgctgaata    3960
ttccttttgt ctccgaccat caggcacctg agtcgctgtc tttttcgtga cattcagttc    4020
gctgcgctca cggctctggc agtgaatggg ggtaaatggc actacaggcg cctttttatgg    4080 attcatgcaa ggaaactacc cataatacaa gaaaagcccg tcacgggctt ctcagggcgt    4140
tttatggcgg gtctgctatg tggtgctatc tgacttttttg ctgttcagca gttcctgccc    4200
tctgattttc cagtctgacc acttcggatt atcccgtgac aggtcattca gactggctaa    4260
tgcacccagt aaggcagcgg tatcatcaac aggcttaccc gtcttactgt cttttctacg    4320
gggtctgacg ctcagtggaa cgaaaactca cgttaaggga ttttggtcat gagattatca    4380
aaaaggatct tcacctagat ccttttttaaat taaaaatgaa gttttaaatc aatctaaagt    4440
```

-continued

```
atatatgagt aaacttggtc tgacagttac caatgcttaa tcagtgaggc acctatctca   4500
gcgatctgtc tatttcgttc atccatagtt gcctgactcc ccgtcgtgta gataactacg   4560
atacgggagg gcttaccatc tggccccagt gctgcaatga taccgcgaga cccacgctca   4620
ccggctccag atttatcagc aataaaccag ccagccggaa gggccgagcg cagaagtggt   4680
cctgcaactt tatccgcctc catccagtct attaattgtt gccgggaagc tagagtaagt   4740
agttcgccag ttaatagttt gcgcaacgtt gttgccattg ctacaggcat cgtggtgtca   4800
cgctcgtcgt ttggtatggc ttcattcagc tccggttccc aacgatcaag gcgagttaca   4860
tgatccccca tgttgtgcaa aaaagcggtt agctccttcg gtcctccgat cgttgtcaga   4920
agtaagttgg ccgcagtgtt atcactcatg gttatggcag cactgcataa ttctcttact   4980
gtcatgccat ccgtaagatg cttttctgtg actggtgagt actcaaccaa gtcattctga   5040
gaatagtgta tgcggcgacc gagttgctct tgcccggcgt caatacggga taataccgcg   5100
ccacatagca gaactttaaa agtgctcatc attggaaaac gttcttcggg gcgaaaactc   5160
tcaaggatct taccgctgtt gagatccagt tcgatgtaac ccactcgtgc acccaactga   5220
tcttcagcat cttttacttt caccagcgtt tctgggtgag caaaaacagg aaggcaaaat   5280
gccgcaaaaa agggaataag ggcgacacgg aaatgttgaa tactcatact cttccttttt   5340
caatattatt gaagcattta tcagggttat tgtctcatga gcggatacat atttgaatgt   5400
atttagaaaa ataaacaaat aggggttccg cgcacatttc cccgaaaagt gccacctgac   5460
gtctaagaaa ccattattat catgacatta acctataaaa ataggcgtat cacgaggccc   5520
tttcgtctcg cgcgtttcgg tgatgacggt gaaaacctct gacacatgca gctcccggag   5580
acggtcacag cttgtctgta agcggatgcc gggagcagac aagcccgtca gggcgcgtca   5640
gcgggtgttg gcgggtgtcg gggctggctt aactatgcgg catcagagca gattgtactg   5700
agagtgcacc atatgcggtg tgaaataccg cacagatgcg taaggagaaa ataccgcatc   5760
aggcgccatt cgccattcag gctgcgcaac tgttgggaag ggcgatcggt gcgggcctct   5820
tcgctattac gccagctggc gaaaggggga tgtgctgcaa ggcgattaag ttgggtaacg   5880
ccagggtttt cccagtcacg acgttgtaaa acgacggcca gtgaattcgt taagacccac   5940
tttcacattt aagttgtttt tctaatccgc atatgatcaa ttcaaggccg aataagaagg   6000
ctggctctgc accttggtga tcaaataatt cgatagcttg tcgtaataat ggcggcatac   6060
tatcagtagt aggtgtttcc ctttcttctt tagcgacttg atgctcttga tcttccaata   6120
cgcaacctaa agtaaaatgc cccacagcgc tgagtgcata taatgcattc tctagtgaaa   6180
aaccttgttg gcataaaaag gctaattgat tttcgagagt ttcatactgt ttttctgtag   6240
gccgtgtacc taaatgtact tttgctccat cgcgatgact tagtaaagca catctaaaac   6300
ttttagcgtt attacgtaaa aaatcttgcc agctttcccc ttctaagggg caaaagtgag   6360
tatggtgcct atctaacatc tcaatggcta aggcgtcgag caaagcccgc ttatttttta   6420
catgccaata caatgtaggc tgctctacac ctagcttctg ggcgagttta cggggttgtta   6480
aaccttcgat tccgacctca ttaagcagct ctaatgcgct gttaatcact ttactttttat   6540
ctaatctaga catcattaat tcctaatttt tgttgacact ctatcattga tagagttatt   6600
tt                                                                   6602
```

<210> SEQ ID NO 29
<211> LENGTH: 6497
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 29

```
accactccct atcagtgata gagaaaagtg aactctagaa ataattttgt ttaactttaa      60
gaaggagata tacatatgaa agctaaagat gttcagccaa ccattattat taataaaaat     120
ggccttatct ctttggaaga tatctatgac attgcgataa acaaaaaaa agtagaaata     180
tcaacggaga tcactgaact tttgacgcat ggtcgtgaaa aattagagga aaaattaaat     240
tcaggagagg ttatatatgg aatcaataca ggatttggag ggaatgccaa tttagttgtg     300
ccatttgaga aaatcgcaga gcatcagcaa atctgttaa cttttctttc tgctggtact     360
ggggactata tgtccaaacc ttgtattaaa gcgtcacaat ttactatgtt acttctgtt     420
tgcaaaggtt ggtctgcaac cagaccaatt gtcgctcaag caattgttga tcatattaat     480
catgacattg ttcctctggt tcctcgctat ggctcagtgg gtgcaagcgg tgatttaatt     540
cctttatctt atattgcacg agcattatgt ggtatcggca agtttatta tgggcgca     600
gaaattgacg ctgctgaagc aattaaacgt gcagggttga caccattatc gttaaaagcc     660
aaagaaggtc ttgctctgat taacggcacc cgggtaatgt caggaatcag tgcaatcacc     720
gtcattaaac tggaaaaact atttaaagcc tcaatttctg cgattgccct tgctgttgaa     780
gcattacttg catctcatga acattatgat gcccggattc aacaagtaaa aaatcatcct     840
ggtcaaaacg cggtggcaag tgcattgcgt aatttattgg caggttcaac gcaggttaat     900
ctattatctg gggttaaaga acaagccaat aaagcttgtc gtcatcaaga aattacccaa     960
ctaaatgata ccttacagga agtttattca attcgctgtg caccacaagt attaggtata    1020
gtgccagaat ctttagctac cgctcggaaa atattggaac gggaagttat ctcagctaat    1080
gataatccat tgatagatcc agaaaatggc gatgttctac acggtggaaa ttttatgggg    1140
caatatgtcg cccgaacaat ggatgcatta aaactggata ttgctttaat tgccaatcat    1200
cttcacgcca ttgtggctct tatgatggat aaccgtttct ctcgtggatt acctaattca    1260
ctgagtccga cacccggcat gtatcaaggt tttaaaggcg tccaactttc tcaaaccgct    1320
ttagttgctg caattcgcca tgattgtgct gcatcaggta ttcataccct cgccacagaa    1380
caatacaatc aagatattgt cagtttaggt ctgcatgccg ctcaagatgt tttagagatg    1440
gagcagaaat tacgcaatat tgtttcaatg acaattctgg tagtttgtca ggccattcat    1500
cttcgcggca atattagtga aattgcgcct gaaactgcta aattttacca tgcagtacgc    1560
gaaatcagtt ctccttttgat cactgatcgt gcgttggatg aagatataat ccgcattgcg    1620
gatgcaatta ttaatgatca acttcctctg ccagaaatca tgctggaaga taagcttgg    1680
cgtaatcatg gtcatagctg tttcctgtgt gaaattgtta tccgctcaca attccacaca    1740
acatacgagc cggaagcata aagtgtaaag cctggggtgc ctaatgagtg agctaactca    1800
cattaattgc gttgcgctca ctgcccgctt tccagtcggg aaacctgtcg tgccagctgc    1860
attaatgaat cggccaacgc gcggggagag gcggtttgcg tattgggcgc tcttccgctt    1920
cctcgctcac tgactcgctg cgctcggtcg ttcggctgcg gcgagcggta tcagctcact    1980
caaaggcggt agtacgggtt ttgctgcccg caaacgggct gttctggtgt tgctagtttg    2040
ttatcagaat cgcagatccg gcttcaggtt tgccggctga aagcgctatt tcttccagaa    2100
ttgccatgat ttttccccca cgggaggcgt cactggctcc cgtgttgtcg gcagctttga    2160
```

```
ttcgataagc agcatcgcct gtttcaggct gtctatgtgt gactgttgag ctgtaacaag    2220
ttgtctcagg tgttcaattt catgttctag ttgctttgtt ttactggttt cacctgttct    2280
attaggtgtt acatgctgtt catctgttac attgtcgatc tgttcatggt gaacagcttt    2340
aaatgcacca aaaactcgta aaagctctga tgtatctatc tttttacac cgttttcatc     2400 tgtgcatatg gacagttttc cctttgatat ctaacggtga acagttgttc tacttttgtt    2460
tgttagtctt gatgcttcac tgatagatac aagagccata agaacctcag atccttccgt    2520
atttagccag tatgttctct agtgtggttc gttgttttg cgtgagccat gagaacgaac     2580
cattgagatc atgcttactt tgcatgtcac tcaaaatttt tgcctcaaaa ctggtgagct    2640 gaattttgc agttaaagca tcgtgtagtg tttttcttag tccgttacgt aggtaggaat     2700
ctgatgtaat ggttgttggt attttgtcac cattcatttt tatctggttg ttctcaagtt    2760
cggttacgag atccatttgt ctatctagtt caacttggaa aatcaacgta tcagtcgggc    2820
ggcctcgctt atcaaccacc aatttcatat tgctgtaagt gtttaaatct ttacttattg    2880
gtttcaaaac ccattggtta agccttttaa actcatggta gttattttca agcattaaca    2940
tgaacttaaa ttcatcaagg ctaatctcta tatttgcctt gtgagttttc ttttgtgtta    3000
gttcttttaa taaccactca taaatcctca tagagtattt gttttcaaaa gacttaacat    3060
gttccagatt atattttatg aattttttta actggaaaag ataaggcaat atctcttcac    3120
taaaaactaa ttctaatttt tcgcttgaga acttggcata gtttgtccac tggaaaatct    3180
caaagccttt aaccaaagga ttcctgattt ccacagttct cgtcatcagc tctctggttg    3240
ctttagctaa tacaccataa gcatttttccc tactgatgtt catcatctga gcgtattggt    3300
tataagtgaa cgataccgtc cgttcttttcc ttgtagggtt ttcaatcgtg gggttgagta    3360
gtgccacaca gcataaaatt agcttggttt catgctccgt taagtcatag cgactaatcg    3420
ctagttcatt tgctttgaaa acaactaatt cagacataca tctcaattgg tctaggtgat    3480
tttaatcact ataccaattg agatgggcta gtcaatgata attactagtc cttttcctt     3540 gagttgtggg tatctgtaaa ttctgctaga cctttgctgg aaaacttgta aattctgcta    3600
gaccctctgt aaattccgct agacctttgt gtgttttttt tgtttatatt caagtggtta    3660
taatttatag aataaagaaa gaataaaaaa agataaaaag aatagatccc agccctgtgt    3720
ataactcact actttagtca gttccgcagt attacaaaag gatgtcgcaa acgctgtttg    3780
ctcctctaca aaacagacct taaaaccta aaggcttaag tagcaccctc gcaagctcgg     3840
gcaaatcgct gaatattcct tttgtctccg accatcaggc acctgagtcg ctgtcttttt    3900
cgtgacattc agttcgctgc gctcacggct ctggcagtga atgggggtaa atggcactac    3960
aggcgccttt tatggattca tgcaaggaaa ctacccataa tacaagaaaa gcccgtcacg    4020
ggcttctcag ggcgttttat ggcgggtctg ctatgtggtg ctatctgact ttttgctgtt    4080
cagcagttcc tgccctctga ttttccagtc tgaccacttc ggattatccc gtgacaggtc    4140
attcagactg gctaatgcac ccagtaaggc agcggtatca tcaacaggct tacccgtctt    4200
actgtctttt ctacggggtc tgacgctcag tggaacgaaa actcacgtta agggattttg    4260
gtcatgagat tatcaaaaag gatcttcacc tagatccttt taaattaaaa atgaagtttt    4320
aaatcaatct aaagtatata tgagtaaact tggtctgaca gttaccaatg cttaatcagt    4380
gaggcaccta tctcagcgat ctgtctattt cgttcatcca tagttgcctg actcccgtc     4440 gtgtagataa ctacgatacg ggagggctta ccatctggcc ccagtgctgc aatgataccg    4500
cgagacccac gctcaccggc tccagattta tcagcaataa accagccagc cggaagggcc    4560
```

```
gagcgcagaa gtggtcctgc aactttatcc gcctccatcc agtctattaa ttgttgccgg    4620
gaagctagag taagtagttc gccagttaat agtttgcgca acgttgttgc cattgctaca    4680
ggcatcgtgg tgtcacgctc gtcgtttggt atggcttcat tcagctccgg ttcccaacga    4740
tcaaggcgag ttacatgatc ccccatgttg tgcaaaaaag cggttagctc cttcggtcct    4800
ccgatcgttg tcagaagtaa gttggccgca gtgttatcac tcatggttat ggcagcactg    4860
cataattctc ttactgtcat gccatccgta agatgctttt ctgtgactgg tgagtactca    4920
accaagtcat tctgagaata gtgtatgcgg cgaccgagtt gctcttgccc ggcgtcaata    4980
cgggataata ccgcgccaca tagcagaact ttaaaagtgc tcatcattgg aaaacgttct    5040
tcggggcgaa aactctcaag gatcttaccg ctgttgagat ccagttcgat gtaacccact    5100
cgtgcaccca actgatcttc agcatctttt actttcacca gcgtttctgg gtgagcaaaa    5160
acaggaaggc aaaatgccgc aaaaaaggga taagggcga cacggaaatg ttgaatactc    5220
atactcttcc ttttcaata ttattgaagc atttatcagg gttattgtct catgagcgga    5280
tacatatttg aatgtattta gaaaaataaa caaatagggg ttccgcgcac atttccccga    5340
aaagtgccac ctgacgtcta agaaaccatt attatcatga cattaaccta taaaaatagg    5400
cgtatcacga ggccctttcg tctcgcgcgt ttcggtgatg acggtgaaaa cctctgacac    5460
atgcagctcc cggagacggt cacagcttgt ctgtaagcgg atgccgggag cagacaagcc    5520
cgtcagggcg cgtcagcggg tgttggcggg tgtcggggct ggcttaacta tgcggcatca    5580
gagcagattg tactgagagt gcaccatatg cggtgtgaaa taccgcacag atgcgtaagg    5640
agaaaatacc gcatcaggcg ccattcgcca ttcaggctgc gcaactgttg ggaagggcga    5700
tcggtgcggg cctcttcgct attacgccag ctggcgaaag ggggatgtgc tgcaaggcga    5760
ttaagttggg taacgccagg gttttcccag tcacgacgtt gtaaaacgac ggccagtgaa    5820
ttcgttaaga cccactttca catttaagtt gttttctaa tccgcatatg atcaattcaa    5880
ggccgaataa gaaggctggc tctgcacctt ggtgatcaaa taattcgata gcttgtcgta    5940
ataatggcgg catactatca gtagtaggtg tttcccttc ttctttagcg acttgatgct    6000
cttgatcttc caatacgcaa cctaaagtaa atgccccac agcgctgagt gcatataatg    6060
cattctctag tgaaaaacct tgttggcata aaaaggctaa ttgattttcg agagtttcat    6120 actgttttc tgtaggccgt gtacctaaat gtacttttgc tccatcgcga tgacttagta    6180
aagcacatct aaaactttta gcgttattac gtaaaaaatc ttgccagctt tccccttcta    6240
aagggcaaaa gtgagtatgg tgcctatcta acatctcaat ggctaaggcg tcgagcaaag    6300
cccgcttatt ttttacatgc caatacaatg taggctgctc tacacctagc ttctgggcga    6360
gtttacgggt tgttaaacct tcgattccga cctcattaag cagctctaat gcgctgttaa    6420
tcactttact tttatctaat ctagacatca ttaattccta atttttgttg acactctatc    6480
attgatagag ttattttt                                                   6497
```

<210> SEQ ID NO 30
<211> LENGTH: 2137
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 30

```
ccagtgaatt cgttaagacc cactttcaca tttaagttgt ttttctaatc cgcatatgat    60
caattcaagg ccgaataaga aggctggctc tgcaccttgg tgatcaaata attcgatagc   120
ttgtcgtaat aatggcggca tactatcagt agtaggtgtt tcccttttct ctttagcgac   180
ttgatgctct tgatcttcca atacgcaacc taaagtaaaa tgcccacag cgctgagtgc    240 atataatgca ttctctagtg aaaaaccttg ttggcataaa aaggctaatt gattttcgag   300
agtttcatac tgttttttctg taggccgtgt acctaaatgt acttttgctc catcgcgatg  360
acttagtaaa gcacatctaa aactttttagc gttattacgt aaaaaatctt gccagctttc  420
cccttctaaa gggcaaaagt gagtatggtg cctatctaac atctcaatgg ctaaggcgtc   480
gagcaaagcc cgcttatttt ttacatgcca atacaatgta ggctgctcta cacctagctt   540
ctgggcgagt ttacggggttg ttaaaccttc gattccgacc tcattaagca gctctaatgc  600
gctgttaatc actttacttt tatctaatct agacatcatt aattcctaat ttttgttgac   660
actctatcat tgatagagtt attttaccac tccctatcag tgatagagaa aagtgaactc   720
tagaaataat tttgtttaac tttaagaagg agatatacat atgaaaaacg cgtcaaccgt   780
atcggaagat actgcgtcga atcaagagcc gacgcttcat cgcggattac ataaccgtca   840
tattcaactg attgcgttgg gtggcgcaat tggtactggt ctgtttcttg gcattggccc   900
ggcgattcag atggcgggtc cggctgtatt gctgggctac ggcgtcgccg ggatcatcgc   960
tttcctgatt atgcgccagc ttggcgaaat ggtggttgag gagccggtat ccggttcatt  1020
tgcccacttt gcctataaat actggggacc gtttgcgggc ttcctctctg gctggaacta  1080
ctgggtaatg ttcgtgctgg tgggaatggc agagctgacc gctgcgggca tctatatgca  1140
gtactggttc ccggatgttc caacgtggat ttgggctgcc gccttcttta ttatcatcaa  1200
cgccgttaac ctggtgaacg tgcgcttata tggcgaaacc gagttctggt ttgcgttgat  1260
taaagtgctg gcaatcatcg gtatgatcgg ctttggcctg tggctgctgt tttctggtca  1320
cggcggcgag aaagccagta tcgacaacct ctggcgctac ggtggtttct tcgccaccgg  1380
ctggaatggg ctgattttgt cgctggcggt aattatgttc tccttcggcg gtctggagct  1440
gattgggatt actgccgctg aagcgcgcga tccggaaaaa agcattccaa agcggtaaa   1500 tcaggtggtg tatcgcatcc tgctgttttta catcggttca ctggtggttt tactggcgct  1560
ctatccgtgg gtggaagtga aatccaacag tagcccgttt gtgatgattt tccataatct  1620
cgacagcaac gtggtagctt ctgcgctgaa cttcgtcatt ctggtagcat cgctgtcagt  1680
gtataacagc ggggtttact ctaacagccg catgctgttt ggccttttctg tgcagggtaa  1740 tgcgccgaag ttttttgactc gcgtcagccg tcgcggtgtg ccgattaact cgctgatgct  1800
ttccggagcg atcacttcgc tggtggtgtt aatcaactat ctgctgccgc aaaaagcgtt  1860
tggtctgctg atggcgctgg tggtagcaac gctgctgttg aactggatta tgatctgtct  1920
ggcgcatctg cgttttcgtg cagcgatgcg acgtcagggg cgtgaaacac agtttaaggc  1980
gctgctctat ccgttcggca actatctctg cattgccttc ctcggcatga ttttgctgct  2040
gatgtgcacg atggatgata tgcgcttgtc agcgatcctg ctgccggtgt ggattgtatt  2100
cctgtttatg gcatttaaaa cgctgcgtcg gaaataa                            2137
```

<210> SEQ ID NO 31
<211> LENGTH: 3383
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 31

```
ggtaccgtca gcataacacc ctgacctctc attaattgtt catgccgggc ggcactatcg      60
tcgtccggcc ttttcctctc ttactctgct acgtacatct atttctataa atccgttcaa     120
tttgtctgtt ttttgcacaa acatgaaata tcagacaatt ccgtgactta agaaaattta     180
tacaaatcag caatatcccc ttaaggagt atataaaggt gaatttgatt tacatcaata      240
agcggggttg ctgaatcgtt aaggtaggcg gtaatagaaa agaaatcgag gcaaaaatga     300
gcaaagtcag actcgcaatt atggatcctc tggccgtcgt attacaacgt cgtgactggg     360
aaaaccctgg cgttacccaa cttaatcgcc ttgcggcaca tccccctttc gccagctggc     420
gtaatagcga gaggcccgc accgatcgcc cttcccaaca gttgcgcagc ctgaatggcg     480
aatggcgctt tgcctggttt ccggcaccag aagcggtgcc ggaaagctgg ctggagtgcg     540
atcttcctga cgccgatact gtcgtcgtcc cctcaaactg gcagatgcac ggttacgatg     600
cgcctatcta caccaacgtg acctatccca ttacggtcaa tccgccgttt gttcccgcgg     660
agaatccgac aggttgttac tcgctcacat ttaatattga tgaaagctgg ctacaggaag     720
gccagacgcg aattattttt gatggcgtta actcggcgtt tcatctgtgg tgcaacgggc     780
gctgggtcgg ttacggccag acagccgttt gccgtctga atttgacctg agcgcatttt      840
tacgcgccgg agaaaaccgc ctcgcggtga tggtgctgcg ctggagtgac ggcagttatc     900
tggaagatca ggatatgtgg cggatgagcg gcatttttccg tgacgtctcg ttgctgcata     960
aaccgaccac gcaaatcagc gatttccaag ttaccactct ctttaatgat gatttcagcc    1020
gcgcggtact ggaggcagaa gttcagatgt acggcgagct gcgcgatgaa ctgcgggtga    1080
cggtttcttt gtggcagggt gaaacgcagg tcgccagcgg caccgcgcct ttcggcggtg    1140
aaattatcga tgagcgtggc ggttatgccg atcgcgtcac actacgcctg aacgttgaaa    1200
atccggaact gtggagcgcc gaaatcccga atctctatcg tgcagtggtt gaactgcaca    1260
ccgccgacgg cacgctgatt gaagcagaag cctgcgacgt cggtttccgc gaggtgcgga    1320
ttgaaaatgg tctgctgctg ctgaacggca agccgttgct gattcgcggc gttaaccgtc    1380
acgagcatca tcctctgcat ggtcaggtca tggatgagca gacgatggtg caggatatcc    1440
tgctgatgaa gcagaacaac tttaacgccg tgcgctgttc gcattatccg aaccatccgc    1500
tgtggtacac gctgtgcgac cgctacggcc tgtatgtggt ggatgaagcc aatattgaaa    1560
cccacggcat ggtgccaatg aatcgtctga ccgatgatcc gcgctggcta cccgcgatga    1620
gcgaacgcgt aacgcggatg gtgcagcgcg atcgtaatca cccgagtgtg atcatctggt    1680
cgctggggaa tgaatcaggc cacggcgcta atcacgacgc gctgtatcgc tggatcaaat    1740
ctgtcgatcc ttcccgcccg gtacagtatg aaggcggcgg agccgacacc acggccaccg    1800
atattatttg cccgatgtac gcgcgcgtgg atgaagacca gcccttcccg gcggtgccga    1860
aatggtccat caaaaaatgg ctttcgctgc ctggagaaat gcgcccgctg atcctttgcg    1920
aatatgccca cgcgatgggt aacagtcttg gcggcttcgc taaatactgg caggcgtttc    1980
gtcagtaccc ccgtttacag gcggcttcg tctgggactg ggtggatcag tcgctgatta    2040
aatatgatga aaacggcaac ccgtggtcgg cttacggcgg tgattttggc gatacgccga    2100
acgatcgcca gttctgtatg aacgctctgg tctttgccga ccgcacgccg catccggcgc    2160
tgacggaagc aaaacaccaa cagcagtatt tccagttccg tttatccggg cgaaccatcg    2220
```

```
aagtgaccag cgaatacctg ttccgtcata gcgataacga gttcctgcac tggatggtgg    2280
cactggatgg caagccgctg gcaagcggtg aagtgcctct ggatgttggc ccgcaaggta    2340
agcagttgat tgaactgcct gaactgccgc agccggagag cgccggacaa ctctggctaa    2400
cggtacgcgt agtgcaacca aacgcgaccg catggtcaga agccggacac atcagcgcct    2460
ggcagcaatg gcgtctggcg gaaaacctca gcgtgacact cccctccgcg tcccacgcca    2520
tccctcaact gaccaccagc ggaacggatt tttgcatcga gctgggtaat aagcgttggc    2580
aatttaaccg ccagtcaggc tttctttcac agatgtggat tggcgatgaa aaacaactgc    2640
tgaccccgct gcgcgatcag ttcacccgtg cgccgctgga taacgacatt ggcgtaagtg    2700
aagcgacccg cattgaccct aacgcctggg tcgaacgctg gaaggcggcg ggccattacc    2760
aggccgaagc ggcgttgttg cagtgcacgg cagatacact tgccgacgcg gtgctgatta    2820
caaccgccca cgcgtggcag catcagggga aaaccttatt tatcagccgg aaaacctacc    2880
ggattgatgg gcacggtgag atggtcatca atgtggatgt tgcggtggca agcgatacac    2940
cgcatccggc gcggattggc ctgacctgcc agctggcgca ggtctcagag cgggtaaact    3000
ggctcggcct ggggccgcaa gaaaactatc ccgaccgcct tactgcagcc tgttttgacc    3060
gctgggatct gccattgtca gacatgtata ccccgtacgt cttcccgagc gaaaacggtc    3120
tgcgctgcgg gacgcgcgaa ttgaattatg cccacacca gtggcgcggc gacttccagt    3180
tcaacatcag ccgctacagc caacaacaac tgatggaaac cagccatcgc catctgctgc    3240
acgcggaaga aggcacatgg ctgaatatcg acggtttcca tatggggatt ggtggcgacg    3300
actcctggag cccgtcagta tcggcggaat ccagctgag cgccggtcgc taccattacc    3360
agttggtctg gtgtcaaaaa taa                                            3383
```

<210> SEQ ID NO 32
<211> LENGTH: 3258
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 32

```
ggtacccatt tcctctcatc ccatccgggg tgagagtctt ttcccccgac ttatggctca      60
tgcatgcatc aaaaaagatg tgagcttgat caaaaacaaa aaatatttca ctcgacagga    120
gtatttatat tgcgcccgtt acgtgggctt cgactgtaaa tcagaaagga gaaacacct     180 atgacgacct acgatcggga tcctctggcc gtcgtattac aacgtcgtga ctgggaaaac    240
cctggcgtta cccaacttaa tcgccttgcg gcacatcccc ctttcgccag ctggcgtaat    300
agcgaagagg cccgcaccga tcgcccttcc caacagttgc gcagcctgaa tggcgaatgg    360
cgctttgcct ggtttccggc accagaagcg gtgccggaaa gctggctgga gtgcgatctt    420
cctgacgccg atactgtcgt cgtcccctca aactggcaga tgcacggtta cgatgcgcct    480
atctacacca acgtgaccta tcccattacg gtcaatccgc cgtttgttcc cgcggagaat    540
ccgacaggtt gttactcgct cacatttaat attgatgaaa gctggctaca ggaaggccag    600
acgcgaatta tttttgatgg cgttaactcg gcgtttcatc tgtggtgcaa cgggcgctgg    660
gtcggttacg gccaggacag ccgtttgccg tctgaatttg acctgagcgc atttttacgc    720
gccggagaaa accgcctcgc ggtgatggtg ctgcgctgga gtgacggcag ttatctggaa    780
gatcaggata tgtggcggat gagcggcatt ttccgtgacg tctcgttgct gcataaaccg    840
```

```
accacgcaaa tcagcgattt ccaagttacc actctcttta atgatgattt cagccgcgcg    900
gtactggagg cagaagttca gatgtacggc gagctgcgcg atgaactgcg ggtgacggtt    960
tctttgtggc agggtgaaac gcaggtcgcc agcggcaccg cgcctttcgg cggtgaaatt   1020
atcgatgagc gtggcggtta tgccgatcgc gtcacactac gcctgaacgt tgaaaatccg   1080
gaactgtgga gcgccgaaat cccgaatctc tatcgtgcag tggttgaact gcacaccgcc   1140
gacggcacgc tgattgaagc agaagcctgc gacgtcggtt ccgcgaggt gcggattgaa   1200 aatggtctgc tgctgctgaa cggcaagccg ttgctgattc gcggcgttaa ccgtcacgag   1260
catcatcctc tgcatggtca ggtcatggat gagcagacga tggtgcagga tatcctgctg   1320
atgaagcaga acaactttaa cgccgtgcgc tgttcgcatt atccgaacca tccgctgtgg   1380
tacacgctgt gcgaccgcta cggcctgtat gtggtggatg aagccaatat tgaaacccac   1440
ggcatggtgc aatgaatcg tctgaccgat gatccgcgct ggctaccgc gatgagcgaa   1500 cgcgtaacgc ggatggtgca gcgcgatcgt aatcacccga gtgtgatcat ctggtcgctg   1560
gggaatgaat caggccacgg cgctaatcac gacgcgctgt atcgctggat caaatctgtc   1620
gatccttccc gcccggtaca gtatgaaggc ggcggagccg acaccacggc caccgatatt   1680
atttgcccga tgtacgcgcg cgtggatgaa gaccagccct cccggcggt gccgaaatgg   1740 tccatcaaaa aatggctttc gctgcctgga gaaatgcgcc cgctgatcct ttgcgaatat   1800
gcccacgcga tgggtaacag tcttggcggc ttcgctaaat actggcaggc gtttcgtcag   1860 taccccgtt tacagggcgg cttcgtctgg gactgggtgg atcagtcgct gattaaatat   1920
gatgaaaacg gcaacccgtg gtcggcttac ggcggtgatt ttggcgatac gccgaacgat   1980
cgccagttct gtatgaacgg tctggtctttt gccgaccgca cgccgcatcc ggcgctgacg   2040
gaagcaaaac accaacagca gtatttccag ttccgttttat ccgggcgaac catcgaagtg   2100
accagcgaat acctgttccg tcatagcgat aacgagttcc tgcactggat ggtggcactg   2160
gatggcaagc cgctggcaag cggtgaagtg cctctggatg ttggcccgca aggtaagcag   2220
ttgattgaac tgcctgaact gccgcagccg gagagcgccg acaactctg gctaacggta   2280 cgcgtagtgc aaccaaacgc gaccgcatgg tcagaagccg gacacatcag cgcctggcag   2340
caatggcgtc tggcggaaaa cctcagcgtg acactcccct ccgcgtccca cgccatccct   2400
caactgacca ccagcggaac ggattttttgc atcgagctgg gtaataagcg ttggcaattt   2460
aaccgccagt caggctttct ttcacagatg tggattggcg atgaaaaaca actgctgacc   2520
ccgctgcgcg atcagttcac ccgtgcgccg ctggataacg acattggcgt aagtgaagcg   2580
acccgcattg accctaacgc ctgggtcgaa cgctggaagg cggcgggcca ttaccaggcc   2640
gaagcggcgt tgttgcagtg cacggcagat acacttgccg acgcggtgct gattacaacc   2700
gcccacgcgt ggcagcatca ggggaaaacc ttatttatca gccggaaaac ctaccggatt   2760
gatgggcacg gtgagatggt catcaatgtg gatgttgcgg tggcaagcga tacaccgcat   2820
ccggcgcgga ttggcctgac ctgccagctg gcgcaggtct cagagcgggt aaactggctc   2880
ggcctggggc cgcaagaaaa ctatcccgac cgccttactg cagcctgttt tgaccgctgg   2940
gatctgccat tgtcagacat gtatacccg tacgtcttcc cgagcgaaaa cggtctgcgc   3000
tgcgggacgc gcgaattgaa ttatggccca ccagtggc gcggcgactt ccagttcaac   3060
atcagccgct acagccaaca acaactgatg gaaaccagcc atcgccatct gctgcacgcg   3120
gaagaaggca catggctgaa tatcgacggt ttccatatgg ggattggtgg cgacgactcc   3180
```
tggagcccgt cagtatcggc ggaattccag ctgagcgccg gtcgctacca ttaccagttg    3240
gtctggtgtc aaaaataa                                                  3258

<210> SEQ ID NO 33
<211> LENGTH: 3386
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 33
ggtaccgtca gcataacacc ctgacctctc attaattgtt catgccgggc ggcactatcg      60
tcgtccggcc ttttcctctc ttactctgct acgtacatct atttctataa atccgttcaa     120
tttgtctgtt ttttgcacaa acatgaaata tcagacaatt ccgtgactta agaaaattta     180
tacaaatcag caatataccc cttaaggagt atataaggt gaatttgatt tacatcaata     240
agcggggttg ctgaatcgtt aaggatccct ctagaaataa ttttgtttaa ctttaagaag     300
gagatataca tatgactatg attacggatt ctctggccgt cgtattacaa cgtcgtgact     360
gggaaaaccc tggcgttacc caacttaatc gccttgcggc acatcccct ttcgccagct     420 ggcgtaatag cgaagaggcc cgcaccgatc gcccttccca acagttgcgc agcctgaatg     480
gcgaatggcg ctttgcctgg tttccggcac cagaagcggg gccggaaagc tggctggagt     540
gcgatcttcc tgacgccgat actgtcgtcg tcccctcaaa ctggcagatg cacggttacg     600
atgcgcctat ctacaccaac gtgacctatc ccattacggt caatccgccg tttgttcccg     660
cggagaatcc gacaggttgt tactcgctca catttaatat tgatgaaagc tggctacagg     720
aaggccagac gcgaattatt tttgatggcg ttaactcggc gtttcatctg tggtgcaacg     780
ggcgctgggt cggttacggc caggacagcc gtttgccgtc tgaatttgac ctgagcgcat     840
ttttacgcgc cggagaaaac cgcctcgcgg tgatggtgct gcgctggagt gacggcagtt     900
atctggaaga tcaggatatg tggcggatga gcggcatttt ccgtgacgtc tcgttgctgc     960
ataaaccgac cacgcaaatc agcgatttcc aagttaccac tctctttaat gatgatttca    1020
gccgcgcggt actggaggca gaagttcaga tgtacggcga gctgcgcgat gaactgcggg    1080
tgacggtttc tttgtggcag ggtgaaacgc aggtcgccag cggcaccgcg cctttcggcg    1140
gtgaaattat cgatgagcgt ggcggttatg ccgatcgcgt cacactacgc ctgaacgttg    1200
aaaatccgga actgtggagc gccgaaatcc gaatctcta tcgtgcagtg gttgaactgc    1260
acaccgccga cggcacgctg attgaagcag aagcctgcga cgtcggtttc gcgaggtgc    1320 ggattgaaaa tggtctgctg ctgctgaacg gcaagccgtt gctgattcgc ggcgttaacc    1380
gtcacgagca tcatcctctg catggtcagg tcatggatga cagacgatg gtgcaggata    1440 tcctgctgat gaagcagaac aactttaacg ccgtgcgctg ttcgcattat ccgaaccatc    1500
cgctgtggta cacgctgtgc gaccgctacg gcctgtatgt ggtggatgaa gccaatattg    1560
aaacccacgg catggtgcca atgaatcgtc tgaccgatga tccgcgctgg ctacccgcga    1620
tgagcgaacg cgtaacgcgg atggtgcagc gcatcgtaa tcacccgagt gtgatcatct    1680
ggtcgctggg gaatgaatca ggccacggcg ctaatcacga cgcgctgtat cgctggatca    1740
aatctgtcga tccttcccgc ccggtacagt atgaaggcgg cggagccgac accacggcca    1800
ccgatattat ttgcccgatg tacgcgcgcg tggatgaaga ccagcccttc ccggcggtgc    1860
cgaaatggtc catcaaaaaa tggctttcgc tgcctggaga aatgcgcccg ctgatccttt    1920

```
gcgaatatgc ccacgcgatg ggtaacagtc ttggcggctt cgctaaatac tggcaggcgt    1980
ttcgtcagta cccccgttta cagggcggct tcgtctggga ctgggtggat cagtcgctga    2040
ttaaatatga tgaaaacggc aacccgtggt cggcttacgg cggtgatttt ggcgatacgc    2100
cgaacgatcg ccagttctgt atgaacggtc tggtctttgc cgaccgcacg ccgcatccgg    2160
cgctgacgga agcaaaacac caacagcagt atttccagtt ccgtttatcc gggcgaacca    2220
tcgaagtgac cagcgaatac ctgttccgtc atagcgataa cgagttcctg cactggatgg    2280
tggcactgga tggcaagccg ctggcaagcg gtgaagtgcc tctggatgtt ggcccgcaag    2340
gtaagcagtt gattgaactg cctgaactgc cgcagccgga gagcgccgga caactctggc    2400
taacggtacg cgtagtgcaa ccaaacgcga ccgcatggtc agaagccgga cacatcagcg    2460
cctggcagca atggcgtctg gcggaaaacc tcagcgtgac actcccctcc gcgtcccacg    2520
ccatccctca actgaccacc agcggaacgg attttgcat cgagctgggt aataagcgtt    2580
ggcaatttaa ccgccagtca ggcttctttt cacagatgtg gattggcgat gaaaaacaac    2640
tgctgacccc gctgcgcgat cagttcaccc gtgcgccgct ggataacgac attggcgtaa    2700
gtgaagcgac ccgcattgac cctaacgcct gggtcgaacg ctggaaggcg gcgggccatt    2760
accaggccga agcggcgttg ttgcagtgca cggcagatac acttgccgac gcggtgctga    2820
ttacaaccgc ccacgcgtgg cagcatcagg ggaaaacctt atttatcagc cggaaaacct    2880
accggattga tgggcacggt gagatggtca tcaatgtgga tgttgcggtg caagcgata    2940 caccgcatcc ggcgcggatt ggcctgacct gccagctggc gcaggtctca gagcgggtaa    3000
actggctcgg cctggggccg caagaaaact atcccgaccg ccttactgca gcctgttttg    3060
accgctggga tctgccattg tcagacatgt atacccgta cgtcttcccg agcgaaaacg    3120
gtctgcgctg cgggacgcgc gaattgaatt atggcccaca ccagtggcgc ggcgacttcc    3180
agttcaacat cagccgctac agccaacaac aactgatgga aaccagccat cgccatctgc    3240
tgcacgcgga agaaggcaca tggctgaata tcgacggttt ccatatgggg attggtggcg    3300
acgactcctg gagcccgtca gtatcggcgg aattccagct gagcgccggt cgctaccatt    3360
accagttggt ctggtgtcaa aaataa                                         3386
```

<210> SEQ ID NO 34
<211> LENGTH: 3261
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 34

```
ggtacccatt tcctctcatc ccatccgggg tgagagtctt ttcccccgac ttatggctca      60
tgcatgcatc aaaaaagatg tgagcttgat caaaaacaaa aaatatttca ctcgacagga    120
gtatttatat tgcgcccgga tccctctaga aataattttg tttaacttta agaaggagat    180
atacatatga ctatgattac ggattctctg gccgtcgtat tacaacgtcg tgactgggaa    240
aaccctggcg ttacccaact taatcgcctt gcggcacatc ccccttttcgc cagctggcgt    300 aatagcgaag aggcccgcac cgatcgccct tcccaacagt tgcgcagcct gaatggcgaa    360
tggcgctttg cctggtttcc ggcaccagaa gcggtgccgg aaagctggct ggagtgcgat    420
cttcctgacg ccgatactgt cgtcgtcccc tcaaactggc agatgcacgg ttacgatgcg    480
```

```
cctatctaca ccaacgtgac ctatcccatt acggtcaatc cgccgtttgt tcccgcggag    540
aatccgacag gttgttactc gctcacattt aatattgatg aaagctggct acaggaaggc    600
cagacgcgaa ttatttttga tggcgttaac tcggcgtttc atctgtggtg caacgggcgc    660
tgggtcggtt acggccagga cagccgtttg ccgtctgaat ttgacctgag cgcattttta    720
cgcgccggag aaaaccgcct cgcggtgatg gtgctgcgct ggagtgacgg cagttatctg    780
gaagatcagg atatgtggcg gatgagcggc attttccgtg acgtctcgtt gctgcataaa    840
ccgaccacgc aaatcagcga tttccaagtt accactctct ttaatgatga tttcagccgc    900
gcggtactgg aggcagaagt tcagatgtac ggcgagctgc gcgatgaact gcgggtgacg    960
gtttctttgt ggcagggtga aacgcaggtc gccagcggca ccgcgccttt cggcggtgaa   1020
attatcgatg agcgtggcgg ttatgccgat cgcgtcacac tacgcctgaa cgttgaaaat   1080
ccggaactgt ggagcgccga atcccgaat ctctatcgtg cagtggttga actgcacacc   1140
gccgacggca cgctgattga agcagaagcc tgcgacgtcg gtttccgcga ggtgcggatt   1200
gaaaatggtc tgctgctgct gaacggcaag ccgttgctga ttcgcggcgt taaccgtcac   1260
gagcatcatc ctctgcatgg tcaggtcatg gatgagcaga cgatggtgca ggatatcctg   1320
ctgatgaagc agaacaactt taacgccgtg cgctgttcgc attatccgaa ccatccgctg   1380
tggtacacgc tgtgcgaccg ctacggcctg tatgtggtgg atgaagccaa tattgaaacc   1440
cacggcatgg tgccaatgaa tcgtctgacc gatgatccgc gctggctacc cgcgatgagc   1500
gaacgcgtaa cgcggatggt gcagcgcgat cgtaatcacc cgagtgtgat catctggtcg   1560
ctggggaatg aatcaggcca cggcgctaat cacgacgcgc tgtatcgctg gatcaaatct   1620
gtcgatcctt cccgcccggt acagtatgaa ggcggcggag ccgacaccac ggccaccgat   1680
attatttgcc cgatgtacgc gcgcgtggat gaagaccagc ccttcccggc ggtgccgaaa   1740
tggtccatca aaaaatggct ttcgctgcct ggagaaatgc gcccgctgat cctttgcgaa   1800
tatgcccacg cgatgggtaa cagtcttggc ggcttcgcta aatactggca ggcgtttcgt   1860
cagtaccccc gtttacaggg cggcttcgtc tgggactggg tggatcagtc gctgattaaa   1920
tatgatgaaa acggcaaccc gtggtcggct tacggcggtg attttggcga tacgccgaac   1980
gatcgccagt tctgtatgaa cggtctggtc tttgccgacc gcacgccgca tccggcgctg   2040
acggaagcaa acaccaaca gcagtatttc cagttccgtt tatccgggcg aaccatcgaa   2100
gtgaccagcg aatacctgtt ccgtcatagc gataacgagt tcctgcactg gatggtggca   2160
ctggatggca agccgctggc aagcggtgaa gtgcctctgg atgttggccc gcaaggtaag   2220
cagttgattg aactgcctga actgccgcag ccggagagcg ccggacaact ctggctaacg   2280
gtacgcgtag tgcaaccaaa cgcgaccgca tggtcagaag ccggacacat cagcgcctgg   2340
cagcaatggc gtctggcgga aaacctcagc gtgacactcc cctccgcgtc ccacgccatc   2400
cctcaactga ccaccagcgg aacggatttt tgcatcgagc tgggtaataa gcgttggcaa   2460
tttaaccgcc agtcaggctt tctttcacag atgtggattg cgatgaaaaa caactgctg   2520 accccgctgc gcgatcagtt caccgtgcg ccgctggata cgacattgg cgtaagtgaa   2580 gcgaccgca ttgaccctaa cgcctgggtc gaacgctgga aggcggcggg ccattaccag   2640
gccgaagcgg cgttgttgca gtgcacggca gatacacttg ccgacgcggt gctgattaca   2700
accgcccacg cgtggcagca tcaggggaaa accttattta tcagccggaa aacctaccgg   2760
attgatgggc acggtgagat ggtcatcaat gtggatgttg cggtggcaag cgatacaccg   2820
catccggcgc ggattggcct gacctgccag ctggcgcagg tctcagagcg ggtaaactgg   2880
```

```
ctcggcctgg ggccgcaaga aaactatccc gaccgcctta ctgcagcctg ttttgaccgc    2940
tgggatctgc cattgtcaga catgtatacc ccgtacgtct tcccgagcga aaacggtctg    3000
cgctgcggga cgcgcgaatt gaattatggc ccacaccagt ggcgcggcga cttccagttc    3060
aacatcagcc gctacagcca acaacaactg atggaaacca gccatcgcca tctgctgcac    3120
gcggaagaag gcacatggct gaatatcgac ggtttccata tggggattgg tggcgacgac    3180
tcctggagcc cgtcagtatc ggcggaattc cagctgagcg ccggtcgcta ccattaccag    3240
ttggtctggt gtcaaaaata a                                              3261
```

<210> SEQ ID NO 35
<211> LENGTH: 3279
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 35

```
ggtaccagtt gttcttattg gtggtgttgc tttatggttg catcgtagta aatggttgta      60
acaaaagcaa ttttccggc tgtctgtata caaaaacgcc gtaaagtttg agcgaagtca     120
ataaactctc tacccattca gggcaatatc tctcttggat ccctctagaa ataattttgt     180
ttaactttaa gaaggagata tacatatgct atgattacgg attctctggc cgtcgtatta     240
caacgtcgtg actgggaaaa ccctggcgtt acccaactta atcgccttgc ggcacatccc     300
cctttcgcca gctggcgtaa tagcgaagag gcccgcaccg atcgcccttc ccaacagttg     360
cgcagcctga atggcgaatg gcgctttgcc tggtttccgg caccagaagc ggtgccggaa     420
agctggctgg agtgcgatct tcctgacgcc gatactgtcg tcgtcccctc aaactggcag     480
atgcacggtt acgatgcgcc tatctacacc aacgtgacct atcccattac ggtcaatccg     540
ccgtttgttc ccgcggagaa tccgacaggt tgttactcgc tcacatttaa tattgatgaa     600
agctggctac aggaaggcca gacgcgaatt atttttgatg gcgttaactc ggcgtttcat     660
ctgtggtgca acgggcgctg ggtcggttac ggccaggaca gccgtttgcc gtctgaattt     720
gacctgagcg cattttttacg cgccggagaa aaccgcctcg cggtgatggt gctgcgctgg     780
agtgacggca gttatctgga agatcaggat atgtggcgga tgagcggcat tttccgtgac     840
gtctcgttgc tgcataaacc gaccacgcaa atcagcgatt ccaagttac cactctcttt     900 aatgatgatt tcagccgcgc ggtactggag gcagaagttc agatgtacgg cgagctgcgc     960
gatgaactgc gggtgacggt ttcttttgtg cagggtgaaa cgcaggtcgc cagcggcacc    1020
gcgcctttcg gcggtgaaat tatcgatgag cgtggcggtt atgccgatcg cgtcacacta    1080
cgcctgaacg ttgaaaatcc ggaactgtgg agcgccgaaa tcccgaatct ctatcgtgca    1140
gtggttgaac tgcacaccgc cgacggcacg ctgattgaag cagaagcctg cgacgtcggt    1200
ttccgcgagg tgcggattga aaatggtctg ctgctgctga acggcaagcc gttgctgatt    1260
cgcggcgtta accgtcacga gcatcatcct ctgcatggtc aggtcatgga tgagcagacg    1320
atggtgcagg atatcctgct gatgaagcag aacaacttta acgccgtgcg ctgttcgcat    1380
tatccgaacc atccgctgtg gtacacgctg tgcgaccgct acggcctgta tgtggtggat    1440
gaagccaata ttgaaaccca cggcatggtg ccaatgaatc gtctgaccga tgatccgcgc    1500
tggctacccg cgatgagcga acgcgtaacg cggatggtgc agcgcgatcg taatcacccg    1560
```

```
agtgtgatca tctggtcgct ggggaatgaa tcaggccacg gcgctaatca cgacgcgctg    1620
tatcgctgga tcaaatctgt cgatccttcc cgcccggtac agtatgaagg cggcggagcc    1680
gacaccacgg ccaccgatat tatttgcccg atgtacgcgc gcgtggatga agaccagccc    1740
ttcccggcgg tgccgaaatg gtccatcaaa aaatggcttt cgctgcctgg agaaatgcgc    1800
ccgctgatcc tttgcgaata tgcccacgcg atgggtaaca gtcttggcgg cttcgctaaa    1860
tactggcagg cgtttcgtca gtaccccgt ttacagggcg gcttcgtctg ggactgggtg    1920
gatcagtcgc tgattaaata tgatgaaaac ggcaacccgt ggtcggctta cggcggtgat    1980
tttggcgata cgccgaacga tcgccagttc tgtatgaacg gtctggtctt tgccgaccgc    2040
acgccgcatc cggcgctgac ggaagcaaaa caccaacagc agtatttcca gttccgttta    2100
tccgggcgaa ccatcgaagt gaccagcgaa tacctgttcc gtcatagcga taacgagttc    2160
ctgcactgga tggtggcact ggatggcaag ccgctggcaa gcggtgaagt gcctctggat    2220
gttggcccgc aaggtaagca gttgattgaa ctgcctgaac tgccgcagcc ggagagcgcc    2280
ggacaactct ggctaacggt acgcgtagtg caaccaaacg cgaccgcatg gtcagaagcc    2340
ggacacatca gcgcctggca gcaatggcgt ctggcggaaa acctcagcgt gacactcccc    2400
tccgcgtccc acgccatccc tcaactgacc accagcggaa cggattttg catcgagctg    2460 ggtaataagc gttggcaatt taaccgccag tcaggctttc tttcacagat gtggattggc    2520
gatgaaaaac aactgctgac cccgctgcgc gatcagttca cccgtgcgcc gctggataac    2580
gacattggcg taagtgaagc gacccgcatt gaccctaacg cctgggtcga acgctggaag    2640
gcggcgggcc attaccaggc cgaagcgcg ttgttgcagt gcacggcaga tacacttgcc    2700
gacgcggtgc tgattacaac cgcccacgcg tggcagcatc aggggaaaac cttatttatc    2760
agccggaaaa cctaccggat tgatgggcac ggtgagatgg tcatcaatgt ggatgttgcg    2820
gtggcaagcg atacaccgca tccggcgcgg attggcctga cctgccagct ggcgcaggtc    2880
tcagagcggg taaactggct cggcctgggg ccgcaagaaa actatcccga ccgccttact    2940
gcagcctgtt ttgaccgctg ggatctgcca ttgtcagaca tgtataccc gtacgtcttc    3000 ccgagcgaaa acggtctgcg ctgcgggacg cgcgaattga attatggccc acaccagtgg    3060
cgcggcgact tccagttcaa catcagccgc tacagccaac aacaactgat ggaaaccagc    3120
catcgccatc tgctgcacgc ggaagaaggc acatggctga atcgacgg tttccatatg    3180 gggattggtg gcgacgactc ctggagcccg tcagtatcgg cggaattcca gctgagcgcc    3240
ggtcgctacc attaccagtt ggtctggtgt caaaaataa                          3279
```

<210> SEQ ID NO 36
<211> LENGTH: 1910
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 36

```
ggtaccgtca gcataacacc ctgacctctc attaattgtt catgccgggc ggcactatcg      60
tcgtccggcc ttttcctctc ttactctgct acgtacatct atttctataa atccgttcaa     120
tttgtctgtt ttttgcacaa acatgaaata tcagacaatt ccgtgactta agaaaattta     180
tacaaatcag caatataccc cttaaggagt atataaggt gaatttgatt tacatcaata     240
agcggggttg ctgaatcgtt aaggatccct ctagaaataa ttttgtttaa ctttaagaag    300
```

```
gagatataca tatgaaagct aaagatgttc agccaaccat tattattaat aaaaatggcc    360
ttatctcttt ggaagatatc tatgacattg cgataaaaca aaaaaaagta gaaatatcaa    420
cggagatcac tgaactttig acgcatggtc gtgaaaaatt agaggaaaaa ttaaattcag    480
gagaggttat atatggaatc aatacaggat ttggagggaa tgccaattta gttgtgccat    540
ttgagaaaat cgcagagcat cagcaaaatc tgttaacttt tctttctgct ggtactgggg    600
actatatgtc caaaccttgt attaaagcgt cacaatttac tatgttactt tctgtttgca    660
aaggttggtc tgcaaccaga ccaattgtcg ctcaagcaat tgttgatcat attaatcatg    720
acattgttcc tctggttcct cgctatggct cagtgggtgc aagcggtgat ttaattcctt    780
tatcttatat tgcacgagca ttatgtggta tcggcaaagt ttattatatg ggcgcagaaa    840
ttgacgctgc tgaagcaatt aaacgtgcag ggttgacacc attatcgtta aaagccaaag    900
aaggtcttgc tctgattaac ggcacccggg taatgtcagg aatcagtgca atcaccgtca    960
ttaaactgga aaaactattt aaagcctcaa tttctgcgat tgcccttgct gttgaagcat   1020
tacttgcatc tcatgaacat tatgatgccc ggattcaaca agtaaaaaat catcctggtc   1080 aaaacgcgt ggcaagtgca ttgcgtaatt tattggcagg ttcaacgcag gttaatctat   1140
tatctggggt taaagaacaa gccaataaag cttgtcgtca tcaagaaatt acccaactaa   1200
atgatacctt acaggaagtt tattcaattc gctgtgcacc acaagtatta ggtatagtgc   1260
cagaatcttt agctaccgct cggaaaatat tggaacggga agttatctca gctaatgata   1320
atccattgat agatccagaa aatggcgatg ttctacacgg tggaaatttt atggggcaat   1380
atgtcgcccg aacaatggat gcattaaaac tggatattgc tttaattgcc aatcatcttc   1440
acgccattgt ggctcttatg atggataacc gtttctctcg tggattacct aattcactga   1500
gtccgacacc cggcatgtat caaggtttta aaggcgtcca actttctcaa accgctttag   1560
ttgctgcaat tcgccatgat tgtgctgcat caggtattca taccctcgcc acagaacaat   1620
acaatcaaga tattgtcagt ttaggtctgc atgccgctca agatgtttta gagatggagc   1680
agaaaattac gcaatattgt ttcaatgacaa ttctggtagt ttgtcaggcc attcatcttc   1740
gcggcaatat tagtgaaatt gcgcctgaaa ctgctaaatt ttaccatgca gtacgcgaaa   1800
tcagttctcc tttgatcact gatcgtgcgt tggatgaaga tataatccgc attgcggatg   1860
caattattaa tgatcaactt cctctgccag aaatcatgct ggaagaataa               1910
```

<210> SEQ ID NO 37
<211> LENGTH: 1785
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic polynucleotide"

<400> SEQUENCE: 37

```
ggtacccatt tcctctcatc ccatccgggg tgagagtctt ttcccccgac ttatggctca     60
tgcatgcatc aaaaaagatg tgagcttgat caaaaacaaa aaatatttca ctcgacagga    120
gtatttatat tgcgcccgga tccctctaga ataattttig tttaacttta agaaggagat    180
atacatatga aagctaaaga tgttcagcca accattatta ttaataaaaa tggccttatc    240
tctttggaag atatctatga cattgcgata aaacaaaaaa agtagaaaat tcaacggag    300 atcactgaac ttttgacgca tggtcgtgaa aaattagagg aaaaattaaa ttcaggagag    360
```

```
gttatatatg gaatcaatac aggatttgga gggaatgcca atttagttgt gccatttgag    420
aaaatcgcag agcatcagca aaatctgtta acttttcttt ctgctggtac tggggactat    480
atgtccaaac cttgtattaa agcgtcacaa tttactatgt tactttctgt ttgcaaaggt    540
tggtctgcaa ccagaccaat tgtcgctcaa gcaattgttg atcatattaa tcatgacatt    600
gttcctctgg ttcctcgcta tggctcagtg ggtgcaagcg gtgatttaat tcctttatct    660
tatattgcac gagcattatg tggtatcggc aaagtttatt atatgggcgc agaaattgac    720
gctgctgaag caattaaacg tgcagggttg acaccattat cgttaaaagc caaagaaggt    780
cttgctctga ttaacggcac ccgggtaatg tcaggaatca gtgcaatcac cgtcattaaa    840
ctggaaaaac tatttaaagc ctcaatttct gcgattgccc ttgctgttga agcattactt    900
gcatctcatg aacattatga tgcccggatt caacaagtaa aaaatcatcc tggtcaaaac    960
gcggtggcaa gtgcattgcg taatttattg gcaggttcaa cgcaggttaa tctattatct   1020
ggggttaaag aacaagccaa taagcttgt cgtcatcaag aaattaccca actaaatgat   1080
accttacagg aagtttattc aattcgctgt gcaccacaag tattaggtat agtgccagaa   1140
tctttagcta ccgctcggaa atattggaa cgggaagtta ctcagctaa tgataatcca   1200 ttgatagatc cagaaaatgg cgatgttcta cacggtggaa attttatggg gcaatatgtc   1260
gcccgaacaa tggatgcatt aaaactggat attgctttaa ttgccaatca tcttcacgcc   1320 attgtgctc ttatgatgga taccgtttc tctcgtggat tacctaattc actgagtccg   1380
acacccggca tgtatcaagg ttttaaaggc gtccaacttt ctcaaaccgc tttagttgct   1440
gcaattcgcc atgattgtgc tgcatcaggt attcataccc tcgccacaga acaatacaat   1500
caagatattg tcagtttagg tctgcatgcc gctcaagatg ttttagagat ggagcagaaa   1560
ttacgcaata ttgtttcaat gacaattctg gtagtttgtc aggccattca tcttcgcggc   1620
aatattagtg aaattgcgcc tgaaactgct aaattttacc atgcagtacg cgaaatcagt   1680
tctcctttga tcactgatcg tgcgttggat gaagatataa tccgcattgc ggatgcaatt   1740
attaatgatc aacttcctct gccagaaatc atgctggaag aataa                  1785
```

<210> SEQ ID NO 38
<211> LENGTH: 1804
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 38

```
ggtaccagtt gttcttattg gtggtgttgc tttatggttg catcgtagta aatggttgta     60
acaaaagcaa ttttccggc tgtctgtata caaaaacgcc gtaaagtttg agcgaagtca    120
ataaactctc tacccattca gggcaatatc tctcttggat ccctctagaa ataattttgt    180
ttaactttaa gaaggagata tacatatgaa agctaaagat gttcagccaa ccattattat    240
taataaaaat ggccttatct ctttggaaga tatctatgac attgcgataa aacaaaaaaa    300
agtagaaata tcaacggaga tcactgaact ttttgacgcat ggtcgtgaaa aattagagga    360
aaaattaaat tcaggagagg ttatatatgg aatcaataca ggatttggag ggaatgccaa    420
tttagttgtg ccatttgaga aaatcgcaga gcatcagcaa aatctgttaa cttttctttc    480
tgctggtact ggggactata tgtccaaacc ttgtattaaa gcgtcacaat ttactatgtt    540
actttctgtt tgcaaaggtt ggtctgcaac cagaccaatt gtcgctcaag caattgttga    600
```

```
tcatattaat catgacattg ttcctctggt tcctcgctat ggctcagtgg gtgcaagcgg    660
tgatttaatt cctttatctt atattgcacg agcattatgt ggtatcggca agtttatta    720 tatgggcgca gaaattgacg ctgctgaagc aattaaacgt gcagggttga caccattatc   780
gttaaaagcc aaagaaggtc ttgctctgat aacggcacc cgggtaatgt caggaatcag    840
tgcaatcacc gtcattaaac tggaaaaact atttaaagcc tcaatttctg cgattgccct   900
tgctgttgaa gcattacttg catctcatga acattatgat gcccggattc aacaagtaaa   960
aaatcatcct ggtcaaaacg cggtggcaag tgcattgcgt aatttattgg caggttcaac  1020
gcaggttaat ctattatctg gggttaaaga acaagccaat aaagcttgtc gtcatcaaga  1080
aattacccaa ctaaatgata ccttacagga agtttattca attcgctgtg caccacaagt  1140
attaggtata gtgccagaat ctttagctac cgctcggaaa atattggaac gggaagttat  1200
ctcagctaat gataatccat tgatagatcc agaaaatggc gatgttctac acggtggaaa  1260
ttttatgggg caatatgtcg cccgaacaat ggatgcatta aaactggata ttgctttaat  1320
tgccaatcat cttcacgcca ttgtggctct tatgatggat aaccgtttct ctcgtggatt  1380
acctaattca ctgagtccga cacccggcat gtatcaaggt tttaaaggcg tccaactttc  1440
tcaaaccgct ttagttgctg caattcgcca tgattgtgct gcatcaggta ttcatccct   1500 cgccacagaa caatacaatc aagatattgt cagtttaggt ctgcatgccg ctcaagatgt  1560
tttagagatg gagcagaaat tacgcaatat tgtttcaatg acaattctgg tagtttgtca  1620
ggccattcat cttcgcggca atattagtga aattgcgcct gaaactgcta aattttacca  1680
tgcagtacgc gaaatcagtt ctcctttgat cactgatcgt gcgttggatg aagatataat  1740
ccgcattgcg gatgcaatta ttaatgatca acttcctctg ccagaaatca tgctggaaga  1800
ataa                                                               1804
```

<210> SEQ ID NO 39
<211> LENGTH: 2170
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 39

```
ttaagaccca ctttcacatt taagttgttt ttctaatccg catatgatca attcaaggcc    60
gaataagaag gctggctctg caccttggtg atcaaataat tcgatagctt gtcgtaataa   120
tggcggcata ctatcagtag taggtgtttc cctttcttct ttagcgactt gatgctcttg   180
atcttccaat acgcaaccta agtaaaatg ccccacagcg ctgagtgcat ataatgcatt    240
ctctagtgaa aaaccttgtt ggcataaaaa ggctaattga ttttcgagag tttcatactg   300
tttttctgta ggccgtgtac ctaaatgtac ttttgctcca tcgcgatgac ttagtaaagc   360
acatctaaaa cttttagcgt tattacgtaa aaaatcttgc cagctttccc cttctaaagg   420
gcaaaagtga gtatggtgcc tatctaacat ctcaatggct aaggcgtcga gcaaagcccg   480 cttattttt acatgccaat acaatgtagg ctgctctaca cctagcttct gggcgagttt    540
acgggttgtt aaaccttcga ttccgacctc attaagcagc tctaatgcgc tgttaatcac   600 tttacttta tctaatctag acatcattaa ttcctaattt ttgttgacac tctatcattg    660
atagagttat tttaccactc cctatcagtg atagagaaaa gtgaactcta gaaataattt   720
```

```
tgtttaactt taagaaggag atatacatat gaacatttca aggagaaagc tacttttagg      780
tgttggtgct gcgggcgttt tagcaggtgg tgcggcttta gttccaatgg ttcgccgtga      840
cggcaaattt gtggaagcta aatcaagagc atcatttgtt gaaggtacgc aagggctct      900 tcctaaagaa gcagatgtag tgattattgg tgccggtatt caagggatca tgaccgctat      960
taaccttgct gaacgtggta tgagtgtcac tatcttagaa aagggtcaga ttgccggtga     1020
gcaatcaggc cgtgcataca gccaaattat tagttaccaa acatcgccag aaatcttccc     1080
attacaccat tatgggaaaa tattatggcg tggcatgaat gagaaaattg gtgcggatac     1140
cagttatcgt actcaaggtc gtgtagaagc gctggcagat gaaaaagcat tagataaagc     1200
tcaagcgtgg atcaaaacag ctaaagaagc ggcaggtttt gatacaccat taaatactcg     1260
catcattaaa ggtgaagagc tatcaaatcg cttagtcggt gctcaaacgc catggactgt     1320
tgctgcattt gaagaagatt caggctctgt tgatcctgaa acaggcacac ctgcactcgc     1380
tcgttatgcc aaacaaatcg gtgtgaaaat ttataccaac tgtgcagtaa gaggtattga     1440
aactgcgggt ggtaaaatct ctgatgtggt gagtgagaaa ggggcgatta aaacgtctca     1500
agttgtactc gctggggta tctggtcgcg tttatttatg ggcaatatgg gtattgatat      1560
cccaacgctc aatgtatatc tatcacaaca acgtgtctca ggggttcctg gtgcaccacg     1620
tggtaatgtg catttaccta atggtattca tttccgcgaa caagcggatg gtacttatgc     1680
cgttgcacca cgtatcttta cgagttcaat agtcaaagat agcttcctgc tagggcctaa     1740
atttatgcac ttattaggtg gcggagagtt accgttggaa ttctctattg gtgaagatct     1800
atttaattca tttaaaatgc cgacctcttg gaatttagat gaaaaaacac cattcgaaca     1860
attccgagtt gccacggcaa cacaaaatac gcaacactta gatgctgttt tccaaagaat     1920
gaaaacagaa ttcccagtat ttgaaaaatc agaagttgtt gaacgttggg gtgccgttgt     1980
gagtccaaca tttgatgaat tacctatcat ttctgaggtc aaagaatacc caggcttagt     2040
gattaacacg gcaacagtgt ggggtatgac agaaggcccg gcagcgggtg aagtgaccgc     2100
tgatattgtc atgggcaaga aacctgttat tgatccaacg ccgtttagtt tggatcgttt     2160
taagaagtaa                                                            2170
```

<210> SEQ ID NO 40
<211> LENGTH: 2624
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 40

```
ttattcacaa cctgccctaa actcgctcgg actcgccccg gtgcattttt taaatactcg      60
cgagaaatag agttgatcgt caaaaccgac attgcgaccg acgtggcga taggcatccg      120 ggtggtgctc aaaagcagct tcgcctgact gatgcgctgg tcctcgcgcc agcttaatac      180
gctaatccct aactgctggc ggaacaaatg cgacagacgc gacggcgaca ggcagacatg      240
ctgtgcgacg ctggcgatat caaaattact gtctgccagg tgatcgctga tgtactgaca      300
agcctcgcgt acccgattat ccatcggtgg atggagcgac tcgttaatcg cttccatgcg      360
ccgcagtaac aattgctcaa gcagatttat cgccagcaat tccgaatagc gcccttcccc      420
ttgtccggca ttaatgattt gcccaaacag gtcgctgaaa tgcggctggt gcgcttcatc      480
cgggcgaaag aaaccggtat tggcaaatat cgacggccag ttaagccatt catgccagta      540
```

```
ggcgcgcgga cgaaagtaaa cccactggtg ataccattcg tgagcctccg gatgacgacc    600
gtagtgatga atctctccag gcgggaacag caaaatatca cccggtcggc agacaaattc    660
tcgtccctga ttttcacca cccctgacc gcgaatggtg agattgagaa tataaccttt    720
cattcccagc ggtcggtcga taaaaaatc gagataaccg ttggcctcaa tcggcgttaa    780
acccgccacc agatgggcgt taaacgagta tcccggcagc aggggatcat tttgcgcttc    840
agccatactt ttcatactcc cgccattcag agaagaaacc aattgtccat attgcatcag    900
acattgccgt cactgcgtct tttactggct cttctcgcta acccaaccgg taaccccgct    960
tattaaaagc attctgtaac aaagcgggac caaagccatg acaaaaacgc gtaacaaaag   1020
tgtctataat cacggcagaa aagtccacat tgattatttg cacggcgtca cactttgcta   1080
tgccatagca tttttatcca taagattagc ggatccagcc tgacgctttt tttcgcaact   1140
ctctactgtt tctccatacc tctagaaata attttgttta actttaagaa ggagatatac   1200
atatgaacat ttcaaggaga aagctacttt taggtgttgg tgctgcgggc gttttagcag   1260
gtggtgcggc tttagttcca atggttcgcc gtgacggcaa atttgtggaa gctaaatcaa   1320
gagcatcatt tgttgaaggt acgcaagggg ctcttcctaa agaagcagat gtagtgatta   1380
ttggtgccgg tattcaaggg atcatgaccg ctattaacct tgctgaacgt ggtatgagtg   1440
tcactatctt agaaaagggt cagattgccg gtgagcaatc aggccgtgca tacagccaaa   1500
ttattagtta ccaaacatcg ccagaaatct tcccattaca ccattatggg aaaatattat   1560
ggcgtggcat gaatgagaaa attggtgcgg ataccagtta tcgtactcaa ggtcgtgtag   1620
aagcgctggc agatgaaaaa gcattagata agctcaagc gtggatcaaa acagctaaag   1680
aagcggcagg ttttgataca ccattaaata ctcgcatcat taaaggtgaa gagctatcaa   1740
atcgcttagt cggtgctcaa acgccatgga ctgttgctgc atttgaagaa gattcaggct   1800
ctgttgatcc tgaaacaggc acacctgcac tcgctcgtta tgccaaacaa atcggtgtga   1860 aaattatac caactgtgca gtaagaggta ttgaaactgc gggtggtaaa atctctgatg   1920
tggtgagtga gaaaggggcg attaaaacgt ctcaagttgt actcgctggg ggtatctggt   1980
cgcgtttatt tatgggcaat atgggtattg atatcccaac gctcaatgta tatctatcac   2040
aacaacgtgt ctcaggggtt cctggtgcac acgtggtaa tgtgcattta cctaatggta   2100
ttcatttccg cgaacaagcg gatggtactt atgccgttgc accacgtatc tttacgagtt   2160
caatagtcaa agatagcttc ctgctagggc ctaaatttat gcacttatta ggtggcggag   2220
agttaccgtt ggaattctct attggtgaag atctatttaa ttcatttaaa atgccgacct   2280
cttggaattt agatgaaaaa acaccattcg aacaattccg agttgccacg gcaacacaaa   2340
atacgcaaca cttagatgct gttttccaaa gaatgaaaac agaattccca gtatttgaaa   2400
aatcagaagt tgttgaacgt tggggtgccg ttgtgagtcc aacatttgat gaattaccta   2460
tcatttctga ggtcaaagaa tacccaggct tagtgattaa cacggcaaca gtgtgggta   2520 tgacagaagg cccggcagcg ggtgaagtga ccgctgatat tgtcatgggc aagaaacctg   2580
ttattgatcc aacgccgttt agtttggatc gttttaagaa gtaa                   2624
```

<210> SEQ ID NO 41
<211> LENGTH: 3206
<212> TYPE: DNA
<213> ORGANISM: Artificial Sequence
<220> FEATURE:
<221> NAME/KEY: source
<223> OTHER INFORMATION: /note="Description of Artificial Sequence:

Synthetic polynucleotide"

<400> SEQUENCE: 41

```
ggtaccagtt gttcttattg gtggtgttgc tttatggttg catcgtagta aatggttgta      60
acaaaagcaa ttttccggc tgtctgtata caaaaacgcc gcaaagtttg agcgaagtca      120
ataaactctc tacccattca gggcaatatc tctcttggat ccaaagtgaa ctctagaaat     180
aattttgttt aactttaaga aggagatata catatgaaag ctaaagatgt tcagccaacc    240
attattatta ataaaaatgg ccttatctct ttggaagata tctatgacat tgcgataaaa     300
caaaaaaag tagaaatatc aacggagatc actgaacttt tgacgcatgg tcgtgaaaaa     360
ttagaggaaa aattaaattc aggagaggtt atatatggaa tcaatacagg atttggaggg    420
aatgccaatt tagttgtgcc atttgagaaa atcgcagagc atcagcaaaa tctgttaact    480
tttctttctg ctggtactgg ggactatatg tccaaacctt gtattaaagc gtcacaattt   540
actatgttac tttctgtttg caaaggttgg tctgcaacca gaccaattgt cgctcaagca   600
attgttgatc atattaatca tgacattgtt cctctggttc ctcgctatgg ctcagtgggt   660
gcaagcggtg atttaattcc tttatcttat attgcacgag cattatgtgg tatcggcaaa    720
gtttattata tgggcgcaga aattgacgct gctgaagcaa ttaaacgtgc agggttgaca    780
ccattatcgt taaaagccaa agaaggtctt gctctgatta acggcacccg ggtaatgtca    840
ggaatcagtg caatcaccgt cattaaactg aaaaactat ttaaagcctc aatttctgcg    900
attgcccttg ctgttgaagc attacttgca tctcatgaac attatgatgc ccggattcaa    960
caagtaaaaa atcatcctgg tcaaaacgcg gtggcaagtg cattgcgtaa tttattggca   1020
ggttcaacgc aggttaatct attatctggg gttaaagaac aagccaataa agcttgtcgt   1080
catcaagaaa ttacccaact aaatgatacc ttacaggaag tttattcaat tcgctgtgca   1140
ccacaagtat taggtatagt gccagaatct ttagctaccg ctcggaaaat attggaacgg   1200
gaagttatct cagctaatga taatccattg atagatccag aaaatggcga tgttctacac   1260
ggtggaaatt ttatggggca atatgtcgcc cgaacaatgg atgcattaaa actggatatt   1320
gctttaattg ccaatcatct tcacgccatt gtggctctta tgatggataa ccgtttctct   1380
cgtggattac ctaattcact gagtccgaca cccggcatgt atcaaggttt taaaggcgtc   1440
caactttctc aaaccgcttt agttgctgca attcgccatg attgtgctgc atcaggtatt   1500
cataccctcg ccacagaaca atacaatcaa gatattgtca gtttaggtct gcatgccgct   1560
caagatgttt tagagatgga gcagaaatta cgcaatattg tttcaatgac aattctggta   1620
gtttgtcagg ccattcatct tcgcggcaat attagtgaaa ttgcgcctga aactgctaaa   1680
ttttaccatg cagtacgcga aatcagttct cctttgatca ctgatcgtgc gttggatgaa   1740
gatataatcc gcattgcgga tgcaattatt aatgatcaac ttcctctgcc agaaatcatg   1800
ctggaagaat aaaagaagga gatatacata tgaaaacgc gtcaaccgta tcggaagata   1860
ctgcgtcgaa tcaagagccg acgcttcatc gcggattaca taaccgtcat attcaactga   1920
ttgcgttggg tggcgcaatt ggtactggtc tgtttcttgg cattggcccg gcgattcaga   1980
tggcgggtcc ggctgtattg ctgggctacg cgtcgccgg gatcatcgct ttcctgatta   2040
tgcgccagct tggcgaaatg gtggttgagg agccggtatc cggttcattt gcccactttg   2100
cctataaata ctggggaccg tttgcgggct tcctctctgg ctggaactac tgggtaatgt   2160
tcgtgctggt gggaatggca gagctgaccg ctgcgggcat ctatatgcag tactggttcc   2220
cggatgttcc aacgtggatt tgggctgccg ccttctttat tatcatcaac gccgttaacc   2280
```

```
tggtgaacgt gcgcttatat ggcgaaaccg agttctggtt tgcgttgatt aaagtgctgg    2340
caatcatcgg tatgatcggc tttggcctgt ggctgctgtt ttctggtcac ggcggcgaga    2400
aagccagtat cgacaacctc tggcgctacg gtggtttctt cgccaccggc tggaatgggc    2460
tgattttgtc gctggcggta attatgttct ccttcggcgg tctggagctg attgggatta    2520
ctgccgctga agcgcgcgat ccggaaaaaa gcattccaaa agcggtaaat caggtggtgt    2580
atcgcatcct gctgttttac atcggttcac tggtggtttt actggcgctc tatccgtggg    2640
tggaagtgaa atccaacagt agcccgtttg tgatgatttt ccataatctc gacagcaacg    2700
tggtagcttc tgcgctgaac ttcgtcattc tggtagcatc gctgtcagtg tataacagcg    2760
gggtttactc taacagccgc atgctgtttg cctttctgt gcagggtaat gcgccgaagt    2820
ttttgactcg cgtcagccgt cgcggtgtgc cgattaactc gctgatgctt ccggagcga    2880 tcacttcgct ggtggtgtta atcaactatc tgctgccgca aaaagcgttt ggtctgctga    2940
tggcgctggt ggtagcaacg ctgctgttga actggattat gatctgtctg gcgcatctgc    3000
gttttcgtgc agcgatgcga cgtcaggggc gtgaaacaca gtttaaggcg ctgctctatc    3060
cgttcggcaa ctatctctgc attgccttcc tcggcatgat tttgctgctg atgtgcacga    3120
tggatgatat gcgcttgtca gcgatcctgc tgccggtgtg gattgtattc ctgtttatgg    3180
catttaaaac gctgcgtcgg aaataa                                         3206
```

<210> SEQ ID NO 42
<211> LENGTH: 3741
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 42

```
ttaggtacgg gctgcccatt tgattttaac gcgttcatca ccatcaaacg gacgaccacg      60
ctggcctttt gcaacccaaa tttcatcgat gcaggtatca ataattgcat tacgcatggt     120
cggggttgca cgcagccaca gttcttcata atcgctgcta tcaacaatcc agctaacatc     180
aactgctgcg cttgcgctgc tttcgctaac tgcatctttg gctgcctgca gggtgctcag     240
tgcttcttga tatgcagggg caaaaaactg ttctgccgga ccatcataaa caccattctg     300
acgatcacgc agcaggcgac ccagattttt ttcggcttca cgaactgcgg cttttgcata     360
cttttcatct tcgcttgcct gcggatgggt cagtgctgcc cagcgatctg caactgcaat     420
aacaaacgga tcatccggtt cgcttgctgc taattttgct gcccaacgaa atgcaacata     480
ttcttcaacg cttttacgtg caacataggt cggtgccgga caaccacctt tcacactgct     540
acgccaacaa cgataaccat taccgctata gctacagcta ccaccacaac ccggacaacg     600
catacgaccg ctcagcagat gtttgcgacg ggtatcatga tcgctaccat ccagcggaac     660
accaacacca tcttcaccct taacggctgc ttttgcggct tcttgttctt catcggtcac     720
cagcggagga ccatgcataa cgctaacacg tttaccttca ccgttataaa aggtcagacg     780
acgctgttta ccatcctgac gacctgtggt ctgccaaccc gcatatgccg gattctgaat     840
catatcacgc acggtaactg caatccacgg accaccggtc gggctcggaa tttcacgggt     900
attcattgca tgtgcggtgc ctgcatagct cagacgatcg gtaaccggca gggtaaaaac     960
cagacgggct gcttctgctt tggtcagacc atcaggacca cccgcatctt catcatctgc    1020
```

```
tgccagttta cgttcatcat attcatcacc ctcttcatca ctaacggtaa ccagaacaac    1080
acgcagacca tacggtgcac gggcattaac ccattcacca ttttcacgct gatgtgcttt    1140
ggtatcacga acacgttcgc tcagtttttc tgcttcttcg cgtgcttctt ctgcacgacg    1200
aatcagttca ccgcgatcac gtttattggt gctatccaga accggacgac cggtatcttc    1260
atcccaacca acagcagac gacgaggcat accatcttcc ggttcgataa ttttcagaat     1320
tgcaccggca ccaccacgat cccaacgatc cagacgataa caccacagtg caccaacttc    1380
accgctttcc agggctttca gtgctttgct ctgatcatca cgtgctttac ctttacgaaa    1440
acggcttgcg ctaccaactt ctttccaaac atgacgaacc tgcatacccca gcagtgctgc   1500 aactttacga cccagggttt cttgtgctgc aatgctaatt tcttgtttac gacgctgacc    1560
tgcaccattt gcacggcttt taactgcttt gcttttacga caaaacaggt caatcagacc    1620
tgcaggatcc ggaccggttt cggtggtcat accaggcata tgtatatctc cttcttaaag    1680
ttaaacaaaa ttatttctag agttcacttt ggatccaaga gagatattgc cctgaatggg    1740
tagagagttt attgacttcg ctcaaacttt gcggcgtttt tgtatacaga cagccggaaa    1800
aattgctttt gttacaacca tttactacga tgcaaccata aagcaacacc accaataaga    1860
acaactggta ccgatattc atatggacca tggcagctag ccctgcaggg tgcactcaga    1920
aaattatttt aaatttcctc ttgtcaggcc ggaataactc cctataatgc gccaccacga    1980
gcgccggatc agggagtgga cggcctggga gcgctacacg ctgtggctgc ggtcggtgct    2040
tattcttcca gcatgatttc tggcagagga agttgatcat taataattgc atccgcaatg    2100
cggattatat cttcatccaa cgcacgatca gtgatcaaag gagaactgat ttcgcgtact    2160
gcatggtaaa atttagcagt ttcaggcgca atttcactaa tattgccgcg aagatgaatg    2220
gcctgacaaa ctaccagaat tgtcattgaa acaatattgc gtaatttctg ctccatctct    2280
aaaacatctt gagcggcatg cagacctaaa ctgacaatat cttgattgta ttgttctgtg    2340
gcgagggtat gaatacctga tgcagcacaa tcatggcgaa ttgcagcaac taaagcggtt    2400
tgagaaagtt ggacgccttt aaaaccttga tacatgccgg gtgtcggact cagtgaatta    2460
ggtaatccac gagagaaacg gttatccatc ataagagcca caatggcgtg aagatgattg    2520
gcaattaaag caatatccag ttttaatgca tccattgttc gggcgacata ttgccccata    2580
aaatttccac cgtgtagaac atcgccattt tctggatcta tcaatggatt atcattagct    2640
gagataactt cccgttccaa tattttccga gcggtagcta aagattctgg cactatacct    2700
aatacttgtg gtgcacagcg aattgaataa acttcctgta aggtatcatt tagttgggta    2760
atttcttgat gacgacaagc tttattggct tgttctttaa ccccagataa tagattaacc    2820
tgcgttgaac ctgccaataa attacgcaat gcacttgcca ccgcgttttg accaggatga    2880
ttttttactt gttgaatccg ggcatcataa tgttcatgag atgcaagtaa tgcttcaaca    2940
gcaagggcaa tcgcagaaat tgaggcttta aatagttttt ccagtttaat gacggtgatt    3000
gcactgattc ctgacattac ccgggtgccg ttaatcagag caagaccttc tttggctttt    3060
aacgataatg gtgtcaaccc tgcacgttta attgcttcag cagcgtcaat ttctgcgccc    3120
atataataaa ctttgccgat accacataat gctcgtgcaa tataagataa aggaattaaa    3180
tcaccgcttg cacccactga gccatagcga ggaaccagag gaacaatgtc atgattaata    3240
tgatcaacaa ttgcttgagc gacaattggt ctggttgcag accaaccttt gcaaacagaa    3300
agtaacatag taaattgtga cgcttttaata caaggtttgg acatatagtc cccagtacca    3360
gcagaaagaa aagttaacag attttgctga tgctctgcga ttttctcaaa tggcacaact    3420
```

```
aaattggcat tccctccaaa tcctgtattg attccatata taacctctcc tgaatttaat    3480
ttttcctcta attttcacg accatgcgtc aaaagttcag tgatctccgt tgatatttct     3540
```
```
aaattggcat tccctccaaa tcctgtattg attccatata taacctctcc tgaatttaat    3480
ttttcctcta attttcacg accatgcgtc aaaagttcag tgatctccgt tgatatttct     3540 acttttttt gttttatcgc aatgtcatag atatcttcca aagagataag gccattttta    3600
ttaataataa tggttggctg aacatcttta gctttcatat gtatatctcc ttcttaaagt    3660
taaacaaaat tatttctaga gcagatcagg gtgcgcaagt tgtcaacgct cccaggagag    3720
ttatcgactt gcgtattagg g                                              3741
```

<210> SEQ ID NO 43
<211> LENGTH: 4794
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 43

```
ttaggtacgg gctgcccatt tgattttaac gcgttcatca ccatcaaacg gacgaccacg      60
ctggcctttt gcaacccaaa tttcatcgat gcaggtatca ataattgcat tacgcatggt     120
cggggttgca cgcagccaca gttcttcata atcgctgcta tcaacaatcc agctaacatc     180
aactgctgcg cttgcgctgc tttcgctaac tgcatctttg gctgcctgca gggtgctcag     240
tgcttcttga tatgcagggg caaaaaactg ttctgccgga ccatcataaa caccattctg     300
acgatcacgc agcaggcgac ccagattttt tccggcttca cgaactgcgg cttttgcata     360
cttttcatct tcgcttgcct gcggatgggt cagtgctgcc cagcgatctg caactgcaat     420
aacaaacgga tcatccggtt cgcttgctgc taattttgct gcccaacgaa atgcaacata     480
ttcttcaacg cttttacgtg caacataggt cggtgccgga caaccacctt tcacactgct     540
acgccaacaa cgataaccat taccgctata gctacagcta ccaccacaac ccggacaacg     600
catacgaccg ctcagcagat gtttgcgacg ggtatcatga tcgctaccat ccagcggaac     660
accaacacca tcttcacctt taacggctgc ttttgcggct tcttgttctt catcggtcac     720
cagcggagga ccatgcataa cgctaacacg tttaccttca ccgttataaa aggtcagacg     780
acgctgttta ccatcctgac gacctgtggt ctgccaaccc gcatatgccg gattctgaat     840
catatcacgc acggtaactg caatccacgg accaccggtc gggctcggaa tttcacgggt     900
attcattgca tgtgcggtgc ctgcatagct cagacgatcg gtaaccggca gggtaaaaac     960
cagacgggct gcttctgctt tggtcagacc atcaggacca cccgcatctt catcatctgc    1020
tgccagttta cgttcatcat attcatcacc ctcttcatca ctaacggtaa ccagaacaac    1080
acgcagacca tacggtgcac gggcattaac ccattccaca ttttcacgct gatgtgcttt    1140
ggtatcacga acacgttcgc tcagttttc tgcttcttcg cgtgcttctt ctgcacgacg     1200
aatcagttca ccgcgatcac gtttattggt gctatccaga accggacgac cggtatcttc    1260
atcccaacca aacagcagac gacgaggcat accatcttcc ggttcgataa ttttcagaat    1320
tgcaccggca ccaccacgat cccaacgatc cagacgataa caccacagtg caccaacttc    1380
accgctttcc agggctttca gtgctttgct ctgatcatca cgtgctttac ctttacgaaa    1440
acggcttgcg ctaccaactt cttccaaac atgacgaacc tgcatacccca gcagtgctgc    1500 aactttacga cccagggttt cttgtgctgc aatgctaatt tcttgtttac gacgctgacc    1560
tgcaccattt gcacggcttt taactgcttt gcttttacga caaaacaggt caatcagacc    1620
```

```
tgcaggatcc ggaccggttt cggtggtcat accaggcata tgtatatctc cttcttaaag    1680
ttaaacaaaa ttatttctag agttcacttt ggatccaaga gagatattgc cctgaatggg    1740
tagagagttt attgacttcg ctcaaacttt gcggcgtttt tgtatacaga cagccggaaa    1800
aattgctttt gttacaacca tttactacga tgcaaccata aagcaacacc accaataaga    1860
acaactggta ccggatattc atatggacca tggcagctag ccctgcaggg tgcactcaga    1920
aaattatttt aaatttcctc ttgtcaggcc ggaataactc cctataatgc gccaccacga    1980
gcgccggatc agggagtgga cggcctggga gcgctacacg ctgtggctgc ggtcggtgct    2040
tacgcgaacg cgaagtccga ctctaagatg tcacggaggt tcaagttacc tttagccgga    2100
agtgctggca ttttgtccaa ttgagactcg tgcaactggt cagcgaactg gtcgtagaaa    2160
tcagccagta catcacaaga ctcatatgtg tcaaccatag tttcgcgcac tgctttgaac    2220
aggttcgcag cgtcagccgg aatggtaccg aaggagtcgt gaatcagtgc aaaagattcg    2280
attccgtact tctcgtgtgc ccacactaca gtcttacgaa ggtggctacc gtcttggctg    2340
tgtacaaagt taggagcgat accagactcc tgtttgtgtg catcaatctc gctatctttg    2400
ttggtgttaa tggtaggctg taagcggaac tgaccgagga acatcaggtt caagcgcgtc    2460
tgaataggct tcttgtattc ctgccacaca gggaaaccat caggagttac ccaatgcaca    2520
gcgcaacgct tgcgaagaat ctctccagtc ttcttatctt tgacctcagc agccagcagc    2580
ttagcagcag acttaagcca gttcattgct tcaaccgcag ctaccaccgt cacgctcaca    2640
gattcccaaa tcagcttagc catgtatcca gcagcctgat tcggctgagt gaacatcaga    2700
cccttgccgg aatcaatagc tggctgaatg gtatcttcca gcacttgttg acggaagccg    2760
aactctttgg acccgtaagc cagcgtcatg actgaacgct tagtcacact gcgagtaaca    2820
ccgtaagcca gccattgacc agccagtgcc ttagtgccca gcttgacttt ctcagagatt    2880
tcaccagtgt tctcatcggt cacggtaact acttcgttat cggtcccatt gattgcgtct    2940
gcttgtagaa tctcgttgac tttcttagca acaatcccgt agatgtcctg aacgtttca    3000 ctaggaagca agttaaccgc gcgaccacct acctcatctc ggagcatcgc ggagaagtgc    3060
tggatgccag agcaagaccc gtcaaacgcc agcggaaggg agcagttata gctcaggccg    3120
tggtgctgta ccccagcgta ctcaaagcag aacgcaagga agcagaacgg agaatcttgc    3180
tcagcccacc aagtgttctc cagtggagac ttagcgcaag ccatgatgtt ctcgtggttt    3240
tcctcaatga acttgatgcg ctcagggaac ggaaccttat cgacaccgc acagtttgca    3300 ccgtggattt tcagccagta gtaaccttcc ttaccgattg gtttaccttt cgccagcgta    3360
agcagtcctt tggtcatatc gttaccttgc gggttgaaca ttgacacagc gtaaacacga    3420
ccgcgccagt ccatgttgta agggaaccag atggccttat ggttagcaaa cttattggct    3480
tgctcaagca tgaactcaag gctgatacgg cgagacttgc gagccttgtc cttgcggtac    3540
acagcagcgg cagcacgttt ccacgcggtg agagcctcag gattcatgtc gatgtcttcc    3600
ggtttcatcg ggagttcttc acgctcaatc gcagggatgt cctcgaccgg acaatgcttc    3660
cacttggtga ttacgttggc gaccgctagg actttcttgt tgattttcca tgcggtgttt    3720
tgcgcaatgt taatcgcttt gtacacctca ggcatgtaaa cgtcttcgta gcgcatcagt    3780
gctttcttac tgtgagtacg caccagcgcc agaggacgac gaccgttagc ccaatagcca    3840
ccaccagtaa tgccagtcca cggcttagga ggaactacgc aaggttggaa catcggagag    3900
atgccagcca gcgcacctgc acgggttgcg atagcctcag cgtattcagg tgcgagttcg    3960
atagtctcag agtcttgacc tactacgcca gcattttggc ggtgtaagct aaccattccg    4020
```

```
gttgactcaa tgagcatctc gatgcagcgt actcctacat gaatagagtc ttccttatgc    4080
cacgaagacc acgcctcgcc accgagtaga cccttagaga gcatgtcagc ctcgacaact    4140
tgcataaatg ctttcttgta gacgtgccct acgcgcttgt tgagttgttc ctcaacgttt    4200
ttcttgaagt gcttagcttc aaggtcacgg atacgaccga agcgagcctc gtcctcaatg    4260
gcccgaccga ttgcgcttgc tacagcctga acggttgtat tgtcagcact ggttaggcaa    4320
gccagagtgg tcttaatggt gatgtacgct acggcttccg gcttgatttc ttgcaggaac    4380
tggaaggctg tcgggcgctt gccgcgctta gctttcactt cctcaaacca gtcgttgatg    4440
cgtgcaatca tcttagggag tagggtagtg atgagaggct tggcggcagc gttatccgca    4500
acctcaccag ctttaagttg acgctcaaac atcttgcgga agcgtgcttc acccatctcg    4560
taagactcat gctcaagggc caactgttcg cgagctaaac gctcaccgta atggtcagcc    4620
agagtgttga acgggatagc agccagttcg atgtcagaga agtcgttctt agcgatgtta    4680
atcgtgttca tatgtatatc tccttcttaa agttaaacaa aattatttct agagcagatc    4740
agggtgcgca agttgtcaac gctcccagga gagttatcga cttgcgtatt aggg          4794
```

<210> SEQ ID NO 44  
<211> LENGTH: 1672  
<212> TYPE: DNA  
<213> ORGANISM: Artificial Sequence  
<220> FEATURE:  
<221> NAME/KEY: source  
<223> OTHER INFORMATION: /note="Description of Artificial Sequence: Synthetic polynucleotide"

<400> SEQUENCE: 44

```
taatacgact cactataggg agaaagtgaa ctctagaaat aatttgttt aactttaaga      60 aggagatata catatgaaag ctaaagatgt tcagccaacc attattatta ataaaaatgg     120
ccttatctct ttggaagata tctatgcat tgcgataaaa caaaaaaaag tagaaatatc     180
aacggagatc actgaacttt tgacgcatgg tcgtgaaaaa ttagaggaaa aattaaattc    240
aggagaggtt atatatgaa tcaatacagg atttggaggg aatgccaatt tagttgtgcc    300
atttgagaaa atcgcagagc atcagcaaaa tctgttaact tttctttctg ctggtactgg    360
ggactatatg tccaaacctt gtattaaagc gtcacaattt actatgttac tttctgtttg    420
caaaggttgg tctgcaacca gaccaattgt cgctcaagca attgttgatc atattaatca    480
tgacattgtt cctctggttc ctcgctatgg ctcagtgggt gcaagcggtg atttaattcc    540
tttatcttat attgcacgag cattatgtgg tatcggcaaa gttattata tgggcgcaga     600 aattgacgct gctgaagcaa ttaaacgtgc agggttgaca ccattatcgt taaaagccaa    660
agaaggtctt gctctgatta acggcacccg ggtaatgtca ggaatcagtg caatcaccgt    720
cattaaactg gaaaaactat ttaaagcctc aatttctgcg attgcccttg ctgttgaagc    780
attacttgca tctcatgaac attatgatgc ccggattcaa caagtaaaaa atcatcctgg    840
tcaaaacgcg gtggcaagtg cattgcgtaa tttattggca ggttcaacgc aggttaatct    900
attatctggg gttaaagaac aagccaataa agcttgtcgt catcaagaaa ttacccaact    960
aaatgatacc ttacaggaag tttattcaat tcgctgtgca ccacaagtat taggtatagt    1020
gccagaatct ttagctaccg ctcggaaaat attggaacgg aagttatct cagctaatga    1080 taatccattg atagatccag aaaatggcga tgttctacac ggtggaaatt ttatggggca    1140
atatgtcgcc cgaacaatgg atgcattaaa actggatatt gctttaattg ccaatcatct    1200
```

| | | |
|---|---|---|
| tcacgccatt gtggctctta tgatggataa ccgtttctct cgtggattac ctaattcact | 1260 |
| gagtccgaca cccggcatgt atcaaggttt taaaggcgtc caactttctc aaaccgcttt | 1320 |
| agttgctgca attcgccatg attgtgctgc atcaggtatt catacctcg ccacagaaca | 1380 |
| atacaatcaa gatattgtca gtttaggtct gcatgccgct caagatgttt tagagatgga | 1440 |
| gcagaaatta cgcaatattg tttcaatgac aattctggta gtttgtcagg ccattcatct | 1500 |
| tcgcggcaat attagtgaaa ttgcgcctga aactgctaaa ttttaccatg cagtacgcga | 1560 |
| aatcagttct cctttgatca ctgatcgtgc gttggatgaa gatataatcc gcattgcgga | 1620 |
| tgcaattatt aatgatcaac ttcctctgcc agaaatcatg ctggaagaat aa | 1672 |

<210> SEQ ID NO 45
<211> LENGTH: 2861
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 45

| | | |
|---|---|---|
| ttattcacaa cctgccctaa actcgctcgg actcgccccg gtgcattttt taaatactcg | 60 |
| cgagaaatag agttgatcgt caaaaccgac attgcgaccg acggtggcga taggcatccg | 120 |
| ggtggtgctc aaaagcagct tcgcctgact gatgcgctgg tcctcgcgcc agcttaatac | 180 |
| gctaatccct aactgctggc ggaacaaatg cgacagacgc gacggcgaca ggcagacatg | 240 |
| ctgtgcgacg ctggcgatat caaaattact gtctgccagg tgatcgctga tgtactgaca | 300 |
| agcctcgcgt acccgattat ccatcggtgg atggagcgac tcgttaatcg cttccatgcg | 360 |
| ccgcagtaac aattgctcaa gcagatttat cgccagcaat tccgaatagc gcccttcccc | 420 |
| ttgtccggca ttaatgattt gcccaaacag gtcgctgaaa tgcggctggt gcgcttcatc | 480 |
| cgggcgaaag aaaccggtat tggcaaatat cgacggccag ttaagccatt catgccagta | 540 |
| ggcgcgcgga cgaaagtaaa cccactggtg ataccattcg tgagcctccg gatgacgacc | 600 |
| gtagtgatga atctctccag gcgggaacag caaaatatca cccggtcggc agacaaattc | 660 |
| tcgtccctga tttttcacca ccccctgacc gcgaatggtg agattgagaa tataaccttt | 720 |
| cattcccagc ggtcggtcga taaaaaaatc gagataaccg ttggcctcaa tcggcgttaa | 780 |
| acccgccacc agatgggcgt taaacgagta tcccggcagc aggggatcat tttgcgcttc | 840 |
| agccatactt tcatactcc cgccattcag agaagaaacc aattgtccat attgcatcag | 900 |
| acattgccgt cactgcgtct tttactggct cttctcgcta acccaaccgg taaccccgct | 960 |
| tattaaaagc attctgtaac aaagcgggac caaagccatg acaaaaacgc gtaacaaaag | 1020 |
| tgtctataat cacggcagaa aagtccacat tgattatttg cacggcgtca cactttgcta | 1080 |
| tgccatagca ttttttatcca taagattagc ggatccagcc tgacgctttt tttcgcaact | 1140 |
| ctctactgtt tctccatacc tctagaaata atttgttta actttaagaa ggagatatac | 1200 |
| atatgcctgg tatgaccacc gaaaccggtc cggatcctgc aggtctgatt gacctgttt | 1260 |
| gtcgtaaaag caaagcagtt aaaagccgtg caaatggtgc aggtcagcgt cgtaaacaag | 1320 |
| aaattagcat tgcagcacaa gaaaccctgg gtcgtaaagt tgcagcactg ctgggtatgc | 1380 |
| aggttcgtca tgtttggaaa gaagttggta gcgcaagccg ttttcgtaaa ggtaaagcac | 1440 |
| gtgatgatca gagcaaagca ctgaaagccc tggaaagcgg tgaagttggt gcactgtggt | 1500 |
| gttatcgtct ggatcgttgg gatcgtggtg gtgccggtgc aattctgaaa attatcgaac | 1560 |

-continued

```
cggaagatgg tatgcctcgt cgtctgctgt ttggttggga tgaagatacc ggtcgtccgg   1620
ttctggatag caccaataaa cgtgatcgcg gtgaactgat tcgtcgtgca gaagaagcac   1680
gcgaagaagc agaaaaactg agcgaacgtg ttcgtgatac caaagcacat cagcgtgaaa   1740
atggtgaatg ggttaatgcc cgtgcaccgt atggtctgcg tgttgttctg gttaccgtta   1800
gtgatgaaga gggtgatgaa tatgatgaac gtaaactggc agcagatgat gaagatgcgg   1860
gtggtcctga tggtctgacc aaagcagaag cagcccgtct ggttttacc ctgccggtta   1920 ccgatcgtct gagctatgca ggcaccgcac atgcaatgaa tacccgtgaa attccgagcc   1980
cgaccggtgg tccgtggatt gcagttaccg tgcgtgatat gattcagaat ccggcatatg   2040
cgggttggca gaccacaggt cgtcaggatg gtaaacagcg tcgtctgacc ttttataacg   2100
gtgaaggtaa acgtgttagc gttatgcatg gtcctccgct ggtgaccgat gaagaacaag   2160
aagccgcaaa agcagccgtt aaaggtgaag atggtgttgg tgttccgctg gatggtagcg   2220
atcatgatac ccgtcgcaaa catctgctga gcggtcgtat gcgttgtccg ggttgtggtg   2280
gtagctgtag ctatagcggt aatggttatc gttgttggcg tagcagtgtg aaaggtggtt   2340
gtccggcacc gacctatgtt gcacgtaaaa gcgttgaaga atatgttgca tttcgttggg   2400
cagcaaaatt agcagcaagc gaaccggatg atccgtttgt tattgcagtt gcagatcgct   2460
gggcagcact gacccatccg caggcaagcg aagatgaaaa gtatgcaaaa gccgcagttc   2520
gtgaagccga aaaaaatctg ggtcgcctgc tgcgtgatcg tcagaatggt gtttatgatg   2580
gtccggcaga acagtttttt gcccctgcat atcaagaagc actgagcacc ctgcaggcag   2640
ccaaagatgc agttagcgaa agcagcgcaa gcgcagcagt tgatgttagc tggattgttg   2700
atagcagcga ttatgaagaa ctgtggctgc gtgcaaccc gaccatgcgt aatgcaatta   2760
ttgatacctg catcgatgaa atttgggttg caaaaggcca gcgtggtcgt ccgtttgatg   2820
gtgatgaacg cgttaaaatc aaatgggcag cccgtaccta a                      2861
```

<210> SEQ ID NO 46
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 46

```
tagaactgat gcaaaaagtg ctcgacgaag gcacacagat gtgtaggctg gagctgcttc   60
```

<210> SEQ ID NO 47
<211> LENGTH: 60
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 47

```
gtttcgtaat tagatagcca ccggcgcttt aatgcccgga catatgaata tcctccttag   60
```

<210> SEQ ID NO 48
<211> LENGTH: 52
<212> TYPE: DNA
<213> ORGANISM: Artificial Sequence
<220> FEATURE:

```
<221> NAME/KEY: source
<223> OTHER INFORMATION: /note="Description of Artificial Sequence:
      Synthetic primer"

<400> SEQUENCE: 48
caacacgttt cctgaggaac catgaaacag tatttagaac tgatgcaaaa ag         52

<210> SEQ ID NO 49
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 49
cgcacactgg cgtcggctct ggcaggatgt ttcgtaatta gatagc                46

<210> SEQ ID NO 50
<211> LENGTH: 36
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 50
atatcgtcgc agcccacagc aacacgtttc ctgagg                            36

<210> SEQ ID NO 51
<211> LENGTH: 47
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 51
aagaatttaa cggagggcaa aaaaaaccga cgcacactgg cgtcggc                47

<210> SEQ ID NO 52
<211> LENGTH: 52
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 52

Leu Asn Pro Leu Ile Asn Glu Ile Ser Lys Ile Ser Ala Ala Gly
1               5                   10                  15

Asn Phe Asp Val Lys Glu Glu Arg Ala Ala Ala Ser Leu Leu Gln Leu
                20                  25                  30

Ser Gly Asn Ala Ser Asp Phe Ser Tyr Gly Arg Asn Ser Ile Thr Leu
            35                  40                  45

Thr Ala Ser Ala
        50

<210> SEQ ID NO 53
<211> LENGTH: 584
<212> TYPE: PRT
<213> ORGANISM: Artificial Sequence
```

```
<220> FEATURE:
<221> NAME/KEY: source
<223> OTHER INFORMATION: /note="Description of Artificial Sequence:
      Synthetic polypeptide"

<400> SEQUENCE: 53

Met Lys Ala Lys Asp Val Gln Pro Thr Ile Ile Ile Asn Lys Asn Gly
1               5                   10                  15

Leu Ile Ser Leu Glu Asp Ile Tyr Asp Ile Ala Ile Lys Gln Lys Lys
            20                  25                  30

Val Glu Ile Ser Thr Glu Ile Thr Glu Leu Leu Thr His Gly Arg Glu
        35                  40                  45

Lys Leu Glu Glu Lys Leu Asn Ser Gly Glu Val Ile Tyr Gly Ile Asn
50                  55                  60

Thr Gly Phe Gly Gly Asn Ala Asn Leu Val Val Pro Phe Glu Lys Ile
65                  70                  75                  80

Ala Glu His Gln Gln Asn Leu Leu Thr Phe Leu Ser Ala Gly Thr Gly
                85                  90                  95

Asp Tyr Met Ser Lys Pro Cys Ile Lys Ala Ser Gln Phe Thr Met Leu
            100                 105                 110

Leu Ser Val Cys Lys Gly Trp Ser Ala Thr Arg Pro Ile Val Ala Gln
        115                 120                 125

Ala Ile Val Asp His Ile Asn His Asp Ile Val Pro Leu Val Pro Arg
130                 135                 140

Tyr Gly Ser Val Gly Ala Ser Gly Asp Leu Ile Pro Leu Ser Tyr Ile
145                 150                 155                 160

Ala Arg Ala Leu Cys Gly Ile Gly Lys Val Tyr Tyr Met Gly Ala Glu
                165                 170                 175

Ile Asp Ala Ala Glu Ala Ile Lys Arg Ala Gly Leu Thr Pro Leu Ser
            180                 185                 190

Leu Lys Ala Lys Glu Gly Leu Ala Leu Ile Asn Gly Thr Arg Val Met
        195                 200                 205

Ser Gly Ile Ser Ala Ile Thr Val Ile Lys Leu Glu Lys Leu Phe Lys
210                 215                 220

Ala Ser Ile Ser Ala Ile Ala Leu Ala Val Glu Ala Leu Leu Ala Ser
225                 230                 235                 240

His Glu His Tyr Asp Ala Arg Ile Gln Gln Val Lys Asn His Pro Gly
                245                 250                 255

Gln Asn Ala Val Ala Ser Ala Leu Arg Asn Leu Leu Ala Gly Ser Thr
            260                 265                 270

Gln Val Asn Leu Leu Ser Gly Val Lys Glu Gln Ala Asn Lys Ala Cys
        275                 280                 285

Arg His Gln Glu Ile Thr Gln Leu Asn Asp Thr Leu Gln Glu Val Tyr
290                 295                 300

Ser Ile Arg Cys Ala Pro Gln Val Leu Gly Ile Val Pro Glu Ser Leu
305                 310                 315                 320

Ala Thr Ala Arg Lys Ile Leu Glu Arg Glu Val Ile Ser Ala Asn Asp
                325                 330                 335

Asn Pro Leu Ile Asp Pro Glu Asn Gly Asp Val Leu His Gly Gly Asn
            340                 345                 350

Phe Met Gly Gln Tyr Val Ala Arg Thr Met Asp Ala Leu Lys Leu Asp
        355                 360                 365

Ile Ala Leu Ile Ala Asn His Leu His Ala Ile Val Ala Leu Met Met
370                 375                 380
```

```
Asp Asn Arg Phe Ser Arg Gly Leu Pro Asn Ser Leu Ser Pro Thr Pro
385                 390                 395                 400

Gly Met Tyr Gln Gly Phe Lys Gly Val Gln Leu Ser Gln Thr Ala Leu
            405                 410                 415

Val Ala Ala Ile Arg His Asp Cys Ala Ala Ser Gly Ile His Thr Leu
            420                 425                 430

Ala Thr Glu Gln Tyr Asn Gln Asp Ile Val Ser Leu Gly Leu His Ala
            435                 440                 445

Ala Gln Asp Val Leu Glu Met Glu Gln Lys Leu Arg Asn Ile Val Ser
450                 455                 460

Met Thr Ile Leu Val Val Cys Gln Ala Ile His Leu Arg Gly Asn Ile
465                 470                 475                 480

Ser Glu Ile Ala Pro Glu Thr Ala Lys Phe Tyr His Ala Val Arg Glu
            485                 490                 495

Ile Ser Ser Pro Leu Ile Thr Asp Arg Ala Leu Asp Glu Asp Ile Ile
            500                 505                 510

Arg Ile Ala Asp Ala Ile Ile Asn Asp Gln Leu Pro Leu Pro Glu Ile
            515                 520                 525

Met Leu Glu Glu Leu Asn Pro Leu Ile Asn Glu Ile Ser Lys Ile Ile
530                 535                 540

Ser Ala Ala Gly Asn Phe Asp Val Lys Glu Glu Arg Ala Ala Ala Ser
545                 550                 555                 560

Leu Leu Gln Leu Ser Gly Asn Ala Ser Asp Phe Ser Tyr Gly Arg Asn
            565                 570                 575

Ser Ile Thr Leu Thr Ala Ser Ala
            580

<210> SEQ ID NO 54
<211> LENGTH: 525
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 54

Met Asn Ile Ser Arg Arg Lys Leu Leu Leu Gly Val Gly Ala Ala Gly
1               5                   10                  15

Val Leu Ala Gly Gly Ala Ala Leu Val Pro Met Val Arg Arg Asp Gly
            20                  25                  30

Lys Phe Val Glu Ala Lys Ser Arg Ala Ser Phe Val Glu Gly Thr Gln
        35                  40                  45

Gly Ala Leu Pro Lys Glu Ala Asp Val Val Ile Ile Gly Ala Gly Ile
    50                  55                  60

Gln Gly Ile Met Thr Ala Ile Asn Leu Ala Glu Arg Gly Met Ser Val
65                  70                  75                  80

Thr Ile Leu Glu Lys Gly Gln Ile Ala Gly Glu Gln Ser Gly Arg Ala
            85                  90                  95

Tyr Ser Gln Ile Ile Ser Tyr Gln Thr Ser Pro Glu Ile Phe Pro Leu
            100                 105                 110

His His Tyr Gly Lys Ile Leu Trp Arg Gly Met Asn Glu Lys Ile Gly
            115                 120                 125

Ala Asp Thr Ser Tyr Arg Thr Gln Gly Arg Val Glu Ala Leu Ala Asp
    130                 135                 140

Glu Lys Ala Leu Asp Lys Ala Gln Ala Trp Ile Lys Thr Ala Lys Glu
```

```
          145                 150                 155                 160
Ala Ala Gly Phe Asp Thr Pro Leu Asn Thr Arg Ile Ile Lys Gly Glu
                    165                 170                 175
Glu Leu Ser Asn Arg Leu Val Gly Ala Gln Thr Pro Trp Thr Val Ala
                    180                 185                 190
Ala Phe Glu Glu Asp Ser Gly Ser Val Asp Pro Glu Thr Gly Thr Pro
                    195                 200                 205
Ala Leu Ala Arg Tyr Ala Lys Gln Ile Gly Val Lys Ile Tyr Thr Asn
                    210                 215                 220
Cys Ala Val Arg Gly Ile Glu Thr Ala Gly Gly Lys Ile Ser Asp Val
225                 230                 235                 240
Val Ser Glu Lys Gly Ala Ile Lys Thr Ser Gln Val Val Leu Ala Gly
                    245                 250                 255
Gly Ile Trp Ser Arg Leu Phe Met Gly Asn Met Gly Ile Asp Ile Pro
                    260                 265                 270
Thr Leu Asn Val Tyr Leu Ser Gln Gln Arg Val Ser Gly Val Pro Gly
                    275                 280                 285
Ala Pro Arg Gly Asn Val His Leu Pro Asn Gly Ile His Phe Arg Glu
                    290                 295                 300
Gln Ala Asp Gly Thr Tyr Ala Val Ala Pro Arg Ile Phe Thr Ser Ser
305                 310                 315                 320
Ile Val Lys Asp Ser Phe Leu Leu Gly Pro Lys Phe Met His Leu Leu
                    325                 330                 335
Gly Gly Gly Glu Leu Pro Leu Glu Phe Ser Ile Gly Glu Asp Leu Phe
                    340                 345                 350
Asn Ser Phe Lys Met Pro Thr Ser Trp Asn Leu Asp Glu Lys Thr Pro
                    355                 360                 365
Phe Glu Gln Phe Arg Val Ala Thr Ala Thr Gln Asn Thr Gln His Leu
                    370                 375                 380
Asp Ala Val Phe Gln Arg Met Lys Thr Glu Phe Pro Val Phe Glu Lys
385                 390                 395                 400
Ser Glu Val Val Glu Arg Trp Gly Ala Val Val Ser Pro Thr Phe Asp
                    405                 410                 415
Glu Leu Pro Ile Ile Ser Glu Val Lys Glu Tyr Pro Gly Leu Val Ile
                    420                 425                 430
Asn Thr Ala Thr Val Trp Gly Met Thr Glu Gly Pro Ala Ala Gly Glu
                    435                 440                 445
Val Thr Ala Asp Ile Val Met Gly Lys Lys Pro Val Ile Asp Pro Thr
                    450                 455                 460
Pro Phe Ser Leu Asp Arg Phe Lys Lys Leu Asn Pro Leu Ile Asn Glu
465                 470                 475                 480
Ile Ser Lys Ile Ile Ser Ala Ala Gly Asn Phe Asp Val Lys Glu Glu
                    485                 490                 495
Arg Ala Ala Ala Ser Leu Leu Gln Leu Ser Gly Asn Ala Ser Asp Phe
                    500                 505                 510
Ser Tyr Gly Arg Asn Ser Ile Thr Leu Thr Ala Ser Ala
                    515                 520                 525

<210> SEQ ID NO 55
<211> LENGTH: 159
<212> TYPE: PRT
<213> ORGANISM: Artificial Sequence
<220> FEATURE:
<221> NAME/KEY: source
<223> OTHER INFORMATION: /note="Description of Artificial Sequence:
```

Synthetic polypeptide"

<400> SEQUENCE: 55

Cys Thr Thr Ala Ala Thr Cys Cys Ala Thr Thr Ala Ala Thr Thr Ala
1               5                   10                  15

Ala Thr Gly Ala Ala Ala Thr Cys Ala Gly Cys Ala Ala Ala Ala Thr
            20                  25                  30

Cys Ala Thr Thr Thr Cys Ala Gly Cys Thr Gly Cys Ala Gly Gly Thr
        35                  40                  45

Ala Ala Thr Thr Thr Thr Gly Ala Thr Gly Thr Thr Ala Ala Ala Gly
    50                  55                  60

Ala Gly Gly Ala Ala Ala Gly Ala Gly Cys Thr Gly Cys Ala Gly Cys
65                  70                  75                  80

Thr Thr Cys Thr Thr Ala Thr Thr Gly Cys Ala Gly Thr Gly Thr Gly
                85                  90                  95

Thr Cys Cys Gly Gly Thr Ala Ala Thr Gly Cys Ala Gly Thr Gly
            100                 105                 110

Ala Thr Thr Thr Thr Cys Ala Thr Ala Thr Gly Gly Ala Cys Gly
        115                 120                 125

Gly Ala Ala Cys Thr Cys Ala Ala Thr Ala Ala Cys Thr Thr Thr Gly
    130                 135                 140

Ala Cys Ala Gly Cys Ala Thr Cys Ala Gly Cys Ala Thr Ala Ala
145                 150                 155

<210> SEQ ID NO 56
<211> LENGTH: 1777
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 56

```
acttttcata ctcccgccat tcagagaaga aaccaattgt ccatattgca tcagacattg     60
ccgtcactgc gtcttttact ggctcttctc gctaacccaa ccggtaaccc cgcttattaa    120
aagcattctg taacaaagcg ggaccaaagc catgacaaaa acgcgtaaca aaagtgtcta    180
taatcacggc agaaaaatga acatttcaag gagaaagcta cttttaggtg ttggtgctgc    240
gggcgtttta gcaggtggtg cggctttagt tccaatggtt cgccgtgacg gcaaatttgt    300
ggaagctaaa tcaagagcat catttgttga aggtacgcaa ggggctcttc ctaaagaagc    360
agatgtagtg attattggtg ccggtattca agggatcatg accgctatta accttgctga    420
acgtggtatg agtgtcacta tcttagaaaa gggtcagatt gccggtgagc aatcaggccg    480
tgcatacagc caaattatta gttaccaaac atcgccagaa atcttcccat acaccatta    540 tgggaaaata ttatggcgtg gcatgaatga gaaaattggt gcggatacca gttatcgtac    600
tcaaggtcgt gtagaagcgc tggcagatga aaaagcatta gataaagctc aagcgtggat    660
caaaacagct aaagaagcgg caggttttga taccaccatta aatactcgca tcattaaagg    720
tgaagagcta tcaaatcgct tagtcggtgc tcaaacgcca tggactgttg ctgcatttga    780
agaagattca ggctctgttg atcctgaaac aggcacacct gcactcgctc gttatgccaa    840
acaaatcggt gtgaaaattt ataccaactg tgcagtaaga ggtattgaaa ctgcgggtgg    900
taaaatctct gatgtggtga gtgagaaagg ggcgattaaa acgtctcaag ttgtactcgc    960 tggggggtatc tggtcgcgtt tatttatggg caatatgggt attgatatcc caacgctcaa   1020
```

| | | |
|---|---|---|
| tgtatatcta tcacaacaac gtgtctcagg ggttcctggt gcaccacgtg gtaatgtgca | 1080 |
| tttacctaat ggtattcatt tccgcgaaca agcggatggt acttatgccg ttgcaccacg | 1140 |
| tatctttacg agttcaatag tcaaagatag cttcctgcta gggcctaaat ttatgcactt | 1200 |
| attaggtggc ggagagttac cgttggaatt ctctattggt gaagatctat ttaattcatt | 1260 |
| taaaatgccg acctcttgga atttagatga aaaacacca ttcgaacaat tccgagttgc | 1320 |
| cacggcaaca caaatacgc aacacttaga tgctgttttc caagaatga aaacagaatt | 1380 |
| cccagtattt gaaaaatcag aagttgttga acgttggggt gccgttgtga gtccaacatt | 1440 |
| tgatgaatta cctatcattt ctgaggtcaa agaataccca ggcttagtga ttaacacggc | 1500 |
| aacagtgtgg ggtatgacag aaggcccggc agcgggtgaa gtgaccgctg atattgtcat | 1560 |
| gggcaagaaa cctgttattg atccaacgcc gtttagtttg gatcgtttta agaagtaact | 1620 |
| taatccatta attaatgaaa tcagcaaaat catttcagct gcaggtaatt ttgatgttaa | 1680 |
| agaggaaaga gctgcagctt ctttattgca gttgtccggt aatgccagtg attttcata | 1740 |
| tggacggaac tcaataactt tgacagcatc agcataa | 1777 |

<210> SEQ ID NO 57
<211> LENGTH: 1963
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 57

| | | |
|---|---|---|
| ggtaccagtt gttcttattg gtggtgttgc tttatggttg catcgtagta aatggttgta | 60 |
| acaaaagcaa ttttccggc tgtctgtata caaaaacgcc gtaaagtttg agcgaagtca | 120 |
| ataaactctc tacccattca gggcaatatc tctcttggat ccctctagaa ataattttgt | 180 |
| ttaactttaa gaaggagata tacatatgaa agctaaagat gttcagccaa ccattattat | 240 |
| taataaaaat ggccttatct ctttggaaga tatctatgac attgcgataa aacaaaaaaa | 300 |
| agtagaaata tcaacggaga tcactgaact tttgacgcat ggtcgtgaaa aattagagga | 360 |
| aaaattaaat tcaggagagg ttatatatgg aatcaataca ggatttggag gaatgccaa | 420 |
| tttagttgtg ccatttgaga aaatcgcaga gcatcagcaa aatctgttaa cttttctttc | 480 |
| tgctggtact ggggactata tgtccaaacc ttgtattaaa gcgtcacaat ttactatgtt | 540 |
| actttctgtt tgcaaaggtt ggtctgcaac cagaccaatt gtcgctcaag caattgttga | 600 |
| tcatattaat catgacattg ttcctctggt tcctcgctat ggctcagtgg gtgcaagcgg | 660 |
| tgatttaatt cctttatctt atattgcacg agcattatgt ggtatcggca agtttatta | 720 |
| tatgggcgca gaaattgacg ctgctgaagc aattaaacgt gcagggttga caccattatc | 780 |
| gttaaaagcc aaagaaggtc ttgctctgat aacggcacc cggtaatgt caggaatcag | 840 |
| tgcaatcacc gtcattaaac tggaaaaact atttaaagcc tcaatttctg cgattgccct | 900 |
| tgctgttgaa gcattacttg catctcatga acattatgat gcccggattc aacaagtaaa | 960 |
| aaatcatcct ggtcaaaacg cggtggcaag tgcattgcgt aatttattgg caggttcaac | 1020 |
| gcaggttaat ctattatctg gggttaaaga acaagccaat aaagcttgtc gtcatcaaga | 1080 |
| aattacccaa ctaaatgata ccttacagga agtttattca attcgctgtg caccacaagt | 1140 |
| attaggtata gtgccagaat ctttagctac cgctcggaaa atattggaac gggaagttat | 1200 |

-continued

```
ctcagctaat gataatccat tgatagatcc agaaaatggc gatgttctac acggtggaaa    1260
ttttatgggg caatatgtcg cccgaacaat ggatgcatta aaactggata ttgctttaat    1320
tgccaatcat cttcacgcca ttgtggctct tatgatggat aaccgtttct ctcgtggatt    1380
acctaattca ctgagtccga cacccggcat gtatcaaggt tttaaaggcg tccaactttc    1440
tcaaaccgct ttagttgctg caattcgcca tgattgtgct gcatcaggta ttcatacgct    1500
cgccacagaa caatacaatc aagatattgt cagtttaggt ctgcatgccg ctcaagatgt    1560
tttagagatg gagcagaaat tacgcaatat tgtttcaatg acaattctgg tagtttgtca    1620
ggccattcat cttcgcggca atattagtga aattgcgcct gaaactgcta aattttacca    1680
tgcagtacgc gaaatcagtt ctcctttgat cactgatcgt gcgttggatg aagatataat    1740
ccgcattgcg gatgcaatta ttaatgatca acttcctctg ccagaaatca tgctggaaga    1800
ataacttaat ccattaatta atgaaatcag caaaatcatt tcagctgcag gtaattttga    1860
tgttaaagag gaaagagctg cagcttcttt attgcagttg tccggtaatg ccagtgattt    1920
ttcatatgga cggaactcaa taactttgac agcatcagca taa                      1963
```

<210> SEQ ID NO 58
<211> LENGTH: 707
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 58

```
Met Asp Ser Cys His Lys Ile Asp Tyr Gly Leu Tyr Ala Leu Glu Ile
1               5                   10                  15

Leu Ala Gln Tyr His Asn Val Ser Val Asn Pro Glu Glu Ile Lys His
            20                  25                  30

Arg Phe Asp Thr Asp Gly Thr Gly Leu Gly Leu Thr Ser Trp Leu Leu
        35                  40                  45

Ala Ala Lys Ser Leu Glu Leu Lys Val Lys Gln Val Lys Lys Thr Ile
    50                  55                  60

Asp Arg Leu Asn Phe Ile Ser Leu Pro Ala Leu Val Trp Arg Glu Asp
65                  70                  75                  80

Gly Arg His Phe Ile Leu Thr Lys Val Ser Lys Glu Ala Asn Arg Tyr
                85                  90                  95

Leu Ile Phe Asp Leu Glu Gln Arg Asn Pro Arg Val Leu Glu Gln Ser
            100                 105                 110

Glu Phe Glu Ala Leu Tyr Gln Gly His Ile Ile Leu Ile Ala Ser Arg
        115                 120                 125

Ser Ser Val Thr Gly Lys Leu Ala Lys Phe Asp Phe Thr Trp Phe Ile
    130                 135                 140

Pro Ala Ile Ile Lys Tyr Arg Lys Ile Phe Ile Glu Thr Leu Val Val
145                 150                 155                 160

Ser Val Phe Leu Gln Leu Phe Ala Leu Ile Thr Pro Leu Phe Phe Gln
                165                 170                 175

Val Val Met Asp Lys Val Leu Val His Arg Gly Phe Ser Thr Leu Asn
            180                 185                 190

Val Ile Thr Val Ala Leu Ser Val Val Val Phe Glu Ile Ile Leu
        195                 200                 205

Ser Gly Leu Arg Thr Tyr Ile Phe Ala His Ser Thr Ser Arg Ile Asp
    210                 215                 220
```

```
Val Glu Leu Gly Ala Lys Leu Phe Arg His Leu Ala Leu Pro Ile
225                 230                 235                 240

Ser Tyr Phe Glu Ser Arg Arg Val Gly Asp Thr Val Ala Arg Val Arg
                245                 250                 255

Glu Leu Asp Gln Ile Arg Asn Phe Leu Thr Gly Gln Ala Leu Thr Ser
            260                 265                 270

Val Leu Asp Leu Leu Phe Ser Phe Ile Phe Ala Val Met Trp Tyr
        275                 280                 285

Tyr Ser Pro Lys Leu Thr Leu Val Ile Leu Phe Ser Leu Pro Cys Tyr
        290                 295                 300

Ala Ala Trp Ser Val Phe Ile Ser Pro Ile Leu Arg Arg Arg Leu Asp
305                 310                 315                 320

Asp Lys Phe Ser Arg Asn Ala Asp Asn Gln Ser Phe Leu Val Glu Ser
                325                 330                 335

Val Thr Ala Ile Asn Thr Ile Lys Ala Met Ala Val Ser Pro Gln Met
            340                 345                 350

Thr Asn Ile Trp Asp Lys Gln Leu Ala Gly Tyr Val Ala Ala Gly Phe
        355                 360                 365

Lys Val Thr Val Leu Ala Thr Ile Gly Gln Gly Ile Gln Leu Ile
        370                 375                 380

Gln Lys Thr Val Met Ile Ile Asn Leu Trp Leu Gly Ala His Leu Val
385                 390                 395                 400

Ile Ser Gly Asp Leu Ser Ile Gly Leu Ile Ala Phe Asn Met Leu
                405                 410                 415

Ala Gly Gln Ile Val Ala Pro Val Ile Arg Leu Ala Gln Ile Trp Gln
                420                 425                 430

Asp Phe Gln Gln Val Gly Ile Ser Val Thr Arg Leu Gly Asp Val Leu
                435                 440                 445

Asn Ser Pro Thr Glu Ser Tyr His Gly Lys Leu Ala Leu Pro Glu Ile
        450                 455                 460

Asn Gly Asn Ile Thr Phe Arg Asn Ile Arg Phe Arg Tyr Lys Pro Asp
465                 470                 475                 480

Ser Pro Val Ile Leu Asp Asn Ile Asn Leu Ser Ile Lys Gln Gly Glu
                485                 490                 495

Val Ile Gly Ile Val Gly Arg Ser Gly Ser Gly Lys Ser Thr Leu Thr
                500                 505                 510

Lys Leu Ile Gln Arg Phe Tyr Ile Pro Glu Asn Gly Gln Val Leu Ile
        515                 520                 525

Asp Gly His Asp Leu Ala Leu Ala Asp Pro Asn Trp Leu Arg Arg Gln
        530                 535                 540

Val Gly Val Val Leu Gln Asp Asn Val Leu Leu Asn Arg Ser Ile Ile
545                 550                 555                 560

Asp Asn Ile Ser Leu Ala Asn Pro Gly Met Ser Val Glu Lys Val Ile
                565                 570                 575

Tyr Ala Ala Lys Leu Ala Gly Ala His Asp Phe Ile Ser Glu Leu Arg
                580                 585                 590

Glu Gly Tyr Asn Thr Ile Val Gly Glu Gln Gly Ala Gly Leu Ser Gly
                595                 600                 605

Gly Gln Arg Gln Arg Ile Ala Ile Ala Arg Ala Leu Val Asn Asn Pro
        610                 615                 620

Lys Ile Leu Ile Phe Asp Glu Ala Thr Ser Ala Leu Asp Tyr Glu Ser
625                 630                 635                 640
```

-continued

```
Glu His Ile Ile Met Arg Asn Met His Lys Ile Cys Lys Gly Arg Thr
                645                 650                 655

Val Ile Ile Ile Ala His Arg Leu Ser Thr Val Lys Asn Ala Asp Arg
            660                 665                 670

Ile Ile Val Met Glu Lys Gly Lys Ile Val Glu Gln Gly Lys His Lys
        675                 680                 685

Glu Leu Leu Ser Glu Pro Glu Ser Leu Tyr Ser Tyr Leu Tyr Gln Leu
    690                 695                 700

Gln Ser Asp
705

<210> SEQ ID NO 59
<211> LENGTH: 478
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 59

Met Lys Thr Trp Leu Met Gly Phe Ser Glu Phe Leu Leu Arg Tyr Lys
1               5                   10                  15

Leu Val Trp Ser Glu Thr Trp Lys Ile Arg Lys Gln Leu Asp Thr Pro
            20                  25                  30

Val Arg Glu Lys Asp Glu Asn Glu Phe Leu Pro Ala His Leu Glu Leu
        35                  40                  45

Ile Glu Thr Pro Val Ser Arg Arg Pro Arg Leu Val Ala Tyr Phe Ile
    50                  55                  60

Met Gly Phe Leu Val Ile Ala Val Ile Leu Ser Val Leu Gly Gln Val
65                  70                  75                  80

Glu Ile Val Ala Thr Ala Asn Gly Lys Leu Thr Leu Ser Gly Arg Ser
                85                  90                  95

Lys Glu Ile Lys Pro Ile Glu Asn Ser Ile Val Lys Glu Ile Ile Val
            100                 105                 110

Lys Glu Gly Glu Ser Val Arg Lys Gly Asp Val Leu Leu Lys Leu Thr
        115                 120                 125

Ala Leu Gly Ala Glu Ala Asp Thr Leu Lys Thr Gln Ser Ser Leu Leu
    130                 135                 140

Gln Thr Arg Leu Glu Gln Thr Arg Tyr Gln Ile Leu Ser Arg Ser Ile
145                 150                 155                 160

Glu Leu Asn Lys Leu Pro Glu Leu Lys Leu Pro Asp Glu Pro Tyr Phe
                165                 170                 175

Gln Asn Val Ser Glu Glu Val Leu Arg Leu Thr Ser Leu Ile Lys
            180                 185                 190

Glu Gln Phe Ser Thr Trp Gln Asn Gln Lys Tyr Gln Lys Glu Leu Asn
        195                 200                 205

Leu Asp Lys Lys Arg Ala Glu Arg Leu Thr Ile Leu Ala Arg Ile Asn
    210                 215                 220

Arg Tyr Glu Asn Leu Ser Arg Val Glu Lys Ser Arg Leu Asp Asp Phe
225                 230                 235                 240

Arg Ser Leu Leu His Lys Gln Ala Ile Ala Lys His Ala Val Leu Glu
                245                 250                 255

Gln Glu Asn Lys Tyr Val Glu Ala Ala Asn Glu Leu Arg Val Tyr Lys
            260                 265                 270

Ser Gln Leu Glu Gln Ile Glu Ser Glu Ile Leu Ser Ala Lys Glu Glu
```

```
                275                 280                 285
Tyr Gln Leu Val Thr Gln Leu Phe Lys Asn Glu Ile Leu Asp Lys Leu
        290                 295                 300
Arg Gln Thr Thr Asp Asn Ile Glu Leu Leu Thr Leu Glu Leu Glu Lys
305                 310                 315                 320
Asn Glu Glu Arg Gln Gln Ala Ser Val Ile Arg Ala Pro Val Ser Gly
                325                 330                 335
Lys Val Gln Gln Leu Lys Val His Thr Glu Gly Gly Val Val Thr Thr
                340                 345                 350
Ala Glu Thr Leu Met Val Ile Val Pro Glu Asp Asp Thr Leu Glu Val
            355                 360                 365
Thr Ala Leu Val Gln Asn Lys Asp Ile Gly Phe Ile Asn Val Gly Gln
    370                 375                 380
Asn Ala Ile Ile Lys Val Glu Ala Phe Pro Tyr Thr Arg Tyr Gly Tyr
385                 390                 395                 400
Leu Val Gly Lys Val Lys Asn Ile Asn Leu Asp Ala Ile Glu Asp Gln
                405                 410                 415
Lys Leu Gly Leu Val Phe Asn Val Ile Val Ser Val Glu Glu Asn Asp
                420                 425                 430
Leu Ser Thr Gly Asn Lys His Ile Pro Leu Ser Ser Gly Met Ala Val
            435                 440                 445
Thr Ala Glu Ile Lys Thr Gly Met Arg Ser Val Ile Ser Tyr Leu Leu
        450                 455                 460
Ser Pro Leu Glu Glu Ser Val Thr Glu Ser Leu His Glu Arg
465                 470                 475

<210> SEQ ID NO 60
<211> LENGTH: 458
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 60

Met Lys Asn Ala Ser Thr Val Ser Glu Asp Thr Ala Ser Asn Gln Glu
1               5                   10                  15
Pro Thr Leu His Arg Gly Leu His Asn Arg His Ile Gln Leu Ile Ala
                20                  25                  30
Leu Gly Gly Ala Ile Gly Thr Gly Leu Phe Leu Gly Ile Gly Pro Ala
            35                  40                  45
Ile Gln Met Ala Gly Pro Ala Val Leu Leu Gly Tyr Gly Val Ala Gly
    50                  55                  60
Ile Ile Ala Phe Leu Ile Met Arg Gln Leu Gly Glu Met Val Val Glu
65                  70                  75                  80
Glu Pro Val Ser Gly Ser Phe Ala His Phe Ala Tyr Lys Tyr Trp Gly
                85                  90                  95
Pro Phe Ala Gly Phe Leu Ser Gly Trp Asn Tyr Trp Val Met Phe Val
                100                 105                 110
Leu Val Gly Met Ala Glu Leu Thr Ala Ala Gly Ile Tyr Met Gln Tyr
            115                 120                 125
Trp Phe Pro Asp Val Pro Thr Trp Ile Trp Ala Ala Ala Phe Phe Ile
    130                 135                 140
Ile Ile Asn Ala Val Asn Leu Val Asn Val Arg Leu Tyr Gly Glu Thr
145                 150                 155                 160
```

```
Glu Phe Trp Phe Ala Leu Ile Lys Val Leu Ala Ile Ile Gly Met Ile
            165                 170                 175

Gly Phe Gly Leu Trp Leu Leu Phe Ser Gly His Gly Gly Glu Lys Ala
        180                 185                 190

Ser Ile Asp Asn Leu Trp Arg Tyr Gly Gly Phe Ala Thr Gly Trp
        195                 200                 205

Asn Gly Leu Ile Leu Ser Leu Ala Val Ile Met Phe Ser Phe Gly Gly
        210                 215                 220

Leu Glu Leu Ile Gly Ile Thr Ala Ala Glu Ala Arg Asp Pro Glu Lys
225                 230                 235                 240

Ser Ile Pro Lys Ala Val Asn Gln Val Val Tyr Arg Ile Leu Leu Phe
            245                 250                 255

Tyr Ile Gly Ser Leu Val Val Leu Leu Ala Leu Tyr Pro Trp Val Glu
            260                 265                 270

Val Lys Ser Asn Ser Ser Pro Phe Val Met Ile Phe His Asn Leu Asp
            275                 280                 285

Ser Asn Val Val Ala Ser Ala Leu Asn Phe Val Ile Leu Val Ala Ser
        290                 295                 300

Leu Ser Val Tyr Asn Ser Gly Val Tyr Ser Asn Ser Arg Met Leu Phe
305                 310                 315                 320

Gly Leu Ser Val Gln Gly Asn Ala Pro Lys Phe Leu Thr Arg Val Ser
            325                 330                 335

Arg Arg Gly Val Pro Ile Asn Ser Leu Met Leu Ser Gly Ala Ile Thr
            340                 345                 350

Ser Leu Val Val Leu Ile Asn Tyr Leu Leu Pro Gln Lys Ala Phe Gly
            355                 360                 365

Leu Leu Met Ala Leu Val Val Ala Thr Leu Leu Leu Asn Trp Ile Met
            370                 375                 380

Ile Cys Leu Ala His Leu Arg Phe Arg Ala Ala Met Arg Arg Gln Gly
385                 390                 395                 400

Arg Glu Thr Gln Phe Lys Ala Leu Leu Tyr Pro Phe Gly Asn Tyr Leu
            405                 410                 415

Cys Ile Ala Phe Leu Gly Met Ile Leu Leu Leu Met Cys Thr Met Asp
            420                 425                 430

Asp Met Arg Leu Ser Ala Ile Leu Leu Pro Val Trp Ile Val Phe Leu
            435                 440                 445

Phe Met Ala Phe Lys Thr Leu Arg Arg Lys
    450                 455
```

<210> SEQ ID NO 61
<211> LENGTH: 456
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 61

```
Met Glu Gly Gln Gln His Gly Glu Gln Leu Lys Arg Gly Leu Lys Asn
1               5                   10                  15

Arg His Ile Gln Leu Ile Ala Leu Gly Gly Ala Ile Gly Thr Gly Leu
            20                  25                  30

Phe Leu Gly Ser Ala Ser Val Ile Gln Ser Ala Gly Pro Gly Ile Ile
        35                  40                  45
```

```
Leu Gly Tyr Ala Ile Ala Gly Phe Ile Ala Phe Leu Ile Met Arg Gln
 50                  55                  60

Leu Gly Glu Met Val Val Glu Pro Val Ala Gly Ser Phe Ser His
 65                  70                  75                  80

Phe Ala Tyr Lys Tyr Trp Gly Ser Phe Ala Gly Phe Ala Ser Gly Trp
                 85                  90                  95

Asn Tyr Trp Val Leu Tyr Val Leu Val Ala Met Ala Glu Leu Thr Ala
                100                 105                 110

Val Gly Lys Tyr Ile Gln Phe Trp Tyr Pro Glu Ile Pro Thr Trp Val
                115                 120                 125

Ser Ala Ala Val Phe Phe Val Val Ile Asn Ala Ile Asn Leu Thr Asn
130                 135                 140

Val Lys Val Phe Gly Glu Met Glu Phe Trp Phe Ala Ile Ile Lys Val
145                 150                 155                 160

Ile Ala Val Val Ala Met Ile Ile Phe Gly Ala Trp Leu Leu Phe Ser
                165                 170                 175

Gly Asn Gly Gly Pro Gln Ala Ser Val Ser Asn Leu Trp Asp Gln Gly
                180                 185                 190

Gly Phe Leu Pro His Gly Phe Thr Gly Leu Val Met Met Met Ala Ile
        195                 200                 205

Ile Met Phe Ser Phe Gly Gly Leu Glu Leu Val Gly Ile Thr Ala Ala
        210                 215                 220

Glu Ala Asp Asn Pro Glu Gln Ser Ile Pro Lys Ala Thr Asn Gln Val
225                 230                 235                 240

Ile Tyr Arg Ile Leu Ile Phe Tyr Ile Gly Ser Leu Ala Val Leu Leu
                245                 250                 255

Ser Leu Met Pro Trp Thr Arg Val Thr Ala Asp Thr Ser Pro Phe Val
                260                 265                 270

Leu Ile Phe His Glu Leu Gly Asp Thr Phe Val Ala Asn Ala Leu Asn
        275                 280                 285

Ile Val Val Leu Thr Ala Ala Leu Ser Val Tyr Asn Ser Cys Val Tyr
        290                 295                 300

Cys Asn Ser Arg Met Leu Phe Gly Leu Ala Gln Gln Gly Asn Ala Pro
305                 310                 315                 320

Lys Ala Leu Ala Ser Val Asp Lys Arg Gly Val Pro Val Asn Thr Ile
                325                 330                 335

Leu Val Ser Ala Leu Val Thr Ala Leu Cys Val Leu Ile Asn Tyr Leu
                340                 345                 350

Ala Pro Glu Ser Ala Phe Gly Leu Leu Met Ala Leu Val Val Ser Ala
                355                 360                 365

Leu Val Ile Asn Trp Ala Met Ile Ser Leu Ala His Met Lys Phe Arg
        370                 375                 380

Arg Ala Lys Gln Glu Gln Gly Val Val Thr Arg Phe Pro Ala Leu Leu
385                 390                 395                 400

Tyr Pro Leu Gly Asn Trp Val Cys Leu Leu Phe Met Ala Ala Val Leu
                405                 410                 415

Val Ile Met Leu Met Thr Pro Gly Met Ala Ile Ser Val Tyr Leu Ile
                420                 425                 430

Pro Val Trp Leu Ile Val Leu Gly Ile Gly Tyr Leu Phe Lys Glu Lys
                435                 440                 445

Thr Ala Lys Ala Val Lys Ala His
                450                 455
```

<210> SEQ ID NO 62
<211> LENGTH: 1582
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 62

```
ggtaccagtt gttcttattg gtggtgttgc tttatggttg catcgtagta aatggttgta      60
acaaaagcaa ttttccggc tgtctgtata caaaaacgcc gtaaagtttg agcgaagtca     120
ataaactctc tacccattca gggcaatatc tctcttggat ccctctagaa ataattttgt     180
ttaactttaa gaaggagata tacatatgaa aaacgcgtca accgtatcgg aagatactgc     240
gtcgaatcaa gagccgacgc ttcatcgcgg attacataac cgtcatattc aactgattgc     300
gttgggtggc gcaattggta ctggtctgtt tcttggcatt ggcccggcga ttcagatggc     360
gggtccggct gtattgctgg gctacggcgt cgccgggatc atcgctttcc tgattatgcg     420
ccagcttggc gaaatggtgg ttgaggagcc ggtatccggt tcatttgccc actttgccta     480
taaatactgg ggaccgtttg cgggcttcct ctctggctgg aactactggg taatgttcgt     540
gctggtggga atggcagagc tgaccgctgc gggcatctat atgcagtact ggttcccgga     600
tgttccaacg tggatttggg ctgccgcctt ctttattatc atcaacgccg ttaacctggt     660
gaacgtgcgc ttatatggcg aaaccgagtt ctggtttgcg ttgattaaag tgctggcaat     720
catcggtatg atcggctttg gcctgtggct gctgttttct ggtcacggcg gcagaaaagc     780
cagtatcgac aacctctggc gctacggtgg tttcttcgcc accggctgga atgggctgat     840
tttgtcgctg gcggtaatta tgttctcctt cggcggtctg gagctgattg ggattactgc     900
cgctgaagcg cgcgatccgg aaaaaagcat tccaaaagcg gtaaatcagg tggtgtatcg     960
catcctgctg ttttacatcg gttcactggt ggttttactg gcgctctatc cgtgggtgga    1020
agtgaaatcc aacagtagcc cgtttgtgat gattttccat aatctcgaca gcaacgtggt    1080
agcttctgcg ctgaacttcg tcattctggt agcatcgctg tcagtgtata acagcggggt    1140
ttactctaac agccgcatgc tgtttggcct ttctgtgcag ggtaatgcgc cgaagttttt    1200
gactcgcgtc agccgtcgcg gtgtgccgat taactcgctg atgctttccg gagcgatcac    1260
ttcgctggtg gtgttaatca actatctgct gccgcaaaaa gcgtttggtc tgctgatggc    1320
gctggtggta gcaacgctgc tgttgaactg gattatgatc tgtctggcgc atctgcgttt    1380
tcgtgcagcg atgcgacgtc aggggcgtga aacacagttt aaggcgctgc tctatccgtt    1440
cggcaactat ctctgcattg ccttcctcgg catgatttg ctgctgatgt gcacgatgga    1500
tgatatgcgc ttgtcagcga tcctgctgcc ggtgtggatt gtattcctgt ttatggcatt    1560
taaaacgctg cgtcggaaat aa                                            1582
```

<210> SEQ ID NO 63
<211> LENGTH: 1573
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 63

```
ggtaccagtt gttcttattg gtggtgttgc tttatggttg catcgtagta aatggttgta      60
```

```
acaaaagcaa ttttccggc tgtctgtata caaaaacgcc gtaaagtttg agcgaagtca      120
ataaactctc tacccattca gggcaatatc tctcttggat ccctctagaa ataattttgt      180
ttaactttaa gaaggagata tacatatgga ggggcagcag catggggagc aactgaagcg      240
cgggttaaaa aatcgtcaca ttcaattaat cgcgctgggc ggagcaattg gtacgggatt      300
gttcctgggt tcagcgagcg tcatccaatc ggcaggtcca gggatcatct tgggatatgc      360
gatcgcaggc tttatcgctt ttcttattat gcgccaatta ggtgagatgg tggtcgagga      420
gcctgtagct ggctccttct cacatttcgc gtacaagtat tggggatcct tgcgggatt       480 tgcttctggt tggaactatt gggttcttta tgtcctggtg gccatggcgg agctgaccgc      540
ggttggaaaa tatatccagt tctggtaccc cgagatcccg acgtgggtct cagccgcggt      600
attctttgtt gttatcaatg caatcaattt aaccaacgta aaagtatttg gtgaaatgga      660
gttctggttc gcgattatca agtaattgc cgtagttgct atgattattt ttggggcatg       720 gttgctttc tcaggaaatg gcggaccaca agcgtcggtt tcaaacctgt gggatcaagg      780
gggattcctg ccgcacggat ttacgggctt ggtgatgatg atggctatca ttatgttttc      840
tttcggtggt cttgaattag tgggtattac cgcagcagag gcagataatc ccgaacaaag      900
catcccaaaa gctactaacc aagttattta ccgtatcctg atttttttata ttggttctct      960 ggcagtcctg ctttccttaa tgccctggac acgtgtaacg gccgatacat ccccttttgt     1020
acttatcttt cacgaactgg gagacacgtt cgtcgccaat gcattaaaca ttgttgtgct     1080
gacagctgcc ttatctgtgt ataatagctg cgtttattgc aattcacgta tgttattcgg     1140
gcttgctcag cagggtaacg cgccaaaggc gttggcctca gtagataagc gcggagtgcc     1200
tgtaaataca attttggtca gcgcattagt cacggctctt tgcgttctga ttaactatct     1260
ggctcctgaa agcgcattcg gattacttat ggccctggtt gtttccgccc tggttatcaa     1320
ttgggcaatg attagttggg cacatatgaa gttccgccgt gctaaacaag aacaaggtgt     1380
cgtaactcgt ttccctgcct tattgtatcc gctggggaat tgggtatgcc ttctttttat     1440
ggccgcagta ctggtaatta tgttgatgac gcccggcatg gctattagtg tataccttat     1500
tccggtatgg ttaatcgtct tgggtatcgg ctacttattt aaagaaaaaa cagcaaaagc     1560
cgtaaaggct cat                                                        1573
```

<210> SEQ ID NO 64
<211> LENGTH: 967
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 64

```
caaatatcac ataatcttaa catatcaata aacacagtaa agtttcatgt gaaaaacatc       60
aaacataaaa tacaagctcg gaatacgaat cacgctatac acattgctaa caggaatgag      120
attatctaaa tgaggattga tatattaatt ggacatacta gttttttttca tcaaaccagt      180 agagataact tccttcacta tctcaatgag gaagaaataa aacgctatga tcagtttcat      240
tttgtgagtg ataaagaact ctatattta agccgtatcc tgctcaaaac agcactaaaa      300
agatatcaac ctgatgtctc attacaatca tggcaattta gtacgtgcaa atatggcaaa      360
ccatttatag ttttttcctca gttggcaaaa aagattttt ttaaccttc ccatactata       420 gatacagtag ccgttgctat tagttctcac tgcgagcttg gtgtcgatat tgaacaaata      480
```

-continued

```
agagatttag acaactctta tctgaatatc agtcagcatt tttttactcc acaggaagct      540
actaacatag tttcacttcc tcgttatgaa ggtcaattac tttttggaa aatgtggacg       600 ctcaaagaag cttacatcaa atatcgaggt aaaggcctat ctttaggact ggattgtatt     660
gaatttcatt taacaaataa aaaactaact tcaaaatata gaggttcacc tgtttatttc     720
tctcaatgga aaatatgtaa ctcatttctc gcattagcct ctccactcat caccoctaaa     780 ataactattg agctatttcc tatgcagtcc caactttatc accacgacta tcagctaatt    840
cattcgtcaa atgggcagaa ttgaatcgcc acggataatc tagacacttc tgagccgtcg    900
ataatattga ttttcatatt ccgtcggtgg tgtaagtatc ccgcataatc gtgccattca    960
catttag                                                              967
```

<210> SEQ ID NO 65
<211> LENGTH: 424
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 65

```
ggatgggggg aaacatggat aagttcaaag aaaaaaaccc gttatctctg cgtgaaagac     60
aagtattgcg catgctggca caaggtgatg agtactctca aatatcacat aatcttaaca    120
tatcaataaa cacagtaaag tttcatgtga aaaacatcaa acataaaata caagctcgga    180
atacgaatca cgctatacac attgctaaca ggaatgagat tatctaaatg aggattgatg    240
tgtaggctgg agctgcttcg aagttcctat actttctaga gaataggaac ttcggaatag   300
gaacttcgga ataggaacta aggaggatat tcatatgtcg tcaaatgggc agaattgaat   360
cgccacggat aatctagaca cttctgagcc gtcgataata ttgattttca tattccgtcg   420
gtgg                                                                424
```

<210> SEQ ID NO 66
<211> LENGTH: 14
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic consensus sequence"
<220> FEATURE:
<221> NAME/KEY: modified_base
<222> LOCATION: (6)..(9)
<223> OTHER INFORMATION: a, c, t, g, unknown or other

<400> SEQUENCE: 66

```
ttgatnnnna tcaa                                                       14
```